US012459883B2

(12) United States Patent
Duke et al.

(10) Patent No.: US 12,459,883 B2
(45) Date of Patent: Nov. 4, 2025

(54) SUBSTITUTED HYDROXYSTILBENE COMPOUNDS AND DERIVATIVES SYNTHESIS AND USES THEREOF

(71) Applicant: Kynan Duke IP, LLC, Greensboro, NC (US)

(72) Inventors: Colin Charles Duke, Randwick (AU); Rujee Kyokajee Duke, Randwick (AU); Van Hoan Tran, Guilford (AU)

(73) Assignee: Kynan Duke IP, LLC, Greensboro, NC (US)

( * ) Notice: Subject to any disclaimer, the term of this patent is extended or adjusted under 35 U.S.C. 154(b) by 700 days.

(21) Appl. No.: 17/788,698

(22) PCT Filed: Dec. 23, 2020

(86) PCT No.: PCT/AU2020/051431
§ 371 (c)(1),
(2) Date: Jun. 23, 2022

(87) PCT Pub. No.: WO2021/127743
PCT Pub. Date: Jul. 1, 2021

(65) Prior Publication Data

US 2023/0159421 A1 May 25, 2023

(30) Foreign Application Priority Data

Dec. 23, 2019 (AU) ................................ 2019904976

(51) Int. Cl.

| | |
|---|---|
| ***C07D 263/58*** | (2006.01) |
| ***A61P 17/00*** | (2006.01) |
| ***A61P 17/06*** | (2006.01) |
| ***A61P 29/00*** | (2006.01) |
| ***A61P 35/00*** | (2006.01) |
| ***C07C 41/26*** | (2006.01) |
| ***C07C 43/23*** | (2006.01) |
| ***C07C 51/367*** | (2006.01) |
| ***C07C 65/28*** | (2006.01) |
| ***C07C 201/12*** | (2006.01) |
| ***C07C 209/04*** | (2006.01) |
| ***C07C 217/80*** | (2006.01) |
| ***C07C 217/82*** | (2006.01) |
| ***C07C 225/06*** | (2006.01) |
| ***C07C 231/12*** | (2006.01) |
| ***C07C 231/14*** | (2006.01) |
| ***C07C 233/01*** | (2006.01) |
| ***C07C 235/74*** | (2006.01) |
| ***C07C 237/04*** | (2006.01) |
| ***C07C 277/08*** | (2006.01) |
| ***C07C 279/18*** | (2006.01) |
| ***C07C 303/40*** | (2006.01) |
| ***C07C 311/08*** | (2006.01) |
| ***C07D 235/26*** | (2006.01) |

(52) U.S. Cl.
CPC .............. *C07C 43/23* (2013.01); *A61P 17/00* (2018.01); *A61P 17/06* (2018.01); *A61P 29/00* (2018.01); *A61P 35/00* (2018.01); *C07C 41/26* (2013.01); *C07C 51/367* (2013.01); *C07C 65/28* (2013.01); *C07C 201/12* (2013.01); *C07C 209/04* (2013.01); *C07C 217/80* (2013.01); *C07C 217/82* (2013.01); *C07C 225/06* (2013.01); *C07C 231/12* (2013.01); *C07C 231/14* (2013.01); *C07C 233/01* (2013.01); *C07C 235/74* (2013.01); *C07C 237/04* (2013.01); *C07C 277/08* (2013.01); *C07C 279/18* (2013.01); *C07C 303/40* (2013.01); *C07C 311/08* (2013.01); *C07D 235/26* (2013.01); *C07D 263/58* (2013.01)

(58) Field of Classification Search
CPC ... C07C 43/253; C07C 37/055; C07C 67/293; C07C 39/215; C07C 41/01; C07C 67/297
See application file for complete search history.

(56) References Cited

U.S. PATENT DOCUMENTS

| | | | |
|---|---|---|---|
| 9,185,909 B2 | 11/2015 | Snyder et al. | |
| 2004/0242696 A1 | 12/2004 | Chaplin et al. | |
| 2010/0247462 A1 | 9/2010 | Snyder et al. | |
| 2015/0307429 A1* | 10/2015 | Duke | ..................... C07C 39/21 568/628 |

FOREIGN PATENT DOCUMENTS

| | | |
|---|---|---|
| CN | 103172512 | 6/2013 |
| CN | 103649031 | 3/2014 |
| CN | 107011127 | 8/2017 |
| JP | 2014519488 | 8/2014 |
| WO | 03018013 | 3/2003 |
| WO | 2012149608 | 11/2012 |

OTHER PUBLICATIONS

Su et al., First total synthesis of two resveratrol derivatives, Journal of Chemical Research, 2004, 2 pages.
El-Feraly et al., Total Synthesis of Notholaenic Acid, Jornal of Natural Products, vol. 48, No. 2, 1985, 6 pages.
Raju et al., Synthesis of 2,3-Disubstituted Carbazoles, Benzo[c-]carbazoles, and Phenanthrenes Through $FeCl_3$—Mediated Cyclization of Triene Frameworks, SynOpen, 2018, 5 pages.
Steynberg et al., Synthesis of Condensed Tannins. Part 18. Stilbenes as Potent Nucleophiles in Regio- and Sterio-specific Condensations: Novel Guibourtinidol-Stilbenes from Gulbourtia coleosperma, Journal of the Chemical Society, Perkin Transactions 1, 1987, pp. 1705-1712.
Hartung et al., Stilbenes as k-Selective, Non-nitrogenous Opioid Receptor Antagonists, Journal of Natural Products, 2014, pp. 311-319.

(Continued)

*Primary Examiner* — Erich A Leeser
(74) *Attorney, Agent, or Firm* — Thorpe North & Western, LLP

(57) ABSTRACT

The present disclosure relates to substituted hydroxystilbene compounds and derivatives, specifically 2-substituted hydroxystilbene compounds and derivatives, the synthesis of such compounds and their use in therapy.

33 Claims, 23 Drawing Sheets

(56) References Cited

OTHER PUBLICATIONS

Munigunti et al., Screening of natural compounds for ligands to PfTrxR by ultrafiltration and LC-MS based binding assay, Journal of Pharmaceutical and Biomedical Analysis 55, 2011, pp. 265-271.
Snyder et al., Total Synthesis of Diverse Carbogenic Complexity within the Resveratrol Class from a Common Building Block, Journal of the American Chemical Society, 2009, pp. 1753-1765.
Qi et al., Design of Chiral Sulfoxide—Olefins as a New Class of Sulfur-Based Olefin Ligands for Asymmetric Catalysis, Organic Letters, vol. 13, No. 13, 2011, pp. 3410-3413.
Wang et al., Stilbene Derivatives from Gnetum montanum Markgr. f. megalocarpum Markgr., Helvetica Chimca Acta, vol. 91, 2008, pp. 159-164.
Abu-Mellal et al., Prenylated cinnamate and stilbenes from Kangaroo Island propolis and their antioxidant activity, Phytochemistry 77 (2012) 251-259.
Abu-Mellal et al., The Pharmacological Effect of Stilbenes Isolated From Kangaroo Island Propolis on Sirt-1 Enzyme Activity, International Journal of Pharmacy and Pharmaceutical Sciences, vol. 8, Issue 8, 2016, 264-267.
Duke et al., A sedge plant as the source of Kangaroo Island propolis rich in prenylated p-coumarate ester and stilbenes, Phytochemistry 134 (2017) 87-97.
Aritomi et al., Stilbene Glucosides in the Bark of Picea Sitchensis, Phytochemistry, vol. 15, 1976, 2006-2008.
Kanekar et al., Regioselective synthesis of phenanthrenes and evaluation of their anti-oxidant based anti-inflammatory potential, European Journal of Medicinal Chemistry 76 (2013) 454-463.
Koolaji et al., Synthesis of C- and O-prenylated tetrahydroxystilbenes and O-prenylated cinnamates and their action towards cancer cells, European Journal of Medicinal Chemistry 63 (2013) 415-422.
McAtee et al., Polycyclic Aromatic Hydrocarbons via Iron(III)-Catalyzed Carbonyl-Olefin Metathesis, Journal of the American Chemical Society 139 (2017) 2960-2963.
Mervic et al., Synthesis of 2,2'-Diacyl-1,1'-biaryls. Regiocontrolled Protection of Ketones in Unsymmetrically Substituted 9, 10-Phenanthrenequinones, J. Org. Chem., vol. 45, No. 23 (1980) 4720-4725.
Snyder et al., Total Synthesis of Resveratrol-Based Natural Products: A Chemoselective Solution, Angew. Chem. Int. Ed. 46 (2007) 8186-8191.
Tanjung et al., Flavonoid and stilbene derivatives from Macaranga trichocarpa, Fitoterapia 126 (2018) 74-77.
Zheng et al., The antioxidative activity of piceatannol and its different derivatives: Antioxidative mechanism analysis, Phytochemistry 156 (2018) 184-192.

* cited by examiner

Concentration-response graphs of compound 1, 8, 20, 27, 28, 31 and 35

Effect of compound 1:

A.

B.

Effect of compound 1:

C.

D.

Effect of compound 8:

A.

B.

Effect of compound 8:

C.

D.

Effect of compound 20:

A.

B.

Effect of compound 20:

C.

D.

Effect of compound 27.

A.

B.

Effect of compound 27.

C.

D.

Effect of compound 28.

A.

B.

Effect of compound 28.

C.

D.

Effect of compound 31

A.

B.

Effect of compound 31.

C.

D.

The effects of compound 35.

A.

B.

The effects of compound 35.

C.

D.

BNA99 Results

Compound 1 [KYN-001]

Compound 20 [KYN-146]

Compound 27 [KYN-149]

Comp. 1 Comp. 20 Comp. 27 TMZ

BNB04

Results

Compound 20

Compound 27

Comp. 1 Comp. 20 Comp. 27 TMZ

BNB18

Results

Compound 20

Compound 27

A. Concentrations of 27 in different tissues from experimental mice.

B. Concentrations of 27 in isolated tissues from the treated groups.

SUBSTITUTED HYDROXYSTILBENE COMPOUNDS AND DERIVATIVES SYNTHESIS AND USES THEREOF

TECHNICAL FIELD

The present disclosure relates to substituted hydroxystilbene compounds and derivatives, specifically 2-substituted hydroxystilbene compounds and derivatives, the synthesis of such compounds and their use in therapy.

BACKGROUND

WO2012/19608 discloses novel prenylated polyhydroxystilbene derivatives and methods of preparing such compounds via multiple steps. One of the steps is an O- to C-prenyl rearrangement step as generally outlined below:

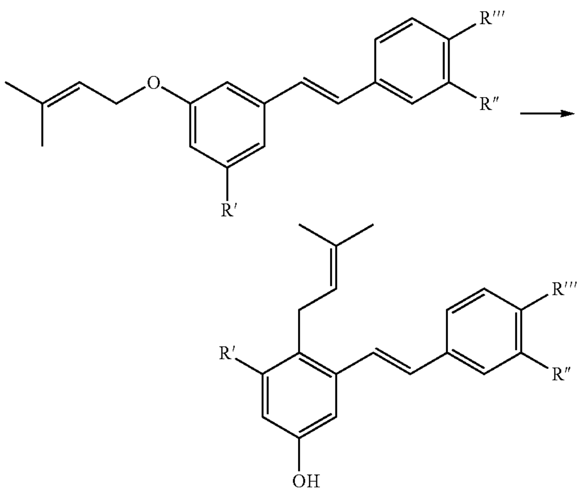

The methods disclosed in WO2012/149608 have a number of disadvantages. The number of synthetic steps from common intermediates to the final prenylated polyhydroxystilbene compounds is high. The rearrangement step is problematic as it is specific mainly to a prenyl group and to a relatively narrow range of other substituent types. The rearrangement methodology requires chromatographic separation and is generally low yielding. Thus, the prior art methods are not suitable to produce a wide range of synthetic derivatives of the prenylated polyhydroxystilbene compounds and are not suitable for large scale synthesis. The content of WO2012/149608 is fully incorporated herein.

A need exists for alternate methods of producing substituted hydroxystilbene compounds and derivatives, specifically 2-substituted hydroxystilbene compounds and derivatives.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each of the appended claims.

SUMMARY

In work leading up to the present disclosure the inventors have synthesised a wide range of 2-substituted hydroxystilbene compounds by a novel process that has provided an efficient and commercially viable pathway to a number of compounds that have importance in medical therapy. The novel process has also provided access to a range of novel compounds that have shown to be potential candidates for use in therapy, such as in the treatment of cancer and skin diseases and disorders.

The present disclosure relates to the synthesis of a compound of formula (I):

Formula (I)

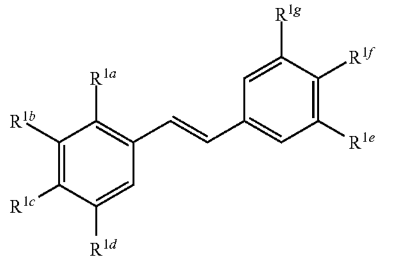

wherein:

$R^{1a}$ is independently allyl, crotyl, prenyl, geranyl, farnesyl, benzyl or 2-alkenyl, 2-alkynyl;

$R^{1b}$ is independently $CF_3$, OH or $OR^2$, $NO_2$, NHEt, $NMe_2$, NMeEt, $NHR^3$, $NMeR^3$, $NHC{=}NH(NH_2)$ or $COOR^2$;

$R^{1c}$ is independently H, alkyl, alkenyl, alkynyl, alkanedienyl, prenyl, geranyl, farnesyl, or benzyl;

$R^{1d}$ is independently $CF_3$, OH or $OR^2$, $NHR^3$, $NO_2$, $NMeR^3$, $NHC{=}NH(NH_2)$ or $COOR^2$;

$R^{1e}$ is independently H, $C_1$-$C_6$ alkyl, OH, $OR^2$, $NO_2$, $NMe_2$, $NHR^3$, $NMeR^3$, NHC(O)H, or $SR^2$;

$R^{1f}$ is independently H, OH, $OR^2$, $NO_2$, $NHR^3$, $NHC{=}NH(NH_2)$, $COOR^2$, COOH;

$R^{1g}$ is independently H, alkyl, $CF_3$, OH or $OR^2$;

and no more than one of $R^{1e}$, $R^{1f}$ or $R^{1g}$ can be H;

or $R^{1e}$ and $R^{1f}$ form a five or six-membered heterocyclic ring containing a carbonyl group or $(CO)CH_2$ group when $R^{1e}$ is independently OH, $NH_2$ or NHMe and $R^{1f}$ is $NH_2$, such that the nitrogen of $R^{1f}$ is bridged with the carbonyl group or $(CO)CH_2$ group to the oxygen or nitrogen of $R^{1e}$;

$R^2$ is independently methyl, ethyl, propyl, isopropyl, butyl, isobutyl, t-butyl, trifluoromethyl, $COCOOR^4$ or an O-protecting group when $R^2$ is attached to an O, wherein the O-protecting group is selected from the group consisting of COMe, t-$BuSi(CH_3)_2$, 2-(trimethylsilyl)ethoxy]methyl (SEM), $CH(OEt)CH_3$, tetrahydropyranyl, or $C(OEt)(CH_3)_2$;

$R^3$ is independently H, $CH_3$, OH, (CO)H, (CO)Me, $SO_2Me$, $CH_2COOH$, $CH_2COOR^2$, $CO(CH_2)_nNH_2$, $CONH_2$, $CO(CH_2)_nCOOH$ or $COCOOR^4$, where n=0, 1 or 2; and $R^4$ is $C_1$-$C_6$ alkyl.

As referred to herein, the 2-substituted hydroxystilbene compound according to formula (I) is represented by two benzene rings which are designated as the A and B ring. The A-ring referred to herein represents the benzene ring bearing substituents, $R^{1a}$, $R^{1b}$, $R^{1c}$ and $R^{1d}$, and the B-ring referred to herein represents the benzene ring bearing the substituents $R^{1e}$, $R^{1f}$ and $R^{1g}$.

The present disclosure utilises a modular approach for synthesising the compound according to formula (I). The A ring and the B ring of the 2-substituted hydroxylstilbene compound are formed from two separate modules, Module A and Module B respectively. Module A is a halo or hydroxyl benzaldehyde derivative and Module B is an aromatic phosphonate derivative. According to the present disclosure, coupling of the halo/hydroxy benzaldehyde (Module A) with the aromatic phosphonate (Module B) affords a 2-halo or 2-hydroxy substituted hydroxystilbene derivative (Module C), as referred to above.

Throughout the specification, 2-halo or 2-hydroxy substituted hydroxystilbene derivative (Module C) may be referred to as 2-halo/hydroxyl substituted hydroxystilbene derivative, 2-halo/hydroxyl hydroxystilbene derivative, 2-halo/hydroxyl hydroxystilbene or Module C and includes both 2-halo substituted hydroxystilbene derivatives and 2-hydroxy substituted hydroxystilbene derivatives and equivalent name variations as before mentioned.

The present inventors have surprisingly found that this methodology allows an alternate synthesis of 2-substituted hydroxystilbene compounds and versatility of substitution at the 2-position of 2-substituted hydroxystilbene compounds, such that the group substituted at the 2-position can be extended beyond the prenyl group. Accordingly, the present disclosure provides a process of preparing a 2-substituted hydroxystilbene compound of formula (I), as described above, where addition of a 2-alkenyl or benzyl group at the $R^{1a}$ position occurs by direct coupling of the 2-alkenyl or benzyl group of a boronic acid/derivative or organostannane compound containing the same with a 2-halo/hydroxy substituted hydroxystilbenene derivative.

In one embodiment, the synthesis of the above compound of formula (I) is advantageously efficient in terms of having a low number of synthetic steps from prepared starting modules, and versatility and flexibility for application in preparing a wide range of synthetic derivatives. In another embodiment, each step of the synthesis starting from the prepared modules is high yielding.

In one embodiment, the method of preparing a compound of formula (I) as defined above, when $R^{1a}$ is a prenyl group results in an improvement in the yield over the steps disclosed in WO2012/149608 which produces a mixture of products.

One embodiment of the present disclosure provides a synthetic method where the O- to C-prenyl rearrangement step disclosed in WO2012/149608 is replaced by a direct coupling of a prenyl group to an aromatic ring by way of coupling of a prenylboronic acids/esters or a prenyltributylstannane with a 2-halo or 2-hydroxyl substituted hydroxystilbenene derivative. Advantageously, groups other than prenyl can be added at the $R^{1a}$ position of the hydroxystilebene structure.

Advantageously, the inventors are able to adopt the versatile methodology disclosed herein to efficiently prepare previously identified 2-prenyl hydroxystilbene compounds which are important in medical therapy on a commercial scale. Due to the versatility of the methodology disclosed herein, the inventors have been able to prepare a wide range of 2-substituted hydroystilbene compounds according to Formula (I) which they were previously unable to prepare using the rearrangement method. The inventors have surprisingly found that the 2-substituted hydroxystilbene compounds according to formula (I) prepared by the methodology disclosed herein, are strong candidates for the development of new therapeutic agents in the treatment of diseases such as cancer and skin disease and disorders such as atopic dermatitis and psoriasis.

In a first aspect, the present disclosure provides a process of synthesising a compound according to formula (I), Formula (I)

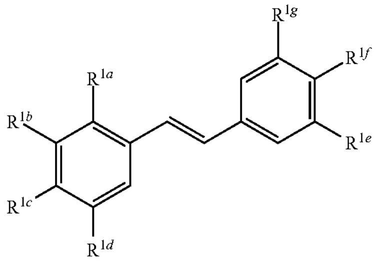

wherein:

$R^{1a}$ is independently allyl, crotyl, prenyl, geranyl, farnesyl, benzyl or 2-alkenyl, 2-alkynyl;

$R^{1b}$ is independently $CF_3$, OH or $OR^2$, $NO_2$, NHEt, $NMe_2$, NMeEt, $NHR^3$, $NMeR^3$, NHC═NH($NH_2$) or $COOR^2$;

$R^{1c}$ is independently H, alkyl, alkenyl, alkynyl, alkanedienyl, prenyl, geranyl, farnesyl, or benzyl;

$R^{1d}$ is independently $CF_3$, OH or $OR^2$, $NHR^3$, $NO_2$, $NMeR^3$, NHC═NH($NH_2$) or $COOR^2$;

$R^{1e}$ is independently H, $C_1$-$C_6$ alkyl, OH, $OR^2$, $NO_2$, $NMe_2$, $NHR^3$, $NMeR^3$, NHC(O)H, or $SR^2$;

$R^{1f}$ is independently H, OH, $OR^2$, $NO_2$, $NHR^3$, NHC═NH($NH_2$), $COOR^2$, COOH;

$R^{1g}$ is independently H, alkyl, $CF_3$, OH or $OR^2$;

and no more than one of $R^{1e}$, $R^{1f}$ or $R^{1g}$ can be H;

or $R^{1e}$ and $R^{1f}$ form a five or six-membered heterocyclic ring containing a carbonyl group or (CO)$CH_2$ group when $R^{1e}$ is independently OH, $NH_2$ or NHMe and $R^{1f}$ is $NH_2$, such that the nitrogen of $R^{1f}$ is bridged with the carbonyl group or (CO)$CH_2$ group to the oxygen or nitrogen of $R^{1e}$;

$R^2$ is independently methyl, ethyl, propyl, isopropyl, butyl, isobutyl, t-butyl, trifluoromethyl, $COCOOR^4$ or an O-protecting group when $R^2$ is attached to an O;

$R^3$ is independently H, $CH_3$, OH, (CO)H, (CO)Me, $SO_2Me$, $CH_2COOH$, $CH_2COOR^2$, $CO(CH_2)_nNH_2$, $CONH_2$, $CO(CH_2)_nCOOH$ or $COCOOR^4$, where n is 0, 1 or 2; and $R^4$ is $C_1$-$C_6$ alkyl;

the process comprising:

i) a step of coupling a compound of formula (II) (Module A) with a compound of formula (III) (Module B) to afford a compound of formula (IV) (Module C):

Module A

Formula (II)

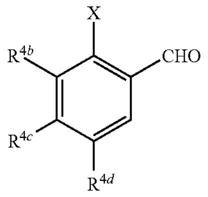

Module B

Formula (III)

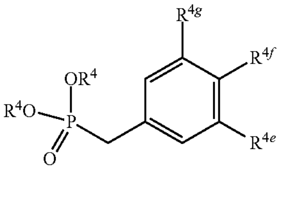

-continued

Module C

Formula (IV)

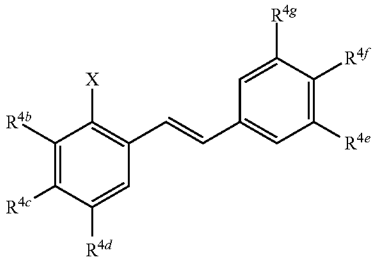

wherein, in Formula II (Module A):

$R^{2b}$ is independently $CF_3$, OH, $OR^2$, $NO_2$, $NMe_2$, NHEt, NMeEt, $NHR^3$ or $NMeR^3$;

$R^{2c}$ is independently H, alkyl, alkenyl, alkynyl, alkanedienyl, prenyl, geranyl, farnesyl, or benzyl;

$R^{2d}$ is independently $CF_3$, OH or $OR^2$, $NO_2$, $NHR^3$, $NMeR^3$, NHC═NH($NH_2$) or $COOR^2$;

X is a halide or a hydroxyl group, wherein the halide is selected from the group consisting of F, Cl, Br, I, and At;

$R^2$ is independently methyl, ethyl, propyl, isopropyl, butyl, isobutyl, t-butyl, trifluoromethyl, or O-protecting group when $R^2$ is attached to an O; and $R^3$ is independently H, OH, $CH_3$, (CO)H, COMe, $SO_2Me$, $COCH_2NH_2$, or $CH_2COOR^2$; and in Formula III (Module B):

$R^{3e}$ is independently H, $C_1$-$C_6$ alkyl, OH, OR, $NO_2$, NHMe, $NMe_2$, $NHR^3$ or $NMeR^3$, $SR^2$;

$R^{3f}$ is independently H, OH, $OR^2$, $NO_2$, $NHR^3$, NHC═NH($NH_2$), COOH or $COOR^2$;

$R^{3g}$ is independently H, alkyl, $CF_3$, OH or $OR^2$;

and no more than one of $R^{3e}$, $R^{3f}$ or $R^{3g}$ can be H;

or $R^{3e}$ and $R^{3f}$ form a five or six-membered heterocyclic ring containing a carbonyl group or (CO)$CH_2$ group when $R^{3e}$ is OH, $NH_2$ or NHMe and $R^{3f}$ is $NH_2$, such that the nitrogen of $R^{3f}$ is bridged with the carbonyl group or (CO)$CH_2$ group to the oxygen or nitrogen of $R^{3e}$;

$R^2$ is independently methyl, ethyl, propyl, isopropyl, butyl, isobutyl, t-butyl, trifluoromethyl or O-protecting group when $R^2$ is attached to an O, $R^3$ is independently H, $CH_3$, OH, (CO)H, COMe, $SO_2Me$, $COCH_2NH_2$, $CH_2COOH$ or $CH_2COOR^2$; and in Formula IV (Module C):

$R^{4b}$ is independently $CF_3$, OH or $OR^2$, $NO_2$, $NMe_2$, NHEt, NMeEt, $NHR^3$ or $NMeR^3$;

$R^{4c}$ is independently H, alkyl, alkenyl, alkynyl, alkanedienyl, prenyl, geranyl, farnesyl or benzyl;

$R^{4d}$ is independently $CF_3$, OH or $OR^2$, $OR^3$, $NO_2$ or $NHR^3$, $NMeR^3$, NHC═NH($NH_2$) or $COOR^2$;

$R^{4e}$ is independently H, $C_1$-$C_6$ alkyl, OH, $OR^2$, $NO_2$, $NMe_2$, $NHR^3$ or $NMeR^3$, $SR^2$;

$R^{4f}$ is independently H, OH, $OR^2$, $NO_2$, $NHR^3$, NHC═NH($NH_2$), COOH or $COOR^2$;

$R^{4g}$ is independently H, alkyl, $CF_3$, OH or $OR^2$;

and no more than one of $R^{4e}$, $R^{4f}$ or $R^{4g}$ can be H;

or $R^{4e}$ and $R^{4f}$ form a five or six-membered heterocyclic ring containing a carbonyl group or (CO)$CH_2$ group when $R^{4e}$ is OH, $NH_2$ or NHMe and $R^{4f}$ is $NH_2$, such that the nitrogen of $R^{4f}$ is bridged with the carbonyl group or (CO)$CH_2$ group to the oxygen or nitrogen of $R^{4e}$;

$R^2$ is independently methyl, ethyl, propyl, isopropyl, butyl, isobutyl, t-butyl, trifluoromethyl or O-protecting group when $R^2$ is attached to an O;

$R^3$ is independently H, $CH_3$, OH, (CO)H, COMe, $SO_2Me$, $COCH_2NH_2$, $CH_2COOH$ or $CH_2COOR^2$; and X is a halide or a hydroxyl group, wherein the halide is selected from the group consisting of F, Cl, Br, I, and At.

The 2-substituted halo/hydroxy hydroxystilbene compounds according to formula (IV) (Module C) undergo a further reaction to afford the compound of Formula (I) as herein described.

In one embodiment, the 2-substituted halo hydroxystilbene compound according to formula (IV) (Module C) undergoes a further coupling reaction with a 2-alkenyl or benzyl boronic acid or ester, a 2-alkenyl or benzyl trifluoroborate compound, or a 2-alkenyl or benzyl organostannane compound to afford the compound of Formula (I)

In another embodiment, when X is a hydroxyl in formula (IV), activation of the hydroxyl to a triflate group (OTf, trifluoromethylsilfonate) is required before coupling with a 2-alkenyl or benzyl boronic acid or ester, a 2-alkenyl or benzyl trifluoroborate compound, or a 2-alkenyl or benzyl organostannane compound to afford the compound of Formula (I).

The compound of formula (IV) or (I) may optionally undergo one or more further reactions, including but not limited to reaction with one or more —$NH_2$, $NO_2$ and/or —OH substituents on formula (IV) or formula (I).

In a second aspect, the present disclosure provides a compound according to formula (I)

Formula (I)

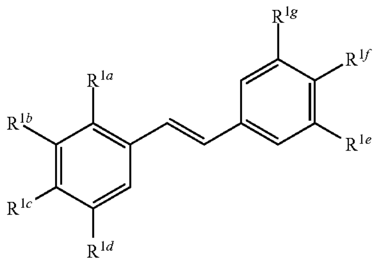

wherein:

$R^{1a}$ is independently allyl, crotyl, prenyl, geranyl, farnesyl, benzyl, 2-alkenyl or 2-alkynyl;

$R^{1b}$ is independently $CF_3$, OH or $OR^2$, $NO_2$, NHEt, $NMe_2$, NMeEt, $NHR^3$, $NMeR^3$, NHC═NH($NH_2$) or $COOR^2$;

$R^{1c}$ is independently H, alkyl, alkenyl, alkynyl, alkanedienyl, prenyl, geranyl, farnesyl, or benzyl;

$R^{1d}$ is independently $CF_3$, OH or $OR^2$, $NHR^3$, $NO_2$, $NMeR^3$, NHC═NH($NH_2$) or $COOR^2$;

$R^{1e}$ is independently H, $C_1$-$C_6$ alkyl, OH, $OR^2$, $NO_2$, $NMe_2$, $NHR^3$ or $NMeR^3$, NHC(O)H or $SR^2$;

$R^{1f}$ is independently H, OH, $OR^2$, $NO_2$, $NHR^3$, NHC═NH($NH_2$), $COOR^2$ or COOH;

$R^{1g}$ is independently H, alkyl, $CF_3$, OH or $OR^2$;

and only one of $R^{1e}$, $R^{1f}$ or $R^{1g}$ can be H;

or $R^{1e}$ and $R^{1f}$ form a five or six-membered heterocyclic ring containing a carbonyl group or (CO)$CH_2$ group when $R^{1e}$ is OH, $NH_2$ or NHMe and $R^{1f}$ is $NH_2$, such that the nitrogen of $R^{1f}$ is bridged with the carbonyl group or $(CO)CH_2$ group to the oxygen or nitrogen of $R^{1e}$;

$R^2$ is independently methyl, ethyl, propyl, isopropyl, butyl, isobutyl, t-butyl, trifluoromethyl, $COCOOR^4$ or an O-protecting group when $R^2$ is attached to an O, wherein the O-protecting group is selected from the group consisting of COMe, t-$BuSi(CH_3)_2$, 2-(trimethylsilyl)ethoxy]methyl (SEM), $CH(OEt)CH_3$, tetrahydropyranyl, or $C(OEt)(CH_3)_2$;

$R^3$ is independently H, $CH_3$, OH, (CO)H, (CO)Me, $SO_2Me$, $CH_2COOH$, $CH_2COOR^2$, $CO(CH_2)_nNH_2$, $CONH_2$, $CO(CH_2)_nCOOH$ or $COCOOR^4$, where n=0, 1 or 2;

$R^4$ is $C_1$-$C_6$ alkyl; and halide is selected from the group consisting of F, Cl, Br, I, and At;

wherein the compound of formula (I) is prepared by a process according to the first aspect as disclosed herein.

In a third aspect, the present disclosure provides a compound according to formula (I)

Formula (I)

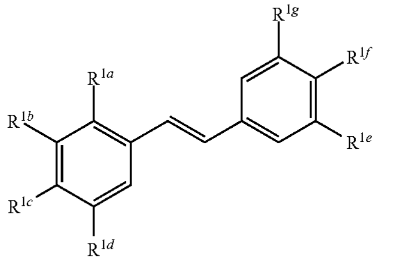

wherein:

$R^{1a}$ is independently allyl, crotyl, prenyl, geranyl, farnesyl, benzyl, 2-alkenyl or 2-alkynyl;

$R^{1b}$ is independently $CF_3$, OH, $OR^2$, $NO_2$, NHEt, $NMe_2$, NMeEt, $NHR^3$, $NMeR^3$, $NHC{=}NH(NH_2)$ or $COOR^2$;

$R^{1c}$ is independently H, alkyl, alkenyl, alkynyl, alkanedienyl, prenyl, geranyl, farnesyl, or benzyl;

$R^{1d}$ is independently $CF_3$, OH, $OR^2$, $NO_2$, $NHR^3$, $NMeR^3$, $NHC{=}NH(NH_2)$ or $COOR^2$;

$R^{1e}$ is independently H, $C_1$-$C_6$ alkyl, OH, $OR^2$, $NO_2$, $NMe_2$, $NHR^3$ or $NMeR^3$, NHC(O)H and $SR^2$;

$R^{1f}$ is independently H, OH, $OR^2$, $NO_2$, $NHR^3$, $NHC{=}NH(NH_2)$, $COOR^2$, COOH;

$R^{1g}$ is independently H, alkyl, $CF_3$, OH or $OR^2$;

and only one of $R^{1e}$, $R^{1f}$ or $R^{1E}$ can be H;

or $R^{1e}$ and $R^{1f}$ form a five or six-membered heterocyclic ring containing a carbonyl group or $(CO)CH_2$ group when $R^{1e}$ is OH, $NH_2$ or NHMe and $R^{1f}$ is $NH_2$, such that the nitrogen of $R^{1f}$ is bridged with the carbonyl group or $(CO)CH_2$ group to the oxygen or nitrogen of $R^{1e}$;

$R^2$ is independently methyl, ethyl, propyl, isopropyl, butyl, isobutyl, t-butyl, trifluoromethyl, $COCOOR^4$ or O-protecting group when $R^2$ is attached to an O, wherein the O-protecting group is selected from the group consisting of COMe, t-$BuSi(CH_3)_2$, 2-(trimethylsilyl)ethoxymethyl (SEM) acetal, $CH(OEt)CH_3$, tetrahydropyranyl, or $C(OEt)(CH_3)_2$;

$R^3$ is independently H, $CH_3$, OH, (CO)H, (CO)Me, $SO_2Me$, $CH_2COOH$, $CH_2COOR^2$, $CO(CH_2)_nNH_2$, $CONH_2$, $CO(CH_2)_nCOOH$ or $COCOOR^4$, where n is 0, 1 or 2;

$R^4$ is $C_1$-$C_6$ alkyl;

halide is selected from the group consisting of F, Cl, Br, I, and At; and only one of $R^{1e}$, $R^{1f}$ or $R^{1g}$ can be H, provided that when $R^{1a}$ and/or $R^{1c}$ is prenyl, $R^{1d}$ is OH, $R^{1f}$ is OH, $R^{1g}$ is H and $R^{1e}$ is OH, OMe or OEt, then $R^{1b}$ cannot be OH or $OR^2$ where R is methyl, ethyl, propyl, isopropyl, butyl, isobutyl, t-butyl, or benzyl.

In a fourth aspect, the present disclosure provides a method for treating cancer comprising administering a therapeutically effective amount of a compound according to the second or third aspect of the present disclosure or a pharmaceutically acceptable salt, solvate or pharmaceutical composition including said compounds to a patient in need.

In a fifth aspect, the present disclosure provides a method for treating a skin disease or disorder comprising administering a therapeutically effective amount of a compound according to the second or third aspect of the present disclosure or a pharmaceutically acceptable salt, solvate or pharmaceutical composition including said compounds to a patient in need.

DESCRIPTION OF EMBODIMENTS

Disclosed herein is a process of synthesising a compound of Formula (I):

Formula (I)

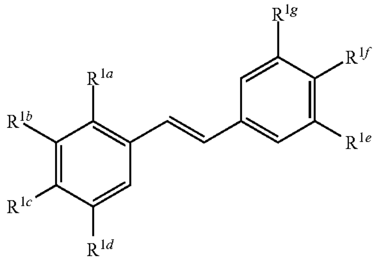

wherein:

$R^{1a}$ is independently allyl, crotyl, prenyl, geranyl, farnesyl, benzyl, 2-alkenyl or 2-alkynyl;

$R^{1b}$ is independently $CF_3$, OH, $OR^2$, $NO_2$, NHEt, $NMe_2$, NMeEt, $NHR^3$, $NMeR^3$, $NHC{=}NH(NH_2)$ or $COOR^2$;

$R^{1c}$ is independently H, alkyl, alkenyl, alkynyl, alkanedienyl, prenyl, geranyl, farnesyl, or benzyl;

$R^{1d}$ is independently $CF_3$, OH, $OR^2$, $NHR^3$, $NO_2$, $NMeR^3$, $NHC{=}NH(NH_2)$ or $COOR^2$;

$R^{1e}$ is independently H, $C_1$-$C_6$ alkyl, OH, $OR^2$, $NO_2$, $NMe_2$, $NHR^3$ or $NMeR^3$, NHC(O)H, $SR^2$;

$R^{1f}$ is independently H, OH, $OR^2$, $NO_2$, $NHR^3$, $NHC{=}NH(NH_2)$, $COOR^2$, COOH;

$R^{1g}$ is independently H, alkyl, $CF_3$, OH or $OR^2$;

and no more than one of $R^{1e}$, $R^{1f}$ or $R^{1g}$ can be H;

or $R^{1e}$ and $R^{1f}$ form a five or six-membered heterocyclic ring containing a carbonyl group or $(CO)CH_2$ group when $R^{1e}$ is independently OH, $NH_2$ or NHMe and $R^{1f}$ is $NH_2$, such that the nitrogen of $R^{1f}$ is bridged with the carbonyl group or $(CO)CH_2$ group to the oxygen or nitrogen of $R^{1e}$;

$R^2$ is independently methyl, ethyl, propyl, isopropyl, butyl, isobutyl, t-butyl, trifluoromethyl, $COCOOR^4$ or O-protecting group when $R^2$ is attached to an O;

$R^3$ is independently H, $CH_3$, OH, (CO)H, (CO)Me, $SO_2Me$, $CH_2COOH$, $CH_2COOR^2$, $CO(CH_2)_nNH_2$, $CONH_2$, $CO(CH_2)_nCOOH$ or $COCOOR^4$, where n is 0, 1 or 2; and $R^4$ is $C_1$-$C_6$ alkyl;

the process comprising:

i) a step of coupling a compound of formula (II) (Module A) with a compound of formula (III) (Module B) to afford a compound of formula (IV) (Module C):

Module A

Formula (II)

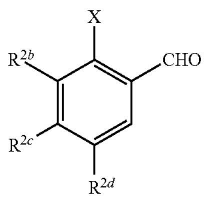

Module B

Formula (III)

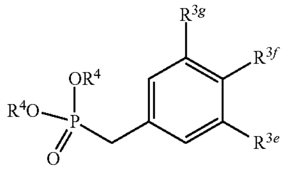

Module C

Formula (IV)

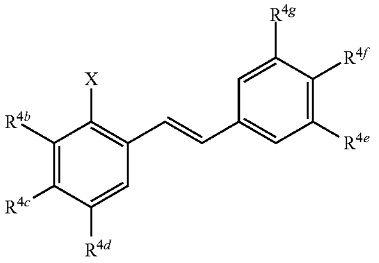

wherein, in Formula II (Module A):

$R^{2b}$ is independently $CF_3$, OH, $OR^2$, $NO_2$, $NMe_2$, NHEt, NMeEt, $NHR^3$ or $NMeR^3$;

$R^{2c}$ is independently H, alkyl, alkenyl, alkynyl, alkanedienyl, prenyl, geranyl, farnesyl, or benzyl;

$R^{2d}$ is independently $CF_3$, OH or $OR^2$, $NO_2$, $NHR^3$, $NMeR^3$, NHC═NH($NH_2$) or $COOR^2$;

X is a halide or a hydroxyl group, wherein the halide is selected from the group consisting of F, Cl, Br, I, and At;

$R^2$ is independently methyl, ethyl, propyl, isopropyl, butyl, isobutyl, t-butyl, trifluoromethyl, or an O-protecting group;

$R^3$ is independently H, OH, $CH_3$, (CO)H, COMe, $SO_2Me$, $COCH_2NH_2$, or $CH_2COOR^2$; and in Formula III (Module B):

$R^{3e}$ is independently H, $C_1$-$C_6$ alkyl, OH, $OR^2$, $NO_2$, NHMe, $NMe_2$, $NHR^3$ or $NMeR^3$, $SR^2$;

$R^{3f}$ is independently H, OH, $OR^2$, $NO_2$, $NHR^3$, NHC═NH($NH_2$), COOH or $COOR^2$;

$R^{3g}$ is independently H, alkyl, $CF_3$, OH, $OR^2$;

and no more than one of $R^{3e}$, $R^{3f}$ or $R^{3g}$ can be H or $R^{3e}$ and $R^{3f}$ form a five or six-membered heterocyclic ring containing a carbonyl group or (CO)$CH_2$ group when $R^{3e}$ is OH, $NH_2$ or NHMe and $R^{3f}$ is $NH_2$, such that the nitrogen of $R^{3f}$ is bridged with the carbonyl group or (CO)$CH_2$ group to the oxygen or nitrogen of $R^{3e}$;

$R^2$ is independently methyl, ethyl, propyl, isopropyl, butyl, isobutyl, t-butyl, trifluoromethyl or an O-protecting group when $R^2$ is attached to an O, $R^3$ is H, $CH_3$, OH, (CO)H, COMe, $SO_2Me$, $COCH_2NH_2$, $CH_2COOH$ and $CH_2COOR^2$; and in Formula IV (Module C):

$R^{4b}$ is independently $CF_3$, OH or $OR^2$, $NO_2$, $NMe_2$, NHEt, NMeEt, $NHR^3$ or $NMeR^3$;

$R^{4c}$ is independently H, alkyl, alkenyl, alkynyl, alkanedienyl, prenyl, geranyl, farnesyl, or benzyl;

$R^{4d}$ is independently $CF_3$, OH, $OR^2$, $OR^3$, $NO_2$ or $NHR^3$, $NMeR^3$, NHC═NH($NH_2$) or $COOR^2$;

$R^{4e}$ is independently H, $C_1$-$C_6$ alkyl, OH, $OR^2$, $NO_2$, $NMe_2$, $NHR^3$ or $NMeR^3$, NHC(O)H or $SR^2$;

$R^{4f}$ is independently H, OH, $OR^2$, $NO_2$, $NHR^3$, NHC═NH($NH_2$), COOH or $COOR^2$;

$R^{4g}$ is independently H, alkyl, $CF_3$, OH or $OR^2$;

or $R^{4e}$ and $R^{4f}$ form a five or six-membered heterocyclic ring containing a carbonyl group or (CO)$CH_2$ group when $R^{4c}$ is OH, $NH_2$ or NHMe and $R^{4f}$ is $NH_2$, such that the nitrogen of $R^{4f}$ is bridged with the carbonyl group or (CO)$CH_2$ group to the oxygen or nitrogen of $R^{4e}$;

$R^2$ is independently methyl, ethyl, propyl, isopropyl, butyl, isobutyl, t-butyl, trifluoromethyl or an O-protecting group when $R^2$ is attached to an O;

$R^3$ is independently H, $CH_3$, OH, (CO)H, COMe, $SO_2Me$, $COCH_2NH_2$, $CH_2COOH$ or $CH_2COOR^2$; and X is a halide or a hydroxyl group, wherein the halide is selected from the group consisting of F, Cl, Br, I, and At.

The O-protecting group may be selected from those known in the art. Suitable protecting O-protecting groups suitable for use in the present application would be know to a person skilled in the art.

The O-protecting group may be COMe, t-BuSi$(CH_3)_2$, 2-(trimethylsilyl)ethoxy]methyl (SEM), CH(OEt)$CH_3$, tetrahydropyranyl, or C(OEt)$(CH_3)_2$.

According to the compounds defined herein by formula (I), formula (III) and formula (IV), $R^{1e, 3e, 4e}$ and $R^{1f, 3f, 4f}$ may form a five or six-membered heterocyclic ring containing a carbonyl group or (CO)$CH_2$ group when $R^{1e, 3e, 4e}$ is OH, $NH_2$ or NHMe and $R^{1f, 3f, 4f}$ is $NH_2$, such that the nitrogen of $R^{1f, 3f, 4f}$ is bridged with the carbonyl group or (CO)$CH_2$ group to the oxygen or nitrogen of $R^{1e, 3e, 4e}$. In one embodiment, the nitrogen of $R^{1f, 3f, 4f}$ is bridged with a carbonyl group or (CO)$CH_2$ group to the oxygen or nitrogen of $R^{1e, 3e, 4e}$ to form a group selected from any one of the groups: —NH—C(O)—O—, —NH—C(O)—$CH_2$—O—, —NH—$CH_2$C(O)—O—, —NH—C(O)—NH—, —NH—C(O) $CH_2$—NH—, —NH—$CH_2$C(O)—NH—, —NH—C(O)—N(Me)—, —NH—C(O) $CH_2$—NMe- or —NH—$CH_2$C(O)—N(Me)—. In one embodiment $R^{1f, 3f, 4f}$ is $NH_2$ and $R^{1e, 3e, 4e}$ is NHMe and the nitrogen of $R^{1f, 3f, 4f}$ is bridged with a carbonyl group to the nitrogen of $R^{1e, 3e, 4e}$ to form —NH—C(O)—N(Me)—such that $R^{1e, 3e, 4e}$ and $R^{1f, 3f, 4f}$ form a five membered heterocyclic ring. In another embodiment $R^{1f, 3f, 4f}$ is $NH_2$ and $R^{1e, 3e, 4e}$ is OH and the nitrogen of $R^{1f, 3f, 4f}$ is bridged with a carbonyl group to the oxygen of $R^{1e, 3e, 4e}$ to form —NH—C(O)—O— such that $R^{1e, 3e, 4e}$ and $R^{1f, 3f, 4f}$ form a five membered heterocyclic ring.

The 2-substituted halo/hydroxy hydroxystilbene compound according to formula (IV) (Module C) undergoes a further reaction to afford the compound of Formula (I) as herein described.

In module A and C, the group X is a halide or hydroxyl group. In one embodiment X is a halide. When X is a halide, formula (II) and (IV) may be referred to as the halide of formula (II) and the halide of formula (IV). In another embodiment X is a hydroxyl group. When X is hydroxyl, formula (II) and (IV) may be referred to as the hydroxyl of formula (II) and the hydroxyl of formula (IV). The hydroxyl of formula (IV) may be activated to the corresponding triflate (trifluoromethylsulfonate) group and may be referred to as the triflate of formula (IV) or the 2-substituted triflate hydroxystilbene of formula (IV).

The conversion of the hydroxyl group to a triflate group may be carried out according to processes known in the art. In one embodiment, when X is hydroxyl, the hydroxyl of formula (IV) is treated with trifluromethansulfonic anhydride in the presence of N-methylmorphine to provide the triflate of formula (IV).

In one embodiment, when X is a halide in formula (IV) (halide of formula (IV)) undergoes a coupling reaction with one of the following:

a) a $R^{1a}$-substituted boronic acid compound or ester;

b) a $R^{1a}$-substituted trifluoroborate compound; or c) a $R^{1a}$-substituted organostannane compound;

to form the compound of formula (I).

In one embodiment, the 2-substituted halo hydroxystilbene compound according to formula (IV) (Module C) undergoes a further coupling reaction with a 2-alkenyl or benzyl boronic acid or ester, to afford the compound of Formula (I). In one embodiment, a 2-substituted halo hydroxystilbene compound according to formula (IV) (Module C) undergoes a further coupling reaction with a 2-alkenyl or benzyl trifluoroborate compound, to afford a compound of Formula (I). In another embodiment, a 2-substituted halo hydroxystilbene compound according to formula (IV) (Module C) undergoes a further coupling reaction with a 2-alkenyl or benzyl organostannane compound, to afford a compound of Formula (I).

In one embodiment, when X is a hydroxyl in formula (IV) (hydroxyl of formula (IV)), activation of the hydroxyl to a triflate group (OTf, trifluoromethyl sulfonate) is required before coupling can occur. In one embodiment, the hydroxyl group of formula (IV) is converted to a triflate (trifluromethylsulfonate) group to form a triflate of formula (IV), and the triflate of formula (I)) undergoes a coupling reaction with one of the following:

a) a $R^{1a}$-substituted boronic acid compound or ester.

b) a $R^{1a}$-substituted trifluoroborate compound; or c) a $R^{1a}$-substituted organostannane compound to form the compound of formula (I).

In one embodiment, a 2-substituted hydroxy hydroxystilbene compound according to formula (IV) (Module C) is activated to a 2-substituted triflate hydroxystilbene which may then undergo a coupling reaction with a 2-alkenyl or benzyl boronic acid or ester to afford a compound of Formula (I). In another embodiment, the triflate of Formula (IV) undergoes a further coupling reaction with a 2-alkenyl or benzyl trifluoroborate compound to afford a compound of Formula (I). In another embodiment, the triflate of Formula (IV) undergoes a further coupling reaction with a 2-alkenyl or benzyl organostannane compound, to afford a compound of Formula (I).

In one embodiment, the halide compound according to formula (IV) or the triflate of formula (IV) as herein described, undergoes a coupling reaction with a $R^{1a}$-substituted boronic acid compound to form a compound of formula (I), wherein $R^{1a}$ is selected from the group consisting of allyl, crotyl, prenyl, geranyl, farnesyl, benzyl, 2-alkenyl, and 2-alkynyl.

In another embodiment, the halide compound according to formula (IV) or the triflate of formula (IV) as herein described, undergoes a coupling reaction with a $R^{1a}$-substituted organostannane compound to form a compound of formula (I), wherein $R^{1a}$ is selected from the group consisting of allyl, crotyl, prenyl, geranyl, farnesyl, benzyl, 2-alkenyl, and 2-alkynyl.

In another embodiment, the halide compound according to formula (IV) or the triflate of formula (IV), as herein described, undergoes a coupling reaction with a $R^{1a}$-substituted trifluoroborate to form a compound of formula (I), wherein $R^{1a}$ is selected from the group consisting of allyl, crotyl, prenyl, geranyl, farnesyl, benzyl, 2-alkenyl, and 2-alkynyl.

In another embodiment, the $R^{1a}$ substituent in formula (II) and (IV) is selected from the group consisting of allyl, crotyl, prenyl, benzyl or 2-alkenyl. In another embodiment, $R^{1a}$ is selected from the group consisting of allyl, crotyl, prenyl or benzyl.

The coupling reaction of a compound of formula (IV) or the triflate of formula (IV) as described herein, with a $R^{1a}$-substituted boronic acid compound, a $R^{1a}$-substituted organostannane compound or a $R^{1a}$-substituted trifluoroborate may be catalysed by a suitable catalyst, including a palladium compound. The palladium catalyst includes but is not limited to tetrakis(triphenylphosphine)palladium(0) and 1,1'-bis(diphenylphosphino) ferrocene]dichloropalladium (II). The coupling reaction described herein may also be carried out in the presence of a base including but not limited to alkali metal carbonates, such as potassium carbonate ($K_2CO_3$), hydrogen carbonates, calcium carbonate, magnesium carbonate and alkylamines including triethylamine.

In one embodiment, the $R^{1a}$-substituted boronic acid compound is a allyl, crotyl, prenyl, benzyl, 2-alkenyl boronic pinacol ester. The prenyl boronic pinacol ester includes but is not limited to 3-methylbut-2-enylboronic acid pinacol ester, crotylboronic pinacol ester, allylboronic pinacol ester, benzylboronic pinacol ester.

In one embodiment, the halide compound according to formula (IV) or the or the triflate of formula (IV) as defined herein, undergoes a coupling reaction with a $R^{1a}$-substituted boronic acid pinacol ester catalysed by a palladium catalyst in the presence of a base. In another embodiment, the halide compound according to formula (IV) undergoes a coupling reaction with a $R^{1a}$-substituted tributylstannane catalysed by tetrakis(triphenylphosphine)palladium(0).

In another embodiment, the halide compound according to formula (IV) or the triflate of formula (IV)) as defined herein, undergoes a coupling reaction with a $R^{1a}$-substituted trifluoroborate. In one specific embodiment, the halide or triflate compound according to formula (IV) undergoes a coupling reaction with potassium allyltrifluoroborate catalysed by 1,1'-bis(diphenylphosphino) ferrocene]dichloropalladium(II) and triethylamine. This coupling method provide an allyl group at $R^{1a}$ position on the A-ring.

In one embodiment, there is provided a process of synthesising a compound of Formula (I)

wherein in Formula (I):

$R^{1a}$ is independently allyl, crotyl, prenyl, benzyl, or 2-alkenyl;

$R^{1b}$ is independently OH, $OR^2$ or NHC(O)Me;

$R^{1c}$ is H;

$R^{1d}$ is independently OH, $NHR^3$, NH(CO)H or $NO_2$;

$R^{1e}$ is independently OH, $OR^2$, $NMe_2$, $NHR^3$, $NMeR^3$, NHC(O)H or $SR^2$;

$R^{1f}$ is independently H, OH, $NO_2$, $OR^2$, $NHR^3$, NHC═NH($NH_2$), or COOH;

$R^{1g}$ is independently H, alkyl, OH or $OR^2$;

and no more than one of $R^{1e}$, $R^{1f}$ or $R^{1g}$ can be H;

or $R^{1e}$ and $R^{1f}$ form a five or six-membered heterocyclic ring containing a carbonyl group when $R^{1e}$ is OH, $NH_2$ or NHMe and $R^{1f}$ is $NH_2$, such that the nitrogen of $R^{1f}$ is bridged with the carbonyl group to the oxygen or nitrogen of $R^{1e}$;

$R^2$ is independently methyl, ethyl, propyl, isopropyl, butyl, isobutyl, t-butyl or an O-protecting group when $R^2$ is attached to an O, wherein the O-protecting group is selected from the group consisting of COMe, t-BuSi$(CH_3)_2$, 2-(trimethylsilyl)ethoxy]methyl (SEM), CH(OEt)$CH_3$, tetrahydropyranyl, or C(OEt)$(CH_3)_2$;

$R^3$ is independently H, $CH_3$, OH, (CO)H, (CO)Me, $SO_2Me$, $CO(CH_2)_nNH_2$, $CH_2COOR^2$, $CO(CH_2)_nCOOH$ or $COCOOR^4$, where n is 0, 1 or 2; and $R^4$ is $C_1$-$C_6$ alkyl;

in Formula II (Module A):

$R^{2b}$ is OH or $OR^2$;

$R^{2c}$ is H;

$R^{2d}$ is independently OH or $OR^2$, $NO_2$, $NHR^3$ or $COOR^2$;

X is a halide (Hal) or hydroxyl group, wherein the halide is selected from the group consisting of F, Cl, Br, I, and At;

$R^2$ is independently methyl, ethyl, propyl, isopropyl, butyl, isobutyl, t-butyl, trifluoromethyl, or an O-protecting group;

$R^3$ is independently H, OH, $CH_3$, (CO)H, COMe, $SO_2Me$, $COCH_2NH_2$, or $CH_2COOR^2$; and in Formula III (Module B):

$R^{3e}$ is independently OH, $OR^2$, $NO_2$, NHMe, $NMe_2$, $NHR^3$ $NMeR^3$ or $SR^2$, $R^{3f}$ is independently H, OH, $OR^2$, $NO_2$, $NHR^3$, NHC═NH($NH_2$), COOH, $COOR^2$;

$R^{3g}$ is independently H, alkyl, OH, $OR^2$;

and no more than one of $R^{3e}$, $R^{3f}$ or $R^{3g}$ can be H;

or $R^{3e}$ and $R^{3f}$ form a five or six-membered heterocyclic ring containing a carbonyl group or (CO)$CH_2$ group when $R^{3e}$ is OH, $NH_2$ or NHMe and $R^{3f}$ is $NH_2$, such that the nitrogen of $R^{3f}$ is bridged with the carbonyl group or (CO)$CH_2$ group to the oxygen or nitrogen of $R^{3e}$;

$R^2$ is independently methyl, ethyl, propyl, isopropyl, butyl, isobutyl, t-butyl, trifluoromethyl or an O-protecting group when $R^2$ is attached to an O, $R^3$ is independently H, $CH_3$, OH, (CO)H, COMe, $SO_2Me$, $COCH_2NH_2$, $CH_2COOH$ or $CH_2COOR^2$; and in Formula IV (Module C):

$R^{4b}$ is OH or $OR^2$, NHC(O)Me;

$R^{4c}$ is H;

$R^{4d}$ is independently OH or $OR^2$, $NO_2$ or $NHR^3$, $NMeR^3$;

$R^{4e}$ is independently OH, $OR^2$, $NO_2$, $NMe_2$, $NHR^3$ or $NMeR^3$, NHC(O)H or $SR^2$;

$R^{4f}$ is independently H, OH, $OR^2$, $NO_2$, $NHR^3$, NHC═NH($NH_2$), COOH or $COOR^2$;

$R^{4g}$ is independently H, alkyl, $CF_3$, OH or $OR^2$;

and no more than one of $R^{4e}$, $R^{4f}$ or $R^{4g}$ can be H;

or $R^{4e}$ and $R^{4f}$ form a five or six-membered heterocyclic ring containing a carbonyl group or (CO)$CH_2$ group when $R^{4e}$ is OH, $NH_2$ or NHMe and $R^{4f}$ is $NH_2$, such that the nitrogen of $R^{4f}$ is bridged with the carbonyl group or (CO)$CH_2$ group to the oxygen or nitrogen of $R^{4e}$;

$R^2$ is independently methyl, ethyl, propyl, isopropyl, butyl, isobutyl, t-butyl, trifluoromethyl or an O-protecting group when $R^2$ is attached to an O;

$R^3$ is independently H, $CH_3$, OH, (CO)H, COMe, $SO_2Me$, $COCH_2NH_2$, $CH_2COOH$ or $CH_2COOR^2$; and X is a halide or hydroxyl group, wherein the halide is selected from the group consisting of F, Cl, Br, I, and At.

In one embodiment, there is provided a synthesis of a compound of Formula (I):

Formula (I)

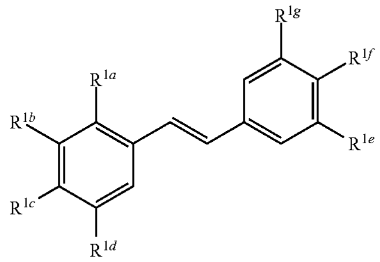

wherein in formula (I):

$R^{1a}$ is independently, crotyl, prenyl, benzyl, or 2-alkenyl;

$R^{1b}$ is $CF_3$, $OR^2$ or NHC(O)Me;

$R^{1c}$ is H;

$R^{1d}$ is independently OH, $NHR^3$, or $NO_2$;

$R^{1e}$ is independently $OR^2$, $NMe_2$, $NHR^3$, or $SR^2$;

$R^{1f}$ is independently H, OH, $NO_2$, $NHR^3$, NHC═NH($NH_2$), or COOH;

$R^{1g}$ is independently H, alkyl, OH or $OR^2$, or $R^{1e}$ and $R^{1f}$ form a five or six-membered heterocyclic ring containing a carbonyl group when $R^{1e}$ is OH, $NH_2$ or NHMe and $R^{1f}$ is $NH_2$, such that the nitrogen of $R^{1f}$ is bridged with the carbonyl group to the oxygen or nitrogen of $R^{1e}$;

$R^2$ is independently methyl, ethyl, propyl, isopropyl, butyl, isobutyl, t-butyl;

$R^3$ is independently H, Me, (CO)H, (CO)Me, $SO_2Me$, $CO(CH_2)$~$NH_2$, $CO(CH_2)_nCOOH$ or $COCOOR^4$ (where n=0, 1 or 2); and $R^4$ is $C_1$-$C_6$ alkyl;

wherein the synthesis comprises:

i) a step of coupling a compound of formula (II) (Module A) with a compound of formula (III) (Module B) to afford a compound of formula (IV) (Module C):

Module A

Formula (II)

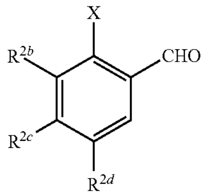

-continued

Module B

Formula (III)

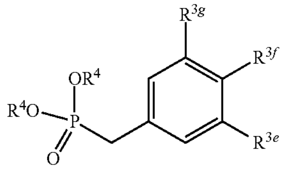

Module C

Formula (IV)

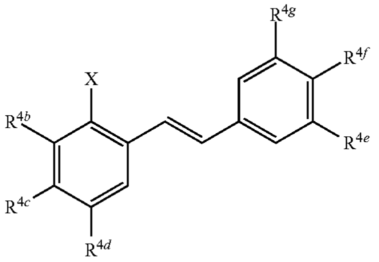

wherein, in Formula II (Module A):

$R^{2b}$ is $CF_3$, OH, $OR^2$, $NO_2$, $NMe_2$, NHEt, NMeEt, $NHR^3$ or $NMeR^3$;

$R^{2c}$ is H, alkyl, alkenyl, alkynyl, alkanedienyl, prenyl, geranyl, farnesyl, or benzyl;

$R^{2d}$ is $CF_3$, OH or $OR^2$, $NO_2$, $NHR^3$, $NMeR^3$, NHC═NH ($NH_2$) or $COOR^2$;

X is a halide (Hal) or hydroxyl group, wherein the halide is selected from the group consisting of F, Cl, Br, I, and At;

$R^2$ is methyl, ethyl, propyl, isopropyl, butyl, isobutyl, t-butyl, trifluoromethyl, or an O-protecting group;

$R^3$ is H, OH, $CH_3$, (CO)H, COMe, $SO_2Me$. $COCH_2NH_2$, or $CH_2COOR^2$; and in Formula III (Module B):

$R^{3e}$ is independently, OH, $OR^2$, $NO_2$, NHMe, $NMe_2$, $NHR^3$ or $NMeR^3$, (CO)H, NHC(O)H or $SR^2$;

$R^{3f}$ is independently H, OH, $OR^2$, $NO_2$, $NHR^3$;

$R^{3g}$ is independently H, alkyl, OH, $OR^2$;

and no more that one of $R^{3e}$, $R^{3f}$ or $R^{3g}$ can be H;

or $R^{3e}$ and $R^{3f}$ form a five or six-membered heterocyclic ring containing a carbonyl group or $(CO)CH_2$ group when $R^{3e}$ is OH, $NH_2$ or NHMe and $R^{3f}$ is $NH_2$, such that the nitrogen of $R^{3f}$ is bridged with the carbonyl group or $(CO)CH_2$ group to the oxygen or nitrogen of $R^{3e}$;

$R^2$ is independently methyl, ethyl, propyl, isopropyl, butyl, isobutyl, t-butyl, trifluoromethyl or an O-protecting group when $R^2$ is attached to an O, $R^3$ is H, $CH_3$, (CO)H, COMe, $SO_2Me$, $COCH_2NH_2$ or $CH_2COOR^2$; and in Formula IV (Module C):

$R^{4b}$ is independently $CF_3$, OH or $OR^2$, NHC(O)Me;

$R^{4c}$ is H;

$R^{4d}$ is OH, $NH_2$, N(CO)H;

$R^{4e}$ is independently OH, $OR^2$, $NO_2$, $NHR^3$ or $NMeR^3$, $SR^2$;

$R^{4f}$ is independently H, OH, $OR^2$, $NO_2$, $NHR^3$;

$R^{4g}$ is independently H, alkyl, $CF_3$, OH, $OR^2$;

and only one of $R^{4e}$, $R^{4f}$ or $R^{4g}$ can be H;

$R^2$ is independently methyl, ethyl, propyl, isopropyl, butyl, isobutyl, t-butyl, trifluoromethyl or an O-protecting group when $R^2$ is attached to an O;

$R^3$ is independently H, (CO)H, COMe, $SO_2Me$, or $CH_2COOR^2$; and

X is a halide or a hydroxyl group, wherein the halide is selected from the group consisting of F, Cl, Br, I, and At.

In one embodiment, there is provided a process of synthesising a compound of Formula (I):

Formula (I)

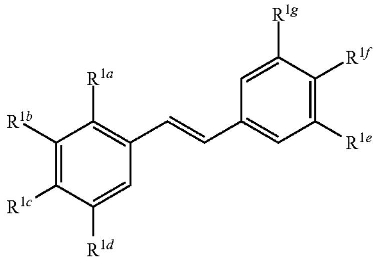

wherein in formula (I):

$R^{1a}$ is independently allyl, crotyl, prenyl, benzyl;

$R^{1b}$ is independently $OR^2$ or NHC(O)Me;

$R^{1c}$ is H;

$R^{1d}$ is independently OH, $NH_2$, N(CO)H;

$R^{1e}$ is independently OH, $OR^2$, $NO_2$, $NHR^3$ or $NMeR^3$, (CO)H, SMe;

$R^{1f}$ is independently H, OH, $OR^2$, $NO_2$, $NHR^3$, NHC═NH($NH_2$), COOH;

$R^{1g}$ is independently H, alkyl, OH, $OR^2$;

$R^2$ is independently methyl, ethyl, propyl, isopropyl, butyl, isobutyl, t-butyl, trifluoromethyl or an O-protecting group when $R^2$ is attached to an O, wherein the O-protecting group is selected from the group consisting of COMe, $t\text{-}BuSi(CH_3)_2$, 2-(trimethylsilyl) ethoxymethyl (SEM) acetal, $CH(OEt)CH_3$, tetrahydropyranyl, or $C(OEt)(CH_3)_2$;

$R^3$ is independently H, $CH_3$, OH, (CO)H, (CO)Me, $SO_2Me$, $CH_2COOR^2$, $COCH_2NH_2$, $CO(CH_2)_nCOOH$ (where n=0, 1 or 2);

wherein the synthesis comprises:

i) a step of coupling a compound of formula (II) (Module A) with a compound of formula (III) (Module B) to afford a compound of formula (V) (Module C):

Module A

Formula (II)

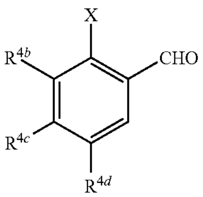

Module B

Formula (III)

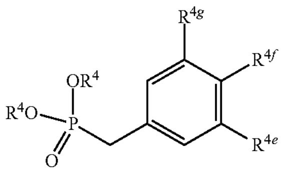

-continued

Module C

Formula (IV)

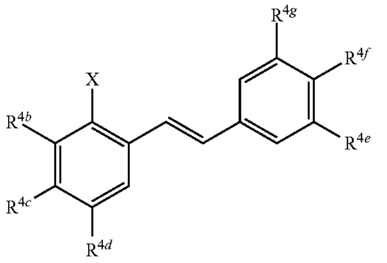

wherein in Formula II:

$R^{2b}$ is $CF_3$, OH or $OR^2$;

$R^{2c}$ is H, $R^{2d}$ is OH or $NH_2$, N(CO)H;

X is a halide (Hal) or hydroxyl group, wherein the halide is selected from the group consisting of F, Cl, Br, I, and At;

a halide selected from the group consisting of F, Cl, Br, I, and At;

$R^2$ is methyl, ethyl, propyl, isopropyl, butyl, isobutyl, t-butyl, trifluoromethyl or O-protecting group when $R^2$ is attached to an O, wherein the O-protecting group is selected from the group consisting of COMe, r-BuSi$(CH_3)_2$, 2-(trimethylsilyl)ethoxymethyl (SEM) acetal, $CH(OEt)CH_3$, tetrahydropyranyl, or $C(OEt)(CH_3)_2$; and in Formula III:

$R^{3e}$ is OH, $OR^2$, $NO_2$, $NHR^3$ or $NMeR^3$, $SR^2$;

$R^{3f}$ is H, OH, OR, $NO_2$, $NHR^3$;

$R^{3g}$ is H, alkyl, OH, $OR^2$;

$R^2$ is methyl, ethyl, propyl, isopropyl, butyl, isobutyl, t-butyl, trifluoromethyl or O-protecting group when $R^2$ is protecting an O, wherein the O-protecting group is selected from the group consisting of COMe, t-BuSi$(CH_3)_2$, 2-(trimethylsilyl)ethoxymethyl (SEM) acetal, $CH(OEt)CH_3$, tetrahydropyranyl, or $C(OEt)(CH_3)_2$; and $R^3$ is H, $CH_3$, (CO)H, COMe, $SO_2Me$ or $CH_2COOR^2$, $COCH_2NH_2$; and in Formula IV;

$R^{4b}$ is $CF_3$, OH or $OR^2$;

$R^{4c}$ is H;

$R^{4d}$ is OH, $NH_2$, N(CO)H;

$R^{4e}$ is OH, $OR^2$, $NO_2$, $NHR^3$ or $NMeR^3$, $SR^2$;

$R^{4f}$ is H, OH, $OR^2$, $NO_2$, $NHR^3$;

$R^{4g}$ is H, alkyl, OH, $OR^2$;

$R^2$ is methyl, ethyl, propyl, isopropyl, butyl, isobutyl, t-butyl, trifluoromethyl or O-protecting group when $R^2$ is attached to an O, wherein the O-protecting group is selected from the group consisting of COMe, t-BuSi$(CH_3)_2$, 2-(trimethylsilyl)ethoxymethyl (SEM) acetal, $CH(OEt)CH_3$, tetrahydropyranyl, or $C(OEt)(CH_3)_2$;

$R^3$ is H, (CO)H, COMe, $SO_2Me$, or $CH_2COOR^2$; and

X is a halide (Hal) or hydroxyl group, wherein the halide is selected from the group consisting of F, Cl, Br, I, and At;

In one embodiment, there is provided a process of synthesising a compound of Formula (I):

Formula (I)

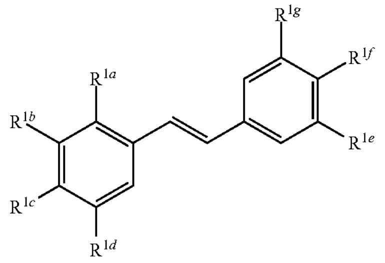

wherein in formula (I):

$R^{1a}$ is allyl, crotyl, prenyl, benzyl;

$R^{1b}$ is $OR^2$, NHC(O)Me $R^{1c}$ is H;

$R^{1d}$ is OH;

$R^{1e}$ is $OR^2$, $NO_2$;

$R^{1f}$ is $NO_2$, $NHR^3$, NHC=NH($NH_2$);

$R^{1g}$ is H, alkyl, OH, $OR^2$;

$R^2$ is methyl, ethyl, propyl, isopropyl, butyl, isobutyl, t-butyl;

$R^3$ is H, (CO)H, (CO)Me, $SO_2Me$, $CH_2COOR^2$, $COCH_2NH_2$, $CO(CH_2)_nCOOH$ (where n=0, 1 or 2);

wherein the synthesis comprises:

i) a step of coupling a compound of formula (II) (Module A) with a compound of formula (III) (Module B) to afford a compound of formula (IV) (Module C):

Module A

Formula (II)

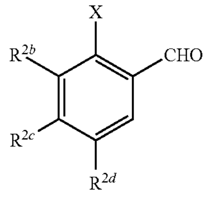

Module B

Formula (III)

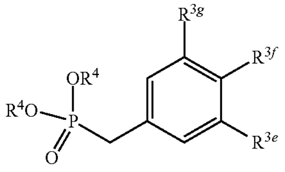

Module C

Formula (IV)

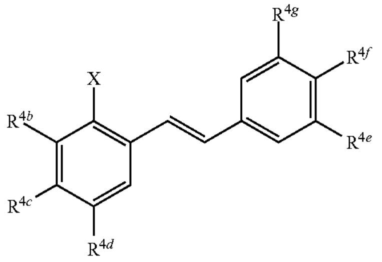

wherein in Formula II:

$R^{2b}$ is $CF_3$, OH or $OR^2$;

$R^{2c}$ is H, $R^{2d}$ is OH or $NH_2$, N(CO)H;

Hal is a halide selected from the group consisting of F, Cl, Br, I, and At;

$R^2$ is methyl, ethyl, propyl, isopropyl, butyl, isobutyl, t-butyl, trifluoromethyl or O-protecting group when $R^2$ is attached to an O, wherein the O-protecting group is selected from the group consisting of COMe, t-BuSi$(CH_3)_2$, 2-(trimethylsilyl)ethoxymethyl (SEM) acetal, $CH(OEt)CH_3$, tetrahydropyranyl, or $C(OEt)(CH_3)_2$; and in Formula III:

$R^{3e}$ is OH, $OR^2$, $NO_2$, $NHR^3$ or $NMeR^3$, $SR^2$;

$R^{3f}$ is H, OH, $OR^2$, $NO_2$, $NHR^3$;

$R^{3g}$ is H, alkyl, OH, $OR^2$;

$R^2$ is methyl, ethyl, propyl, isopropyl, butyl, isobutyl, t-butyl, trifluoromethyl or O-protecting group when $R^2$ is protecting an O, wherein the O-protecting group is selected from the group consisting of COMe, t-BuSi$(CH_3)_2$, 2-(trimethylsilyl)ethoxymethyl (SEM) acetal, $CH(OEt)CH_3$, tetrahydropyranyl, or $C(OEt)(CH_3)_2$; and $R^3$ is H, $CH_3$, (CO)H, COMe, $SO_2Me$ or $CH_2COOR^2$, $COCH_2NH_2$; and in Formula IV:

$R^{4b}$ is $CF_3$, OH or $OR^2$;

$R^{4c}$ is H;

$R^{4d}$ is OH, $NH_2$, N(CO)H;

$R^{4e}$ is OH, $OR^2$, $NO_2$, $NHR^3$ or $NMeR^3$, $SR^2$;

$R^{4f}$ is H, OH, $OR^2$, $NO_2$, $NHR^3$;

$R^{4g}$ is H, alkyl, OH, $OR^2$;

$R^2$ is methyl, ethyl, propyl, isopropyl, butyl, isobutyl, t-butyl, trifluoromethyl or O-protecting group when $R^2$ is attached to an O, wherein the O-protecting group is selected from the group consisting of COMe, t-BuSi$(CH_3)_2$, 2-(trimethylsilyl)ethoxymethyl (SEM) acetal, $CH(OEt)CH_3$, tetrahydropyranyl, or $C(OEt)(CH_3)_2$;

$R^3$ is H, (CO)H, COMe, $SO_2Me$, or $CH_2COOR^2$; and

Hal is a halide selected from the group consisting of F, Cl, Br, I, and At;

wherein formula IV is coupled with a $R^{1a}$ boronic pinacol ester selected from the group consisting of 3-methylbut-2-enylboronic acid pinacol ester, crotylboronic pinacol ester, allylboronic pinacol ester and benzylboronic pinacol ester, catalysed by a palladium catalyst in the presence of a base, to produce the compound of formula (I).

In one embodiment, there is provided a process of synthesising a compound of Formula (I): wherein in formula (I):

$R^{1a}$ is crotyl, prenyl;

$R^{1b}$ is $OR^2$;

$R^{1c}$ is H;

$R^{1d}$ is OH, $R^{1e}$ is $OR^2$;

$R^{1f}$ is $NO_2$, $NHR^3$, $NHC{=}NH(NH_2)$;

$R^{1g}$ is H;

$R^2$ is methyl, ethyl;

$R^3$ is H, (CO)H, (CO)Me, $SO_2Me$, $CH_2COOR^2$, $COCH_2NH_2$, $CO(CH_2)_nCOOH$ (where n=0, 1 or 2); and in Formula II:

$R^{2b}$ is OH or $OR^2$;

$R^{2c}$ is H;

$R^{2d}$ is OH, OSEM;

Halide is Br;

$R^2$ is methyl or ethyl; and in Formula III:

$R^{3e}$ is OH, $OR^2$;

$R^{3f}$ is, $NO_2$, $NHR^3$; $NHC{=}NH(NH_2)$, $R^{3g}$ is H;

$R^2$ is methyl, ethyl, and $R^3$ is H, (CO)H, COMe, $SO_2Me$ or $CH_2COOR^2$, $COCH_2NH_2$ or $CO(CH_2)_nCOOH$ where n is 0, 1 or 2; and in Formula IV:

$R^{4b}$ is, $OR^2$;

$R^{4c}$ is H;

$R^{4d}$ is OH;

$R^{4e}$ is $OR^2$, $R^{4f}$ is, $NO_2$, $NHR^3$, $NHC{=}NH(NH_2)$;

$R^{4g}$ is H;

$R^2$ is methyl, ethyl, $R^3$ is H, (CO)H, COMe, $SO_2Me$, or $CH_2COOR^2$, $COCH_2NH_2$, $CO(CH_2)_nCOOH$ and Halide is, Br;

wherein formula IV is coupled with a $R^{1a}$ boronic pinacol ester selected from the group consisting of 3-methyl-but-2-enylboronic acid pinacol ester, crotylboronic pinacol ester, allylboronic pinacol ester and benzylboronic pinacol ester, catalysed by a palladium catalyst in the presence of a base, to produce the compound of formula (I).

In one embodiment of the above process, $R^{1f}$ in formula (I) is $NO_2$. The compound of formula (I) may be further reacted with a reducing agent to convert the $NO_2$ group to an $NH_2$ group. This allows for the formation of amine compounds such as compounds 23 and 24. In one embodiment the compound of formula (I) where $R^{1f}$ is $NH_2$, is further reacted with methane sulfonyl chloride in the presence of a base, such as triethylamine, to form a compound of formula (I) where $R^{1f}$ is $NHSO_2Me$. This allows for the formation of amine compounds such as compounds 25 and 24. In another embodiment, the compound of formula (I) where $R^{1f}$ is $NH_2$, is further reacted with ethyl formate to form a compound of formula (I) where $R^{1f}$ is NH(CO)H. This allows for the formation of amine compounds such as compounds 27 and 28. Preliminary results have indicated that compounds 27 and 28 are potential lead candidates for therapeutic use in treating atopic dermatitis and psoriasis.

In one embodiment, there is provided a process of synthesising a compound of Formula (I): wherein in formula (I):

$R^{1a}$ is crotyl, prenyl;

$R^{1b}$ is $OR^2$, $R^{1c}$ is H;

$R^{1d}$ is OH;

$R^{4e}$ and $R^{4f}$ form a five or six-membered heterocyclic ring containing a carbonyl group when $R^{4e}$ is OH or $NH_2$ and $R^{4f}$ is $NH_2$, such that the nitrogen of $R^{4f}$ is bridged with the carbonyl group to the oxygen or nitrogen of $R^{4e}$;

$R^{1g}$ is H;

$R^2$ is methyl, ethyl;

$R^3$ is H, (CO)H, (CO)Me, $SO_2Me$, $CH_2COOR^2$, $COCH_2NH_2$ or $CO(CH_2)_nCOOH$ (where n=0, 1 or 2);

in Formula II;

$R^{2b}$ is $OR^2$;

$R^{2c}$ is H;

$R^{2d}$ is OSEM;

Hal is Br;

$R^2$ is methyl or ethyl, and in Formula III:

$R^{3e}$ and $R^{3f}$ form a five or six-membered heterocyclic ring containing a carbonyl group when $R^{3e}$ is OH or $NH_2$ and $R^{3f}$ is $NH_2$, such that the nitrogen of $R^{3f}$ is bridged with the carbonyl group to the oxygen or nitrogen of $R^{3e}$;

$R^{3g}$ is H; and in Formula IV;

$R^{4b}$ is, $OR^2$;

$R^{4c}$ is H;

$R^{4d}$ is OSEM;

$R^{4e}$ and $R^{4f}$ form a five or six-membered heterocyclic ring containing a carbonyl group when $R^{4e}$ is OH or $NH_2$ and $R^{4f}$ is $NH_2$, such that the nitrogen of $R^{4f}$ is bridged with the carbonyl group to the oxygen or nitrogen of $R^{4e}$;

$R^{4g}$ is H;

$R^2$ is methyl, ethyl;

and

Halide is Br;

wherein formula (IV) is coupled with a $R^{1a}$ boronic pinacol ester selected from the group consisting of 3-methylbut-2-enylboronic acid pinacol ester, crotylboronic pinacol ester, allylboronic pinacol ester and benzylboronic pinacol ester, catalysed by a palladium catalyst in the presence of a base, to produce the compound of formula (I).

In one specific embodiment of the above process, formula (IV) is coupled with 3-methylbut-2-enylboronic acid pinacol ester and catalysed by tetrakis(triphenylphosphine)palladium(0) in the presence of potassium carbonate. In one embodiment, the compound of formula (I) is selected from compounds 51 and 52.

In one embodiment of the process of synthesising a compound of Formula (I), the compound according to formula (I) is selected from the group consisting of:

1 [KYN-001]

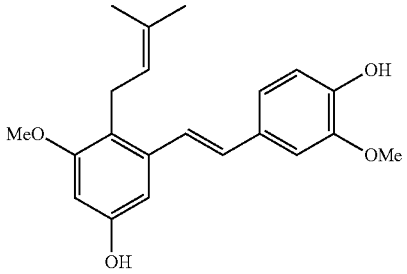

2 [KYN-138]

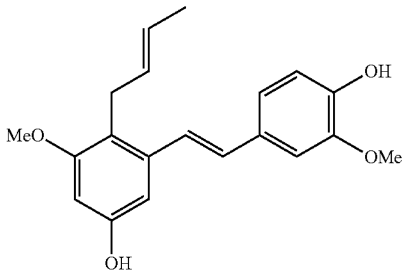

-continued

3 [KYN-139]

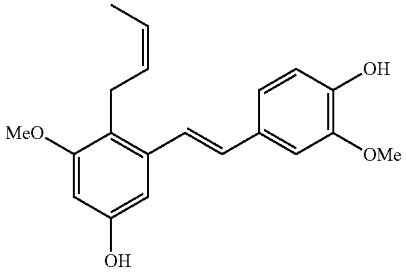

4 [KYN-140]

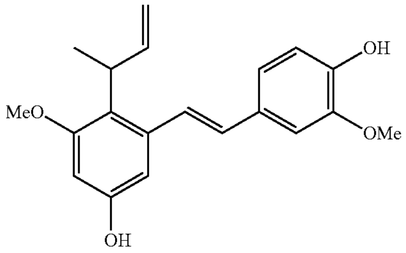

5 [KYN-153]

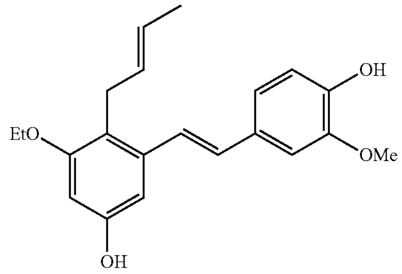

6 [KYN-134]

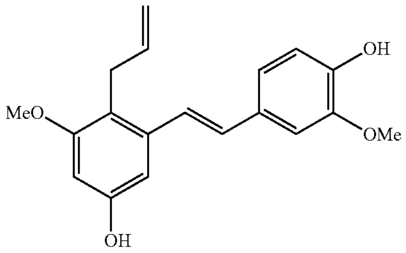

7 [KYN-136]

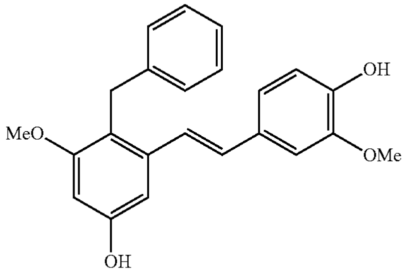

8 [KYN-119]

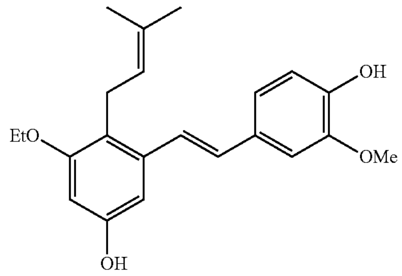

-continued
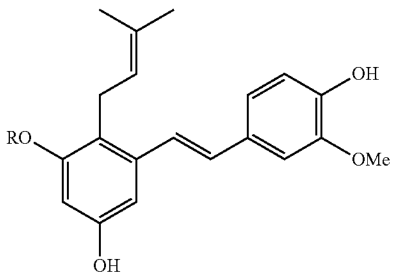
9 [KYN-130] R = n-propyl
10 [KYN-131] R = iso-propyl
11 [KYN-132] R = $CF_3$
12 [KYN-133]
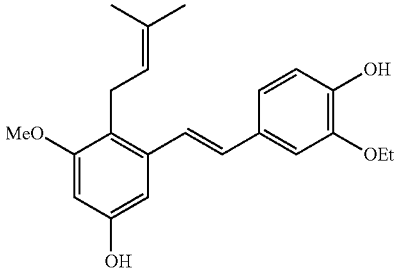
13 [KYN-114]
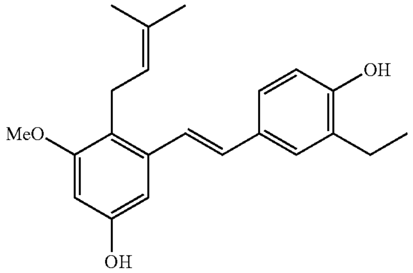
14 [KYN-118]
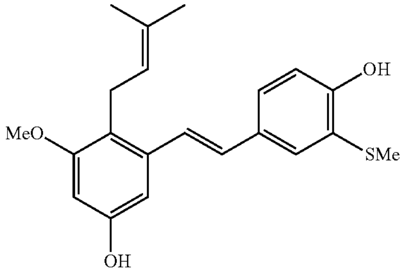
15 [KYN-158]
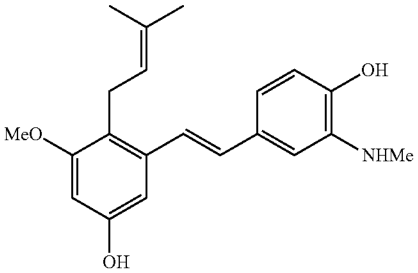
-continued
16 [KYN-157]
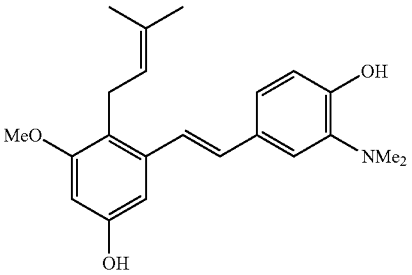
17 [KYN-120]
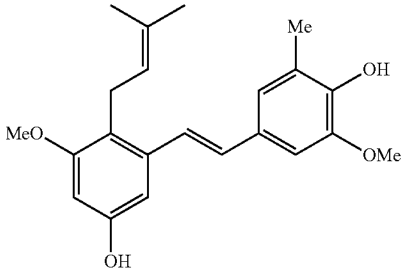
18 [KYN-156]
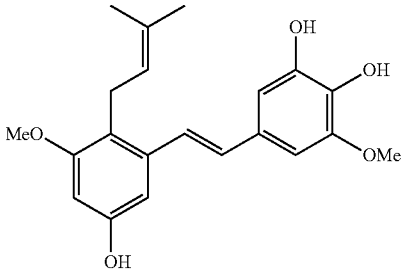
19 [KYN-160]
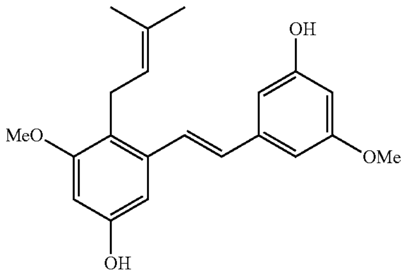
20 [KYN-146]
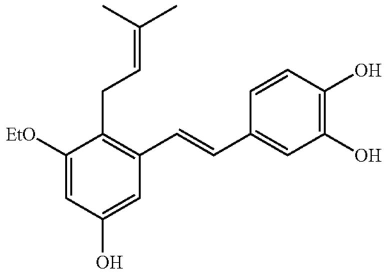

-continued
21 [KYN-154]
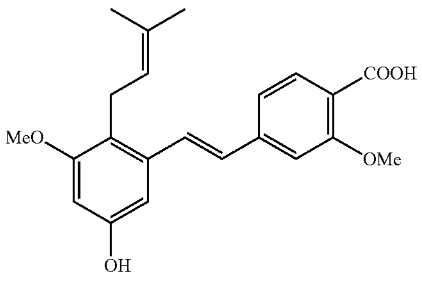
22 [KYN-124]
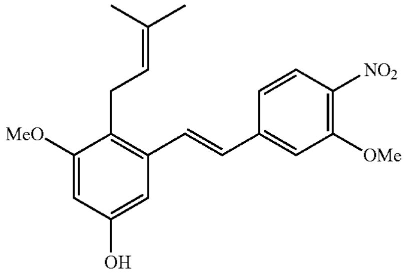
23 [KYN-125]
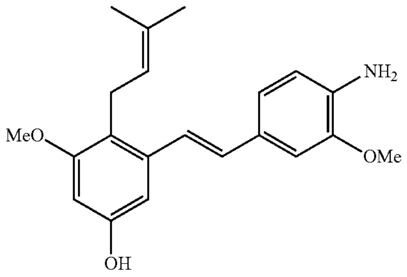
24 [KYN-141]
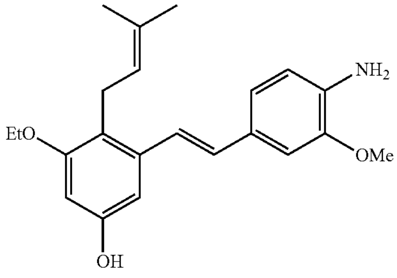
25 [KYN-137]
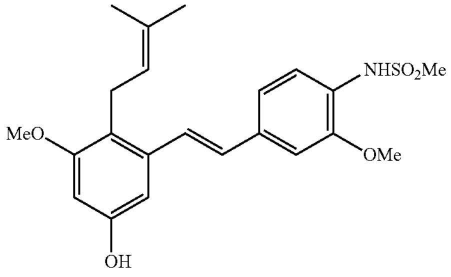
-continued
26 [KYN-129]
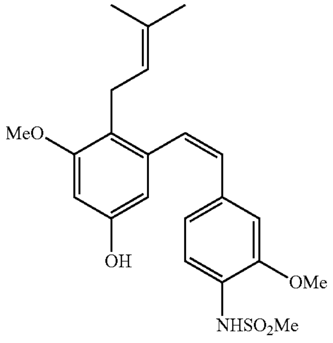
27 [KYN-149]
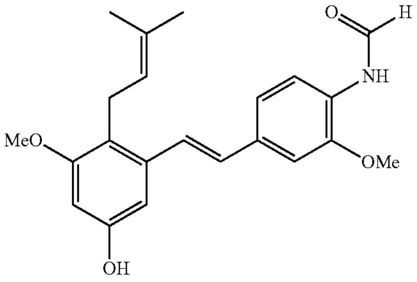
28 [KYN-143]
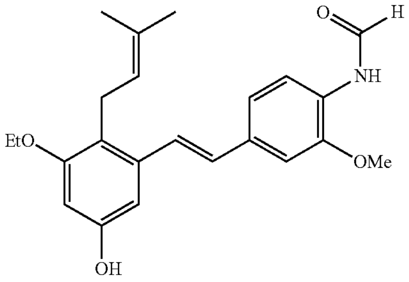
29 [KYN-128]
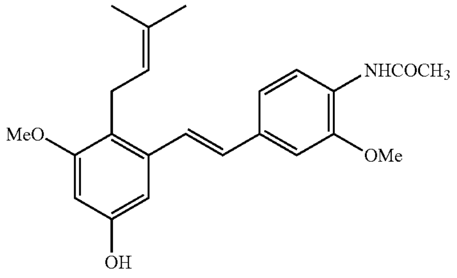
30 [KYN-142]
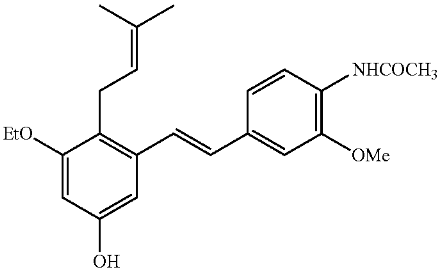

-continued
31 [KYN-151]
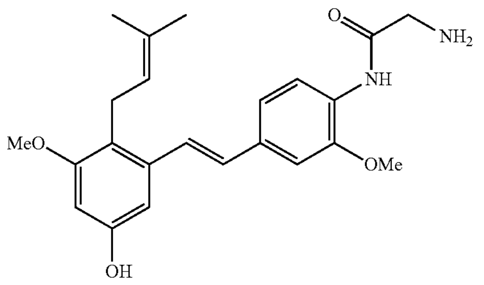
32 [KYN-148]
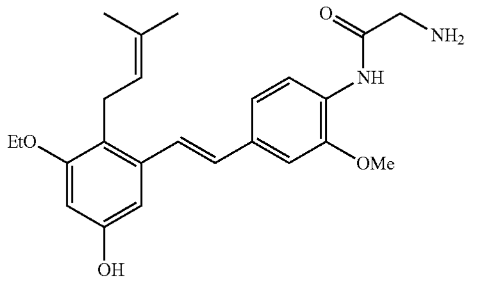
33 [KYN-126]
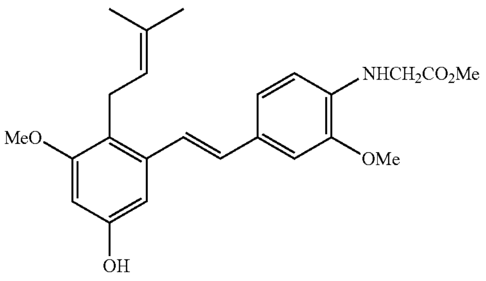
34 [KYN-147]
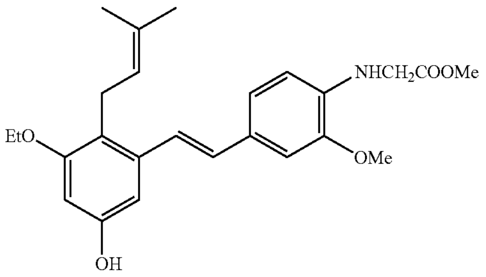
35 [KYN-152]
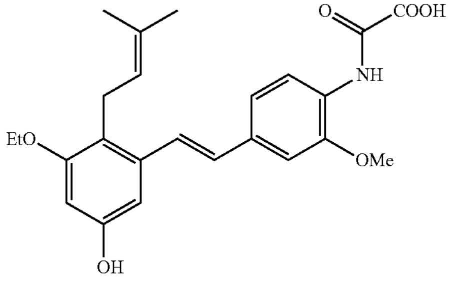
-continued
36 [KYN-150]
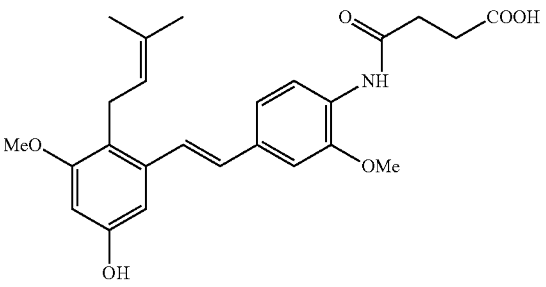
37 [KYN-144]
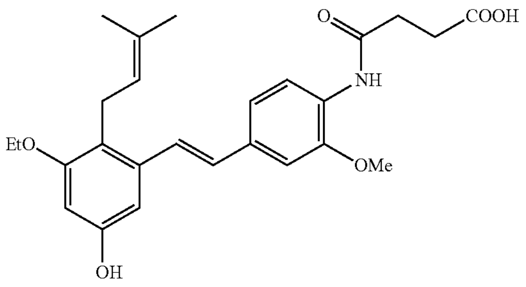
38 [KYN-155]
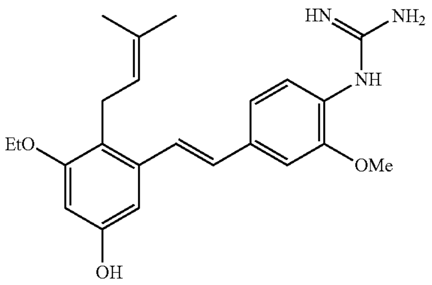
39 [KYN-165]
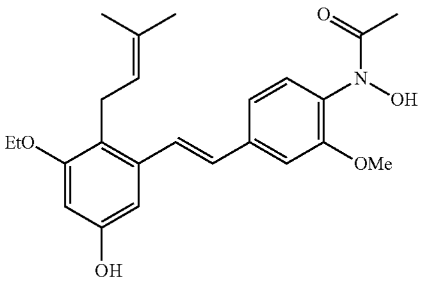
40 [KYN-159]
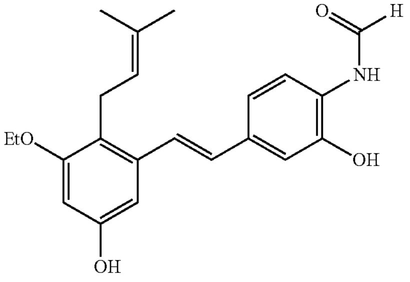

41 [KYN-161]
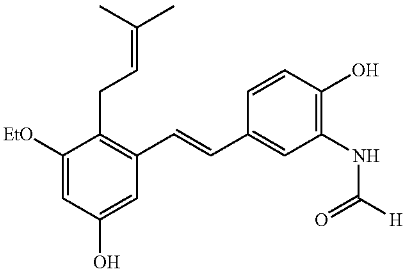
42 [KYN-162]
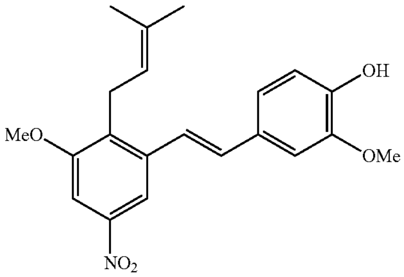
43 [KYN-163]
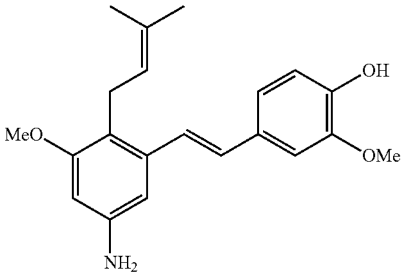
44 [KYN-164]
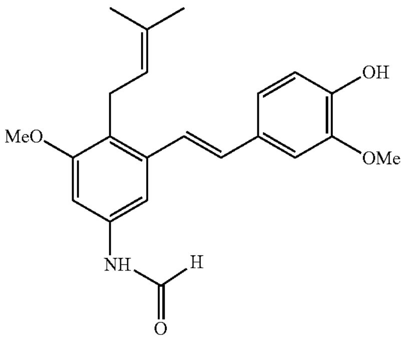
45 [KYN-112]
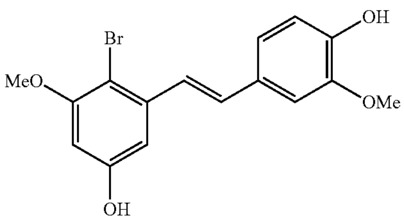
46 [KYN-145]
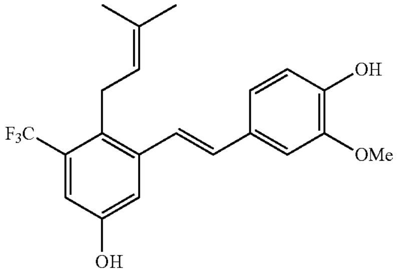
47 [KYN-167]
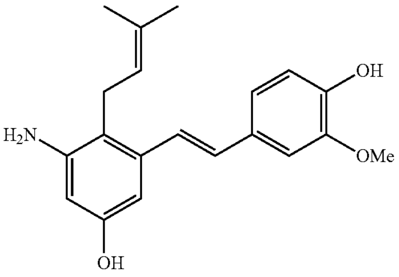
48 [KYN-168]
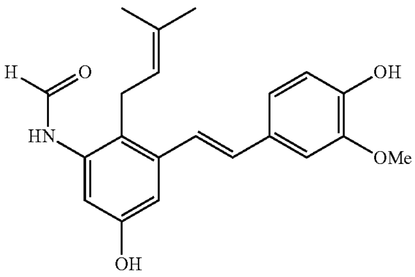
49 [KYN-169]
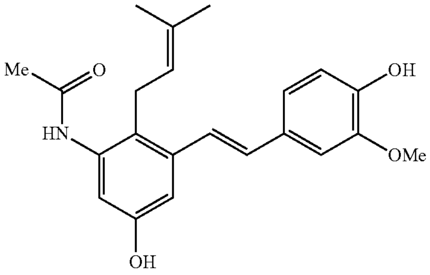
50 [KYN-170]
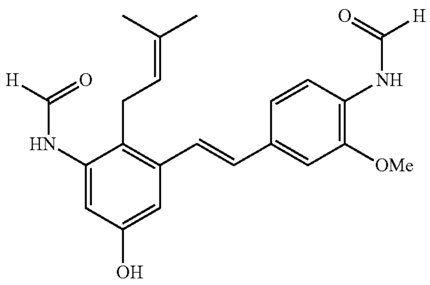

-continued

51 [KYN-166]

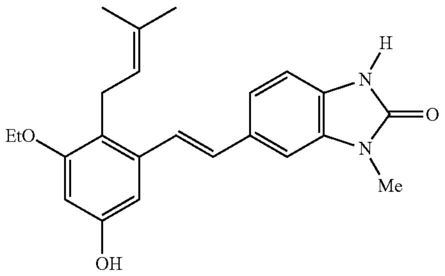

52 [KYN-171]

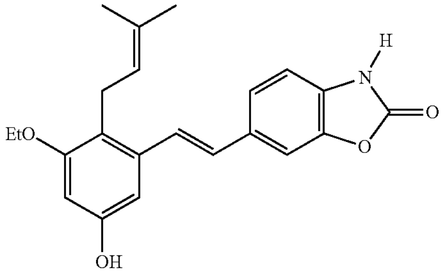

In one embodiment of the process of synthesising a compound of Formula (I), the compound according to formula (I) is selected from the group consisting of: compounds 22, 23, 24, 25, 26 27, 28, 29, 30, 31, 36, 24, 33, 34, 35, 36, 37, 38, 39, 40, The compound of formula (IV) or (I) may optionally undergo one or more further reactions, including but not limited to reaction with one or more —$NH_2$, $NO_2$ and/or —OH substituents on formula (IV) or formula (I). In one embodiment, this further reaction occurs at the $R^{1f}$ substituent of formula (I). In one embodiment, one or more —OH substituents one or formula (IV) or formula (I), may be converted to methoxyoxoacetamido (—NHC(O)C(O)$OCH_3$) substituents by reaction of the compound containing the OH substituent with methyl chlorooxoacetate in the presence of a base, such as triethylamine. In one embodiment, this further reaction occurs at the $R^{1f}$ substituent of formula (I).

In one embodiment, one or more —$NH_2$ substituents may be converted to methyl oxalate substituents by reaction of the compound containing the $NH_2$ substituent with methyl chlorooxoacetate in the presence of a base, such as triethylamine. In one embodiment, this further reaction occurs at the $R^{1f}$ substituent of formula (I).

In one embodiment, one or more methoxyoxoacetamido substituents are hydrolysed to —NHC(O)C(O)OH substituents by reaction of the compound containing the N methoxyoxoacetamido substituent with a base, for example LiOH. In one embodiment, this further reaction occurs at the $R^{1f}$ substituent of formula (I).

In one embodiment, one or more methyl oxalate substituents may be hydrolysed to —OH substituents by reaction of the compound containing the methyl oxalate substituent with a base, for example LiOH. In one embodiment, this further reaction occurs at the $R^{1f}$ substituent of formula (I).

In one embodiment, one or more —$NH_2$ substituents may be converted to guanidine (—NHC(NH)$NH_2$) substituents by reaction of the compound containing the $NH_2$ substituent with cyanamide in the presence of an acid, such as p-toluenesulfonic acid. In one embodiment, this further reaction occurs at the Ru substituent of formula (I).

In one embodiment, one or more —$NH_2$ substituents may be converted to formamide (—NHC(O)H) substituents by reaction of the compound containing the $NH_2$ substituent with ethyl formate. In one embodiment, this further reaction occurs at the $R^{1f}$ substituent of formula (I).

In one embodiment, one or more —$NH_2$ substituents may be converted to an acetamido (—NHC(O)$CH_3$) substituents by reaction of the compound containing the $NH_2$ substituent with acetic anhydride in the presence of a base such as DIPEA (diisopropylethylamine). In one embodiment, this further reaction occurs at the $R^{1f}$ substituent of formula (I).

In one embodiment, one or more —$NH_2$ substituents may be converted to an amide derivative (—NHC(O)$CH_2CH_2$C(O)OH) substituents by reaction of the compound containing the $NH_2$ substituent with succinic anhydride in the presence of a base such as DIPEA (diisopropylethylamine). In one embodiment, this further reaction occurs at the $R^{1f}$ substituent of formula (I).

In one embodiment, one or more —$NH_2$ substituents may be converted to methyl amine substituents (—NHMe) by reaction of the compound containing the $NH_2$ substituent with formaldehyde in the presence of triacetoxyborohydride. In one embodiment, this further reaction occurs at the $R^{1f}$ substituent of formula (I).

In one embodiment, one or more —OH substituents may be converted to acetate (—OC(O)$CH_3$) substituents by reaction of the compound containing the —OH substituent with acetic anhydride in the presence of a base such as DIPEA (diisopropylethylamine). In one embodiment, this further reaction occurs at the $R^{1f}$ substituent of formula (I).

In one embodiment, one or more acetate substituents may be hydrolysed to form —OH substituents by reaction of the compound containing the acetate substituent with a base, for example, LiOH. In one embodiment, this further reaction occurs at the $R^{1f}$ substituent of formula (I).

In one embodiment, one or more —$NO_2$ substituents may be reduced to amine substituents by, for example, reaction of the compound containing the $NO_2$ substituent with Zn in the presence of ammonium chloride. In one embodiment, this further reaction occurs at the $R^{1f}$ substituent of formula (I).

Module A

In one embodiment of the process disclosed herein, the compound according to formula (II) is Module A Formula (II)

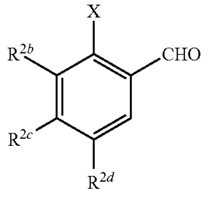

wherein $R^{2b}$=OMe $R^{2d}$=OH or OSEM $R^{2c}$=H

Hal is Br

In one embodiment of the process disclosed herein, the compound according to formula (II) may be prepared according to the steps comprising i) bromination of a mono- or di-hydroxyl substituted toluene compound; ii) protection of one hydroxyl group and/or alkylation of the other hydroxyl group; iii) removal of protecting group; iv) acylation of a hydroxyl group; v) dibromination of the aromatic methyl; vi) hydrolysis of the dibromomethyl to form an aldehyde; and vii) protection of the hydroxyl. In one embodiment, there is provided in step i) bromination of a di-hydroxyl substituted toluene compound. In one embodiment of the process disclosed herein, the compound according to formula (II) may be prepared according to the steps comprising i) bromination of a di-hydroxyl substituted toluene compound at a position adjacent to the C-bonded substituent with a brominating agent; ii) protection of a hydroxyl group with an O-protecting group followed by alkylation with an a C1-C3alkyl halogen; iii) removal of the O-protecting group in the presence of a base; iv) acylation of hydroxyl group using acetic anhydride in the presence of a base; v) dibromination of the aromatic methyl group using a brominating agent to form a dibromomethyl group; vi) hydrolysis of the dibromomethyl group to form an aldehyde; and vii) protection of the hydroxyl group by reaction with a suitable compound able to provide an O-protecting group including but not limited to COMe, t-BuSi$(CH_3)_2$, 2-(trimethylsilyl)ethoxymethyl (SEM), CH(OEt)$CH_3$, tetrahydropyranyl, or C(OEt)$(CH_3)$. In one embodiment, there is provided in step vii), protection of the hydroxyl group by reaction with 2-(trimethylsilyl)ethoxymethyl (SEM) chloride to provide a 2-(trimethylsilyl)ethoxymethyl (SEM) acetal protecting group. In one specific embodiment, the compound according to formula (II) is Module A and is prepared according to the following process:

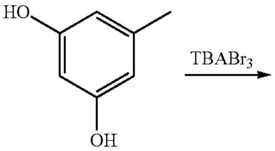

A1

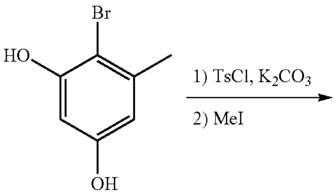

A2

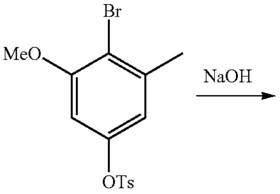

A3

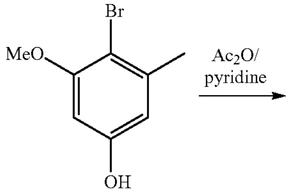

A4

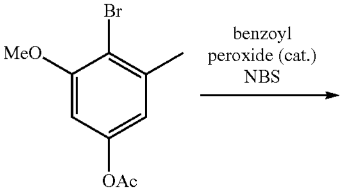

A5

-continued

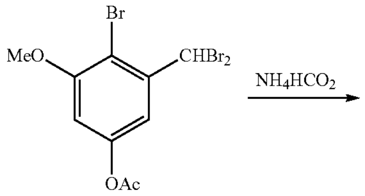

A6

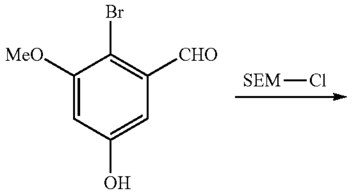

A7

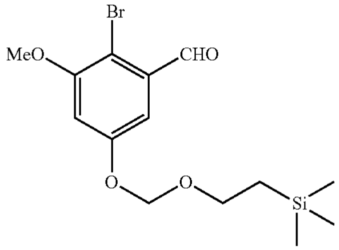

A8 (Module A)

Module B

In one embodiment of the process disclosed herein, the compound according to formula (III) may be prepared starting with a di-, or tri-substituted hydroxyl and/or alkoxyl substituted benzaldehyde compound, according to the steps comprising i) protection of the hydroxyl group; ii) reduction of the aromatic aldehyde to a benzyl alcohol; iii) coupling of the benzyl alcohol with a trialkylphosphonate and zinc (II) iodide to form a dialkylbenzylphosphonate.

In one embodiment, the compound according to formula (III) is Module B:

Module B

Formula (III)

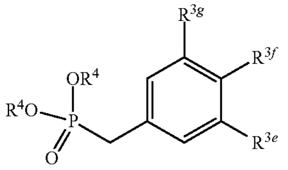

wherein $R^{3g}$=H $R^{3f}$=OSEM $R^{3e}$=OMe

R4=Et

In one embodiment of the process disclosed herein, the compound according to formula (III) is Module B and is prepared according to the following process:

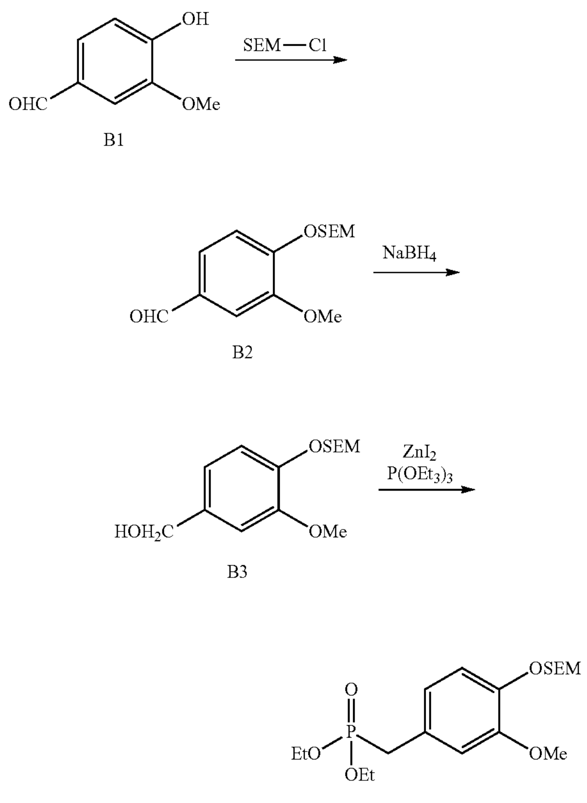

B1

B2

B3

B4 (Module B)

Module C

In one embodiment, the compound according to formula (IV) is Module C:

Module C

Formula (IV)

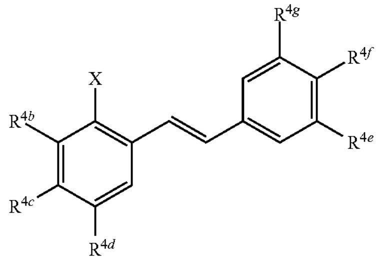

Wherein $R^{4b}$=OMe $R^{4c}$=H $R^{4d}$=OSEM, OH $R^{4g}$=H $R^{4e}$=OMe $R^{4f}$=OSEM Hal=Br In one embodiment of the process disclosed herein, the compound according to formula (IV) is prepared according to the following process:

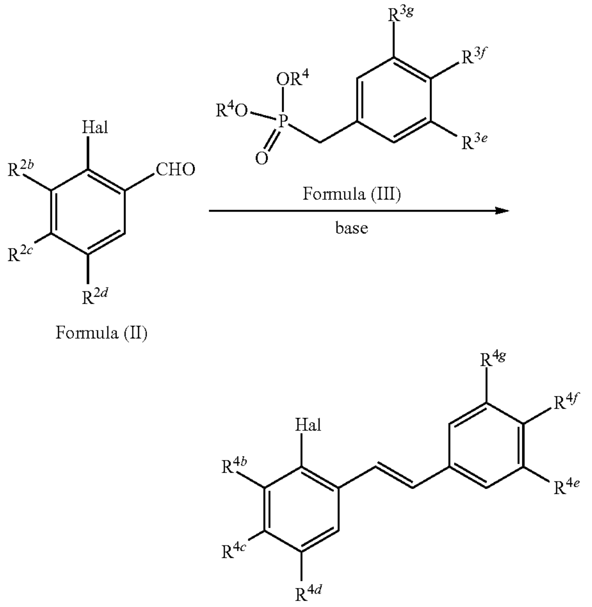

Formula (II)

Formula (III)

Formula (IV)

wherein the base can be, but is not limited to, NaH and wherein the formula (II) (III) and (IV) are as defined herein.

In one embodiment of the process disclosed herein, formula (II) is Module A, formula (III) is Module B and formula (IV) is Module C according to the following:

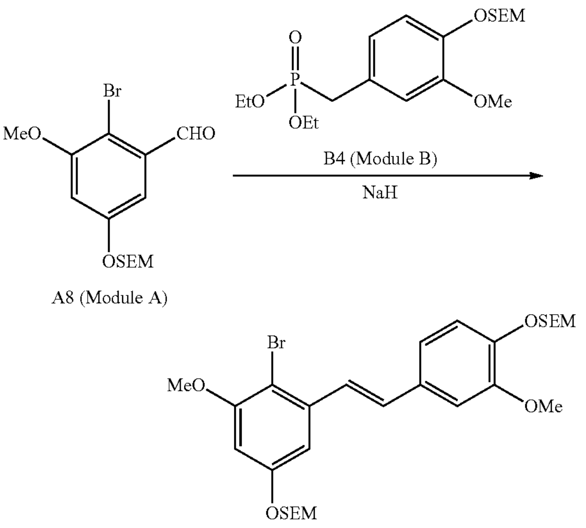

A8 (Module A)

B4 (Module B)

C1 (Module C)

Cross coupling alkylation of the aryl halide, Module C, can be achieved with for, example, an alkyl boronic acid. As an example of the process disclosed herein, there is provided the following embodiment:

i) Module C is coupled with 3-methylbut-2-enylboronic acid pinacol ester in the presence of tetrakis(triphenylphosphine) palladium(0) and potassium carbonate to afford compound 1.1;

ii) compound 1.1 is treated with tetrabutylammonium fluoride to afford compound 1, according to the following:

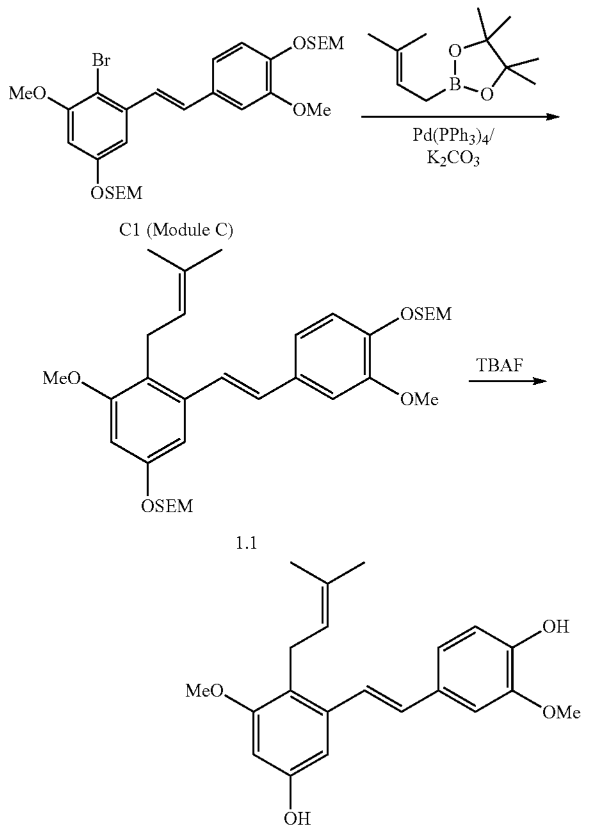

C1 (Module C)

1.1

Compound 1

Compounds and Compositions

Disclosed herein is a compound according to formula (I)

Formula (I)

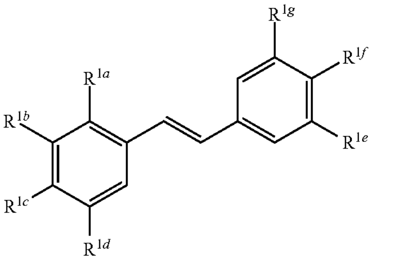

prepared by a process disclosed herein, wherein:

$R^{1a}$ is Hal, allyl, crotyl, prenyl, geranyl, farnesyl, benzyl, 2-alkenyl, 2-alkynyl;

$R^{1b}$ is $CF_3$, OH or $OR^2$, $NO_2$, NHEt, $NMe_2$, NMeEt, $NHR^3$, $NMeR^3$, NHC═NH($NH_2$) or $COOR^2$;

$R^{1c}$ is H, alkyl, alkenyl, alkynyl, alkanedienyl, prenyl, geranyl, farnesyl, or benzyl;

$R^{1d}$ is $CF_3$, OH or $OR^2$, $NHR^3$, $NO_2$, $NMeR^3$, NHC═NH ($NH_2$) or $COOR^2$;

$R^{1e}$ is H, $C_1$-$C_6$ alkyl, OH, $OR^2$, $NO_2$, $NMe_2$, $NHR^3$ or $NMeR^3$, $SR^2$;

$R^{1f}$ is H, OH, $OR^2$, $NO_2$, $NHR^3$, NHC═NH($NH_2$), $COOR^2$, COOH;

$R^{1g}$ is H, alkyl, $CF_3$, OH or $OR^2$;

$R^2$ is methyl, ethyl, propyl, isopropyl, butyl, isobutyl, t-butyl, trifluoromethyl, $COCOOR^4$ or O-protecting group when attached to an O, wherein the O-protecting group is selected from the group consisting of COMe, t-BuSi$(CH_3)_2$, 2-(trimethylsilyl)ethoxy]methyl (SEM) acetal, CH(OEt)$CH_3$, tetrahydropyranyl, or C(OEI) $CH_3)_2$;

$R^3$ is H, $CH_3$, OH, (CO)H, (CO)Me, $SO_2Me$, $CH_2COOH$, $CH_2COOR^2$, $CO(CH_2)_nNH_2$, $CONH_2$, $CO(CH_2)_n$ COOH or $COCOOR^4$ (where n=0, 1 or 2);

$R^4$ is $C_1$-$C_6$ alkyl; and

Hal is a halide selected from the group consisting of F, Cl, Br, I, and At;

only one of $R^{1e}$, $R^{1f}$ or $R^{1g}$ can be H; and when $R^{1e}$ is OH, $NH_2$ or NHMe and $R^{1f}$ is $NH_2$, the nitrogen of $R^{1f}$ is bridged with a carbonyl group or $(CO)CH_2$ group to the oxygen or nitrogen of $R^{1e}$ to form a five or six-membered heterocyclic ring.

Also disclosed herein is a compound according to formula (I):

Formula (I)

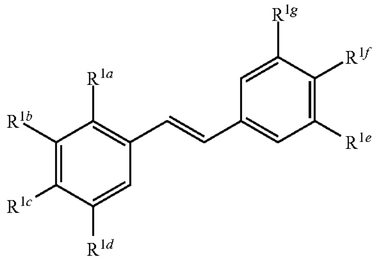

wherein:

$R^{1a}$ is Hal, allyl, crotyl, prenyl, geranyl, farnesyl, benzyl, 2-alkenyl, 2-alkynyl;

$R^{1b}$ is $CF_3$, OH or $OR^2$, $NO_2$, NHEt, $NMe_2$, NMeEt, $NHR^3$, $NMeR^3$, NHC═NH($NH_2$) or $COOR^2$;

$R^{1c}$ is H, alkyl, alkenyl, alkynyl, alkanedienyl, prenyl, geranyl, farnesyl, or benzyl;

$R^{1d}$ is $CF_3$, OH or $OR^2$, $NO_2$, $NHR^3$, $NMeR^3$, NHC═NH ($NH_2$) or $COOR^2$;

$R^{1e}$ is H, $C_1$-$C_6$ alkyl, OH, $OR^2$, $NO_2$, $NMe_2$, $NHR^3$ or $NMeR^3$, $SR^2$;

$R^{1f}$ is H, OH, $OR^2$, $NO_2$, $NHR^3$, NHC═NH($NH_2$), $COOR^2$, COOH;

$R^{1g}$ is H, alkyl, $CF_3$, OH or $OR^2$;

$R^2$ is methyl, ethyl, propyl, isopropyl, butyl, isobutyl, t-butyl, trifluoromethyl, $COCOOR^4$ or O-protecting group when attached to an O, wherein the O-protecting group is selected from the group consisting of COMe, t-BuSi$(CH_3)_2$, 2-(trimethylsilyl)ethoxy]methyl (SEM) acetal, CH(OEt)$CH_3$, tetrahydropyranyl, or C(OEt) $CH_3)_2$;

$R^3$ is H, $CH_3$, OH, (CO)H, (CO)Me, $SO_2Me$, $CH_2COOH$, $CH_2COOR^2$, $CO(CH))_nNH_2$, $CONH_2$, $CO(CH_2)_n$ COOH or $COCOOR^4$ (where n=0, 1 or 2);

$R^4$ is $C_1$-$C_6$ alkyl; and

Hal is a halide selected from the group consisting of F, Cl, Br, I, and At;

only one of $R^{1e}$, $R^{1f}$ or $R^{1g}$ can be H, when $R^{1e}$ is OH, $NH_2$ or NHMe and $R^{1f}$ is $NH_2$, the nitrogen of $R^{1f}$ is bridged with a carbonyl group or $(CO)CH_2$ group to the oxygen or nitrogen of $R^{1e}$ to form a five or six-membered heterocyclic ring;

provided that when $R^{1a}$ and/or $R^{1c}$ is prenyl, $R^{1d}$ is OH, $R^{1f}$ is OH, $R^{1g}$ is H and $R^{1e}$ is OH, OMe or OEt, then $R^{1b}$ cannot be OH, OR where R=methyl, ethyl, propyl, isopropyl, butyl, isobutyl, t-butyl, or benzyl.

In one specific embodiment, there is provided a compound of formula (I) wherein:

$R^{1a}$ is allyl, prenyl, benzyl, 2-alkenyl;

$R^{1b}$ is $CF_3$, OH or $OR^2$;

$R^{1c}$ is H;

$R^{1d}$ is OH, $NH_2$, N(CO)H;

$R^{1e}$ is OH, $OR^2$, $NO_2$, $NHR^3$ or $NMeR^3$, (CO)H, SMe;

$R^{1f}$ is H, OH, $OR^2$, $NO_2$, $NHR^3$, NHC═NH($NH_2$), COOH;

$R^{1g}$ is H, alkyl, OH;

$R^2$ is methyl, ethyl, propyl, isopropyl, butyl, isobutyl, t-butyl;

$R^3$ is H, $CH_3$, OH, (CO)H, (CO)Me, $SO_2Me$, $CH_2COOR^2$, $COCH_2NH_2$, $CO(CH_2)_nCOOH$ (where n=0, 1 or 2).

provided that when $R^{1a}$ or $R^{1c}$ is prenyl, $R^{1d}$ is OH, $R^{1f}$ is OH, $R^{1g}$ is H and $R^{1e}$ is OH, OMe or OEt, then $R^{1b}$ cannot be OR where R=methyl, ethyl, isopropyl, propyl, butyl, isobutyl, t-butyl, or benzyl.

In one embodiment, formula (I) is a compound selected from the group consisting of compounds 2 to 7, 11, 13 to 19, 21 to 44, 46 to 49, 50, 51, 52 [KYN 138, 139, 140, 153, 134, 136, 132, 114, 118, 158, 157, 120, 156, 160, 154, 124, 125, 141, 137, 129, 149, 143, 128, 142, 151, 148, 126, 147, 152, 150, 144, 155, 165, 159, 161, 162, 163, 164, 145, 167, 168, 169, 166, 171, KYN-170] as disclosed herein.

Also disclosed herein are embodiments wherein one of $R^{1b}$ and $R^{1d}$ of Formula (I) are a substituent other than OH or $OR^2$. In one embodiment, at least one of $R^{1b}$ or $R^{1d}$ is $CF_3$, $NO_2$, $NHR^3$, $NMeR^3$, NHC═NH($NH_2$) or COOR. Accordingly, there is also provided a compound according to formula (I):

Formula (I)

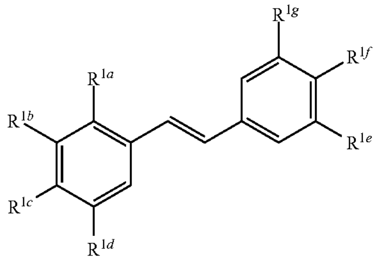

wherein:

$R^{1a}$ is Hal, allyl, crotyl, prenyl, geranyl, farnesyl, benzyl, 2-alkenyl, 2-alkynyl;

$R^{1b}$ is $CF_3$, OH or $OR^2$, $NO_2$, NHEt, $NMe_2$, NMeEt, $NHR^3$, $NMeR^3$, NHC═NH($NH_2$) or $COOR^2$;

$R^{1c}$ is H, alkyl, alkenyl, alkynyl, alkanedienyl, prenyl, geranyl, farnesyl, or benzyl;

$R^{1d}$ is $CF_3$, OH or $OR^2$, $NO_2$, $NHR^3$, $NMeR^3$, NHC═NH($NH_2$) or $COOR^2$;

$R^{1e}$ is H, $C_1$-$C_6$ alkyl, OH, $OR^2$, $NO_2$, $NMe_2$, $NHR^3$ or $NMeR^3$, $SR^2$;

$R^{1f}$ is H, OH, $OR^2$, $NO_2$, $NHR^3$, NHC═NH($NH_2$), $COOR^2$, COOH;

$R^{1g}$ is H, alkyl, $CF_3$, OH or $OR^2$;

wherein at least one of $R^{1b}$ or $R^{1d}$ is $CF_3$, $NO_2$, $NHR^3$, $NMeR^3$, NHC═NH($NH_2$) or $COOR^2$;

$R^2$ is methyl, ethyl, propyl, isopropyl, butyl, isobutyl, t-butyl, trifluoromethyl, $COCOOR^4$ or O-protecting group, wherein the O-protecting group is selected from the group consisting of COMe, t-BuSi($CH_3$)$_2$, 2-(trimethylsilyl)ethoxy]methyl (SEM) acetal, CH(OEt)$CH_3$, tetrahydropyranyl, or C(OEt)($CH_3$)$_2$;

$R^3$ is H, $CH_3$, OH, (CO)H, (CO)Me, $SO_2Me$, $CH_2COOH$, $CH_2COOR^2$, $CO(CH_2)_nNH_2$, $CONH_2$, $CO(CH_2)_n$COOH or $COCOOR^4$ (where n=0, 1 or 2);

$R^4$ is $C_1$-$C_6$ alkyl; and

Hal is a halide selected from the group consisting of F, Cl, Br, I, and At;

only one of $R^{1e}$, $R^{1f}$ or $R^{1g}$ can be H, when $R^{1e}$ is OH, $NH_2$ or NHMe and $R^{1f}$ is $NH_2$, the nitrogen of $R^{1f}$ is bridged with a carbonyl group or (CO)$CH_2$ group to the oxygen or nitrogen of $R^{1e}$ to form a five or six-membered heterocyclic ring.

In one embodiment, Formula (I) is a compound selected from compounds 11, 43, 44, 46, 47, 48, 49, 50 [KYN-132, 163, 164, 145, 167, 168, 169 [KYN-170] as disclosed herein.

Also disclosed herein are embodiments where the substituent $R^{1f}$ on the B-ring is not H, OH or $OR^2$ and $R^{1e}$ is not H. In one embodiment, there is provided a compound of formula (I)

Formula (I)

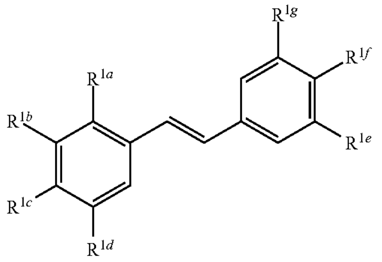

wherein:

$R^{1a}$ is Hal, allyl, crotyl, prenyl, geranyl, farnesyl, benzyl, 2-alkenyl, 2-alkynyl;

$R^{1b}$ is $CF_3$, OH or $OR^2$, $NO_2$, NHMe, NHEt, $NMe_2$, NMeEt, $NHR^3$, $NMeR^3$, NHC═NH($NH_2$) or COOR2, NHR3, $NMeR^3$, NHC═NH($NH_2$) or $COOR^2$;

$R^{1c}$ is H, alkyl, alkenyl, alkynyl, alkanedienyl, prenyl, geranyl, farnesyl, or benzyl;

$R^{1d}$ is $CF_3$, OH or $OR^2$, $NHR^3$, $NO_2$, $NH_2$, NHMe, NHC═NH($NH_2$) or $COOR^2$;

$R^{1e}$ is OH, $OR^2$;

$R^{1f}$ is $NO_2$, $NHR^3$, NHC═NH($NH_2$), $COOR^2$, COOH, $NHSO_2Me$, NHC(O)($CH_2$)COOH, NHC(O)COOH, NHC(O)($CH_2$)$NNH_2$, NHC(O)$CH_2NH_2$, $NHCH_2COOMe$, NHC(O)H, NHC(O)$CH_3$, NHC(O)($CH_2$)$_2$COOH, NHC(NH)$NH_2$;

$R^{1g}$ is H;

$R^2$ is methyl, ethyl, propyl, isopropyl, butyl, isobutyl, t-butyl, trifluoromethyl or O-protecting group, wherein the O-protecting group is selected from the group consisting of COMe, t-BuSi($CH_3$)$_2$, 2-(trimethylsilyl)ethoxy]methyl (SEM) acetal, CH(OEt)$CH_3$, tetrahydropyranyl, or C(OEt)($CH_3$)$_2$;

$R^3$ is H, $CH_3$, OH, (CO)H, (CO)Me, $SO_2Me$, $CH_2COOH$, $CH_2COOR^2$, $COCH_2NH_2$, $CONH_2$, $CO(CH_2)_nCOOH$, $CO(CH_2)_nCOOR^4$ (where n=0, 1 or 2);

$R^4$ is C1-C6 alkyl;

Hal is a halide selected from the group consisting of F, Cl, Br, I, and At;

only one of $R^{1e}$, $R^{1f}$ or $R^{1g}$ can be H, and when $R^{1e}$ is OH, $NH_2$ or NHMe and $R^{1f}$ is $NH_2$, the nitrogen of $R^{1f}$ is bridged with a carbonyl group or $(CO)CH_2$ group to the oxygen or nitrogen of $R^{1e}$ to form a five or six-membered heterocyclic ring.

In one embodiment, Formula (I) is a compound selected from compounds 21 to 40, 50, 51, 52 [KYN-154, 124, 125, 141, 137, 129, 149, 143, 128, 142, 151, 148, 126, 147, 152, 150, 144, 155, 165, 159, 166, 170, 171] as disclosed herein.

Also disclosed herein are embodiments where the substituent $R^{1e}$ on the B-ring is not H, OH or $OR^2$ and $R^{1fe}$ is not H. In one embodiment, there is provided a compound of formula (I):

Formula (I)

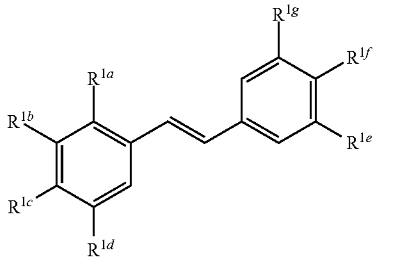

wherein;

$R^{1a}$ is Hal, allyl, crotyl, prenyl, geranyl, farnesyl, benzyl, 2-alkenyl, 2-alkynyl;

$R^{1b}$ is $CF_3$, OH or $OR^2$, $NO_2$, NHMe, NHEt, $NMe_2$, NMeEt, $NHR^3$, $NMeR^3$, NHC═NH($NH_2$) or COOR2, NHR3, $NMeR^3$, NHC═NH($NH_2$) or $COOR^2$;

$R^{1c}$ is H, alkyl, alkenyl, alkynyl, alkanedienyl, prenyl, geranyl, farnesyl, or benzyl;

$R^{1d}$ is $CF_3$, OH or $OR^2$, $NHR^3$, $NO_2$, $NH_2$, NHMe, NHC═NH($NH_2$) or $COOR^2$;

$R^{1e}$ is $C_1$-$C_6$ alkyl, $NO_2$, $NH_2$, NHMe, $NMe_2$, $NHR^3$ or $NMeR^3$, $SR^2$;

$R^{1f}$ is OH, $OR^2$;

$R^{1g}$ is H;

$R^2$ is methyl, ethyl, propyl, isopropyl, butyl, isobutyl, t-butyl, trifluoromethyl or O-protecting group, wherein the O-protecting group is selected from the group consisting of COMe, t-BuSi$(CH_3)_2$, 2-(trimethylsilyl) ethoxy]methyl (SEM) acetal, CH(OEt)$CH_3$, tetrahydropyranyl, or C(OEt)$(CH_3)_2$;

$R^3$ is H, $CH_3$, OH, (CO)H, (CO)Me, $SO_2Me$, $CH_2COOH$, $CH_2COOR^2$, $COCH_2NH_2$, $CONH_2$, $CO(CH_2)_nCOOH$ (where n=0, 1 or 2); and Hal is a halide selected from the group consisting of F, Cl, Br, I, and At;

only one of $R^{1e}$, $R^{1f}$ or $R^{1g}$ can be H, when $R^{1e}$ is OH, $NH_2$ or NHMe and $R^{1f}$ is $NH_2$, the nitrogen of $R^{1f}$ is bridged with a carbonyl group or $(CO)CH_2$ group to the oxygen or nitrogen of $R^{1e}$ to form a five or six-membered heterocyclic ring.

In one embodiment, Formula (I) is a compound selected from compound 13 to 16, 41 [KYN-114, 118, 158, 157, 161] as disclosed herein.

Also disclosed herein are embodiments where there is no prenyl group on the A or B-ring. In one embodiment, there is provided a compound of formula (I):

Formula (I)

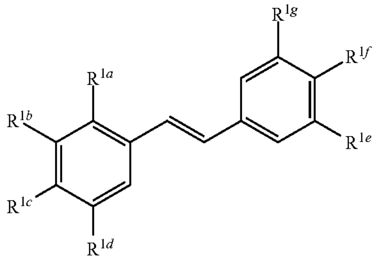

wherein:

$R^{1a}$ is Hal, allyl, crotyl, geranyl, farnesyl, benzyl, 2-alkenyl, 2-alkynyl;

$R^{1b}$ is $CF_3$, OH or $OR^2$, $NO_2$, NHMe, NHEt, $NMe_2$, NMeEt, $NHR^3$, $NMeR^3$, NHC═NH($NH_2$) or $COOR^2$;

$R^{1c}$ is H, alkyl, alkenyl, alkynyl, alkanedienyl, geranyl, farnesyl, or benzyl;

$R^{1d}$ is $CF_3$, OH or $OR^2$, $NHR^3$, $NO_2$, $NH_2$, NHMe, NHC═NH($NH_2$) or $COOR^2$;

$R^{1e}$ is H, OH, $OR^2$, $NO_2$, $NH_2$, NHMe, $NMe_2$, $NHR^3$ or $NMeR^3$, $SR^2$;

$R^{1f}$ is H, OH, $OR^2$, $NO_2$, $NH_2$, NHMe, $NHR^3$, NHC═NH ($NH_2$), $COOR^2$, COOH;

$R^{1g}$ is H, alkyl, $CF_3$, OH or $OR^2$;

$R^2$ is methyl, ethyl, propyl, isopropyl, butyl, isobutyl, t-butyl, trifluoromethyl, C(O)C(O)$OR^4$ or O-protecting group, wherein the O-protecting group is selected from the group consisting of COMe, t-BuSi$(CH_3)_2$, 2-(trimethylsilyl)ethoxy]methyl (SEM) acetal, CH(OEt)$CH_3$, tetrahydropyranyl, or C(OEt)$(CH_3)_2$;

$R^3$ is H, $CH_3$, OH, (CO)H, (CO)Me, $SO_2Me$, $CH_2COOH$, $CH_2COOR^2$, $COCH_2NH_2$, $CONH_2$, $CO(CH_2)_nCOOH$ (where n=0, 1 or 2);

$R^4$ is C1-C6 alkyl; and

Hal is a halide selected from the group consisting of F, Cl, Br, I. and At;

only one of $R^{1e}$, $R^{1f}$ or $R^{1g}$ can be H, and when $R^{1e}$ is OH, $NH_2$ or NHMe and $R^{1f}$ is $NH_2$, the nitrogen of $R^{1f}$ is bridged with a carbonyl group or $(CO)CH_2$ group to the oxygen or nitrogen of $R^{1e}$ to form a five or six-membered heterocyclic ring.

In a specific embodiment, there is provided a compound according to Formula (I), wherein:

$R^{1a}$ is allyl, crotyl, geranyl, farnesyl, benzyl, 2-alkenyl, 2-alkynyl;

$R^{1b}$ is $CF_3$, OH, $OR^2$;

$R^{1c}$ is H;

$R^{1d}$ is OH or $OR^2$, $NH_2$, NH(CO)H;

$R^{1e}$ is $OR^2$, $R^4$, $NO_2$, $NH_2$, NHMe, $NMe_2$, $SR^2$;

$R^{1f}$ is OH, $OR^2$, $NO_2$, $NH_2$, NHMe, $NHR^3$, NHC═NH ($NH_2$), $COOR^2$, COOH;

$R^{1g}$ is H;

$R^2$ is methyl, ethyl, propyl, isopropyl, butyl, isobutyl, t-butyl, trifluoromethyl, C(O)C(O)$OR^4$ or O-protecting group, wherein the protecting group is selected from the group consisting of COMe, t-BuSi$(CH_3)_2$, 2-(trimethylsilyl)ethoxymethyl (SEM) acetal, CH(OEt)$CH_3$, tetrahydropyranyl, or C(OEt)$(CH_3)_2$;

$R^3$ is H, $CH_3$, OH, (CO)H, (CO)Me, $SO_2Me$, $CH_2COOH$, $CH_2COOR^2$, $COCH_2NH_2$, $CONH_2$, $CO(CH_2)_nCOOH$ (where n=0, 1 or 2);

$R^4$ is C1-C6 alkyl;

and

Hal is a halide selected from the group consisting of F, Cl, Br, I, and At;

only one of $R^{1e}$, $R^{1f}$ or $R^{1g}$ can be H, when $R^{1e}$ is OH, $NH_2$ or NHMe and $R^{1f}$ is $NH_2$, the nitrogen of $R^{1f}$ is bridged with a carbonyl group or $(CO)CH_2$ group to the oxygen or nitrogen of $R^{1e}$ to form a five or six-membered heterocyclic ring.

In one embodiment, Formula (I) is a compound selected from compound 2, 3, 4, 5, 6, 7 [KYN-138, 139, 140, 153, 134, 136] as disclosed herein.

In another embodiment, there is provided a compound of formula (I) wherein:

$R^{1a}$ is prenyl;

$R^{1b}$ is $OR^2$;

$R^{1c}$ is H;

$R^{1d}$ is OH;

$R^{1e}$ is $OR^2$;

$R^{1f}$ is $NHR^3$, $NHC{=}NH(NH_2)$;

$R^{1g}$ is H;

$R^2$ is methyl, ethyl, propyl, isopropyl, butyl, isobutyl, t-butyl; and $R^3$ is H, $CH_3$, OH, (CO)H, (CO)Me, $SO_2Me$, $CH_2COOR^2$, $COCH_2NH_2$, $CO(CH_2)_nCOOH$ (where n=0, 1 or 2).

In yet another embodiment, there is provided a compound of formula (I) wherein:

$R^{1a}$ is prenyl;

$R^{1b}$ is $OR^2$;

$R^{1c}$ is H;

$R^{1d}$ is OH;

$R^{1e}$ is $OR^2$;

$R^{1f}$ is OH;

$R^{1g}$ is alkyl, OH;

$R^2$ is methyl, ethyl, propyl, isopropyl, butyl, isobutyl, t-butyl; and alkyl is methyl, ethyl, propyl, isopropyl, butyl, isobutyl, t-butyl.

Also disclosed herein is a compound according to formula (I) having at least one formamide group and/or ethoxide group on the A and/or B ring. In one embodiment, the A-ring has at least one ethoxide substituent. The ethoxide substituent may be at the $R^{1b}$ or $R^{1d}$ position on the A-ring. In another embodiment, the A-ring has a formamide substituent. In another embodiment the B-ring has a formamide substituent. In another embodiment, the A-ring has at least one ethoxide substituent and the B-ring has a formamide substituent. In a specific embodiment, the compound of formula (I) may be selected from compounds 8, 20, 24, 27, 28, 30, 32, 34, 35, 37 to 41, 50, 51 [KYN-119, 146, 141, 149, 143, 142, 148, 147, 152, 144, 155, 165, 159, 161, 170].

Methods of Treatment

There is provided a method for treating cancer comprising administering a therapeutically effective amount of a compound of formula (I) as disclosed herein or a pharmaceutically acceptable salt, solvate or pharmaceutical composition including said compounds to a patient in need.

Preliminary Results

Discussion

WO2012/149608 discloses the anticancer activity of specific prenylated polyhydroxystilbene derivatives. In particular, compound 1 [KYN-001], as disclosed herein, was found to have potent activity in the inhibition of cancerous cells. The activity of the compounds of the present disclosure have been compared to compound 1.

Preliminary studies indicate that compounds where $R^{1b}$=OEt and/or at least one phenolic OH is replaced by a formamide group are very effective cancer inhibitors. From Table 6, $IC_{50}$ values for 42 cancer cell lines (average activity), the order of potency is 28>27>8>20>1. Compound 28 with formamide and OEt was most active followed by 27 with $R^{1b}$=OMe and formamide.

BRIEF DESCRIPTION OF DRAWINGS

FIG. 13.1 shows the effect of compound 1 on: A. CCL2 release from inflammation induced by IL-4, IL-13, IL-22 and IFN-γ in human keratinocytes, B. IL-8 release from inflammation induced by IL-17 and TNF-α in human keratinocytes, C. IL-17A release from inflammation induced by CD3, CD28 and IL-23 in human PBMC, D. IL-4 and IL-2 release from inflammation induced by CD2, CD3 and CD28 in T-cells. Effects of the compound 1 on cell viability in each assay were parallelly assessed.

FIG. 13.2 shows the effect of compound 8 on: A. CCL2 release from inflammation induced by IL-4, IL-13, IL-22 and IFN-γ in human keratinocytes, B. IL-8 release from inflammation induced by IL-17 and TNF-α in human keratinocytes, C. IL-17A release from inflammation induced by CD3, CD28 and IL-23 in human PBMC, D. IL-4 and IL-2 release from inflammation induced by CD2, CD3 and CD28 in T-cells. Effects of the compound 8 on cell viability in each assay were parallelly assessed.

FIG. 13.3 shows the effect of Compound 20 on: A. CCL2 release from inflammation induced by IL-4, IL-13, IL-22 and IFN-γ in human keratinocytes, B. IL-8 release from inflammation induced by IL-17 and TNF-α in human keratinocytes, C. IL-17A release from inflammation induced by CD3, CD28 and IL-23 in human PBMC. D. IL-4 and IL-2 release from inflammation induced by CD2, CD3 and CD28 in T-cells. Effects of the compound 20 on cell viability in each assay were parallelly assessed.

FIG. 13.4 shows the effect of Compound 27 on: A. CCL2 release from inflammation induced by IL-4, IL-13, IL-22 and IFN-γ in human keratinocytes, B. IL-8 release from inflammation induced by IL-17 and TNF-α in human keratinocytes, C. IL-17A release from inflammation induced by CD3, CD28 and IL-23 in human PBMC. D. IL-4 and IL-2 release from inflammation induced by CD2, CD3 and CD28 in T-cells. Effects of the compound 27 on cell viability in each assay were parallelly assessed.

FIG. 13.5 shows the effect of Compound 28 on: A. CCL2 release from inflammation induced by IL-4, IL-13, IL-22 and IFN-γ in human keratinocytes, B. IL-8 release from inflammation induced by IL-17 and TNF-α in human keratinocytes, C. IL-17A release from inflammation induced by CD3, CD28 and IL-23 in human PBMC, D. IL-4 and IL-2 release from inflammation induced by CD2, CD3 and CD28 in T-cells. Effects of the compound 28 on cell viability in each assay were parallelly assessed.

FIG. 13.6 shows the effect of Compound 31 on: A. CCL2 release from inflammation induced by IL-4, IL-13, IL-22 and IFN-γ in human keratinocytes, B. IL-8 release from inflammation induced by IL-17 and TNF-α in human keratinocytes, C. IL-17A release from inflammation induced by CD3, CD28 and IL-23 in human PBMC, D. IL-4 and IL-2 release from inflammation induced by CD2, CD3 and CD28 in T-cells. Effects of the compound 31 on cell viability in each assay were parallelly assessed.

FIG. 13.7 shows the effect of Compound 35 on: A. CCL2 release from inflammation induced by IL-4, IL-13, IL-22 and IFN-γ in human keratinocytes, B. IL-8 release from inflammation induced by IL-17 and TNF-α in human keratinocytes, C. IL-17A release from inflammation induced by CD3, CD28 and IL-23 in human PBMC, D. IL-4 and IL-2 release from inflammation induced by CD2, CD3 and CD28 in T-cells. Effects of the compound 35 on cell viability in each assay were parallelly assessed.

FIG. 14. Concentration dependent inhibition of compound 1 [KYN-001], 20 [KYN-146] and 27 [KYN-149] towards three patients derived glioblastoma multiforme (GBM) cell samples designated as A. BNA99; B. BNB04 and C. BNB18.

Figure 15:
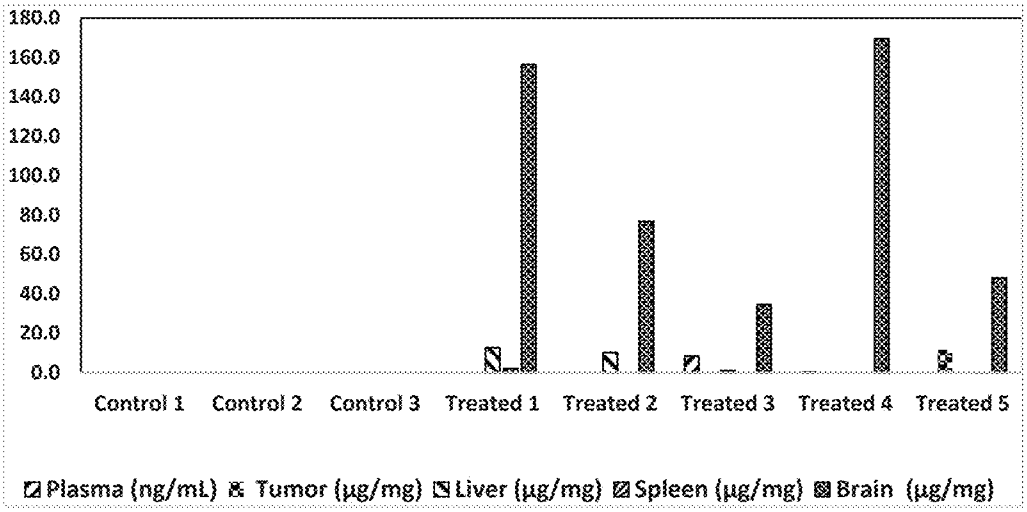
Figure 15:
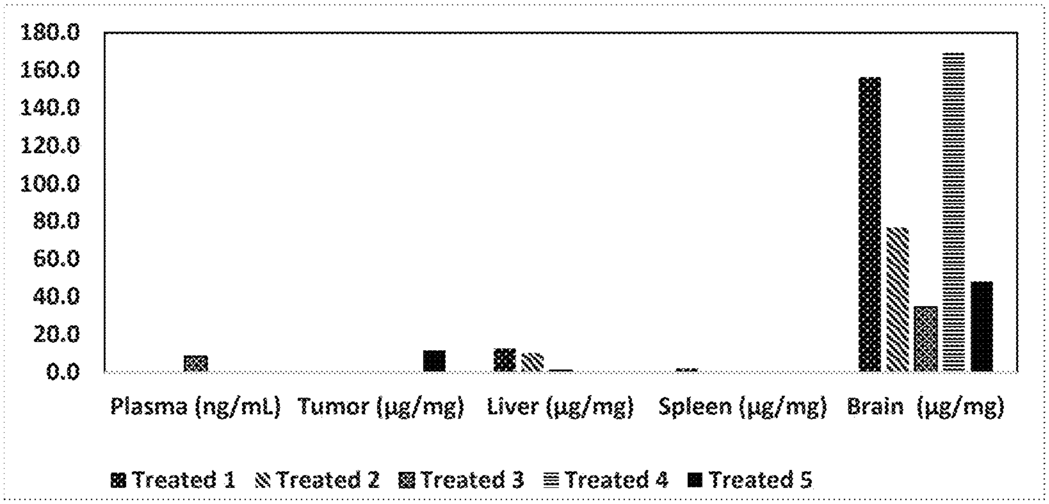

FIG. 15. Concentrations of compound 27 in different tissue samples isolated from treated mice.

Figure 16:

FIG. 16. Histochemical analysis of tumor samples from treated 1 and 2 mice

Figure 17:
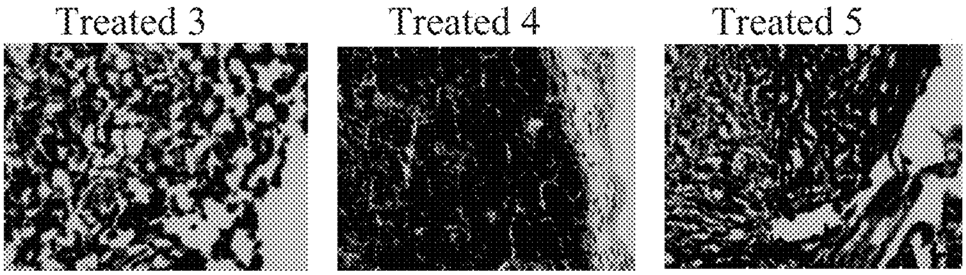

FIG. 17. Histochemical analysis of samples from treated 3, 4 and 5 mice

Figure 18:
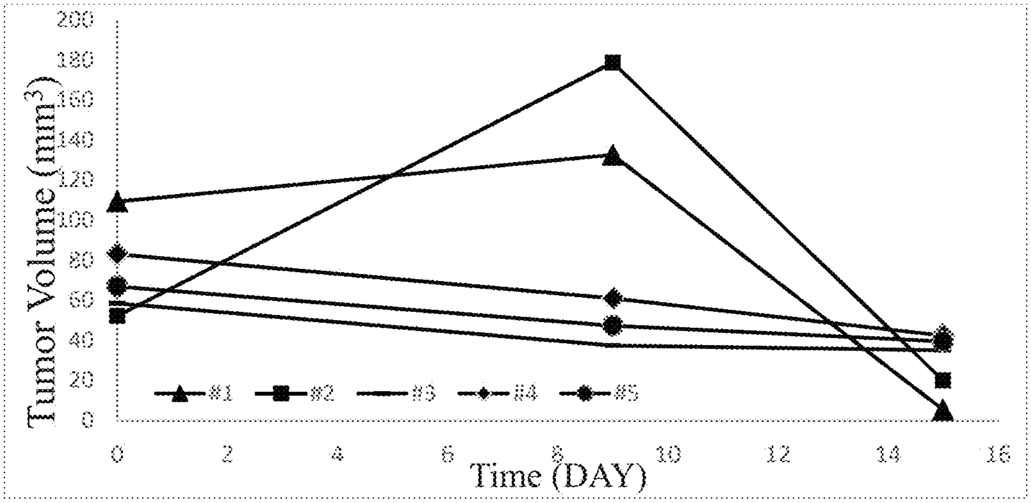

FIG. 18. Effect of compound 27 on melanoma B16F10 xenografted in BALB/c mice

DEFINITION

Unless specifically defined otherwise, all technical and scientific terms used herein shall be taken to have the same meaning as commonly understood by one of ordinary skill in the art (e.g., chemistry, biochemistry, medicinal chemistry, microbiology and the like). Although methods and materials similar or equivalent to those described herein can be used in the practice or testing of the present invention, suitable methods and materials are described below. In case of conflict, the present specification, including definitions, will control. In addition, the materials, methods, and examples are illustrative only and not intended to be limiting.

As used herein, the term "and/or", e.g., "X and/or Y" shall be understood to mean either "X and Y" or "X or Y" and shall be taken to provide explicit support for both meanings or for either meaning, e.g. A and/or B includes the options i) A, ii) B or iii) A and B.

As used herein, the term about, unless stated to the contrary, refers to +/−20%, typically +/−10%, typically +/−5%, of the designated value.

As used herein, the terms "a", "an" and "the" include both singular and plural aspects, unless the context clearly indicates otherwise.

It is to be appreciated that certain features that are, for clarity, described herein in the context of separate embodiments, may also be provided in combination in a single embodiment. Conversely, various features that are, for brevity, described in the context of a single embodiment, may also be provided separately or in any sub-combination.

Throughout the present specification, various aspects and components of the invention can be presented in a range format. The range format is included for convenience and should not be interpreted as an inflexible limitation on the scope of the invention. Accordingly, the description of a range should be considered to have specifically disclosed all the possible sub-ranges as well as individual numerical values within that range, unless specifically indicated. For example, description of a range such as from 1 to 5 should be considered to have specifically disclosed sub-ranges such as from 1 to 3, from 1 to 4, from 1 to 5, from 2 to 4, from 2 to 5, from 3 to 5 etc., as well as individual and partial numbers within the recited range, for example, 1, 2, 3, 4, 5, 5.5 and 6, unless where integers are required or implicit from context. This applies regardless of the breadth of the disclosed range. Where specific values are required, these will be indicated in the specification.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

As used herein, the term "halogen" means fluorine, chlorine, bromine, iodine or astatine.

As used herein, the term "hydrocarbon" encompass a chemical compound composed of hydrogen and carbon atoms.

As used herein, the term "alkyl" encompasses both straight-chain (i.e., linear) and branched-chain hydrocarbon groups. Examples of alkyl groups include, but are not limited to, methyl, ethyl, n-propyl, iso-propyl, n-butyl, t-butyl, i-butyl, sec-butyl, pentyl, and hexyl groups. In one example, the alkyl group is of one to six carbon atoms (i.e. $C_{1-6}$alkyl).

As used herein, the term "alkoxy" refers to the group —O-alkyl, where "alkyl" is as described above. Examples of alkoxy groups include, but are not limited to, methoxy, ethoxy, propoxy, and butoxy groups. In one example, the alkoxy group is of one to six carbon atoms (i.e. —O—$C_{1-6}$alkyl).

As used herein, the term "alkenyl" refers to both straight and branched chain unsaturated hydrocarbon groups with at least one carbon-carbon double bond. Examples of alkenyl groups include, but are not limited to, ethenyl, propenyl, butenyl, pentenyl, and hexenyl groups. In one example, the alkenyl group is of two to six carbon atoms (i.e. $C_{2-6}$alkenyl). The term "2-alkenyl" refers to an alkene substituent that has a double bond at the 2 position from its attachment point. It includes allyl, crotyl, prenyl, geranyl, and farnesyl groups As used herein, the term "alkynyl" refers to both straight and branched chain unsaturated hydrocarbon groups with at least one carbon-carbon triple bond. Examples of alkynyl groups include, but are not limited to, ethynyl, propynyl, butynyl, pentynyl, and hexynyl groups. In one example, the alkynyl group is of two to six carbon atoms (i.e. $C_{2-6}$alkynyl).

As used herein, the term "haloalkyl" refers to an alkyl group having at least one halogen substituent, where "alkyl" and "halogen" are as described above. Similarly, the term "dihaloalkyl" means an alkyl group having two halogen substituents, and the term "trihaloalkyl" means an alkyl group having three halogen substituents. Examples of haloalkyl groups include fluoromethyl, chloromethyl, bromomethyl, iodomethyl, fluoropropyl, and fluorobutyl groups. Examples of dihaloalkyl groups include difluoromethyl and difluoroethyl groups. Examples of trihaloalkyl groups include trifluoromethyl and trifluoroethyl groups. In one example, the haloalkyl group is of one to six carbon atoms (i.e. $C_{1-6}$haloalkyl).

As used herein, the term "heterocyclyl" refers to an aromatic or non-aromatic cyclic group which is analogous to a carbocyclic group, but in which from one to three of the carbon atoms is/are replaced by one or more heteroatoms independently selected from nitrogen, oxygen, or sulfur. A heterocyclyl group may, for example, be monocyclic or polycyclic (e.g. bicyclic). A heteroatom may be N, O, or S.

While it is possible that, for use in therapy a therapeutically effective amount of the compounds as defined herein, or a pharmaceutically acceptable salt or solvate thereof, may be administered as the raw chemical; in one aspect of the present invention the active ingredient is presented as a pharmaceutical composition. Thus, in a further embodiment the invention provides a pharmaceutical composition comprising a compound of formula (I) as disclosed herein, or a pharmaceutically acceptable salt or solvate thereof, in admixture with one or more pharmaceutically acceptable carriers, diluents, or excipients. The carrier(s), diluent(s) or excipient(s) must be acceptable in the sense of being compatible with the other ingredients of the formulation and not deleterious to the recipient thereof.

When applicable, the compounds of the present invention, including the compounds of formula (I) may be in the form of and/or may be administered as a pharmaceutically acceptable salt.

As used herein the term "pharmaceutically acceptable salt" refers to salts which are toxicologically safe for systemic administration. The pharmaceutically acceptable salts may be selected from alkali or alkaline earth metal salts, including, sodium, lithium, potassium, calcium, magnesium and the like, as well as non-toxic ammonium, quaternary ammonium, and amine cations, including, but not limited to ammonium, tetramethylammonium, tetraethylammonium, methylamine, dimethylamine, trimethylamine, triethylamine, ethylamine, triethanolamine and the like.

As used herein the term "pharmaceutically acceptable excipient" refers to a solid or liquid filler, diluent or encapsulating substance that may be safely used in systemic administration. Depending upon the particular route of administration, a variety of carriers, well known in the art may be used. These carriers or excipients may be selected from a group including sugars, starches, cellulose and its derivatives, malt, gelatine, talc, calcium sulfate, vegetable oils, synthetic oils, polyols, alginic acid, phosphate buffered solutions, emulsifiers, isotonic saline, and pyrogen-free water.

As used herein, the term "solvate" refers to a complex of variable stoichiometry formed by a solute (in this invention, a compound of formula (I) or (Ia) or a salt or physiologically functional derivative thereof) and a solvent. Such solvents for the purpose of the invention may not interfere with the biological activity of the solute. Examples of suitable solvents include, but are not limited to, water, methanol, ethanol and acetic acid. In particular the solvent used is a pharmaceutically acceptable solvent. Examples of suitable pharmaceutically acceptable solvents include, without limitation, water, ethanol, acetic acid, glycerol, liquid polyethylene glycols and mixtures thereof. A particular solvent is water.

Administration of compounds of the formula (I) may be in the form of a "prodrug". A prodrug is an inactive form of a compound which is transformed in vivo to the active form. Suitable prodrugs include esters, phosphonate esters etc, of the active form of the compound.

It should be understood that in addition to the ingredients particularly mentioned above, the formulations may include other agents conventional in the art having regard to the type of formulation in question.

The compounds of the present disclosure may be suitable for the treatment of diseases in a human or animal patient. In one embodiment, the patient is a mammal including a human, horse, dog, cat, sheep, cow, or primate. In one embodiment the patient is a human. In a further embodiment, the patient is not a human.

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein the term "treatment" refers to defending against or inhibiting a symptom, treating a symptom, delaying the appearance of a symptom, reducing the severity of the development of a symptom, and/or reducing the number or type of symptoms suffered by an individual, as compared to not administering a pharmaceutical composition comprising a compound of the invention. The term treatment encompasses the use in a palliative setting Those skilled in the art will appreciate that in the preparation of the compounds of the invention it may be necessary and/or desirable to protect one or more sensitive groups in the molecule to prevent undesirable side reactions. Suitable protecting groups for use according to the present invention are well known to those skilled in the art and may be used in a conventional manner. See, for example, "Protective groups in organic synthesis" by T. W. Greene and P. G. M. Wuts (John Wiley & sons 1991) or "Protecting Groups" by P J. Kocienski (Georg Thieme Verlag 1994). Examples of suitable amino protecting groups include acyl type protecting groups (e.g. formyl, trifluoroacetyl, acetyl), aromatic urethane type protecting groups (e.g. benzyloxycarbonyl (Cbz) and substituted Cbz), aliphatic urethane protecting groups (e.g. 9-fluorenylmethoxycarbonyl (Fmoc), t-butyloxycarbonyl (Boc), isopropyloxycarbonyl, cyclohexyloxycarbonyl) and alkyl type protecting groups (e.g. benzyl, trityl, chlorotrityl).

According to the fourth aspect of the disclosure, the compounds according to formula (I) are suitable for use in the treatment of cancer. The cancers to be treated include leukemia, non-small cell lung cancer, colon cancer, CNS cancer, melanoma, ovarian cancer, renal cancer, prostate cancer or breast cancer. Most preferably, the cancer to be treated is leukemia or melanoma.

The antitumor effect of the compounds of the present invention may be applied as a sole therapy or may involve, in addition, one or more other substances and/or treatments. Such conjoint treatment may be achieved by way of the simultaneous, sequential or separate administration of the individual components of the treatment. In the field of medical oncology it is normal practice to use a combination of different forms of treatment to treat each patient with cancer such as a combination of surgery, radiotherapy and/or chemotherapy. In particular, it is known that irradiation or treatment with antiangiogenic and/or vascular permeability reducing agents can enhance the amount of hypoxic tissue within a tumour. Therefore the effectiveness of the compounds of the present invention may be improved by conjoint treatment with radiotherapy and/or with an antiangiogenic agent.

The individual components of such combinations can be administered separately at different times during the course of therapy or concurrently in divided or single combination forms. The present invention is therefore to be understood as embracing all such regimes of simultaneous or alternating treatment and the term “administering” is to be interpreted accordingly. It will be understood that the scope of combinations of the compounds of this invention with other anti-neoplastic agents includes in principle any combination with any pharmaceutical composition useful for treating cancer.

When combined m the same formulation it will be appreciated that the two compounds must be stable and compatible with each other and the other components of the formulation and may be formulated for administration. When formulated separately they may be provided in any convenient formulation, conveniently in such a manner as are known for such compounds in the art.

Pharmaceutical compositions of the invention may be formulated for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Therefore, the pharmaceutical compositions of the invention may be formulated, for example, as tablets, capsules, powders, granules, lozenges, creams or liquid preparations, such as oral or sterile parenteral solutions or suspensions. Such pharmaceutical formulations may be prepared by any method known in the art of pharmacy, for example by bringing into association the active ingredient with the carrier(s) or excipient(s). Such pharmaceutical formulations may be prepared as enterically coated granules, tablets or capsules suitable for oral administration and delayed release formulations.

When a compound is used in combination with a second therapeutic agent active against the same disease, the dose of each compound may differ from that when the compound is used alone. Appropriate doses will be readily appreciated by those skilled in the art.

MODES FOR CARRYING OUT THE INVENTION

In order to better understand the nature of the invention a number of examples will now be described as follows:

Preparation of Module A

Module A is represented by formula (II) of the present disclosure as herein described.

In one embodiment, Module A is represented by A7 and A8 and is prepared according to the following process.

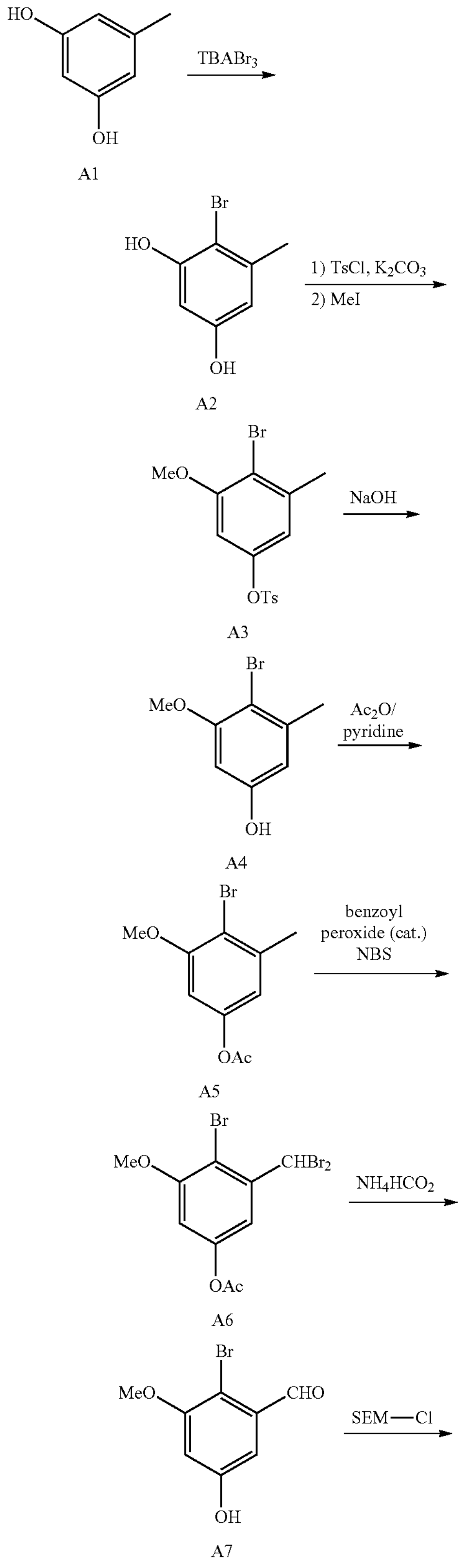

-continued

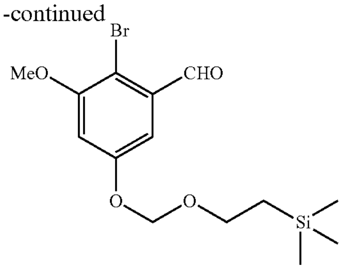

A8

4-Bromo-5-methylbenzene-1,3-diol (A2)

Tetrabutylammonium tribromide (120 g, 248 mmol, 1.0 equiv) in a 3 to 2 mixture of dichloromethane and methanol (300 mL) was added dropwise to a solution of compound A1 (30 g, 242 mmol, 1.0 equiv) in 3 to 2 mixture of dichloromethane and methanol (200 mL) at 15° C. over 3 hours. The resulting mixture was slowly warmed up to room temperature and stirred for 16 hours. The solvents were removed under reduced pressure. Water (200 mL) was added to the residue. The mixture was extracted with ethyl acetate (2×250 mL) and methyl tert-butyl ether (500 mL). The combined organic layers was washed with 2.5% sodium bicarbonate (3×500 mL), dried over sodium sulfate, filtered and concentrated under reduced pressure. The residue was purified over silica gel (2.5 kg), eluting with a gradit of 0 to 50% ethyl acetate in heptanes to give compound A2 (36.83 g, 75% yield) as an off-white solid. (LM-1-96).

Additional compound A1 (270 g, 2175 mmol, 1.0 equiv) was processed in the same manner. The reaction mixture was concentrated under reduced pressure. The residue was dissolved in dichloromethane (3 L) and purified over silica gel (6 kg), eluting with a gradient of 0 to 100% ethyl acetate in heptanes to give partially purified compound A2 (407 g, ~70% purity). This crude product was recrystallized twice in 1 to 3 mixture of in methanol and water (1.2 L). The solid was filtered, rinsed with water (500 mL) and dried under high-vacuum at 45° C. for 16 hours to give compound A2 (163.78 g 37% yield) as an off-white solid. (LM-1-100).

4-Bromo-3-methoxy-5-methylphenyl 4-methylbenzenesulfonate (A3)

Potassium carbonate (886 g, 6402 mmol, 6.5 equiv) was added to a solution of compound A2 (200 g, 985 mmol, 1.0 equiv) in acetone (15 L). After stirring for 30 minutes, p-toluenesulfonyl chloride (187.8 g, 985 mmol, 1.0 equiv) was added and the resulting mixture was refluxed for 16 hours. Methyl iodide (166 mL, 2660 mmol, 2.7 equiv) was added to the reaction and refluxing was continued for an additional 24 hours. The reaction mixture was cooled to room temperature, filtered and the solids were rinsed with acetone (4 L). The filtrate was concentrated under reduced pressure. The residue was dissolved in dichloromethane (2 L) and passed through silica gel (6 kg), eluting with a gradient of 0 to 15% ethyl acetate in heptanes (16 L) to give compound A3 (350 g, ~60% purity), which was used subsequently. (LM-6-1).

4-Bromo-3-methoxy-5-methylphenol (A4)

6M Sodium hydroxide (108 mL, 8.0 equiv) was added to a solution of crude compound A3 (30 g, 1.0 equiv) in 1 to 1 mixture of tetrahydrofuran and methanol (400 mL). After refluxing for 16 hours. LCMS indicated the reaction was complete. Another batch of crude compound A3 (300 g) was processed in the same manner and both batches were combined for work-up. After the mixture was cooled to room temperature, acetonitrile (4 L) was added and the mixture was washed with heptanes (2×4 L). The heptane layers were discarded. The tetrahydrofuran/methanol/acetonitrile/water mixture was acidify with 1N hydrochloride acid (~6.2 L) to pH=7, saturated with sodium chloride (3 kg) and extracted with ethyl acetate (2×4 L). The combined organic layers was concentrated under reduced pressure. The residue was diluted in water (500 mL) and extracted with ethyl acetate (3×1 L). The combined organic layers were dried over sodium sulfate, filtered and concentrated under reduced pressure. The residue was diluted with acetonitrile (1 L) and heptanes (500 mL), and the layers were separated. The heptanes layer was discarded. The acetonitrile layer was passed through a pad of silica gel (300 g), which was, eluted with ethyl acetate (2 L). The filtrate was concentrated under reduced, pressure. The resulting solid was triturated with 10% ethyl acetate in heptanes. (1.1 L) to give compound A4 (96.6 g, 45% yield over 2 steps) as an off-white solid. (LM-6-12, LM-6-14)

4-Bromo-3-methoxy-5-methylphenyl acetate (A5)

Acetic anhydride (63.1 mL, 668 mmol, 1.5 equiv) was added to a solution of compound A4 (96.6 g, 445 mmol, 1.0 equiv) in a mixture of pyridine (377 ml) and dichloromethane (1000 mL) at room temperature. The resulting mixture was stirred for 16 hours. Ice water (500 mL) was added to quench the reaction. The organic layer was washed with ice cold 1N HCl (3×500 mL), saturated sodium bicarbonate (500 mL), saturated brine (500 mL), dried over sodium sulfate, filtered and concentrated under reduced pressure. The residue was further dried under high-vacuum at 45° C. for 16 hours to give compound A5 (114.53 g, 99% yield) as an off-white solid, which was used subsequently. (LM-6-15).

4-Bromo-3-(dibromomethyl)-5-methoxyphenyl acetate (A6)

N-Bromosuccinimide (82.6 g, 464 mmol, 2.1 equiv) and benzoyl peroxide (5.35 g, 22.1 mmol, 0.1 equiv) were sequentially added to a solution of compound A5 (57.27 g, 221 mmol, 1.0 equiv) in carbon tetrachloride (1 L). The resulting mixture was refluxed for 24 hours, at which time LCMS analysis indicated the reaction was complete. Another batch of compound A5 (57.27 g) was processed in the same manner and both batches were combined for work-up. After the mixture was cooled to room temperature, sodium bisulfite (250 g) was added and the reaction mixture was stirred for 24 hours at room temperature (test on wet starch paper showed no peroxide). The resulting mixture was filtered through Celite (200 g), which was rinsed with dichloromethane (2 L). The filtrate was concentrated under reduced pressure to give crude compound A6 as a yellow solid, which was used subsequently. (LM-6-17)

2-Bromo-5-hydroxy-3-methoxybenzaldehyde (A7)

Ammonium formate (153 g, 2431 mmol, 5.5 equiv) and a 1 to 1 mixture of ethanol and water (600 mL) was added to a solution of compound A6 (~442 mmol, 1.0 equiv) in ethanol (800 mL) at 50° C. The resulting mixture was refluxed for 70 hours. LCMS analysis indicated the reaction was complete. The reaction mixture was cooled to room temperature and concentrated hydrochloric acid (15 mL) was added. Solvents were removed under reduced pressure. The residue was diluted in water (500 mL), extracted with ethyl acetate (2×1 L) and methyl tert-butyl ether (2×1 L). The aqueous layer was filtered through a pad of Celite (50 g), which was rinsed with ethyl acetate (2 L). The organic layer was separated. All organic layers were combined, dried over sodium sulfate, filtered and concentrated under reduced pressure. The residue was passed through a pad of silica gel (300 g), which was eluted with tetrahydrofuran (3 L) and ethyl acetate (4 L). The filtrate was concentrated under reduced pressure to give crude compound A7 (141 g) as a black oil, which was used subsequently. (LM-6-18)

2-Bromo-3-methoxy-5-((2-(trimethylsilyl)ethoxy) methoxy)benzaldehyde (A8 Representative of Module A)

Diisopropylethylamine (16.5 mL, 94.7 mmol, 1.5 equiv) and 2-(trimethylsilyl)ethoxymethyl chloride (13.4 mL, 75.6 mmol, 1.2 equiv) were added sequentially to a solution of crude compound A7 (20 g, ~63 mmol, 1.0 equiv) in 1 to 1 mixture of anhydrous tetrahydrofuran and dichloromethane (200 mL) at room temperature. After stirring at room temperature for 16 hours, LCMS analysis indicated ~65% conversion of the reaction. Additional diisopropylethylamine (16.5 mL, 94.7 mmol, 1.5 equiv) and 2-(trimethylsilyl) ethoxymethyl chloride (13.4 mL, 75.6 mmol, 1.2 equiv) were added and the mixture was stirred for additional 24 hours. Saturated sodium bicarbonate (250 mL) was added to quench the reaction and the organic solvent was removed under reduced pressure. The remaining aqueous layer was extracted with methyl tert-butyl ether (500 mL). The organic layer was dried over sodium sulfate, filtered and concentrated under reduced pressure. The residue was purified on an Interchim automated system (330 g column), eluting with a gradient of 0 to 20% ethyl acetate in heptanes to give A8 (representative of Module A) (8.44 g) as a white solid. (LM-6-20) Additional crude compound 7 (120 g) was processed in the same manner. Saturated sodium bicarbonate (250 mL) was added to quench the reaction and the solvent was removed under reduced pressure. The remaining aqueous layer was diluted with water (250 mL), saturated brine (250 mL) and was extracted with methyl tert-butyl ether (2×1 L). The combined organic layers was dried over sodium sulfate, filtered and concentrated under reduced pressure. The residue was filtered through a pad of silica gel (1 kg), which was eluted with 20% ethyl acetate in heptanes. The filtrate was concentrated under reduced pressure. The residue was equally divided in to 6 portions. Each portion was purified on an Interchim automated system (330 g column), eluting with a gradient of 0 to 20% ethyl acetate in heptanes. All isolated compound Intermediate A was further purified by trituration with 5% dichloromethane in hexanes (300 mL) to give A8 (representative of Module A) (26.73 g, 99% purity and 42.72 g, ~90% purity) as a white solid after drying under vacuum at 45° C. for 16 hours. The combined yield was 43% over 3 steps. (LM-6-21)

White Solid, Melting Point 58.3-59.1° C.; HPLC Analysis: 99.6% purity; Wavelength 254 nm, bandwidth 4; Column: SorbTech C18AQ, 2.1×50 mm, 3 μm; Retention Time: 10.80 min; Mobile Phase: ACN/formic acid/water; Mass Spectrum (positive mode) m/z=378.0 $(M+H_2O)^+$; $C_{14}H_{21}BrO_4Si$; $^1H$ NMR (400 MHz, $CDCl_3$) δ=10.40 (s, 1H), 7.20 (d, J=2.8 Hz, 1H), 6.84 (d, J=2.7 Hz, 1H), 5.25 (s, 2H), 3.92 (s, 3H), 3.78-3.73 (m, 2H), 0.97-0.93 (m, 2H), 0.00 (s, 9H); $^{13}C$ NMR (100 MHz, $CDCl_3$) δ=191.82, 157.76, 157.12, 134.85, 109.31, 107.49, 106.62, 93.06, 66.72, 56.65, 18.02, −1.43.

In another embodiment, Module A is represented by A9 which is prepared according to the following process:

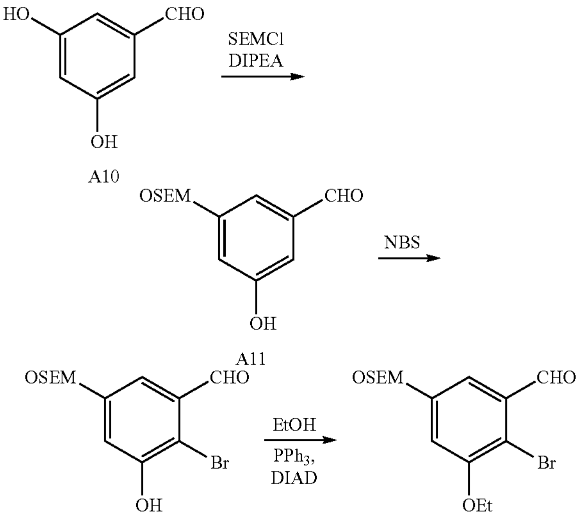

A10

A11

A12

A9 (Module A)

3-Hydroxy-5-((2-(trimethylsilyl)ethoxy)methoxy) benzaldehyde (A11)

N,N-Diisopropylethylamine (122 mL, 700 mmol, 1.4 equiv) was added to a solution of compound A10 (69.06 g, 500 mmol, 1.0 equiv) in anhydrous dimethylformamide (400 mL) at room temperature. 2-(Trimethylsilyl)ethoxymethyl chloride (106.2 mL, 600 mmol, 1.2 equiv) was added dropwise over 30 minutes. The resulting mixture was stirred at room temperature for 70 hours. Water (1.5 L) was added and the mixture was extracted with methyl tert-butyl ether (2×2.5 L). The combined organic layers was dried over sodium sulfate, filtered and concentrated under reduced pressure. The residue was divided into 3 equal 3 portions. Each portion was purified on an Interchim automated system (330 g column), eluting with a gradient of 0 to 50% ethyl acetate in heptanes to give compound A11 (49.64 g, 26% yield, 71% purity by QNMR) as a yellow oil. (LM-6-84)

2-Bromo-3-hydroxy-5-((2-(trimethylsilyl)ethoxy) methoxy)benzaldehyde (A12)

Compound A11 (49.64 g, 71% purity by QNMR, 131.3 mmol, 1.0 equiv) was put under high vacuum (0.5 Torr) at 50° C. for 2 hours to remove residual 2-(trimethylsilyl) ethanol. After cooling to room temperature, anhydrous dichloromethane (700 mL) was added and the mixture was cooled to −17° C. N-Bromosuccinimide (25.12 g, 141.1 mmol, 1.07 equiv) in anhydrous dichloromethane (1 L) was added dropwise over 1 hour while keeping the temperature between −15° C. and −20° C. After the addition, NMR analysis indicated the reaction was not complete (16% compound A11 remained). Additional N-bromosuccinimide (4.62 g, 26 mmol, 0.2 equiv) in anhydrous dichloromethane (200 mL) was added dropwise over 10 minutes. The resulting mixture was stirred at −17° C. for another 30 minutes.

Water (800 mL) was added and the mixture was warmed up to room temperature. The organic layer was washed with saturated brine (1 L), dried over sodium sulfate, filtered and concentrated under reduced pressure. The residue was divided into 5 equal portions. Each portion was purified on an Interchim automated system (2×120 g column stack), eluting with a gradient of 0 to 12% ethyl acetate in heptanes to give compound A12 (35.84 g, 79% yield) as a yellow oil. (LM-6-87)

2-Bromo-3-ethoxy-5-((2-(trimethylsilyl)ethoxy) methoxy)benzaldehyde (A9, Module A)

Triphenylphosphine (40.6 g, 154.8 mmol, 1.5 equiv) and ethanol (9 mL, 154.8 mmol, 1.5 equiv) were added to a solution of compound A12 (35.84 g, 103.2 mmol, 1.0 equiv) in anhydrous tetrahydrofuran (1 L). After cooling to 0° C. for 10 minutes, diisopropyl azodicarboxylate (31 mL, 154.8 mmol, 1.5 equiv) was added dropwise over 15 minutes. The resulting mixture was slowly warmed up to room temperature and stirred for 16 hours. The solvent was removed under reduced pressure. The residue was divided into 5 equal portions. Each portion was purified on an Interchim automated system (2×120 g column stack), eluting with 5% ethyl acetate in heptanes to give A9 (17.5 g, 45% yield) as a yellow solid. (LM-6-88)

Preparation of Module B

Module B is represented by formula (III) of the present disclosure as herein described.

In one embodiment, Module B is represented by B4 which is prepared according to the below process:

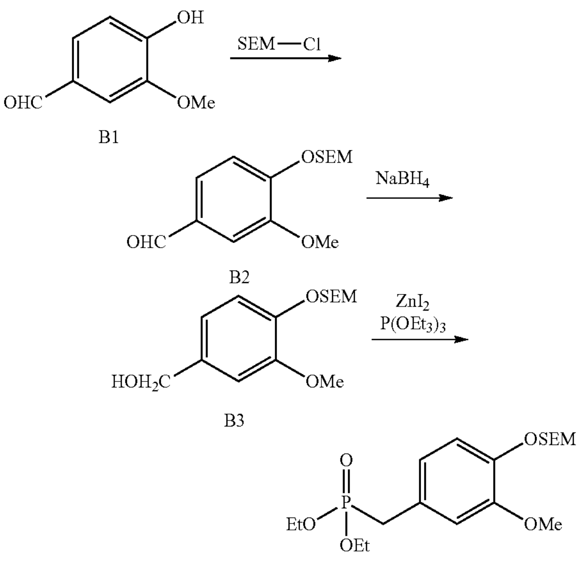

B1

B2

B3

B4

3-Methoxy-4-((2-(trimethylsilyl)ethoxy)methoxy) benzaldehyde (B2)

N,N-Diisopropylethylamine (1224 g, 9.47 mol, 1.2 equiv) and 2-(trimethylsilyl)-ethoxymethyl chloride (1315 g, 7.89 mol, 1.0 equiv) were sequentially added to a solution of compound B1 (1200 g, 7.84 mol, 1.0 equiv) in anhydrous dichloromethane (12 L). After stirring at room temperature overnight, the mixture was poured into a separatory funnel containing saturated sodium bicarbonate (20 L). The layers were separated and the aqueous layer was extracted with dichloromethane (2×5 L). The combined organic layers were concentrated under reduced pressure. The residue was combined with 2 other reactions of equal scale and purified over silica gel (2 kg), eluting with a gradient of 0 to 50% MTBE in heptanes to give compound B2 (2200 g, 99% yield) as a pale-yellow oil. (EK-22-137)

(3-Methoxy-4-((2-(trimethylsilyl)ethoxy)methoxy) phenyl)methanol (B3)

Sodium borohydride (250 g, 6.61 mol) was added portion-wise over 20 minutes while keeping the temp below 20° C. to a solution of compound B2 (2000 g, 7.10 mol) in methanol (8 L). After stirring overnight, water (1 L) was added slowly over 20 minutes. The mixture was combined with a reaction of equal scale and concentrated under reduced pressure to remove most of the methanol. The slurry was poured into a separatory funnel and diluted with MTBE (8 L). The layers were separated and the aqueous layer was back extracted with MTBE (2×4 L). The combined organic layers were washed with saturated brine (4 L), dried over sodium sulfate (200 g) and concentrated under reduced pressure to give compound B3 (1970 g, 98% yield) as a yellow oil which was used subsequently. (EK-22-153)

Diethyl (3-methoxy-4-((2-(trimethylsilyl)ethoxy) methoxy)benzyl) phosphonate (B4, Module B)

A 22 L flask was charged with THF (7 L) and zinc(II) iodide (2.24 kg, 2.03 mol, 2 equiv), the addition exothermed to 40° C. Triethyl phosphite (1.17 kg, 7.03 mol, 2 equiv) and compound B3 (1000 g, 3.52 mol, 1 equiv) in THF (1 L) were sequentially added. After heating at 65° C. for 16 hours, the reaction was cooled to room temperature and diluted with water (5 L). Potassium carbonate (1.2 kg, 8.68 mol, 2.47 equiv) was added in portions over 5 minutes adjusting the pH to 9. There was no foaming observed during the addition. The salts were filtered and the filter cake was washed with MTBE (2×4 L). The combined filtrates were washed with saturated brine (4 L), dried over sodium sulfate (500 g) and concentrated under reduced pressure. The resulting oil was purified over silica gel (2.0 kg), eluting with a gradient of 25 to 100% ethyl acetate in heptanes to give B4 (1035 g, 72% yield) as a yellow oil. (EK-22-154) $C_{18}H_{33}PSiO_6$ $^1H$ NMR (400 MHz, $CDCl_3$) δ=7.11 (d, J=8.2 Hz, 1H), 6.89 (m, 1H), 6.80 (dm, J=8.2 Hz, 1H), 5.26 (s, 2H), 4.08-3.98 (m, 4H), 3.88 (s, 3H), 3.82 (m, 2H), 3.10 (d, J=21.1 Hz, 2H), 1.26 (t, J=7.1 Hz, 6H), 0.98-0.93 (m, 2H), 0.00 (s, 9H).

Preparation of Module C

Module C is represented by formula (IV) of the present disclosure as herein described.

In one embodiment, Module C is represented by $C_1$ which is prepared according to the below process:

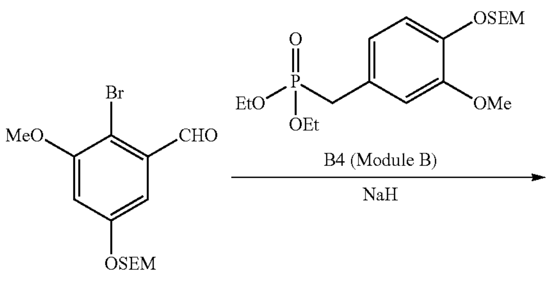

A8 (Module A)

-continued

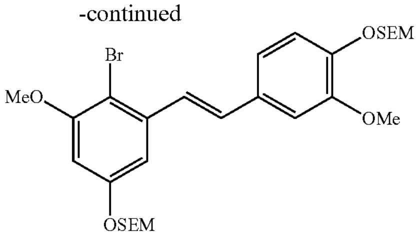

C1 (Module C)

(E)-(2-((4-(2-bromo-3-methoxy-5-((2-(trimethylsilyl)ethoxy) methoxy)styryl)-2-methoxyphenoxy)methoxy)ethyl)trimethylsilane (C1)

A 60% dispersion of sodium hydride in mineral oil (1.07 g, 26.7 mmol, 2 equiv) was added in one portion to a solution of B4 (5.4 g, 13.4 mmol, 1.0 equiv) in anhydrous tetrahydrofuran (120 mL) at 0° C. The mixture was warmed to room temperature and stirred 30 minutes. A solution of A8 (4.82 g, 13.4 mmol, 1 equiv) in anhydrous tetrahydrofuran (30 mL) was then added dropwise and the mixture was stirred at room temperature for 16 hours at which time LCMS analysis indicated that ~30% conversion to Module C. Additional 60% dispersion of sodium hydride in mineral oil (1.07 g, 26.7 mmol, 2 equiv) was added, resulting in ~50% conversion after 8 hours by LCMS analysis. Additional 60% dispersion of sodium hydride in mineral oil (2.14 g, 53.4 mmol, 4 equiv) was added, resulting in complete conversion after 16 hours by LCMS analysis. The reaction was carefully quenched with saturated brine (100 mL, 1 drop per minute for the first 5 mL brine) at 0° C. The mixture was extracted with ethyl acetate (2×500 mL). The combined organic layers were dried over sodium sulfate, filtered, and concentrated under reduced pressure. The residue was purified on an Interchim automated chromatography system (220 column), eluting with a gradient of 0 to 20% ethyl acetate in heptanes to give $C_1$ (5.2 g, 64% yield) as a yellow oil. (LM-6-27) $C_{28}H_{43}BrSiO_6$ $^1H$ NMR (400 MHz, $CDCl_3$) δ=7.39 (d, J=16.1 Hz, 1H), 7.17 (d, J=8.3 Hz, 1H), 7.09 (d, J=1.7 Hz, 1H), 7.07 (dd, J=2.0, 8.6 Hz, 1H), 6.99 (d, J=2.4 Hz, 1H), 6.96 (d, J=16.2 Hz, 1H), 6.56 (d, J=2.7 Hz, 1H), 5.29 (s, 2H), 5.25 (s, 2H), 3.94 (s, 3H), 3.88 (s, 3H), 3.83-3.77 (m, 4H), 1.00-0.94 (m, 4H), 0.02 (s, 9H), 0.00 (s, 9H). In another embodiment, Module C is represented by C2 which is prepared according to the below process:

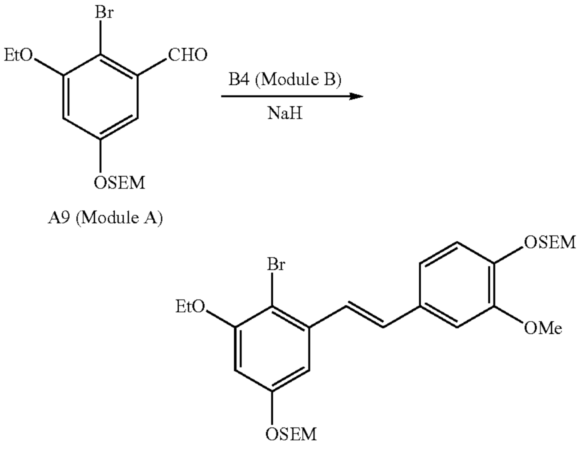

A9 (Module A)

C2 (Module C)

(E)-(2-((4-(2-Bromo-3-ethoxy-5-((2-(trimethylsilyl) ethoxy)methoxy)styryl)-2-methoxyphenoxy) methoxy)ethyl)trimethylsilane (C2)

A 60% dispersion of sodium hydride in mineral oil (750 Mg, 18.8 mmol, 2 equiv) was added in one portion to a solution of compound B4 (3.8 g, 9.4 mmol, 1.0 equiv) in anhydrous tetrahydrofuran (150 mL) at 0° C. The mixture was warmed up to room temperature and stirred 30 minutes. A solution of D4 (3.52 g, 9.4 mmol, 1 equiv) in anhydrous tetrahydrofuran (50 mL) was then added dropwise and the mixture was stirred at room temperature for 16 hours. The reaction was carefully quenched with saturated brine (150 mL, 1 drop per minute for the first 5 mL) at 0° C. The mixture was extracted with methyl tert-butyl ether (2×150 mL). The combined organic layers was dried over sodium sulfate, filtered, and concentrated under reduced pressure. The residue was purified on an Interchim automated chromatography system (120 column), eluting with a gradient of 0 to 15% ethyl acetate in heptanes to give $C_2$ (1.69 g, 29% yield) as a yellow oil. (LM-6-80).

Preparation of Compound 1 [KYN-001]

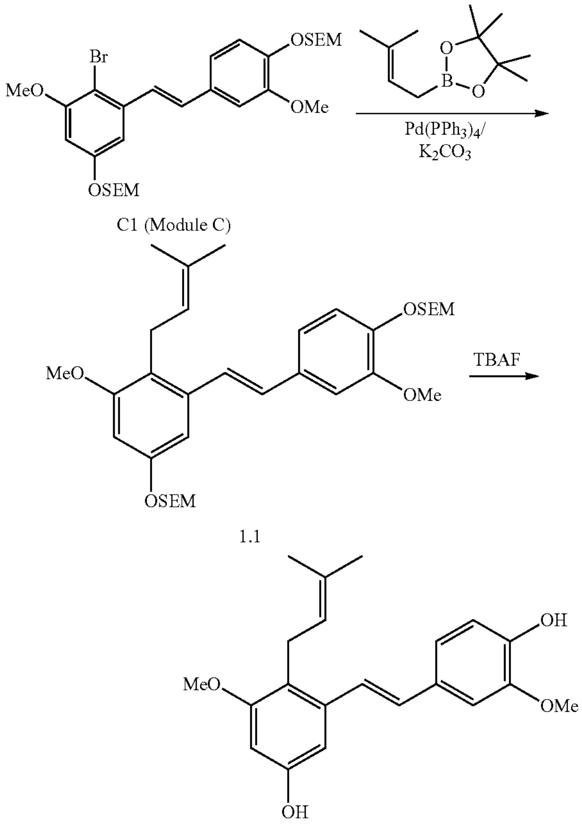

C1 (Module C)

1.1

Compound 1

(E)-(2-((2-methoxy-4-(3-methoxy-2-(3-methylbut-2-en-1-yl)-5-((2-(trimethylsilyl)ethoxy)methoxy) styryl)phenoxy)methoxy)ethyl)trimethylsilane (1-1)

Tetrakis(triphenylphosphine)palladium(0) (29 mg, 0.025 mmol, 0.05 equiv), potassium carbonate (138 mg, 1 mmol, 2 equiv), 3-methylbut-2-enylboronic acid pinacol ester (147 mg, 0.75 mmol, 1.5 equiv) and water (5 mL) were added sequentially to a solution of C1 (306 mg, 0.5 mmol, 1 equiv) in tetrahydrofuran (5 mL). After sparging with nitrogen for 10 minutes, the reaction was heated at 50° C. for 20 hours. After cooling to room temperature, the mixture was extracted with ethyl acetate (15 mL) and the organic layer was concentrated under reduced pressure. The residue was purified on an Interchim automated chromatography system (40 g column), eluting with a gradient of 0 to 20% ethyl acetate in heptanes to give compound 1-1 (190 mg, 63% yield) as a yellow oil. (LM-6-29)

(E)-3-(4-hydroxy-3-methoxystyryl)-5-methoxy-4-(3-methylbut-2-en-1-yl)phenol (1)

1M Tetrabutylammonium fluoride in tetrahydrofuran (4.43 mL, 4.43 mmol, 14 equiv) was added to compound 1-1 (190 mg, 0.32 mmol, 1 equiv) at room temperature. After heating at 67° C. for 16 hours, the mixture was cooled to room temperature and diluted with water (4 mL). The mixture was extracted with ethyl acetate (15 mL) and the organic layer was concentrated under reduced pressure. The residue was purified twice on an Interchim automated chromatography system (2×25 columns), eluting each time with a gradient of 0 to 60% ethyl acetate in heptanes to give compound 1 (60 mg, 56% yield) as an off-white solid after drying under vacuum at 40° C. for 16 hours. (LM-6-30)

White solid, melting point 132.3-134.0° C.; HPLC Analysis: 96.3% purity; Wavelength 254 nm, bandwidth 4; Column: SorbTech C18AQ, 2.1×50 mm, 3 μm; Retention Time: 8.4 min; Mobile Phase: ACN/formic acid/water; Mass Spectrum (positive mode) m/z=341.2 $(M+H)^+$; $C_{21}H_{24}O_4$; $^1H$ NMR (400 MHz, $CDCl_3$) δ=7.15 (d, J=16.0 Hz, 1H), 7.00 (br s, 1H), 6.99 (dd, J=2.0, 8.2 Hz, 1H), 6.90 (d, J=8.2 Hz, 1H), 6.85 (d, J=16.1 Hz, 1H), 6.66 (d, J=2.6 Hz, 1H), 6.36 (d, J=2.4 Hz, 1H), 5.12 (tm, J=6.8 Hz, 1H), 3.94 (s, 3H), 3.80 (s, 3H), 3.41 (br d, J=6.7 Hz, 2H), 1.81 (s, 3H), 1.68 (d, J=1.1 Hz, 3H); $^{13}C$ NMR (100 MHz, $CDCl_3$) δ=158.52, 154.37, 146.65, 145.54, 138.13, 130.59, 130.40, 130.24, 124.24, 123.63, 120.65, 120.55, 114.53, 108.22, 103.85, 98.17, 55.86, 55.69, 25.78, 24.45, 17.97.

Preparation of Compound 2, 3 and 4:

4-((E)-but-2-en-1-yl)-3-((E)-4-hydroxy-3-methoxystyryl)-5-methoxyphenol (2) [KYN-138]

4-((Z)-but-2-en-1-yl)-3-((E)-4-hydroxy-3-methoxystyryl)-5-methoxyphenol (3) [KYN-139]

(E)-4-(but-3-en-2-yl)-3-(4-hydroxy-3-methoxystyryl)-5-methoxyphenol (4) [KYN-140]

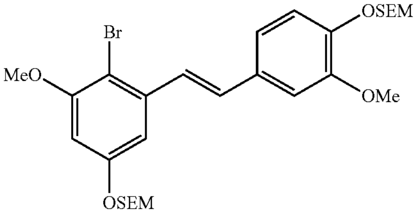

C1 (Module C)

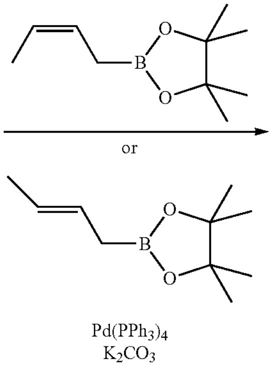

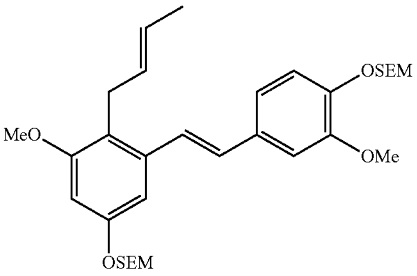

2-1

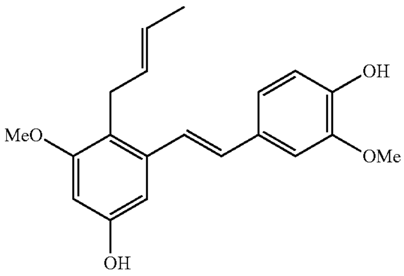

2

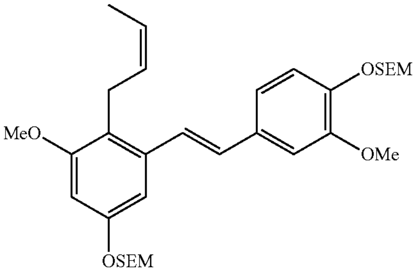

3-1

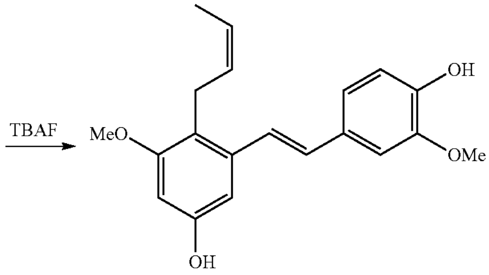

3

-continued

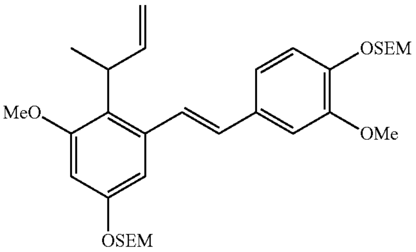

4-1

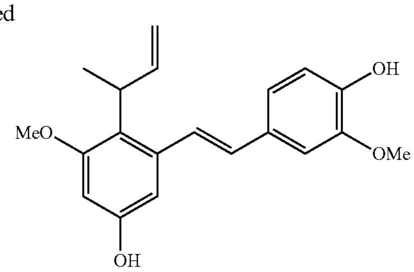

4

(2-((4-((E)-2-((E)-but-2-en-1-yl)-3-methoxy-5-((2-(trimethylsilyl)ethoxy) methoxy)styryl)-2-methoxy-phenoxy)methoxy)ethyl)trimethylsilane (2-1)

(2-((4-((E)-2-((Z)-but-2-en-1-yl)-3-methoxy-5-((2-(trimethylsilyl)ethoxy) methoxy)styryl)-2-methoxy-phenoxy)methoxy)ethyl)trimethylsilane (3-1)

(E)-(2-((4-(2-(but-3-en-2-yl)-3-methoxy-5-((2-(trimethylsilyl)ethoxy) methoxy)styryl)-2-methoxyphenoxy)methoxy)ethyl)trimethylsilane (4-1)

Tetrakis(triphenylphosphine)palladium(0) (116 mg, 0.1 mmol, 0.05 equiv), potassium carbonate (553 mg, 4 mmol, 2 equiv), trans-crotylboronic acid pinacol ester (728 mg, 4 mmol, 2 equiv) and water (10 mL) were added sequentially to a solution of $C_1$ (1.22 g, 2 mmol, 1 equiv) in tetrahydrofuran (10 mL). After sparging with nitrogen for 10 minutes, the reaction was heated at 77° C. for 20 hours. Another batch of $C_1$ (1.22 g) with cis-crotylboronic acid pinacol ester (2 equiv) was processed in the same manner and both batches were combined for work-up. After cooling to room temperature, the mixture was extracted with ethyl acetate (2×50 mL) and the organic layer was concentrated under reduced pressure. The residue was purified on an Interchim automated chromatography system (80 column), eluting with a gradient of 0 to 15% ethyl acetate in heptanes to give a mixture of compound 2-1, 3-1 and 4-1 (2.2 g, 94% yield) as a yellow oil. (LM-6-42, LM-6-43)

4-((E)-but-2-en-1-yl)-3-((E)-4-hydroxy-3-methoxystyryl)-5-methoxyphenol (2)/4-((Z)-but-2-en-1-yl)-3-((E)-4-hydroxy-3-methoxystyryl)-5-methoxyphenol 3)/(E)-4-(but-3-en-2-yl)-3-(4-hydroxy-3-methoxystyryl)-5-methoxyphenol (4)

1M Tetrabutylammonium fluoride in tetrahydrofuran (52.5 mL, 52.5 mmol, 14 equiv) was added to a mixture of compounds 2, 3 and 4 (2.2 g, 3.75 mmol, 1 equiv) at room temperature. After heating at 67° C. for 16 hours, the mixture was cooled to room temperature and diluted with water (50 mL). The mixture was extracted with dichloromethane (2×150 mL) and the organic layer was concentrated under reduced pressure. The residue was purified three times on an Interchim automated chromatography system (3×80 columns), eluting each time with a gradient of 0 to 60% ethyl acetate in heptanes to a mixture of compounds 2, 3 and 4 (760 mg) as a yellow oil. This mixture of oil was subjected to supercritical fluid chromatography (Lotus Separations) to give three compounds, which were appeared as black residue oils. These residues were individually re-purified on an InterChim automated chromatography system (25 column), eluting with a gradient of 0 to 60% ethyl acetate in heptanes to give compounds 2 (90 mg, 7% yield), 3 (60 mg, 5% yield) and 4 (290 mg, 24% yield), respectively, as off-white solids after drying under vacuum at 40° C. for 16 hours. (LM-6-44)

The following SFC separation (conditions listed below) yielded 400 mg of peak-1 (4, LM-6-44-P1), 108 mg of peak-2 (2, LM-6-44-P2), and 110 mg of peak-3 (3, LM-6-44-P3). Chromatograms are included in this report.

| Preparative Method: | Analytical Method: |
|---|---|
| SFC-B (2 × 25 cm)<br>40% methanol (no additive)/$CO_2$,<br>100 bar<br>65 mL/min, 220 nm<br>inj vol.: 0.5 mL, 15 mg/mL ethanol | SFC-B(15 × 0.46 cm)<br>40% methanol (no additive)/$CO_2$,<br>100 bar<br>3.5 mL/min, 220, 254 and 280 nm |

Figure 1:
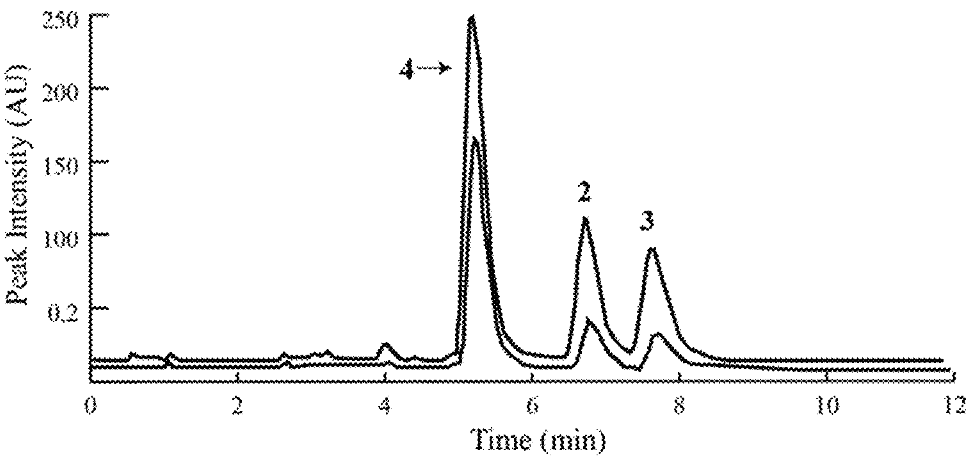
FIG. 1 is a chromatogram of LM-6-44 (mixture of compounds 2, 3 and 4), before separation.

FIG. 1 shows LM-6-44 (mixture of compounds 2, 3 and 4), before separation

Figure 2:
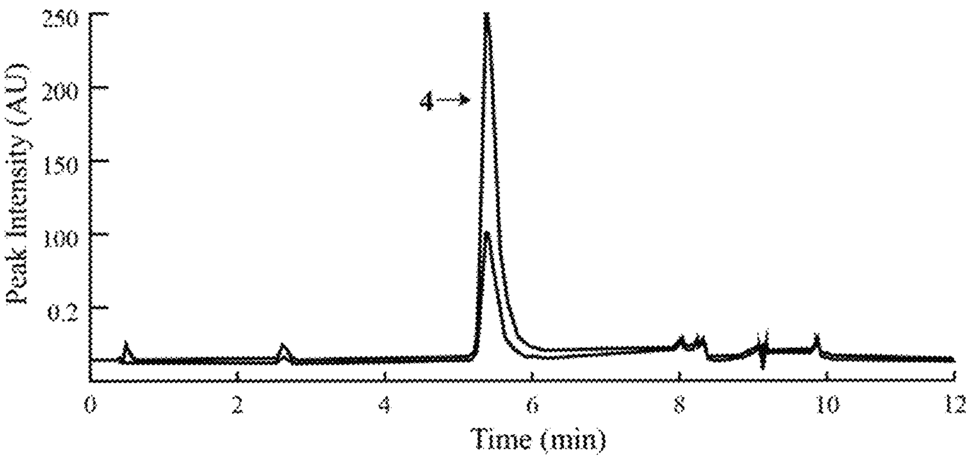
FIG. 2 is a chromatogram of LM-6-44-P1 (compound 4), after separation.

FIG. 2 shoes LM-6-44-P1 (compound 4), after separation.

Figure 3:
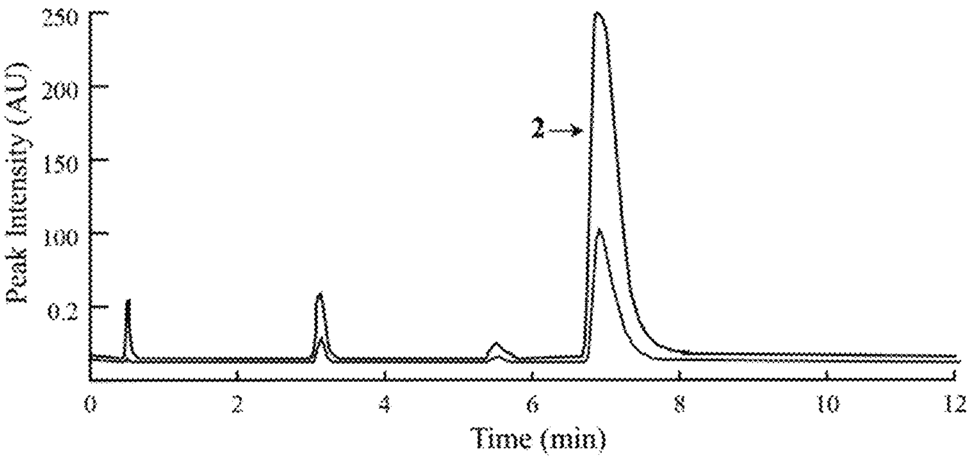
FIG. 3 is a chromatogram of LM-6-44-P2 (compound 2), after separation

FIG. 3 shows LM-6-44-P2 (compound 2), after separation.

Figure 4:
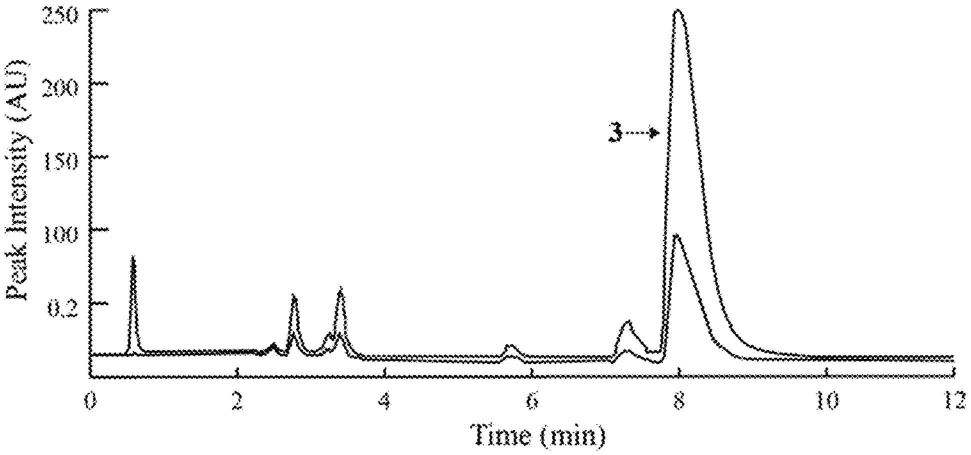
FIG. 4 is a chromatogram of LM-6-44-P3 (compound 3), after separation

FIG. 4 shows LM-6-44-P3 (compound 3), after separation:

Structure Data:

4-((E)-but-2-en-1-yl)-3-((E)-4-hydroxy-3-methoxystyryl)-5-methoxyphenol (Compound 2) [KYN-138]

Off-white solid; HPLC Analysis: 96.3% purity; Wavelength 254 nm, bandwidth 4; Column: SorbTech C18AQ, 2.1×50 mm, 3 μm; Retention Time: 8.1 min; Mobile Phase: ACN/formic acid/water; Mass Spectrum (positive mode) m/z=327.2 $(M+H)^+$; $C_{20}H_{22}O_4$; $^1H$ NMR (400 MHz, $CDCl_3$) δ=7.17 (d, J=16.1 Hz, 1H), 7.03-6.98 (m, 2H), 6.93-6.89 (m, 1H), 6.86 (d, J=16.1 Hz, 1H), 6.67 (d, J=2.3 Hz, 1H), 6.36 (d, J=2.4 Hz, 1H), 5.67 (s, 1H), 5.59-5.49 (m, 1H), 5.47-5.36 (m, 1H), 4.73 (s, 1H), 3.94 (s, 3H), 3.80 (s, 3H), 3.41 (td, J=1.3, 5.9 Hz, 2H), 1.63 (qd, J=1.4, 6.2 Hz, 3H); $^{13}C$ NMR (100 MHz, $CDCl_3$) δ=158.63, 154.50, 146.67, 145.59, 138.42, 130.41, 130.31, 129.67, 124.93, 124.34, 120.35, 119.57, 114.59, 108.56, 103.91, 98.24, 55.89, 55.78, 28.29, 17.91.

4-((Z)-but-2-en-1-yl)-3-((E)-4-hydroxy-3-methoxystyryl)-5-methoxyphenol (Compound 3) [KYN-139]

Off-white solid; HPLC Analysis: 98.8% purity; Wavelength 254 nm, bandwidth 4; Column: SorbTech C18AQ, 2.1×50 mm, 3 μm; Retention Time: 8.2 min; Mobile Phase:

ACN/formic acid/water; Mass Spectrum (positive mode) m/z=327.2 $(M+H)^+$; $C_{20}H_{22}O_4$; $^1H$ NMR (400 MHz, $CDCl_3$) δ=7.15 (d, J=16.0 Hz, 1H), 7.01-6.97 (m, 2H), 6.90 (d, J=7.9 Hz, 1H), 6.85 (d, J=16.0 Hz, 1H), 6.66 (d, J=2.3 Hz, 1H), 6.36 (d, J=2.4 Hz, 1H), 5.68 (s, 1H), 5.53-5.32 (m, 2H), 4.87 (s, 1H), 3.93 (s, 3H), 3.80 (s, 3H), 3.48 (d, J=6.7 Hz, 2H), 1.81 (qd, J=1.2, 6.4 Hz, 3H); $^{13}C$ NMR (100 MHz, $CDCl_3$) δ=158.60, 154.49, 146.68, 145.58, 138.29, 130.56, 130.24, 129.71, 124.20, 122.99, 120.59, 120.16, 114.56, 108.29, 104.00, 98.23, 55.86, 55.69, 23.37, 12.99.

(E)-4-(but-3-en-2-yl)-3-(4-hydroxy-3-methoxystyryl)-5-methoxyphenol (Compound 4) [KYN-140]

Off-white solid; HPLC Analysis: 96.1% purity; Wavelength 254 nm, bandwidth 4; Column: SorbTech C18AQ, 2.1×50 mm, 3 μm; Retention Time: 8.2 min; Mobile Phase: ACN/formic acid/water; Mass Spectrum (positive mode) m/z=327.2 $(M+H)^+$; $C_{20}H_{22}O_4$; $^1H$ NMR (400 MHz, $CDCl_3$) δ=7.32 (d, J=16.0 Hz, 1H), 6.99-6.95 (m, 2H), 6.92-6.89 (m, 1H), 6.74 (d, J=16.0 Hz, 1H), 6.61 (d, J=2.4 Hz, 1H), 6.37 (d, J=2.4 Hz, 1H), 6.22 (ddd, J=4.8, 10.5, 17.4 Hz, 1H), 5.67 (s, 1H), 5.10-5.03 (m, 2H), 4.85 (s, 1H), 4.15 (tdq, J=2.1, 4.6, 7.0 Hz, 1H), 3.94 (s, 3H), 3.78 (s, 3H), 1.39 (d, J=7.1 Hz, 3H); $^{13}C$ NMR (100 MHz, $CDCl_3$) δ=158.72, 154.52, 146.69, 145.51, 143.90, 138.85, 130.37, 130.14, 125.60, 124.11, 120.38, 114.56, 111.76, 108.30, 105.18, 98.73, 55.86, 55.70, 34.49, 18.55.

4-((E)-But-2-en-1-yl)-3-ethoxy-5-((E)-4-hydroxy-3-methoxystyryl)phenol (Compound 5) [KYN-153]

(2-((4-((E)-2-((E)-But-2-en-1-yl)-3-ethoxy-5-((2-(trimethylsilyl)ethoxy)methoxy)styryl)-2-methoxyphenoxy)methoxy)ethyl)trimethylsilane (5-1)

Tetrakis(triphenylphosphine)palladium(0) (156 mg, 0.14 mmol, 0.05 equiv), potassium carbonate (1.12 g, 8.1 mmol, 3 equiv), trans-crotylboronic acid pinacol ester (1.48 g, 8.1 mmol, 3 equiv) and water (10 mL) were added sequentially to a solution of C2 (1.69 g, 2.7 mmol, 1 equiv) in 1,4-dioxane (15 mL). After sparging with nitrogen for 10 minutes, the reaction was heated at 95° C. for 16 hours. After cooling to room temperature, the mixture was extracted with methyl tert-butyl ether (2×20 mL) and the combined organic layers was-concentrated under reduced pressure. The residue was purified on an Interchim-automated chromatography system (40 g column), eluting with a gradient of 0 to 20% ethyl acetate in heptanes to give a mixture of compound 5-1, 5-2 and 5-3 (1.54 g, 89% yield) as a yellow oil. (LM-6-82)

4-((E)-But-2-en-1-yl)-3-ethoxy-5-((E)-4-hydroxy-3-methoxystyryl)phenol (5)

1M Tetrabutylammonium fluoride in tetrahydrofuran (33.5 mL, 33.5 mmol, 14 equiv) was added to a mixture of compound 5-1, 5-2 and 5-3 (1.44 g, 2.4 mmol, 1 equiv) in tetrahydrofuran (50 mL) at room temperature. After heating at 67° C. for 16 hours, the mixture was cooled to room temperature and diluted with ethyl acetate (200 mL). The mixture was washed with saturated brine (50 mL) and the organic layer was dried over sodium sulfate, filtered, and concentrated under reduced pressure. The residue was puri-

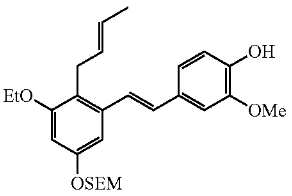

5-1

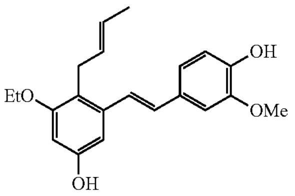

Compound 5

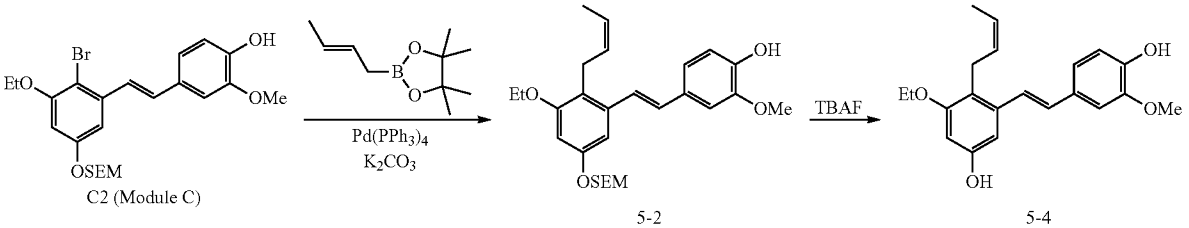

C2 (Module C)

5-2

5-4

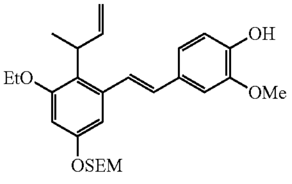

5-3

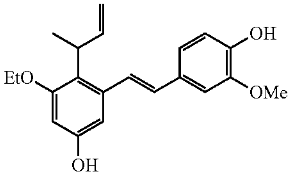

5-5 fied twice on an Interchim automated chromatography system (2×40 g column stack, 2×25 g column stack), eluting each time with a gradient of 0 to 100% ethyl acetate in heptanes to a mixture of compound 5, 5-4 and 5-5 (610 mg) as a yellow oil. This mixture of oil was subjected to supercritical fluid chromatography (Lotus Separations) to give three compounds, which were appeared as black residue oils. The LM-6-85-P2 residue was re-purified on an InterChim automated chromatography system (25 column), eluting with a gradient of 0 to 60% ethyl acetate in hexanes to give compound 5 (60 mg, 7% yield) as an off-white solid after drying under vacuum at 40° C. for 16 hours. (LM-6-85) The following SFC separation (conditions listed below) yielded 425 mg of peak-1 (5-5, LM-6-85-P1), 88 mg of peak-2 (5, LM-6-85-P2), and 70 mg of peak-3 (5-4, LM-6-85-P3). Peak-2 was reworked to enhance the purity.

Chromatograms are included in this report.

| Preparative Method: | Analytical Method: |
|---|---|
| SFC-B (2 × 25 cm) | SFC-B(15 × 0.46 cm) |
| 45% methanol/$CO_2$, 100 bar | 40% methanol/$CO_2$, 120 bar |
| 80 mL/min, 220 nm | 3 mL/min, 220, 254 and 280 nm |
| inj vol.: 0.5 mL, 20 mg/mL ethanol 1 | |

Figure 5:
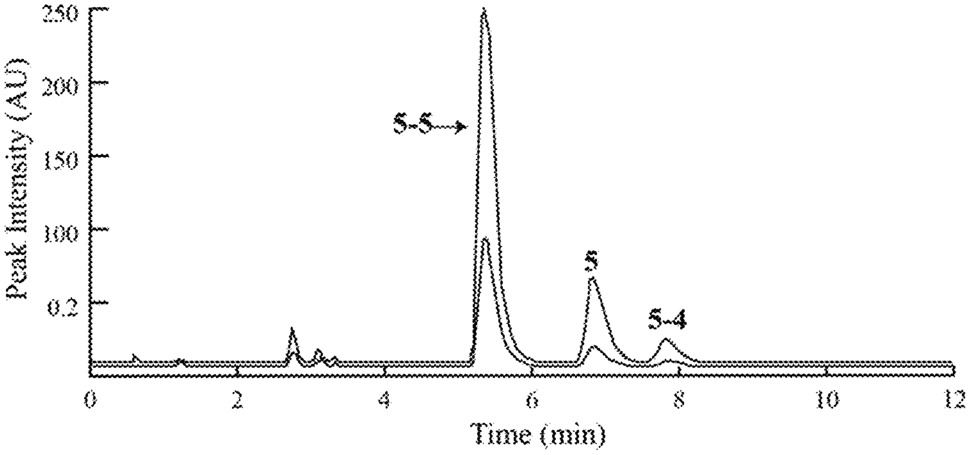
FIG. 5 is a chromatogram LM-6-85 (mixture of compound 5, E-5-4 and E-5-5), before separation.

FIG. 5 shows LM-6-85 (mixture of compound 5, E-5-4 and E-5-5), before separation.

Figure 6:
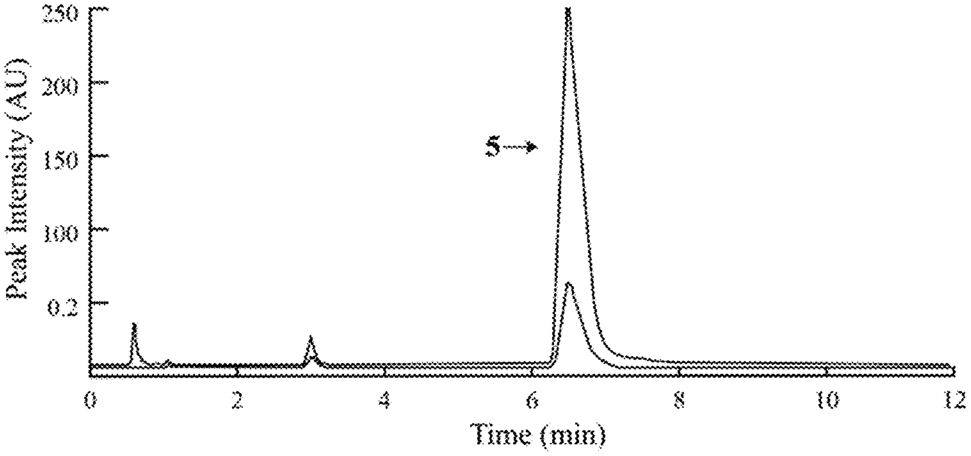
FIG. 6 is a chromatogram LM-6-85-P2 (compound 5), after separation.

FIG. 6 shows LM-6-85-P2 (compound 5), after separation.

Figure 7:
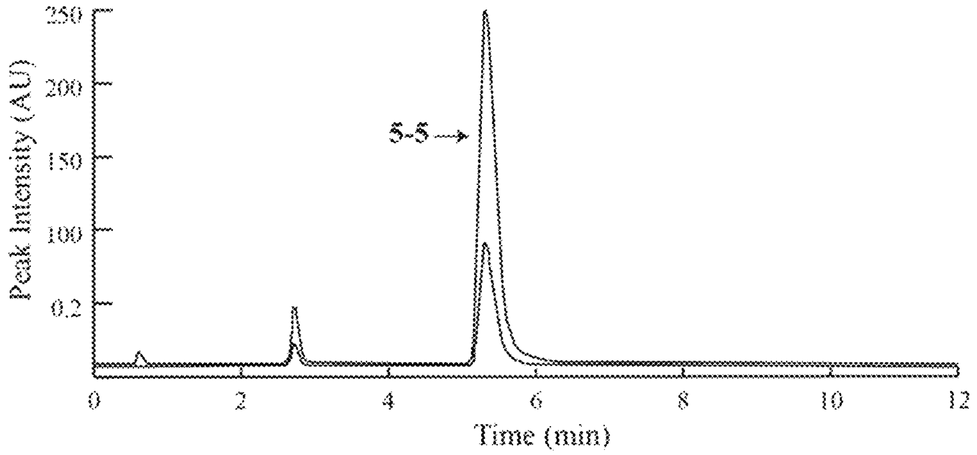
FIG. 7 is a chromatogram LM-6-85-P1 (compound 5-5), after separation.

FIG. 7 shows LM-6-85-P1 (compound 5-5), after separation.

Figure 8:
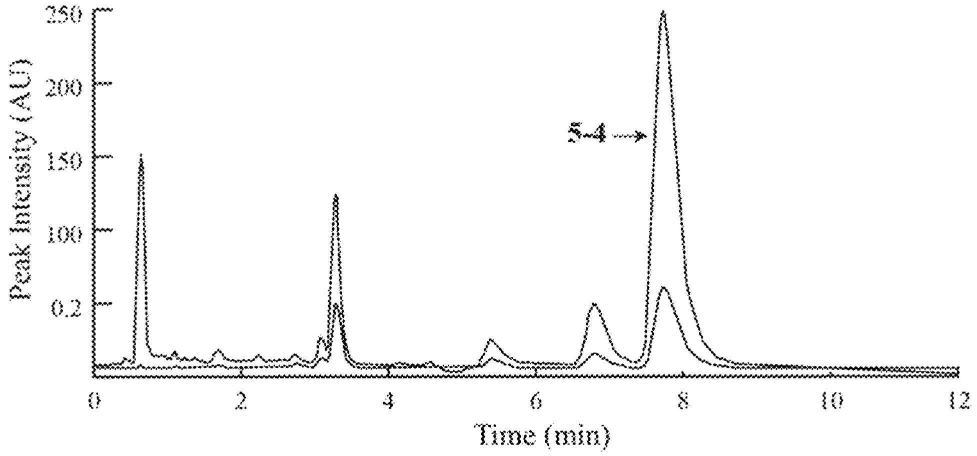
FIG. 8 is a chromatogram LM-6-85-P3 (compound 5-4), after separation.

FIG. 8 shows LM-6-85-P3 (compound 5-4), after separation.

Structure Data:

Compound 5 [KYN-153]

Off-white solid; HPLC Analysis: 97.7% purity; Wavelength 254 nm, bandwidth 4; Column: SorbTech C18AQ, 2.1×50 mm, 3 μm; Retention Time: 8.6 min; Mobile Phase: ACN/formic acid/water; Mass Spectrum (positive mode) m/z=341.2 $(M+H)^+$; $C_{21}H_{24}O_4$; NMR (400 MHz, $CDCl_3$) δ=7.19 (d, J=16.1 Hz, 1H), 7.03-6.98 (m, 2H), 6.92 (d, J=8.2 Hz, 1H), 6.85 (d, J=16.1 Hz, 1H), 6.65 (d, J=2.4 Hz, 1H), 6.34 (d, J=2.4 Hz, 1H), 5.66 (s, 1H), 5.59-5.40 (m, 2H), 4.70 (s, 1H), 4.00 (q, J=7.0 Hz, 2H), 3.95 (s, 3H), 3.42 (br d, J=5.9 Hz, 2H), 1.65-1.61 (m, 3H), 1.41 (t, J=7.0 Hz, 3H); $^{13}C$ NMR (100 MHz, $CDCl_3$) δ=157.95, 154.40, 146.68, 145.57, 138.31, 130.35, 130.29, 129.79, 124.88, 124.43, 120.34, 119.89, 114.59, 108.54, 103.84, 99.17, 63.99, 55.89, 28.49, 17.90, 14.87.

Preparation of (E)-4-allyl-3-(4-hydroxy-3-methoxystyryl)-5-methoxyphenol (6) [KYN-134]

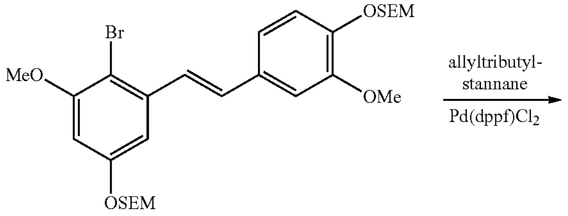

C1 (Module C)

-continued

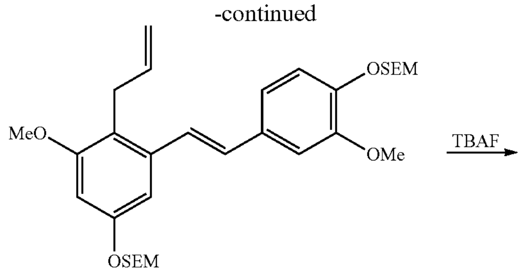

6-1

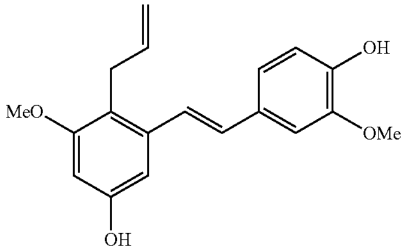

Compound 6

(E)-(2-((4-(2-allyl-3-methoxy-5-((2-(trimethylsilyl) ethoxy)methoxy)styryl)-2-methoxyphenoxy) methoxy)ethyl)trimethylsilane (6-1)

[1,1'-Bis(diphenylphosphino)ferrocene]dichloropalladium(II) (46 mg, 0.063 mmol, 0.25 equiv) and allyltributylstannane (248 mg, 0.75 mmol, 3 equiv) were added to a solution of compound $C_1$ (Module C) (153 mg, 0.25 mmol, 1 equiv) in anhydrous dimethylformamide (3 mL). After sparging with nitrogen for 10 minutes, the reaction was heated at 100° C. for 16 hours. The reaction mixture was cooled to room temperature, loaded to a 12 g dry-load cartridge with silica gel (10 g) and purified on an Interchim automated chromatography system (25 column), eluting with a gradient of 0 to 40% ethyl acetate in heptanes to give compound 6-1 (140 mg, 98% yield) as a yellow oil. (LM-6-33)

(E)-4-allyl-3-(4-hydroxy-3-methoxystyryl)-5-methoxyphenol (6) [KYN-134]

1M Tetrabutylammonium fluoride in tetrahydrofuran (3.5 mL, 3.5 mmol, 14 equiv) was added to compound 6-1 (140 mg, 0.25 mmol, 1 equiv) at room temperature, and the mixture was heated at 67° C. for 16 hours. After the mixture was cooled to room temperature, water (4 mL) was added to quench the reaction. The mixture was extracted with ethyl acetate (15 mL) and the organic layer was concentrated under reduced pressure. The residue was purified twice on an Interchim automated chromatography system (2×25 columns), eluting each time with a gradient of 0 to 60% ethyl acetate in heptanes to give compound 6 (34 mg, 45% yield) as an off-white solid after drying under vacuum at 35° C. for 16 hours. (LM-6-34)

White solid; HPLC Analysis: 96.3% purity; Wavelength 254 nm, bandwidth 4; Column: SorbTech C18AQ, 2.1×50 mm, 3 μm; Retention Time: 7.48 min; Mobile Phase: ACN/formic acid/water; Mass Spectrum (positive mode) m/z=313.1 $(M+H)^+$; $C_{19}H_{20}O_4$ $^1H$ NMR (400 MHz, $CDCl_3$) δ=7.14 (d, J=16.2 Hz, 1H), 7.00 (dd, J=1.5, 7.7 Hz, 1H), 6.98 (s, 1H), 6.90 (d, J=7.8 Hz, 11H), 6.85 (d, J=16.1 Hz, 1H), 6.67 (d, J=2.5 Hz, 1H), 6.36 (d, J=2.2 Hz, 1H), 5.94 (ddt, J=5.9, 10.2, 17.0 Hz, 1H), 5.66 (br s, 1H), 4.99 (dq, J=1.7, 8.5 Hz, 1H), 4.96 (dq, J=1.7, 17.1 Hz, 1H), 4.76 (br s, 1H), 3.93 (s, 3H), 3.79 (s, 3H), 3.48 (dt, J=1.7, 5.8 Hz, 2H).

$^{13}C$ NMR (100 MHz, $CDCl_3$) δ=158.73, 154.70, 146.70, 145.64, 138.71, 137.25, 130.63, 130.26, 124.22, 120.43, 118.57, 114.61, 114.40, 108.56, 104.03, 98.25, 55.92, 55.80, 29.50.

Preparation of (E)-4-benzyl-3-(4-hydroxy-3-methoxystyryl)-5-methoxyphenol (7) [KYN-136]

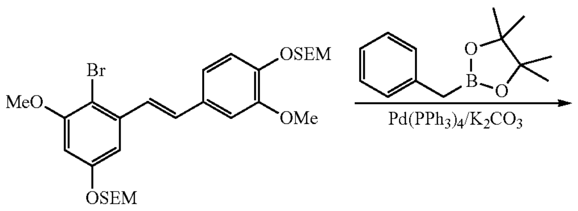

C1 (Module C)

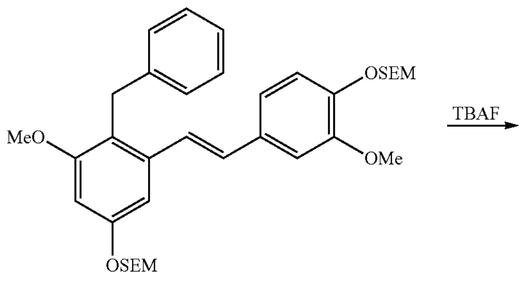

7-1

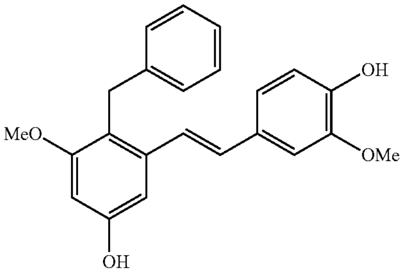

Compound 7

(E)-(2-((4-(2-benzyl-3-methoxy-5-((2-(trimethylsilyl)ethoxy)methoxy)styryl)-2-methoxyphenoxy)methoxy)ethyl)trimethylsilane (Compound 7-1)

Tetrakis(triphenylphosphine)palladium(0) (16 mg, 0.014 mmol, 0.05 equiv), potassium carbonate (77 mg, 0.56 mmol, 2 equiv), benzylboronic acid pinacol ester (122 mg, 0.56 mmol, 2 equiv) and water (5 mL) were added sequentially to a solution of compound C1 (170 mg, 0.28 mmol, 1 equiv) in tetrahydrofuran (5 mL). After sparging with nitrogen for 10 minutes, the reaction was heated at 77° C. for 16 hours. After cooling to room temperature, the mixture was extracted with ethyl acetate (15 mL) and the organic layer was concentrated under reduced pressure. The residue was purified on an Interchim automated chromatography system (40 g column), eluting with a gradient of 0 to 50% ethyl acetate in heptanes to give compound 7-1 (172 mg, 99% yield) as a yellow oil. (LM-6-35)

(E)-4-benzyl-3-(4-hydroxy-3-methoxystyryl)-5-methoxyphenol (7) [KYN-136]

1M Tetrabutylammonium fluoride in tetrahydrofuran (3.92 mL, 3.92 mmol, 14 equiv) was added to compound 7-1 (172 mg, 0.28 mmol, 1 equiv) at room temperature. After heating at 67° C. for 16 hours, the mixture was cooled to room temperature and diluted with water (4 mL). The mixture was extracted with ethyl acetate (15 mL) and the organic layer was concentrated under reduced pressure. The residue was purified twice on an Interchim automated chromatography system (40 & 25 columns), eluting each time with a gradient of 0 to 60% ethyl acetate in heptanes to give compound 7 (37 mg, 37% yield) as an off-white solid after drying under vacuum at 35° C. for 16 hours. (LM-6-36)

Off-white solid; HPLC Analysis: 96.4% purity; Wavelength 254 nm, bandwidth 4; Column: SorbTech C18AQ, 2.1×50 mm, 3 μm; Retention Time: 8.0) min; Mobile Phase: ACN/formic acid/water; Mass Spectrum (positive mode) m/z=363.1 $(M+H)^+$; $C_{23}H_{22}O_4$;

$^1H$ NMR (400 MHz, $CDCl_3$) δ=7.24-7.00 (m, 2H), 7.18-7.10 (m, 3H), 7.09 (d, J=16.1 Hz, 1H), 6.89 (dd, J=1.7, 8.6 Hz, 1H), 6.85 (d, J=8.1 Hz, 1H), 6.85 (d, J=1.7 Hz), 6.82 (d, J=15.9 Hz), 6.68 (d, J=2.5 Hz, 1H), 6.39 (d, J=2.5 Hz, 1H), 5.65 (br s, 1H), 4.87 (br s, 1H), 4.10 (s, 2H), 3.87 (s, 3H), 3.77 (s, 3H).

$^{13}C$ NMR (100 MHz, $CDCl_3$) δ=159.03, 154.85, 146.63, 145.58, 141.66, 138.83, 130.62, 130.12, 128.22, 128.16, 125.55, 124.31, 120.60, 119.60, 114.48, 108.23, 104.06, 98.21, 55.83, 55.72, 30.92.

Preparation of (E)-3-Ethoxy-5-(4-hydroxy-3-methoxystyryl)-4-(3-methylbut-2-en-1-yl)phenol (8) [KYN-119]

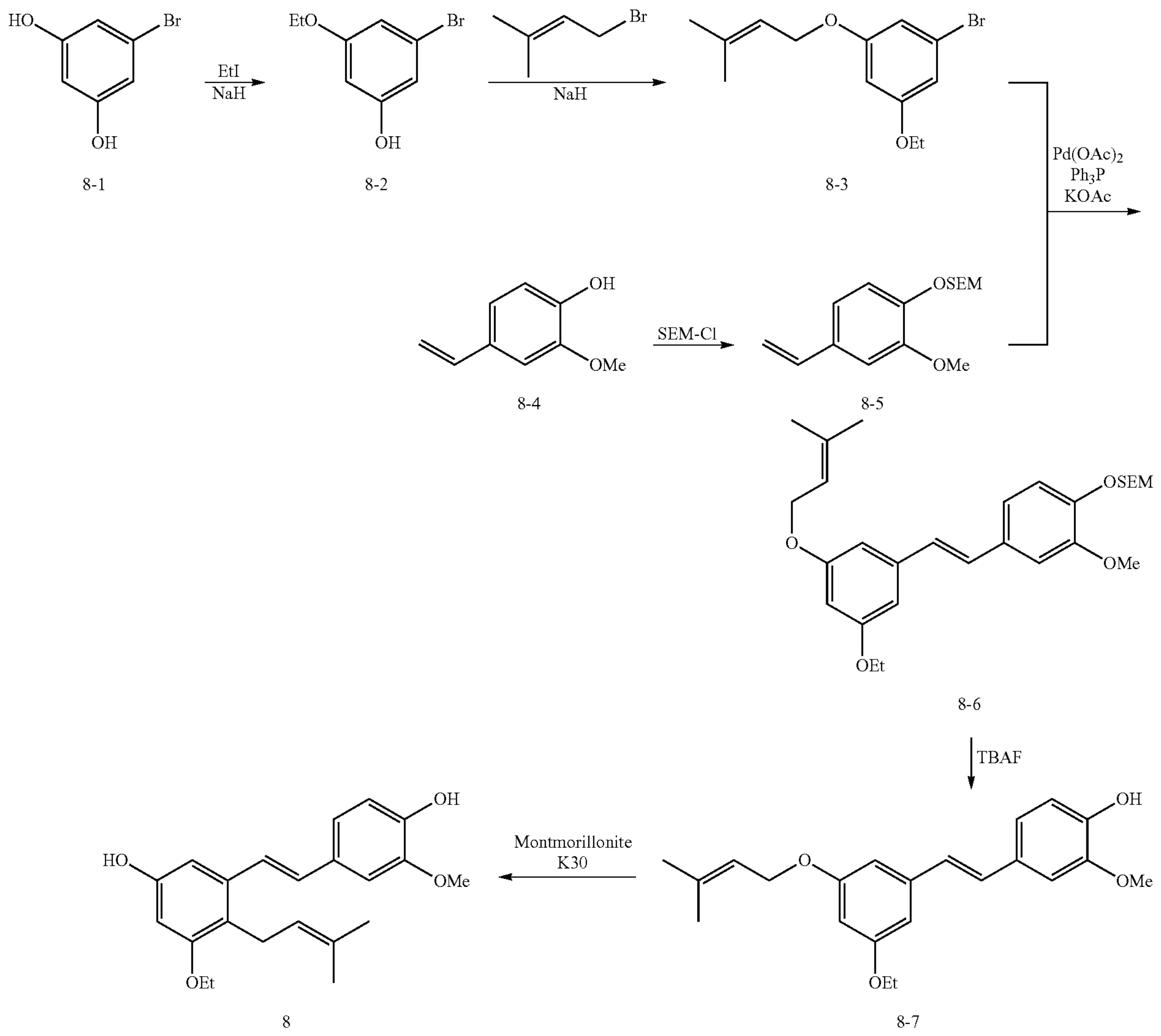

8-1 8-2 8-3 8-4 8-5 8-6 8-7 8

3-Bromo-5-ethoxyphenol (8-2)

A 60% dispersion of sodium hydride (2.9 g, 73.62 mmol, 1.1 equiv) in mineral oil was added in several portions to a solution of compound 8-1 (12.65 g, 66.93 mmol, 1 equiv) in anhydrous tetrahydrofuran (700 mL) at room temperature. After stirring at room temperature for 15 minutes, ethyl iodide (5.38 mL, 66.93 mmol, 1 equiv) was added. The resulting solution was heated at 50° C. for 8 hours. The reaction was cooled to room temperature and transferred to a separatory funnel containing saturated ammonium chloride solution (500 mL). Ethyl acetate (1 L) was added and the organic layer separated. The aqueous layer was extracted with ethyl acetate (3×400 mL) and the combined organic layers were dried over sodium sulfate, filtered and concentrated under reduced pressure. The residue was purified on an Interchim automated chromatography system (Sorbtech 120 g column), eluting with a gradient of 0 to 50% ethyl acetate in heptanes to give compound 8-2 (4.37 g, 31% yield) as a yellow oil. (TA-1-107)

1-Bromo-3-ethoxy-5-((3-methylbut-2-en-1-yl)oxy)benzene (8-3)

A 60% dispersion of sodium hydride (1.1 g, 28.64 mmol, 1.1 equiv) in mineral oil and 3,3-dimethylallyl bromide (4.27 g, 28.6 mmol, 1.1 equiv) were sequentially added to a solution of compound 8-2 (5.65 g, 26.03 mmol, 1 equiv) in anhydrous THF (500 mL). The reaction mixture was heated at 50° C. and stirred overnight. The reaction was cooled to room temperature and transferred to a separatory funnel containing saturated ammonium chloride solution (400 mL). Ethyl acetate (700 mL) was added and the organic layer was separated. The aqueous layer was extracted with ethyl acetate (3×200 mL) and the combined organic layers were dried with sodium sulfate, filtered and concentrated under reduced pressure. The residue was purified on an Interchim automated chromatography system (Sorbtech 120 g column), eluting with a gradient of 0 to 20% ethyl acetate in heptanes to give compound 8-3 (6.8 g, 88% yield) as a yellow oil. (TA-1-102).

(2-((2-Methoxy-4-vinylphenoxy)methoxy)ethyl) trimethylsilane (8-5)

N,NDiisopropylethylamine (8.8 mL, 50 mmol, 1.5 equiv) and 2-(trimethylsilyl)ethoxymethyl chloride (7.1 mL, 40 mmol, 1.2 equiv) were sequentially added to a solution of compound 8-4 (5 g, 33.33 mmol, 1.0 equiv) in anhydrous dichloromethane (50 mL) at room temperature. After stirring at room temperature overnight, saturated ammonium chloride (50 mL) was added to quench the reaction. The aqueous layer was extracted with dichloromethane (2×50 mL). The combined organic layers were dried over sodium sulfate, filtered and concentrated under reduced pressure. The residue was purified on an Interchim automated chromatography system (Sorbtech 24 g column), eluting with a gradient of 0 to 10% ethyl acetate in heptanes to give compound 8-5 (6.5 g, 70% yield) as a clear oil. (NK-1-45)

(E)-(2-((4-(3-Ethoxy-5-((3-methylbut-2-en-1-yl)oxy) styryl)-2-methoxyphenoxy)methoxy)ethyl)trimethylsilane (8-6)

Compound 8-5 (1.49 g, 5.32 mmol, 1.2 equiv), triphenylphosphine (110 mg, 0.443 mmol, 0.1 equiv), potassium acetate (868 mg, 8.86 mmol, 2 equiv) and palladium acetate (50 mg, 0.221 mmol, 0.05 equiv) were added to a solution of compound 8-3 (1.26 g, 4.43 mmol, 1.0 equiv) in anhydrous toluene (30 mL). The reaction mixture was sparged with nitrogen for 15 minutes. After refluxing (110° C.) for 16 hours, the reaction mixture was cooled to room temperature and filtered through celite (~5 g). The filtrate was transferred to a separatory funnel containing saturated sodium bicarbonate (30 mL). The organic layer was separated and the aqueous layer was extracted with ethyl acetate (2×20 mL). The combined organic layers were dried over sodium sulfate, filtered and concentrated under reduced pressure. Another batch using compound 3 (1.26 g) was processed in a similar way. The combined residue was purified on an Interchim automated chromatography system (Sorbtech 24 g column), eluting with a gradient of 0 to 20% ethyl acetate in heptanes to give compound 8-6 (960 mg, 22% yield) as a pale yellow oil. (NK-1-49)

(E)-4-(3-Ethoxy-5-((3-methylbut-2-en-1-yl)oxy) styryl)-2-methoxyphenol (8-7)

1M tetrabutylammonium fluoride in THF (14.0 mL, 13.88 mmol, 7 equiv) was added to a solution of compound 8-6 (960 mg, 1.98 mmol, 1 equiv) in anhydrous THF (40 mL) at room temperature. The mixture was refluxed overnight (66° C.), at which point LCMS indicated that the reaction was complete. After the mixture was cooled to room temperature, water (10 mL) was added to quench the reaction. The volatiles were removed under reduced pressure followed by the addition of ethyl acetate (15 mL). The organic layer was separated and the aqueous layer was extracted with ethyl acetate (2×15 mL). The combined organic layers were dried over sodium sulfate, filtered and concentrated under reduced pressure. The residue was purified on an Interchim automated chromatography system (Sorbtech 12 g column), eluting with a gradient of 0 to 50% ethyl acetate in heptanes to give compound 8-7 (503 mg, 71% yield) as a yellow oil. (NK-1-44)

(E)-3-Ethoxy-5-(4-hydroxy-3-methoxystyryl)-4-(3-methylbut-2-en-1-yl)phenol (8) [KYN-119]

Montmorillonite K30 powder (500 mg) was added to a solution of compound 8-7 (500 mg, 1.41 mmol) in anhydrous dichloromethane (20 mL) at room temperature and the mixture was stirred at room temperature overnight. No product formation was observed by LCMS. The mixture was filtered and fresh Montmorillonite K30 powder (500 mg) was added and the mixture was stirred at room temperature overnight, at which point LCMS indicated that 30-40% of desired compound 8 was formed, along with two regioisomers and unreacted starting compound 7 as byproducts. The mixture was filtered and the solid was washed with dichloromethane (2×15 mL). The filtrate was concentrated under reduced pressure. The residue was purified on an Interchim automated chromatography system (Sorbtech 24 g column), eluting with a gradient of 0 to 50% ethyl acetate in heptanes. Trituration with 30% dichloromethane in heptanes (10 mL) gave pure compound 8 [KYN-119] (60 mg, 12% yield) as a white solid. (NK-1-52-C)

Beige solid, melting point 133.9-134.7° C.; HPLC Analysis: 96.7% purity; Wavelength 254 nm, bandwidth 4; Column: SorbTech C18AQ, 2.1×50 mm, 3 μm; Retention Time: 9.10 min; Mobile Phase: ACN/formic acid/water; Mass Spectrum (positive mode) m/z=355.2 $(M+H)^+$; $C_{22}H_{26}O_4$; $^1H$ NMR (400 MHz, $CDCl_3$) δ=7.16 (d, J=16.1 Hz, 1H), 7.00 (br s, 1H), 6.99 (dd, J=1.9, 9.0 Hz, 1H), 6.90 (d, J=8.4 Hz, 1H), 6.84 (d, J=16.1 Hz, 1H), 6.64 (d, J=2.4 Hz, 1H), 6.33 (d, J=2.4 Hz, 1H), 5.13 (tm, J=1.4, 7.0 Hz, 1H), 3.98 (q, J=7.0 Hz, 2H), 3.93 (s, 3H), 3.43 (d, J=7.0 Hz, 2H), 1.81 (d, J=1.0 Hz, 3H), 1.67 (d, J=1.2 Hz, 3H), 1.41 (t, J=7.0 Hz, 3H); $^{13}C$ NMR (100 MHz, $CDCl_3$) δ=157.88, 154.27, 146.68, 145.53, 138.12, 130.40, 130.34, 130.32, 124.39, 123.74, 120.89, 120.55, 114.56, 108.32, 103.86, 99.12, 63.94, 55.88, 25.78, 24.54, 18.01, 14.89.

Compound 8 (KYN-119) can also be synthesised by the modular methodology of the present disclosure using equivalents to Module A, B and C and subsequent cross coupling alkylation of the aryl halide.

Preparation (E)-3-(4-Hydroxy-3-methoxystyryl)-4-(3-methylbut-2-en-1-yl)-5-propoxyphenol (9) [KYN-130]

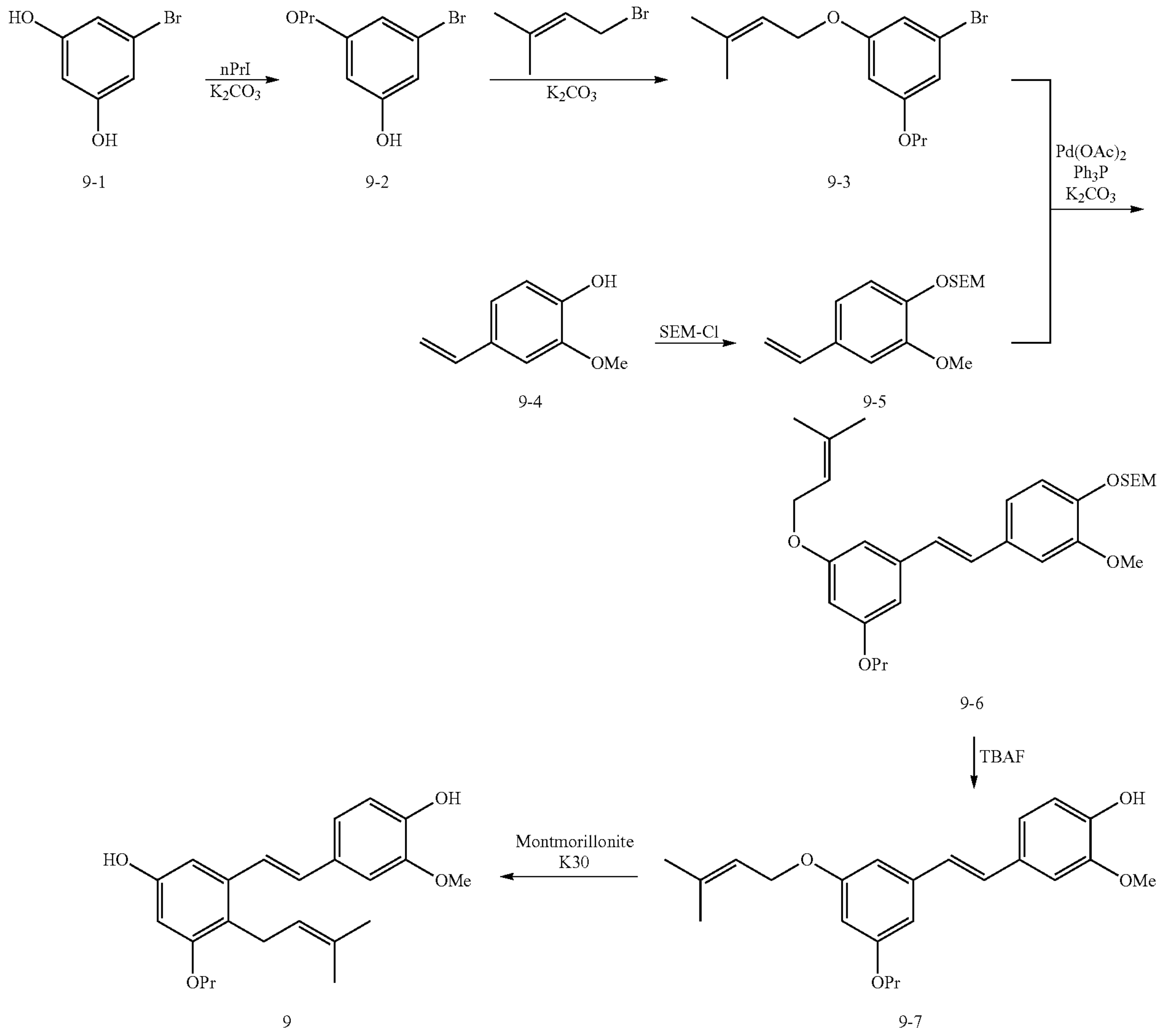

9-1, 9-2, 9-3, 9-4, 9-5, 9-6, 9-7, 9

3-Bromo-5-propoxyphenol (9-2)

Potassium carbonate (21.9 g, 158.73 mmol, 1.2 equiv) and propyl iodide (15 mL, 158.73 mmol, 1.2 equiv) were added sequentially to a solution of compound 9-1 (10.0 g, 52.91 mmol, 1 equiv) in acetonitrile (300 mL) at room temperature. The resulting suspension was refluxed (80° C.) for 16 hours. After cooling to room temperature the reaction mixture was filtered and the filtrate was concentrated under reduced pressure. The residue was dissolved in ethyl acetate (150 mL) and transferred to a separatory funnel containing 1M hydrochloric acid solution (100 mL). The layers were separated and the aqueous layer was extracted with ethyl acetate (2×100 mL). The combined organic layers were dried over sodium sulfate, filtered, and concentrated under reduced pressure. The residue was purified on a Reveleris automated chromatography system (Sorbtech 40 g column), eluting with a gradient of 0 to 30% ethyl acetate in heptanes to obtain compound 9-2 (11.3 g, 37% yield) as a light brown oil (NRK-1-89).

1-Bromo-3-((3-methylbut-2-en-1-yl)oxy)-5-propoxybenzene (9-3)

Potassium carbonate (10.1 g, 73.36 mmol, 1.5 equiv) and 3,3-dimethylallyl bromide (6.8 mL, 58.70 mmol, 1.2 equiv) were added sequentially to a solution of compound 9-2 (11.3 g, 48.91 mmol, 1 equiv) in acetonitrile (200 mL) at room temperature. The resulting suspension was refluxed (80° C.) for 16 hours. After cooling to room temperature the reaction mixture was filtered and the filtrate was concentrated under reduced pressure to obtain compound 9-3 (16.0 g, 99% yield) as a light brown oil (NRK-1-90) which was used subsequently, (E)(2-((2-methoxy-4-(3-((3-methylbut-2-en-1-yl)oxy)-5-propoxystyryl)phenoxy)methoxy)ethyl)trimethylsilane (9-6)

(2-((2-Methoxy-4-vinylphenoxy)methoxy)ethyl)trimethylsilane (9-5, see 8-5 for prep) (12.3 g, 4.15 mmol, 1.1 equiv), triphenylphosphine (2.1 g, 8.02 mmol, 0.2 equiv), potassium carbonate (11 g, 80.26 mmol, 2 equiv) and palladium acetate (910 mg, 4.01 mmol, 0.1 equiv) were added to a solution of compound 9-3 (12.0 g, 40.13 mmol, 1.0 equiv) in anhydrous toluene (300 mL) at room temperature. The reaction mixture was sparged with nitrogen for 15 minutes. After refluxing (110° C.) for 16 hours, the reaction mixture was cooled to room temperature and filtered through celite (~30 g). The filtrate was transferred to a separatory funnel containing saturated sodium bicarbonate solution (200 mL). The layers were separated and the aqueous layer was extracted with ethyl acetate (2×100 mL). The combined organic layers were dried over sodium sulfate, filtered, and concentrated under reduced pressure. The residue was purified on a Reveleris automated chromatography system (Sorbtech 80 g column), eluting with a gradient of 0 to 20% ethyl acetate in heptanes to give compound 9-6 (6.25 g, 31% yield) as a light brown oil. (NRK-1-91)

(E)-2-methoxy-4-(3-((3-methylbut-2-en-1-yl)oxy)-5-propoxystyryl)phenol (8-7)

1M Tetrabutylammonium fluoride in THF (139 mL, 138.59 mmol, 7 equiv) was added to a solution of compound 9-6 (9.86 g, 19.8 mmol, 1 equiv) in anhydrous THF (200 mL) at room temperature. The mixture was refluxed (66° C.) for 16 hours, at which point LCMS indicated that the reaction was complete. After the mixture was cooled to room temperature, water (20 mL) was added. The volatiles were removed under reduced pressure followed by the addition of ethyl acetate (150 mL). The layers were separated and the aqueous layer was extracted with ethyl acetate (2×100 mL). The combined organic layers were dried over sodium sulfate, filtered, and concentrated under reduced pressure. The residue was purified on a Reveleris automated chromatography system (Sorbtech 80 g column), eluting with a gradient of 0 to 50% ethyl acetate in heptanes to give compound 9-7 (6.66 g, 92% yield) as a yellow solid. (NRK-1-92)

(E)-3-(4-hydroxy-3-methoxystyryl)-4-(3-methylbut-2-en-1-yl)-5-propoxyphenol (9) [KYN-130]

Montmorillonite K30 powder (6.66 g) was added to a solution of compound 8-7 (6.66 g, 18.09 mmol) in anhydrous dichloromethane (200 mL) at room temperature. After stirring at room temperature overnight, LCMS indicated that 3040% of desired compound 9 had formed, along with two regioisomers and unreacted starting compound 9-7 as byproducts. The mixture was filtered through celite, which was washed with dichloromethane (2×50 mL). The filtrate was concentrated under reduced pressure. The residue was purified on a Reveleris automated chromatography system (Sorbtech 80 g column), eluting with a gradient of 0 to 20% ethyl acetate in heptanes. The product was triturated with 30% dichloromethane in heptanes (20 mL) to give pure compound 9 [KYN-130] (1.02 g, 15% yield) as a white solid. (NRK-1-95-C)

White solid, melting point 141.6-142.8° C.; HPLC Analysis: 99.48% purity; Wavelength 254 nm, bandwidth 4; Column: SorbTech C18AQ, 2.1×50 mm, 3 μm; Retention Time: 9.4 min; Mobile Phase: ACN/formic acid/water; Mass Spectrum (negative mode) m/z=367.2 $(M-H)^-$; $C_{23}H_{28}O_4$; $^1H$ NMR (400 MHz, $CDCl_3$) δ=7.16 (d, J=16.1 Hz, 1H), 7.00 (br s, 1H), 6.99 (dd, J=2.0, 8.2 Hz, 1H), 6.90 (d, J=8.3 Hz, 1H), 6.84 (d, J=15.9 Hz, 1H), 6.64 (d, J=2.5 Hz, 1H), 6.33 (d, J=2.4 Hz, 1H), 5.14 (tm, J=7.0 Hz, 1H), 3.93 (s, 3H), 3.88 (t, 6.4 Hz, 2H), 3.43 (d, J=6.8 Hz, 2H), 1.83 (m, J=6.4, 7.6 Hz, 2H), 1.81 (d, J=1.0 Hz, 3H), 1.67 (d, J=1.2 Hz, 3H), 1.04 (t, J=7.5 Hz, 3H); $^{13}C$ NMR (100 MHz, $CDCl_3$) δ=158.02, 154.27, 146.68, 145.57, 138.14, 130.36, 130.33, 130.31, 124.42, 123.84, 120.88, 120.55, 114.56, 108.32, 103.75, 98.97, 69.90, 55.90, 25.78, 24.57, 22.68, 18.01, 10.68.

Compound 9 (KYN-130) can also be synthesised by the modular methodology of the present disclosure using equivalents to Module A, B and C and subsequent cross coupling alkylation of the aryl halide.

Preparation of 3-(4-Hydroxy-3-methoxystyryl)-5-isopropoxy-4-(3-methylbut-2-en-1-yl)phenol (10) [KYN-131]

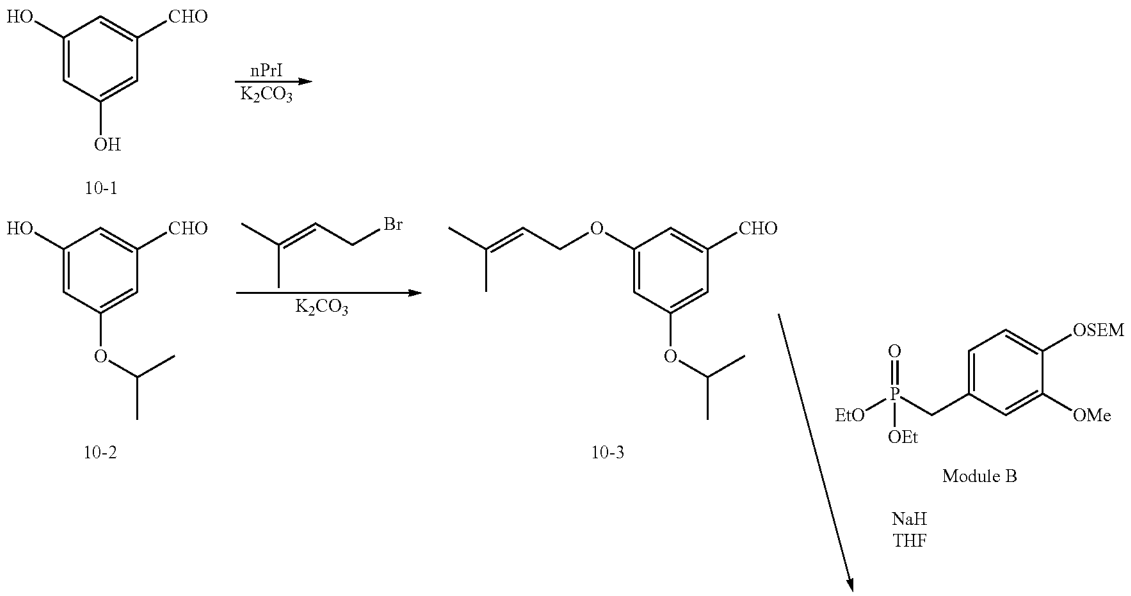

10-1

10-2

10-3

-continued

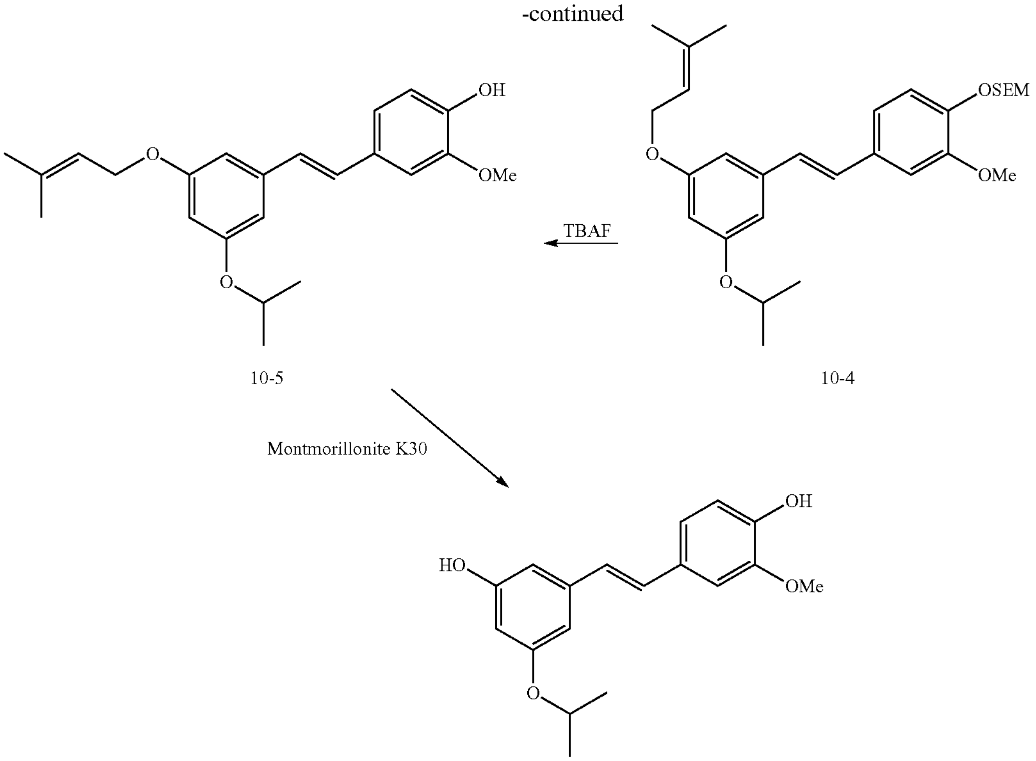

10-5 10-4

10

3-Hydroxy-5-isopropoxybenzaldehyde (10-2)

A mixture of compound 10-1 (3 g, 21.7 mmol, 1 equiv), potassium carbonate (4.5 g, 32.6 mmol, 1.5 equiv) and isopropyl iodide (2.1 mL, 21.7 mmol, 1 equiv) in N,N'-dimethylformamide (60 mL) was heated at 70° C. for 16 hours. Additional isopropyl iodide (1.05 Ml, 10.9 mmol, 0.5 equiv) was added and the reaction was continued for 2 hours. After cooling to room temperature, the pH was adjusted to 4 with 6 N HCl. The remaining solid was removed by filtration. The filtrate was extracted with ethyl acetate (4×50 mL). The combined organic layers were washed with saturated brine (50 mL), dried over sodium sulfate, filtered, and concentrated under reduced pressure. The residue was purified on an InterChim automated chromatography system (40 g SorbTech column), eluting with a gradient of 0 to 70% ethyl acetate in heptanes to give compound 10-2 (1.13 g, 29% yield) as a brown solid. (QZH-RCI-4).

3-Isopropoxy-5-((3-methylbut-2-en-1-yl)oxy)benzaldehyde (10-3)

A mixture of compound 10-2 (1.13 g, 6.27 mmol, 1 equiv), potassium carbonate (1.73 g, 12.5 mmol, 2 equiv) and 1-bromo-3-methylbut-2-ene (0.87 mL, 7.53 mmol, 1.2 equiv) in acetone (35 mL) was refluxed for 16 hours. After cooling to room temperature, the reaction was diluted with water (50 mL) and extracted with ethyl acetate (2×50 mL). The combined organic layers were washed with saturated brine (30 mL), dried over sodium sulfate, filtered, and concentrated under reduced pressure. The residue was purified on a Büchi automated chromatography system (24 g SorbTech column), eluting with a gradient of 0 to 50% ethyl acetate in heptanes to give compound 10-3 (1.33, 86% yield) as a yellow oil. (QZH-RCI-6).

2-((4-(3-Isopropoxy-5-((3-methylbut-2-en-1-yl)oxy)styryl)-2-methoxyphenoxy)methoxy)ethyl)trimethylsilane (10-4)

A solution of Module B (2.17 g, 5.36 mmol, 1 equiv) in tetrahydrofuran (10 mL) was added to a suspension of a 60% dispersion of sodium hydride in mineral oil (0.43 g, 10.7 mmol, 2 equiv) in tetrahydrofuran (30 mL) at 0° C. The reaction was stirred at 0° C. for 1 hour. A solution of compound 10-3 (1.33 g, 5.36 mmol, 1 equiv) in tetrahydrofuran (10 mL) was added and the reaction was allowed to warm to room temperature overnight. The reaction was diluted with water (50 mL) and extracted with ethyl acetate (3×30 mL). The combined organic layers were washed with saturated brine (50 mL), dried over sodium sulfate, filtered, and concentrated under reduced pressure. The residue was purified on a Büchi automated chromatography system (24 g RediSep column), eluting with a gradient of 0 to 10% ethyl acetate in heptanes to give compound 10-4 (1.65 g, 62% yield) as a yellow oil. (QZH-RCI-9).

4-(3-Isopropoxy-5-((3-methylbut-2-en-1-yl)oxy)styryl)-2-methoxyphenol (10-5)

A solution of compound 10-4 (1.65 g, 3.3 mmol, 1 equiv) and 1.0 M tetrabutylammonium fluoride in tetrahydrofuran (16.5 mL, 16.5 mmol, 5 equiv) in tetrahydrofuran (20 mL) was refluxed overnight. After cooling to room temperature, the reaction was diluted with water (100 mL) and extracted with ethyl acetate (3×100 mL). The combined organic layers were washed with saturated brine (50 mL), dried over sodium sulfate and concentrated under reduced pressure. The residue was purified on a Büchi automated chromatography system (12 g RediSep column), eluting with a gradient of 0 to 30% ethyl acetate in heptanes to give Compound 10-5 (0.85 g, 70% yield) as a brown oil. (QZH-RCI-10)

3-(4-Hydroxy-3-methoxystyryl)-5-isopropoxy-4-(3-methylbut-2-en-1-yl)phenol (10) [KYN-131]

Montmorillonite K10 powder (1 g, Sigma-Aldrich, catalog #69866) was added to a solution of compound 10-5 (0.85 g, 2.3 mmol, 1 equiv) in anhydrous dichloromethane (10 mL). The reaction was stirred at room temperature for 16 hours, at which point the LC/MS indicates >90% conversion of the starting material. The solid was removed by filtration and the filter cake was rinsed with dichloromethane (100 mL). The filtrate was concentrated under reduced pressure. The residue was initially purified on a Büchi automated chromatography system (25 g SorbTech column), eluting with a gradient of 0 to 30% ethyl acetate in heptanes. The fractions that contains product (>85% purity by LC/MS) were collected and again purified on an InterChim automated chromatography system (25 g InterChim 20 to 45 microns silica gel column), eluting with a gradient of 0 to 30% ethyl acetate in heptanes to give Compound 10 [KYN-131] (75 mg, 9% yield, 99.2% purity by HPLC) as an off-white solid. (QZH-RCI-12).

Off-white solid; HPLC Analysis: 99.2% purity; Wavelength 254 nm, bandwidth 4; Column: SorbTech C18AQ, 2.1x50 mm, 3 μm; Retention Time: 9.2 min; Mobile Phase: ACN/formic acid/water; $C_{23}H_{28}O_4$; $^1H$ NMR (400 MHz, $CDCl_3$) δ=7.15 (d, J=16.1 Hz, 1H), 7.00 (br s, 1H), 6.99 (dd, J=2.0, 8.0 Hz, 1H), 6.90 (d, J=8.3 Hz, 1H), 6.85 (d, J=16.1 Hz, 1H), 6.64 (d, J=2.4 Hz, 1H), 6.35 (d, J=2.2 Hz, 1H), 5.12 (tm, J=1.4, 7.0 Hz, 1H), 4.49 (septet, J=6.0 Hz, 1H), 3.94 (s, 3H), 3.41 (d, J=6.9 Hz, 2H), 1.82 (d, J=1.0 Hz, 3H), 1.67 (d, J=1.2 Hz, 3H), 1.34 (d, J=6.1 Hz, 6H); $^{13}C$ NMR (100 MHz, $CDCl_3$) δ=156.75, 154.19, 146.68, 145.57, 138.37, 130.34, 130.27, 130.23, 124.52, 123.87, 121.87, 120.55, 114.55, 108.32, 103.95, 100.46, 70.35, 55.90, 25.78, 24.69, 22.17, 18.10.

Compound 10 (KYN-131) can also be synthesised by the modular methodology of the present disclosure using equivalents to Module A. B and C and subsequent cross coupling alkylation of the aryl halide.

Preparation of (E)-3-(4-Hydroxy-3-methoxystyryl)-4-(3-methylbut-2-en-1-yl)-5-(trifluoromethoxy)phenol (11) [KYN-132]

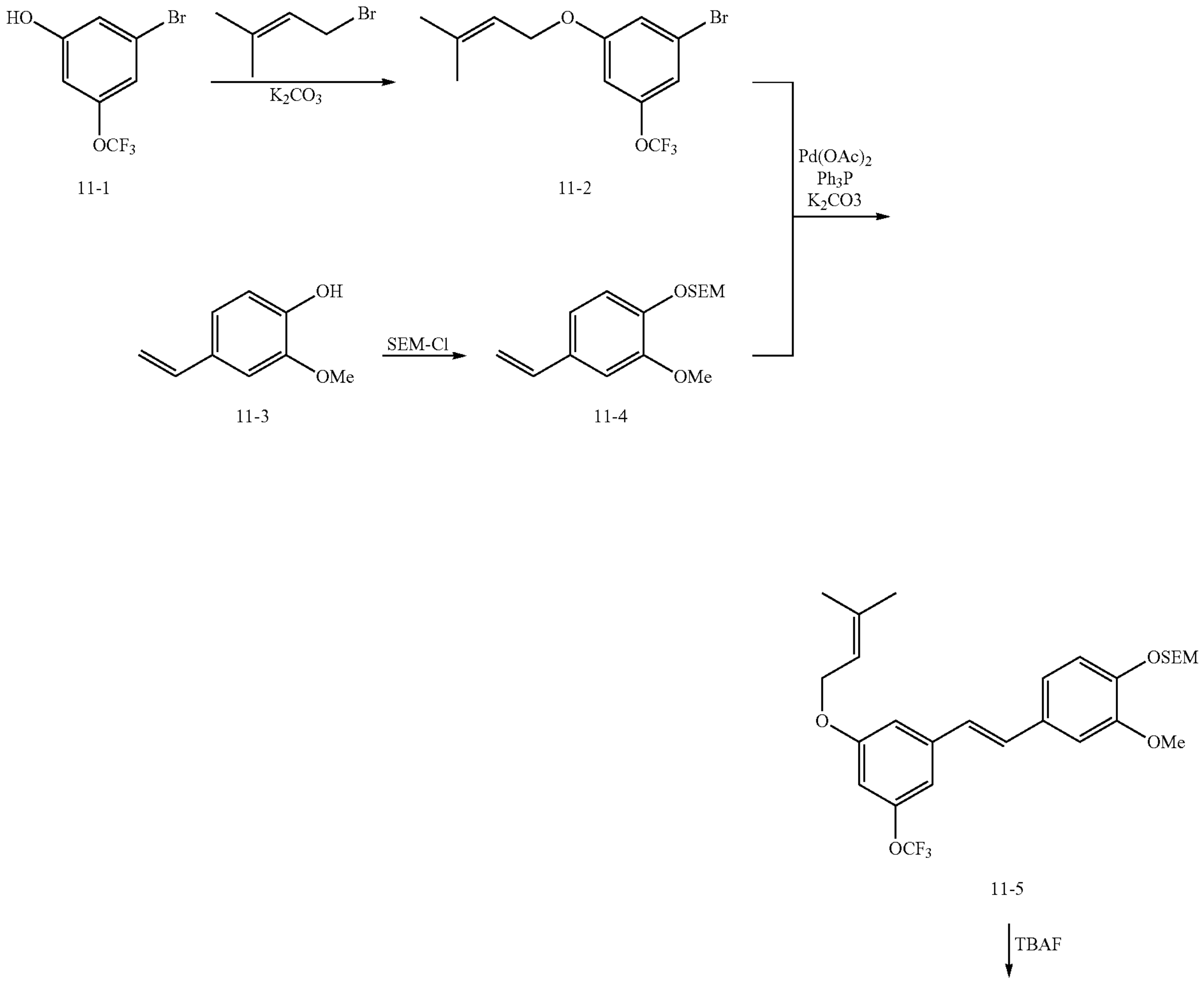

11-1 11-2 11-3 11-4 11-5

-continued

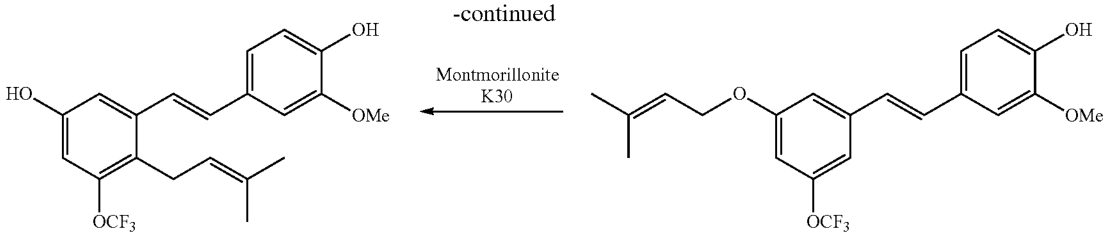

11 11-6

1-Bromo-3-((3-methylbut-2-en-1-yl)oxy-5-(trifluoromethoxy)benzene (11-2)

Potassium carbonate (5.36 g, 38.9 mmol, 2 equiv) and 3,3-dimethylallyl bromide (2.9 mL, 23.34 mmol, 1.2 equiv) were added sequentially to a solution of compound 11-1 (5.0 g, 19.45 mmol, 1 equiv) in acetonitrile (100 mL) at room temperature. The resulting suspension was heated to reflux (80° C.) for 16 hours. After cooling to room temperature, the reaction mixture was filtered and the filtrate was concentrated under reduced pressure. The crude residue was dissolved in ethyl acetate (100 mL) and washed with 1M hydrochloric acid solution (2×50 mL). The organic layer was dried over sodium sulfate and evaporated under reduced pressure to obtain compound 11-2 (5.0 g, 79% yield) as a pale yellow oil (NRK-1-96) which was used subsequently.

(E)-(2-((2-methoxy-4-(3-((3-methylbut-2-en-1-yl)oxy)-5-(trifluoromethoxy)styryl)phenoxy)methoxy)ethyl)trimethylsilane (11-5)

(2-((2-Methoxy-4-vinylphenoxy)methoxy)ethyl)trimethylsilane (11-4, see 8-5 for prep) (4.30 g, 15.38 mmol, 1.0 equiv), triphenylphosphine (800 mg, 3.07 mmol, 0.2 equiv), potassium carbonate (4.25 g, 30.76 mmol, 2 equiv) and palladium acetate (350 mg, 1.6 mmol, 0.1 equiv) were added to a solution of compound 11-2 (5.0 g, 15.38 mmol, 1.0 equiv) in anhydrous toluene (150 mL) at room temperature. The reaction mixture was sparged with nitrogen for 15 minutes. After refluxing (110° C.) for 16 hours, the reaction mixture was cooled to room temperature and filtered through celite (~20 g). The filtrate was transferred to a separatory funnel containing saturated sodium bicarbonate (100 mL). The layers were separated and the aqueous layer was extracted with ethyl acetate (2×50 mL). The combined organic layers were dried over sodium sulfate, filtered and concentrated under reduced pressure. The residue was purified on a Reveleris automated chromatography system (Sorbtech 80 g column), eluting with a gradient of 0 to 20% ethyl acetate in heptanes to give compound 11-5 (4.89 g, 61% yield) as a light brown oil. (NRK-1-97)

(E)-2-methoxy-4-(3-((3-methylbut-2-en-1-yl)oxy)-5-(trifluoromethoxy)styryl)phenol (11-6)

1M Tetrabutylammonium fluoride solution in THF (66 mL, 65.24 mmol, 7 equiv) was added to a solution of compound 11-5 (4.89 g, 9.32 mmol, 1 equiv) in anhydrous THF (200 mL) at room temperature. After refluxing (66° C.) for 16 hours. LCMS analysis indicated that the reaction was complete. The mixture was cooled to room temperature and diluted with water (20 mL). The volatiles were removed under reduced pressure and the residue was diluted with ethyl acetate (150 mL). The layers were separated and the aqueous layer was extracted with ethyl acetate (2×100 mL). The combined organic layers were dried over sodium sulfate, filtered and concentrated under reduced pressure. The residue was purified on a Reveleris automated chromatography system (Sorbtech 80 g column), eluting with a gradient of 0 to 50% ethyl acetate in heptanes to give compound 11-6 (3.2 g, 87% yield) as a pale yellow oil. (NRK-1-98)

(E)-3-(4-hydroxy-3-methoxystyryl)-4-(3-methylbut-2-en-1-yl)-5-(trifluoromethoxy)phenol (11) [KYN-132]

Montmorillonite K30 powder (3.2 g) was added to a solution of Compound 11-6 (3.2 g, 8.89 mmol) in anhydrous dichloromethane (100 mL) at room temperature and the mixture was stirred at room temperature overnight. LCMS indicated that 10-15% of desired compound 11 was formed, along with two regio-isomers and unreacted starting compound 11-6 as by-products. The mixture was filtered and treated with fresh montmorillonite K30 powder (3.2 g) at room temperature for an additional 24 hours. The reaction mixture was filtered and solid was washed with dichloromethane (2×50 mL). The combined filtrate was concentrated under reduced pressure. The residue was first purified on a Reveleris automated chromatography system (Sorbtech 80 g column), eluting with a gradient of 0 to 20% ethyl acetate in heptanes to give several mixed fractions containing compound 11. The fractions were pooled together and the resulting material was purified on a Reveleris automated chromatography system (Redisep Rf Gold HP C18, 100 g column), eluting with a gradient of 0 to 80% acetonitrile in water. The product was triturated with 30% dichloromethane in heptanes (10 mL) to give pure compound 11 (60 mg, 1.7% yield) as a white solid. (NRK-1-99-C)

White solid, melting point 141.6-142.6° C.; HPLC Analysis: 98.81% purity; Wavelength 254 nm, bandwidth 4; Column: SorbTech C18AQ, 2.1×50 mm, 3 μm; Retention Time: 9.8 min; Mobile Phase: ACN/formic acid/water; Mass Spectrum (negative mode) m/z=393.0 $(M-H)^-$; $C_{21}H_{21}F_3O_4$; $^1H$ NMR (400 MHz, $CDCl_3$) δ=7.09 (d, J=15.9 Hz, 1H), 7.00 (dd, J=1.8, 7.1 Hz, 1H), 6.99 (br s, 1H), 6.99 (m, 1H), 6.92 (d, J=8.9 Hz, 1H), 6.87 (d, J=16.1 Hz, 1H), 6.69 (m, 1H), 5.07 (tm, J=6.9 Hz, 1H), 3.94 (s, 3H), 3.42 (d, J=6.9 Hz, 2H), 1.80 (s, 3H), 1.69 (s, 3H); $^{19}F$ NMR (376 MHz, $CDCl_3$) δ=−56.88 (s, 3F); $^{13}C$ NMR (100 MHz, $CDCl_3$) δ=153.95, 148.13, 146.73, 145.92, 139.81, 131.69, 131.66, 129.80, 124.31, 123.25, 122.29, 120.77, 114.64, 110.74, 108.43, 106.97, 55.90, 25.68, 25.02, 17.93.

Compound 11 (KYN-132) can also be synthesised by the modular methodology of the present disclosure using equivalents to Module A, B and C and subsequent cross coupling alkylation of the aryl halide.

Preparation of 3-(3-Ethoxy-4-hydroxystyryl)-5-methoxy-4-(3-methylbut-2-en-1-yl)phenol (12) [KYN-133]

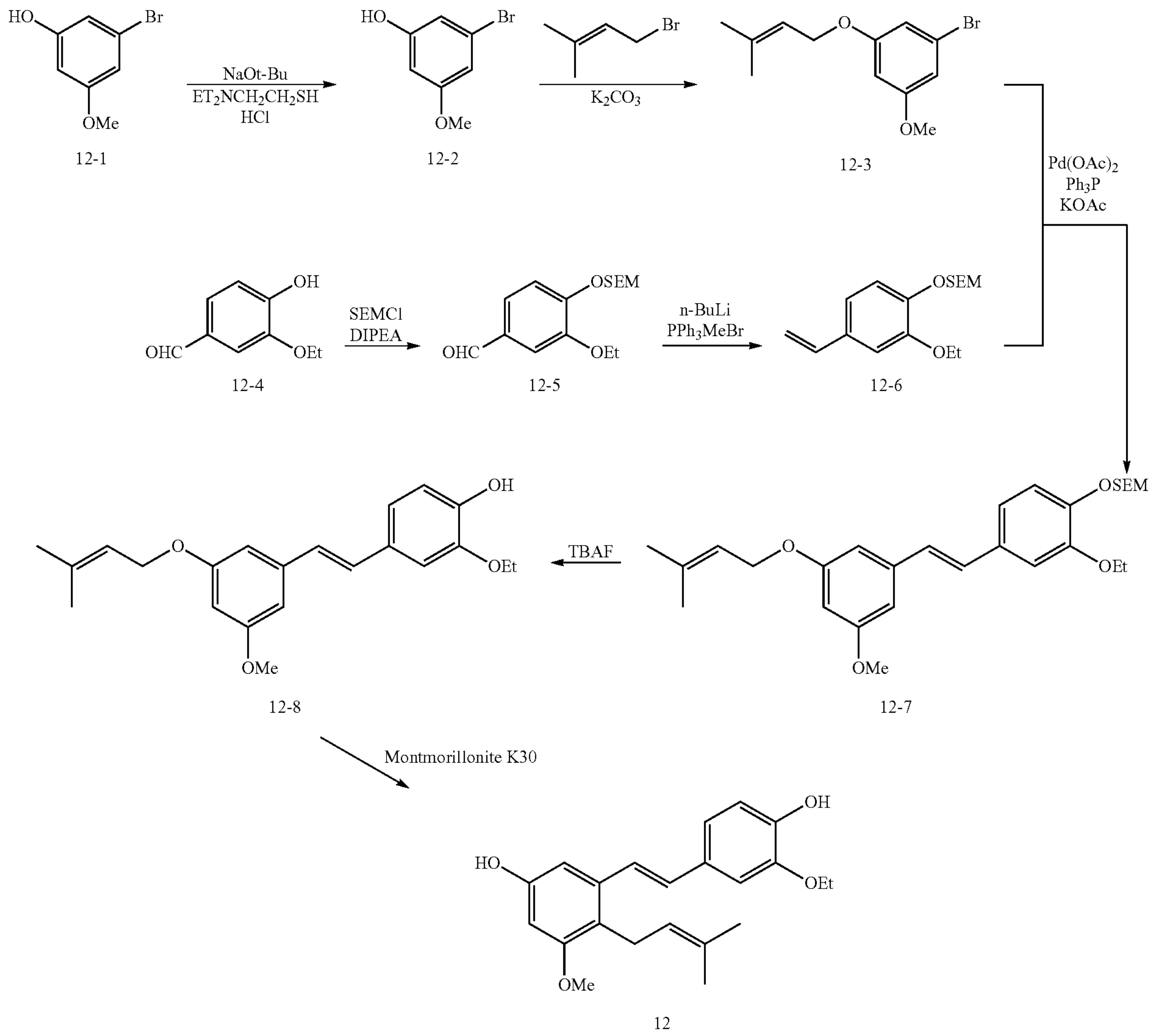

3-Bromo-5-methoxyphenol (12-2)

A mixture of 2-(diethylamino)ethanethiol hydrochloride (46.92 g, 276.5 mmol, 1.2 equiv) in DMF (1000 mL) was cooled in an ice-bath, and sodium I-butoxide (55.3 g, 576 mmol, 2.5 equiv) was added in portions while keeping the temperature below 25° C. After stirring for 5 minutes, the reaction was warmed to room temperature. After 5 minutes. Compound 12-1 (50 g, 230.4 mmol, 1.0 equiv) was added, and the mixture was refluxed (138° C.) for 3 hours at which time LCMS analysis indicated that the reaction was complete. The reaction mixture was cooled to 0° C. and adjusted to pH 1 with of 1M HCl (~1000 mL), while maintaining the temperature below 20° C. The mixture was extracted with ethyl acetate (4×1 L) and the combined organic layers were dried over sodium sulfate, filtered and concentrated under reduced pressure. Additional compound 1 (25 g) was processed in a similar way and combined with the above residue. The combined residue was purified on an Interchim automated chromatography system (Sorbtech 330 g column), eluting with a gradient of 10 to 20% ethyl acetate in heptanes to give Compound 12-2 (60 g, 86% yield) as a light brown solid. (NK-1-5)

1-Bromo-3-methoxy-5-((3-methylbut-2-en-1-yl)oxy)benzene (12-3)

Potassium carbonate powder (82 g, 594.20 mmol, 2 equiv) and 3,3-dimethylallyl bromide (53 g, 355.7 mmol, 1.2 equiv) were added sequentially to a solution of Compound 12-2 (60 g, 297.02 mmol, 1.0 equiv) in acetone (500 mL) at room temperature. After refluxing (55° C.) overnight, the reaction was cooled to room temperature and filtered. The filtrate was concentrated under reduced pressure and the residue was purified on an Interchim automated chromatography system (Sorbtech 220 g column), eluting with a gradient of 0 to 20% ethyl acetate in heptanes to give Compound 12-3 (60 g, 75% yield) as a light brown oil. (NK-1-8)

3-Ethoxy-4-((2-(trimethylsilyl)ethoxy)methoxy)benzaldehyde (12-5)

2-(Trimethylsilyl)ethoxymethyl chloride (3.4 mL, 19 mmol, 1.05 equiv) was added to a solution of Compound 12-4 (3 g, 18.1 mmol, 1 equiv) and N,N'-diisopropylethylamine (9.5 mL, 54.3 mmol, 3 equiv) in dichloromethane (60 mL) at room temperature. The reaction was stirred for 16 hours, at which point LC/MS analysis indicates the reaction was completed. The reaction mixture was washed sequentially with water (100 mL), saturated ammonium chloride (100 mL) and saturated brine (50 mL). The organic layer was dried over sodium sulfate, filtered and concentrated under reduced pressure to give Compound 12-5 (6 g, >theory) as an orange oil, which was used subsequently. (QZH-RCI-34).

(2-((2-Ethoxy-4-vinylphenoxy)methoxy)ethyl)trimethylsilane (12-6)

2.5 M n-Butyllithium in hexane (8 mL, 20 mmol, 1.1 equiv) was added to a mixture of methyltriphenylphosphonium bromide (7.1 g, 20 mmol, 1.1 equiv) in tetrahydrofuran (90 mL) at 0° C. After stirring for 30 minutes, a solution of Compound 12-5 (6 g, 18.1 mmol, 1 equiv) in tetrahydrofuran (20 mL) was added while at such a rate as to maintain the internal temperature of the reaction below 5° C. Hexane (150 mL) was added and the solid resulting solid was filtered. The filtrate was concentrated under reduced pressure. The residue was purified on a Büchi automated chromatography system (80 g column), eluting with a gradient of 0 to 30% ethyl acetate in heptanes to give Compound 12-6 (4.43 g, 84% yield) as a clear oil. (QZH-RCI-35).

((2-((2-Ethoxy-4-(3-methoxy-5-((3-methylbut-2-en-1-yl)oxy)styryl)phenoxy)methoxy)ethyl)trimethylsilane (12-7)

A mixture of Compound 12-6 (4.43 g, 15 mmol, 1 equiv), 1-bromo-3-methoxy-5-((3-methylbut-2-en-1-yl)oxy)benzene (12-3) (4.3 g, 15.8 mmol, 1.05 equiv), palladium(II) acetate (0.34 g, 1.5 mmol, 0.1 equiv), triphenylphosphine (0.79 g, 3 mmol, 0.2 equiv) and potassium carbonate (4.14 g, 30 mmol, 2 equiv) in toluene (130 mL) was sparged with nitrogen for ten minutes. After refluxing for 16 hours, the reaction was cooled to room temperature and diluted with heptanes (150 mL). The solids were removed by filtration and discarded. The filtrate was concentrated under reduced pressure and the residue was purified on a Büchi automated chromatography system (120 g column), eluting with a gradient of 0 to 25% ethyl acetate in heptanes to give Compound 12-7 (3.18 g, 44% yield) as a brown oil. (QZH-RCI-37).

2-Ethoxy-4-(3-methoxy-5-((3-methylbut-2-en-1-yl)oxy)styryl)phenol (12-8)

A solution of Compound 12-7 (3.18 g, 6.56 mmol, 1 equiv) and 1.0 M tetrabutylammonium fluoride in tetrahydrofuran (45.9 mL, 45.9 mmol, 7 equiv) in tetrahydrofuran (32 mL) was refluxed overnight. After cooling to room temperature, water (100 mL) and saturated ammonium chloride (200 mL) was added. The reaction mixture was extracted with ethyl acetate (3×100 mL). The combined organic layers were washed with saturated brine (50 mL), dried over sodium sulfate and concentrated under reduced pressure. The residue was purified on a Büchi automated chromatography system (24 g column), eluting with a gradient of 0 to 35% ethyl acetate in heptanes to give Compound 12-8 (1.76 g, 76% yield) as a yellow oil. (QZH-RCI-38).

3-(3-Ethoxy-4-hydroxystyryl)-5-methoxy-4-(3-methylbut-2-en-1-yl)phenol (12) (KYN-133)

Montmorillonite K10 powder (1.76 g, Sigma-Aldrich, catalog #69866) was added to a solution of Compound 12-8 (1.76 g, 4.96 mmol, 1 equiv) in anhydrous dichloromethane (10 mL). The reaction was stirred at room temperature for 24 hours, at which point the LC/MS analysis indicates >90% conversion of the starting material. The reaction mixture was directly absorbed on Celite (25 g) and purified on a Büchi automated chromatography system (80 g column), eluting with a gradient of 0 to 35% ethyl acetate in heptanes to give Compound 12 [KYN-133] (0.17 g, 10% yield, 99.4% purity by HPLC %) as an off-white solid. (QZH-RCI-38).

Off-white solid, melting point 126.6-129.1° C.; HPLC Analysis: 99.4% purity; Wavelength 254 nm, bandwidth 4; Column: SorbTech C18AQ, 2.1×50 mm, 3 μm; Retention Time: 9.1 min; Mobile Phase: ACN/formic acid/water; Mass Spectrum (positive mode) m/z=355.2 $(M+H)^+$; $C_{22}H_{26}O_4$; $^1H$ NMR (400 MHz, $CDCl_3$) δ=7.12 (d, J=16.2 Hz, 1H), 6.98 (s, 1H), 6.97 (dd, J=2.0, 8.5 Hz, 1H), 6.90 (dm, J=8.6 Hz, 1H), 6.82 (d, J=15.9 Hz, 1H), 6.64 (d, J=2.4 Hz, 1H), 6.34 (d, J=2.4 Hz, 1H), 5.74 (s, 1H), 5.13 (tm, J=1.4, 6.9 Hz, 1H), 4.85 (s, 1H), 4.14 (q, J=6.9 Hz, 2H), 3.78 (s, 3H), 3.40 (d, J=6.9 Hz, 2H), 1.80 (d, J=0.8 Hz, 3H), 1.67 (d, J=1.2 Hz, 3H), 1.46 (t, J=7.1 Hz, 3H); $^{13}C$ NMR (100 MHz, $CDCl_3$) δ=158.54, 154.34, 145.93, 145.65, 138.17, 130.58, 130.46, 130.24, 124.19, 123.66, 120.71, 120.44, 114.50, 109.28, 103.94, 98.23, 64.49, 55.68, 25.74, 24.45, 17.93, 14.87.

The compound 12 (KYN-133) can also be synthesised by the modular methodology of the present disclosure using equivalents to Module A, B and C and subsequent cross coupling alkylation of the aryl halide.

Preparation of (E)-3-(3-Ethyl-4-hydroxystyryl)-5-methoxy-4-(3-methylbut-2-en-1-yl)phenol (13) [KYN-114]

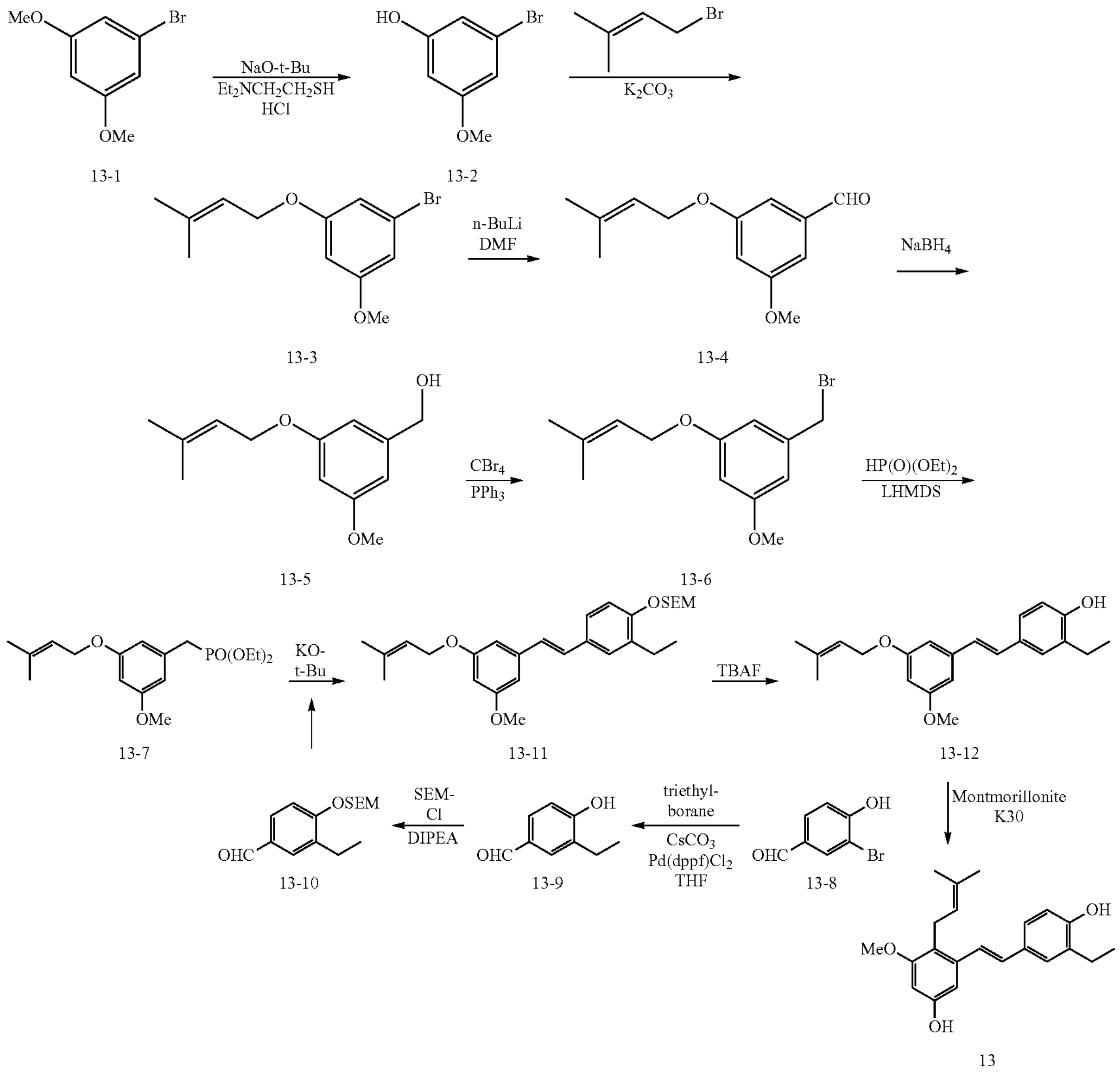

3-Bromo-5-methoxyphenol (13-2)

Sodium t-butoxide (332.05 g, 3455.3 mmol, 2.5 equiv) was added in portions while keeping the temperature below 25° C. to a mixture of 2-(diethylamino)ethanethiol hydrochloride (281.48 g, 1658.5 mmol, 1.2 equiv) in DMF (3000 mL) in an ice-bath. After 5 minutes, the reaction was warmed to room temperature and stirred an additional 5 minutes. Compound 13-1 (300 g, 1382.1 mmol, 1.0 equiv) was added and the mixture was refluxed (138° C.) for 3 hours, at which time LCMS indicated that the reaction was complete. After cooling to room temperature, the mixture was cooled in an ice-bath and 1M HCl (~30001 mL) was added adjusting to pH 1. The mixture was extracted with ethyl acetate (3x5 L) and the combined organic layers were washed with saturated brine (4 L), dried over sodium sulfate, filtered, and concentrated under reduced pressure. The residue was purified over silica gel (2.6 kg), eluting with a gradient of 0 to 25% ethyl acetate in heptanes to give compound 13-2 (257.1 g, 92% yield) as a brown solid. (GB-27-172)

1-Bromo-3-methoxy-5-((3-methylbut-2-en-1-yl)oxy)benzene (13-3)

Powdered potassium carbonate\(350.0 g, 2532.5 mmol, 2 equiv) and 3,3-dimethylallyl bromide (226.45 g, 1519.5 mmol, 1.2 equiv) were added sequentially to a solution of compound 13-2 (257.1 g, 1266.2 mmol, 1.0 equiv) in acetone (7500 mL) at room temperature. After refluxing overnight, the reaction was cooled to room temperature and filtered. The filtrate was concentrated under reduced pressure and the residue was purified on a Biotage-150 column, eluting with a gradient of 0 to 10% ethyl acetate in heptanes to give compound 13-3 (358.0 g, >100% yield) as a brown oil. (GB-27-174)

3-Methoxy-5-((3-methylbut-2-en-1-yl)oxy)benzaldehyde (13-4): 2.5M n-Butyllithium in hexanes (557 mL, 1392.6 mmol, 1.1 equiv) was added dropwise, while keeping the temperature below −70° C., to a solution of compound 13-3 (358.0 g, ~1266.2 mmol, 1.0 equiv) in anhydrous THF (7000 mL) at −75° C. After stirring at −75° C. for 30 minutes, anhydrous DMF (147 mL, 1899.0 mmol, 1.5 equiv) was added dropwise while keeping the temperature below −70° C. The resulting mixture was allowed to slowly warm to room temperature overnight. Ice-cold water (500 mL) was added to quench the reaction. The mixture was diluted with ethyl acetate (5 L) and the layers were separated. The organic layer was washed with saturated brine (500 mL). The combined aqueous layers were extracted with ethyl acetate (2×500 mL). The combined organic layers were dried over sodium sulfate, filtered and concentrated under reduced pressure. The residue was purified on a Biotage-150 column, eluting with a gradient of 0 to 20% ethyl acetate in heptanes to give compound 13-4 (221.5 g, 79% overall yield for two steps) as a yellow oil. (GB-27-175)

(3-Methoxy-5-((3-methylbut-2-en-1-yl)oxy)phenyl) methanol (13-5)

Sodium borohydride (38.04 g, 1005.6 mmol, 1.0 equiv) was added in portions, while keeping the temperature below 10° C., to a solution of compound 13-4 (221.5 g, 1005.6 mmol, 1.0 equiv) in methanol (3500 mL) at 0° C. After stirring at 5-10° C. for 1 hour, water (200 mL) was added to quench the reaction. The mixture was concentrated under reduced pressure to remove most of methanol. The residue was diluted with ethyl acetate (2.5 L) and washed with saturated brine (600 mL). The aqueous layer was extracted with ethyl acetate (2×500 mL). The combined organic layers were dried over sodium sulfate, filtered and concentrated under reduced pressure to give compound 13-5 (218.61 g, 98% yield) as a yellow oil, which was used subsequently. (GB-27-178)

1-(Bromomethyl)-3-methoxy-5-((3-methylbut-2-en-1-yl)oxy)benzene (13-6)

Carbon tetrabromide (358.76 g, 1081.84 mmol, 1.1 equiv) was added to a solution of compound 13-5 (218.61 g, 983.49 mmol, 1.0 equiv) in dichloromethane (4400 mL) at room temperature. The resulting mixture was cooled to 0° C., and triphenylphosphine (283.76 g, 1081.84 mmol, 1.1 equiv) was added in portions. After stirring at room temperature for 4 hours, the mixture was concentrated under reduced pressure. The residue was purified on a Biotage-150 column, eluting with a gradient of 0 to 10% ethyl acetate in heptanes to give compound 13-6 (273.76 g, 97% yield) as a yellow oil. (GB-27-181) Note: Compound 13-6 appears unstable when purified on some prepacked silica gel columns.

Diethyl (3-methoxy-5-((3-methylbut-2-en-1-yl)oxy) benzyl)phosphonate (13-7)

1M lithium hexamethyldisilylazide in THF (6.57 mL, 6.57 mmol, 1.8 equiv) was added to a solution of diethyl phosphite (0.94 mL, 7.3 mmol, 2.0 equiv) in anhydrous THF (20 mL) at 0° C. After stirring at 0° C. for 30 minutes, a solution of compound 13-6 (1.04 g, 3.65 mmol, 1.0 equiv) in anhydrous THF (10 mL) was added and the mixture was stirred at room temperature overnight. The reaction was quenched with water (30 mL) and the mixture was washed with saturated brine (30 mL). The aqueous layer was extracted with ethyl acetate (2×60 mL). The combined organic layers were dried over sodium sulfate, filtered and concentrated under reduced pressure. The residue was purified on an Interchim automated chromatography system (400 g column), eluting with a gradient of 0 to 10% methanol in dichloromethane to give compound 13-7 (1.10 g, 88% yield) as a brown oil. (LM-1-41)

3-Ethyl-4-hydroxybenzaldehyde (13-9): [1,1'-Bis(diphenylphosphino)ferrocene]dichloropalladium(II) (2.18 g, 2.98 mmol, 0.05 equiv) and cesium carbonate (38.9 g, 119.4 mmol, 2 equiv) were added to a solution of 3-bromo-4-hydroxylbenzaldehyde (13-8) (12 g, 59.7 mmol, 1 equiv) in anhydrous THF (150 mL). 1M Triethylborane solution in THF (119.4 mL, 119.4 mmol, 1.8 equiv) was added and the mixture was refluxed (66° C.) overnight. After cooling room temperature, the reaction was diluted with water (100 mL) and extracted with ethyl acetate (2×250 mL). The combined organic layers were washed with saturated brine (200 mL), dried over sodium sulfate, and concentrated under reduced pressure. Crude residue was purified initially on an InterChim Automated Chromatography System (220 g column), eluting with a gradient of 0 to 40% ethyl acetate in heptanes. A second purification on an InterChim Automated Chromatography System (80 g column), eluting with a gradient of 0 to 40% ethyl acetate in heptanes to give compound 13-9 (5.21 g, 58% yield) as a brown oil. (LM-1-2)

3-Ethyl-4-((2-(trimethylsilyl)ethoxy)methoxy)benzaldehyde (13-10): 2-(Trimethylsilyl)ethoxymethylchloride (6.1 mL, 34.52 mmol, 1.1 equiv) was added to a solution of compound 13-9 (4.71 g, 31.38 mmol, 1 equiv) in anhydrous dichloromethane (120 mL). Diisopropylethylamine (8.2 mL, 47.07 mmol, 1.5 equiv) was added and the mixture was stirred for 2 hours at room temperature. The reaction mixture was quenched with saturated sodium bicarbonate (50 mL) and extracted with ethyl acetate (2×100 mL). The combined organic layers were dried over sodium sulfate and concentrated under reduced pressure. The crude residue was purified initially on an InterChim Automated Chromatography System (220 g column), eluting with a gradient of 0 to 20% ethyl acetate in heptanes. A second purification on an InterChim Automated Chromatography System (120 g column), eluting with a gradient of 0 to 20% ethyl acetate in heptanes to give compound 13-10 (6.77 g, 77% yield) as a clear oil. (LM-1-4)

(E)-(2-((2-Ethyl-4-(3-methoxy-5-((3-methylbut-2-en-1-yl)oxy)styryl)phenoxy)methoxy)ethyl)trimethylsilane (13-11)

1.0M Potassium t-butoxide solution in THF (11.7 mL, 11.68 mmol, 2 equiv) was added dropwise to a cooled solution of diethyl (3-methoxy-5-((3-methylbut-2-en-1-yl)oxy)benzyl)phosphonate (13-7) (2 g, 5.84 mmol, 1 equiv) in anhydrous THF (20 mL) at 0° C. After stirring for 15 minutes at room temperature, a solution of compound 9 (2.5 g, 8.76 mmol, 1.5 equiv) in anhydrous THF (5 mL) was added dropwise. The reaction mixture was stirred overnight at room temperature then quenched with saturated brine (50 mL) and extracted with ethyl acetate (200 mL). The organic layer was dried over sodium sulfate and concentrated under reduced pressure. The crude residue was purified on an Interchim Automated Chromatography System (80 g column), eluting with a gradient of 0 to 30% ethyl acetate in heptanes to give compound 13-11 (1.32 g, 48% yield) as a clear oil. (CSK-2-97)

(E)-2-Ethyl-4-(3-methoxy-5-((3-methylbut-2-en-1-yl)oxy)styryl)phenol (13-12)

1.0M Tetrabutylammonium fluoride in THF (19.7 mL, 19.7 mmol, 7 equiv) was added to a solution of compound 13-11 (1.32 g, 2.81 mmol, 1 equiv) in anhydrous THF (20 mL) and resulting mixture was refluxed overnight. Reaction mixture was cooled to room temperature and diluted with water (25 mL). The mixture was extracted with ethyl acetate (100 mL). The organic layer was washed with saturated brine (25 mL), dried over sodium sulfate, and concentrated under reduced pressure. The crude residue was purified initially on an InterChim Automated Chromatography System (80 g column), eluting with a gradient of 0 to 100% ethyl acetate in heptanes. A second purification on an InterChim Automated Chromatography System (40 g column), eluting with a gradient of 0 to 30% ethyl acetate in heptanes gave compound 13-12 (770 mg, 80% yield) as a thick clear oil. (CSK-2-98)

(E)-3-(3-Ethyl-4-hydroxystyryl)-5-methoxy-4-(3-methylbut-2-en-1-yl)phenol (13) [KYN-114]

Montmorillonite K30 (620 mg) was added to a solution of compound 13-12 (620 mg, 1.83 mmol, 1 equiv) in anhydrous dichloromethane (12 mL) and resulting mixture was stirred at room temperature overnight. Mixture was filtered through a Celite pad, which was rinsed with dichloromethane (50 mL). The filtrate was concentrated under reduced pressure. The crude residue was purified on an Interchim Automated Chromatography System (25 g column) eluting with a gradient of 0 to 30% ethyl acetate in heptanes to give compound 13 [KYN-114] (120 mg, 19% yield) as an off-white solid. (CSK-2-99) $^{1}H$ NMR (400) MHz, Methanol-$d_3$) δ=7.22 (d, J=2.2 Hz, 1H), 7.13 (dd, J=2.0, 8.3 Hz, 1H), 7.11 (d, J=16.1 Hz, 1H), 6.83 (d, J=16.1 Hz, 1H), 6.72 (d, J=8.3 Hz, 1H), 6.63 (d, J=2.2 Hz, 1H), 6.33 (d, J=2.2 Hz, 1H), 5.06 (septett, J=1.4, 6.8 Hz, 1H), 3.77 (s, 3H), 3.37 (br d, J=6.6 Hz, 2H), 2.62 (q, J=7.5 Hz, 2H), 1.80 (d, J=1.0 Hz, 3H), 1.67 (d, J=1.2 Hz, 3H), 1.21 (t, J=7.5 Hz, 3H); $^{13}C$ NMR (100 MHz, Methanol-$d_3$) δ=159.69, 157.12, 156.09, 139.51, 131.92, 131.12, 130.70, 128.30, 126.20, 125.49, 124.54, 115.95, 104.67, 98.95, 55.96, 25.87, 25.09, 24.26, 18.06, 14.68.

The compound of KYN-114 can also be synthesised by the modular methodology of the present disclosure using equivalents to Module A, B and C and subsequent cross coupling alkylation of the aryl halide.

Preparation of (E)-3-(4-hydroxy-3-(methylthio)styryl)-5-methoxy-4-(3-methylbut-2-en-1-yl)phenol (14) [KYN-118]

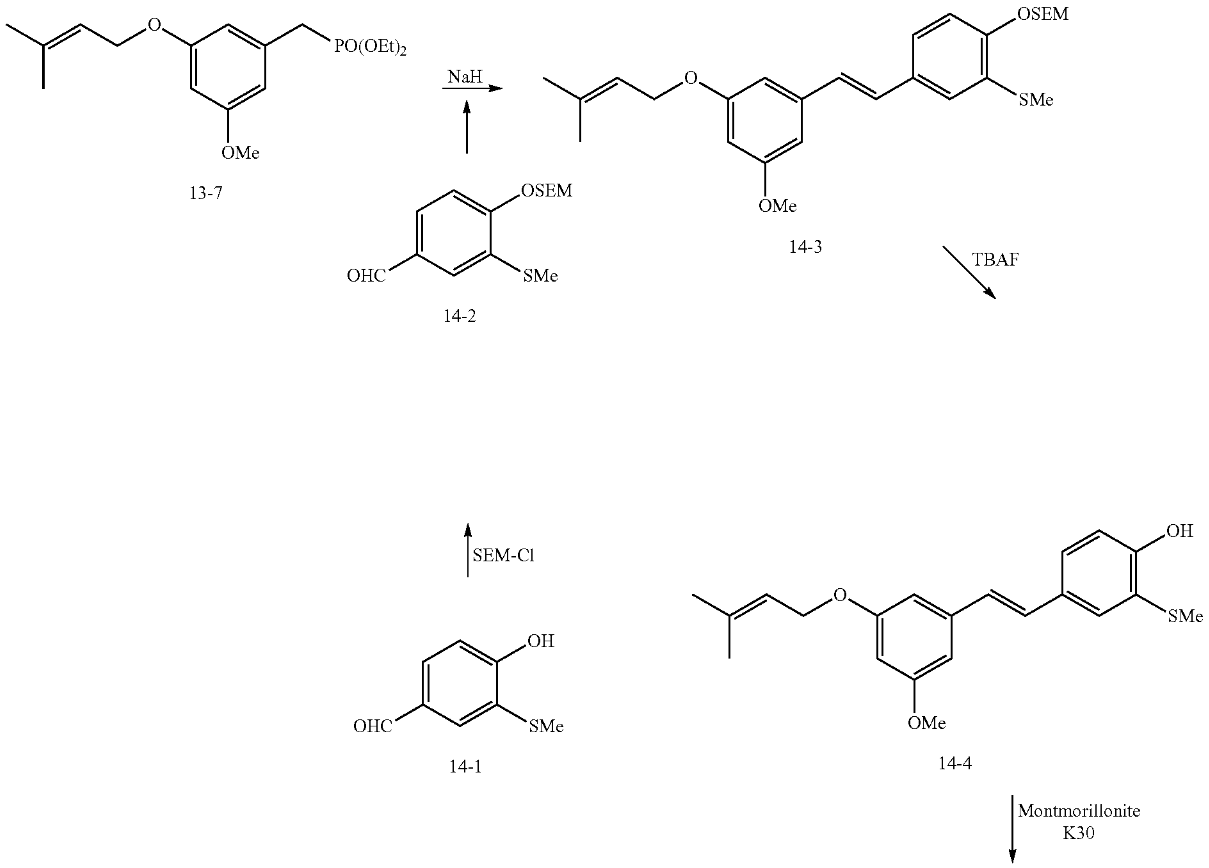

13-7 14-2 14-3 14-1 14-4

-continued

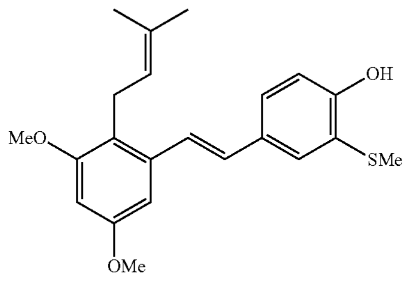

14

3-(Methylthio)-4-((2-(trimethylsilyl)ethoxy)methoxy)benzaldehyde (14-2)

N,N-Diisopropylethylamine (0.78 mL, 4.46 mmol, 1.5 equiv) and 2-(trimethylsilyl)ethoxymethyl chloride (0.63 mL, 3.57 mmol, 1.2 equiv) were added sequentially to a solution of compound 14-1 (0.50 g, 2.97 mmol, 1.0 equiv) in anhydrous dichloromethane (30 mL) at room temperature and stirred at room temperature overnight. Another reaction of equal scale was combined and quenched with saturated sodium bicarbonate (50 mL). The layers were separated and the aqueous layer was extracted with dichloromethane (2×50 mL). The combined organic layers were dried over sodium sulfate, filtered and concentrated under reduced pressure. The residue was purified on an Interchim automated chromatography system (80 g column), eluting with a gradient of 0 to 20% ethyl acetate in heptanes to give compound 14-2 (1.67 g, 94% yield) as a pale yellow oil. (LM-1-39 and LM-1-40)

(E)-(2-((4-(3-Methoxy-5-((3-methylbut-2-en-1-yl)oxy)styryl)-2-(methylthio)phenoxy)methoxy)ethyl)trimethylsilane (14-3)

A solution of compound 13-7 (1.1 g, 3.2 mmol, 1.0 equiv) in anhydrous THF (10 mL) was added dropwise to 60% dispersion of sodium hydride in mineral oil (257 mg, 6.4 mmol, 2.0 equiv) in anhydrous THE (20 mL) at 0° C. The mixture was warmed to room temperature and stirred for 30 minutes. A solution of compound 14.2 (0.955 g, 3.2 mmol, 1.0 equiv) in anhydrous THF (10 mL) was then added dropwise and the mixture was stirred at room temperature overnight. The reaction was quenched with water (30 mL) and the mixture was washed with saturated brine (70 mL).

The aqueous layer was extracted with ethyl acetate (2×100 mL). The combined organic layers were dried over sodium sulfate, filtered and concentrated under reduced pressure. The residue was purified on an Interchim automated chromatography system (40 g column), eluting with a gradient of 0 to 20% ethyl acetate in heptanes to give compound 14-3 (1.01 g, 79% yield based on 0.17 g recovered starting material compound 14.2) as a yellow oil. (LM-1-42)

(E)-4-(3-Methoxy-5-((3-methylbut-2-en-1-yl)oxy)styryl)-2-(methylthio)phenol (14.4)

1M Tetrabutylammonium fluoride in THF (7 mL, 7 mmol, 7 equiv) was added to a solution of compound 14.3 (0.486 g, 1.0 mmol, 1.0 equiv) in anhydrous THF (10 mL) at room temperature. After refluxing overnight, the mixture was cooled to room temperature and diluted with water (20 mL) and ethyl acetate (50 mL). The layers were separated and the organic layer was washed with saturated brine (30 mL). The combined aqueous layers were extracted with ethyl acetate (2×50 mL). The combined organic layers were dried over sodium sulfate, filtered and concentrated under reduced pressure. The residue was purified on an Interchim automated chromatography system (25 g column), eluting with a gradient of 0 to 30% ethyl acetate in heptanes to give compound 14.4 (0.25 g, 70% yield) as a brown oil. (LM-1-43)

(E)-3-(4-Hydroxy-3-(methylthio)styryl)-5-methoxy-4-(3-methylbut-2-en-1-yl)phenol (14): Montmorillonite K30 powder (Aldrich #69866, 0.25 g) was added to a solution of compound 14.4 (0.25 g, 0.7 mmol) in anhydrous dichloromethane (15 mL) at room temperature, and the mixture was stirred at room temperature overnight, at which point LCMS indicated that the reaction was complete. The mixture was filtered and the solid rinsed with dichloromethane (2×15 mL). The combined filtrate was concentrated under reduced pressure. The residue was purified on an Interchim automated chromatography system (25 g column, 20-45 um), eluting with a gradient of 0 to 40% ethyl acetate in heptanes to give a mixture of compounds 14A, 14B and 14 (0.18 g, 70% combined yield). (LM-1-44)

Additional compound 14-4 (0.27 g) of 11 used) was processed in same manner, and to give a mixture of compounds 14A, 14B and 14 (0.22 g, 81% combined yield). (LM-1-46)

Crude compounds 14A, 14B and 14 (LM-1-44 and LM-1-46) were further purified on an Interchim automated chromatography system (25 g column, 20-45 um), eluting with a gradient of 0 to 40% ethyl acetate in heptanes to give compound 14B (50 mg, 10% yield) as a pale-yellow solid, compound 14B (100 mg, 19% yield) as a pale-yellow solid and compound 14 (170 mg, 33% yield) as a white solid. (LM-1-54A, LM-1-54B and LM-1-54C). Note: The three compounds structures were determined at the University of Florida by NMR.

Compound 14 can also be synthesised by the modular methodology of the present disclosure using equivalents to Module A, B and C and subsequent cross coupling alkylation of the aryl halide.

(E)-3-(4-Hydroxy-3-(methylthio)styryl)-5-methoxy-4-(3-methylbut-2-en-1-yl)phenol (14) [KYN-118]

White solid, melting point 124.5-125.2° C.; HPLC Analysis: 98.9% purity; Wavelength 254 nm, bandwidth 4; Column: SorbTech C18AQ, 2.1×50 mm, 3 μm; Retention Time: 9.00 min; Mobile Phase: ACN/formic acid/water; Mass Spectrum (positive mode) m/z=357.1 $(M+H)^+$; $C_{21}H_{24}O_3S$; $^1H$ NMR (400 MHz, $CDCl_3$) δ=7.60 (d, J=2.2 Hz, 1H), 7.37 (dd, J=2.2, 8.3 Hz, 1H), 7.17 (d, J=16.2 Hz, 1H), 6.98 (d, J=8.3 Hz, 1H), 6.82 (d, J=16.1 Hz, 1H), 6.66 (s, 1H), 6.65 (d, J=2.5 Hz, 1H), 6.36 (d, J=2.5 Hz, 1H), 5.11 (septett, J=1.3, 6.8 Hz, 1H), 4.71 (br s, 1H), 3.80 (s, 3H), 3.41 (br d, J=6.8 Hz, 2H), 2.36 (s, 3H), 1.81 (d, J=1.0 Hz, 3H), 1.68 (d, J=1.2 Hz, 3H); $^{13}C$ NMR (100 MHz, $CDCl_3$) δ=158.61, 155.89, 154.39, 138.04, 132.98, 131.00, 130.83, 129.29, 128.98, 125.01, 123.58, 121.37, 120.92, 115.13, 103.93, 98.39, 55.74, 25.79, 24.47, 19.90, 17.98.

(E)-3-(4-Hydroxy-3-(methylamino)styryl)-5-methoxy-4-(3-methylbut-2-en-1-yl)phenol (15) [KYN-158]

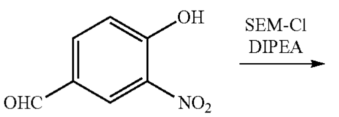

15-1

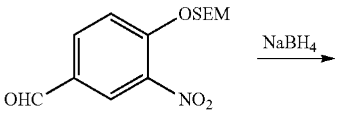

15-2

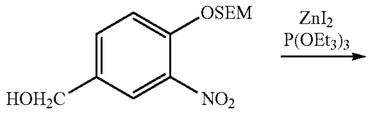

15-3

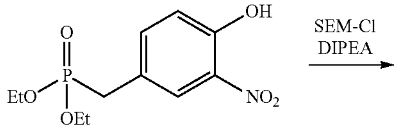

15-4

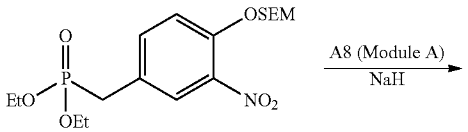

15-5

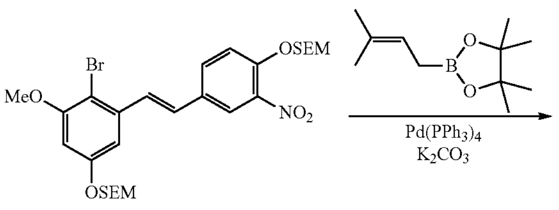

15-6

-continued

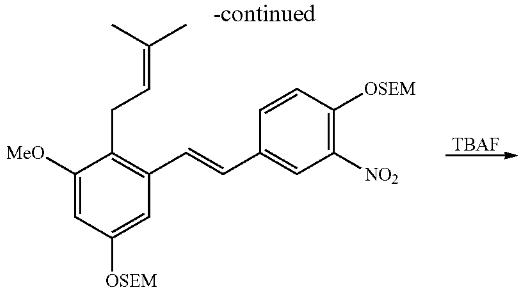

15-7

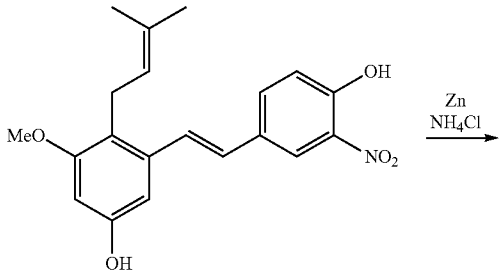

15-8

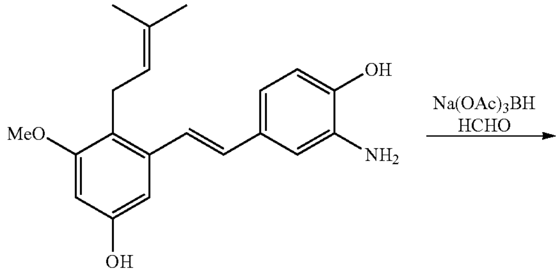

15-9

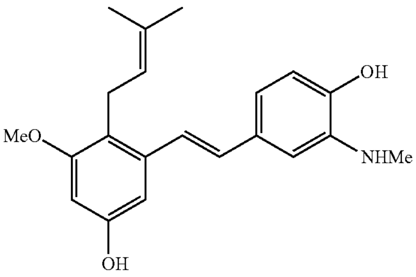

15

3-Nitro-4-((2-(trimethylsilyl)ethoxy)methoxy)benzaldehyde (15-2)

2-(Trimethylsilyl)ethoxymethyl chloride (17.9 g, 166.70 mmol, 1.2 equiv) and N,N-diisopropylethylamine (24.0 mL, 134.73 mmol, 1.5 equiv) were sequentially added to a solution of compound 15-1 (15.0 g, 89.82 mmol, 1.0 equiv) in dichloromethane (150 mL) at room temperature. After stirring for 16 hours, the reaction mixture was diluted with saturated sodium bicarbonate (150 mL). The layers were separated and the aqueous layer was extracted with dichloromethane (2×100 mL). The combined organic layers were dried over sodium sulfate, filtered and concentrated under reduced pressure. The residue was purified on a Reveleris automated chromatography system (Sorbtech 80 g column), eluting with a gradient of 0 to 20% ethyl acetate in heptanes to give compound 15-2 (23.5 g, 88% yield) as a yellow oil (NRK-1-179).

(3-Nitro-4-((2-(trimethylsilyl)ethoxy)methoxy)phenyl)methanol (15-3)

Sodium borohydride (2.92 g, 79.12 mmol, 1.0 equiv) was added in two portions to a solution of compound 15-2 (23.5 g, 79.12 mmol, 1.0 equiv) in methanol at 0° C. The resulting solution was stirred at room temperature for 1 hour. The reaction mixture was quenched with water (20 mL). The volatiles were removed under reduced pressure and the resulting crude residue was dissolved in ethyl acetate (150 mL) and washed with saturated ammonium chloride (100 mL). The aqueous layer was extracted with ethyl acetate (2×100 mL). The combined organic layers were dried over sodium sulfate and evaporated under reduced pressure to give compound 15-3 (23.7 g, 99% yield) as an orange oil, which was used subsequently. (NRK-1-120)

Diethyl (4-hydroxy-3-nitrobenzyl)phosphonate (15-4)

Zinc iodide (21.31 g, 66.80 mmol, 2.0 equiv) was added to triethylphosphite (11.5 mL, 66.80 mmol, 2.0 equiv). After stirring for 15 minutes at room temperature a solution of compound 15-3 (10.0 g, 33.40 mmol, 1.0 equiv) in anhydrous tetrahydrofuran (100 mL) was added. The resulting solution was refluxed (66° C.) for 4 hours. After cooling to room temperature, the volatiles were removed under reduced pressure. The crude residue was dissolved in ethyl acetate (150 mL) and washed with 1M sodium hydroxide (150 mL). The aqueous layer was neutralized with 1M HCL (250 mL). The resulting aqueous layer was extracted with ethyl acetate (3×200 mL). The combined organic layers were dried over sodium sulfate and evaporated under reduced pressure to give compound 15-4 (7.12 g, 76% yield) as a yellow oil, which was used subsequently. (NRK-1-187)

Diethyl (3-nitro-4-((2-(trimethylsilyl)ethoxy)methoxy)benzyl)phosphonate (15-5)

2-(Trimethylsilyl)ethoxymethyl chloride (4.1 g, 24.63 mmol, 1.0 equiv) and N,N-diisopropylethylamine (6.5 mL, 36.94 mmol, 1.5 equiv) were sequentially added to a solution of compound 15-4 (7.12 g, 24.63 mmol, 1.0 equiv) in dichloromethane (100 mL) at room temperature. After stirring for 20 hours, the reaction mixture was diluted with saturated sodium bicarbonate (100 mL). The layers were separated and the aqueous layer was extracted with dichloromethane (2×50 mL).—The combined organic layers were dried over sodium sulfate, filtered and concentrated under reduced pressure to give compound 15-5 (9.45 g, 92% yield) as a yellow oil, which was used subsequently. (NRK-1-189)

(E)-(2-((4-(2-Bromo-3-methoxy-5-((2-(trimethylsilyl)ethoxy)methoxy)styryl)-2-nitrophenoxy)methoxy)ethyl)trimethylsilane (15-6)

A 60% dispersion of sodium hydride in mineral oil (3.6 g, 90.24 mmol, 4 equiv) was added in 5 portions to a solution of compound 15-5 (9.45 g, 22.56 mmol, 1.0 equiv) in anhydrous tetrahydrofuran (100 mL) at 0° C. The mixture was warmed up to room temperature and stirred for 30 minutes. A solution of A8 (Module A) (8.15 g, 22.56 mmol, 1 equiv) in anhydrous tetrahydrofuran (20 mL) was added dropwise and the mixture was stirred at room temperature for 16 hours. The reaction was carefully quenched with saturated brine (20 mL, 1 drop per minute for the first 5 mL brine) at 0° C. The volatiles were removed under reduced pressure. Saturated ammonium chloride (100 mL) was added. The mixture was extracted with ethyl acetate (2×50 mL). The combined organic layers were dried over sodium sulfate, filtered and concentrated under reduced pressure. The residue was first purified on a Reveleris automated chromatography system (Sorbtech 330 g column), eluting with a gradient of 0 to 10% ethyl acetate in heptanes. The product was further purified on a Reveleris automated chromatography system (Sorbtech 330 g column) eluting with a gradient of 0 to 10% ethyl acetate in heptanes to give compound 15-6 (1.63 g, 12% yield) as a yellow oil. (NRK-1-190)

(E)-(2-((4-(3-Methoxy-2-(3-methylbut-2-en-1-yl)-5-((2-(trimethylsilyl)ethoxy)methoxy)styryl)-2-nitrophenoxy)methoxy)ethyl)trimethylsilane (15-7)

Tetrakis(triphenylphosphine)palladium(0) (300 mg, 0.26 mmol, 0.1 equiv), potassium carbonate (710 mg, 5.2 mmol, 2 equiv), 3-methylbut-2-enylboronic acid pinacol ester (1.01 g, 5.2 mmol, 2 equiv) and water (2 mL) were added sequentially to a solution of compound 15-6 (1.6 g, 2.60 mmol, 1 equiv) in 1,4-dioxane (20 mL) in a sealed tube. After sparging with nitrogen for 10 minutes, the reaction was heated at 100° C. for 16 hours. After cooling to room temperature, the reaction mixture was filtered through Celite. The filtrate was evaporated under reduced pressure. The residue was suspended in saturated sodium bicarbonate (100 mL) and extracted with ethyl acetate (3×50 mL). The combined organic layers were dried over sodium sulfate, filtered and concentrated under reduced pressure. The residue was purified on a Reveleris automated chromatography system (Sorbtech 80 g column), eluting with a gradient of 0 to 10% ethyl acetate in heptanes to give compound 15-7 (1.8 g, >100% yield) as an orange oil. (NRK-6-25)

(E)-3-(4-Hydroxy-3-nitrostyryl)-5-methoxy-4-(3-methylbut-2-en-1-yl)phenol (15-8)

1M Tetrabutylammonium fluoride in tetrahydrofuran (41 mL, 40.92 mmol, 14 equiv) was added to a solution of compound 15-7 (1.8 g, 2.92 mmol, 1 equiv) in tetrahydrofuran (20 mL) at room temperature. After heating at 67° C. for 16 hours, the mixture was cooled to room temperature and diluted with water (20 mL) and saturated ammonium chloride (100 mL). The volatiles were removed under reduced pressure and the remaining aqueous layer was extracted with ethyl acetate (2×50 mL). The combined organic layers were dried over sodium sulfate, filtered and concentrated under reduced pressure. The residue was purified on a Reveleris automated chromatography system (Sorbtech 80 g column), eluting with a gradient of 0 to 80% ethyl acetate in heptanes to give compound 15-8 (370 mg, 36% yield) as a yellow solid. (NRK-6-26)

(E)-3-(3-Amino-4-hydroxystyryl)-5-methoxy-4-(3-methylbut-2-en-1-yl)phenol (15-9)

Activated zinc powder (680 mg, 10.4 mmol, 10.0 equiv), ammonium chloride (560 mg, 10.4 mmol, 10.0 equiv) and water (6 mL) were added sequentially to a solution of compound 15-8 (370 mg, 1.04 mmol, 1.0 equiv) in tetrahydrofuran (20 mL) at room temperature. The resulting suspension was stirred at room temperature for 16 hours. The suspension was filtered through Celite and the solids were washed with ethyl acetate (20 mL). The filtrate was evaporated to dryness under reduced pressure. The residue was suspended in saturated ammonium chloride (50 mL) and extracted with ethyl acetate (2×30 mL). The combined organic layers were dried over sodium sulfate, filtered and concentrated under reduced pressure to give compound 15-9 (270 mg, 81% yield) as an off white solid, which was used subsequently. (NRK-6-32)

(E)-3-(4-Hydroxy-3-(methylamino)styryl)-5-methoxy-4-(3-methylbut-2-en-1-yl)phenol (15)

37% wt % Aqueous formaldehyde (52 μL, 0.62 mmol, 2.0 equiv) and sodium triacetoxyborohydride (262 mg, 1.24 mmol, 4.0 equiv) were sequentially added to a solution of compound 15-9 (100 mg, 0.31 mmol, 1.0 equiv) in dichloromethane (10 mL). The reaction mixture was stirred at room temperature for 16 hours. The reaction mixture was diluted with dichloromethane (20 mL) and washed with saturated sodium bicarbonate (15 mL). The aqueous layer was extracted with dichloromethane (2×10 mL). The combined organic layers were dried over sodium sulfate, filtered and concentrated under reduced pressure. The residue was initially purified on a Reveleris automated chromatography system (Sorbtech 24 g column), eluting with a gradient of 0 to 100% ethyl acetate in heptanes to give compound 15 [KYN-158] (52 mg, 52% yield) as an off white solid. (NRK-6-40)

NOTE: In a trial run, compound 15-9 (50 mg) was converted to compound 15 using conditions as described above. Purification of crude 15 obtained from this reaction on a Reveleris automated chromatography system (Redisep Rf Gold HP C18, 50 g column), eluting with a gradient of 0 to 80% acetonitrile in water, resulted in the formation of an impurity (with mass m/z=2M−1). LCMS analysis indicated that the ratio of this impurity over 15, increased over a period of time. A similar result was obtained when a solution of compound 15 was allowed to stand in methanol for 16 hours, thus suggesting that compound 15 might be unstable in solution.

(E)-3-(3-(Dimethylamino-4-hydroxystyryl)-5-methoxy-4-(3-methylbut-2-en-1-yl)phenol (16) [KYN-157]

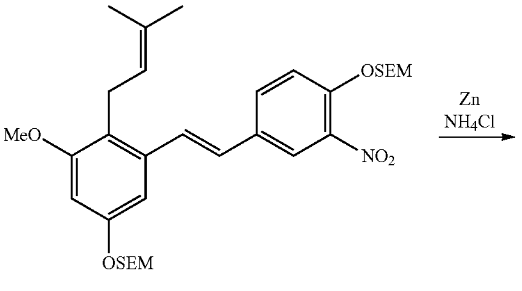

15-7

-continued

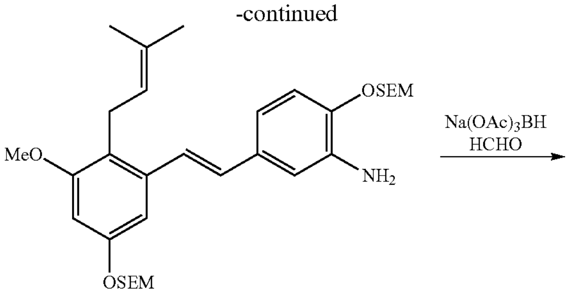

16-1

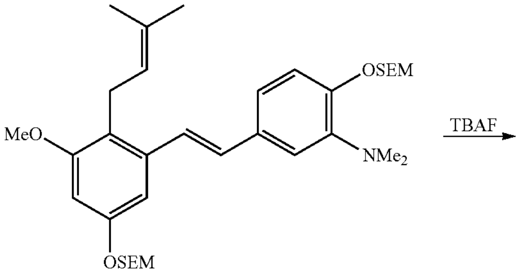

16-2

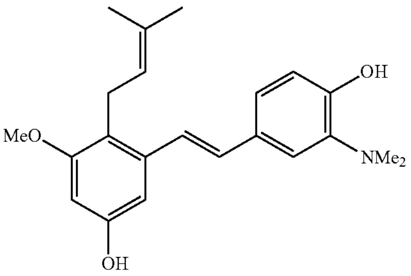

16

(E)-5-(3-Methoxy-2-(3-methylbut-2-en-1-yl)-5-((2-(trimethylsilyl) ethoxy)methoxy)styryl)-2-((2-(trimethylsilyl)ethoxy)methoxy)aniline) (16-1)

Activated zinc powder (1.89 g, 29.1 mmol, 10.0 equiv), ammonium chloride (1.57 g, 29.1 mmol, 10.0 equiv) and water (3 mL) were added sequentially to a solution of compound 15-7 (1.79 g, 2.91 mmol, 1.0 equiv) in tetrahydrofuran (50 mL) at room temperature. The resulting suspension was stirred at room temperature for 16 hours. The suspension was filtered and the solids were washed with ethyl acetate (20 mL). The filtrate was evaporated to dryness under reduced pressure. The residue was suspended in saturated ammonium chloride (30 mL), and extracted with ethyl acetate (3×50 mL). The combined organic layers were dried over sodium sulfate, filtered and concentrated under reduced pressure to give compound 16-1 (1.7 g, 99% yield) as a light yellow oil, which was used subsequently. (NRK-1-199)

(E)-5-(3-Methoxy-2-(3-methylbut-2-en-1-yl)-5-((2-(trimethylsilyl)ethoxy)methoxy)styryl)-N,N-dimethyl-2-((2-(trimethylsilyl)ethoxy)methoxy)aniline (16-2)

37% wt % Aqueous formaldehyde (37 μL, 0.46 mmol, 1.0 equiv) and sodium triacetoxyborohydride (1% mg, 0.92 mmol, 2.0 equiv) were sequentially added to a solution of compound 16-1 (267 mg, 0.46 mmol, 1.0 equiv) in dichloromethane (10 mL). The reaction mixture was stirred at room temperature for 30 minutes. LCMS analysis indicated the formation of both mono and di N-methylated products. Additional formaldehyde solution (0.5 mL, excess) was added to the reaction mixture and stirred at room temperature for 16 hours. The reaction mixture was diluted with dichloromethane (20 mL) and washed with saturated sodium bicarbonate (20 mL). The aqueous layer was extracted with dichloromethane (2×20 mL). The combined organic layers were dried over sodium sulfate, filtered and concentrated under reduced pressure. The residue was initially purified on a Reveleris automated chromatography system (Sorbtech 24 g column), eluting with a gradient of 0 to 15% ethyl acetate in heptanes. The resulting product was further purified on a Reveleris automated chromatography system (Sorbtech 24 g column), eluting with a gradient of 0 to 15% ethyl acetate in heptanes to give compound 16-2 (194 mg, 69% yield) as a light yellow oil. (NRK-1-198)

(E)-3-(3-(Dimethylamino)-4-hydroxystyryl)-5-methoxy-4-(3-methylbut-2-en-1-yl)phenol (16) [KYN-157]: 1M Tetrabutylammonium fluoride in tetrahydrofuran (4.5 mL, 4.42 mmol, 14 equiv) was added to a solution of compound 16-2 (194 mg, 0.32 mmol, 1 equiv) in tetrahydrofuran (10 mL) at room temperature. After heating at 67° C. for 8 hours, the mixture was cooled to room temperature and diluted with water (20 mL) and saturated ammonium chloride (20 mL).

The volatiles were removed under reduced pressure and the remaining aqueous layer was extracted with ethyl acetate (3×30 mL). The combined organic layers were dried over sodium sulfate, filtered and concentrated under reduced pressure. The residue was purified on a Reveleris automated chromatography system (Redisep Rf Gold HP C18, 50 g column), eluting with a gradient of 0 to 60% acetonitrile in water to give compound 16 [KYN-157] (40 mg, 36% yield) as a pale yellow solid. (NRK-1-201)

Pale yellow solid, melting point 45-53° C.; HPLC Analysis: 97.0% purity; Wavelength 210 nm, bandwidth 4; Column: Water Atlantis T3, 2.1×50 mm, 3 μm; Retention Time: 5.75 min; Mobile Phase: ACN/formic acid/water; Mass Spectrum (positive mode) m/z=354.2 $(M+H)^+$; $C_{22}H_{27}NO_3$; $^1H$ NMR (400 MHz, $CDCl_3$) δ=7.31 (d, J=2.0 Hz, 1H), 7.17 (dd, J=2.0, 8.3 Hz, 1H), 7.14 (d, J=16.1 Hz, 1H), 6.92 (d, J=8.3 Hz, 1H), 6.84 (d, J=16.0 Hz, 1H), 6.67 (d, J=2.3 Hz, 1H), 6.37 (d, J=2.3 Hz, 1H), 5.12 (septett, J=1.3, 6.8 Hz, H), 3.79 (s, 3H), 3.41 (br d, J=6.8 Hz, 2H), 2.69 (s, 6H), 1.82 (s, 3H), 1.69 (d, J=1.0 Hz, 3H); $^{13}C$ NMR (100 MHz, $CDCl_3$) δ=158.55, 154.55, 151.23, 140.76, 138.25, 130.52, 130.27, 130.07, 124.75, 124.06, 123.76, 120.54, 118.70, 114.21, 103.93, 98.24, 55.69, 45.14 (2C), 25.77, 24.47, 17.98.

Preparation of Compound 17 [KYN-120]

(E)-4-(5-Hydroxy-3-methoxy-2-(3-methylbut-2-en-1-yl)styryl)-2-methoxy-6-methylphenol (17)

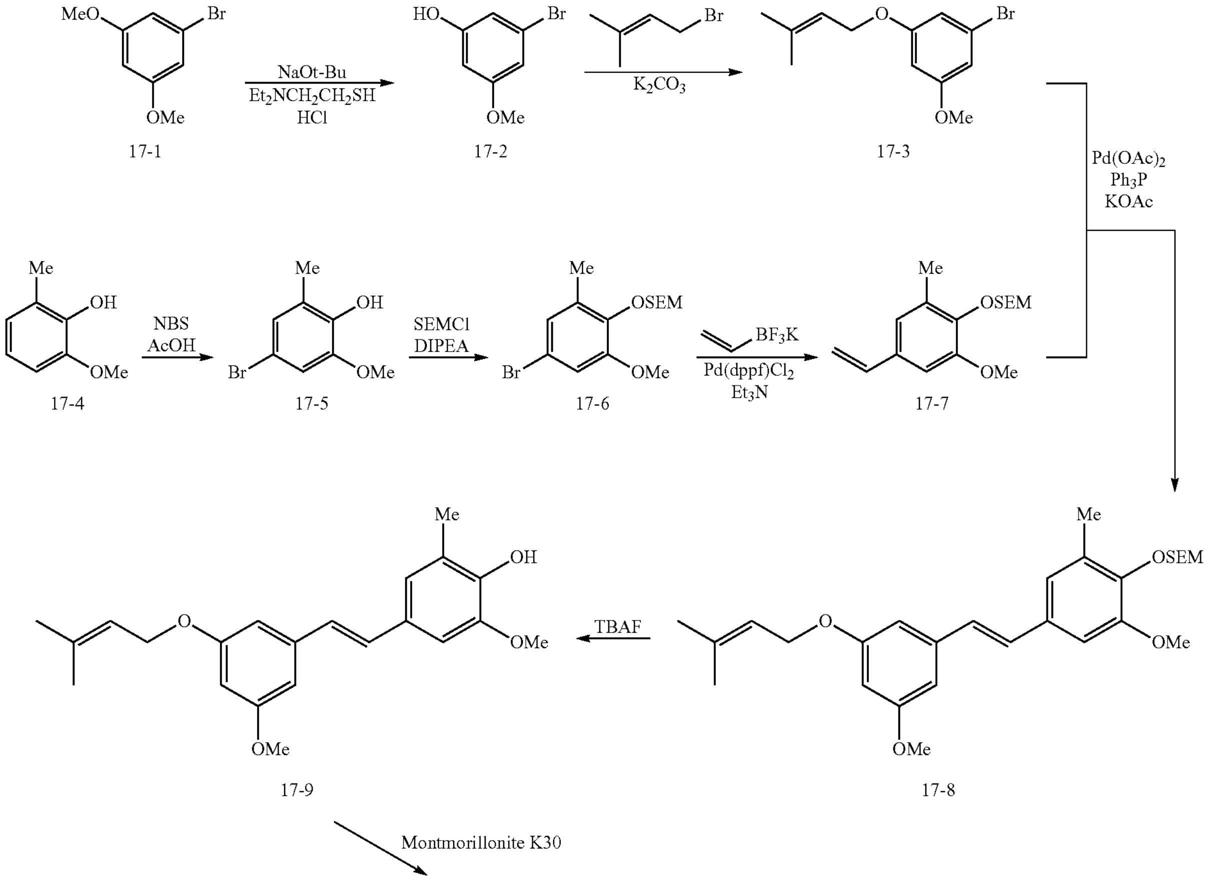

17-1 17-2 17-3 17-4 17-5 17-6 17-7 17-8 17-9

-continued

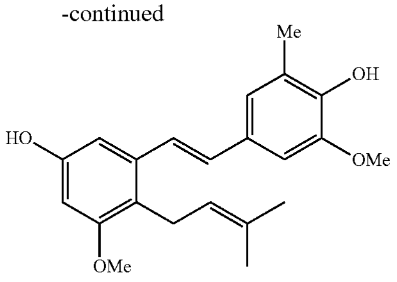

17

4-Bromo-2-methoxy-6-methylphenol (17-5)

N-Bromosuccinimide (5.15 g, 28.98 mmol, 1 equiv) was added to a solution of compound 17-4 (4 g, 28.98 mmol, 1.0 equiv) in acetic acid (60 mL) at room temperature. After stirring at room temperature overnight, the volatiles were removed under reduced pressure. The residue was diluted with water (200 mL) and extracted with ethyl acetate (3×60 mL). The combined organic layer was washed with saturated sodium bicarbonate (100 mL) dried over sodium sulfate filtered, and concentrated under reduced pressure. The residue was purified on an Interchim automated chromatography system (Sorbtech 12 g column), eluting with a gradient of 0 to 20% ethyl acetate in heptanes to give compound 17-5 (7 g, 99% yield) as a colorless oil. (NK-1-35)

(2-((4-Bromo-2-methoxy-6-methylphenoxy)methoxy)ethyl)trimethylsilane (17-6)

N,N-Diisopropylethylamine (3.6 mL, 20.73 mmol, 1.5 equiv) and 2-(trimethylsilyl)ethoxymethyl chloride (2.9 mL, 16.58 mmol, 1.2 equiv) were sequentially added to a solution of compound 17-5 (3 g, 13.82 mmol, 1.0 equiv) in anhydrous dichloromethane (60 mL) at room temperature. After stirring overnight, saturated ammonium chloride (100 mL) was added. The aqueous layer was extracted with dichloromethane (3×50 mL). The combined organic layers were dried over sodium sulfate, filtered and concentrated under reduced pressure. The residue was purified on an Interchim automated chromatography system (Sorbtech 12 g column), eluting with a gradient of 0 to 20% ethyl acetate in heptanes to give compound 17-6 (2.37 g, 88% yield) as a pale-yellow oil. (NK-1-29)

(2-((2-Methoxy-6-methyl-4-vinylphenoxy)methoxy)ethyl)trimethylsilane (17-7)

Potassium vinyltrifluoroborate (1.08 g, 8.06 mmol, 1.4 equiv), triethylamine (1.3 mL, 9.2 mmol, 1.6 equiv) and $Pd(dppf)Cl_2$ (210 mg, 0.029 mmol, 0.05 equiv) were added to a solution of compound 17-6 (2.0 g, 5.75 mmol, 1.0 equiv) in 2-propanol (40 mL). After sparging with nitrogen for 10 minutes, the mixture was refluxed (80° C.) for 16 hours. The reaction was cooled to room temperature and filtered through celite (~5 g). The filtrate was concentrated under reduced pressure, diluted with saturated sodium bicarbonate (20 mL) and extracted with ethyl acetate (3×20 mL). The combined organic layers were dried over sodium sulfate, filtered and concentrated under reduced pressure. The residue was purified on an Interchim automated chromatography system (Sorbtech 24 g column), eluting with a gradient of 0 to 20% ethyl acetate in heptanes to give compound 17-7 (1.06 g, 65% yield) as a colorless oil. (NK-1-34)

(E)-(2-((2-Methoxy-4-(3-methoxy-5-((3-methylbut-2-en-1-yl)oxy)styryl)-6-methylphenoxy)methoxy)ethyl)trimethylsilane (17-8)

1-Bromo-3-methoxy-5-((3-methylbut-2-en-1-yl)oxy)benzene (17-3) (1.49 g, 5.26 mmol, 1.2 equiv), triphenylphosphine (114 mg, 0.438 mmol, 0.1 equiv), potassium acetate (850 mg, 8.76 mmol, 2 equiv) and palladium acetate (50 mg, 0.219 mmol, 0.05 equiv) were added to a solution of compound 17-7 (1.29 g, 4.38 mmol, 1.0 equiv) in anhydrous toluene (60 mL). After sparging with nitrogen for 15 minutes, the mixture was refluxed (110° C.) for 16 hours. The reaction mixture was cooled to room temperature and filtered through celite (~5 g). The filtrate was transferred to a separatory funnel containing saturated sodium bicarbonate 20 mL). The organic layer was separated and the aqueous layer was extracted with ethyl acetate (2×20 mL). The combined organic layers were dried over sodium sulfate, filtered and concentrated under reduced pressure. The residue was purified on an Interchim automated chromatography system (Sorbtech 24 g column), eluting with a gradient of 0 to 30% ethyl acetate in heptanes to give compound 17-8 (420 mg, 20% yield) as a colorless oil. (NK-1-40)

1M Tetrabutylammonium fluoride in THF (6.1 mL, 6.06 mmol, 7 equiv) was added to a solution of compound 17-8 (420 mg, 0.86 mmol, 1 equiv) in anhydrous THF (40 mL) at room temperature. After refluxing overnight (66° C.), LCMS indicated that the reaction was complete. The mixture was cooled to room temperature and diluted with water (10 mL). The organic volatiles were removed under reduced pressure and diluted with ethyl acetate (20 mL). The organic layer was separated and the aqueous layer was extracted with ethyl acetate (2×20 mL). The combined organic layers were dried over sodium sulfate, filtered and concentrated under reduced pressure. The residue was purified on an Interchim automated chromatography system (Sorbtech 14 g column), eluting with a gradient of 0 to 50% ethyl acetate in heptanes to give Compound 17-9 (220 mg, 73% yield) as a yellow oil. (NK-1-41)

(E)-4-(5-Hydroxy-3-methoxy-2-(3-methylbut-2-en-1-yl)styryl)-2-methoxy-6-methylphenol (17) [KYN-120]

Montmorillonite K30 powder (220 mg) was added to a solution of Compound 17-9 (220 mg, 0.45 mmol) in anhydrous dichloromethane (20 mL) at room temperature. After stirring at room temperature overnight, LCMS indicated that 30-40% of desired compound 10 was formed, along with two regioisomers and unreacted starting compound 9. The mixture was filtered, washed with dichloromethane (2×15 mL) and the filtrate was concentrated under reduced pressure. The residue was purified on an Interchim automated chromatography system (Sorbtech 12 g column), eluting with a gradient of 0 to 50% ethyl acetate in heptanes. Trituration with 30% dichloromethane in heptanes (10 mL) gave pure compound 17 [KYN-120] (38 mg, 17% yield) as a white solid. (NK-1-42-S3)

White solid, melting point 140.3-140.4° C.; HPLC Analysis: 97.6% purity; Wavelength 210 nm, bandwidth 4; Column: SorbTech C18AQ, 2.1×50 mm, 3 μm; Retention Time: 9.29 min; Mobile Phase: ACN/formic acid/water, Mass Spectrum (positive mode) m/z=355 $(M+H)^+$; $C_{22}H_{26}O_4$; $^1H$ NMR (400 MHz, $CDCl_3$) δ=7.14 (d, J=16.1 Hz, 1H), 6.88 (m, 1H), 6.87 (m, 1H), 6.83 (d, J=16.1 Hz, 1H), 6.65 (d, J=2.5 Hz, 1H), 6.35 (d, J=2.5 Hz, 1H), 5.72 (d, J=0.5 Hz, 1H), 5.13 (tm, J=1.4, 6.9 Hz, 1H), 4.60 (s, 1H), 3.92 (s, 3H), 3.80 (s, 3H), 3.42 (br d, J=6.9 Hz, 2H), 2.27 (s, 3H), 1.82 (d, J=1.0 Hz, 3H), 1.69 (d, J=1.2 Hz, 3H); $^{13}C$ NMR (100 MHz, $CDCl_3$) δ=158.58, 154.34, 146.37, 143.77, 138.32, 130.62, 130.53, 129.17, 124.00, 123.87, 123.73, 122.35, 120.71, 105.96, 103.87, 98.13, 56.00, 55.71, 25.78, 24.49, 17.97, 15.45.

Compound 17 can also be synthesised by the modular methodology of the present disclosure using equivalents to Module A, B and C and subsequent cross coupling alkylation of the aryl halide.

(E)-5-(5-Hydroxy-3-methoxy-2-(3-methylbut-2-en-1-yl)styryl)-3-methoxybenzene-1,2-diol (18) [KYN-156]

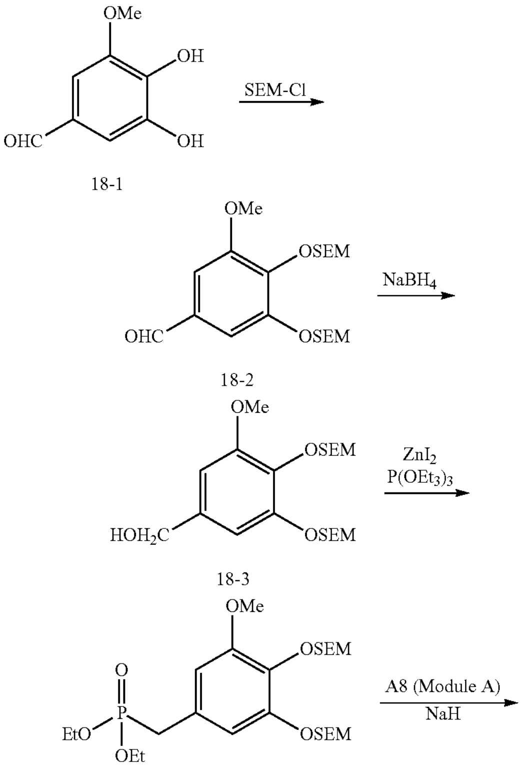

18-1

18-2

18-3

18-4

-continued

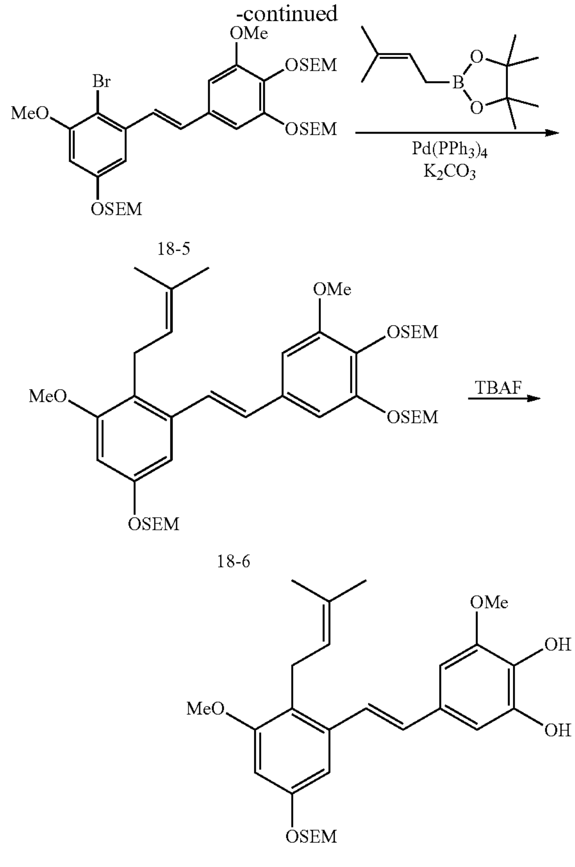

18-5

18-6

18

3-Methoxy-4,5-bis((2-(trimethylsilyl)ethoxy)methoxy)benzaldehyde (18-2)

N,N-Diisopropylethylamine (3.14 mL, 18 mmol, 3.0 equiv) and 2-(trimethylsilyl)ethoxymethyl chloride (2.53 mL, 14.3 mmol, 2.4 equiv) were added sequentially to a solution of compound 18-1 (1.0 g, 6 mmol, 1.0 equiv) in a 1:1:2 mixture of anhydrous tetrahydrofuran/dimethylformamide/dichloromethane (80 mL) at room temperature. After stirring at room temperature for 16 hours, a saturated sodium bicarbonate (100 mL) was added to quench the reaction. The layers were separated and the aqueous layer was extracted with methyl tert-butyl ether (2×250 mL). The combined organic layers were dried over sodium sulfate, filtered, and concentrated under reduced pressure. The residue was purified on an Interchim automated chromatography system (80 g column), eluting with a gradient of 0 to 35% ethyl acetate in heptanes to give compound 18-2 (2 g, 78% yield) as a colorless oil. (LM-6-96)

(3-Methoxy-4,5-bis((2-(trimethylsilyl)ethoxy)methoxy)phenyl)methanol (18-3)

Sodium borohydride (176 mg, 4.66 mmol, 1.0 equiv) was added in one portion solution of compound 18-2 (2 g, 4.66 mmol, 1.0 equiv) in methanol (50 mL) at 0° C. After stirring at 0° C. for 1 hour, water (50 mL) was added to quench the reaction. The mixture was concentrated under reduced pressure to remove most of methanol. The residue was diluted with saturated brine (50 mL) and extracted with ethyl acetate (2×100 mL). The combined organic layers was dried over sodium sulfate, filtered and concentrated under reduced pressure to give compound 18-3 (2 g) as a colorless oil, which was used subsequently. (LM-6-104).

Diethyl (3-methoxy-4,5-bis((2-(trimethylsilyl) ethoxy)methoxy)benzyl)phosphonate (18-4)

Zinc iodide (2.97 g, 9.32 mmol, 2.0 equiv) and triethyl phosphite (1.6 mL, 9.32 mmol, 2.0 equiv) were added sequentially to a solution of compound 18-3 (2 g, 4.66 mmol, 1.0 equiv) in anhydrous tetrahydrofuran (100 mL) at room temperature. The mixture was refluxed (68° C.) for 16 hours. After cooling to room temperature, water (50 mL), potassium carbonate (1.61 g, 2.5 equiv) and methyl tert-butyl ether (200 mL) were added sequentially. The mixture was filtered through a pad of Celite (20 g), which was rinsed with ethyl acetate (300 mL). The layers were separated and the organic layer was washed with saturated brine (100 mL), dried over sodium sulfate, filtered and concentrated under reduced pressure. The residue was purified on an Interchim automated chromatography system (80 g column), eluting with a gradient of 0 to 100% ethyl acetate in heptanes, to give mixture of compound 4A and 4B (1 g). N,NDiisopropylethylamine (2.52 mL, 14.4 mmol, 6 equiv) and 2-(trimethylsilyl)ethoxymethyl chloride (2.04 mL, 11.2 mmol, 4.8 equiv) were added successively to a solution of compounds 4A and 4B (1 g, 2.4 mmol, 1.0 equiv) in anhydrous dichloromethane (100 mL) at room temperature. After stirring at room temperature for 16 hours, saturated sodium bicarbonate (100 mL) was added to quench the reaction. The layers were separated and the aqueous layer was extracted with dichloromethane (2×100 mL). The combined organic layers was dried over sodium sulfate, filtered and concentrated under reduced pressure. The residue was purified on an Interchim automated chromatography system (80 g column), eluting with a gradient of 0 to 100% ethyl acetate in heptanes to give compound 18-4 (1.15 g, 45% yield over three steps) as a colorless oil. (LM-8-4, LM-8-5)

(E)-(((((5-(2-Bromo-3-methoxy-5-((2-(trimethylsilyl)ethoxy)methoxy)styryl)-3-methoxy-1,2-phenylene)bis(oxy))bis(methylene))bis(oxy))bis(ethane-2,1-diyl))bis(trimethylsilane) (18-5)

A 60% dispersion of sodium hydride in mineral oil (168 mg, 4.2 mmol, 2 equiv) was added in one portion to a solution of compound 18-4 (1.15 g, 2.1 mmol, 1.0 equiv) in anhydrous tetrahydrofuran (50 mL) at 0° C. The mixture was warmed up to room temperature and stirred 30 minutes. A solution of Intermediate A (754 mg, 2.1 mmol, 1 equiv) in anhydrous tetrahydrofuran (20 mL) was added dropwise and the mixture was stirred at room temperature for 16 hours. The reaction was carefully quenched with saturated brine (20 mL, 1 drop per minute for the first 5 mL brine) at 0° C. The mixture was extracted with methyl tert-butyl ether (2×150 mL). The combined organic layers was dried over sodium sulfate, filtered and concentrated under reduced pressure. The residue was purified on an Interchim automated chromatography system (80 g column), eluting with a gradient of 0 to 20% ethyl acetate in heptanes to give compound 18-5 (1.18 g, 75% yield) as a colorless oil. (LM-8-6)

(E)-(((((3-Methoxy-5-(3-methoxy-2-(3-methylbut-2-en-1-yl)-5-((2-(trimethylsilyl)ethoxy)methoxy)styryl)-1,2-phenylene)bis(oxy))bis(methylene))bis(oxy))bis(ethane-2,1-diyl))bis(trimethylsilane) (18-6)

Tetrakis(triphenylphosphine)palladium(0) (90 mg, 0.078 mmol, 0.05 equiv), potassium carbonate (428 mg, 3.1 mmol, 2 equiv), 3-methylbut-2-enylboronic acid pinacol ester (611 mg, 3.1 mmol, 2 equiv) and water (4 mL) were added sequentially to a solution of compound 18-5 (1.18 g, 1.56 mmol, 1 equiv) in 1,4-dioxane (12 mL). After sparging with nitrogen for 10 minutes, the reaction was heated at 95° C. for 16 hours. After cooling to room temperature, the mixture was extracted with methyl tert-butyl ether (2×20 mL). The combined organic layers was dried over sodium sulfate, filtered and concentrated under reduced pressure. The residue was purified on an Interchim automated chromatography system (80 g column), eluting with a gradient of 0 to 20% ethyl acetate in heptanes to give compound 18-6 (1 g, 86% yield) as a colorless oil. (LM-8-7)

(E)-5-(5-Hydroxy-3-methoxy-2-(3-methylbut-2-en-1-yl)styryl)-3-methoxybenzene-1,2-diol (18) [KYN-156]

1M Tetrabutylammonium fluoride in tetrahydrofuran (25.3 mL, 25.3 mmol, 21 equiv) was added to a solution of compound 18-6 (900 mg, 1.2 mmol, 1 equiv) in tetrahydrofuran (25 mL) at room temperature. After heating at 67° C. for 16 hours, the mixture was cooled to room temperature and diluted with water (20 mL) and saturated brine (20 mL). The mixture was extracted with ethyl acetate (300 mL). The organic layer was dried over sodium sulfate, filtered and concentrated under reduced pressure. The residue was purified three times on an Interchim automated chromatography system (80 g column, 2×40 g column stacked, 2×25 g column stacked), eluting each time with a gradient of 0 to 100% ethyl acetate m heptanes to give compound 18 (70 mg, ~85% purity). This crude compound 18 was equally divided in to 7 portions. Each portion was purified on a reverse ACCQPrep HP125 automated chromatography system (SunFire Prep C18 OBD 5 μm 19×250 mm column), eluting with a gradient of 0 to 100% acetonitrile in water to give compound 18 (50 mg). This material was further purified on an Interchim automated chromatography system (25 g column), eluting with a gradient of 0 to 100% ethyl acetate in hexanes to give compound 18 [KYN-156](27 mg, 6.3% yield) as an off-white solid after drying under vacuum at 40° C. for 16 hours. (LM-8-9).

Off white solid; HPLC Analysis: 96.0% purity; Wavelength 254 nm, bandwidth 4; Column: Luna C18(2), 2.0×20 mm, 3 μm; Retention Time: 7.7 min; Mobile Phase: ACN/formic acid/water; Mass Spectrum (positive mode) m/z=357.1 $(M+H)^+$; $C_{21}H_{24}O_5$; $^1H$ NMR (400 MHz, Acetone-$d_6$) δ=8.08 (s, 1H), 7.72-7.41 (m, 2H), 7.19 (d, J=16.1 Hz, 1H), 6.84 (d, J=16.0 Hz, 1H), 6.75-6.72 (m, 2H), 6.72 (d, J=2.3 Hz, 1H), 6.40 (d, J=2.2 Hz, 1H), 5.09 (septett, J=1.3, 7.0 Hz, 1H), 3.86 (s, 3H), 3.78 (s, 3H), 3.41 (br d, J=7.0 Hz, 2H), 1.82 (d, J=0.7 Hz, 3H), 1.64 (d, J=1.1 Hz, 3H); $^{13}C$ NMR (100 MHz, Acetone-$d_6$) δ=158.88, 156.66, 148.63, 145.92, 138.33, 134.46, 130.72, 129.84, 129.52, 124.69, 124.46, 119.36, 107.91, 104.14, 102.28, 98.62, 55.95, 55.38, 25.38, 24.37, 17.58.

(E)-3-(3-Hydroxy-5-methoxystyryl)-5-methoxy-4-(3-methylbut-2-en-1-yl)phenol (19) [KYN-160]

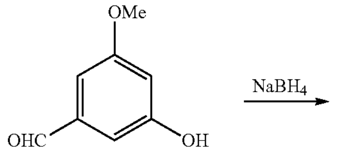

19-1

-continued

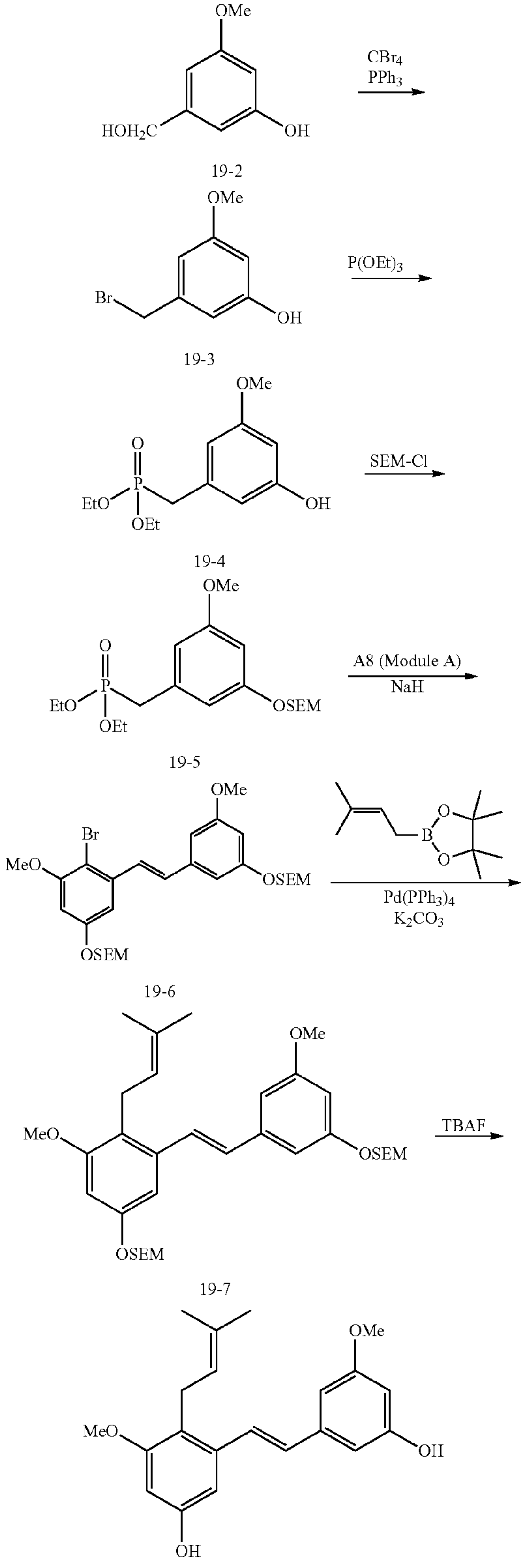

19-2

19-3

19-4

19-5

19-6

19-7

19

3-(Hydroxymethyl)-5-methoxyphenol (19-2)

Sodium borohydride (263 mg, 4.66 mmol, 1.0 equiv) was added in one portion to a solution of compound 19-1 (1.06 g, 7 mmol, 1.0 equiv) in methanol (70 mL) at 0° C. After stirring at 0° C. for 1 hour, water (50 mL) was added to quench the reaction. The mixture was concentrated under reduced pressure to remove most of methanol. The residue was diluted with saturated brine (50 mL) and extracted with ethyl acetate (2×100 mL). The combined organic layers were dried over sodium sulfate, filtered and concentrated under reduced pressure. The residue was purified on an InterChim automated chromatography system (40 g column), eluting with a gradient of 0 to 100% ethyl acetate in heptanes to give compound 19-2 (1.07 g, 99% yield) as a white solid. (LM-8-17)

3-(Bromomethyl)-5-methoxyphenol (19-3)

Carbon tetrabromide (2.55 g, 7.7 mmol, 1.1 equiv) was added to a solution of compound 19-2 (1.06 g, 7 mmol, 1.0 equiv) in a 1 to 2 mixture of anhydrous tetrahydrofuran and dichloromethane (75 mL) at room temperature. The mixture cooled in an ice-bath, and triphenylphosphine (2.02 g, 7.7 mmol, 1.1 equiv) was added in one portion. The mixture was then warmed up to room temperature and stirred for 2 hours. The solvent was removed under reduced pressure. The residue was purified on an InterChim automated chromatography system (80 g column), eluting with a gradient of 0 to 50% ethyl acetate in heptanes to give compound 19-3 (1.18 g, 79% yield) as an off-white solid. (LM-8-18)

Diethyl (3-hydroxy-5-methoxybenzyl)phosphonate (19-4)

Triethylphosphite (2.8 mL, 16.3 mmol, 3 equiv) were added to a solution of compound 19-3 (1.18 g, 5.4 mmol, 1.0 equiv) in anhydrous toluene (100 mL) at room temperature. After refluxing (110° C.) for 16 hours, the reaction was cooled to room temperature and the solvent was removed under reduced pressure. The residue was purified on an InterChim automated chromatography system (80 g column), eluting with a gradient of 0 to 100% ethyl acetate in heptanes to give compound 19-4 (1.32 g, 89% yield) as a colorless oil. (LM-8-19)

Diethyl (3-methoxy-5-((2-(trimethylsilyl)ethoxy)methoxy)benzyl) phosphonate (19-5)

N,N-Diisopropylethylamine (3.1 mL, 24 mmol, 5 equiv) and 2-(trimethylsilyl)ethoxymethyl chloride (3.4 mL, 19.3 mmol, 4 equiv) were added sequentially to a solution of compound 19-4 (1.32 g, 4.8 mmol, 1.0 equiv) in anhydrous dichloromethane (50 mL) at room temperature. After stirring at room temperature for 16 hours, saturated sodium bicarbonate (50 mL) was added to quench the reaction. The layers were separated and the aqueous layer was extracted with dichloromethane (2×200 mL). The combined organic layers were dried over sodium sulfate, filtered and concentrated under reduced pressure. The residue was purified on an InterChim automated chromatography system (80 g column), eluting with a gradient of 0 to 100% ethyl acetate in heptanes to give compound 19-5 (1.27 g, 65% yield) as a colorless oil. (LM-8-20)

(E)-(2-((3-(2-Bromo-3-methoxy-5-((2-(trimethylsilyl)ethoxy)methoxy)styryl)-5-methoxyphenoxy)methoxy)ethyl)trimethylsilane (19-6)

A 60% dispersion of sodium hydride in mineral oil (204 mg, 5.1 mmol, 2 equiv) was added in one portion to a solution of compound 19-5 (1.03 g, 2.55 mmol, 1.0 equiv) in anhydrous tetrahydrofuran (50 mL) at 0° C. The mixture was warmed up to room temperature and stirred 30 minutes. A solution of A8 (Module A) (0.92 mg, 2.55 mmol, 1 equiv) in anhydrous tetrahydrofuran (20 mL) was added dropwise and the mixture was stirred at room temperature for 16 hours. The reaction was carefully quenched with saturated brine (20 mL, 1 drop per minute for the first 5 mL brine) at 0° C. The mixture was extracted with methyl tert-butyl ether (2×150 mL). The combined organic layers were dried over sodium sulfate, filtered and concentrated under reduced pressure. The residue was purified on an InterChim automated chromatography system (80 g column), eluting with a gradient of 0 to 20% ethyl acetate in heptanes to give compound 19-6 (1.23 g, 79% yield) as a colorless oil. (LM-8-21)

(E)-(2-((3-Methoxy-5-(3-methoxy-2-(3-methylbut-2-en-1-yl)-5-((2-(trimethylsilyl)ethoxy)methoxy)styryl)phenoxy)methoxy)ethyl)trimethylsilane (19-7)

Tetrakis(triphenylphosphine)palladium(0) (116 mg, 0.1 mmol, 0.05 equiv), potassium carbonate (553 mg, 4 mmol, 2 equiv), 3-methylbut-2-enylboronic acid pinacol ester (785 mg, 4 mmol, 2 equiv) and water (5 mL) were added sequentially to a solution of compound 19-6 (1.23 g, 2 mmol, 1 equiv) in 1,4-dioxane (15 mL). After sparging with nitrogen for 10 minutes, the reaction was heated at 95° C. for 16 hours. After cooling to room temperature, the mixture was extracted with methyl tert-butyl ether (2×20 mL) and the combined organic layers were dried over sodium sulfate, filtered and concentrated under reduced pressure. The residue was purified on an InterChim automated chromatography system (80 g column), eluting with a gradient of 0 to 15% ethyl acetate in heptanes to give compound 19-7 (1.1 g, 91% yield) as a colorless oil. (LM-8-22)

(E)-3-(3-Hydroxy-5-methoxystyryl)-5-methoxy-4-(3-methylbut-2-en-1-yl)phenol (19) [KYN-160]

1M Tetrabutylammonium fluoride in tetrahydrofuran (25.6 mL, 25.6 mmol, 14 equiv) was added to a solution of compound 19-7 (1.1 g, 1.83 mmol, 1 equiv) in tetrahydrofuran (25 mL) at room temperature. After heating at 67° C. for 16 hours, the mixture was cooled to room temperature and diluted with water (20 mL) and saturated brine (20 mL). The mixture was extracted with ethyl acetate (300 mL) and the organic layer was dried over sodium sulfate, filtered and concentrated under reduced pressure. The residue was purified twice on an InterChim automated chromatography system (120 g column, 2×25 g column stacked), eluting each time with a gradient of 0 to 100% ethyl acetate in heptanes to give compound 19 (110 mg, 17% yield) as an off-white solid after drying under vacuum at 40° C. for 16 hours. (LM-8-23).

E)-4-(3-Ethoxy-S-hydroxy-2-(3-methylbut-2-en-1-yl)styryl)benzene-1,2-diol (20) [KYN-146]

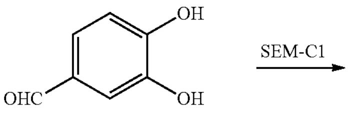

20-1

-continued

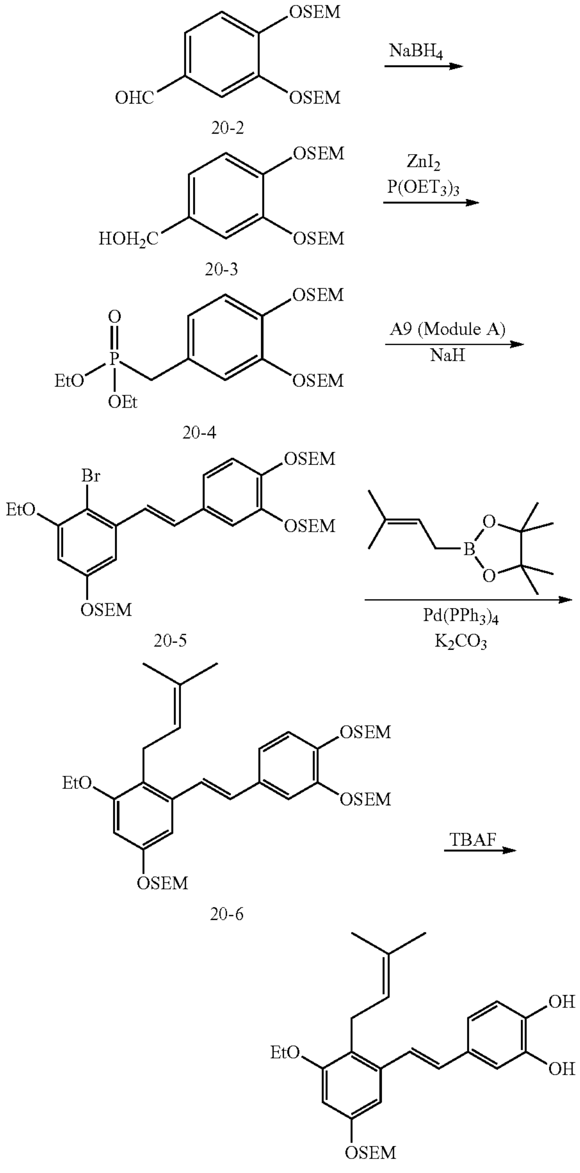

20-2

20-3

20-4

20-5

20-6

20

3,4-Bis((2-(trimethylsilyl)ethoxy)methoxy)benzaldehyde (20-2): N,N-Diisopropylethylamine (37.8 mL, 217.2 mmol, 3.0 equiv) and 2-(trimethylsilyl)ethoxymethyl chloride (29.0 g, 173.8 mmol, 2.4 equiv) were added sequentially to a solution of compound 20-1 (10.0 g, 72.4 mmol, 1.0 equiv) in anhydrous dichloromethane (200 mL) at room temperature. After stirring at room temperature for 16 hours, saturated sodium bicarbonate solution (150 mL) was added. The layers were separated and the aqueous layer was extracted with dichloromethane (2×150 mL). The combined organic layers was dried over sodium sulfate, filtered and concentrated under reduced pressure. The residue was purified on an Interchim automated chromatography system (120 g column), eluting with a gradient of 0 to 50% ethyl acetate in heptanes to give compound 20-2 (28.03 g, 97% yield) as a yellow oil. (LM-1-75)

(3,4-Bis((2-(trimethylsilyl)ethoxy)methoxy)phenyl) methanol (20-3): Sodium borohydride (2.66 g, 70.3 mmol, 1.0 equiv) was added in one portion to a solution of compound 20-2 (28.03 g, 70.3 mmol, 1.0 equiv) in methanol (200 mL) at 0° C. After stirring at 0° C. for 1 hour, water (75 mL) was added to quench the reaction. The mixture was concentrated under reduced pressure to remove most of methanol. The residue was diluted with saturated brine (75 mL) and extracted with ethyl acetate (2×200 mL). The combined organic layers was dried over sodium sulfate, filtered and concentrated under reduced pressure. The residue was purified on an Interchim automated chromatography system (120 g column), eluting with a gradient of 0 to 100% ethyl acetate in heptanes to give compound 20-3 (26.84 g, 95% yield) as a yellow oil. (LM-1-80)

Diethyl (3,4-bis((2-(trimethylsilyl)ethoxy)methoxy) benzyl)phosphonate (20-4)

Zinc iodide (42.77 g, 134.0 mmol, 2.0 equiv) and triethyl phosphite (23 mL, 134.0 mmol, 2.0 equiv) were added sequentially to a solution of compound 20-3 (26.84 g, 67.0 mmol, 1.0 equiv) in anhydrous tetrahydrofuran (400 mL) at room temperature. The mixture was refluxed (68° C.) for 4 hours, at which time LCMS analysis indicated that the reaction was complete. After cooling to room temperature, the mixture was concentrated under reduced pressure to remove most of tetrahydrofuran. The residue was diluted with saturated sodium bicarbonate (150 mL) and extracted with methyl tert-butyl ether (2×400 mL). The combined organic layers was dried over sodium sulfate, filtered and concentrated under reduced pressure. The residue was purified on an Interchim automated chromatography system (220 g column), eluting with a gradient of 0 to 100% ethyl acetate in heptanes to give compound 20-4 (24.18 g, 69% yield) as a yellow oil. (LM-1-82)

(E)-(((((4-(2-Bromo-3-ethoxy-5-((2-trimethylsilyl) ethoxy)methoxy)styryl)-1,2-phenylene)bis(oxy))bis (methylene))bis(oxy))bis(ethane-2,1-diyl))bis(trimethylsilane) (20-5)

A 60% dispersion of sodium hydride in mineral oil (2.43 g, 60.6 mmol, 2 equiv) was added in one portion to a solution of compound 20-4 (15.76 g, 30.3 mmol, 1.0 equiv) in anhydrous tetrahydrofuran (300 mL) at 0° C. The mixture was warmed to room temperature and stirred 30 minutes. A solution containing compound A9 (Module A) (11.36 g, 30.3 mmol, 1 equiv) in anhydrous tetrahydrofuran (100 mL) was added dropwise and the mixture was stirred at room temperature for 16 hours. The reaction was carefully quenched with saturated brine (250 mL, 1 drop per minute for the first 5 mL brine) at 0° C. The mixture was extracted with methyl tert-butyl ether (2×500 mL). The combined organic layers was dried over sodium sulfate, filtered and concentrated under reduced pressure. The residue was purified on an Interchim automated chromatography system (330 column), eluting with a gradient of 0 to 15% ethyl acetate in heptanes to give compound 20-5 (15.5 g, 69% yield) as a yellow oil. (LM-6-89)

(E)-(((((4-(3-ethoxy-2-(3-methylbut-2-en-1-yl)-5-((2-(trimethylsilyl)ethoxy)methoxy)styryl)-1,2-phenylene)bis(oxy))bis(methylene))bis(oxy))bis(ethane-2,1-diyl))bis(trimethylsilane) (20-6)

Tetrakis(triphenylphosphine)palladium(0) (1.21 g, 1.05 mmol, 0.05 equiv), potassium carbonate (5.78 g, 41.8 mmol, 2 equiv), 3-methylbut-2-enylboronic acid pinacol ester (8.2 g, 41.8 mmol, 2 equiv) and water (50 mL) were added sequentially to a solution of compound 20-5 (15.5 g, 20.9 mmol, 1 equiv) in 1,4-dioxane (150 mL). After sparging with nitrogen for 10 minutes, the reaction was heated at 95° C. for 16 hours. After cooling to room temperature, the mixture was extracted with methyl tert-butyl ether (2×300 mL). The combined organic layers was dried over sodium sulfate, filtered and concentrated under reduced pressure. The residue was purified on an Interchim automated chromatography system (330 column), eluting with a gradient of 0 to 15% ethyl acetate in heptanes to give a compound 20-6 (15.28 g, 99% yield) as a yellow oil. (LM-6-90)

(E)-4-(3-Ethoxy-5-hydroxy-2-(3-methylbut-2-en-1-yl)styryl)benzene-1,2-diol (20) [KYN-146]

1M Tetrabutylammonium fluoride in tetrahydrofuran (513 mL, 513 mmol, 21 equiv) was added to a mixture of compound 20-6 (17.86 g, 24.4 mmol, 1 equiv) in tetrahydrofuran (500 mL) at room temperature. After heating at 67° C. for 16 hours, the mixture was cooled to room temperature and diluted with water (350 mL) and saturated brine (350 mL). The mixture was extracted with methyl tertbutyl ether (1.5 L) and ethyl acetate (1.5 L). The combined organic layers were dried over sodium sulfate, filtered and concentrated under reduced pressure. The residue was purified three times on an Interchim automated chromatography system (2×40 g column stacked, 2×80 g column stacked, 2×40 g column stacked), eluting each time with a gradient of 0 to 100% ethyl acetate in heptanes, to give a mixture of SEM protected compounds (3.94 g) and compound 20 (1.5 g, ~70% purity). This crude compound 20 was further purified on a reverse Interchim automated chromatography system (300 g column), eluting with a gradient of 0 to 100% acetonitrile in water to give compound 20 (480 mg). The mixture of SEM-protected compounds (3.94 g) was treated with 1M tetrabutylammonium fluoride in tetrahydrofuran (58.7 mL, 58.7 mmol, 7.0 equiv) and processed in the same manner to give compound 20 (450 mg). All SEM-protected material was combined (480 mg, 450 mg and 130 mg, LM-6-69) and purified on an Interchim automated chromatography system (40 g column), eluting with a gradient of 0 to 55% ethyl acetate in hexanes to give compound 20 [KYN-146] (1.0 g, 10% yield in total) as an off-white solid after drying under vacuum at 40° C. for 16 hours. (LM-6-91).

Structure Data:

Compound 20 [KYN-146]

Off-white solid; HPLC Analysis: 96.3% purity; Wavelength 254 nm, bandwidth 4; Column: SorbTech C18AQ, 2.1×50 mm, 3 μm; Retention Time: 8.3 min; Mobile Phase: ACN/formic acid/water; Mass Spectrum (positive mode) m/z=341.2 $(M+H)^+$; $C_{21}H_{24}O_4$; $^1H$ NMR (400 MHz, Acetone-$d_6$) δ=7.98 (br s, 2H), 7.18 (d, J=16.1 Hz, 1H), 7.08 (d, J=2.1 Hz, 1H), 6.90 (ddd, J=0.4, 2.1, 8.1 Hz, 1H), 6.87-6.80 (m, 2H), 6.70 (d, J=2.3 Hz, 1H), 6.37 (d, J=2.3 Hz, 1H), 5.11 (septett, J=1.3, 7.0 Hz, 1H), 3.99 (q, J=7.0 Hz, 2H), 3.42 (d, J=7.0 Hz, 2H), 1.81 (d, J=0.9 Hz, 3H), 1.64 (d, J=1.1 Hz, 3H), 1.38 (t, J=7.0 Hz, 3H); $^{13}C$ NMR (100 MHz, Acetone-$d_6$) δ=158.18, 156.56, 145.65, 145.59, 138.34, 130.60, 130.33, 129.87, 124.65, 124.23, 119.52, 119.50, 115.75, 113.29, 104.08, 99.43, 63.86, 25.40, 24.44, 17.65, 14.75.

(E)-4-(5-Hydroxy-3-methoxy-2-(3-methylbut-2-en-1-yl)styryl)-2-methoxybenzoic acid (21) [KYN-154]

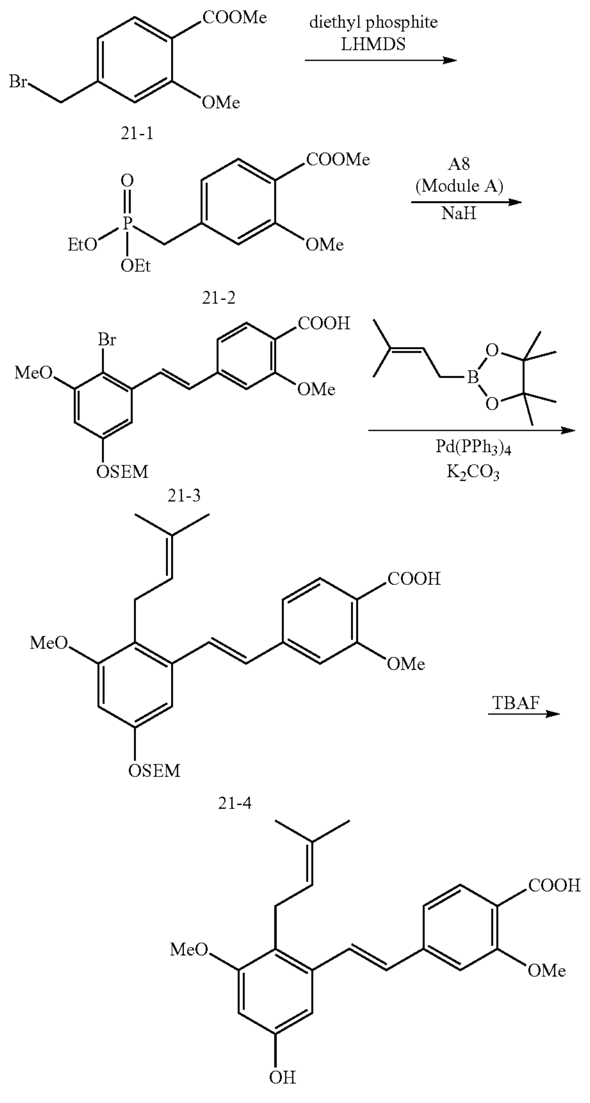

21-1

21-2

21-3

21-4

21

Methyl 4-((diethoxyphosphoryl)methyl)-2-methoxybenzoate (21-2)

1M Lithium bis(trimethylsilyl)amide in tetrahydrofuran (7 mL, 7 mmol, 1.8 equiv) was added to a solution of diethyl phosphite (1 mL, 7.7 mmol, 2.0 equiv) in anhydrous tetrahydrofuran (30 mL) at 0° C. After stirring at 0° C. for 30 minutes, a solution of compound 21-1 (1 g, 3.9 mmol, 1 equiv) in anhydrous tetrahydrofuran (10 mL) was added dropwise and the mixture was stirred at room temperature for 16 hours. The reaction was diluted with saturated brine (50 mL) and extracted with ethyl acetate (2×300 mL). The combined organic layers were dried over sodium sulfate, filtered and concentrated under reduced pressure. The residue was purified on an Interchim automated chromatography system (40 column), eluting with a gradient of 0 to 100% ethyl acetate in heptanes to give compound 21-2 (1.22 g, 99% yield) as a colorless oil. (LM-6-92)

(E)-4-(2-Bromo-3-methoxy-5-((2-(trimethylsilyl)ethoxy)methoxy)styryl)-2-methoxybenzoic acid (21-3)

A 60% dispersion of sodium hydride in mineral oil (160 mg, 4 mmol, 2 equiv) was added in one portion to a solution of compound 21-2 (0.63 g, 2 mmol, 1.0 equiv) in anhydrous tetrahydrofuran (30 mL) at 0° C. The mixture was warmed up to room temperature and stirred 30 minutes. A solution of A8 (Module A) (0.72 g, 2 mmol, 1 equiv) in anhydrous tetrahydrofuran (10 mL) was added dropwise and the mixture was stirred at room temperature for 16 hours. The reaction was diluted with saturated brine (20 mL, 1 drop per minute for the first 5 mL brine) at 0° C. The mixture was extracted with methyl tert-butyl ether (2×50 mL). The combined organic layers were dried over sodium sulfate, filtered, and concentrated under reduced pressure. The residue was purified on an Interchim automated chromatography system (40 column), eluting with a gradient of 0 to 100% ethyl acetate in heptanes to give compound 21-3 (0.55 g, 55% yield) as a yellow solid. (LM-6-93)

(E)-2-Methoxy-4-(3-methoxy-2-(3-methylbut-2-en-1-yl)-5-((2-(trimethylsilyl)ethoxy)methoxy)styryl)benzoic acid (21-4)

Tetrakis (triphenylphosphine)palladium(0) (58 mg, 0.05 mmol, 0.05 equiv), potassium carbonate (415 mg, 3 mmol, 3 equiv), 3-methylbut-2-enylboronic acid pinacol ester (392 mg, 2 mmol, 2 equiv) and water (4 mL) were added sequentially to a solution of compound 21-3 (509 mg, 1 mmol, 1 equiv) in 1,4-dioxane (12 mL). After sparging with nitrogen for 10 minutes, the reaction was heated at 95° C. for 16 hours. After cooling to room temperature, the mixture was extracted with ethyl acetate (2×20 mL) and the combined organic layers was concentrated under reduced pressure. The residue was purified on an Interchim automated chromatography system (25 g column), eluting with a gradient of 0 to 80% ethyl acetate in heptanes to give compound 21-4 (490 mg, 98% yield) as a yellow oil. (LM-6-94)

(E)-4-(5-Hydroxy-3-methoxy-2-(3-methylbut-2-en-1-yl)styryl)-2-methoxybenzoic acid (21) [KYN-154]

1M Tetrabutylammonium fluoride in tetrahydrofuran (7 mL, 7 mmol, 7 equiv) was added to a mixture of compound 21-4 (490 mg, 1 mmol, 1 equiv) in tetrahydrofuran (20 mL) at room temperature. After heating at 67° C. for 16 hours, the mixture was cooled to room temperature and diluted with ethyl acetate (200 mL). The mixture was washed with saturated brine (50 mL) and the organic layer was dried over sodium sulfate, filtered and concentrated under reduced pressure. The residue was purified twice on an Interchim automated chromatography system (2×25 g column stacked), eluting each time with a gradient of 0 to 100% ethyl acetate in heptanes and twice on a reverse Interchim automated chromatography system (50 g column), eluting each time with a gradient of 0 to 100% acetonitrile in water to give compound S10 (70 mg, ~70% purity). This material was equally divided in to 8 portions. Each portion was purified on a reverse ACCQPrep HP125 automated chromatography system (SunFire Prep C18 OBD 5 μm 19×250 mm column), eluting with a gradient of 0 to 100% acetonitrile in water to give compound 21 [KYN-154] (30 mg, 8% yield) as an off-white solid after lyophilization for 16 hours. (LM-6-95).

Off-white solid; HPLC Analysis: 98.8% purity; Wavelength 254 nm, bandwidth 4; Column: SorbTech C18AQ, 2.1×50 mm, 3 μm; Retention Time: 8.4 min; Mobile Phase: ACN/formic acid/water; Mass Spectrum (positive mode) m/z=369.2 $(M+H)^+$; $C_{22}H_{24}O_5$; $^1H$ NMR (400 MHz, Acetone-$d_6$) δ=7.92 (d, J=8.1 Hz, 1H), 7.58 (d, J=16.1 Hz, 1H), 7.38 (d, J=1.1 Hz, 1H) 7.30 (dd, J=1.2, 8.2 Hz, 1H) 7.05 (d, J=16.3 Hz, 1H), 6.78 (d, J=2.3 Hz, 1H), 6.48 (d, J=2.2 Hz, 1H), 5.08 (septett, J=1.3, 7.0 Hz, 1H), 4.09 (s, 3H), 3.80 (s, 3H), 3.45 (br d, J=6.8 Hz, 2H), 1.81 (s, 3H), 1.64 (d, J=1.0 Hz, 3H); $^{13}C$ NMR (100 MHz, Acetone-$d_6$) δ=165.55, 159.48, 158.97, 156.82, 144.29, 137.40, 133.08, 130.20, 130.14, 129.15, 124.52, 120.27, 119.38, 118.33, 110.57, 104.49, 99.64, 56.36, 55.46, 25.36, 24.36, 17.57.

Preparation of Compound 22 [KYN-124] and Compound 23 [KYN-125]

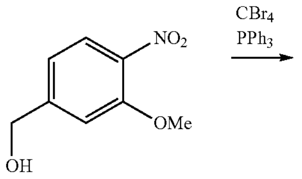

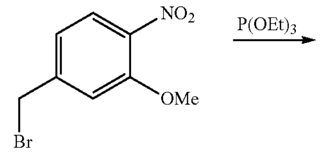

22-1

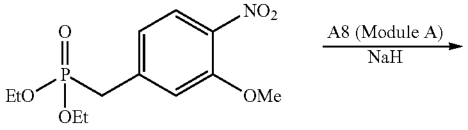

22-2

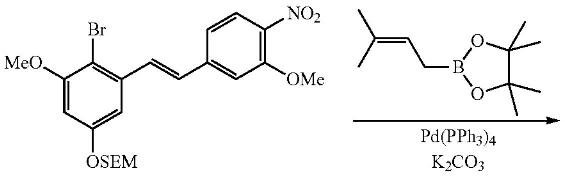

22-3

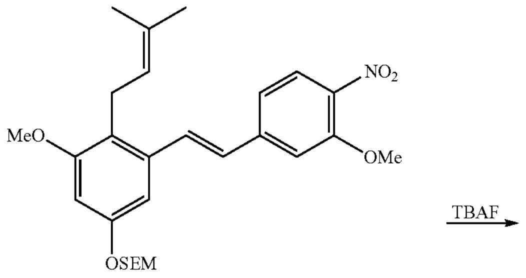

22-4

-continued

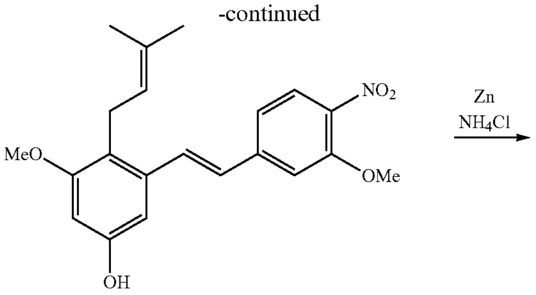

22

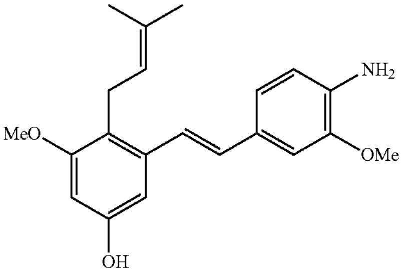

23

4-(Bromomethyl)-2-methoxy-1-nitrobenzene (22-1)

Carbon tetrabromide (21.7 g, 65.5 mmol, 1.2 equiv) was added in 5 portions to a solution of 3-methoxy-4-nitrobenzyl alcohol (10 g, 54.5 mmol, 1.0 equiv) and triphenylphosphine (17.2 g, 65.5 mmol, 1.2 equiv) in dichloromethane (300 mL) at 0° C. After stirring at room temperature for 16 hours, the reaction mixture was concentrated under reduced pressure. The residue was purified on an InterChim automated chromatography system (330 g column), eluting with a gradient of 0 to 50% ethyl acetate in heptanes, to give compound 22-1 (12.8 g, 95% yield) as a yellow solid (CH-LM-02-26)

Diethyl (3-methoxy-4-nitrobenzyl)phosphonate (22-2)

Triethyl phosphite (26.8 mL, 156 mmol, 3.0 equiv) was added to a solution of compound 22-1 (12.8 g, 52 mmol, 1.0 equiv) in toluene (400 mL). After refluxing (110° C.) for 40 hours, NMR analysis indicated the reaction was complete. The reaction mixture was cooled to room temperature and concentrated under reduced pressure. The residue was purified on an InterChim automated chromatography system (330 g column), eluting with a gradient of 0 to 100% ethyl acetate in heptanes followed by 10% methanol in dichloromethane to give compound 22-2 (15.5 g, 98% yield) a pale yellow oil (CH-LM-02-27).

(E)-(2-((4-Bromo-3-methoxy-5-(3-methoxy-4-nitrostyryl)phenoxy)methoxy)ethyl)trimethylsilane (22-3)

A 60% dispersion of sodium hydride in mineral oil (6.1 g, 153.3 mmol, 3.0 equiv) was added in 3 portions to a solution of compound 22-2 (15.5 g, 51.1 mmol, 1.0 equiv) in anhydrous tetrahydrofuran (450 mL) at 0° C. The mixture was warmed up to room temperature and stirred for 30 minutes. A solution of Intermediate A (18.5 g, 51.1 mmol, 1.0 equiv) in anhydrous tetrahydrofuran (150 mL) was added dropwise and the mixture was stirred at room temperature for 16 hours. The reaction was carefully quenched with water (500 mL, 1 drop per minute for the first 5 mL water) at 0° C. and extracted with methyl tert-butyl ether (1.5 L) and ethyl acetate (1 L). The combined organic layers were dried over sodium sulfate, filtered and concentrated under reduced pressure. The residue was purified in three equal portions on an InterChim automated chromatography system (3×330 g column), eluting with a gradient of 10 to 50% ethyl acetate in heptanes, to give compound 22-3 (9.9 g, 38% yield) as a yellow solid. (CH-LM-02-28)

(E)-(2-((3-Methoxy-5-(3-methoxy-4-nitrostyryl)-4-(3-methylbut-2-en-1-yl) phenoxy)methoxy)ethyl) trimethylsilane (22-4)

Tetrakis(triphenylphosphine) palladium(0) (2.1 g, 1.8 mmol, 0.05 equiv), potassium carbonate (10 g, 72 mmol, 2.0 equiv), 3-methylbut-2-enylboronic acid pinacol ester (14.1 g, 72 mmol, 2.0 equiv) and water (90 mL) were added sequentially to a solution of compound 22-3 (18.3 g, 36 mmol, 1.0 equiv) in 1,4-dioxane (270 mL) in a sealed tube. After sparging with nitrogen for 10 minutes, the reaction was heated at 100° C. for 16 hours. After cooling to room temperature, the reaction mixture was extracted with methyl tert-butyl ether (500 mL). The organic layer was dried over sodium sulfate, filtered and concentrated under reduced pressure. The residue was purified in two equal portions on an InterChim automated chromatography system (2×220 g column), eluting with a gradient of 0 to 12% ethyl acetate in heptanes to give compound 22-4 (15.1 g, 84% yield) as a yellow solid. (CH-LM-02-29)

(E)-3-Methoxy-5-(3-methoxy-4-nitrostyryl)-4-(3-methylbut-2-en-1-yl)phenol (22): 1M Tetrabutylammonium fluoride in tetrahydrofuran (366 mL, 366 mmol, 7.0 equiv) was added to a solution of compound 22-4 (26.1 g, 52.3 mmol, 1.0 equiv) in tetrahydrofuran (400 mL) at room temperature. After heating at 68° C. for 16 hours, the mixture was cooled to room temperature and diluted with water (100 mL). The volatiles were removed under reduced pressure. The residue was diluted with saturated ammonium chloride (250 mL) and extracted with ethyl acetate (2×500 mL). The combined organic layers were dried over sodium sulfate, filtered and concentrated under reduced pressure. The residue was purified in three equal portions on an InterChim automated chromatography system (3×330 g column), eluting with a gradient of 30 to 100% ethyl acetate in heptanes to give compound 22 (17.1 g, 89% yield) as a yellow solid. (CH-LM-02-30) Yellow solid, melting point 167.1-169.0° C.: HPLC Analysis: 99.2% purity; Wavelength 210 nm, bandwidth 4; Column: SorbTech C18AQ, 2.1×50 mm, 3 μm; Retention Time: 9.77 min; Mobile Phase: ACN/formic acid/water; Mass Spectrum (positive mode) m/z=370.1 $(M+H)^+$; $C_{21}1H_2NO_5$; $^1H$ NMR (400 MHz, $CDCl_3$) δ=7.91 (d, J=8.3 Hz, 1H), 7.43 (d, J=16.1 Hz, 1H), 7.12 (ddd, J=0.5, 1.7, 8.3 Hz, 1H), 7.11 (br d, J=1.5 Hz, 1H), 6.91 (d, J=16.1 Hz, 1H), 6.68 (d, J=2.4 Hz, 1H), 6.42 (d, J=2.4 Hz, 1H), 5.09 (tm, J=6.8 Hz, 1H), 4.76 (s, 1H), 4.01 (s, 3H), 3.82 (s, 3H), 3.43 (d, J=6.8 Hz, 2H), 1.80 (d, J=0.7 Hz, 3H), 1.68 (d, J=1.2 Hz, 3H); $^{13}C$ NMR (100 MHz, $CDCl_3$) δ=158.67, 154.55, 153.70, 144.15, 138.12, 136.81, 130.97, 130.89, 128.38, 126.57, 123.42, 121.71, 118.09, 111.20, 104.15, 99.44, 56.45, 55.76, 25.74, 24.46, 17.99.

(E)-3-(4-Amino-3-methoxystyryl)-5-methoxy-4-(3-methylbut-2-en-1-yl)phenol (23) [KYN-125]

Zinc powder (30.3 g, 463 mmol, 10.0 equiv), ammonium chloride (25 g, 463 mmol, 10.0 equiv) and water (70 mL) were added sequentially to a solution of compound 22 (17.1 g, 46.3 mmol, 1.0 equiv) in tetrahydrofuran (700 mL) at room temperature. The resulting suspension was stirred at room temperature for 4 hours. The suspension was filtered and the solids were washed with ethyl acetate (1 L). The filtrate was evaporated to dryness under reduced pressure. The residue was purified in five equal portions on an InterChim automated chromatography system (5×120 g column), eluting each time with a gradient of 0 to 40% ethyl acetate in heptanes to give compound 23 (10.5 g, 67% yield) as an off-white solid. (CH-LM-02-31). Melting point 159.3-163.3° C.; HPLC Analysis: 94.8% purity; Wavelength 210 nm, bandwidth 4; Column: SorbTech C18AQ, 2.1×50 mm, 3 μm; Retention Time: 7.80 min; Mobile Phase: ACN/formic acid/water; Mass Spectrum (positive mode) m/z=340.2 $(M+H)^+$; $C_{21}H_{25}NO_3$; $^1H$ NMR (400 MHz, $CDCl_3$) δ=7.10 (d, J=16.1 Hz, 1H), 6.95 (d, J=1.7 Hz, 1H), 6.92 (dd, J=1.9, 7.9 Hz, 1H), 6.81 (d, J=15.9 Hz, 1H), 6.69 (d, J=7.8 Hz, 1H), 6.62 (d, J=2.5 Hz, 1H), 6.34 (d, J=2.4 Hz, 1H), 5.12 (tm, J=1.5, 6.9 Hz, 1H), 3.89 (s, 3H), 3.80 (s, 3H), 3.41 (d, J=6.6 Hz, 2H), 1.81 (d, J=1.0 Hz, 3H), 1.67 (d, J=0.9 Hz, 3H); $^{13}C$ NMR (100 MHz, $CDCl_3$) δ=158.56, 154.40, 147.42, 138.48, 136.08, 130.88, 130.49, 128.67, 123.77, 122.88, 120.54, 120.50, 114.86, 108.07, 103.83, 97.97, 55.69, 55.45, 25.77, 24.48, 17.97.

(E)-3-(4-Amino-3-methoxystyryl)-5-ethoxy-4-(3-methylbut-2-en-1-yl)phenol (24) [KYN-141]

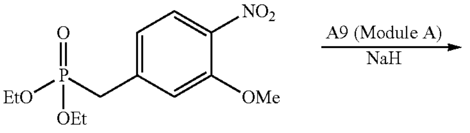

22-2

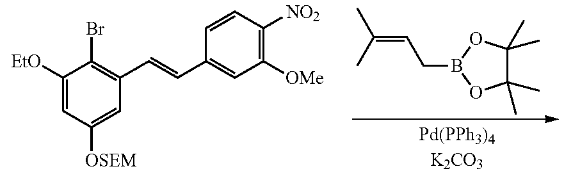

24-1

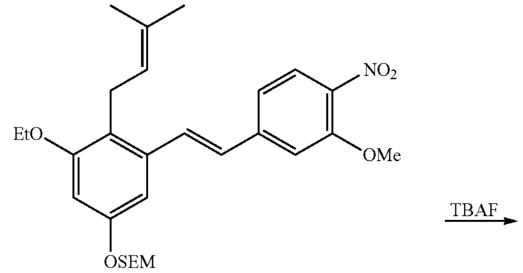

24-2

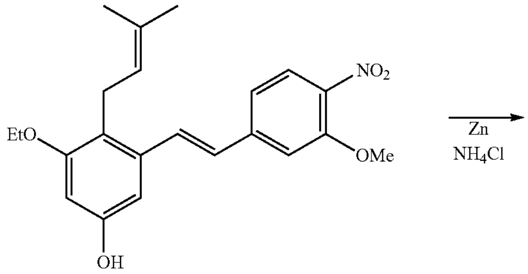

24-3

-continued

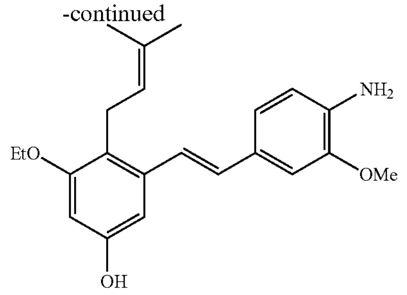

24

(E)-(2-((4-Bromo-3-ethoxy-5-(3-methoxy-4-nitrostyryl)phenoxy)methoxy)ethyl)trimethylsilane (24-1)

A 60% dispersion of sodium hydride in mineral oil (2.7 g, 67.3 mmol, 3.0 equiv) was added in 3 portions to a solution of compound 22-2 (6.8 g, 22.4 mmol, 1.0 equiv) in anhydrous tetrahydrofuran (200 mL) at 0° C. The mixture was warmed up to room temperature and stirred for 30 minutes. A solution of compound A9 (Module A) (8.4 g, 22.4 mmol, 1.0 equiv) in anhydrous tetrahydrofuran (50 mL) was added dropwise and the mixture was stirred at room temperature for 16 hours. The reaction was carefully quenched with water (200 mL, 1 drop per minute for the first 5 mL water) at 0° C. and extracted with methyl tert-butyl ether (1 L) and ethyl acetate (500 mL). The combined organic layers was dried over sodium sulfate, filtered and concentrated under reduced pressure. The residue was purified on an InterChim automated chromatography system (220 g column), eluting with a gradient of 0 to 20% ethyl acetate in heptanes to give compound 24-1 (9.04 g, 77% yield) as a yellow solid. (LM-8-98).

(E)-(2-((3-Ethoxy-5-(3-methoxy-4-nitrostyryl)-4-(3-methylbut-2-en-1-yl)phenoxy)methoxy)ethyl)trimethylsilane (24-2)

Tetrakis (triphenylphosphine) palladium(0) (1 g, 0.86 mmol, 0.05 equiv), potassium carbonate (4.76 g, 34.47 mmol, 2.0 equiv), 3-methylbut-2-enylboronic acid pinacol ester (6.76 g, 34.47 mmol, 2.0 equiv) and water (30 mL) were added sequentially to a solution of compound 24-1 (9.04 g, 17.24 mmol, 1.0 equiv) in 1,4-dioxane (120 mL) in a sealed tube. After sparging with nitrogen for 10 minutes, the reaction was heated at 100° C. for 16 hours. After cooling to room temperature, the reaction mixture was extracted with methyl tert-butyl ether (200 mL). The organic layer was dried over sodium sulfate, filtered and concentrated under reduced pressure. The residue was purified on an InterChim automated chromatography system (2×200 g column stacked), eluting with a gradient of 0 to 7% ethyl acetate in heptanes to give compound 24-2 (8.84 g, 99% yield) as a yellow oil. (LM-8-99).

(E)-3-Ethoxy-5-(3-methoxy-4-nitrostyryl)-4-(3-methylbut-2-en-1-yl)phenol (24-3): 1M Tetrabutylammonium fluoride in tetrahydrofuran (130 mL, 130 mmol, 7.0 equiv) was added to a solution of compound 24-2 (9.53 g, 18.55 mmol, 1.0 equiv) in tetrahydrofuran (200 mL) at room temperature. After heating at 68° C. for 16 hours, the mixture was cooled to room temperature and diluted with water (50 mL). The volatiles were removed under reduced pressure. The residue was diluted with saturated ammonium chloride (250 mL)

and extracted with ethyl acetate (2×400 mL). The combined organic layers were dried over sodium sulfate, filtered and concentrated under reduced pressure. The residue was purified on an InterChim automated chromatography system (330 g column), eluting with a gradient of 0 to 60% ethyl acetate in heptanes to give compound 24-3 (5.05 g, 71% yield) as a yellow solid. (LM-8-100).

(E)-3-(4-Amino-3-methoxystyryl)-5-ethoxy-4-(3-methylbut-2-en-1-yl)phenol (24): Zinc powder (8.61 g, 131.7 mmol, 10.0 equiv), ammonium chloride (7.1 g, 131.7 mmol, 10.0 equiv) and water (20 mL) were added sequentially to a solution of compound 24-3 (5.05 g, 13.17 mmol, 1.0 equiv) in tetrahydrofuran (200 mL) at room temperature. The resulting suspension was stirred at room temperature for 16 hours. The suspension was filtered through a pad of Celite (50 g), which was rinsed with ethyl acetate (400 mL). The filtrate was evaporated to dryness under reduced pressure. The residue was purified twice on an InterChim automated chromatography system (2×120 g column stacked), eluting each time with a gradient of 0 to 100% ethyl acetate in heptanes to give compound 24 (4.56 g, 98% yield) as an off white solid. (LM-8-101). Off white solid, melting point 187-196° C.; HPLC Analysis: 97.9% purity; Wavelength 210 nm, bandwidth 4; Column: SorbTech C18AQ, 2.1×50 mm, 3 μm; Retention Time: 8.3 min; Mobile Phase: ACN/formic acid/water; Mass Spectrum (positive mode) m/z=354.2 $(M+H)^+$; $C_{22}H_{27}NO_3$; $^1H$ NMR (400 MHz, $CDCl_3$) δ=7.11 (br d, J=16.0 Hz, 1H), 6.95 (br s, 1H), 6.92 (br d, J=7.7 Hz, 1H), 6.80 (br d, J=16.0 Hz, 1H), 6.70 (br d, J=7.9 Hz, 1H), 6.59 (br s, 1H), 6.31 (br s, 1H), 5.14 (br t, J=5.9 Hz, 1H), 4.90 (br s, 1H), 3.99 (q, J=6.6 Hz, 2H), 3.90 (s, 5H), 3.42 (br d, J=6.1 Hz, 2H), 1.91-1.74 (m, 3H), 1.74-1.61 (m, 3H), 1.41 (br t, J=6.8 Hz, 3H); $^{13}C$ NMR (100 MHz, $CDCl_3$) δ=157.88, 154.28, 147.40, 138.44, 136.10, 130.80, 130.30, 128.66, 123.84, 122.96, 120.67, 120.51, 114.83, 108.10, 103.74, 98.82, 63.90, 55.46, 25.79, 24.55, 18.03, 14.93.

(E)-N-(4-(5-hydroxy-3-methoxy-2-(3-methylbut-2-en-1-yl)styryl)-2-methoxyphenyl)methanesulfonamide (25) [KYN-137] and (Z)—N-(4-(5-hydroxy-3-methoxy-2-(3-methylbut-2-en-1-yl)styryl)-2-methoxyphenyl)methanesulfonamide (26) [KYN-129]

(E*Z*)-3-methoxy-5-(3-methoxy-4-(methylsulfonamido)styryl)-4-(3-methylbut-2-en-1-yl)phenyl methane sulfonate (25 and 26)

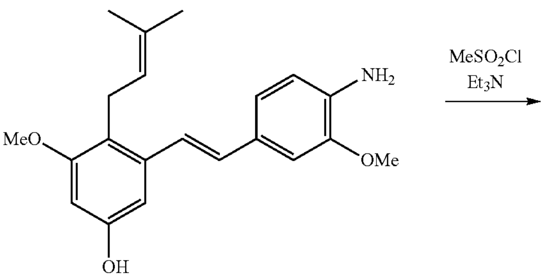

23

-continued

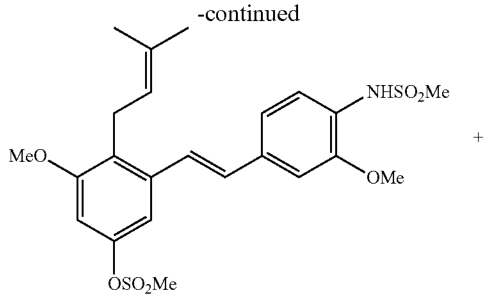

25-1

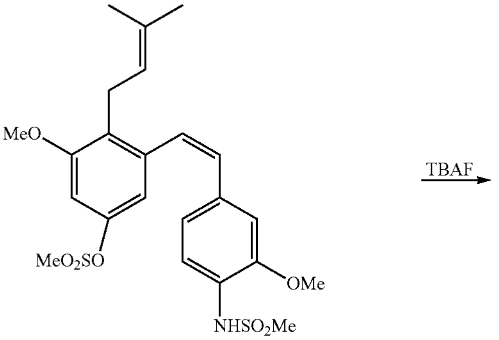

TBAF 26-1

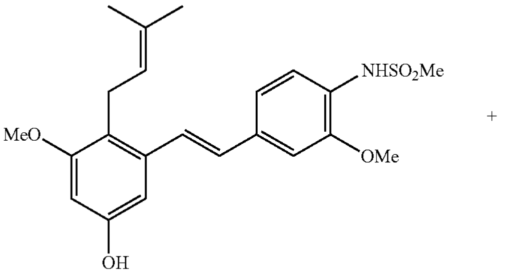

25

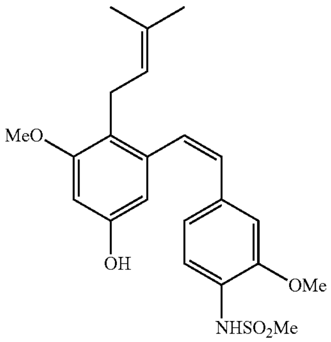

26

Triethylamine (0.15 mL, 1.08 mmol, 3 equiv) and methane sulfonyl chloride (0.1 mL, 0.70 mmol, 2 equiv) were sequentially added to a solution of compound 23 (120 mg, 0.36 mmol, 1.0 equiv) in anhydrous THF (10 mL) at room temperature. After refluxing (66° C.) for 16 hours, the reaction mixture was cooled to room temperature and the volatiles were removed under reduced pressure. The residue was dissolved in ethyl acetate (20 mL) and washed with saturated sodium bicarbonate (20 mL). The aqueous layer was extracted with ethyl acetate (2×15 mL). The combined organic layers were dried over sodium sulfate, filtered and concentrated under reduced pressure. The residue was purified on an Interchim automated chromatography system (Sorbtech 24 g column), eluting with a gradient of 0 to 30% ethyl acetate in heptanes to give compounds 25-1 and 26-1 (100 mg, 66% yield) as a white solid. (NRK-1-74)

1M Tetrabutylammonium fluoride solution in THF (2 mL, 1.63 mmol, 7 equiv) was added to a solution of compounds 25-1 and 26-1 (100 mg, 0.234 mmol, 1 equiv) in anhydrous THF (10 mL) at room temperature. After refluxing (66° C.) for 16 hours. LCMS analysis indicated that the reaction was complete. After the mixture was cooled to room temperature and diluted with saturated ammonium chloride (10 mL). The volatiles were removed under reduced pressure and the residue was diluted with ethyl acetate (20 mL). The layers were separated and the aqueous layer was extracted with ethyl acetate (2×15 mL). The combined organic layers were dried over sodium sulfate, filtered and concentrated under reduced pressure. The residue was purified on a Reveleris automated chromatography system (RediSep Rf Gold HP C18, 50 g column), eluting with a gradient of 0 to 40% acetonitrile in water to give compound 25 [KYN-137] (15.0 mg) as an off white solid and compound 26 [KYN-129] (19 mg, 22% yield) as a light brown oil.

(E)-N-(4-(5-hydroxy-3-methoxy-2-(3-methylbut-2-en-1-yl)styryl)-2-methoxyphenyl)methanesulfonamide (25) [KYN-137]

Off white solid; melting point 170.7-173.5° C.; HPLC Analysis: 92.4% purity; Wavelength 210 nm, bandwidth 4; Column: SorbTech C18AQ, 2.1×50 mm, 3 μm; Retention Time: 8.4 min; Mobile Phase: ACN/formic acid/water; Mass Spectrum (positive mode) m/z=418.1 $(M+H)^+$; $C_{22}H_{27}NO_5S$; $^1H$ NMR (400 MHz, $CDCl_3$) δ=7.50 (d, J=8.2 Hz, 1H), 7.27 (s, 1H), 7.26 (s, 1H), 7.25-7.22 (m, 1H), 7.02 (d, J=1.6 Hz, 1H), 6.88 (d, J=16.0 Hz, 1H), 6.68 (d, J=2.3 Hz, 1H), 6.39 (d, J=2.3 Hz, 1H), 5.11 (tseptets, J=1.3, 6.8 Hz, 1H), 4.92 (br s, 1H), 3.93 (s, 3H), 3.81 (s, 3H), 3.42 (br d, J=6.7 Hz, 2H), 2.97 (s, 3H), 1.81 (s, 3H), 1.68 (d, J=1.0 Hz, 3H); $^{13}C$ NMR (100 MHz, $CDCl_3$) δ=158.60, 154.52, 149.51, 137.63, 135.35, 130.67, 129.64, 126.58, 125.48, 123.62, 120.99, 120.75, 120.06, 108.33, 104.01, 98.68, 55.77, 55.72, 39.14, 25.76, 24.47, 17.99.

(Z)—N-(4-(5-hydroxy-3-methoxy-2-(3-methylbut-2-en-1-yl)styryl)-2-methoxyphenyl)methanesulfonamide (26) [KYN-129]

Light brown oil; HPLC Analysis: 97.8% purity; Wavelength 254 nm, bandwidth 4; Column: SorbTech C18AQ, 2.1×50 mm, 3 μm; Retention Time: 9.2 min; Mobile Phase: ACN/formic acid/water; Mass Spectrum (positive mode) m/z=418.1 $(M+H)^+$; $C_{22}H_{27}NO_5S$; $^1H$ NMR (400 MHz, $CDCl_3$) δ=7.31 (d, J=8.3 Hz, 1H), 6.77 (dd, J=1.7, 8.4 Hz, 1H), 6.66 (d, J=1.7 Hz, 1H), 6.63 (d, J=12.3 Hz, 1H), 6.50 (d, J=12.2 Hz, 1H), 6.35 (d, J=2.5 Hz, 1H), 6.19 (d, J=2.2 Hz, 1H), 5.08 (tm, J=1.4, 6.9 Hz, 1H), 3.79 (s, 3H), 3.50 (s, 3H), 3.27 (br d, J=7.1 Hz, 2H), 2.90 (s, 3H), 1.68 (s, 3H), 1.58 (d, J=0.9 Hz, 3H); $^{13}C$ NMR (100 MHz, $CDCl_3$) δ=158.87, 154.74, 148.69, 138.86, 134.39, 130.97, 129.90, 129.71, 124.78, 122.90, 122.67, 120.75, 120.01, 111.24, 107.31, 98.13, 55.65, 55.32, 39.14, 25.75, 25.66, 17.87.

(E)-N-(4-(S-Hydroxy-3-methoxy-2-(3-methylbut-2-en-1-yl)styryl)-2-methoxyphenyl)formamide (27) [KYN-149]

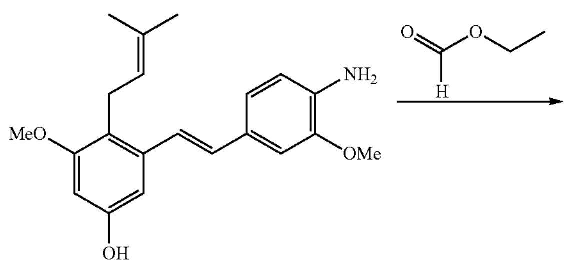

23

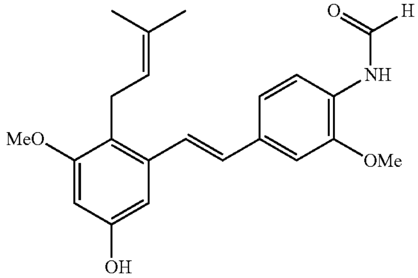

27

Compound 23 [KYN-125] (120 mg, 0.35 mmol, 1.0 equiv) was added to ethyl formate (15 mL) to obtain a cloudy solution, which was heated at 55° C. for 20 hours (clear solution on heating). The reaction mixture was cooled to room temperature and evaporated to dryness under reduced pressure. The residue was dissolved in ethyl acetate (20 mL) and washed with saturated ammonium chloride (20 mL). The aqueous layer was extracted with ethyl acetate (2×20 mL). The combined organic layers were dried over sodium sulfate, filtered and concentrated under reduced pressure. The residue was initially purified on a Reveleris automated chromatography system (Sorbtech 24 g column), eluting with a gradient of 0 to 60% ethyl acetate in heptanes. The product was triturated with 10% ethyl acetate in heptanes (10 mL) to afford compound 27 (50 mg, 38% yield) as an of T-white solid. (NRK-1-159).

(E)-N-(4-(5-hydroxy-3-methoxy-2-(3-methylbut-2-en-1-yl)styryl)-2-methoxyphenyl)formamide (27) [KYN-149]

White solid, melting point 181.2-181.7° C.; HPLC Analysis: 99.6% purity; Wavelength 210 nm, bandwidth 4; Column: SorbTech C18AQ, 2.1×50 mm, 3 µm; Retention Time: 8.4 min; Mobile Phase: ACN/formic acid/water; Mass Spectrum (negative mode) m/z=733.3 $(2M-H)^-$; $C_{22}H_{25}NO_4$; $^1H$ NMR (400 MHz, DMSO-$d_6$) δ=9.69 (s, 1H), 9.24 (s, 1H), 8.30 (d, J=1.8 Hz, 1H), 8.16 (d, J=8.2 Hz, 1H) 7.31-7.22 m, 2H), 7.09 (d, J=8.6 Hz, 1H), 6.90 (d, J=16.1 Hz, 1H), 6.64 (d, J=2.1 Hz, 1H), 6.35 (d, J=2.2 Hz, 1H), 5.00 (septt, J=1.4, 6.8 Hz, 1H), 3.91 (s, 3H), 3.73 (s, 3H), 3.36 (br d, J=6.7 Hz, 2H), 1.76 (s, 3H), 1.60 (s, 3H); $^{13}C$ NMR (100 MHz, DMSO-$d_6$) δ=160.45, 158.45, 156.69, 149.10, 137.43, 133.78, 129.85, 127.03, 125.99, 124.50, 120.63, 119.75, 118.74, 109.00, 104.13, 99.16, 56.25, 55.91, 25.96, 24.28, 18.21.

E)-N-(4-(3-Ethoxy-5-hydroxy-2-(3-methylbut-2-en-1-yl)styryl)-2-methoxyphenyl)formamide (28) [KYN-143]

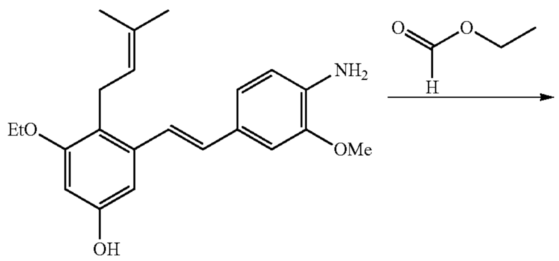

24

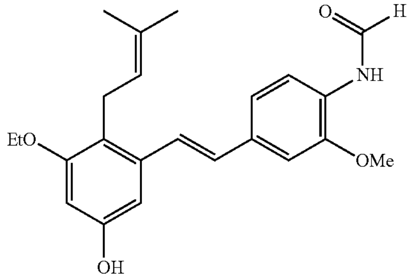

28

(E)-N-(4-(3-Ethoxy-5-hydroxy-2-(3-methylbut-2-en-1-yl)styryl)-2-methoxyphenyl)formamide (28) [KYN-143]

Compound 24 (100 mg, 0.29 mmol, 1.0 equiv) was added to ethyl formate (10 mL) to obtain a cloudy solution, which was heated at 55° C. for 20 hours (clear solution on heating). The reaction mixture was cooled to room temperature and evaporated to dryness under reduced pressure. The residue was dissolved in ethyl acetate (20 mL) and washed with saturated ammonium chloride (20 mL). The aqueous layer was extracted with ethyl acetate (2×20 mL). The combined organic layers were dried over sodium sulfate, filtered and concentrated under reduced pressure. The residue was initially purified on a Reveleris automated chromatography system (Sorbtech 12 g column), eluting with a gradient of 0 to 50% ethyl acetate in heptanes. The product was triturated with 10% ethyl acetate in heptanes (10 mL) to afford compound 28 [KYN-143] (45 mg, 64% yield) as an off-white solid. (NRK-1-145).

Off white solid, melting point 173-176° C.; HPLC Analysis: 98.9% purity; Wavelength 210 nm, bandwidth 4; Column: SorbTech C18AQ, 2.1×50 mm, 3 µm; Retention Time: 9.0 min; Mobile Phase: ACN/formic acid/water; Mass Spectrum (negative mode) m/z=761.3 $(M-H)^-$; $C_{23}H_{27}NO_4$; $^1H$ NMR (400 MHz, DMSO-$d_6$) δ=9.69 (s, 1H), 9.20 (s, 1H), 8.30 (d, J=1.7 Hz, 1H), 8.16 (d, J=8.3 Hz, 1H), 7.29 (d, J=16.1 Hz, 1H), 7.25 (d, J=1.1 Hz, 1H), 7.10 (br d, J=8.3 Hz, 1H), 6.90 (d, J=16.0 Hz, 1H), 6.62 (d, J=2.1 Hz, 1H), 6.32 (d, J=2.0 Hz, 1H), 5.01 (br t, J=7.0 Hz, 1H), 3.95 (q, J=7.0 Hz, 2H), 3.91 (s, 3H), 3.37 (br d, J=6.7 Hz, 2H), 1.76 (s, 3H), 1.60 (s, 3H), 1.33 (t. J=6.9 Hz, 3H); $^{13}C$ NMR (100 MHz, DMSO-$d_6$) δ=160.44, 157.71, 156.59, 149.09, 137.40, 133.79, 129.74 (2C), 127.01, 126.04, 124.52, 120.62, 119.72, 118.90, 109.03, 104.1, 99.96, 63.74, 56.27, 25.99, 24.34, 18.25, 15.25.

(E)-N-(4-(5-hydroxy-3-methoxy-2-(3-methylbut-2-en-1-yl)styryl)-2-methoxyphenyl)acetamide (29) [KYN-128]

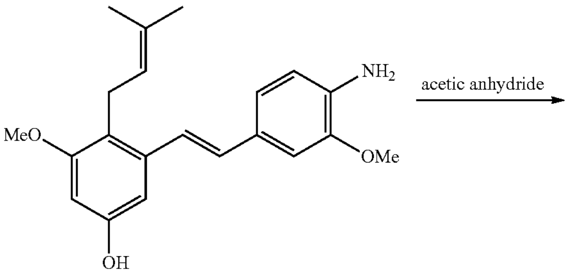

23

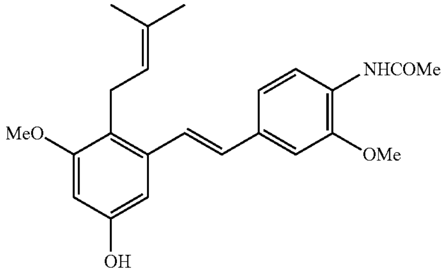

29

N,N-Diisopropylethylamine (0.1 mL, 0.38 mmol, 2 equiv) and acetic anhydride (0.1 mL, 0.38 mmol, 2 equiv) were sequentially added to a solution of Compound 23 [KYN-125] (65 mg, 0.19 mmol, 1.0 equiv) in anhydrous THF (10 mL) at room temperature. After refluxing (66° C.) for 16 hours, the reaction mixture was cooled to room temperature and the volatiles were removed under reduced pressure. The residue was dissolved in ethyl acetate (20 mL) and washed with saturated sodium bicarbonate (20 mL). The aqueous layer was extracted with ethyl acetate (2×10 mL). The combined organic layers were dried over sodium sulfate, filtered and concentrated under reduced pressure. The residue was purified on an Interchim automated chromatography system (RediSep Rf Gold HP C18, 50 g column), eluting with a gradient of 0 to 80% acetonitrile in water to give relatively pure Compound 29, which was further purified by trituration with 30% dichloromethane in heptanes (10 mL) to give pure Compound 29 [KYN-128] (17 mg, 23% yield) as a white solid. (NRK-1-66) Off white grey solid, melting point 205.7-205.9° C.; HPLC Analysis: 97.4% purity; Wavelength 210 nm, bandwidth 4; Column: SorbTech C18AQ, 2.1×50 mm, 3 μm; Retention Time: 8.4 min; Mobile Phase: ACN/formic acid/water; Mass Spectrum (positive mode) m/z=382.2 $(M+H)^+$; $C_{23}H_{27}NO_4$; $^1H$ NMR (400 MHz, $CDCl_3$) δ=8.40 (d, J=8.8 Hz, 1H), 7.84 (s, 1H), 7.23 (d, J=16.1 Hz, 1H), 7.04 (d, J=1.8 Hz, 1H), 7.03 (dd, J=1.7, 6.0 Hz, 1H), 6.88 (d, J=16.1 Hz, 1H), 6.79 (d, J=2.3 Hz, 1H), 6.39 (d, J=2.3 Hz, 1H), 6.24 (s, 1H), 5.12 (tm, J=1.4, 6.8 Hz, 1H), 3.93 (s, 3H), 3.81 (s, 3H), 3.42 (d, J=6.7 Hz, 2H), 2.24 (s, 3H), 1.81 (d, J=0.6 Hz, 3H), 1.67 (d, J=1.0 Hz, 3H); $^{13}C$ NMR (100 MHz, $CDCl_3$) δ=168.65, 158.58, 155.07, 147.91, 137.68, 133.65, 130.42, 129.84, 127.11, 125.77, 123.86, 120.71, 120.44, 119.67, 106.87, 103.98, 98.62, 55.68, 55.65, 25.75, 24.88, 24.45, 17.98.

(E)-N-(4-(3-Ethoxy-5-hydroxy-2-(3-methylbut-2-en-1-yl)styryl)-2-methoxyphenyl)acetamide (30) [KYN-142]

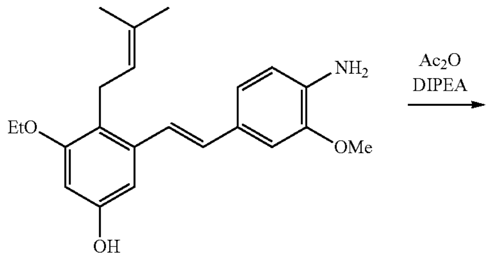

24

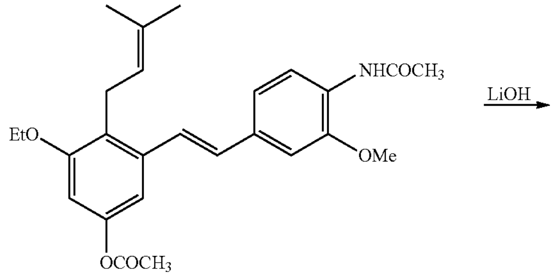

30-1

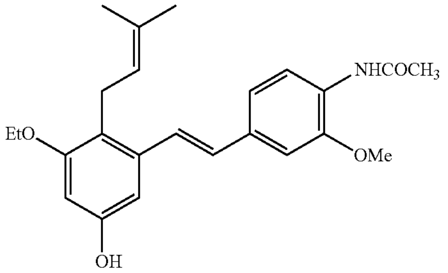

30

(E)-3-(4-Acetamido-3-methoxystyryl)-5-ethoxy-4-(3-methylbut-2-en-1-yl)phenyl acetate (30-1)

N,N-Diisopropylethylamine (0.25 mL, 1.36 mmol, 4 equiv) and acetic anhydride (0.1 mL, 0.75 mmol, 2.2 equiv) were sequentially added to a solution of compound 24 (120 mg, 0.34 mmol, 1.0 equiv) in anhydrous THF (20 mL) at room temperature. After refluxing (66□C) for 16 hours, the reaction mixture was cooled to room temperature and the volatiles were removed under reduced pressure. The residue was dissolved in ethyl acetate (20 mL) and washed with saturated sodium bicarbonate (20 mL). The aqueous layer was extracted with ethyl acetate (2×10 mL). The combined organic layers were dried over sodium sulfate, filtered and concentrated under reduced pressure to give compound 30-1 (136 mg, 92% yield) as a pale yellow solid, which was used subsequently. (NRK-1-133)

(E)-N-(4-(3-ethoxy-5-hydroxy-2-(3-methylbut-2-en-1-yl)styryl)-2-methoxyphenyl)acetamide (30) [KYN-142]

1M Lithium hydroxide (1.6 mL, 1.55 mmol, 5.0 equiv) was added to a solution of compound 30-1 (136 mg, 0.31 mmol, 1.0 equiv) in tetrahydrofuran (10 mL) at room temperature. The resulting solution was stirred at room temperature for 4 hours. The volatiles were removed under reduced pressure. The residue was dissolved in ethyl acetate (20 mL) and washed with saturated ammonium chloride (10 mL). The aqueous layer was extracted with ethyl acetate (2×10 mL). The combined organic layers were dried over sodium sulfate, filtered and concentrated under reduced pressure. The residue was purified on a Reveleris automated chromatography system (Sorbtech 12 g column), eluting with a gradient of 0 to 50% ethyl acetate in heptanes. The product was triturated with diethyl ether (5 mL) to give pure compound 30 [KYN-142](20 mg, 17% yield) as a white solid. (NRK-1-135)

Off white solid, melting point 188-189° C.; HPLC Analysis: 99.3% purity; Wavelength 210 nm, bandwidth 4; Column: SorbTech C18AQ, 2.1×50 mm, 3 μm; Retention Time: 9.0 min; Mobile Phase: ACN/formic acid/water; Mass Spectrum (positive mode) m/z=396.2 $(M+H)^+$; $C_{24}H_{29}NO_4$; $^1H$ NMR (400 MHz, $CDCl_3$) δ=8.41 (d, J=8.1 Hz, 1H), 7.85 (s, 1H), 7.26-7.22 (m, 1H), 7.06-7.00 m, 2H), 6.88 (d, J=16.0 Hz, 1H), 6.79 (d, J=2.1 Hz, 1H), 6.42-6.31 (m, 2H), 5.14 (septett, J=1.2, 6.8 Hz, 1H), 4.00 (q, J=6.9 Hz, 2H), 3.93 (s, 3H), 3.44 (br d, J=6.7 Hz, 2H), 2.24 (s, 3H), 1.82 (s, 3H), 1.68 (s, 3H), 1.42 (t, J=7.0 Hz, 3H); $^{13}C$ NMR (100 MHz, $CDCl_3$) δ=168.71, 157.91, 155.05, 147.92, 137.60, 133.73, 130.22, 129.71, 127.06, 125.90, 123.96, 120.78, 120.55, 119.67, 106.82, 103.91, 99.52, 63.88, 55.68, 25.79, 24.88, 24.53, 18.04, 14.93.

(E)-2-Amino-N-(4-(5-hydroxy-3-methoxy-2-(3-methylbut-2-en-1-yl)styryl)-2-methoxyphenyl)acetamide (31) [KYN-151]

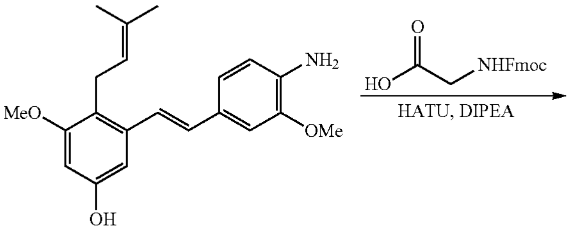

23

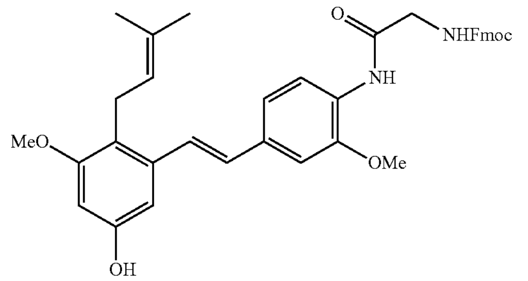

+

31-1

-continued

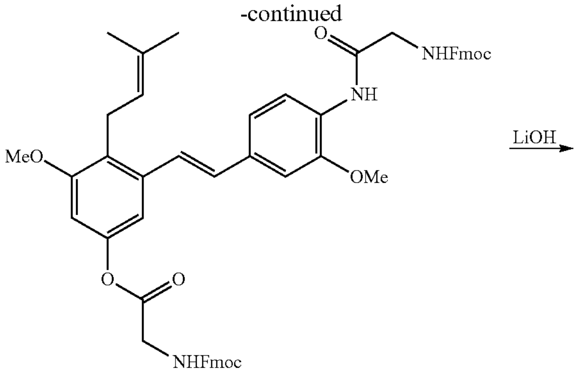

31-2

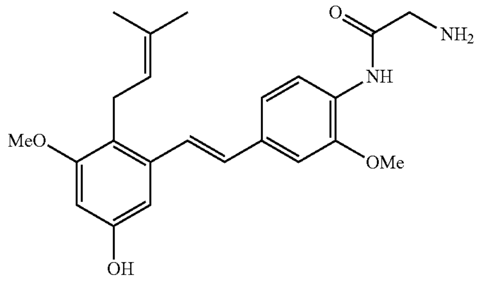

31

(9H-Fluoren-9-yl)methyl (E)-(2-((4-(5-hydroxy-3-methoxy-2-(3-methylbut-2-en-1-yl)styryl)-2-methoxyphenyl)amino)-2-oxoethyl)carbamate Fmocglycine (520 mg, 1.76 mmol, 3.0 equiv), N,N-Diisopropylethylanine (0.5 mL, 2.95 mmol, 5.0 equiv) and 1-*ibis*(dimethylamino)methylene-1H-1,2,3-triazolo[4,5-b] pyridinium 3-oxid hexafluorophosphate (HATU) (900 mg, 2.36 mmol, 4.0 equiv) were sequentially added to a solution of (E)-3-(4-amino-3-methoxystyryl)-5-methoxy-4-(3-methylbut-2-en-1-yl)phenol (compound 23) [KYN-125] (200 mg, 0.59 mmol, 1.0 equiv) in dichloromethane (10 mL). The resulting solution was stirred at room temperature for 16 hours. LC-MS analysis indicated the formation of compound 11 and compound 12. The reaction mixture was diluted with dichloromethane (20 mL) and washed with saturated sodium bicarbonate (30 mL). The aqueous layer was extracted with dichloromethane (2×20 mL). The combined organic layers were dried over sodium sulfate, filtered and concentrated under reduced pressure. The residue was purified on a Reveleris automated chromatography system (Sorbtech 24 g column), eluting with a gradient of 0 to 60% ethyl acetate in heptanes to give a mixture of compound 31-1 and compound 31-2 (330 mg) as an off white solid (NRK-1-161).

(E)-2-amino-N-(4-(5-hydroxy-3-methoxy-2-(3-methylbut-2-en-1-yl)styryl)-2-methoxyphenyl)acetamide (31): 1M lithium hydroxide (5 mL) was added to a solution of compound 31-1 and compound 31-2 (330 mg) in tetrahydrofuran at room temperature. After stirring for 16 hours, the volatiles were removed under reduced pressure. The residue was dissolved in ethyl acetate (30 mL) and washed with saturated ammonium chloride (30 mL). The aqueous layer was extracted with ethyl acetate (2×20 mL). The combined organic layers were dried over sodium sulfate, filtered and concentrated under reduced pressure. The residue was purified on a Reveleris automated chromatography system (Sorbtech 24 g column), eluting with a gradient of 0 to 5% methanol in dichloromethane containing 1% of 7M ammonia in methanol to give compound 31 (25.0 mg, 23% yield over 2 steps) as an off white solid (NRK-1-164).

(E)-2-amino-N-(4-(5-hydroxy-3-methoxy-2-(3-methylbut-2-en-1-yl)styryl)-2-methoxyphenyl)acetamide (31) [KYN-151]

Off white solid, melting point 196.0-201.9° C.; HPLC Analysis: 98.7% purity; Wavelength 210 nm, bandwidth 4; Column: SorbTech C18AQ, 2.1×50 mm, 3 μm; Retention Time: 5.78 min; Mobile Phase: ACN/formic acid/water; Mass Spectrum (positive mode) m/z=397.2 $(M+H)^+$; $C_{23}H_{28}N_2O_4$; $^1H$ NMR (400 MHz, DMSO-$d_6$) δ=10.10 (br s, 1H), 9.24 (s, 1H), 8.29 (d, J=8.3 Hz, 1H), 7.30-7.23 (m, 2H), 7.10 (dd, J=1.7, 8.4 Hz, 1H), 6.90 (d, J=16.0 Hz, 1H), 6.63 (d, J=2.2 Hz, 1H), 6.35 (d, J=2.2 Hz, 1H), 5.00 (septt, J=1.2, 7.0 Hz, 1H), 3.92 (s, 3H), 3.73 (s, 3H), 3.38-3.33 (m, 2H), 3.28-3.24 (m, 2H), 2.33 (br s, 2H), 1.76 (s, 3H), 1.60 (s, 3H); $^{13}C$ NMR (100 MHz, DMSO-$d_6$) δ=171.88, 158.45, 156.68, 148.71, 137.47, 133.12, 129.92, 129.83, 127.42, 125.67, 124.51, 119.96, 118.87, 118.69, 108.71, 104.09, 99.11, 56.30, 55.91, 45.67, 25.95, 24.28, 18.20.

(E)-2-Amino-N-(4-(3-ethoxy-5-hydroxy-2-(3-methylbut-2-en-1-yl)styryl)-2-methoxyphenyl)acetamide (32) [KYN-148]

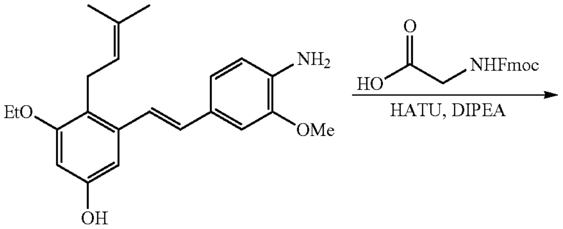

24

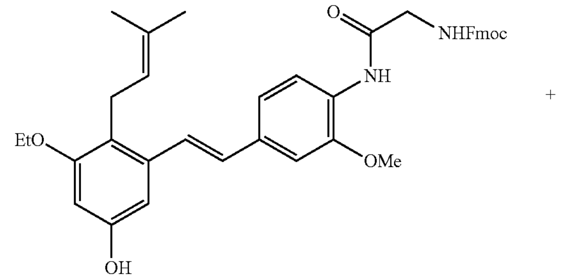

32-1

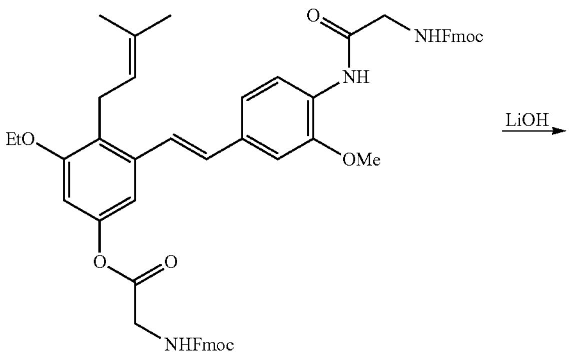

32-2

-continued

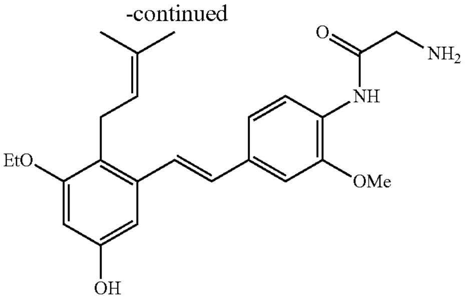

32

(9H-Fluoren-9-yl)methyl (E)-(2-((4-(3-ethoxy-5-hydroxy-2-(3-methylbut-2-en-1-yl)styryl)-2-methoxyphenyl)amino)-2-oxoethyl)carbamate (12)

Fmocglycine (500 mg, 1.71 mmol, 3.0 equiv), N,N-Diisopropylethylamine (0.5 mL, 2.85 mmol, 5.0 equiv) and 1-[Bis(dimethylamino)methylene]-1H-1,2,3-triazolo[4,5-b] pyridinium 3-oxid hexafluorophosphate (HATU) (860 mg, 2.28 mmol, 4.0 equiv) were sequentially added to a solution of compound 24 (200 mg, 0.57 mmol, 1.0 equiv) in dichloromethane (10 mL). The resulting solution was stirred at room temperature for 16 hours. LC-MS analysis indicated the formation of compound 32-1 and compound 32-2. The reaction mixture was diluted with dichloromethane (20 mL) and washed with saturated sodium bicarbonate (30 mL). The aqueous layer was extracted with dichloromethane (2×20 mL). The combined organic layers were dried over sodium sulfate, filtered and concentrated under reduced pressure. The residue was purified on a Reveleris automated chromatography system (Sorbtech 24 g column), eluting with a gradient of 0 to 60% ethyl acetate in heptanes to give a mixture of compound 32-1 and compound 32-2 (550 mg) as an off white solid (NRK-1-158).

(E)-2-Amino-N-(4-(3-ethoxy-5-hydroxy-2-(3-methylbut-2-en-1-yl)styryl)-2-methoxyphenyl)acetamide (32) [KYN-148]

1M lithium hydroxide solution (5 mL) was added to a solution of compound 32-1 and compound 32-2 (550 mg) in tetrahydrofuran (20 mL) at room temperature. After stirring for 16 hours, the volatiles were removed under reduced pressure. The crude was dissolved in ethyl acetate (30 mL) and washed with saturated ammonium chloride (30 mL). The aqueous layer was extracted with ethyl acetate (2×20 mL). The combined organic layers were dried over sodium sulfate, filtered and concentrated under reduced pressure. The residue was first triturated with 30% ethyl acetate in heptanes (30 mL) to afford a beige solid, which was further purified on a Reveleris automated chromatography system (Sorbtech 24 g column), eluting with a gradient of 0 to 5% methanol in dichloromethane containing 1% of 7M ammonia in methanol to give compound 32 [KYN-148] (30.0 mg, 13% yield over 2 steps) as an off white solid (NRK-1-162).

Off white solid, melting point 200.0-203.7° C.; HPLC Analysis: 99.5% purity; Wavelength 210 nm, bandwidth 4; Column: SorbTech C18AQ, 2.1×50 mm, 3 μm; Retention Time: 8.25 min; Mobile Phase: ACN/formic acid/water; Mass Spectrum (positive mode) m/z=411.2 $(M+H)^+$; $C_{24}H_{30}N_2O_4$; $^1H$ NMR (400 MHz, DMSO-d) δ=10.08 (br s, 1H), 9.20 (s, 1H), 8.29 (d, J=8.3 Hz, 1H), 7.32-7.23 (m, 2H), 7.11 (dd, J=1.5, 8.4 Hz, 1H), 6.90 (d, J=16.0 Hz, 1H), 6.63 (d, J=2.1 Hz, 1H), 6.32 (d, J=2.1 Hz, 1H), 5.01 (br t, J=7.0 Hz, 1H), 3.95 (q, J=6.8 Hz, 2H), 3.92 (s, 3H), 3.40-3.34 (m, 2H), 3.29-3.24 (m, 2H), 2.33 (br s, 2H), 1.77 (s, 3H), 1.61 (s, 3H), 1.33 (t, J=6.9 Hz, 3H); $^{13}$C NMR (100 MHz, DMSO-$d_6$) δ=171.88, 157.72, 156.59, 148.71, 137.46, 133.14, 129.87, 129.73, 127.41, 125.74, 124.54, 119.93, 118.86, 108.74, 104.08, 99.92, 63.74, 56.32, 45.67, 25.99, 24.35, 18.25, 15.25.

Methyl (E)-(4-(5-hydroxy-3-methoxy-2-(3-methyl-but-2-en-1-yl)styryl)-2-methoxyphenyl)glycinate (33) [KYN-126]

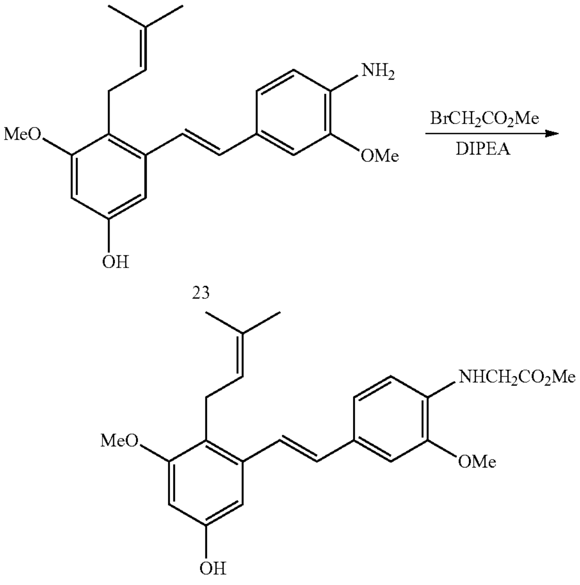

23

33

N,N-Diisopropylethylamine (0.5 mL, 2.92 mmol, 4 equiv) and methyl bromoacetate (0.2 mL, 2.21 mmol, 3 equiv) were sequentially added to a solution of compound 23 [KYN-125] in anhydrous THF (10 mL) at room temperature. After refluxing (66° C.) for 16 hours, the reaction was cooled to room temperature and the volatiles were removed under reduced pressure. The residue was dissolved in ethyl acetate (30 mL) and washed with saturated sodium bicarbonate (20 mL). The aqueous layer was extracted with ethyl acetate (2×30 mL). The combined organic layers were dried over sodium sulfate, filtered and concentrated under reduced pressure. The residue was purified on an Interchim automated chromatography system (RediSep Rf Gold HP C18, 50 g column), eluting with a gradient of 0 to 70% acetonitrile in water to give compound 33 [KYN-126] (180 mg, 59% yield) as an off white solid. (NRK-1-65-1).

Off white grey solid, melting point 147.3-160.2° C.; HPLC Analysis: 98.1% purity; Wavelength 210 nm, bandwidth 4; Column: Luna C18(2), 2.0×20 mm, 3 μm; Retention Time: 3.84 min; Mobile Phase: ACN/formic acid/water; Mass Spectrum (positive mode) m/z=412.2 $(M+H)^+$; $C_{24}H_{29}NO_5$; $^1$H NMR (400 MHz, $CDCl_3$) δ=7.10 (d, J=16.2 Hz, 1H), 6.97 (dd, J=1.6, 6.7 Hz, 1H), 6.96 (br s, 1H), 6.84 (d, J=15.8 Hz, 1H), 6.65 (d, J=2.4 Hz, 1H), 6.45 (d, J=8.6 Hz, 1H), 6.34 (d, J=2.4 Hz, 1H), 5.13 (tm, J=1.5, 6.9 Hz, 1H), 4.92 (br t, J=4.3 Hz, 1H), 4.75 (br s, 1H), 3.98 (d, J=5.1 Hz, 2H), 3.91 (s, 3H), 3.80 (s, 3H), 3.79 (s, 3H), 3.41 (d, J=6.6 Hz, 2H), 1.82 (d, J=0.7 Hz, 3H), 1.68 (d, J=1.2 Hz, 3H); $^{13}$C NMR (100 MHz, $CDCl_3$) δ=171.44, 158.55, 154.37, 147.19, 138.52, 137.00, 130.88, 130.47, 127.54, 123.79, 122.63, 120.85, 120.50, 109.64, 107.10, 103.78, 97.92, 55.69, 55.47, 52.26, 45.43, 25.76, 24.47, 17.98.

Methyl (E)-(4-(3-ethoxy-5-hydroxy-2-(3-methylbut-2-en-1-yl)styryl)-2-methoxyphenyl)glycinate (34) [KYN-147]

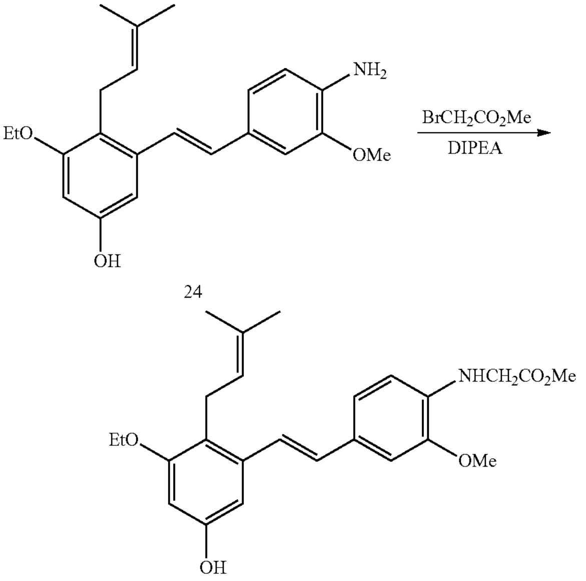

24

34

Methyl (E)-(4-(3-ethoxy-5-hydroxy-2-(3-methylbut-2-en-1-yl)styryl)-2-methoxyphenyl)glycinate (34) [KYN-147]

N,N-Diisopropylethylamine (0.4 mL, 2.24 mmol, 4 equiv) and methyl bromoacetate (0.21 mL, 1.68 mmol, 3 equiv) were sequentially added to a solution of compound 24 (200 mg, 0.56 mmol, 1.0 equiv) in anhydrous THF (20 mL) at room temperature. After refluxing (66° C.) for 16 hours, the reaction mixture was cooled to room temperature and the volatiles were removed under reduced pressure. The residue was dissolved in ethyl acetate (30 mL) and transferred to a separatory funnel containing saturated sodium bicarbonate solution (20 mL). The layers were separated and the aqueous layer was extracted with ethyl acetate (2×30 mL). The combined organic layers were dried over sodium sulfate, filtered, and concentrated under reduced pressure. The residue was initially purified on a Reveleris automated chromatography system (Redisep Rf Gold HP C18, 50 g column), eluting with a gradient of 0 to 60% acetonitrile in water. The product was triturated with 10% ethyl acetate in heptanes (10 mL) to give compound 34 [KYN-147] (40 mg, 17% yield) as an off white solid. (NRK-1-151)

Off white solid, melting point 144-169° C.; HPLC Analysis: 97.3% purity; Wavelength 254 nm, bandwidth 4; Column: SorbTech C18AQ, 2.1×50 mm, 3 μm; Retention Time: 10.06 min; Mobile Phase: ACN/formic acid/water; Mass Spectrum (positive mode) m/z=426.2 $(M+H)^+$; $C_{25}H_{31}NO_5$;

$^1$H NMR (400 MHz, $CDCl_3$) δ=7.11 (d, J=16.0 Hz, 1H), 6.99-6.94 (m, 2H), 6.84 (br d, J=16.0 Hz, 1H), 6.63 (d, J=2.3 Hz, 1H), 6.45 (d, J=8.6 Hz, 1H), 6.31 (d, J=2.4 Hz, 1H), 5.14 (septett, J=1.3, 7.0 Hz, 1H), 4.92 (br s, 1H), 4.73 (br s, 1H), 3.99 (q, J=7.0 Hz, 2H), 3.97 (s, 2H), 3.91 (s, 3H), 3.79 (s, 3H), 3.43 (br d, J=6.8 Hz, 2H), 1.82 (s, 3H), 1.68 (d, J=0.9 Hz, 3H), 1.41 (t, J=7.0 Hz, 3H); $^{13}$C NMR (100 MHz, $CDCl_3$) δ=171.44, 157.88, 154.27, 147.20, 138.45, 136.96, 130.77, 130.28, 127.59, 123.86, 122.74, 120.82, 120.65, 109.66, 107.14, 103.69, 98.79, 63.91, 55.48, 52.25, 45.44, 25.79, 24.54, 18.04, 14.92.

(E)-2-((4-(3-Ethoxy-5-hydroxy-2-(3-methylbut-2-en-1-yl)styryl)-2-methoxyphenyl)amino)-2-oxoacetic acid (35) [KYN-152]

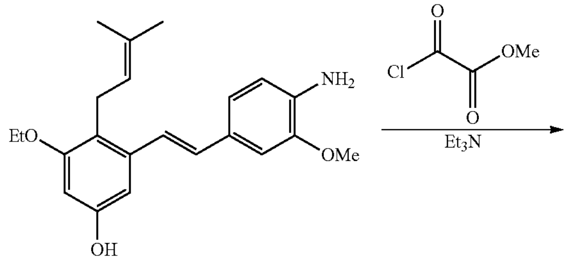

24

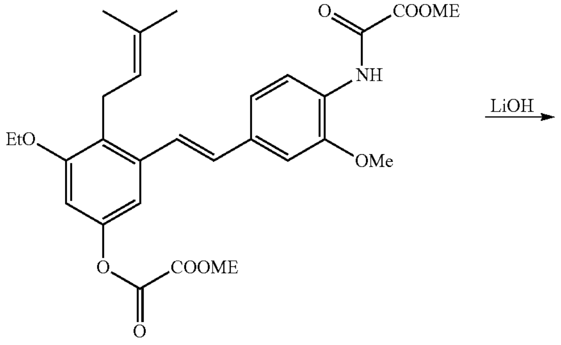

35-1

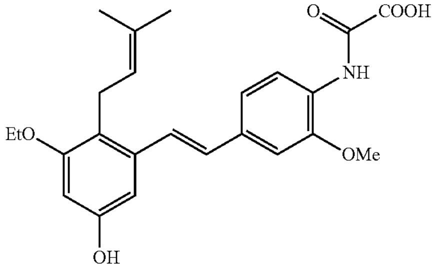

35

(E)-3-Ethoxy-5-(3-methoxy-4-(2-methoxy-2-oxoacetamido)styryl)-4-(3-methylbut-2-en-1-yl)phenyl methyl oxalate (35-1)

Methyl chlorooxoacetate (0.1 mL, 0.85 mmol, 2.5 equiv) was added to a solution of triethylamine (0.25 mL, 1.7 mmol, 5.0 equiv) and compound 24 [KYN-141] (120 mg, 0.34 mmol, 1.0 equiv) in tetrahydrofuran (20 mL) at 5° C. The reaction mixture was warmed to room temperature and stirred for 16 hours. The reaction mixture was filtered and the filtrate was concentrated under reduced pressure. The residue was dissolved in ethyl acetate (20 mL) and washed with saturated ammonium chloride (20 mL). The aqueous layer was extracted with ethyl acetate (2×20 mL). The combined organic layers were dried over sodium sulfate, filtered and concentrated under reduced pressure. The residue was purified on a Reveleris automated chromatography system (Sorbtech 24 g column), eluting with a gradient of 0 to 60% ethyl acetate in heptanes to give compound 35-1 (130.0 mg, 73%) as a beige solid (NRK-1-168).

(E)-2-((4-(3-Ethoxy-5-hydroxy-2-(3-methylbut-2-en-1-yl)styryl)-2-methoxyphenyl)amino)-2-oxoacetic acid (35) [KYN-152]

1M lithium hydroxide (0.75 mL, 0.75 mmol, 3.0 equiv) was added to a solution of compound 35-1 (130 mg, 0.25 mmol, 1.0 equiv) in tetrahydrofuran (20 mL) at room temperature. After stirring for 16 hours, the volatiles were removed under reduced pressure. The residue was dissolved in ethyl acetate (30 mL) and washed with 1M HCl (10 mL). The aqueous layer was extracted with ethyl acetate (2×30 mL). The combined organic layers were dried over sodium sulfate, filtered and concentrated under reduced pressure. The residue was triturated with 10% ethyl acetate in heptanes (20 mL) to give compound 35 [KYN-152] (42.0 mg, 38% yield) as an off white solid (NRK-1-170).

Off white solid, melting point 207.8-207.9° C.; HPLC Analysis: 99.1% purity; Wavelength 210 nm, bandwidth 4; Column: SorbTech C18AQ, 2.1×50 mm, 3 μm; Retention Time: 8.24 min; Mobile Phase: ACN/formic acid/water; Mass Spectrum (negative mode) m/z=424.1 $(M-H)^-$; $C_{24}H_{27}NO_6$; $^1$H NMR (400 MHz, DMSO-$d_6$) δ=9.63 (s, 1H), 9.21 (br s, 1H), 8.10 (d, J=8.3 Hz, 1H), 7.38-7.29 (m, 2H), 7.18 (br d, J=8.4 Hz, 1H), 6.93 (d, J=16.1 Hz, 1H), 6.63 (d, J=2.0 Hz, 1H), 6.33 (d, J=2.1 Hz, 1H) 5.01 (br t, J=7.0 Hz, 1H), 4.06-3.91 (m, 5H), 3.38 (br d, J=6.8 Hz, 2H), 1.76 (s, 3H), 1.60 (s, 3H), 1.33 (t, J=6.9 Hz, 3H); $^{13}$C NMR (100 MHz, DMSO-$d_6$) δ=162.25, 157.73, 156.61, 156.08, 149.59, 137.30, 135.11, 129.78, 129.62, 126.77, 125.77, 124.51, 120.32, 119.82, 119.04, 109.14, 104.17, 100.10, 63.75, 56.53, 25.99, 24.35, 18.26, 15.25.

(E)-4-((4-(5-Hydroxy-3-methoxy-2-(3-methylbut-2-en-1-yl)styryl)-2-methoxyphenyl)amino)-4-oxobutanoic acid (compound 36) [KYN-150]

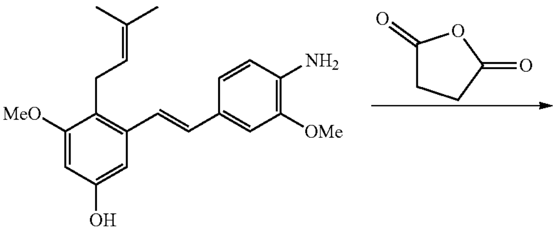

23

-continued

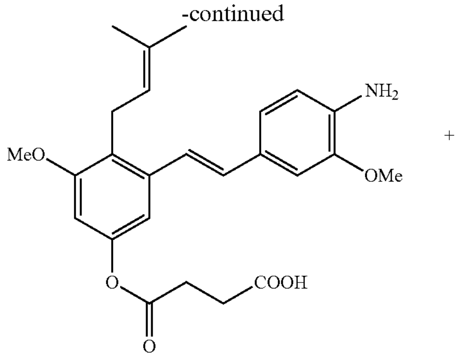

36-1

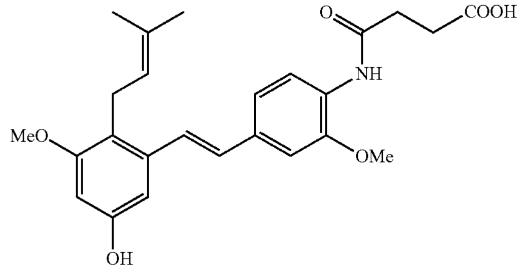

36

Succinic anhydride (140 mg, 1.4 mmol, 4.0 equiv) and N,N-diisopropylethylamine (0.36 mL, 2.1 mmol, 6.0 equiv) were sequentially added to a solution of (E)-3-(4-amino-3-methoxystyryl)-5-methoxy-4-(3-methylbut-2-en-1-yl)phenol (compound 23) [KYN-125] (120 mg, 0.35 mmol, 1.0 equiv) in toluene (20 mL). The resulting cloudy solution was refluxed (110° C.) for 16 hours (clear solution on heating). The reaction mixture was cooled to room temperature and diluted with ethyl acetate (20 mL). The organic layer was washed with saturated ammonium chloride (20 mL). The aqueous layer was extracted with ethyl acetate (2×20 mL). The combined organic layers were dried over sodium sulfate, filtered and concentrated under reduced pressure to give a mixture of compound 36-1 and compound 36 (210 mg) as a light brown oil. The residue was dissolved in tetrahydrofuran (10 mL) and treated with 1M lithium hydroxide (1.0 mL) at room temperature for 16 hours. The reaction mixture was evaporated to dryness and the resulting residue was dissolved in ethyl acetate (20 mL). The organic layer was washed with saturated ammonium chloride (20 mL). The organic layer was dried over sodium sulfate and concentrated under reduced pressure. The residue was triturated with 10% ethyl acetate in heptanes (10 mL). The product was suspended in diethyl ether (10 mL) and stirred at room temperature for 16 hours. The suspension was filtered to afford compound 36 (60 mg, 40% yield over 2 steps) as a light grey solid. (NRK-1-163).

(E)-N-((4-(3-methoxy-5-hydroxy-2-(3-methylbut-2-en-1-yl)styryl)-2methoxyphenyl)amino)-4-oxobutanoic acid (compound 36) [KYN-150]

Light grey solid, melting point 169.4-175.7° C.; HPLC Analysis: 97.8% purity; Wavelength 210 nm, bandwidth 4; Column: SorbTech C18AQ, 2.1×50 mm, 3 μm; Retention Time: 7.98 min; Mobile Phase: ACN/formic acid/water; Mass Spectrum (negative mode) m/z=438.2 $(M-H)^-$; $C_{25}H_{29}NO_6$; $^1H$ NMR (400 MHz, Acetonitrile-$d_3$) δ=8.25 (br s, 1H), 8.21 (br d, J=8.3 Hz, 1H), 7.28 (d, J=16.1 Hz, 1H), 7.17 (d, J=1.7 Hz, 1H), 7.07 (dd, J=1.8, 8.4 Hz, 1H), 6.94 (d, J=16.1 Hz, 1H), 6.68 (d, J=2.3 Hz, 1H), 6.39 (d, J=2.3 Hz, 1H), 5.05 (septt, J=1.4, 6.8 Hz, 1H), 3.92 (s, 3H), 3.77 (s, 3H), 3.41 (br d, J=6.8 Hz, 2H), 2.70-2.65 (m, 2H), 2.64-2.60 (m, 2H), 1.80 (d, J=0.7 Hz, 3H), 1.64 (d, J=1.1 Hz, 3H); $^{13}C$ NMR (100 MHz, Acetonitrile-$d_3$) δ=174.42, 171.50, 159.61, 156.96, 138.79, 131.50, 130.93, 128.74, 126.52, 124.90, 120.85, 120.77, 120.69, 109.17, 104.80, 99.68, 56.67, 56.39, 32.51, 29.64, 25.88, 24.99, 18.23.

(E)-4-((4-(3-Ethoxy-5-hydroxy-2-(3-methylbut-2-en-1-yl)styryl)-2-methoxyphenyl)amino)-4-oxobutanoic acid (37) [KYN-144]

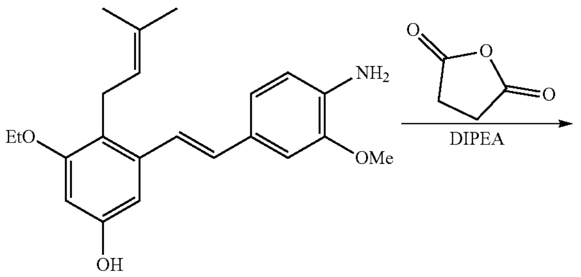

24

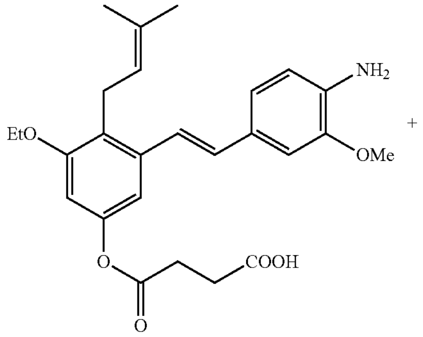

37-1

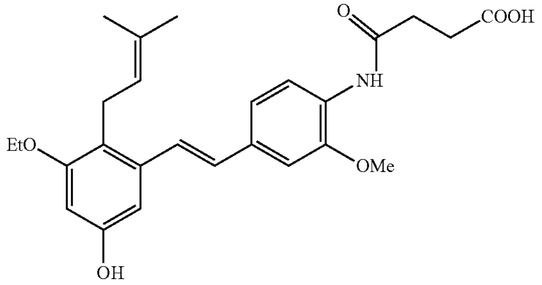

37

(E)-4-((4-(3-Ethoxy-5-hydroxy-2-(3-methylbut-2-en-1-yl)styryl)-2-methoxyphenyl)amino)-4-oxobutanoic acid (compound 37) [KYN-144]

Succinic anhydride (58 mg, 0.58 mmol, 2.0 equiv) and N,N-diisopropylethylamine (0.15 mL, 0.87 mmol, 3.0 equiv) were sequentially added to a solution of compound 24 (100 mg, 0.29 mmol, 1.0 equiv) in toluene (20 mL). The resulting cloudy solution was refluxed (110° C.) for 16 hours (clear solution on heating). The reaction mixture was cooled to room temperature and diluted with ethyl acetate (20 mL).

The organic layer was washed with saturated ammonium chloride (20 mL). The aqueous layer was extracted with ethyl acetate (2×20 mL). The combined organic layers were dried over sodium sulfate, filtered and concentrated under reduced pressure to give a mixture of compound 37-1 and compound 37 (165 mg) as a light brown solid. The residue was dissolved in tetrahydrofuran (10 mL) and treated with 1M lithium hydroxide solution (1.0 mL) at room temperature for 16 hours. The reaction mixture was evaporated to dryness and the resulting residue was dissolved in ethyl acetate (20 mL). The organic layer was washed with saturated ammonium chloride (20 mL). The organic layer was collected, dried over sodium sulfate and concentrated under reduced pressure. The residue was triturated with 10% ethyl acetate in heptanes (10 mL). The product was suspended in diethyl ether (10 mL) and stirred at room temperature for 16 hours. The suspension was filtered to afford compound 37 [KYN-144] (40 mg, 31% yield over 2 steps) as a light grey solid. (NRK-1-148)

Light grey solid, melting point 173-180° C.; HPLC Analysis: 96.4% purity; Wavelength 254 nm, bandwidth 4; Column: SorbTech C18AQ, 2.1×50 mm, 3 μm; Retention Time: 8.52 min; Mobile Phase: ACN/formic acid/water; Mass Spectrum (negative mode) m/z=452.2 $(M-H)^-$; $C_{26}H_{31}NO_6$; $^1H$ NMR (400 MHz, Acetonitrile-$d_3$) δ=8.25 (br s, 1H), 8.21 (br d, J=8.3 Hz, 1H), 7.29 (d, J=16.1 Hz, 1H), 7.17 (d, J=1.7 Hz, 1H), 7.07 (dd, J=1.7, 8.3 Hz, 1H), 6.94 (d, J=16.1 Hz, 1H), 6.67 (d, J=2.3 Hz, 1H), 6.36 (d, J=2.3 Hz, 1H), 5.07 (septett, J=1.5, 7.0 Hz, 1H), 3.99 (q, J=7.0 Hz, 2H), 3.92 (s, 3H), 3.43 (br d, J=7.0 Hz, 2H), 2.70-2.65 (m, 2H), 2.64-2.60 (m, 2H), 1.80 (s, 3H), 1.64 (d, J=1.0 Hz, 3H), 1.37 (t, J=7.0 Hz, 3H); $^{13}C$ NMR (100 MHz, Acetonitrile-$d_3$) δ=174.41, 171.48, 158.91, 156.86, 149.80, 138.77, 134.49, 131.38, 130.85, 128.72, 126.61, 124.95, 120.95, 120.84, 120.68, 109.18, 104.74, 100.55, 64.93, 55.67, 32.52, 29.64, 25.90, 25.07, 18.32, 15.30.

(E)-1-(4-(3-Ethoxy-5-hydroxy-2-(3-methylbut-2-en-1-yl)styryl)-2-methoxyphenyl)guanidine (38) [KYN-155]

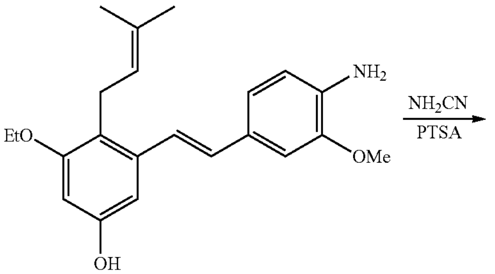

24

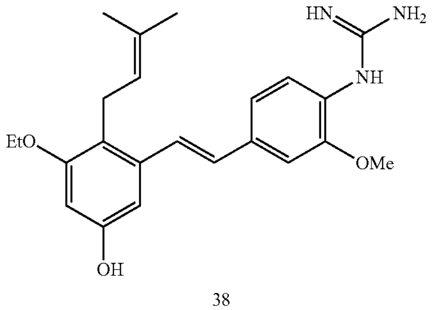

38

(E)-1-(4-(3-ethoxy-5-hydroxy-2-(3-methylbut-2-en-1-yl)styryl)-2-methoxyphenyl)guanidine (38) [KYN-155]

Cyanamide (237 mg, 5.66 mmol, 20.0 equiv) and p-toluenesulfonic acid (1.07 g, 5.66 mmol, 20.0 equiv) were added to a solution of compound 24 (100 mg, 0.28 mmol, 1.0 equiv) in ethanol (50 mL).

After refluxing (79° C.) for 16 hours, additional cyanamide (237 mg, 5.66 mmol, 20.0 equiv) and p-toluenesulfonic acid (1.07 g, 5.66 mmol, 20.0 equiv) were added to the reaction mixture, which was refluxed an additional 16 hours. The reaction mixture was cooled to room temperature and the volatiles were removed under reduced pressure. The residue was dissolved in ethyl acetate (50 mL) and washed with saturated sodium bicarbonate (50 mL). The aqueous layer was extracted with ethyl acetate (2×30 mL). The combined organic layers were dried over sodium sulfate, filtered and concentrated under reduced pressure. Additional compound 24 (100 mg) was converted to compound 38 in a similar manner. The combined residue was first purified on a Reveleris automated chromatography system (Sorbtech 24 g column), eluting with a gradient of 0 to 15% methanol in dichloromethane containing 5% of 7M ammonia in methanol to afford relatively pure 38. The product was further purified on a Reveleris automated chromatography system (Redisep Rf Gold HP C18, 50 g column), eluting with a gradient of 0 to 45% acetonitrile in water containing 10 mM ammonium bicarbonate and 5% methanol to afford compound 38 [KYN-155] (37.0 mg, 16% yield) as a white solid (NRK-1-177).

White solid, melting point 130.5-130.6° C.; HPLC Analysis: 99.7% purity; Wavelength 210 nm, bandwidth 4; Column: SorbTech C18AQ, 2.1×50 mm, 3 μm; Retention Time: 6.45 min; Mobile Phase: ACN/formic acid/water; Mass Spectrum (positive mode) m/z=396.2 $(M+H)^+$; $C_{23}H_{29}N_3O_3$; $^1H$ NMR (400 MHz, DMSO-$d_4$) δ=7.20 (d, J=16.0 Hz, 1H), 7.11 (s, 1H), 7.01 (d, J=7.5 Hz, 1H), 6.96-6.80 (m, 2H), 6.62 (d, J=2.2 Hz, 1H), 6.30 (d, J=2.2 Hz, 1H), 5.06-4.98 (m, 1H), 3.94 (q, J=6.9 Hz, 2H), 3.82-3.72 (m, 3H), 3.35 (br d, J=6.8 Hz, 2H), 1.77 (s, 3H), 1.61 (s, 3H), 1.33 (t. J=6.9 Hz, 3H); $^{13}C$ NMR (100 MHz, DMSO-$d_6$) δ=157.70, 156.60, 153.04, 137.68, 130.36, 129.71, 124.83, 124.59, 124.37, 120.26, 118.60, 110.05, 103.97, 99.72, 63.74, 55.76, 25.99, 24.34, 18.27, 15.27.

(E)-N-(4-(3-ethoxy-5-hydroxy-2-(3-methylbut-2-en-1-yl)styryl)-2-methoxyphenyl)-N-hydroxyacetamide (compound 39) [KYN-165]

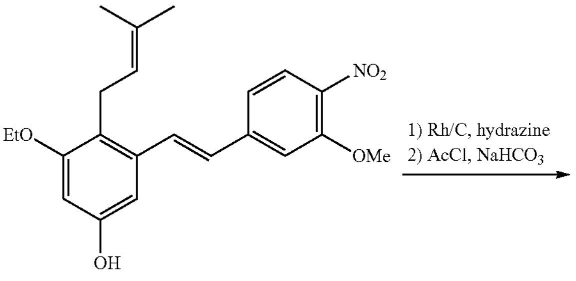

24-3

-continued

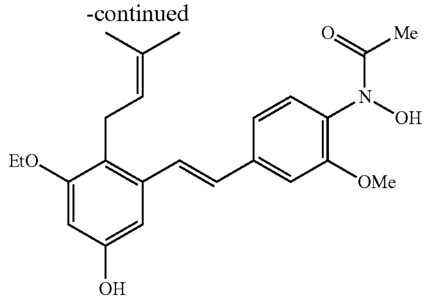

39

5% Rhodium on activated charcoal (5 mg, 0.672 μmol, 0.003 equiv) and hydrazine monohydrate (27 mg, 0.27 mmol, 1.2 equiv) were added to a solution of compound 24-3 (86 mg, 0.224 mmol, 1.0 equiv) in tetrahydrofuran (8 mL) at 0° C. After stirring at 0° C. for 1 hour, sodium bicarbonate (75 mg, 0.896 mmol, 4 equiv) and acetyl chloride (53 mg, 0.672 mmol, 3 equiv) were sequentially added to the reaction. The mixture was warmed to room temperature and stirred for 1 hour. The suspension was diluted with ethyl acetate (30 mL) and washed with saturated ammonium chloride (10 mL). The organic layer was dried over sodium sulfate, filtered and concentrated under reduced pressure. The residue was purified on an InterChim automated chromatography system (25 g column), eluting with a gradient of 0 to 100% ethyl acetate in heptanes, to give compound 39 (44 mg, 44% yield) as an off-white oil. (LM-8-65)

HPLC Analysis: 97.2% purity; Wavelength 254 nm, bandwidth 4; Column: Waters Atlantis T3, 2.1×50 mm, 3 μm; Retention Time: 8.3 min; Mobile Phase: ACN/formic acid/water; Mass Spectrum (positive mode) m/z=412.2 $(M+H)^+$; $C_{24}H_{29}NO_5$; $^1H$ NMR (400 MHz, $CDCl_3$) δ=9.69-7.44 (m, 1H), 7.40-7.28 (m, 2H), 7.08 (br d, J=6.6 Hz, 1H), 7.02 (s, 1H), 6.87 (br d, J=15.4 Hz, 1H), 6.70 (br s, 1H), 6.41 (br s, 1H), 5.12 (br t. J=6.7 Hz, 1H), 3.98 (q, J=6.9 Hz, 2H), 3.86 (s, 3H), 3.43 (br d, J=6.5 Hz, 2H), 1.97 (br s, 3H), 1.80 (s, 3H), 1.67 (s, 3H), 1.40 (t, J=6.9 Hz, 3H); $^{13}C$ NMR (100 MHz, $CDCl_3$) δ=167.75, 157.86, 155.23, 154.91, 141.36, 136.98, 130.47, 130.07, 128.96, 126.01, 123.73, 120.97, 119.27, 109.83, 104.13, 100.11, 63.93, 55.75, 25.75, 24.48, 19.41, 18.01, 14.87.

(E)-N-(4-(3-Ethoxy-5-hydroxy-2-(3-methylbut-2-en-1-yl)styryl)-2-hydroxyphenyl)formamide (40) [KYN-159]

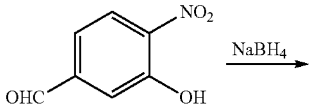

40-1

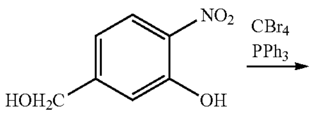

40-2

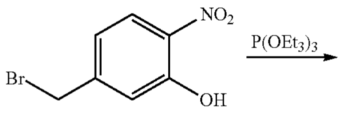

40-3

-continued

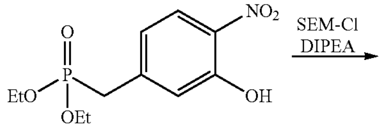

40-4

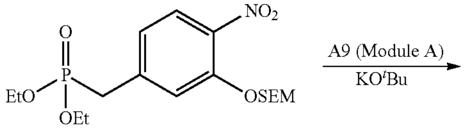

40-5

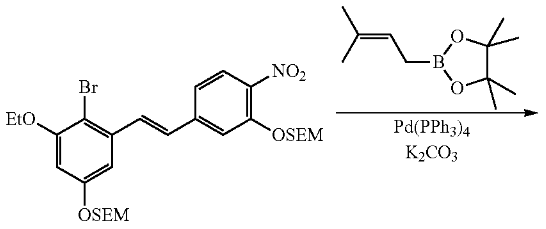

40-6

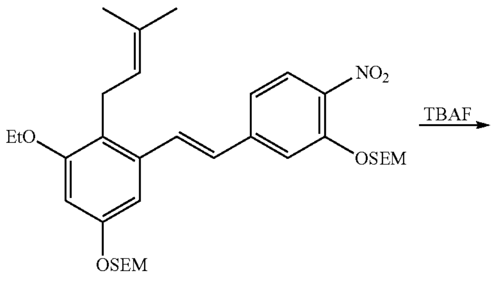

40-7

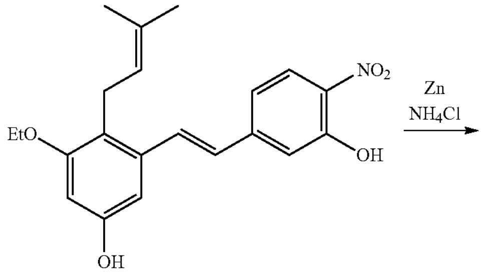

40-8

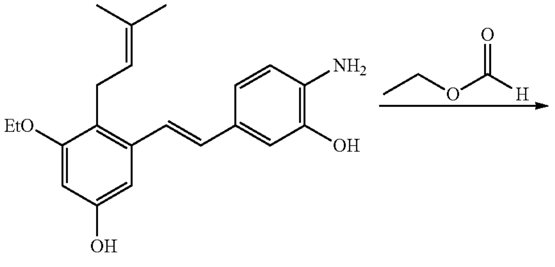

40-9

-continued

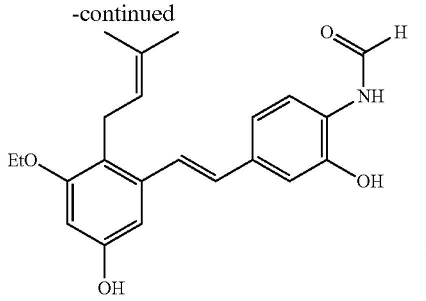

40

5-(hydroxymethyl)-2-nitrophenol (40-2): Sodium borohydride (2.27 g, 59.88 mmol, 1.0 equiv) was added in two portions to a solution of compound 40-1 (10.0 g, 59.88 mmol, 1.0 equiv) in methanol at 0° C. The resulting solution was stirred at room temperature for 1 hour. The reaction mixture was quenched by the addition of water (20 mL). The volatiles were removed under reduced pressure and the resulting crude residue was dissolved in ethyl acetate (150 mL) and washed with 1M HCl (100 mL). The aqueous layer was extracted with ethyl acetate (2×100 mL). The combined organic layers were dried over sodium sulfate and evaporated under reduced pressure to give compound 40-2 (9.98 g, 98% yield) as a yellow solid (NRK-1-202), which was used subsequently.

5-(Bromomethyl)-2-nitrophenol (40-3): Carbon tetrabromide (4.05 g, 12.18 mmol, 2.0 equiv) was added in 4 portions to a solution of compound 40-2 (1.0 g, 6.09 mmol, 1.0 equiv) and triphenylphosphine (3.19 g, 12.18 mmol, 2.0 equiv) in dichloromethane (50 mL) at 0° C. The resulting solution was stirred at room temperature for 16 hours. The reaction mixture was quenched by the addition of 1M HCl (40 mL). The layers were separated and the aqueous layer was extracted with dichloromethane (2×20 mL). The combined organic layers were dried over sodium sulfate and evaporated under reduced pressure. The residue was purified on a Reveleris automated chromatography system (Sorbtech 40 g column), eluting with a gradient of 0 to 40% ethyl acetate in heptanes to give compound 40-3 (1.5 g, 92% yield) as a yellow solid (NRK-6-23).

Diethyl (3-hydroxy-4-nitrobenzyl)phosphonate (40-4): Triethylphosphite (3.3 mL, 19.39 mmol, 3.0 equiv) was added to a solution of compound 40-3 (1.5 g, 6.46 mmol, 1.0 equiv) in toluene (30 mL). The resulting solution was refluxed (110° C.) for 20 hours. After cooling to room temperature, the volatiles were removed under reduced pressure. The crude residue was dissolved in dichloromethane (50 mL) and washed with 1M sodium hydroxide (100 mL). The aqueous layer was neutralized with 1M hydrochloric acid (150 mL). The resulting aqueous layer was extracted with ethyl acetate (3×100 mL). The combined organic layers were dried over sodium sulfate and evaporated under reduced pressure to give compound 40-4 (1.0 g, 56% yield) as a yellow solid, which was used subsequently. (NRK-6-24)

Diethyl (4-nitro-3-((2-(trimethylsilyl)ethoxy)methoxy)benzyl)phosphonate (40-5): 2-(Trimethylsilyl)ethoxymethyl chloride (0.6 mL, 3.46 mmol, 1.0 equiv) and N,N-diisopropylethylamine (0.9 mL, 5.19 mmol, 1.5 equiv) were sequentially added to a solution of compound 40-4 (1.0 g, 3.46 mmol, 1.0 equiv) in dichloromethane (50 mL) at room temperature. After stirring for 20 hours, the reaction mixture was diluted with saturated sodium bicarbonate (30 mL). The layers were separated and the aqueous layer was extracted with dichloromethane (2×20 mL). The combined organic layers were dried over sodium sulfate, filtered and concentrated under reduced pressure to give compound 5 (1.02 g, 71% yield) as a yellow oil, which was used subsequently. (NRK-6-29)

(E)-(2-((5-(2-Bromo-3-ethoxy-5-((2-(trimethylsilyl)ethoxy)methoxy)styryl)-2-nitrophenoxy)methoxy)ethyl)trimethylsilane (40-6): Potassium tert-butoxide (800 mg, 7.06 mmol, 2 equiv) was added in 3 portions to a solution of compound 5 (1.02 g, 3.53 mmol, 1.0 equiv) in anhydrous tetrahydrofuran (50 mL) at 0° C. The mixture was warmed up to room temperature and stirred for 30 minutes. A solution of Module D (1.32 g, 3.53 mmol, 1 equiv) in anhydrous tetrahydrofuran (20 mL) was added dropwise and the mixture was stirred at room temperature for 16 hours. The reaction was carefully quenched with saturated brine (20 mL, 1 drop per minute for the first 5 mL brine) at 0° C. The volatiles were removed under reduced pressure. Saturated ammonium chloride (50 mL) was added and the mixture was extracted with ethyl acetate (2×60 mL). The combined organic layers were dried over sodium sulfate, filtered and concentrated under reduced pressure. The residue was purified on a Reveleris automated chromatography system (Sorbtech 40 g column), eluting with a gradient of 0 to 20% ethyl acetate in heptanes to give compound 40-6 (867 mg, 39% yield) as a yellow oil. (NRK-6-31)

(E)-(2-((5-(3-Ethoxy-2-(3-methylbut-2-en-1-yl)-5-((2-(trimethylsilyl)ethoxy) methoxy)styryl)-2-nitrophenoxy)methoxy)ethyl)trimethylsilane (40-7): Tetrakis (triphenylphosphine)palladium(0) (156 mg, 0.14 mmol, 0.1 equiv), potassium carbonate (373 mg, 2.7 mmol, 2 equiv), 3-methylbut-2-enylboronic acid pinacol ester (530 mg, 2.7 mmol, 2 equiv) and water (3 mL) were added sequentially to a solution of compound 40-6 (867 mg, 1.4 mmol, 1 equiv) in 1,4-dioxane (30 mL) in a sealed tube. After sparging with nitrogen for 10 minutes, the reaction was heated at 100° C. for 16 hours. LCMS analysis indicated formation of the desired compound 40-7 (70% conversion). Additional 3-methylbut-2-enylboronic acid pinacol ester (530 mg, 2.7 mmol, 2 equiv) was added, and the reaction mixture was heated at 100° C. for 16 hours. After cooling to room temperature, the reaction mixture was filtered through Celite and the filtrate evaporated under reduced pressure. The residue was suspended in saturated ammonium chloride (20 mL) and extracted with ethyl acetate (3×30 mL). The combined organic layers were dried over sodium sulfate, filtered and concentrated under reduced pressure. The residue was purified on a Reveleris automated chromatography system (Sorbtech 40 g column), eluting with a gradient of 0 to 30% ethyl acetate in heptanes to give compound 40-7 (852 mg, 99% yield) as a yellow oil. (NRK-6-37)

(E)-3-Ethoxy-5-(3-hydroxy-4-nitrostyryl)-4-(3-methylbut-2-en-1-yl)phenol (40-8): 1M Tetrabutylammonium fluoride in tetrahydrofuran (19 mL, 18.90 mmol, 14 equiv) was added to a solution of compound 40-7 (852 mg, 1.36 mmol, 1 equiv) in tetrahydrofuran (20 mL) at room temperature. After heating at 67° C. for 16 hours, the mixture was cooled to room temperature and diluted with water (10 mL) and saturated ammonium chloride (30 mL). The volatiles were removed under reduced pressure and the remaining aqueous layer was extracted with ethyl acetate (3×20 mL). The combined organic layers were dried over sodium sulfate, filtered and concentrated under reduced pressure. The residue was purified on a Reveleris automated chromatography system (Sorbtech 40 g column), eluting with a gradient of 0 to 80% ethyl acetate in heptanes to give compound 40-8 (410 mg, 83% yield) as a yellow solid. (NRK-6-26)

(E)-3-(4-Amino-3-hydroxystyryl)-5-ethoxy-4-(3-methyl-but-2-en-1-yl)phenol (40-9): Activated zinc powder (730 mg, 11.1 mmol, 10.0 equiv), ammonium chloride (590 mg, 11.1 mmol, 10.0 equiv) and water (5 mL) were added sequentially to a solution of compound 40-8 (410 mg, 1.11 mmol, 1.0 equiv) in tetrahydrofuran (20 mL) at room temperature. The resulting suspension was stirred at room temperature for 16 hours. The suspension was filtered and the solids were washed with ethyl acetate (20 mL). The filtrate was evaporated to dryness under reduced pressure. The residue was suspended in saturated ammonium chloride (20 mL) and extracted with ethyl acetate (3×20 mL). The combined organic layers were dried over sodium sulfate, filtered and concentrated under reduced pressure. The residue was purified on a Reveleris automated chromatography system (Sorbtech 24 g column), eluting with a gradient of 0 to 80% ethyl acetate in heptanes to give compound 40-9 (234 mg, 63% yield) as a pale yellow solid. (NRK-6-39)

(E)-N-(4-(3-Ethoxy-5-hydroxy-2-(3-methylbut-2-en-1-yl)styryl)-2-hydroxyphenyl)formamide (40) [KYN-159]: Compound 40-9 (100 mg, 0.3 mmol, 1.0 equiv) was added to ethyl formate (10 mL) and the reaction was heated at 55° C. for 20 hours. The reaction mixture was cooled to room temperature and evaporated to dryness under reduced pressure. The residue was dissolved in ethyl acetate (20 mL) and washed with saturated ammonium chloride (20 mL). The aqueous layer was extracted with ethyl acetate (2×15 mL). The combined organic layers were dried over sodium sulfate, filtered and concentrated under reduced pressure. The residue was purified on a Reveleris automated chromatography system (Sorbtech 24 g column), eluting with a gradient of 0 to 80% ethyl acetate in heptanes. The product was triturated with 10% ethyl acetate in heptanes (10 mL) to afford compound 40 (74 mg, 69% yield) as an off-white solid. (NRK-6-41).

Off-white solid: melting point 157.9-162.90; HPLC Analysis: 97.0% purity; Wavelength 210 nm, bandwidth 4; Column: Waters Atlantis T3, 2.1×50 mm, 3 μm; Retention Time: 8.4 min; Mobile Phase: ACN/formic acid/water; Mass Spectrum (positive mode) m/z=368.2 $(M+H)^+$; $C_{22}H_{25}NO_4$; $^1H$ NMR (400 MHz, DMSO-do) δ=10.04 (br s, 1H), 9.63 (s, 1H), 9.19 (br s, 1H), 8.28 (d, J=1.7 Hz, 1H), 8.04 (d, J=8.3 Hz, 1H), 7.16 (d, J=16.1 Hz, 1H), 7.05 (d, J=1.7 Hz, 1H), 6.97 (dd, J=1.7, 8.3 Hz, 1H), 6.83 (d, J=16.1 Hz, 1H), 6.62 (d, J=2.2 Hz, 1H), 6.31 (d, J=2.1 Hz, 1H), 5.02 (br t, J=7.0 Hz, 1H), 3.94 (q, J=6.9 Hz, 2H), 3.34 (br s, 2H), 1.75 (s, 3H), 1.62 (s, 3H), 1.33 (t, J=6.9 Hz, 3H); $^{13}C$ NMR (100 MHz, DMSO-$d_6$) δ=160.41, 157.69, 156.59, 147.23, 137.32, 133.69, 130.08, 129.78, 126.32, 125.48, 124.32, 121.06, 118.76, 118.45, 112.80, 104.10, 99.93, 63.75, 25.99, 24.29, 18.28, 15.25.

(E)-N-(5-(3-Ethoxy-5-hydroxy-2-(3-methylbut-2-en-1-yl)styryl)-2-hydroxyphenyl)formamide (41) [KYN-161]

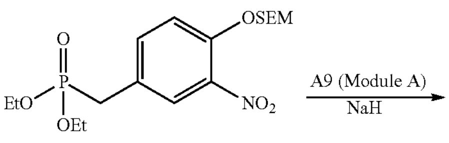

15-5

-continued

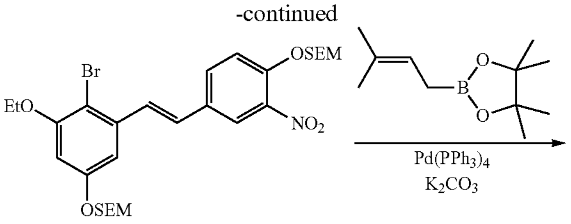

41-1

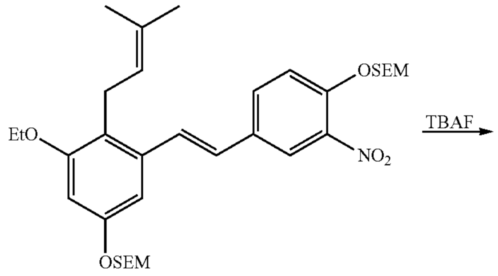

41-2

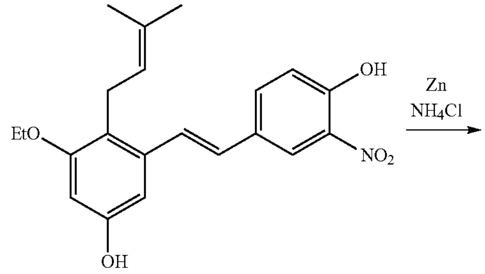

41-3

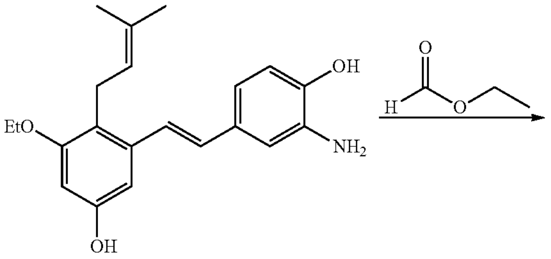

41-4

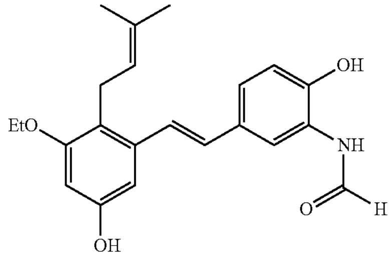

41

(E)-(2-((4-(2-Bromo-3-ethoxy-5-((2-(trimethylsilyl)ethoxy) methoxy)styryl)-2-nitrophenoxy)methoxy)ethyl)trimethylsilane (41-1)

A 60% dispersion of sodium hydride in mineral oil (1.09 g, 45.52 mmol, 4 equiv) was added in 2 portions to a solution of compound 15-5 (3.29 g, 11.38 mmol, 1.0 equiv) in anhydrous tetrahydrofuran (60 mL) at 0° C. The mixture was warmed to room temperature and stirred for 30 minutes. A solution of Module D (4.3 g, 11.38 mmol, 1 equiv) in anhydrous tetrahydrofuran (20 mL) was added dropwise and the mixture was stirred at room temperature for 16 hours. The reaction was carefully quenched with saturated brine (20 mL, 1 drop per minute for the first 5 mL brine) at 0° C. The volatiles were removed under reduced pressure. Saturated ammonium chloride (60 mL) was added and the mixture was extracted with ethyl acetate (3×50 mL). The combined organic layers were dried over sodium sulfate, filtered and concentrated under reduced pressure. The residue was purified on a Reveleris automated chromatography system (Sorbtech 80 g column), eluting with a gradient of 0 to 10% ethyl acetate in heptanes to give compound 41-1 (740 mg, 16% yield) as a yellow oil. (NRK-6-48)

(E)-(2-((4-(3-Ethoxy-2-(3-methylbut-2-en-1-yl)-5-((2-(trimethylsilyl)ethoxy)methoxy)styryl)-2-nitrophenoxy) methoxy)ethyl)trimethylsilane (41-2)

Tetrakis(triphenylphosphine)palladium(0) (120 mg, 0.1 mmol, 0.1 equiv), potassium carbonate (276 mg, 2.0 mmol, 2 equiv), 3-methylbut-2-enylboronic acid pinacol ester (400 mg, 2.0 mmol, 2 equiv) and water (2 mL) were added sequentially to a solution of compound 41-1 (640 mg, 1.0 mmol, 1 equiv) in 1,4-dioxane (10 mL) in a sealed tube. After sparging with nitrogen for 10 minutes, the reaction was heated at 100° C. for 16 hours. After cooling to room temperature, the reaction mixture was filtered through Celite. The filtrate was concentrated under reduced pressure. The residue was suspended in saturated sodium bicarbonate (30 mL) and extracted with ethyl acetate (3×30 mL). The combined organic layers was dried over sodium sulfate, filtered and concentrated under reduced pressure. The residue was purified on a Reveleris automated chromatography system (Sorbtech 40 g column), eluting with a gradient of 0 to 20% ethyl acetate in heptanes to give compound 41-2 (525 mg, 71% yield) as a yellow oil. (NRK-6-53)

(E)-3-Ethoxy-5-(4-hydroxy-3-nitrostyryl)-4-(3-methylbut-2-en-1-yl)phenol (41-3)

1M Tetrabutylammonium fluoride in tetrahydrofuran (12 mL, 11.68 mmol, 14 equiv) was added to a solution of compound 41-2 (525 mg, 0.84 mmol, 1 equiv) in tetrahydrofuran (12 mL) at room temperature. After heating at 67° C. for 16 hours, the mixture was cooled to room temperature and diluted with water (20 mL) and 1M HCL (30 mL). The volatiles were removed under reduced pressure and the remaining aqueous layer was extracted with ethyl acetate (3×30 mL). The combined organic layers were dried over sodium sulfate, filtered and concentrated under reduced pressure. The residue was purified on a Reveleris automated chromatography system (Sorbtech 80 g column), eluting with a gradient of 0 to 60% ethyl acetate in heptanes to give compound 41-3 (120 mg, 40% yield) as a yellow solid. (NRK-6-54)

(E)-3-(3-Amino-4-hydroxystyryl)-5-ethoxy-4-(3-methylbut-2-en-1-yl)phenol (41-4)

Activated zinc powder (210 mg, 3.26 mmol, 10.0 equiv), ammonium chloride (176 mg, 3.26 mmol, 10.0 equiv) and water (2 mL) were added sequentially to a solution of compound 41-3 (120 mg, 0.326 mmol, 1.0 equiv) in tetrahydrofuran (10 mL) at room temperature. The resulting suspension was stirred at room temperature for 16 hours. The suspension was filtered through Celite, which was washed with ethyl acetate (20 mL). The filtrate was concentrated to dryness under reduced pressure. The residue was suspended in saturated ammonium chloride (20 mL) and extracted with ethyl acetate (3×30 mL). The combined organic layers were dried over sodium sulfate, filtered and concentrated under reduced pressure. The residue was purified on a Reveleris automated chromatography system (Sorbtech 24 g column), eluting with a gradient of 0 to 60% ethyl acetate in heptanes to give compound 41-4 (100 mg, 910% yield) as a pale yellow solid. (NRK-6-55)

(E)-N-(5-(3-Ethoxy-5-hydroxy-2-(3-methylbut-2-en-1-yl)styryl)-2-hydroxyphenyl)formamide (41) [KYN-161]

A solution of compound 41-4 (100 mg, 0.3 mmol, 1.0 equiv) in ethyl formate (10 mL) was heated at 55° C. for 20 hours. The reaction mixture was cooled to room temperature and concentrated to dryness under reduced pressure. The residue was dissolved in ethyl acetate (30 mL) and washed with saturated ammonium chloride (30 mL). The aqueous layer was extracted with ethyl acetate (2×30 mL). The combined organic layers were dried over sodium sulfate, filtered and concentrated under reduced pressure. The residue was purified on a Reveleris automated chromatography system (Sorbtech 24 g column), eluting with a gradient of 0 to 60% ethyl acetate in heptanes to afford compound 41 (80 mg, 73% yield) as a pale yellow solid. (NRK-6-57).

Pale yellow solid; HPLC Analysis: 97.5% purity; Wavelength 254 nm, bandwidth 4; Column: Waters Atlantis T3, 2.1×50 mm, 3 μm; Retention Time: 8.3 min; Mobile Phase: ACN/formic acid/water; Mass Spectrum (positive mode) m/z=368.2 $(M+H)^+$; $C_{22}H_{25}NO_4$; $^1H$ NMR (400 MHz, DMSO-$d_6$) δ=10.08 (br s, 1H), 9.58 (s, 1H), 9.16 (br s, 1H), 8.31 (d, J=1.7 Hz, 1H), 8.28 (d, J=2.1 Hz, 1H), 7.20-7.02 (m, 2H), 6.91-6.78 (m, 2H), 6.63-6.58 (m, 1H), 6.30 (d, J=2.2 Hz, 1H), 5.00 (br t, J=7.0 Hz, 1H), 3.94 (q, J=6.9 Hz, 2H), 3.35 (br s, 1H), 3.31-3.28 (m, 1H), 1.77-1.70 (m, 3H), 1.67-1.47 (m, 3H), 1.33 (t, J=7.0 Hz, 3H); $^{13}C$ NMR (100 MHz, DMSO-$d_6$) δ=160.55, 157.67, 156.57, 147.20, 137.62, 130.08, 128.90, 126.77, 124.51, 124.29, 123.97, 123.49, 118.83, 118.52, 115.61, 103.97, 99.69, 63.74, 25.96, 24.34, 18.24, 15.26.

(E)-2-Methoxy-4-(3-methoxy-2-(3-methylbut-2-en-1-yl)-5-nitrostyryl)phenol (42) [KYN-162]

(E)-4-(5-Amino-3-methoxy-2-(3-methylbut-2-en-1-yl)styryl)-2-methoxyphenol (S16) (43) [KYN-163]

(E)-N-(3-(4-Hydroxy-3-methoxystyryl)-5-methoxy-4-(3-methylbut-2-en-1-yl)phenyl)formamide (S17) (44) [KYN-164]

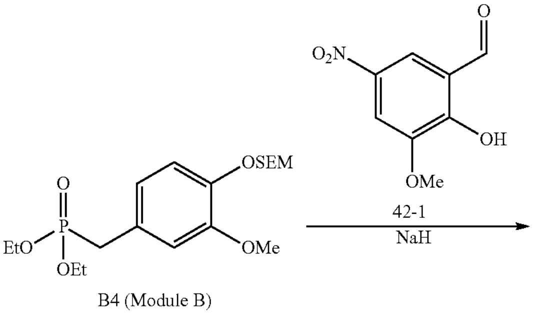

B4 (Module B)

-continued

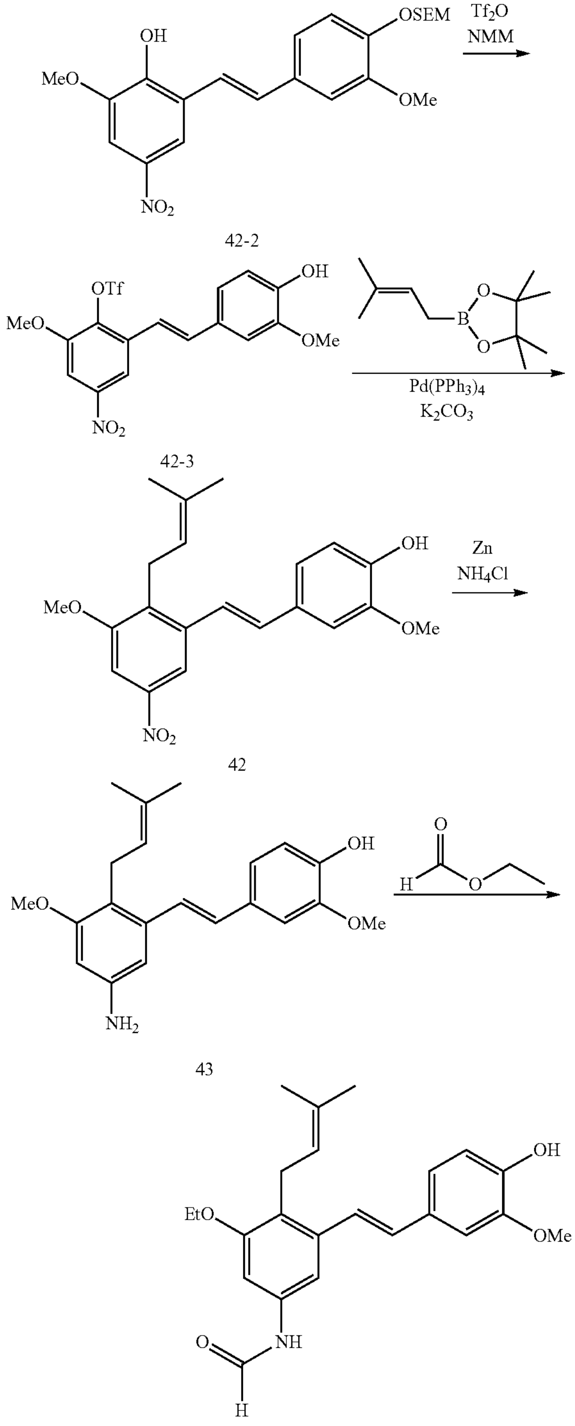

42-2

42-3

42

43

44

(E)-2-Methoxy-6-(3-methoxy-4-((2-(trimethylsilyl)ethoxy)methoxy)styryl)-4-nitrophenol (42-2): A 60% dispersion of sodium hydride in mineral oil (14.2 g, 356 mmol, 9 equiv) was added in one portion to a solution of B4 (Module B) (16 g, 39.5 mmol, 1 equiv) in anhydrous tetrahydrofuran (400 mL) at 0° C. The mixture was warmed up to room temperature and stirred 30 minutes. A solution of compound 42-1 (11.7 g, 59.3 mmol, 1.5 equiv) in anhydrous tetrahydrofuran (100 mL) was added dropwise and the mixture was refluxed (68° C.) for 16 hours. LCMS analysis indicated ~15% conversion to the product. Additional 60% dispersion of sodium hydride in mineral oil (4.7 g, 119 mmol, 3 equiv) was added and the mixture was refluxed (68° C.) for an additional 24 hours. The reaction was cooled to 0° C. and carefully quenched with water (40 mL, 1 drop per minute for the first 10 mL and then diluted with saturated ammonium chloride solution (2 L). The mixture was extracted with methyl tert-butyl ether (2 L) and ethyl acetate (3 L). The combined organic layers were dried over sodium sulfate, filtered and concentrated under reduced pressure. The residue was purified twice on an Interchim automated chromatography system (2×120 g column, stacked), eluting each time with a gradient of 0 to 100% ethyl acetate in heptanes to give compound 42-2 (2.8 g, 16% yield) as a yellow solid. (LM-8-46)

(E)-2-(4-Hydroxy-3-methoxystyryl)-6-methoxy-4-nitrophenyl tifluoromethanesulfonate (42-3): Trifluoromethanesulfonic anhydride (1.9 g, 6.7 mmol, 1.07 equiv) was added dropwise over 5 minutes, maintaining the reaction temperature at 0° C., to a solution of compound 42-2 (2.8 g, 6.26 mol, 1.0 equiv) and N-methylmorpholine (1.03 mL, 9.4 mmol, 1.5 equiv) in dichloromethane (100 mL) at 0° C. After stirring at 0° C. for 3 hours, the reaction mixture was quenched by addition of 10% citric acid (100 mL) over 15 minutes maintaining the reaction temperature below 5° C. The layers were separated and the aqueous layer was extracted with dichloromethane (2×100 mL). The combined organic layers were dried over sodium sulfate, filtered and concentrated under reduced pressure. The residue was purified on an Interchim automated chromatography system (80 g column), eluting with a gradient of 0 to 60% ethyl acetate in heptanes to give compound 42-3 (2.26 g, 80% yield) as a yellow solid. (LM-8-47)

(E)-2-Methoxy-4-(3-methoxy-2-(3-methylbut-2-en-1-yl)-5-nitrostyryl)phenol (42) [KYN-162]: Tetrakis(triphenylphosphine)palladium(0) (237 mg, 0.2 mmol, 0.05 equiv), potassium carbonate (1.2 g, 8.2 mmol, 2 equiv), 3-methylbut-2-enylboronic acid pinacol ester (1.6 g, 8.2 mmol, 2 equiv) and water (11 mL) were added sequentially to a solution of compound 42-3 (1.83 g, 4.1 mmol, 1 equiv) in 1,4-dioxane (33 mL). After sparging with nitrogen for 10 minutes, the reaction was heated at 95° C. for 16 hours. After cooling to room temperature, the mixture was diluted with saturated ammonium chloride solution (30 mL) and extracted with methyl tert-butyl ether (2×100 mL). The combined organic layers were dried over sodium sulfate, filtered, and concentrated under reduced pressure. The residue was purified on an Interchim automated chromatography system (120 g column), eluting with a gradient of 0 to 60% ethyl acetate in heptanes to give compound 42 (0.82 g, 54% yield) as a yellow oil. HPLC Analysis: 97.3% purity; Wavelength 254 nm, bandwidth 4; Column: Waters Atlantis T3, 2.1×50 mm, 3 μm; Retention Time: 10.7 min; Mobile Phase: ACN/formic acid/water; Mass Spectrum (positive mode) m/z=370.2 $(M+H)^+$; $C_{21}H_{23}NO_5$; $^1H$ NMR (400 MHz, $CDCl_3$) δ=8.10 (d, J=2.2 Hz, 1H), 7.59 (d, J=2.2 Hz, 1H), 7.18-7.13 (m, 1H), 7.08-7.01 (m, 3H), 6.94 (d, J=8.2 Hz, 1H), 5.71 (s, 1H), 5.07 (sptt, J=1.3, 6.8 Hz, 1H), 3.95 (s, 3H), 3.93 (s, 3H), 3.55 (br d, J=6.8 Hz, 2H), 1.84 (d, J=0.9 Hz, 3H), 1.70 (d, J=1.1 Hz, 3H); $^{13}C$ NMR (100 MHz, $CDCl_3$) δ=157.84, 147.03, 146.73, 146.17, 138.48, 135.17, 132.87, 132.61, 129.45, 122.31, 121.10, 120.63, 114.73, 113.29, 108.83, 103.38, 56.10, 55.91, 25.75, 25.52, 18.09.

(E)-4-(5-Amino-3-methoxy-2-(3-methylbut-2-en-1-yl)styryl)-2-methoxyphenol (43) [KYN-163]: Water (6 mL), ammonium chloride (613 mg, 11.4 mmol, 10 equiv) and zinc powder (743 mg, 11.4 mmol, 10 equiv) were added sequentially to a solution of compound 42 (420 mg, 1.14 mmol, 1 equiv) in tetrahydrofuran (60 mL) at room temperature. The resulting suspension was stirred at room temperature for 3 hours. The suspension was filtered through Celite, which was washed with ethyl acetate (50 mL). The filtrate was evaporated to dryness under reduced pressure. The residue was purified on an Interchim automated chromatography system (80 g column), eluting with a gradient of 0 to 100% ethyl acetate in heptanes to give compound 43 (60 mg, >95% purity and 180 mg, ~90% purity; 62% yield) as an off-white solid after drying under vacuum at 40° C. for 16 hours. (LM-8-53).

Off-white solid; HPLC Analysis: 97.6% purity; Wavelength 254 nm, bandwidth 4; Column: Waters Atlantis T3, 2.1×50 mm, 3 μm; Retention Time: 6.7 min; Mobile Phase: ACN/formic acid/water; Mass Spectrum (positive mode) m/z=340.2 $(M+H)^+$; $C_{21}H_{25}NO_3$; $^1H$ NMR (400 MHz, DMSO-$d_6$) δ=9.08 (s, 1H), 7.12-7.04 (m, 2H), 6.91 (dd, J=1.9, 8.3 Hz, 1H), 6.81-6.73 (m, 2H), 6.43 (d, J=2.0 Hz), 6.17 (d, J=2.0 Hz), 4.99 (sptt, J=1.3, 6.8 Hz, 1H), 4.88 (s, 2H), 3.81 (s, 3H), 3.69 (s, 3H), 3.28 (br d, J=7.0 Hz, 2H), 1.75 (d, J=0.6 Hz, 3H), 1.60 (d, J=0.7 Hz, 3H); $^{13}C$ NMR (100 MHz, DMSO-$d_6$) δ=158.21, 148.28, 147.79, 146.99, 137.40, 129.49, 129.22, 125.10, 124.35, 120.35, 116.08, 115.59, 110.09, 103.11, 97.74, 55.99, 55.68, 55.36, 25.97, 24.18, 18.18.

(E)-N-(3-(4-Hydroxy-3-methoxystyryl)-5-methoxy-4-(3-methylbut-2-en-1-yl)phenyl)formamide (44) [KYN-164]: A solution of compound 43 (90 mg, 0.27 mmol, 1.0 equiv) in ethyl formate (10 mL) was heated at 55° C. for 20 hours. The reaction mixture was cooled to room temperature and evaporated to dryness under reduced pressure. The residue was purified on an Interchim automated chromatography system (25 g column), eluting with a gradient of 0 to 60% ethyl acetate in heptanes to give compound 44 (80 mg, 82% yield) as an off-white solid after drying under vacuum at 40° C. for 16 hours. (LM-8-57).

Off-white solid: HPLC Analysis: 97.3% purity; Wavelength 254 nm, bandwidth 4; Column: Waters Atlantis T3, 2.1×50 mm, 3 μm; Retention Time: 6.7 min; Mobile Phase: ACN/formic acid/water; Mass Spectrum (positive mode) m/z=368.2 $(M+H)^+$; $C_{22}H_{25}NO_4$; $^1H$ NMR (400 MHz, DMSO-$d_6$) δ=10.08 (s, 1H), 9.98 (d, J=11.1 Hz, 1H), 9.15 (s, 1H), 8.90-8.80 (m, 1H), 8.27 (d, J=1.8 Hz, 1H), 7.42 (d, J=1.8 Hz), 7.22-7.11 (m, 2H), 7.07-6.91 (m, 2H), 6.87-6.70 (m, 2H), 5.04-4.96 (m, 1H), 3.82 (s, 3H), 3.78-3.74 (m, 3H), 3.40 (br d, J=6.7 Hz, 2H), 1.77 (s, 3H), 1.61 (s, 3H); $^{13}C$ NMR (100 MHz, DMSO-$d_6$) δ=163.17, 159.99, 157.64, 148.30, 147.31, 137.64, 137.56, 137.52, 130.91, 130.48, 129.07, 123.75, 123.72, 123.52, 123.08, 120.66, 120.60, 116.09, 110.38, 108.53, 101.90, 56.19, 56.03, 56.00, 25.94, 24.56, 18.24.

(E)-4-Bromo-3-(4-hydroxy-3-methoxystyryl)-5-methoxyphenol (45) [KYN-112]

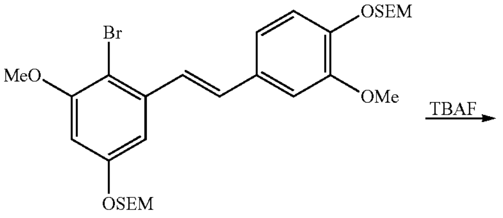

C1 (Module C)

-continued

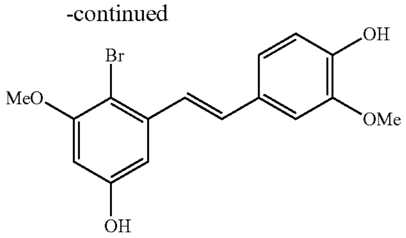

45

1.0M Tetrabutylammonium fluoride in THF (2.3 mL, 2.29 mmol, 7 equiv) was added to a solution of (E)-(2-((4-(2-Bromo-3-methoxy-5-((2-(trimethylsilyl)ethoxy)methoxy)styryl)-2-methoxyphenoxy)methoxy)ethyl)trimethylsilane (C1) (200 mg, 0.327 mmol, 1 equiv) in anhydrous THF (5 mL) and refluxed overnight. After cooling to room temperature, the reaction mixture was quenched with water (25 mL) and extracted with ethyl acetate (100 mL). Organic layer was washed with saturated brine (25 mL), dried over sodium sulfate and concentrated under reduced pressure. The residue was purified twice on an AnaLogixs automated system (12 g column), eluting each time with a gradient of 0 to 100% ethyl acetate in heptanes to give Compound 45 [KYN-112] (21 mg, 18% yield) as brown film. (CSK-2-95)

HPLC Analysis: 94.3% purity; Wavelength 210 nm, bandwidth 4; Column: SorbTech C18AQ, 2.1×50 mm, 3 μm; Retention Time: 7.0 min; Mobile Phase: ACN/formic acid/water; Mass Spectrum (negative mode) m/z=349/351 $(M-H)^-$; $C_{16}H_{15}BrO_4$; $^1H$ NMR (400 MHz, Methanol-$d_3$) δ=7.31 (d, J=16.2 Hz, 1H), 7.10 (d, J=2 Hz, 1H), 7.00 (dd, J=2.0, 8.1 Hz, 1H), 6.93 (d, J=16.1 Hz, 1H), 6.79 (d, J=8.0 Hz, 1H), 6.75 (d, J=2.7 Hz, 1H), 6.40 (d, J=2.7 Hz, 1H), 3.90 (s, 3H), 3.82 (s, 3H); $^{13}C$ NMR (100 MHz, Methanol-$d_3$) δ=158.69, 158.32, 149.15, 148.08, 140.14, 132.49, 130.67, 126.01, 121.41, 116.38, 110.75, 105.77, 103.89, 100.20, 56.57, 56.37.

Preparation of Compound 46 [KYN-145]-(E)-3-(4-hydroxy-3-methoxystyryl)-4-(3-methylbut-2-en-1-yl)-5-(trifluoromethyl)phenol (46) [KYN-145]

Proposed Modular Synthesis

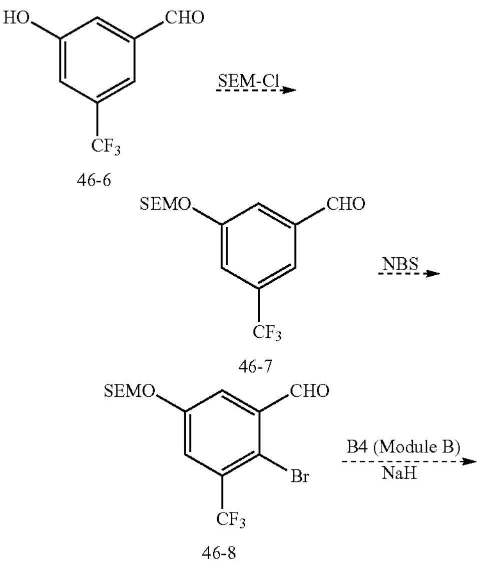

46-6

46-7

46-8

-continued
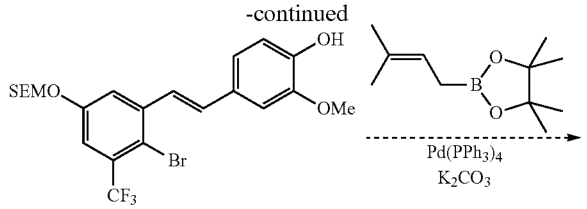
46-9
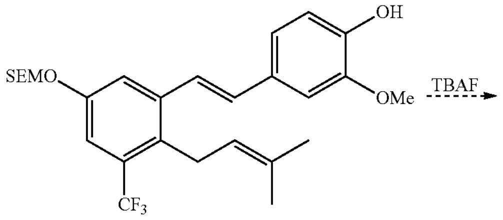
46-10
-continued
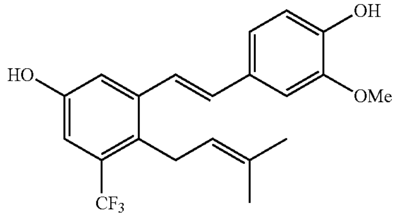
46
The following key steps for the modular synthesis is proposed as follows. Reaction of 2-bromo-3-trifluoromethyl-5-((2-trimethylsilyl)ethoxy)methoxy)benzaldehyde (Module A) with B4 (Module B) in the presence of sodium hydride to give the Module C product which may be converted to compound 46 in 2 steps.
Preparation by the Rearrangement Method
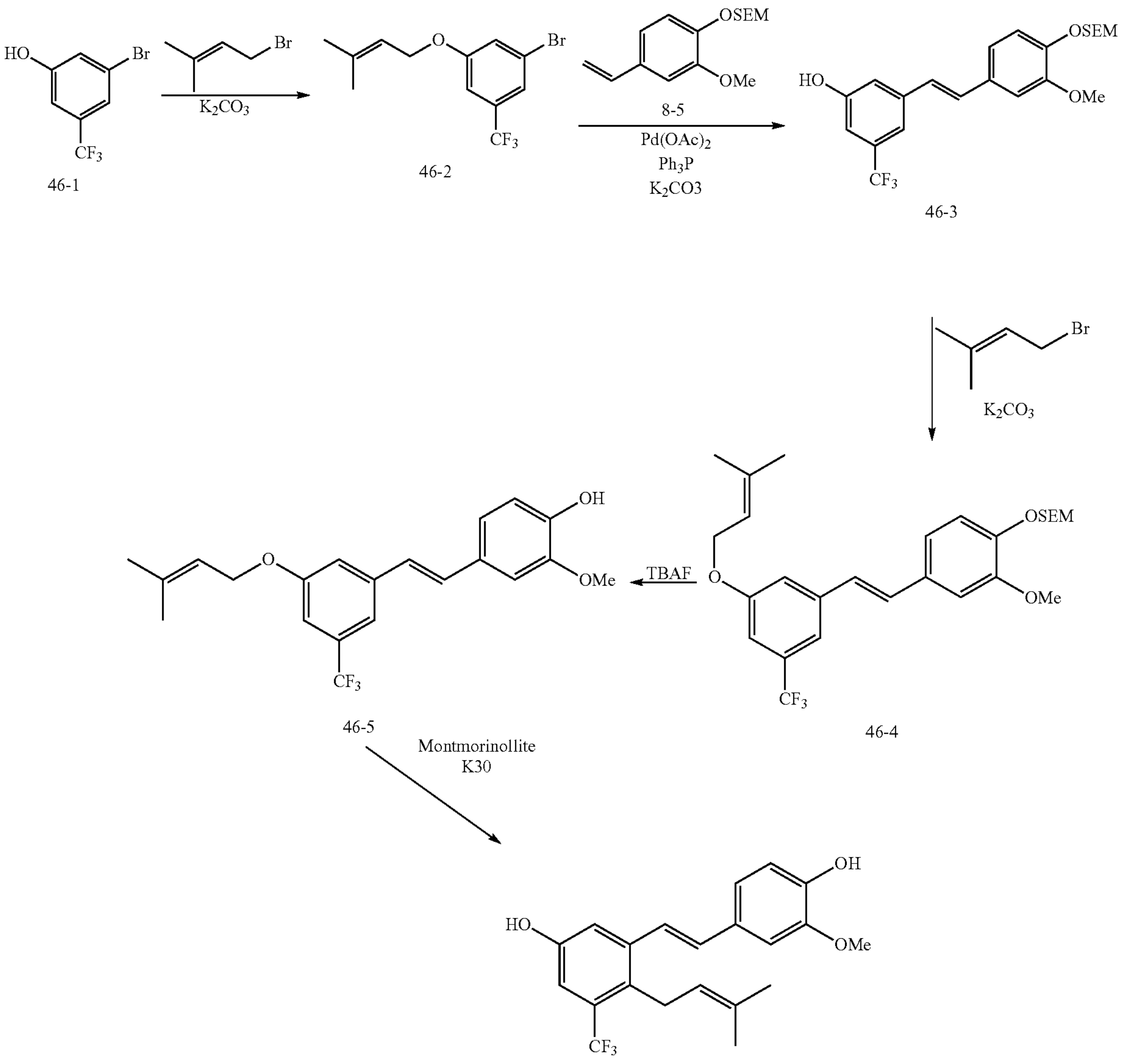
46-1
46-2
46-3
46-4
46-5
46

1-Bromo-3-((3-methylbut-2-en-1-yl)oxy)-5-(trifluoromethyl)benzene (46-2)

Potassium carbonate (28 g, 206 mmol, 2 equiv) and 3,3-dimethylallyl bromide (18.5 g, 124.48 mmol, 1.2 equiv) were added sequentially to a solution of compound 46-1 (25.0 g, 107.73 mmol, 1 equiv) in acetonitrile (100 mL) at room temperature. The resulting suspension was refluxed (80° C.) for 16 hours. After cooling to room temperature, the reaction mixture was filtered and the filtrate was concentrated under reduced pressure. The crude residue was dissolved in ethyl acetate (300 mL) and washed with 1M hydrochloric acid solution (2×70 mL). The organic layer was dried over sodium sulfate and evaporated under reduced pressure to obtain compound 46-2 (31.0 g, 99% yield) as a pale yellow oil (NRK-1-106) which was used subsequently.

(E)-3-(3-methoxy-4-((2-(trimethylsilyl)ethoxy)methoxy)styryl)-5-(trifluoromethyl)phenol (46-3)

(2-((2-Methoxy-4-vinylphenoxy)methoxy)ethyl)trimethylsilane (8-5) (3.97 g, 14.20 mmol, 1.0 equiv), triphenylphosphine (750 m, 2.84 m mol 0.2 equiv), potassium carbonate (4.25 g, 30.76 mmol, 2 equiv) and palladium acetate (320 mg, 1.42 mmol, 0.1 equiv) were added to a solution of compound 46-2 (5.0 g, 14.20 mmol, 1.0 equiv) in anhydrous toluene (100 mL) at room temperature. The reaction mixture was sparged with nitrogen for 15 minutes. After refluxing (110° C.) for 16 hours, the reaction mixture was cooled to room temperature and filtered through celite (~20 g). The filtrate was transferred to a separatory funnel containing saturated sodium bicarbonate (150 mL). The layers were separated and the aqueous layer was extracted with ethyl acetate (2×50 mL). The combined organic layers were dried over sodium sulfate, filtered, and concentrated under reduced pressure. The residue was purified on a Reveleris automated chromatography system (Sorbtech 40 g column) eluting with a gradient of 0 to 50% ethyl acetate in heptanes to give Compound 46-3 (5.25 g, 85% yield) as a pale yellow oil. (NRK-1-107)

(E)-(2-((2-methoxy-4-(3-((3-methylbut-2-en-1-yl)oxy)-5-(trifluoromethyl)styryl)phenoxy)methoxy)ethyl)trimethylsilane (46-4)

Potassium carbonate (3.36 g, 24.40 mmol, 2 equiv) and 3,3-dimethylallyl bromide (2.18 g, 14.64 mmol, 1.2 equiv) were added successively to a solution of Compound 46-3 (5.25 g, 12.20 mmol, 1 equiv) in acetonitrile (150 mL) at room temperature. After refluxing (80° C.) for 16 hours, the reaction was cooled to room temperature and filtered. The filtrate was concentrated under reduced pressure. The crude residue was dissolved in ethyl acetate (100 mL) and washed with 1M hydrochloric acid solution (2×50 mL). The organic layers was dried over sodium sulfate and evaporated under reduced pressure to give Compound 46-4 (5.0 g, 80% yield) as a pale yellow oil, which was used subsequently. (NRK-1-111)

(E)-2-methoxy-4-(3-((3-methylbut-2-en-1-yl)oxy)-5-(trifluoromethyl)styryl)phenol (46-5)

1M Tetrabutylammonium fluoride in THF (69 mL, 68.78 mmol, 7 equiv) was added to a solution of Compound 46-4 (5.0 g, 9.82 mmol, 1 equiv) in anhydrous THF (200 mL) at room temperature. After refluxing (66° C.) for 16 hours, analysis LCMS indicated that the reaction was complete.

The mixture was cooled to room temperature and diluted with water (20 mL). The volatiles were removed under reduced pressure. The mixture was diluted with ethyl acetate (150 mL). The layers were separated and the aqueous layer was extracted with ethyl acetate (2×100 mL). The combined organic layers were dried over sodium sulfate, filtered, and concentrated under reduced pressure. The residue was purified on a Reveleris automated chromatography system (Sorbtech 80 g column) eluting with a gradient of 0 to 20% ethyl acetate in heptanes to give Compound 46-5 (3.25 g, 87% yield) as a pale yellow solid. (NRK-1-113)

(E)-3-(4-hydroxy-3-methoxystyryl)-4-(3-methylbut-2-en-1-yl)-5-(trifluoromethyl)phenol (46) [KYN-145]

Montmorillonite K30 powder (3.25 g) was added to a solution of Compound 46-7 (3.2 g, 8.89 mmol) in anhydrous dichloromethane (200 mL) at room temperature. After stirring overnight. LCMS analysis indicated that 10-15% of desired Compound 46 was formed, along with two regioisomers and unreacted starting Compound 46-5 as byproducts. The mixture was filtered and treated with fresh montmorillonite K30 powder (3.2 g) at room temperature for an additional 24 hours. The reaction mixture was filtered and the solids were washed with dichloromethane (2×50 mL). The combined filtrates was concentrated under reduced pressure. The residue was first purified on a Reveleris automated chromatography system (Sorbtech 80 g column), eluting with a gradient of 0 to 50% ethyl acetate in heptanes to give several mixed fractions containing Compound 46. The fractions were collected and purified again on a Reveleris automated chromatography system (Sorbtech 24 g column), eluting with a gradient of 0 to 40% ethyl acetate in heptanes. All the fractions that containing Compound 46 (along with another isomer) were collected and purified again on a Reveleris automated chromatography system (Redisep 100 g C-18 column), eluting with a gradient of 0 to 100% acetonitrile in water to give Compound 46 (118 mg, 85% purity by HPLC, 3% yield) as a yellow solid. This material was dissolved in ethyl acetate (3 mL) and heptanes (7 mL), and the solution was slowly evaporated to a volume of ~3 mL overnight at room temperature to give a layer of crystals in bottom of solution. The solid was collected to give Compound 46 [KYN-145] (34 mg, 96.5% purity by HPLC) as an off-white solid. (NRK-1-115) and (QZH-RCI-47).

Off-white solid; HPLC Analysis: 96.5% purity; Wavelength 210 nm, bandwidth 4; Column: SorbTech C18AQ, 2.1×50 mm, 3 μm; Retention Time: 11.9 min; Mobile Phase: ACN/formic acid/water; Mass Spectrum (positive mode) m/z=379.1 $(M+H)^+$; $C_{21}H_{21}F_3O_3$; $^1H$ NMR (400 MHz, $CD_3OD$) δ=7.33 (d, J=16.1 Hz, 1H), 7.21 (br m, 1H), 7.19 (s, 1H), 7.12 (br m, 1H), 6.88 (d, J=16.2 Hz, 1H), 6.88 (br m, 1H), 6.64 (s, 1H), 5.21 (tm, J=1.5, 7.1 Hz, 1H), 3.90 (s, 3H), 3.36 (br d, J=7.1 Hz, 2H), 1.78 (d, J=1.0 Hz, 3H), 1.73 (d, J=0.9 Hz, 3H); $^{19}F$ NMR (376 MHz, $CD_3OD$) δ=−64.35 (s, 3F); $^{13}C$ NMR (100 MHz, $CD_3OD$) δ=159.66, 148.18, 147.81, 142.37, 134.79, 133.34, 133.01, 132.66, 129.41, 128.29, 127.12, 126.81, 125.22, 117.72, 117.28, 114.99, 114.95, 111.53, 111.49, 110.19, 56.78, 32.91, 25.99, 18.15.

The compound of 46 KYN-145 can also be synthesised by the modular methodology of the present disclosure using equivalents to Module A, B and C and subsequent cross coupling alkylation of the aryl halide.

(E)-3-Amino-5-(4-hydroxy-3-methoxystyryl)-4-(3-methylbut-2-en-1-yl)phenol (47) (E)-N-(5-Hydroxy-3-(4-hydroxy-3-methoxystyryl)-2-(3-methylbut-2-en-1-yl)phenyl)formamide (48)

(E)-N-(5-Hydroxy-3-(4-hydroxy-3-methoxystyryl)-2-(3-methylbut-2-en-1-yl)phenyl)acetamide (49)

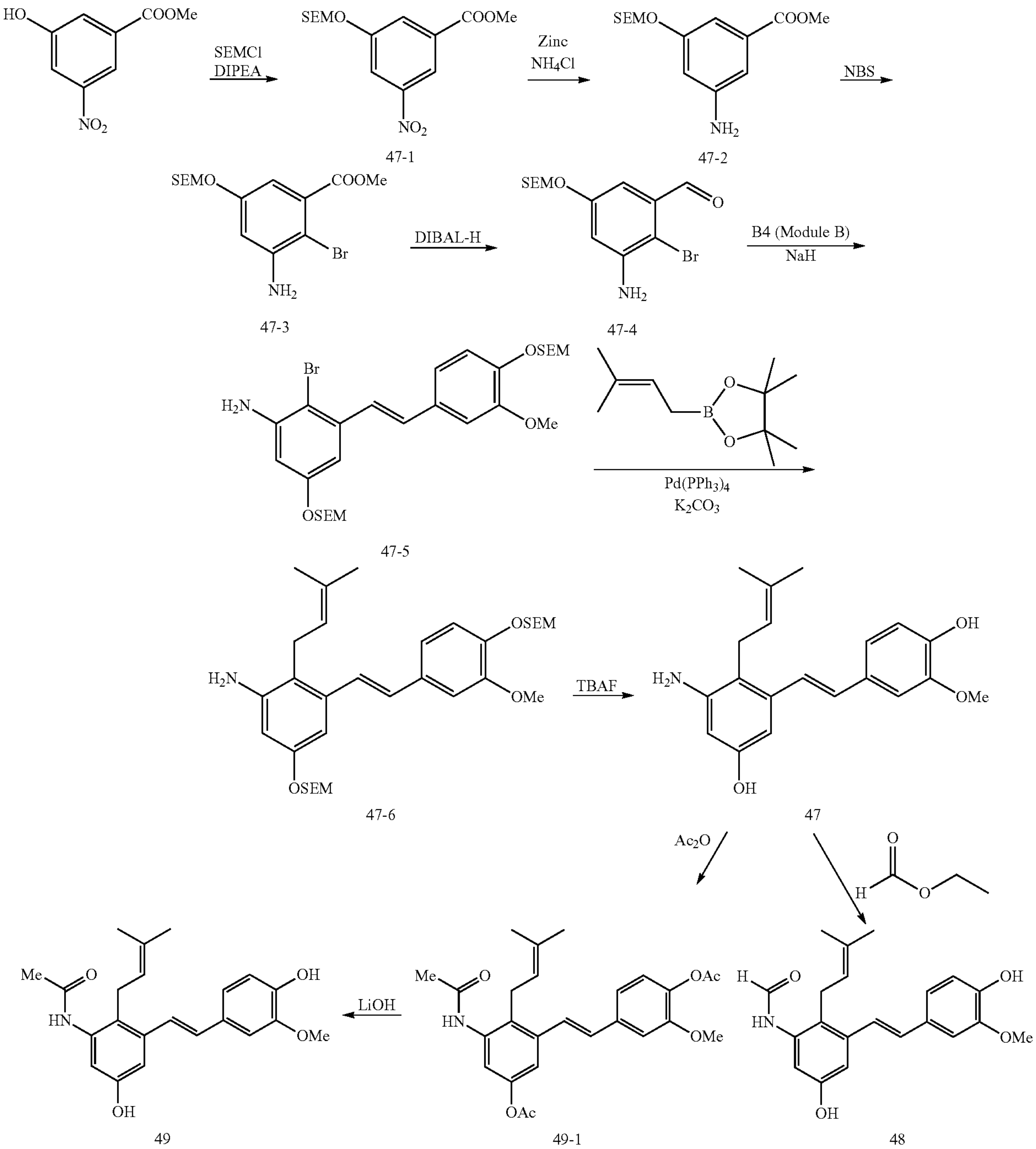

Methyl 3-nitro-5-((2-(trimethylsilyl)ethoxy)methoxy) benzoate (47-1): N,N-Diisopropylethylamine (10.3 mL, 59 mmol, 3 equiv) and 2-(trimethylsilyl)-ethoxymethyl chloride (5.2 mL, 29.6 mmol, 1.5 equiv) were sequentially added to a solution of methyl 3-nitro-5-hydroxybenzoate (3.88 g, 19.7 mol, 1.0 equiv) in anhydrous dichloromethane (200 mL). After stirring at room temperature for 16 hours, saturated sodium bicarbonate (250 mL) was added. The layers were separated and the aqueous layer was extracted with dichloromethane (250 mL). The combined organic layers were dried over sodium sulfate, filtered, concentrated under reduced pressure. The residue was purified on an InterChim automated chromatography system (120 g column), eluting with a gradient of 0 to 30% ethyl acetate in heptanes to give compound 47-1 (6.12 g, 95% yield) as a colorless oil. (CHLM-02-9).

Methyl 3-amino-5-((2-(trimethylsilyl)ethoxy)methoxy) benzoate (47-2): Zinc powder (18.33 g, 280 mmol, 15.0 equiv), ammonium chloride (15.1 g, 280 mmol, 15.0 equiv) and water (20 mL) were added sequentially to a solution of compound 47-1 (6.12 g, 18.7 mmol, 1.0 equiv) in tetrahydrofuran (200 mL) at room temperature. The resulting suspension was refluxed (68° C.) for 5 hours. The suspension was cooled to room temperature, diluted with ethyl acetate (500 mL), filtered through Celite, which was washed with ethyl acetate (500 mL). The filtrate was evaporated to dryness under reduced pressure. The residue was purified on an InterChim automated chromatography system (2×120 g column stacked), eluting with a gradient of 0 to 60% ethyl acetate in heptanes to give compound 47-2 (4.76 g, 86% yield) as a pale yellow oil. (CH-LM-02-10).

Methyl 3-amino-2-bromo-5-((2-(trimethylsilyl)ethoxy)methoxy)benzoate (47-3): N-Bromosuccinimide (2.85 g, 16 mmol, 1.0 equiv) was added portion wise to a solution of compound 47-2 (4.76 g, 16 mmol, 1.0 equiv) in anhydrous dichloromethane (500 mL) at 0° C. After stirring at 0° C. for 1 hour, ice-cold water (500 mL) was added and the mixture was warmed to room temperature. The layers were separated and the organic layer was washed with saturated sodium bicarbonate (500 mL), dried over sodium sulfate, filtered and concentrated under reduced pressure. The residue was purified on an InterChim automated chromatography system (2×120 g column stacked), eluting with a gradient of 0 to 20% ethyl acetate in heptanes to give compound 47-3 (5.05 g, 84% yield) as a pale yellow oil. (CH-LM-02-14).

3-Amino-2-bromo-5-((2-(trimethylsilyl)ethoxy)methoxy)benzaldehyde (47-4): 1M Diisobutylaluminum hydride in toluene (26.84 mL, 26.84 mmol, 2.0 equiv) was added dropwise to a solution of compound 47-3 (5.05 g, 13.42 mmol, 1.0 equiv) in toluene (250 mL) at −78° C. The resulting mixture was stirred at −78° C. for 3 hours. Saturated potassium sodium tartrate (120 mL) was added dropwise and the mixture was slowly warmed to room temperature. After stirring for 16 hours, methyl tert-butyl ether (300 mL) was added. The layers were separated and the organic layer was dried over sodium sulfate, filtered and concentrated under reduced pressure. The residue was purified on an InterChim automated chromatography system (2×120 g column stacked), eluting with a gradient of 0 to 60% ethyl acetate in heptanes to give compound 47-4 (3.25 g, 70% yield) as a yellow oil. (CH-LM-02-16).

(E)-2-Bromo-3-(3-methoxy-4-((2-(trimethylsilyl)ethoxy)methoxy)styryl)-5-((2-(trimethylsilyl)ethoxy)methoxy)aniline (47-5): A 60% dispersion of sodium hydride in mineral oil (1.34 g, 33.6 mmol, 4.0 equiv) was added in one portion to a solution of Module B (3.4 g, 8.4 mmol, 1.0 equiv) in anhydrous tetrahydrofuran (150 mL) at 0° C. The mixture was warmed up to room temperature and stirred for 30 minutes. A solution of compound 47-4 (3.25 g, 9.4 mmol, 1.12 equiv) in anhydrous tetrahydrofuran (50 mL) was added dropwise and the mixture was stirred at room temperature for 16 hours. The reaction was carefully quenched with water (250 mL, 1 drop per minute for the first 5 mL water) at 0° C. and extracted with methyl tert-butyl ether (400 mL) and ethyl acetate (400 mL). The combined organic layers was dried over sodium sulfate, filtered and concentrated under reduced pressure. The residue was purified on an InterChim automated chromatography system (2×120 g column stacked), eluting with a gradient of 0 to 30% ethyl acetate in heptanes to give compound 47-5 (2.6 g, 52% yield) as a yellow solid. (CH-LM-02-17)

(E)-3-(3-Methoxy-4-((2-(trimethylsilyl)ethoxy)methoxy)styryl)-2-(3-methylbut-2-en-1-yl)-5-((2-(trimethylsilyl)ethoxy)methoxy)aniline (47-6)

Tetrakis(triphenylphosphine) palladium(0) (252 mg, 0.22 mmol, 0.05 equiv), potassium carbonate (1.2 g, 8.71 mmol, 2.0 equiv), 3-methylbut-2-enylboronic acid pinacol ester (1.71 g, 8.71 mmol, 2.0 equiv) and water (15 mL) were added sequentially to a solution of compound 47-5 (2.6 g, 4.36 mmol, 1.0 equiv) in 1,4-dioxane (45 mL) in a sealed tube. After sparging with nitrogen for 10 minutes, the reaction was heated at 100° C. for 16 hours. After cooling to room temperature, the reaction mixture was extracted with methyl tert-butyl ether (100 mL). The organic layer was dried over sodium sulfate, filtered and concentrated under reduced pressure. The residue was purified on an InterChim automated chromatography system (120 g column), eluting with a gradient of 0 to 35% ethyl acetate in heptanes to give compound 47-6 (2.07 g, 81% yield) as a yellow solid. (CH-LM-02-18)

(E)-3-Amino-5-(4-hydroxy-3-methoxystyryl)-4-(3-methylbut-2-en-1-yl)phenol (47) [KYN-167]: 1M Tetrabutylammonium fluoride in tetrahydrofuran (35 mL, 35 mmol, 14.0 equiv) was added to a solution of compound 47-6 (1.47 g, 2.51 mmol, 1.0 equiv) in tetrahydrofuran (120 mL) at room temperature. After heating at 68° C. for 16 hours, the mixture was cooled to room temperature and diluted with water (50 mL). The volatiles were removed under reduced pressure. The residue was diluted with saturated ammonium chloride (150 mL) and extracted with ethyl acetate (2×300 mL). The combined organic layers were dried over sodium sulfate, filtered and concentrated under reduced pressure. The residue was purified on an InterChim automated chromatography system (80 g column) eluting with a gradient of 0 to 100% ethyl acetate in heptanes. The product fractions were combined, concentrated under reduced pressure and further purified on an InterChim automated chromatography system (RediSep Rf GOLD 100 g HP C18 column), eluting with a gradient of 0 to 100% acetonitrile in water to give compound 47 (148 mg, 18% yield) as an off-white solid. (CH-LM-02-22) Another batch of compound 11 (400 mg) was processed in the same manner to give compound 47 (15 mg, 7% yield) as an off-white solid. (CH-LM-02-19) HPLC Analysis: 99.2% purity; Wavelength 254 nm, bandwidth 4; Column: Waters Atlantis T3, 2.1×50 mm, 3 μm; Retention Time: 6.1 min; Mobile Phase: ACN/formic acid/water; Mass Spectrum (positive mode) m/z=326.2 $(M+H)^+$; $C_{20}H_{23}NO_3$; $^1H$ NMR (400 MHz, DMSO-$d_6$) δ=9.06 (br s, 1H), 8.72 (br s, 1H), 7.12-7.05 (m, 2H), 6.91 (dd, J=1.9, 8.3 Hz, 1H), 6.77-6.70 (m, 2H), 6.27 (d, J=2.3 Hz), 6.06 (d, J=2.3 Hz), 4.99 (sptt, J=1.3, 6.7 Hz, 1H), 4.62 (s, 2H), 3.81 (s, 3H), 3.24-3.17 (m, 2H), 1.77 (s, 3H), 1.64 (s, 3H); $^{13}C$ NMR (100 MHz, DMSO-$d_7$) δ=156.14, 148.25, 147.75, 146.90, 137.67, 129.92, 129.60, 129.53, 124.97, 124.23, 120.36, 116.04, 114.60, 110.16, 101.93, 101.72, 56.03, 25.98, 25.57, 18.26.

(E)-N-(5-Hydroxy-3-(4-hydroxy-3-methoxystyryl)-2-(3-methylbut-2-en-1-yl)phenyl)formamide (48): Compound 47 (49 mg, 0.15 mmol, 1.0 equiv) was added to ethyl formate (10 mL) to obtain a cloudy solution, which was heated at 55° C. (clear solution on heating). After 24 hours, the reaction mixture was cooled to room temperature and evaporated to dryness under reduced pressure. The residue was purified on an InterChim automated chromatography system (RediSep Rf GOLD 100 g HP C18 column), eluting with a gradient of 0 to 100% acetonitrile in water to give compound 48 (25 mg, 47% yield) as an off-white solid after lyophilization. (CH-LM-02-23) HPLC Analysis: 99.8% purity; Wavelength 254 nm, bandwidth 4; Column: Waters Atlantis T3, 2.1×50 mm, 3 μm; Retention Time: 6.6 min; Mobile Phase: ACN/formic acid/water; Mass Spectrum (positive mode) m/z=354.2 $(M+H)^+$; $C_{21}H_{23}NO_4$; $^1H$ NMR (400 MHz, DMSO-$d_6$) δ=9.66-9.45 (m, 1H), 9.23 (br s, 2H), 8.26-8.19 (m, 1H), 7.17-7.06 (m, 3H), 6.99-6.85 (m, 2H), 6.83 (d, J=2.7 Hz, 1H), 6.76 (d, J=8.1 Hz), 6.49 (d, J=2.3 Hz, 1H), 4.95 (br s, 1H), 3.81 (s, 3H), 3.39-3.33 (m, 2H), 1.78-1.73 (m, 3H), 1.64-1.59 (m, 3H); $^{13}C$ NMR (100 MHz, DMSO-$d_6$) δ=163.08, 159.42, 155.17, 154.60, 147.22, 146.16, 137.35, 135.29, 130.02, 129.59, 129.53, 129.34, 128.21, 128.11, 122.94, 122.89, 122.79, 122.64, 122.56, 121.68, 119.68, 119.63, 115.00, 110.26, 109.37, 109.21, 108.56, 55.00, 54.96, 24.88, 17.32.

(E)-3-Acetamido-5-(4-acetoxy-3-methoxystyryl)-4-(3-methylbut-2-en-1-yl)phenyl acetate (49-1)

N,N-Diisopropylethylamine (0.32 mL, 1.8 mmol, 6 equiv) and acetic anhydride (0.1 mL, 1 mmol, 3.3 equiv) were sequentially added to a solution of compound 47 (98 mg, 0.3 mmol, 1.0 equiv) in anhydrous tetrahydrofuran (50 mL) at room temperature. After refluxing (66° C.) for 16 hours, the reaction mixture was cooled to room temperature and the volatiles were removed under reduced pressure. The residue was dissolved in ethyl acetate (20 mL) and washed with saturated sodium bicarbonate (20 mL). The aqueous layer was extracted with ethyl acetate (2×10 mL). The combined organic layers were dried over sodium sulfate, filtered and concentrated under reduced pressure to give compound 49-1 (135 mg, 99% yield) as a pale yellow solid, which was used subsequently. (CH-LM-02-24)

(E)-N-(5-hydroxy-3-(4-hydroxy-3-methoxystyryl)-2-(3-methylbut-2-en-1-yl)phenyl)acetamide (49) [KYN-169]

1M Lithium hydroxide (1.27 mL, 1.27 mmol, 5.0 equiv) was added to a solution of compound 49-1 (115 mg, 0.255 mmol, 1.0 equiv) in a 5 to 1 mixture of tetrahydrofuran and methanol (30 mL) at room temperature. The resulting solution was stirred at room temperature for 1 hour. Another batch of compound 49-1 (20 mg) was processed in the same manner. Two batches were combined and the volatiles were removed under reduced pressure. The residue was dissolved in ethyl acetate (50 mL) and washed with saturated ammonium chloride (30 mL). The aqueous layer was extracted with ethyl acetate (2×50 mL). The combined organic layers were dried over sodium sulfate, filtered and concentrated under reduced pressure. The residue was purified on an InterChim automated chromatography system (RediSep Rf GOLD 100 g HP C18 column), eluting with a gradient of 0 to 100% acetonitrile in water to give compound 49 (50 mg, 46% yield) as an off-white solid after lyophilization. (CH-LM-02-25) Off-white solid melting point 87.3-193.8° C. (decomp.); HPLC Analysis: 99.3% purity; Wavelength 254 nm, bandwidth 4; Column: Waters Atlantis T3, 2.1×50 mm, 3 μm; Retention Time: 6.6 min; Mobile Phase: ACN/formic acid/water; Mass Spectrum (positive mode) m/z=368.2 $(M+H)^+$; $C_{22}H_{25}NO_4$; $^1H$ NMR (400 MHz, DMSO-$d_6$) δ=9.19 (s, 2H), 9.14 (br s, 1H), 7.18-7.09 (m, 2H), 6.95 (dd, J=1.8, 8.2 Hz, 1H), 6.91-6.79 (m, 2H), 6.76 (d, J=8.1 Hz, 1H), 6.70 (d, J=2.2 Hz, 1H), 4.94 (sptt, J=1.2, 6.8 Hz, 1H), 3.81 (s, 3H), 3.37-3.32 (m, 2H), 2.01 (s, 3H), 1.75 (s, 3H), 1.60 (s, 3H); $^{13}C$ NMR (100 MHz, DMSO-$d_6$) δ=168.82, 155.54, 148.27, 147.17, 138.26, 137.47, 130.43, 129.96, 129.34, 124.94, 124.37, 123.98, 120.64, 116.05, 113.45, 110.34, 109.99, 56.06, 26.29, 25.98, 23.67, 18.29.

(E)-N-(5-Hydroxy-3-(4-formamido-3-methoxystyryl)-2-(3-methylbut-2-en-1-yl)phenyl)formamide (50) [KYN-170]

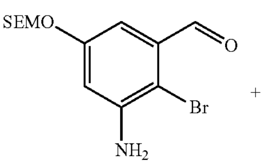

47-4

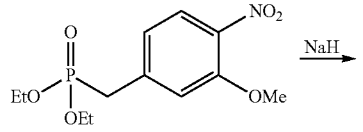

22-2

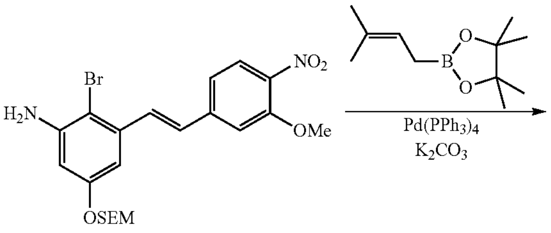

50-1

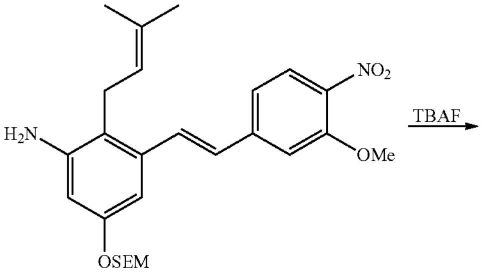

50-2

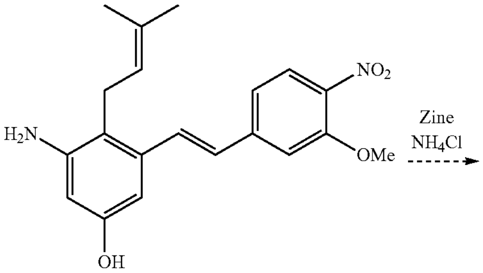

50-3

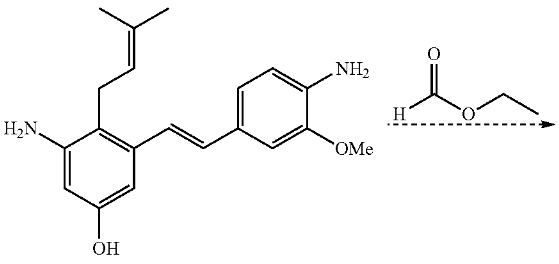

50-4

-continued

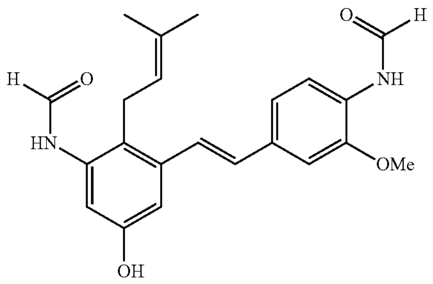

50

Compound 47-4 (3.8 g) was treated with sodium hydride (7.2 equiv) and compound 22-2 (1.8 equiv) at room temperature in tetrahydrofuran for 16 hours to give compound 50-1 (4.6 g, 85% yield).

Compound 50-1 (4.6 g) is being treated with tetrakis (triphenylphosphine)palladium(0) (0.05 equiv), potassium carbonate (2 equiv and 3-methylbut-2-enylboronic acid pinacol ester (2 equiv) in a 3 to 1 mixture of dioxane/water at 100° C. towards compound 50-2 (3.99 g, 89% yield). Compound 50-2 (0.79 g) was treated with 1M tetrabutylammonium fluoride in tetrahydrofuran (7 equiv) at 68° C. for 16 hours towards compound 50-3.

(E)-6-(3-Ethoxy-5-hydroxy-2-(3-methylbut-2-en-1-yl)styryl)-1-methyl-1,3-dihydro-2H-benzo[d]imidazol-2-one (51) [KYN-166]

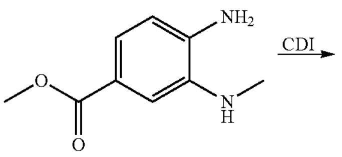

51-1

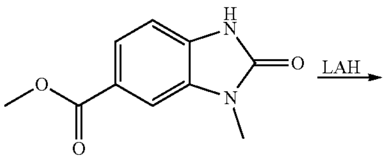

51-2

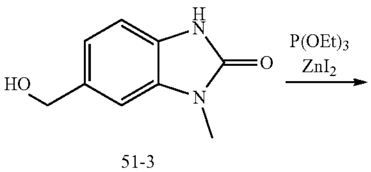

51-3

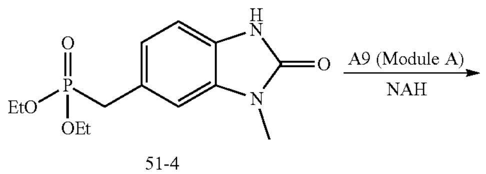

51-4

-continued

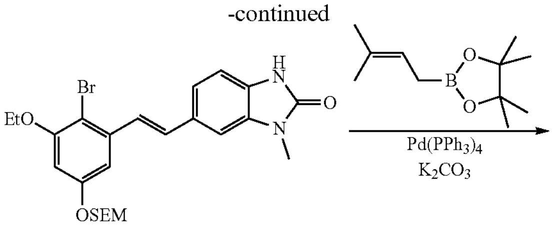

51-5

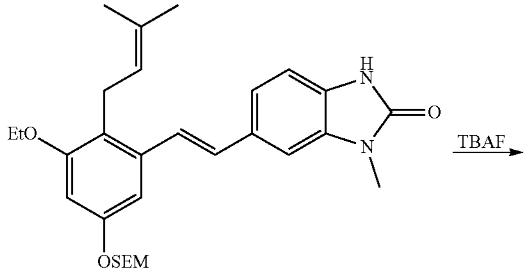

51-6

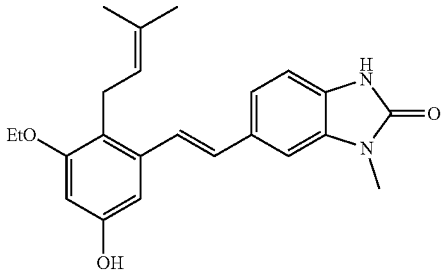

51

Methyl 3-methyl-2-oxo-2,3-dihydro-1H-benzo[d]imidazole-5-carboxylate (51-2): A mixture of compound 51-1 (10.4 g, 57.7 mmol, 1 equiv), carbonyldiimidazole (14.0 g, 86.5 mmol, 1.5 equiv) in N,N'-dimethylformamide (104 mL) was heated to 80° C. for 2 hours at which time LC/MS analysis indicated the reaction was complete. After cooling to room temperature, the solvent was removed under reduced pressure. 1N HCl (100 mL) and water (80 mL) were added to the residue and the resulting mixture was stirred at room temperature for 1 hour. The solid was filtered and dried under vacuum at 40° C. for 16 hours to give compound 51-2 (11.5 g, 97% yield) as a white solid. (YZ-3-165).

6-(Hydroxymethyl)-1-methyl-1,3-dihydro-2H-benzo[d]imidazol-2-one (51-3): 1M Lithium aluminum hydride in tetrahydrofuran (83.7 mL, 83.7 mmol, 1.5 equiv) was added slowly to a solution of compound 51-2 (11.5 g, 55.8 mmol, 1 equiv) in anhydrous tetrahydrofuran (230 mL) at −79° C. The reaction was gradually warmed to room temperature over 4 hours and stirred overnight, at which point LC/MS analysis indicated the reaction was complete. Water (10 mL), 1N sodium hydroxide aqueous solution (5 mL) were added sequentially to the reaction mixture. The mixture was stirred at room temperature for 30 minutes and filtered. The filtrate was concentrated under reduced pressure. The residue was purified on an Interchim automated chromatography system (330 g Sorbtech silica gel column), eluting with a gradient of 0 to 10% methanol in dichloromethane to give compound 51-3 (7.2 g, 72% yield) as a white solid. (YZ-3-166).

Diethyl ((3-methyl-2-oxo-2,3-dihydro-1H-benzo[d]imidazol-5-yl)methyl)phosphonate (51-4): Triethyl phosphite (13.8 mL, 13.4 g, 40.4 mmol, 2 equiv) was added to a solution of compound 51-3 (7.2 g, 40.4 mmol, 1 equiv) and zinc iodide (25.8 g, 80.8 mmol, 2 equiv) in anhydrous tetrahydrofuran (72 mL). The reaction mixture was stirred at 70° C. for 4 hours. 1H-NMR analysis indicated that the reaction was complete. After cooling to room temperature, the reaction mixture was diluted with methyl tert-butyl ether (200 mL) and filtered. The filtrate was concentrated under reduced pressure. The residue was purified on an Interchim automated chromatography system (330 g Sorbtech silica gel column), eluting with a gradient of 0 to 6% methanol in dichloromethane to give compound 51-4 (2.7 g, 22% yield) as a white solid. (YZ-3-167).

(E)-6-(2-Bromo-3-ethoxy-5-((2-(trimethylsilyl)ethoxy) methoxy)styryl)-1-methyl-1,3-dihydro-2H-benzo[d]imidazol-2-one (51-5): Potassium tert-butoxide (3.0 g, 27.2 mmol, 3 equiv) was added to a solution of compound 51-4 (2.7 g, 9.0 mmol, 1 equiv) in anhydrous dimethoxyethane (35 mL) at 0° C. After stirring for 30 minutes at 0° C., a solution of Module D (3.7 g, 10.0 mmol, 1.1 equiv) was added portionwise. The reaction mixture was gradually warmed up to room temperature and stirred for 20 hours. LC/MS analysis indicated that the reaction was complete. The reaction mixture was diluted with methyl tert-butyl ether (200 mL) and saturated ammonium chloride (200 mL). The layers were separated and the aqueous layer was extracted with additional methyl tert-butyl ether (200 mL). The combined organic layers were dried over sodium sulfate and concentrated under reduced pressure. The crude product was purified on a Biotage automatic chromatography system (330 g Sorbtech silica gel column), eluting with a gradient of 25 to 60% ethyl acetate in heptane to give compound 51-5 (300 mg, 6% yield) as an off-white solid. (YZ-3-168).

(E)-6-(3-Ethoxy-2-(3-methylbut-2-en-1-yl)-5-((2-(trimethylsilyl) ethoxy)methoxy)styryl)-1-methyl-1,3-dihydro-2H-benzo[d]imidazol-2-one (51-6): A 3 to 1 mixture of mixture of dioxane and water (16 mL) was sparged with nitrogen for 30 minutes. Compound 51-5 (290 mg, 0.56 mmol, 1 equiv), potassium carbonate (32 mg, 1.12 mmol, 2 equiv), tetrakis(triphenylphosphine)palladium(0) (32 mg, 0.03 mmol, 0.05 equiv) and 4,4,5,5-tetramethyl-2-(3-methylbut-2-en-1-yl)-1,3,2-dioxaborolane (220 g, 1.12 mmol, 2 equiv) were added sequentially. The reaction mixture was stirred at 100° C. for 7 hours. LC/MS analysis indicated that the reaction was complete. The reaction mixture was diluted with methyl tert-butyl ether (100 mL) and water (100 mL). The layers were separated and the aqueous layer was extracted with additional methyl tert-butyl ether (100 mL). The combined organic layers were dried over sodium sulfate and concentrated under reduced pressure. The crude product was purified on a Biotage automatic chromatography system (40 g Sorbtech silica gel column), eluting with a gradient of 10 to 40% ethyl acetate in heptane to give compound 51-6 (160 mg, 56% yield) as an off-white solid. (YZ-3-170).

(E)-6-(3-Ethoxy-5-hydroxy-2-(3-methylbut-2-en-1-yl) styryl)-1-methyl-1,3-dihydro-2H-benzo[d]imidazol-2-one (51) [KYN-166]: 1M Tetrabutylammonium fluoride in tetrahydrofuran (2.0 mL, 2.0 mmol, 7 equiv) was added to an solution of compound 51-6 (145 mg, 0.29 mmol, 1 equiv) in tetrahydrofuran (3 mL). After stirring at 70° C. for 24 hours. LC/MS analysis indicated that the reaction was complete. The reaction mixture cooled to room temperature and diluted with ethyl acetate (100 mL) and saturated brine (100 mL). The layers were separated and the aqueous layer was extracted with additional ethyl acetate (100 mL). The combined organic layers were dried over sodium sulfate and concentrated under reduced pressure. The crude product was purified on an Interchim automated chromatography system (80 g Sorbtech silica gel column), eluting with a gradient of 0 to 5% methanol in dichloromethane to give compound 51 (29 mg, 27% yield, 98.4% purity) as an off-white solid. (YZ-3-172). HPLC Analysis: 97.3% purity; Wavelength 254 nm, bandwidth 4; Column: Waters Atlantis T3, 2.1×50 mm, 3 μm; Retention Time: 8.4 min; Mobile Phase: ACN/formic acid/water; Mass Spectrum (positive mode) m/z=379.2 $(M+H)^+$; $C_{23}H_{26}N_2O_3$ $^1H$ NMR (400 MHz, DMSO-$d_6$) δ=7.32 (s, 1H), 7.27 (d, J=16.1 Hz, 1H), 7.16 (d, J=7.9 Hz, 1H), 6.97 (s, 1H), 6.94 (d, J=6.6 Hz, 1H), 6.63 (d, J=2.1 Hz, 1H), 6.31 (d, J=2.0 Hz, 1H), 5.02 (br t, J=6.8 Hz, 1H), 4.25-3.69 (m, 4H), 3.42-3.34 (m, 2H), 1.77 (s, 3H), 1.61 (s, 3H), 1.33 (t, J=6.9 Hz, 3H); $^{13}C$ NMR (100 MHz, DMSO-$d_6$) δ=157.77, 156.49, 155.02, 137.69, 132.04, 130.90, 130.62, 129.79, 128.52, 124.59, 121.14, 118.77, 109.10, 105.26, 103.95, 99.67, 63.77, 26.89, 26.03, 24.37, 18.27, 18.28.

(E)-6-(3-Ethoxy-5-hydroxy-2-(3-methylbut-2-en-1-yl)styryl)benzo[d]oxazol-2(3H)-one (52) [KYN-171]

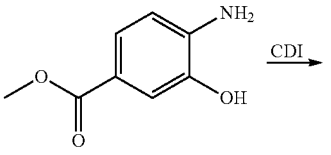

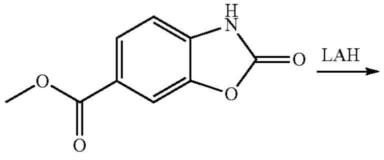

52-1

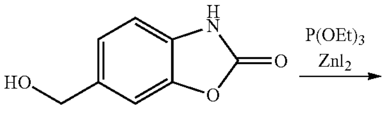

52-2

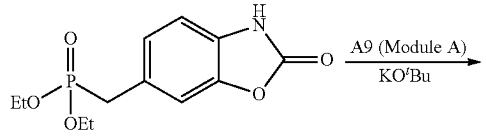

52-3

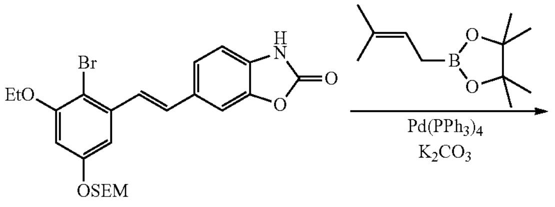

52-4

-continued

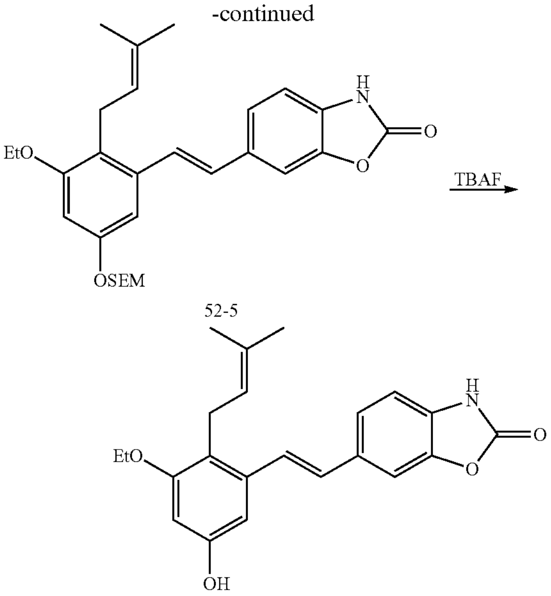

52-5

52

Methyl 2-oxo-2,3-dihydrobenzo[d]oxazole-6-carboxylate (52-1): A mixture of methyl 4-amino-3-hydroxybenzoate (10 g, 59.8 mmol, 1 equiv), carbonyldiimidazole (14.5 g, 89.7 mmol, 1.5 equiv) in N,N'-dimethylformamide (100 mL) was heated to 80° C. for 2 hours at which time LC/MS analysis indicated the reaction was complete. After cooling to room temperature, the solvent was removed under reduced pressure. 1N HCl (120 mL) was added to the residue and the resulting mixture was stirred for 3 hours at room temperature. The solid was filtered and dried under vacuum at 40° C. for 16 hours to give compound 52-1 (11.6 g, 99% yield, 97% purity) as an off-white solid. (CH-QZH-01-17).

6-(Hydroxymethyl)benzo[d]oxazol-2(3H)-one (52-2): 1M lithium aluminum hydride in tetrahydrofuran (39 mL, 39 mmol, 1.5 equiv) was added at a rate maintaining the reaction temperature below 5° C. to a mixture of compound 52-1 (5 g, 25.6 mmol, 1 equiv) in tetrahydrofuran (120 mL) at 0° C. The reaction was stirred at room temperature for overnight, at which point LC/MS analysis indicated the reaction was complete. The reaction was cooled to 5° C., water (1.5 mL), 4N sodium hydroxide solution (3 mL) and water (6 mL) was added sequentially. The mixture was stirred at room temperature for 30 minutes and filtered. The filtrate was concentrated under reduced pressure. The residue was purified on an Interchim automated chromatography system (220 g Sorbtech silica gel column), eluting with a gradient of 0 to 10% methanol in dichloromethane to give compound 52-2 (1.03 g, 24% yield) as a yellow solid. (CH-QZH-01-021).

Diethyl ((2-oxo-2,3-dihydrobenzo[d]oxazol-6-yl)methyl) phosphonate (52-3): Triethyl phosphite (3.8 mL, 3.73 g, 22.48 mmol, 2 equiv) was added to a solution of compound 52-2 (1.86 g, 11.24 mmol, 1 equiv) and zinc iodide (7.18 g, 22.48 mmol, 2 equiv) in tetrahydrofuran (55 mL). The reaction mixture was stirred at 70° C. for 3 hours. 1H-NMR analysis indicated that the reaction was complete. After cooling to room temperature, the reaction was diluted with methyl tert-butyl ether (200 mL) and filtered. The filtrate was concentrated under reduced pressure. The residue was purified on an Interchim automated chromatography system (220 g Sorbtech silica gel column), eluting with a gradient of 0 to 5% methanol in dichloromethane to give compound 52-3 (1.9 g, 59% yield) as an off-white solid. (YZ-3-151).

(E)-6-(2-Bromo-3-ethoxy-5-((2-(trimethylsilyl)ethoxy) methoxy)styryl)benzo[d]oxazol-2(3H)-one (52-4): Potassium tert-butoxide (2.10 g, 18.96 mmol, 3 equiv) was added to a solution of compound 52-3 (1.8 g, 6.30 mmol, 1 equiv) in anhydrous dimethoxyethane (53 mL) at 0° C. After stirring for 1 hour at 0° C., a solution of Module D (2.61 g, 6.96 mmol, 1.1 equiv) in anhydrous dimethoxyethane (10 mL) was added slowly. The reaction mixture was gradually warmed up to room temperature and stirred for 2 days. LC/MS analysis indicated that the reaction was complete. The reaction mixture was diluted with methyl tert-butyl ether (200 mL) and saturated ammonium chloride aqueous solution (200 mL). The layers were separated and the aqueous layer was extracted with additional methyl tert-butyl ether (200 mL). The combined organic layers were dried over sodium sulfate and concentrated under reduced pressure. The crude product was purified on a Biotage automatic chromatography system (220 g Sorbtech silica gel column), eluting with a gradient of 5 to 30% ethyl acetate in heptane to give compound 52-4 (0.94 g, 29% yield) as an off-white solid. (YZ-3-155).

(E)-6-(3-Ethoxy-2-(3-methylbut-2-en-1-yl)-5-((2-(trimethylsilyl)ethoxy)methoxy)styryl)benzo[d]oxazol-2(3H)-one (52-5): A mixture of dioxane/water (45 mL/15 mL) was sparged with nitrogen for 30 minutes. Compound 52-4 (0.94 g, 1.86 mmol, 1 equiv), potassium carbonate (0.51 g, 3.72 mmol, 2 equiv), tetrakis(triphenylphosphine)palladium(0) (0.11 g, 0.08 mmol, 0.05 equiv) and 4,4,5,5-tetramethyl-2-(3-methylbut-2-en-1-yl)-1,3,2-dioxaborolane (0.73 g, 3.72 mmol, 2 equiv) were added sequentially. The reaction mixture was stirred at 100° C. for 20 hours. LC/MS analysis indicated that the reaction was complete. The reaction mixture was diluted with methyl tert-butyl ether (200 mL) and water (200 mL). The layers were separated and the aqueous layer was extracted with additional methyl tert-butyl ether (200 mL). The combined organic layers were dried over sodium sulfate and concentrated under reduced pressure. The crude product was purified on a Biotage automatic chromatography system (220 g Sorbtech silica gel column), eluting with a gradient of 5 to 30% ethyl acetate in heptane to give compound 52-5 (0.54 g, 59% yield) as a white solid. (YZ-3-156).

(E)-6-(3-Ethoxy-5-hydroxy-2-(3-methylbut-2-en-1-yl) styryl)benzo[d]oxazol-2(3H)-one (52): 1M tetrabutylammonium fluoride in tetrahydrofuran (4.9 mL, 4.94 mmol, 7 equiv) was added to an solution of compound 52-5 (0.35 g, 0.71 mmol, 1 equiv) in anhydrous tetrahydrofuran (5 mL). The reaction mixture was stirred at 70° C. for 24 hours. LC/MS analysis indicated that trace product was generated but the majority of starting material remained unreacted. The volume of the reaction mixture was concentrated under reduced pressure to ~1 mL and stirred at 70° C. for another 24 hours. LC/MS analysis indicated that the reaction was complete. The reaction mixture was diluted with ethyl acetate (100 mL) and saturated brine (100 mL). The layers were separated and the aqueous layer was extracted with additional ethyl acetate (100 mL). The combined organic layers were dried over sodium sulfate and concentrated under reduced pressure. The crude product was purified on an Interchim automated chromatography system (80 g Sorbtech silica gel column), eluting with a gradient of 0 to 2% methanol in dichloromethane to give compound 52 (58 mg, >95% purity, and 78 mg, ~70% purity, 53% overall yield) as a white solid. (YZ-3-158). HPLC Analysis: 97.0% purity; Wavelength 254 nm, bandwidth 4; Column: Waters Atlantis T3, 2.1×50 mm, 3 μm; Retention Time: 8.9 min; Mobile Phase: ACN/formic acid/water; Mass Spectrum (positive mode) m/z=366.2 $(M+H)^+$; $C_{22}H_{23}NO_4$; $^1H$ NMR (400 MHz, DMSO-$d_6$) δ=11.65 (br s, 1H), 9.20 (br s, 1H), 7.56 (s, 1H), 7.38-7.23 (m, 2H), 7.07 (d, J=8.1 Hz, 1H), 6.95 (d, J=16.0 Hz, 1H), 6.66-6.58 (m, 1H), 6.36-6.27 (m, 1H), 5.01 (br t, J=6.4 Hz, 1H), 3.94 (q, J=6.8 Hz, 2H), 3.41-3.34 (m, 2H), 1.74 (s, 3H), 1.60 (s, 3H), 1.33 (t, J=6.8 Hz, 3H); $^{13}C$ NMR (100 MHz, DMSO-$d_6$) δ=157.70, 156.57, 154.94, 144.44, 137.36, 132.39, 130.35, 129.81, 129.71, 125.91, 124.51, 123.41, 118.94, 110.22, 107.20, 104.16, 99.96, 63.74, 25.98, 24.27, 18.25, 15.25.

Cellular Studies

In Vitro Studies Related to Compounds 1 to 15 in Human Cancer Cell Lines

Introduction

Compounds 1 to 15 were evaluated and their effect on cancer growth examined in cell viability assays on multiple cancer types (Tables 1 to 5). Cancer cells including pancreatic, bladder, kidney, colon, breast, lung, liver and osteosarcomas obtained from ATCC (American Type Culture Collection) were authenticated before use by Short Tandem Repeat genomic analysis (Reid Y, Storts D, Riss T and Minor L. Authentication of Human Cell Lines by STR DNA Profiling Analysis. 2013 May 1. In: Markossian S, Sittampalam G S, Grossman A, et al., editors. Assay Guidance Manual. Bethesda (Md.): Eli Lilly & Company and the National Center for Advancing Translational Sciences; 2004). Experimental protocol for each cancer cell line was verified and optimized according to literature reports before use (Tables 1 to 3).

Cell Culture/Molecular Biology Protocols

Cryopreservation of Mammalian Cell Lines

Cancer cells were grown on a 100 mm plate according to the manufacturer specification. After culture media removal, cells were split by washing in PBS (lx), then trypsin (1 mL) was added followed by 2-5 min incubation at 37° C. Cells were resuspended in cell culture media, then transferred into a 15 mL Falcon tube and then centrifuged for 5 min at 1,000 rpm at room temperature (RT). The supernatant was removed, and cell pellet was resuspended in Fetal Bovine Serum (900 μL). The cell suspension (900 μL) was transferred into 1 mL cryovial containing DMSO (100 μL). Care was taken to ensure that cells in freezing media had minimal exposure at RT (<10 min). Cryovials were then transferred into an isopropanol-containing CoolCell and stored at −80° C. The CoolCell ensures that the temperature decreases steadily by 1° C./minute. Cryovials were removed from the CoolCell after 24 h, then transferred into liquid nitrogen for long term storage. A minimum of 4 aliquots were banked in LN2 for each cell line.

Thawing and Passaging Cancer Cells

Cryovial was removed from the LN2 tank and hold in RT until the sides were thawed but center remained frozen. A warm media (9 mL) was added dropwise to the partially frozen cells. The cell suspension is centrifuged for 5 min at 1,000 rpm at RT. Supernatant was removed, and cell pellet resuspended in a 1 mL medium. The suspension was transferred into 100 mm culture plate and incubated at 37° C. for 24 h. Upon strong attachment, cells were given fresh medium. Change of media was repeated every 3 days until the cell density reached confluency. Sub-culturing was carried out when cells reached approximately 80% confluent (80% of surface of flask covered by cell monolayer). Split ratios 1:3 up to 1:10 were used to ensure cells readiness for an experiment. Sub-culture was carried out to 10 passages or less.

Cell Viability Assay 1.7*103 cells/well were seeded in quadruplicates in 96-well plate after plating. Drugs were added at 5 μM and 2-fold dilutions over 18 concentrations (0.000038146-5 μM concentration range) to generate a dose-response curve. Cell growth was assessed on day 1, 3 and 5 after drug treatments using the CellTiter Glo Luminescence Cell Viability Assay (Promega) according to manufacturer's protocol. Thermo Scientific Varioskan LUX Multimode Microplate instrument was used for plate reading. Data are expressed as mean luminescence (arbitrary units)±S.D.

$IC_{50}$ Calculation

Cell Viability Assays were employed to determine the concentration of Compound 1 (KYN-001) and analogues where the response is reduced by half. For each treatment of cancer cells, 1, 2, 5, 10 and 20 μM solutions of compounds were applied. GraphPad Prism 7 software was used to fit dose response curves. Relative Luminescence Units were plotted against the log values of the doses used and the nonlinear regression model was used for data analysis Results Effect of Compound 1 (KYN-001) and Analogues on Cancer Cells' Viability The time- and dose-dependent effect of exogenously added compounds on cancer cell proliferation was assessed using CellTiter Glo Luminescence Cell Viability Assay. The concentration of the drug where the response is reduced by half ($IC_{50}$) was calculated in all cases. The inhibitory action of Compound 1 (KYN-001) analogues compared to that of the parent compounds 1 (KYN-001), 8 (KYN-119) and 27 (KYN-149) is shown in Tables 1 to 5.

Compound 8 [KYN-119] was the most potent (lowest $IC_{50}$) amongst the compounds evaluated in all cell lines tested in Tables 1 and 2. Compounds 17[KYN-120], 23 (KYN-125), 29 (KYN-128) and 33 (KYN-126) were marginally less potent than the parent compound 1. Loss of the anti-proliferative effect was observed in the case of Compound 22 (KYN-124).

The protocol for cell proliferation was optimized for Compound 8 (KYN-119) to enable a more accurate assessment of its low $IC_{50}$ value. In this protocol, 18 dosages (2 fold dilutions ranging from 0.000038146 to 5 μM) were applied to cells seeded in 96-well plates, and Luminescence was measured after 1, 3 and 5 days upon treatments. It is notable that neither 1 nor 8 affect cell viability on Day 1 upon treatment at dosages <1 μM. This observation suggests that at <1 μM dosages, compounds 1 (KYN-001) and 8 (KYN-119) are not toxic to cells.

A comparative study on 1 [KYN-001] and 8 [KYN-119] was carried out on 83 cancer cell lines (Table 3). Potent activity was shown by 1 [KYN-001] with $IC_{50}$ values in the range 0.01 to 0.1 μM towards the following cell lines:—Tongue SCC-15, CAL 27, UPCI:SCC090, SCC-4; Leiomyosarcoma SK-UT-1B, SK-LMS-1; Bladder UMUC_3, SCABER, 5637, RT-112; Breast MDA-MB-231; Liver SNU-423, SNU-398, Huh7; Connective Tissue Sarcoma TE 381.T, HT-1080; Osteosarcomas MG3, KHOS_N/P; Lung NCI-H661, NCI-H1299, NCI-H2126, BEAS-2B, NCI-H1048; Hypo-pharynx UPCI:SCC152; Fibrosarcomas SW 684; Liposarcoma 93T449, 94T778; Pharynx FADU; Rhabomyosarcoma SJCRH30, CCL 166; Kidney CCL 166. On the average the activity of 8 [KYN-119] was 10 fold more potent than 1 [KYN-001]. Very potent activity was shown by 8 [KYN-119] with $IC_{50}$ values in the range 0.001 to 0.01 μM towards the following cell lines:—Lung NCI-H2126, NCI-H1299; Bladder RT-112, 5637, UMUC_3; Osteosarcomas T1-73, MG3; Fibrosarcomas SW 684; Rhabomyosarcoma CCL 166; Liver SNU-398; Breast MDA-MB-231; Kidney Caki-1; Pancreatic CAPAN-2. Potent activity was shown by 8 [KYN-119] with $IC_{50}$ values in the range 0.01 to 0.1 μM towards the following cell lines:—Bladder SCABER, HT-1197, T24, J82; Colon SW_480, HT_116; Connective Tissue Sarcoma HT-1080; Ewing's Sarcoma HTB-166; Hypo-pharynx UPCI:SCC152; Kidney ACHN, SK-NEP-1, 769-P, 786-O; Leiomyosarcoma SK-LMS-1; Liposarcoma 93T449, 94T778; Liver HepG2, Huh7, SNU-475, JHH-6; Lung NCI-H661, NCI-H1048, BEAS-2B, NCI-H1437, NCI-H1563, NCI-H1573, A549; Osteosarcomas KHOS_N/P, SAOS-2, Hs888.T, HOS_CRL_1543, KHOS_312H, U2OS; Pancreatic PANC-1, MIA PaCa-2, CFPAC; Pharynx FADU; Rhabomyosarcoma TE 159.T, A-204, SJCRH30, Hs 729; Tongue SCC-15, SCC-4, UPCI:SCC090, CAL 27, SCC-9.

The analogues of compound 1 [KYN-001], including compounds 8 [KYN-129], 12 [KYN-130] and 13 [KYN-131] were tested for their efficacy on cancer cell viability using the optimized cell proliferation protocol together with Compounds 1 [KYN-001] and 9 [KYN-119], and the results are shown in Table 4. None of these compounds is more effective than 9 [KYN-119]. Compounds 12 [KYN-130] and 13 [KYN-131] exhibited a similar activity as 1 [KYN-001] on cancer cell growth inhibition upon 3 Days of treatment. Total loss of the anti-proliferative effect was observed in compound 8 [KYN-129].

Comparative assessment of 1 [KYN_001] and 8 [KYN-119], and their analogues, $IC_{50}$ values (μM) towards A498 and MIA PaCa-2 cancer cell lines was made over 8 experiments (Table 5A and 5B).

Activity shown towards A498 cells in the potent range of $IC_{50}$ value less than 0.1 μM was only observed for compound 30 [KYN-142]. Order of activity (high to low) for compounds in the moderately potent range of 0.1 to 1 μM are as follows:—2, 3, 4, 7, 8, 9, 10, 11, 12, 17, 20, 23, 27, 28, 29, 33, 34, 38 [KYN-155, 131, 138, 120, 130, 143, 136, 132, 125, 128, 119, 139, 146, 140, 133, 147, 149, 126]. Activity shown towards MIA PaCa-2 cells in the highly potent range of $IC_{50}$ value, less than 0.001 μM, was only observed for 28 [KYN-143]. Order of activity for compounds with $IC_{50}$ values in the very potent 0.01 to 0.1 μM range are as following:—1, 5, 8, 10, 20, 27, 30 [KYN-149, 119, 153, 146, 142, 001, 131]. Compounds with $IC_{50}$ values in the potent 0.1 to 1 μM range are as following:—2, 3, 4, 9, 11, 23, 29, 32, 34 [KYN-130, 138, 147, 132, 125, 128, 139, 148, 140].

Cancer cell viability inhibition Structure-Activity Relationships (SARs) for compounds 1 to 49 and 51 [KYN-001, KYN-119, KYN-120, KYN-124, KYN-125, KYN-126, KYN-128 to KYN-134, KYN-136 to KYN-169] based on $IC_{50}$ values in Tables 1 to 5.

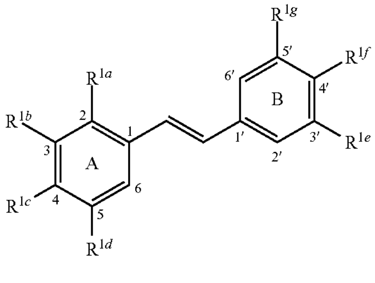

Based on the lead compound 1 [KYN-001] analogues with variations in chemical structure were prepared to vary substituents on the stilbene core to improve and optimise biological activity, bioavailability and solubility properties.

Variation of the prenyl substituent of 1 [KYN-001] ($R^{1a}$=prenyl) was carried out by organic synthesis to give the following analogues:—45 [KYN-112] ($R^{1a}$=Br), 7 [KYN-136] ($R^{1a}$=benzyl), 6 [KYN-134] ($R^{1a}$=allyl), 2 [KYN-138] ($R^{1a}$=E-crotyl ((E)-but-2-en-1-yl)), 3 [KYN-139] ($R^{1a}$=Z-crotyl ((Z)-but-2-en-1-yl)), 4 [KYN-140] ($R^{1a}$=iso-crotyl (but-3-en-2-yl)). In general, all the variations showed reduced biological activity (Tables 1, 4 and 5) except for 2 [KYN-138] with the E-crotyl group that show biological activity comparable with 1 [KYN-001]. 2 [KYN-138] is calculated to be less lipophilic and about 3 times more water soluble than 1 [KYN-001], indicating that it may have better bioavailability and pharmacokinetic properties.

The following analogues were prepared with variation to the $R^{1b}$ substituent of 1 [KYN-001] (R=OMe):—8 [KYN-119] (R=OEt), 9 [KYN-130] (R=propoxy), 10 [KYN-131] (R=iso-propoxy), 11 [KYN-132] (R=trifluoromethoxy), 46 [KYN-145](R=trifluoromethyl). Replacement of the methoxy group with a trifluoromethyl group resulted in a complete loss of biological activity towards the cell lines tested. 8 [KYN-119] with the ethoxy group showed an average 10 fold enhancement of cancer cell viability inhibition over the 83 cell lines (Table 3). Further extension of the alkyl group size as for 9 [KYN-130] (R=propoxy) and 10 [KYN-131] (R=iso-propoxy) resulted in comparable or weaker biological activity and, also, these compounds are calculated to be significantly more lipophilic than 1 [KYN-001] and much less water soluble.

The 1 [KYN-001] ($R^{1e}$=OMe) analogue 12 [KYN-133] ($R^{1e}$=OEt), from the cell lines tested, showed an approximately 10 fold reduction in cancer cell viability inhibition. This is in sharp contrast to the 10 fold enhancement seen with 8 [KYN-119] with the ethoxy group variation from 1 [KYN-001]. Other 1 [KYN-001] ($R^{1e}$=OMe) analogues, [KYN-158] ($R^{1e}$=NHMe), 16 [KYN-157] ($R^{1e}$=NHMe), 41 [KYN-161] ($R^{1e}$=NHMe) tested as inactive or weakly active.

1 [KYN-001] analogues were prepared with variation to the $R^{1f}$ substituent of 1 [KYN-001] ($R^{1f}$=OH). Replacement of the hydroxyl group with an amino group provides an extra valency for addition of extra chemical structure. The analogue with an amino group 23 [KYN-125] showed activity similar to but overall reduced on the cell lines tested compared with 1 [KYN-001]. With extra valency available through the nitrogen a series of amino derivatives of 23 [KYN-125] were prepared as compounds 25, 26, 27, 29, 31, 33, 36 [KYN-126, 128, 129, 137, 149, 150, 151]. The acetamide derivative 29 [KYN-128] ($R^{1f}$=—(CO)$CH_3$) showed similar activity to 1 [KYN-001] and the formamide derivative 27 [KYN-149] ($R^{1f}$=—(CO)H) tested on two cell lines showed on $IC_{50}$ value of 0.015 μM towards MIA PaCa-2 cells approximately 5 fold more potent than 1 [KYN-001]. All amino derivatives larger than acetamide, overall, showed weaker inhibition or were inactive. Replacement of the $R^{1f}$ hydroxy group of 1 [KYN-001] with a carboxy group gave an analogue 21 [KYN-154] ($R^{1f}$—=COOH) with $IC_{50}$ greater than 3 μM on two cell lines, A498 and MIA PaCa-2. Replacement of the $R^{1g}$ hydrogen atom of 1 [KYN-001] with a methyl group to give an analogue 17 [KYN-120] ($R^{1g}$=$CH_3$) resulted in an approximately 3 fold reduction in inhibitory activity towards the six cell lines tested (Table 2). A similar loss of activity was observed for analogue 18 [KYN-156] ($R^{1g}$=OH) with an additional hydroxyl group ((Table 5A). Moving the $R^{1f}$ hydroxy group of 1 [KYN-001] as in analogue 19 [KYN-160]($R^{1g}$=OH) also strongly weakened activity in the cell lines tested.

Where a single change in substituent was made with respect to the 1 [KYN-001] chemical structure two substituent changes were found to independently enhance cancer cell viability inhibition, $R^{1d}$=OEt as observed with compound 8 [KYN-119] ($R^{1b}$=OEt) and $R^{1f}$=NH(CO)H as observed with compound 27 [KYN-149] ($R^{1f}$=—NH(CO)H). A compound was prepared with both of these substituent changes, 28 [KYN-143] ($R^{1b}$=OEt; $R^{1f}$=NH(CO)H) and found to much enhanced inhibition towards A498 ($IC_{50}$ 0.18 μM) and MIA PaCa-2 ($IC_{50}$ 0.00094 μM) cell lines. These inhibition values compare favourably with compound 8 [KYN-119] which showed less inhibition towards the A498 ($IC_{50}$ 0.36 μM) and MIA PaCa-2 ($IC_{50}$ 0.025 μM) cell lines. Replacing the $R^{1e}$ methoxy group of 28 [KYN-143] with a hydroxyl group as in analogue 40 [KYN-159] ($R^{1e}$=OH) very strongly weakened activity in the two cell lines tested (Table 5A). The N-hydroxy derivative of the hydroxy group of 28 [KYN-143] as in analogue 39 [KYN-165] ($R^{1f}$=N(OH)(CO)H) resulted in the almost complete loss of anticancer activity in the two cell lines tested (Table 5B).

Replacement of the $R^{1d}$ hydroxyl group of 1 [KYN-001] with a nitro group gave an analogue 42 [KYN-162] ($R^{1d}$=$NO_2$) which resulted in almost complete loss of anticancer activity towards two cell lines (Table 5A). No significant enhancement of activity was observed when the $R^{1d}$ nitro group was converted to an amino 43 [KYN-163] ($R^{1d}$=$NH_2$) and further into a formamide group 44 [KYN-164] ($R^{1d}$=NH(CO)H) (Table 5A).

Replacement of the $R^{1b}$ hydroxyl group of 1 [KYN-001] with an amino group gave an analogue 47 [KYN-167] ($R^{1b}$=$NH_2$) which gave indeterminate anticancer activity response towards two cell lines (Table 5B). Formamide and acetamide derivatives were prepared as 48 [KYN-168] ($R^{1b}$=NH(CO)H) and 49 [KYN-169] ($R^{1b}$=NH(CO)Me), respectively, which were determined to have anticancer activities comparable to 1 [KYN-001] for two cancer cell lines (Table 5A).

An analogue of 8 [KYN-119] with a 5-membered heterocyclic ring fused through joining $R^{1e}$ and $R^{1f}$, compound 51 [KYN-166] and compound 52 [KYN-171] showed no significant activity towards the two cell lines tested (Table 5A).

TABLE 1

$IC_{50}$ values (μM) of Compounds 1, 13, 14, 45 [KYN-001, 112, 114, 118] on Day 3 upon drug treatment (based on 10 dosages ranging from 0.0001-20 μM [31 Oct. 2018]

| | | Cancer | | | | |
|---|---|---|---|---|---|---|
| Compound Number | Cell Line/KYN code | Colon SW_480 | Pancreatic MIA PaCa-2 | Breast MDA-MB-231 | Bladder RT-112 | Kidney CRL-1611 |
| 1 | KYN-001 | 0.298 | 0.204 | 0.0293 | 0.105 | 0.0937 |
| 13 | KYN-114 | 26.47 | 3.003 | N/A | 0.949 | 2.12 |
| 14 | KYN-118 | N/A | 3.47 | ~10.6 | 1.33 | 2.96 |
| 45 | KYN-112 | 10.8 | 20.4 | ~10.3 | N/A | N/A |

TABLE 2

$IC_{50}$ values (μM) of Compounds 1, 17, 22, 23, 29, 33 on Day 5 upon drug treatment (based on 10 dosages ranging from 0.0001-20 μM and, for Compound 8, 18 dosages ranging from 0.000038146 to 5 μM) [31 Oct. 2018, corrected 9 Jun. 2019]

| | | Cancer | | | | | |
|---|---|---|---|---|---|---|---|
| Comp. | Cell Line | Bladder 5637 | Bladder RT-112 | Breast MDA-MB-231 | Colon HCT_116 | Kidney ACHN | Pancreatic MIA PaCa-2 |
| 1 | KYN-001 | 0.0306 | 0.0287 | 0.0573 | 0.165 | 0.0897 | 0.0507 |
| 8 | KYN-119 | ~0.00943 | ~0.00565 | ~0.00000253 | 0.028 | ~0.0000135 | ~0.00047 |
| 17 | KYN-120 | 0.104 | 0.115 | 0.246 | 0.353 | 0.283 | 0.182 |
| 22 | KYN-124 | N/A | N/A | 6.2 | N/A | N/A | N/A |
| 23 | KYN-125 | 0.0653 | 0.0682 | 0.138 | 0.474 | 0.26 | 0.18 |
| 29 | KYN-128 | 0.0674 | 0.0764 | 0.155 | 0.627 | 0.281 | 0.185 |
| 33 | KYN-126 | 0.0859 | 0.0955 | 0.169 | 0.68 | 2.84 | 0.0968 |

TABLE 3

Effect of 1 [KYN-001] and 8 [KYN-119] compounds on cancer cells' viability as assessed by CellGlow Titer Assay calculated as $IC_{50}$ µM. Cells were treated with 18 (2-fold) dilutions (concentration range: 5-0.00003 µM) 24 h after plating and luminesence measurements were performed upon 3 Days of treatment. Combined results from 7 experiments reported; 31 Oct. 18, 19 Dec. 18, 15 May 19, 4 Jun. 19, 6 Jun. 19, 8 Jun. 19, 19 Jun. 19.

| | | Compound 1 [KYN-001] | | | Compound 8 [KYN-119] | | | Fold |
|---|---|---|---|---|---|---|---|---|
| Cancer | Cell Line | Average $IC_{50}$ µM | STDev | n | Average | STDev | n | $IC_{50}$ |
| Bladder | 5637 | 0.0347 | 0.0044 | 2 | 0.00391 | 0.00064 | 2 | 8.9 |
| Bladder | HT_1376 | N/A | | 0 | 0.610 | | 1 | |
| Bladder | HT-1197 | 0.258 | | 1 | 0.0115 | | 1 | 22 |
| Bladder | J82 | 0.184 | | 1 | 0.0465 | | 1 | 4.0 |
| Bladder | RT-112 | 0.0529 | 0.045 | 3 | 0.00363 | 0.00066 | 2 | 15 |
| Bladder | RT4 | N/A | | 0 | 1.67 | | 1 | |
| Bladder | SCABER | 0.0337 | | 1 | 0.0101 | | 1 | 3.3 |
| Bladder | SW780 | 0.712 | | 1 | 0.217 | | 1 | 3.3 |
| Bladder | T24 | 0.129 | | 1 | 0.0225 | | 1 | 5.8 |
| Bladder | TCCSUP | 0.294 | | 1 | 0.112 | | 1 | 2.6 |
| Bladder | UMUC_3 | 0.0313 | | 1 | 0.00548 | | 1 | 5.7 |
| Bladder | UMUC-14 | 1.16 | | 1 | 0.563 | | 1 | 2.1 |
| Breast | MCF7 | 0.694 | 0.19 | 2 | 0.136 | 0.028 | 2 | 5.1 |
| Breast | MDA-MB-231 | 0.0326 | 0.0046 | 3 | 0.00848 | 0.0050 | 2 | 3.8 |
| Colon | HCT_116 | 0.416 | 0.077 | 2 | 0.0355 | 0.020 | 2 | 12 |
| Colon | SW_480 | 0.179 | 0.11 | 3 | 0.0179 | 0.0030 | 2 | 10 |
| Connective Tissue Sarcoma | HT-1080 | 0.0367 | | 1 | 0.0173 | | 1 | 2.1 |
| Connective Tissue Sarcoma | TE 381.T | 0.0357 | | 1 | 0.00750 | | 1 | 4.8 |
| Ewing's Sarcoma | HTB-166 | 0.257 | | 1 | 0.0492 | | 1 | 5.2 |
| Fibrosarcomas | SW 684 | 0.0552 | | 1 | 0.00463 | | 1 | .12 |
| Hypo-pharynx | UPCI: SCC152 | 0.0463 | | 1 | 0.0230 | | 1 | 2.0 |
| Kidney | 769-P | N/A | | 0 | 0.0337 | | 1 | |
| Kidney | 786-O | 0.334 | | 1 | 0.0648 | | 1 | 5.1 |
| Kidney | A-498 | 2.81 | 4.8 | 5 | 0.329 | 0.25 | 4 | 8.5 |
| Kidney | ACHN | 0.494 | 0.0027 | 2 | 0.0104 | 0.0011 | 3 | 48 |
| Kidney | Caki-1 | 0.103 | | 1 | 0.00890 | | 1 | 12 |
| Kidney | Caki-2 | 1.12 | | 1 | 0.281 | | 1 | 4.0 |
| Kidney | CRL-1611 | 0.0937 | | 1 | | | | |
| Kidney | HTB-45 | 1.73 | | 1 | 0.463 | | 1 | 3.7 |
| Kidney | SK-NEP-1 | 0.158 | | 1 | 0.0178 | | 1 | 8.9 |
| Leiomyosarcoma | SK-LMS-1 | 0.0659 | | 1 | 0.0175 | | 1 | 3.8 |
| Leiomyosarcoma | SK-UT-1B | 0.0226 | | 1 | 0.00639 | | 1 | 3.5 |
| Liposarcoma | 93T449 | 0.0555 | | 1 | 0.0151 | | 1 | 3.7 |
| Liposarcoma | 94T778 | 0.0845 | | 1 | 0.0257 | | 1 | 3.3 |
| Liver | HepG2 | 0.212 | 0.0030 | 2 | 0.0202 | 0.00005 | 2 | 11 |
| Liver | Huh7 | 0.0789 | 0.0017 | 2 | 0.0206 | 0.00049 | 2 | 3.8 |
| Liver | JHH-5 | N/A | | 0 | 4.37 | 3.5 | 2 | |
| Liver | JHH-6 | 0.172 | 0.0008 | 2 | 0.0364 | 0.0022 | 2 | 4.7 |
| Liver | JHH-7 | 0.696 | 0.87 | 2 | 0.519 | 0.16 | 2 | 1.3 |
| Liver | SNU-398 | 0.0429 | 0.0002 | 2 | 0.00815 | 0.00014 | 2 | 5.3 |
| Liver | SNU-423 | 0.0338 | 0.0002 | 2 | 0.00623 | 0.00029 | 2 | 5.4 |
| Liver | SNU-475 | 0.239 | 0.21 | 2 | 0.0324 | 0.00037 | 2 | 7.4 |
| Lung | A549 | 0.163 | 0.039 | 2 | 0.0309 | 0.00066 | 2 | 5.3 |
| Lung | BEAS-2B | 0.0764 | 0.0017 | 2 | 0.0150 | 0.00054 | 2 | 5.1 |
| Lung | NCI-H1048 | 0.0917 | | 1 | 0.0145 | 0.0035 | 2 | 6.3 |
| Lung | NCI-H1299 | 0.0624 | 0.0026 | 2 | 0.00856 | 0.00001 | 2 | 7.3 |
| Lung | NCI-H1437 | 0.347 | | 1 | 0.0166 | | 1 | 21 |
| Lung | NCI-H1563 | 0.449 | | 1 | 0.0195 | | 1 | 23 |
| Lung | NCI-H1573 | 0.217 | 0.016 | 2 | 0.0205 | 0.00080 | 2 | 11 |
| Lung | NCI-H2126 | 0.0754 | | 1 | 0.00173 | | 1 | 44 |
| Lung | NCI-H596 | 0.303 | 0.12 | 2 | 0.115 | 0.034 | 2 | 2.6 |
| Lung | NCI-H661 | 0.0366 | 0.0025 | 2 | 0.0115 | 0.0011 | 2 | 3.2 |
| Osteosarcomas | HOS_CRL_1543 | 0.358 | 0.32. | 3 | 0.0320 | 0.0023 | 3 | 11 |
| Osteosarcomas | Hs888.T | 0.210 | 0.049 | 2 | 0.0261 | 0.0020 | 2 | 8.1 |
| Osteosarcomas | KHOS_312H | 0.356 | 0.25 | 2 | 0.0367 | 0.00071 | 3 | 9.7 |
| Osteosarcomas | KHOS_N/P | 0.0687 | 0.0090 | 3 | 0.0105 | 0.00011 | 3 | 6.6 |
| Osteosarcomas | MG3 | 0.0359 | 0.0041 | 3 | 0.00688 | 0.00039 | 3 | 5.2 |
| Osteosarcomas | SAOS-2 | 0.110 | 0.046 | 2 | 0.0154 | 0.0020 | 3 | 7.2 |
| Osteosarcomas | SJSA_1 | 2.30 | | 1 | 9.58 | 6.7 | 2 | 0.2 |
| Osteosarcomas | T1-73 | 0.804 | | 1 | 0.00393 | 0.00022 | 2 | 205 |
| Osteosarcomas | U2OS | 0.325 | 0.25 | 3 | 0.0368 | 0.0040 | 3 | 8.8 |
| Pancreatic | AsPC-1n | N/A | | 0 | 2.00 | 1.4 | 3 | |
| Pancreatic | BxPC3 | 1.06 | 0.48 | 2 | 0.355 | 0.082 | 2 | 3.0 |
| Pancreatic | CAPAN-1 | 6.22 | 6.7 | 2 | 4.69 | | 1 | 1.3 |
| Pancreatic | CAPAN-2 | 0.182 | 0.12 | 3 | 0.00975 | 0.00062 | 3 | 19 |
| Pancreatic | CFPAC | 0.492 | 0.15 | 3 | 0.0824 | 0.013 | 3 | 6.0 |

TABLE 3-continued

Effect of 1 [KYN-001] and 8 [KYN-119] compounds on cancer cells' viability as assessed by CellGlow Titer Assay calculated as $IC_{50}$ μM. Cells were treated with 18 (2-fold) dilutions (concentration range: 5-0.00003 μM) 24 h after plating and luminesence measurements were performed upon 3 Days of treatment. Combined results from 7 experiments reported; 31 Oct. 18, 19 Dec. 18, 15 May 19, 4 Jun. 19, 6 Jun. 19, 8 Jun. 19, 19 Jun. 19.

| | | Compound 1 [KYN-001] | | | | | | Fold |
|---|---|---|---|---|---|---|---|---|
| | | Average | | | Compound 8 [KYN-119] | | | |
| Cancer | Cell Line | $IC_{50}$ μM | STDev | n | Average | STDev | n | $IC_{50}$ |
| Pancreatic | HPAC | 4.99 | 5.2 | 2 | 1.97 | 1.4 | 2 | 2.5 |
| Pancreatic | HPAFII | 1.07 | 0.63 | 2 | 0.403 | 0.15 | 3 | 2.7 |
| Pancreatic | MIA PaCa-2 | 0.127 | 0.057 | 6 | 0.0181 | 0.015 | 4 | 7.0 |
| Pancreatic | PANC-1 | 0.107 | 0.043 | 2 | 0.0115 | 0.0025 | 2 | 9.3 |
| Pharynx | DETROIT | 1.17 | | 1 | 0.438 | | 1 | 2.7 |
| Pharynx | FADU | 0.0744 | | 1 | 0.0371 | | 1 | 2.0 |
| Rhabomyosarcoma | A-204 | N/A | | 0 | 0.0307 | | 1 | |
| Rhabomyosarcoma | CCL 166 | 0.0960 | | 1 | 0.00605 | | 1 | 16 |
| Rhabomyosarcoma | Hs 729 | 0.383 | | 1 | 0.0649 | | 1 | 5.9 |
| Rhabomyosarcoma | SJCRH30 | 0.082.3 | | 1 | 0.0434 | | 1 | 1.9 |
| Rhabomyosarcoma | TE 159.T | 0.147 | | 1 | 0.0196 | | 1 | 7.5 |
| Tongue | CAL 27 | 0.0568 | | 1 | 0.0383 | | 1 | 1.5 |
| Tongue | SCC-15 | 0.0170 | | 1 | 0.0149 | | 1 | 1.1 |
| Tongue | SCC-25 | 0.744 | | 1 | 0.276 | | 1 | 2.7 |
| Tongue | SCC-4 | 0.100 | | 1 | 0.0239 | | 1 | 4.2 |
| Tongue | SCC-9 | 0.181 | | 1 | 0.0755 | | 1 | 2.4 |
| Tongue | UPCI: SCC090 | 0.0901 | | 1 | 0.0260 | | 1 | 3.5 |
| Average fold | | | | | | | | 10.0 |

$0.005\%-4.88\times10^{-6}\%-3\times10^{-8}\%$ DMSO concentrations served as negative controls in the assay, as these dilutions correspond to the highest, median and lowest concentration of DMSO in the range of 18 drug concentrations tested)

$IC_{50}$ (μM) values correspond to log(inhibitor) vs. response (four parameters) and dose-response graphs were generated using GraphPad Prism8.

TABLE 4

Effect of compounds on cancer cells' viability as assessed by CellGlow Titer Assay calculated as $IC_{50}$ μM. Cells were treated with 18 (2-fold) dilutions (concentration range: 5-0.00003 μM) 24 h after plating and luminesence measurements were performed upon 3 Days of treatment. Combined results from experiments reported; 4 Jun. 19, 6 Jun. 19, 8 Jun. 19.

| | | | Cancer | | | | | |
|---|---|---|---|---|---|---|---|---|
| Cpd | KYN # | Cell Line | Bladder RT-112 | Kidney ACHN | Kidney A-498 | Pancreatic MIA PaCa-2 | Pancreatic CAPAN-1 | Lung NCI-H1299 |
| 1 | KYN-001 | Average | 0.027 | 0.496 | 0.109 | 0.888 | 1.46 | 0.0642 |
| | | STDev | 0.002.9 | | 0.0437 | 0.733 | | |
| | | n | 2 | 1 | 3 | 3 | 1 | 1 |
| 8 | KYN-119 | Average | 0.00409 | 0.0098 | 0.0103 | 0.2099 | 2.45 | 0.00856 |
| | | STDev | | 0.0004 | 0.0005 | | 3.17 | |
| | | n | 1 | 2 | 2 | 1 | 2 | |
| 2 | KYN-138 | Exp D | | | 0.117 | 0.119 | | |
| 4 | KYN-139 | Exp D | | | 0.361 | 0.381 | | |
| 5 | KYN-140 | Exp D | | | 0.667 | 0.755 | | |
| 6 | KYN-134 | Exp C | 0.862 | | 1.59 | | | |
| 7 | KYN-136 | Exp C | 0.17 | | 0.288 | | | |
| 9 | KYN-130 | Exp A | 0.022 | 0.609 | 0.019 | | N/A | |
| 10 | KYN-131 | Exp A | 0.0256 | 0.0409 | 0.0371 | | 2.237 | |
| 11 | KYN-132 | Exp B | 0.0392 | | 0.104 | 0.665 | | 0.193 |
| 12 | KYN-133 | Exp B | 0.347 | | 0.822 | N/A | | 0.827 |
| 25 | KYN-137 | Exp D | | | N/A | 7.74 | | |
| 26 | KYN-129 | Exp A | N/A | N/A | N/A | | N/A | |
| 46 | KYN-145 | Exp C | N/A | | N/A | | | |

TABLE 5A

Effect of compounds on cancer cells' viability as assessed by CellGlow Titer Assay. Comparative assessment of $IC_{50}$s (μM) of 1 [KYN-001] and 27 [KYN-149], and their analogues. Cells were treated with 11 dilutions (concentration range: 3-0.00001 μM) Combined results from seven experiments reported;

| Compound | Cell Line | Cancer Kidney A-498 | Cancer Pancreatic MIA PaCa-2 | Compound | Cell Line | Cancer Kidney A-498 | Cancer Pancreatic MIA PaCa-2 |
|---|---|---|---|---|---|---|---|
| 1 KYN-001 | Exp E | 0.0522 | 0.0645 | 2 KYN-138 | Exp E | 0.132 | 0.135 |
| | Exp F | 1.354 | 0.0697 | 3 KYN-153 | Exp G | 1.194 | 0.0275 |
| | Exp G | 1.596 | 0.0847 | 4 KYN-139 | Exp E | 0.545 | 0.52 |
| | Exp H | 1.271 | 0.0663 | 5 KYN-140 | Exp E | 0.754 | 0.746 |
| | Exp I | 1.612 | 0.1054 | 6 KYN-134 | Exp E | 1.09 | 1.28 |
| | Exp J | 1.557 | 0.0725 | 7 KYN-136 | Exp E | 0.199 | N/A |
| | Exp K | 0.5509 | 0.1012 | 9 KYN-130 | Exp E | 0.147 | 0.115 |
| | average | 1.1419 | 0.0806 | 10 KYN-131 | Exp E | 0.126 | 0.0812 |
| | STD Dev | 0.6052 | 0.0169 | 11 KYN-132 | Exp E | 0.202 | 0.207 |
| | | | | 12 KYN-133 | Exp E | 0.91 | 1.09 |
| | | | | 15 KYN-158 | Exp J | >3 | >3 |
| | | | | 16 KYN-157 | Exp I | >3 | >3 |
| 8 KYN-119 | Exp E | 0.0404 | 0.0408 | 17 KYN-120 | Exp E | 0.142 | 1.15 |
| | Exp F | 0.414 | 0.0152 | 18 KYN-156 | Exp I | ~3 | ~1 |
| | Exp G | 0.604 | 0.0243 | 19 KYN-160 | Exp J | >3 | 0.9213 |
| | Exp H | 0.37 | 0.0178 | 20 KYN-146 | Exp F | 0.714 | 0.0473 |
| | Exp I | 0.721 | 0.0345 | 21 KYN-154 | Exp H | ~3 | >3 |
| | average | 0.43 | 0.0255 | 22 KYN-124 | Exp E | N/A | N/A |
| | STD Dev | 0.26 | 0.0109 | 23 KYN-125 | Exp E | 0.234 | 0.352 |
| | | | | 24 KYN-141 | Exp E | N/A | N/A |
| | | | | 25 KYN-137 | Exp E | 15 | N/A |
| | | | | 26 KYN-129 | Exp E | N/A | N/A |
| 27 KYN-149 | Exp G | 0.932 | 0.0147 | 28 KYN-143 | Exp F | 0.181 | 0.000936 |
| | Exp J | 0.9844 | 0.01341 | 29 KYN-128 | Exp E | 0.27 | 0.491 |
| | Exp K | 0.2688 | 0.0168 | 30 KYN-142 | Exp E | 0.0479 | 0.0608 |
| | average | 0.7284 | 0.0150 | 31 KYN-151 | Exp G | >3 | 3.18 |
| | STD Dev | 0.3989 | 0.0017 | 32 KYN-148 | Exp G | 1.835 | 0.54 |
| | | | | 33 KYN-126 | Exp E | 0.988 | 2.04 |
| | | | | 34 KYN-147 | Exp F | 0.915 | 0.173 |
| | | | | 35 KYN-152 | Exp G | >3 | N/A |
| | | | | 36 KYN-150 | Exp G | N/A | N/A |
| | | | | 37 KYN-144 | Exp F | N/A | >3 |
| | | | | 38 KYN-155 | Exp H | ~0.1 | >3 |
| | | | | 40 KYN-159 | Exp J | 2.926 | >3 |
| | | | | 41 KYN-161 | Exp J | N/A | >3 |
| | | | | 42 KYN-162 | Exp K | ~3 | N/A |
| | | | | 43 KYN-163 | Exp K | ~3 | ~3 |
| | | | | 44 KYN-164 | Exp K | 2.042 | 1.157 |
| | | | | 46 KYN-145 | Exp E | N/A | N/A |

TABLE 5B

Effect of compounds on cancer cells' viability as assessed by CellGlow Titer Assay. Comparative assessment of $IC_{50}$s (μM) of 1 [KYN-001] and 27 [KYN-149], and their analogues. Cells were treated with 11 dilutions (concentration range: 3-0.00001 μM) Combined results from three experiments reported;

| Compound | Cancer Cell Line Exprmnt | Pancreatic MIA PaCa-2 CRL-1420 | Brain U-87 MG HTB-14 | Breast 4T1 |
|---|---|---|---|---|
| 1 KYN-001 | Exp N | 0.07244 | 0.1867 | 0.1171 |
| 27 KYN-149 | Exp N | 0.01474 | 0.03007 | 0.02923 |
| 1 KYN-001 | Exp L | 0.1432 | 0.2812 | |
| 1 KYN-001 | Exp M | 0.7713 | 1.603 | |
| 27 KYN-149 | Exp L | 0.002868 | 0.00986 | |
| 27 KYN-149 | Exp M | 0.01052 | 0.02182 | |
| 39 KYN-165 | Exp L | >3 | ~3 | |
| 47 KYN-167 | Exp M | N/A | N/A | |

TABLE 5B-continued

Effect of compounds on cancer cells' viability as assessed by CellGlow Titer Assay. Comparative assessment of $IC_{50}$s (μM) of 1 [KYN-001] and 27 [KYN-149], and their analogues. Cells were treated with 11 dilutions (concentration range: 3-0.00001 μM) Combined results from three experiments reported;

| Compound | Cancer Cell Line Exprmnt | Pancreatic MIA PaCa-2 CRL-1420 | Brain U-87 MG HTB-14 | Breast 4T1 |
|---|---|---|---|---|
| 48 KYN-168 | Exp M | 0.4856 | 0.555 | |
| 49 KYN-169 | Exp M | 0.5312 | 1.405 | |
| 51 KYN-166 | Exp L | N/A | ~3 | |

TABLE 6

Effect of compounds on cancer cells' viability as assessed by CellGlow Titer Assay. Comparative assessment of $IC_{50}$s (μM) of Compound 1 [KYN-001] and Compound 8 [KYN-119], and their analogues. Cells were treated with 11 dilutions (concentration range: 3-0.00001 μM);

| | | Compound/$IC_{50}$ (μM) | | | | |
|---|---|---|---|---|---|---|
| Cancer Type | Cancer Cell Line | 1 KYN-001 | 8 KYN-119 | 20 KYN-146 | 27 KYN-149 | 28 KYN-143 |
| SARCOMAS | | | | | | |
| Osteosarcoma | MG-63/CRL-1427 | 0.0441 | 0.0182 | 0.0313 | 0.0825 | 0.0048 |
| Osteosarcoma | Saos-2/HTB-85 | 0.173 | 0.0791 | 0.1291 | 0.0424 | 0.0233 |
| Muscle Ewing's Sarcoma | A-673/CRL-1598 | 0.471 | 0.1573 | 0.3116 | 0.2291 | 0.1117 |
| Bone Ewing's Sarcoma | RD-ES/HTB-166 | 0.3098 | 0.1629 | 0.3379 | 0.133 | 0.0651 |
| Muscle Rhabdomyosarcoma | A-204/HTB-82 | 0.1987 | 0.0678 | 0.131 | 0.0524 | 0.0253 |
| Rhabdomyosarcoma | TE 159.T/CRL-7752 | N/A | N/A | N/A | 0.031 | N/A |
| HEAD and NECK CANCERS | | | | | | |
| squamous cell carcinoma - hypopharynx | UPCI: SCC152/CRL-3240 | 0.1404 | 0.0549 | 0.1491 | 0.0366 | 0.0205 |
| squamous cell carcinoma - base of the tongue | UPCI: SCC090/CRL-3239 | 0.0009 | 0.0005 | 0.0478 | 0.02 | 0.0561 |
| squamous cell carcinoma - pharynx | Fadu/HTB-43 | 0.1386 | 0.0541 | 0.0801 | 0.0286 | 0.0118 |
| pharyngeal carcinoma | Detroit 562/CCL-138 | 0.131 | 0.0766 | 0.1224 | 0.0203 | 0.0114 |
| squamous cell carcinoma - tongue | CAL 27/CRL-2095 | 0.0894 | 0.0309 | 0.0409 | 0.015 | 0.005 |
| squamous cell carcinoma - tongue | SCC-4/CRL-1624 | 0.0395 | 0.0232 | 0.0313 | 0.0114 | 0.0031 |
| NEUROBLASTOMAS | | | | | | |
| | CHP-212/CRL-2273 | 0.0281 | 0.0098 | 0.0261 | 0.0057 | 0.003 |
| | BE(2)-C/CRL-2268 | 0.0671 | 0.0259 | 0.0548 | 0.0136 | 0.0112 |
| | SK-N-DZ/CRL-2149 | 0.132 | 0.0501 | 0.1401 | 0.0326 | 0.0164 |
| | SK-N-FI/CRL-2142 | 0.1157 | 0.0266 | 0.0485 | 0.0157 | 0.0097 |
| PANCREATIC CANCER | | | | | | |
| | MIA PaCa-2/CRL-1420 | 0.1089 | 0.0234 | 0.0549 | 0.0214 | 0.0129 |
| | PANC-1/CRL-1469 | 0.1101 | 0.0314 | 0.0416 | 0.0288 | 0.0178 |
| | BxPC-3/CRL-1687 | 0.9436 | 0.3873 | 1.412 | 0.3021 | 0.1747 |
| | Capan-1/HTB-79 | 2.67 | 2.319 | 2.237 | 0.7918 | 0.7348 |
| | HPAF-II/CRL-1997 | 0.417 | 0.242 | 0.6378 | 0.1019 | 0.1106 |
| LUNG CANCER | | | | | | |
| | NCI-H1437/CRL-5872 | 0.1428 | 0.0327 | 0.0732 | 0.0322 | 0.0259 |
| | NCI-H2126/CCL-256 | 0.1055 | 0.0331 | 0.097 | 0.031 | 0.0107 |
| | NCI-H1563/CRL-5875 | 0.1838 | 0.0545 | 0.0741 | 0.0598 | 0.0159 |
| | NCI-H1573/CRL-5877 | 0.2728 | 0.0335 | 0.0558 | 0.048 | 0.0212 |
| LIVER CANCER | | | | | | |
| | Hep G2/HB-8065 | 0.5773 | 0.296 | 0.2345 | 0.2514 | 0.0991 |
| | SNU-398/CRL-2233 | 0.2077 | 0.0746 | 0.1105 | 0.054 | 0.0327 |
| | SNU-423/CRL-2238 | 0.2033 | 0.0797 | 0.1194 | 0.0535 | 0.0275 |
| | SNU-449/CRL-2234 | 0.0818 | 0.0325 | 0.064 | 0.0151 | 0.0102 |
| KIDNEY CANCER | | | | | | |
| | 769-P/CRL-1933 | 0.3627 | 0.109 | 0.1737 | 0.1101 | 0.0401 |
| | A-498/HTB-44 | 1.073 | 0.4012 | 0.6204 | 0.6418 | 0.198 |
| | ACHN/CRL-1611 | 0.2412 | 0.0757 | 0.0834 | 0.0267 | 0.0188 |
| | Caki-1/HTB-46 | 0.12 | 0.0279 | 0.0963 | 0.0154 | 0.0072 |
| | Caki-2/HTB-47 | 0.4263 | 0.5236 | 0.3023 | 1.553 | 0.0698 |
| COLON CANCER | | | | | | |
| | SW480/CCL-228 | 0.2246 | 0.1086 | 0.1577 | 0.0896 | 0.03 |
| | SW620/CCL-227 | 0.1209 | 0.0355 | 0.1027 | 0.0317 | 0.018 |
| | HT-29/HTB-38 | 1.563 | 0.9394 | 1.992 | 0.4315 | 0.3248 |
| BLADDER CANCER | | | | | | |
| | UM-UC-3/CRL-1749 | 0.3327 | 0.0548 | 0.1258 | 0.0302 | 0.0213 |
| | RT4/HTB-2 | 1.384 | 0.9682 | 2.012 | 0.4529 | 0.463 |
| | T24/HTB-4 | 0.1823 | 0.0611 | 0.1113 | 0.0325 | 0.0221 |
| | HT-1197/CRL-1473 | 0.1081 | 0.0485 | 0.0617 | 0.0171 | 0.0122 |
| | SCaBER/HTB-3 | 0.065 | 0.0273 | 0.0537 | 0.0109 | 0.006 |

Day 3 upon treatment of MIA PaCa_2 pancreatic cancer cells, 24 h after plating (11 dilutions), as assessed by CellTiter Glow Assay.

$IC_{50}$ (μM) values correspond to log(inhibitor) vs. response (four parameters) and dose-response graphs were generated using GraphPad Prism8.

Compounds 23, 29 and 33 were prepared to give compounds with improved bioavailability pharmaco-kinetic properties (more optimal log P and water solubility) compared with the lead anticancer compounds 1 and 8.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

Evaluation of Compound 1 to Treat Skin Diseases

Aim

To evaluate compounds 1, 8, 20, 27, 28, 31 and 35 with skin disease relevant in vitro assays. Evaluation was conducted by LEO Pharma Open Innovation, USA.

Specific Objectives

1. Determination of inhibition of CCL2 release from IL-4, IL-13, IL-22 and IFN-γ-stimulated primary human keratinocytes [assay number 1280] and determination of the effect on cell viability [assay number 1243].
2. Determination of inhibition of IL-8 release from IL-17A and TNFα-induced primary human keratinocytes [assay number 1250] and determination of the effect on cell viability [assay number 1244].
3. Determination of inhibition of IL-17A secretion from human PBMC stimulated with antiCD3/antiCD28-coated beads [assay number 1321] and determination of the effect on cell viability [assay number 1322].
4. Determination of inhibition of IL-4 and IL-2 secretion from human CD4-positive T-cells stimulated with antiCD2/antiCD3/antiCD28-coated beads [assay number 1297, 1298] and determination of the effect on cell viability [assay number 1299].

Disease Relevance Summary

1. Compounds which inhibit keratinocyte CCL2 secretion may be expected to have efficacy in atopic dermatitis.
2. Compounds which inhibit keratinocyte IL-8 secretion may be expected to have efficacy in psoriasis.
3. Compounds which inhibit IL-17A secretion may be expected to have efficacy in psoriasis.
4. Compounds which inhibit IL-4 secretion may be expected to have efficacy in atopic dermatitis. Compounds which also inhibit IL-2 secretion have a broader immunosuppressive effect since IL-2 is an autocrine growth factor for T-cells.

Results

Compound 28 [KYN-143] Example Concentration Effect Plots:

1. CCL2 Release

Figure 9:
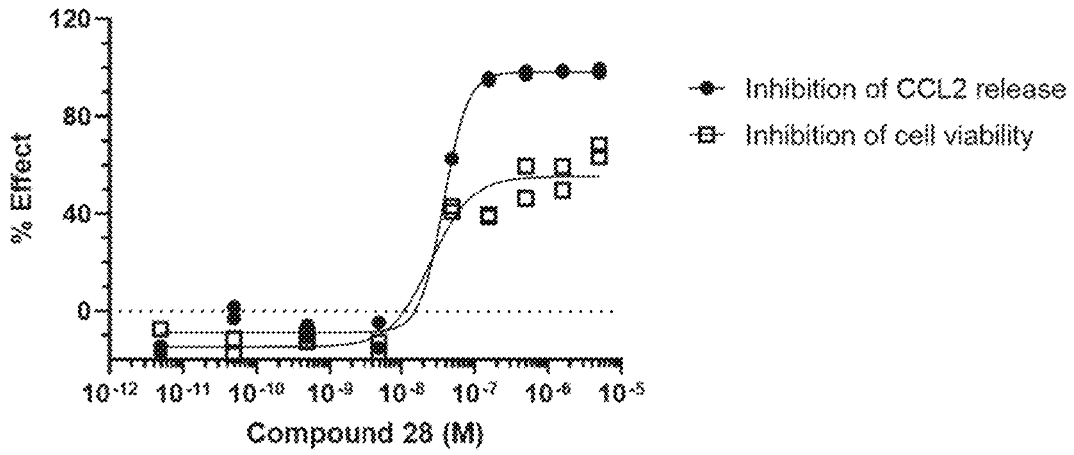
FIG. 9 shows the % effect of varying concentrations of compound 28 on inhibition of CCL2 release and inhibition of cell viability.

FIG. 9 shows the % effect of varying concentrations of compound 28 on inhibition of CCL2 release and inhibition of cell viability.

Discussion: Compound 28 showed medium potency reduction of CCL2 release with a similar reduction of cell viability. Without being bound by theory, the inventors believe that since plateaus at a partial level of cell viability from maximum are probably not due to cytotoxicity, but instead possibly part of the molecule/target MoA.

2. IL-8 Release

Figure 10:
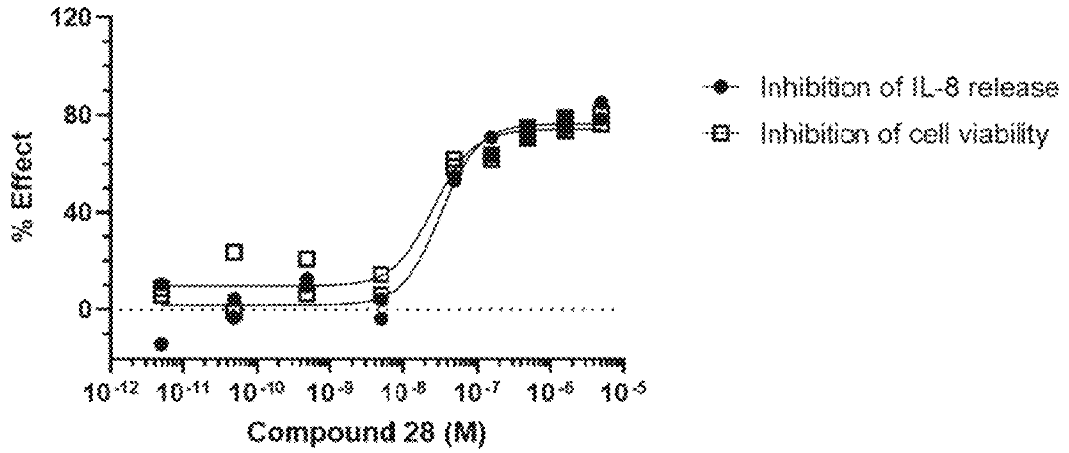
FIG. 10 shows the % effect of varying concentrations of compound 28 on inhibition of IL-8 release and inhibition of cell viability.

FIG. 10 shows the % effect of varying concentrations of compound 28 on inhibition of IL-8 release and inhibition of cell viability.

Discussion: Compound 28 showed medium potency reduction of IL-8 release, similar to that obtained for reduction of CCL2 release. However, compound 28, displayed similar effect in both reduction of IL-8 and cell viability in this assay. Without being bound by theory, the inventors believe this possibly indicates a keratinocyte-related mechanism, but with lesser efficacy on IL-8 release, than CCL2 as described above and shown in FIG. 9.

3. IL-17A Release

Figure 11:
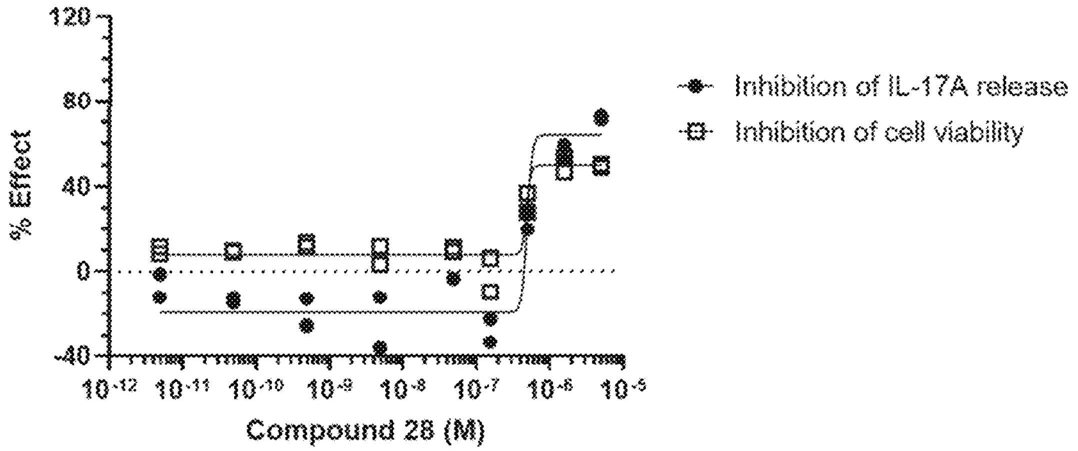
FIG. 11 shows the % effect of varying concentrations of compound 28 for inhibition of IL-17A release and inhibition of cell viability.

FIG. 11 shows the % effect of varying concentrations of compound 28 for inhibition of IL-17A release and inhibition of cell viability.

Discussion: Compound 28 showed low potency reduction of IL-17A release.

4. II-2 and IL-4 Release

Figure 12:
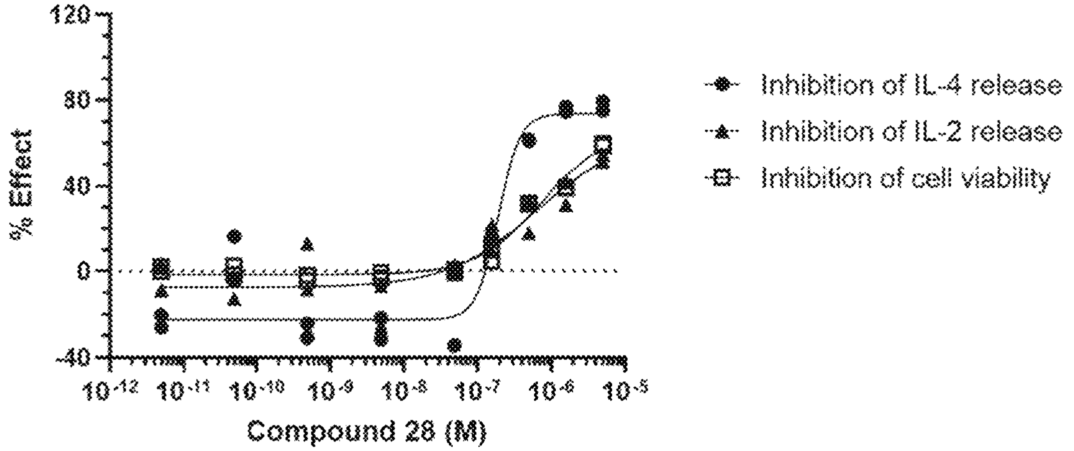
FIG. 12 shows the % effect of varying concentrations of compound 28 for inhibition of IL-2 and IL-4 release and inhibition of cell viability.
Figure 13A:
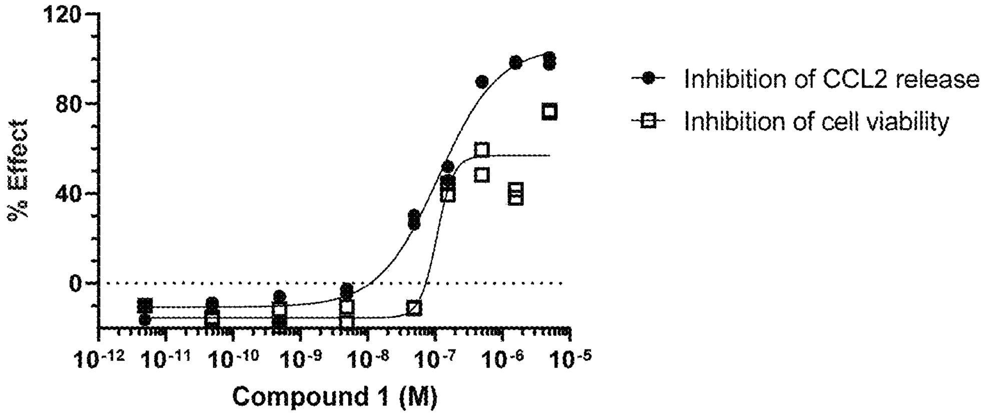
FIG. 13 shows Concentration-response graphs for compounds 1, 8, 20, 27, 28, 31 and 35.
Figure 13A:
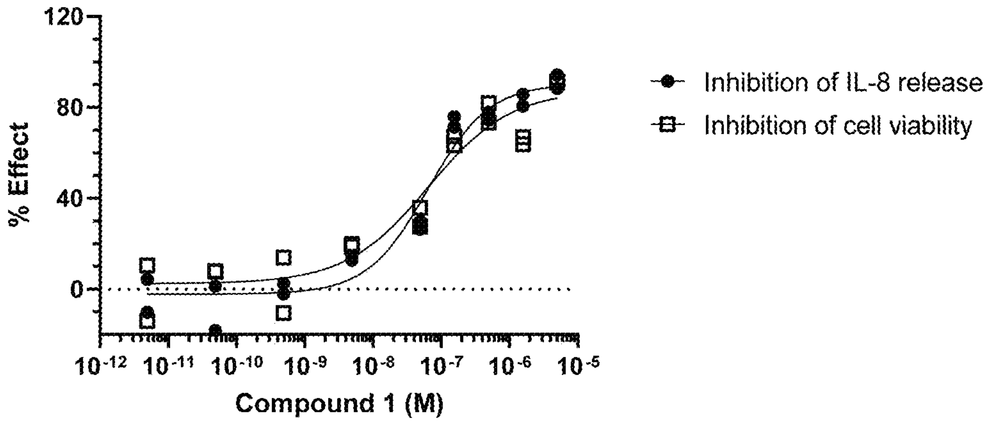
Figure 13B:
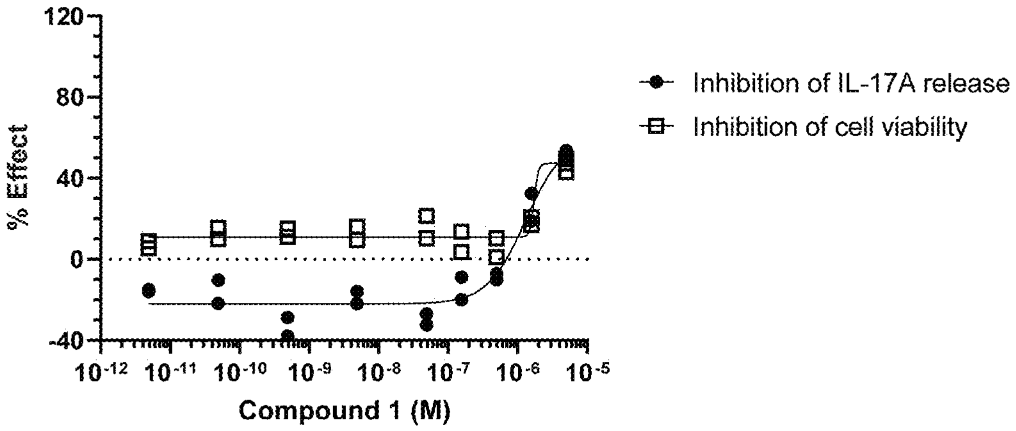
Figure 13B:
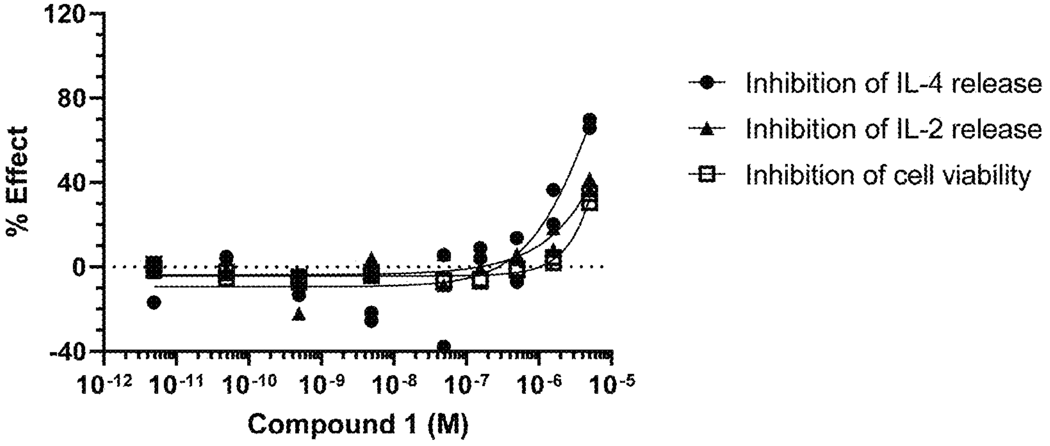
Figure 13C:
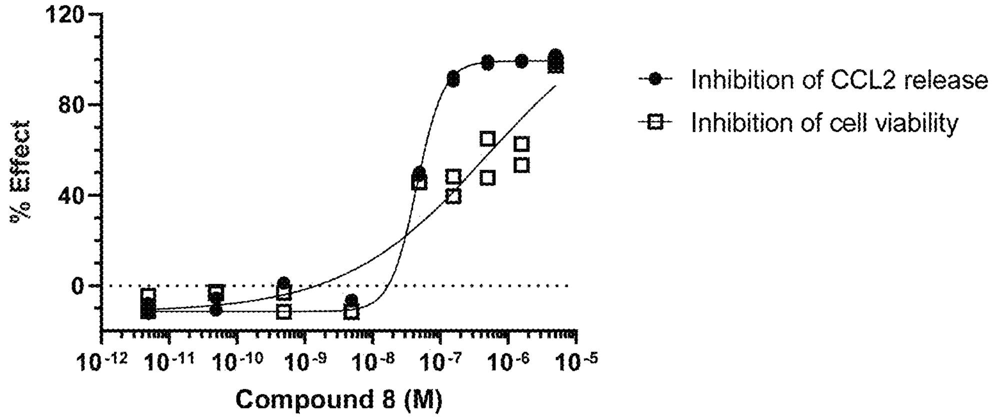
Figure 13C:
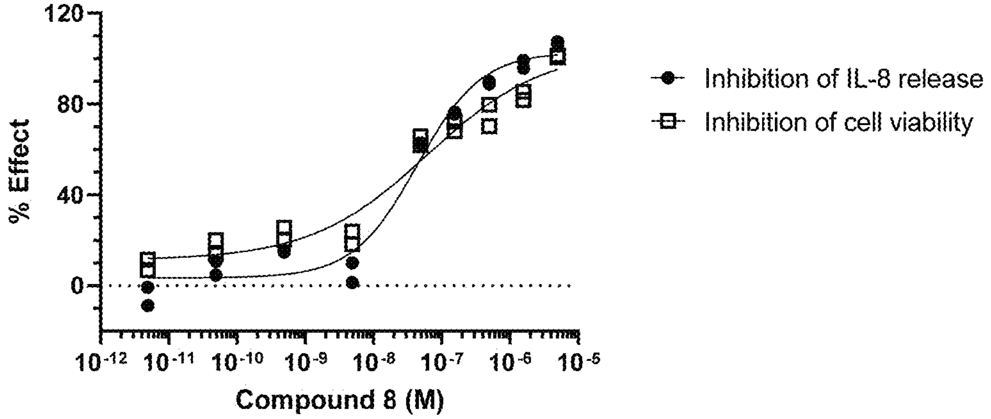
Figure 13D:
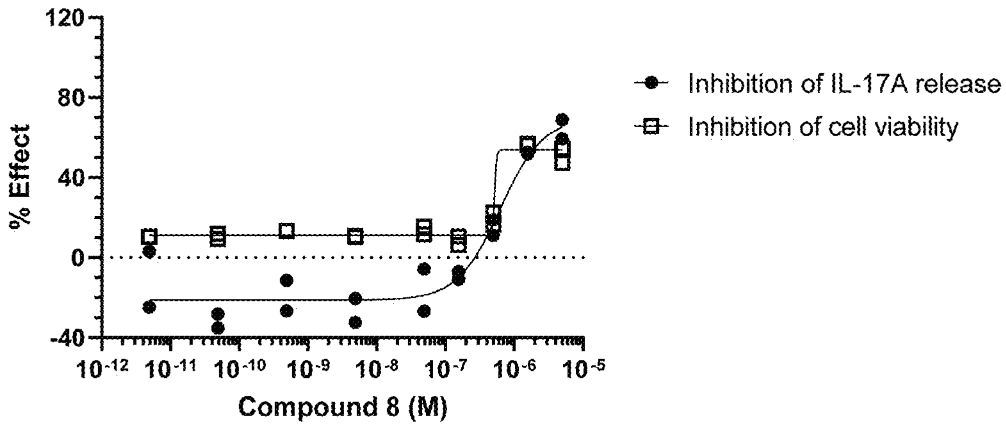
Figure 13D:
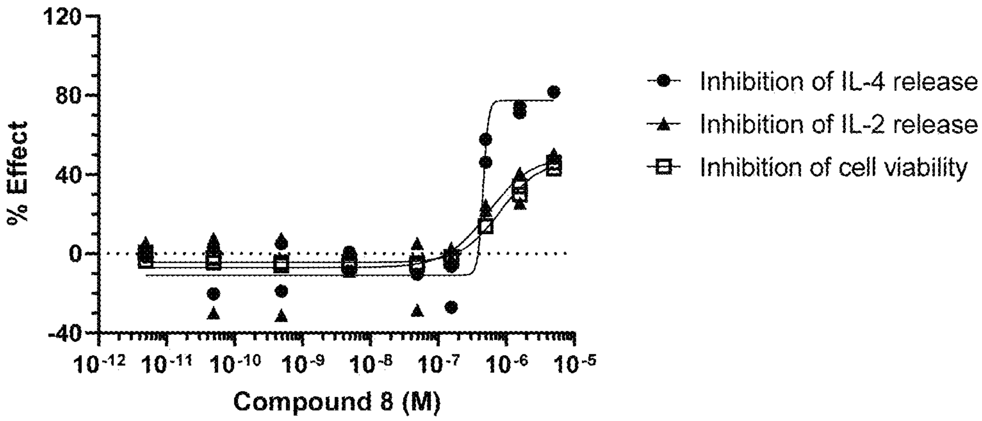
Figure 13E:
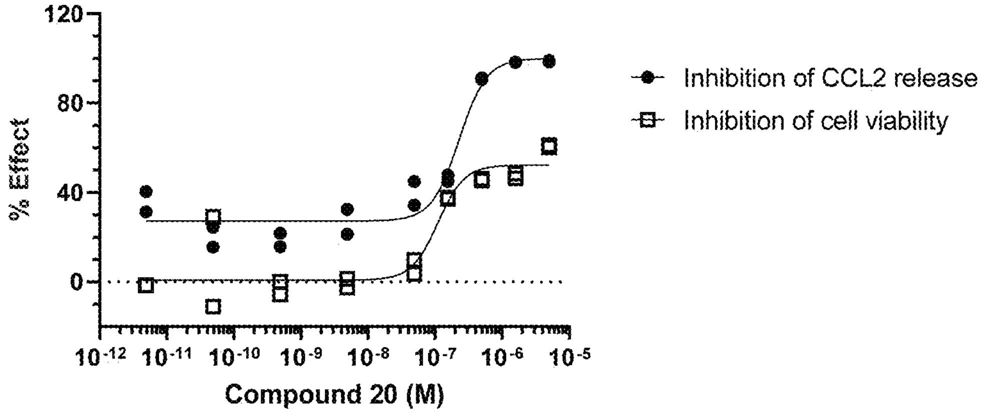
Figure 13E:
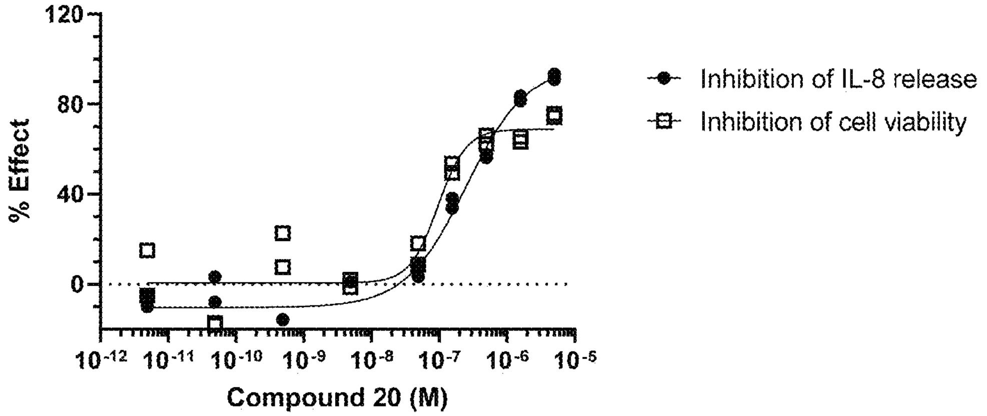
Figure 13F:
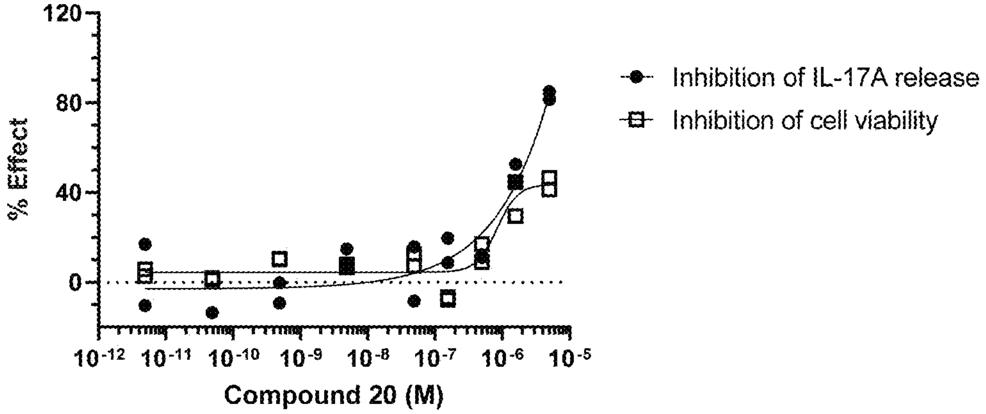
Figure 13F:
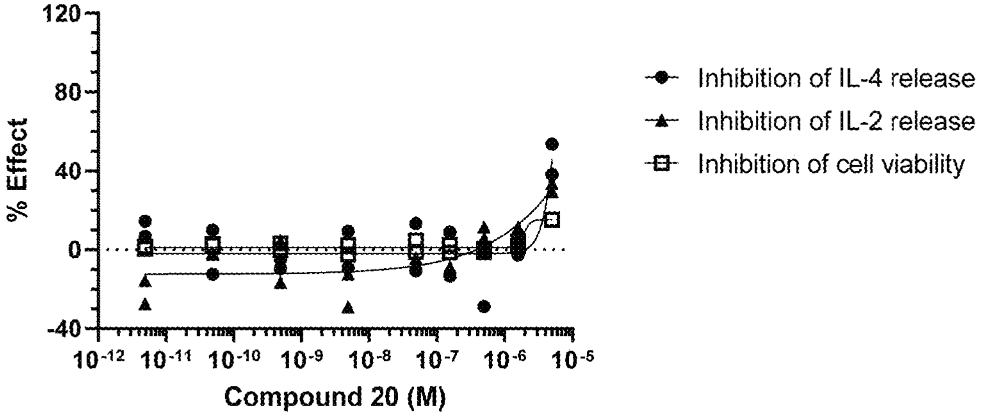
Figure 13G:
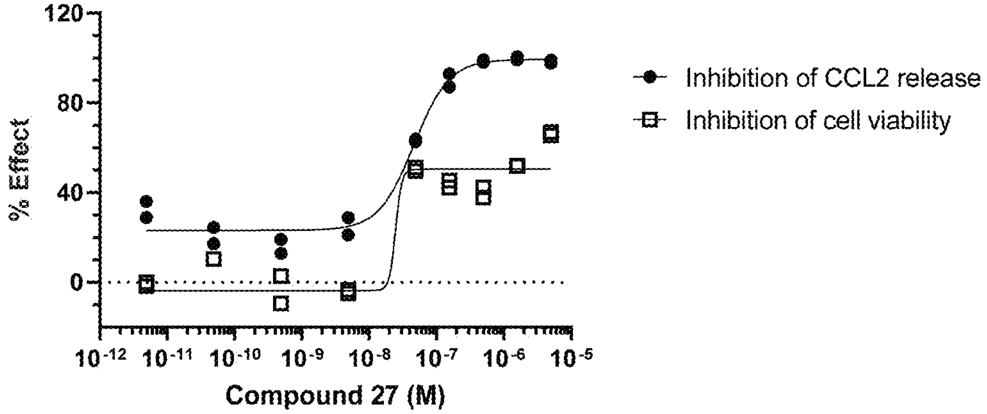
Figure 13G:
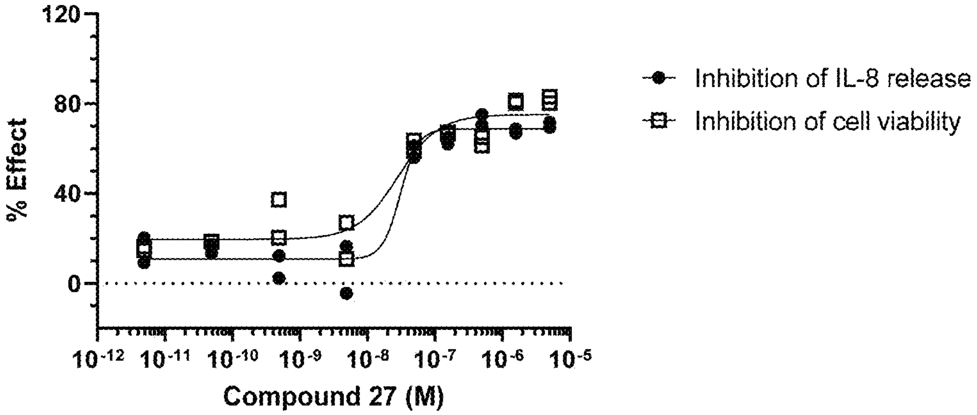
Figure 13H:
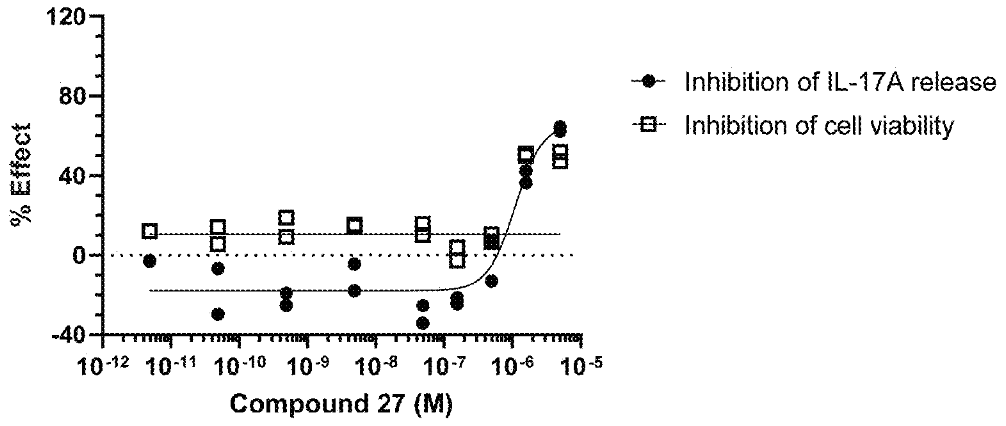
Figure 13H:
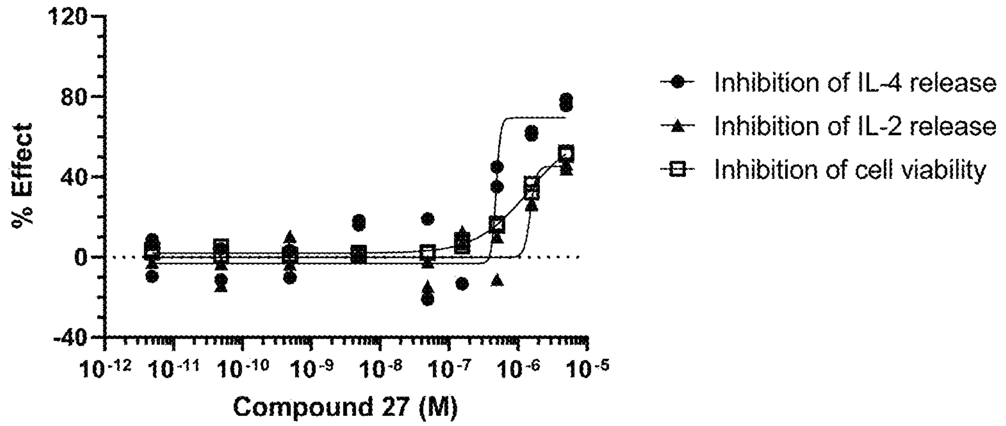
Figure 13I:
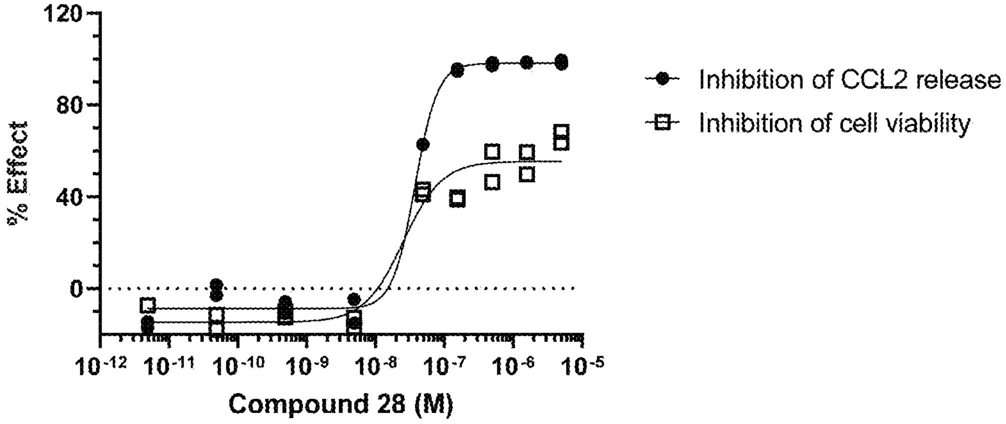
Figure 13I:
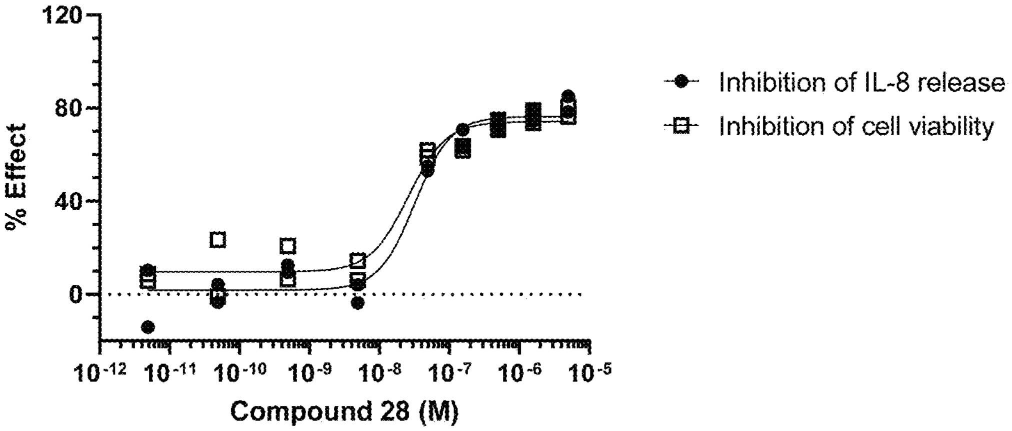
Figure 13J:
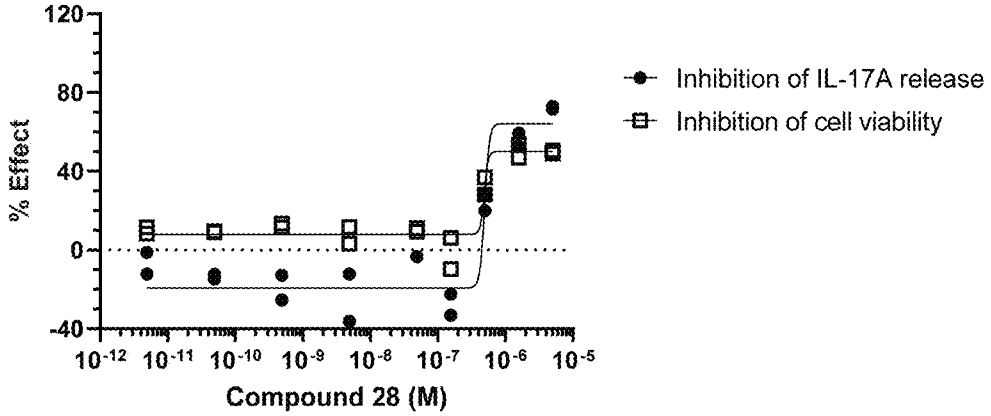
Figure 13J:
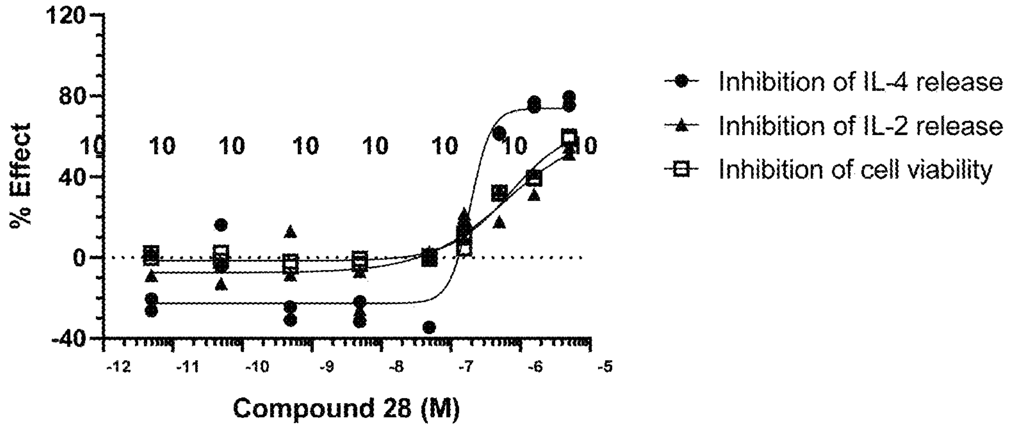
Figure 13K:
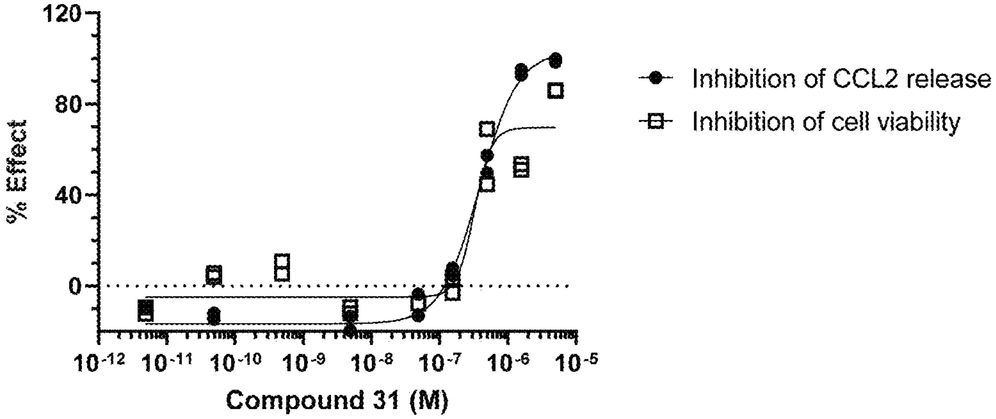
Figure 13K:
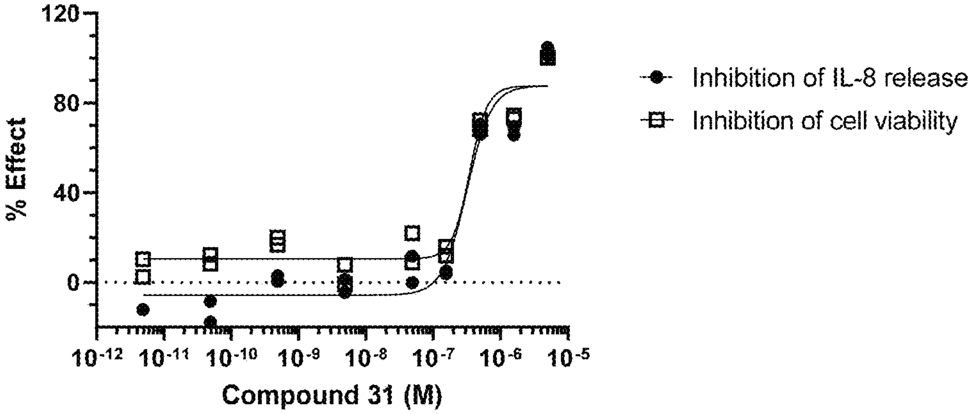
Figure 13L:
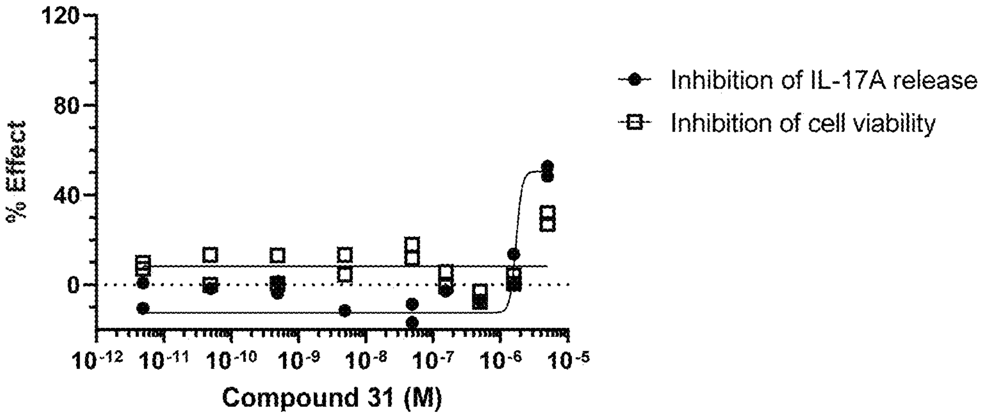
Figure 13L:
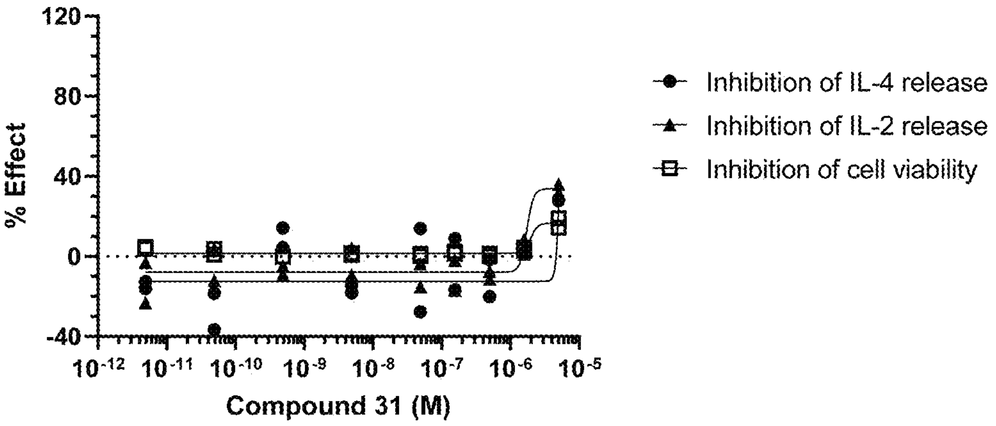
Figure 13M:
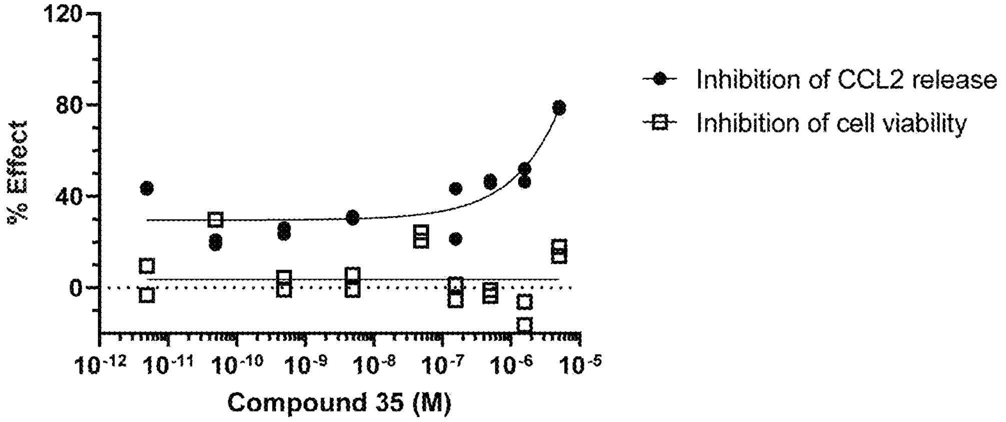
Figure 13M:
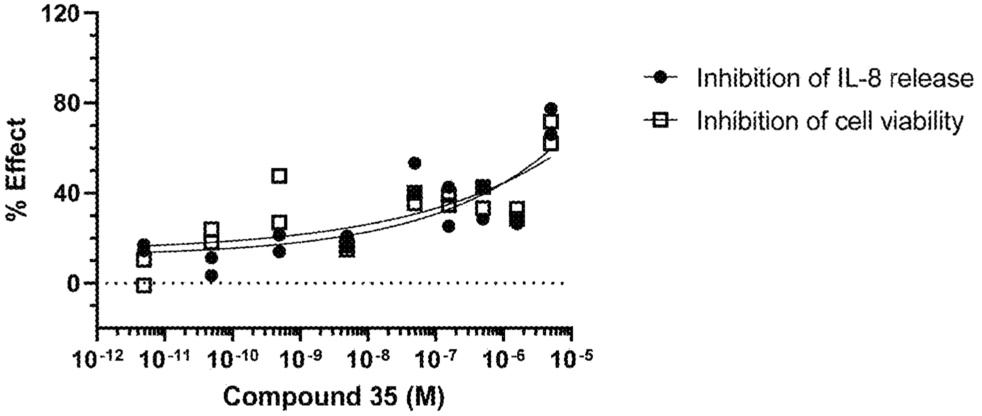
Figure 13N:
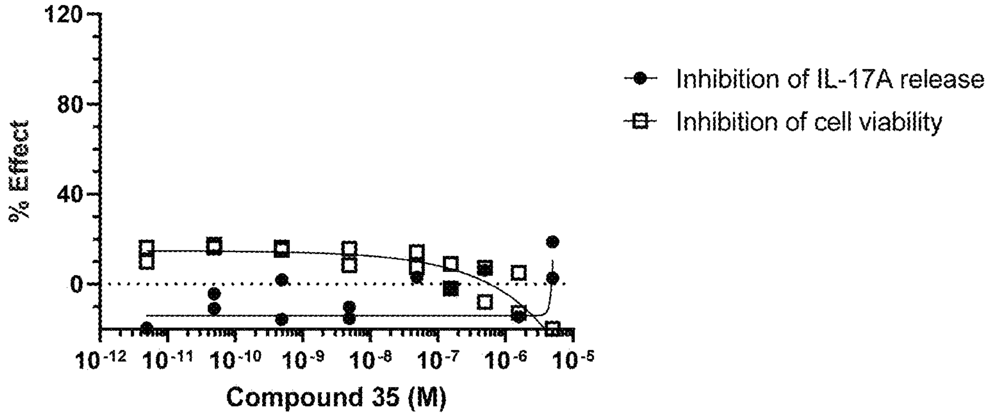
Figure 13N:
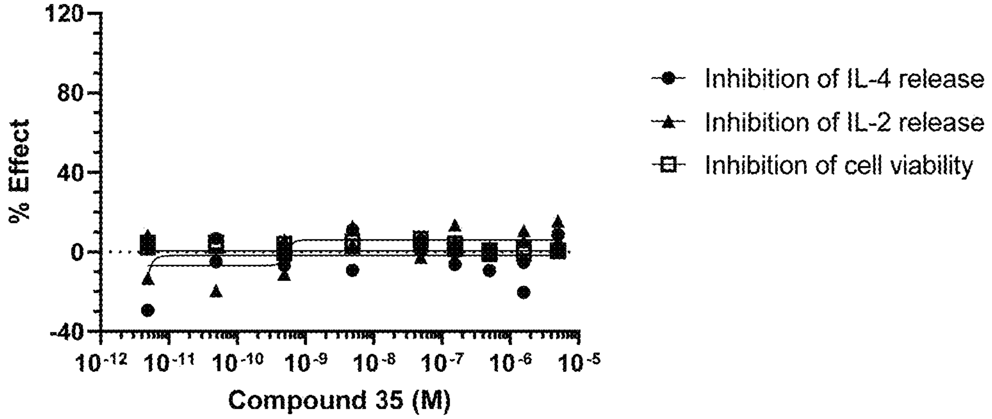
Figure 14A:
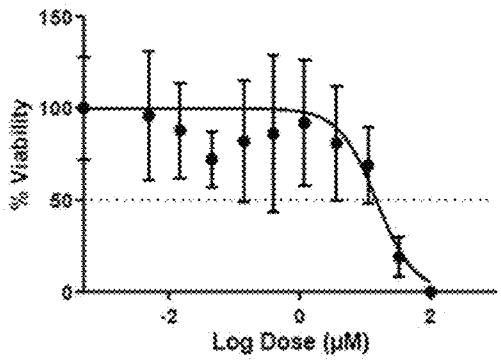
Figure 14A:
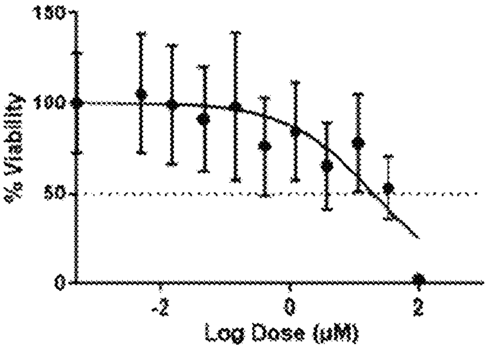
Figure 14A:
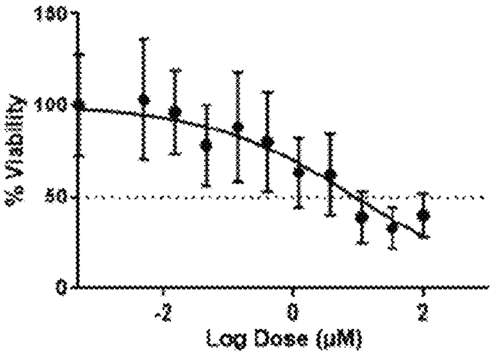
Figure 14A:
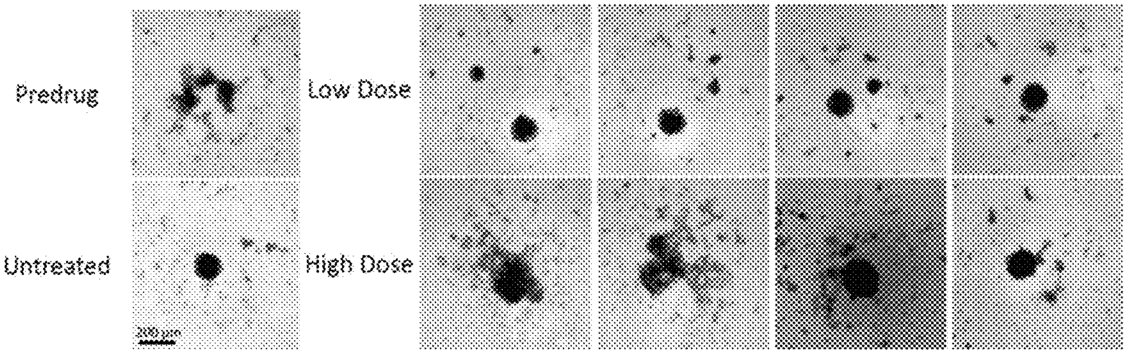
Figure 14B:
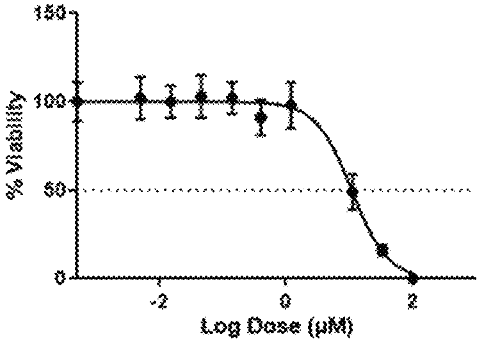
Figure 14B:
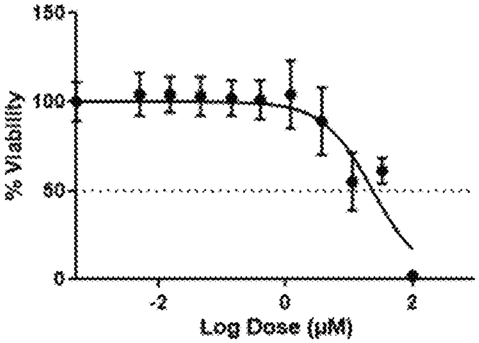
Figure 14B:
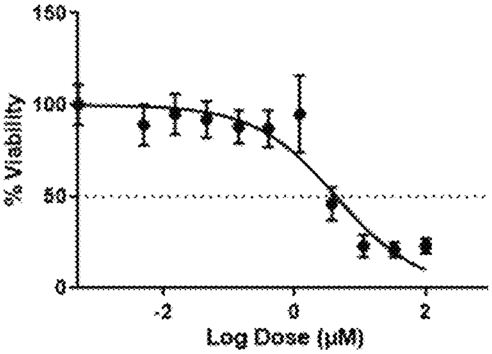
Figure 14B:
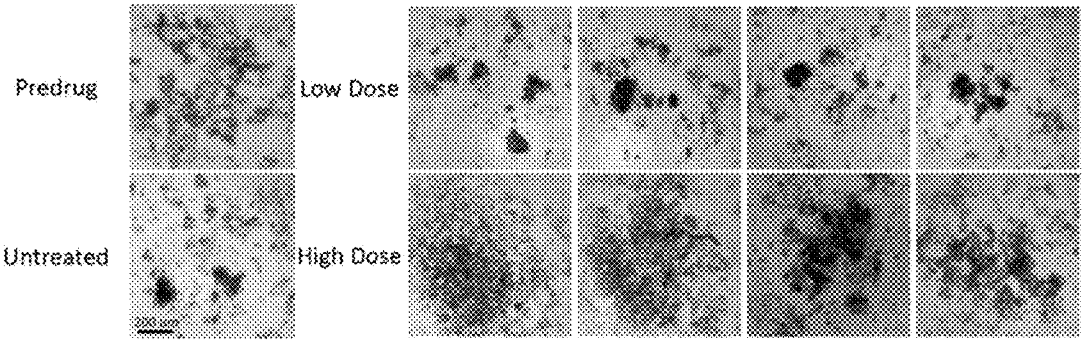
Figure 14C:
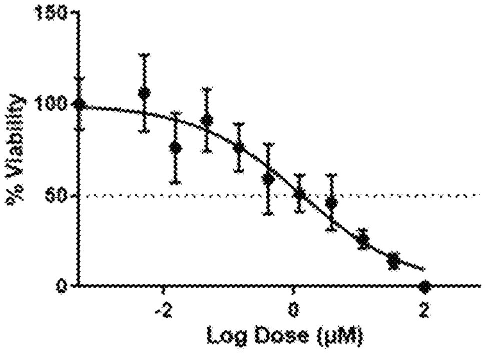
Figure 14C:
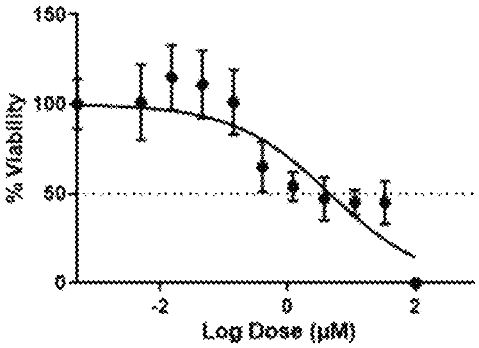
Figure 14C:
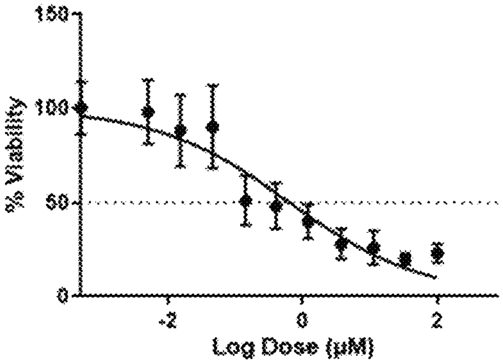
Figure 14C:
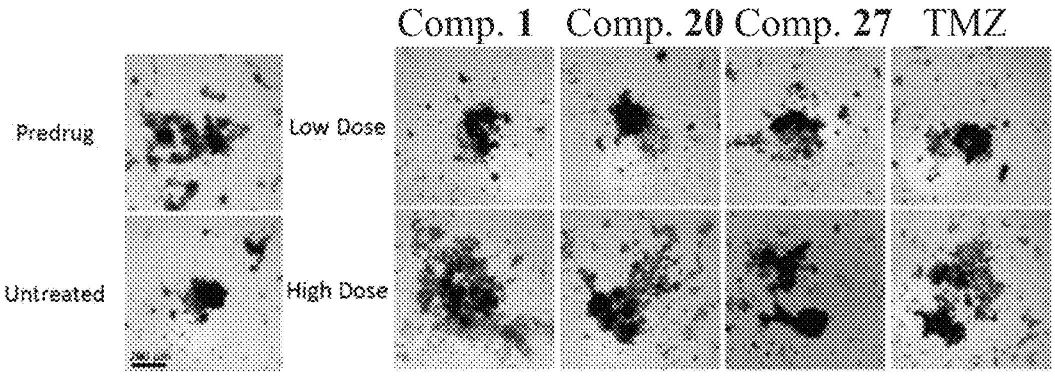

FIG. 12 shows the % effect of varying concentrations of compound 28 for inhibition of IL-2 and IL-4 release and inhibition of cell viability.

Discussion: Compound 28 showed medium potency effect specifically on IL-4 release and a lower potency effect on IL-2 and cell proliferation. Without being bound by theory, the inventors believe that there seem to be a specific effect on IL-4 release in the T cells.

FIG. 13 shows Concentration-response graphs for compounds 1, 8, 20, 27, 28, 31 and 35.

Discussion Compounds 1 (KYN-001), 8 (KYN-119), 20 (KYN-146), 27 (KYN-149), 28 (KYN-143), 31 (KYN-151) and 35 (KYN-152) share a similar profile where a more pronounced effect with lower $EC_{50}$ values can be noticed in the CCL2-release assay, followed by IL-8 and IL-4; less than 100% reduction of cell viability except compound 8 and compound 31 (Table 7, FIG. 13). A general cytotoxic effect is common in tested molecules and may reach 100% but this is not the case for these compounds. This could indicate a specific mode-of-action that is affecting cell viability without being cytotoxic. Furthermore, there seem to be a specific effect on IL-4 release in the T cells, but with less potency. Compounds 28 (KYN-143) and 27 (KYN-149) stand out as the more potent molecules in these assays, closely followed by 8 (KYN-119) (Table 7). Compound 28 (KYN-143) inhibited keratinocyte CCL2 secretion at $EC_{50}$ 40 nM with 100% maximum efficacy and cell viability at $EC_{50}$ 124 nM with 68% maximum reduction of cell viability. Compounds 27 [KYN-149] inhibited keratinocyte CCL2 secretion at $EC_{50}$ 32 nM with 100% maximum efficacy and cell viability at $EC_{50}$ 41 nM with 67% maximum reduction of cell viability.

Compound 28 [KYN-143] inhibited IL-8 release from IL-17A and TNFα-induced primary human keratinocytes at $EC_{50}$ 44 nM with 85% maximum efficacy and cell viability at $EC_{50}$ 35 nM with 81% maximum reduction of cell viability. Compounds 27 [KYN-149] inhibited IL-8 release from IL-17A and TNFα-induced primary human keratinocytes at $EC_{50}$ 46 nM with 75% maximum efficacy and cell viability at $EC_{50}$ 32 nM with 83% maximum reduction of cell viability.

Compound 28 [KYN-143] inhibited IL-17A secretion from human PBMC stimulated with antiCD3/antiCD28-coated beads at $EC_{50}$ 526 nM with 73% maximum efficacy and cell viability at $EC_{50}$ 659 nM with 54% maximum reduction of cell viability.

Compounds 27 [KYN-149] and other candidate compounds were significantly less effective.

For inhibition of IL-2 secretion from human CD4-positive T-cells stimulated with antiCD2/antiCD3/antiCD28-coated beads, none of the candidate compounds were effective in this assay.

Compound 28 [KYN-143] inhibited of IL-4 secretion from human CD4-positive T-cells stimulated with antiCD2/antiCD3/antiCD28-coated beads at $EC_{50}$ 278 nM with 80% maximum efficacy and cell viability at $EC_{50}$ 2360 nM with 60% maximum reduction of cell viability. Compounds 27 [KYN-149] inhibited of IL-4 secretion from human CD4-positive T-cells stimulated with antiCD2/antiCD3/antiCD28-coated beads at $EC_{50}$ 507 nM with 79% maximum efficacy and cell viability at $EC_{50}$ 4350 nM with 52% maximum reduction of cell viability.

Overall, the results indicate that compounds 28 [KYN-143] and 27 [KYN-149] are lead candidates for effective treatment of atopic dermatitis and psoriasis.

TABLE 7

Compounds 1, 8, 20, 27, 28, 31 and 35 assay results for inhibition of release/secretion of CCl2, IL-8, IL-17, IL-2 and IL-4 from cells and effects of the compounds on the viability of the cells.

| | | CCL2 | | | |
|---|---|---|---|---|---|
| | Name | nM Abs $EC_{50}$: CCL2 (1280) | % Max Eff.: CCL2 (1280) | nM Abs $EC_{50}$: Viab (1243) | % Max Eff.: Viab (1243) |
| 1 | KYN-001 | 123 | 101 | 202 | 77 |
| 8 | KYN-119 | 50 | 102 | 235 | 99 |
| 20 | KYN-146 | 108 | 99 | 442 | 61 |
| 27 | KYN-149 | 32 | 100 | 41 | 67 |
| 28 | KYN-143 | 40 | 100 | 124 | 68 |
| 31 | KYN-151 | 445 | 100 | 431 | 86 |
| 35 | KYN-152 | 1130 | 79 | 5000 | 30 |

| | | IL-8 | | | |
|---|---|---|---|---|---|
| | Name | nM Abs $EC_{50}$: IL-8 (1250) | % Max Eff.: IL-8 (1250) | nM Abs $EC_{50}$: Viab (1244) | % Max Eff.: Viab (1244) |
| 1 | KYN-001 | 80 | 94 | 90 | 92 |
| 8 | KYN-119 | 37 | 107 | 32 | 101 |
| 20 | KYN-146 | 321 | 93 | 221 | 76 |
| 27 | KYN-149 | 46 | 75 | 32 | 83 |
| 28 | KYN-143 | 44 | 85 | 35 | 81 |
| 31 | KYN-151 | 364 | 105 | 416 | 100 |
| 35 | KYN-152 | 2950 | 77 | 5000 | 72 |

| | | IL-17 | | | |
|---|---|---|---|---|---|
| | Name | nM Abs $EC_{50}$: IL-17 (1321) | % Max Eff.: IL-17 (1321) | nM Abs $EC_{50}$: Viab (1322) | % Max Eff.: Viab (1322) |
| 1 | KYN-001 | 4430 | 54 | 5000 | 50 |
| 8 | KYN-119 | 1550 | 69 | 582 | 57 |
| 20 | KYN-146 | 1650 | 85 | 5000 | 47 |
| 27 | KYN-149 | 2120 | 65 | 5000 | 52 |
| 28 | KYN-143 | 526 | 73 | 659 | 54 |
| 31 | KYN-151 | 4870 | 53 | 5000 | 32 |
| 35 | KYN-152 | 5000 | 19 | 5000 | 18 |

| | | IL-2 | | IL-4 | | | |
|---|---|---|---|---|---|---|---|
| | Name | nM Abs $EC_{50}$: IL-2 (1297) | % Max Eff.: IL-2 (1297) | nM Abs $EC_{50}$: IL-4 (1298) | % Max Eff.: IL-4 (1298) | nM Abs $EC_{50}$: Viab (1299) | % Max Eff.: Viab (1299) |
| 1 | KYN-001 | 5000 | 42 | 2930 | 70 | 5000 | 35 |
| 8 | KYN-119 | 5000 | 51 | 503 | 82 | 5000 | 46 |
| 20 | KYN-146 | 5000 | 34 | 5000 | 54 | 5000 | 15 |
| 27 | KYN-149 | 5000 | 46 | 507 | 79 | 4350 | 52 |
| 28 | KYN-143 | 4260 | 55 | 278 | 80 | 2360 | 60 |
| 31 | KYN-151 | 5000 | 36 | 5000 | 29 | 5000 | 19 |
| 35 | KYN-152 | 5000 | 16 | 5000 | 11 | 5000 | 7 |

Abs $EC_{50}$: Half maximal effective concentration (nM) relative to control
Max Eff.: Highest effect of molecule as a percentage of control maximum effect Methods 1. Keratinocyte CCL2 Release Inhibition of CCL2 release from IL-4, IL-13, IL-22 and IFN-γ-stimulated primary human keratinocytes LEO Pharma Open Innovation assay number 1280

Disease Relevance

The inflammatory skin disease atopic dermatitis (AD) is characterized by the T-cell cytokines including IL-4, IL-13, IL-22 and IFN-γ. In the present assay, keratinocytes are stimulated with a mixture of these cytokines, and the release of CCL2 (also called monocyte chemoattractant protein 1 (MCP-1)) is measured in the culture supernatant by proximity homogenous time-resolved fluorescence (HTRF). The purpose of the assay is to measure if test compounds inhibit the levels of CCL2 released by the keratinocytes. Compound which inhibit keratinocyte CCL2 secretion may be expected to have efficacy in atopic dermatitis.

A known steroid, Betamethasone, inhibits CCL2 release in this assay with an $EC_{50}$ of approximately 15 nM, and an Emax (plateau of the fitted curve) of approximately 60%. A high Emax shows that the compound inhibits a large proportion of the secreted CCL2. A low $EC_{50}$ value indicates that the compound is potent and to perform the inhibition at low concentrations.

| Key assay parameters | Description |
|---|---|
| Human primary keratinocytes (HEKa) | Cells are frozen in passage 2. Cells are used in passage 3-6 |
| IL-4, IL-13, IL-22 and IFN-γ | Atopic dermatitis-like stimulation: Recombinant human interleukin (IL) 4, 13 and 22 at 10 ng/mL and Interferon-γ at 1 ng/mL |
| Effect | Inhibition of AD stimuli induced CCL2 release from HEKa cells |
| Positive control (~100% effect) | AD-like stimulation + Terfenadine (CAS: 50679-08-8) at 10 microM |
| Negative control (~0% effect) | AD-like stimulation and 0.1% DMSO |
| Reference compound | Betamethasone (CAS: 378-44-9) |
| Incubation time | 48 h |
| Capacity, run-time and requirements | The assay takes 3 days to perform. |

Method Description

Cell Culture:

HEKa are human epidermal keratinocytes isolated from adult skin. The cells have been cryopreserved at the end of the primary culture stage in a medium containing 10% DMSO. Sterile cell culture work applies.

Initiating Cultures from Cryopreserved HEKa Cells:

- Thaw a vial of the frozen HEKa stock in a 37° C. water/bead bath.
- Transfer the cell suspension into 30 ml T75 cell culture flask.
- Take 15 ml out and dispense over into 2×T75 (15 ml each).
- Set up for assay 5-6 days later or pass it on.

Maintenance of Stock Cultures

- Change the culture medium to freshly supplemented medium, 24 to 36 hours after establishing a secondary culture from cryopreserved cells. For subsequent subcultures, change the medium 48-72 hours after establishing the subculture.
- Only passage up to 3-5 in the assay.

Subculture of HEKa

- View and confirm 80% confluence.
- Remove all of the culture medium from the flask.
- Add 3 ml of TrypLE Express solution to the flask. Rock the flask to ensure that the entire surface is covered.
- Immediately remove all 3 ml of TrypLE Express solution from the flask.
- Add 1½ ml (T75) (3 ml T175) of fresh TrypLE Express solution to the flask.
- View the culture under a microscope. Incubate the flask at room temperature until the cells have become completely round, approximately 8-10 minutes.
- Tap the flask very gently to dislodge cells from the surface of the flask.
- Add 3-4 ml (T75) (7 ml T175) of Trypsin Neutralizer solution to the flask and transfer the detached cells to a sterile conical tube.
- Centrifuge the cells at 170×g for 7-10 minutes. Observe the cell pellet.
- Remove the supernatant from the tube, being careful not to dislodge the cell pellet.
- Resuspend the cell pellet in 15 ml medium with HKGS supplemented (cat no S-001-K) but without hydrocortisone (when use for assay). Pipette the cells up and down with a 10 ml pipette to ensure a homogeneous cell suspension.
- Determine the concentration of cells in the suspension.
- Dilute the cells in supplemented medium and seed new culture in a T175 flask. Incubate the cultures in a 37° C., 5% $CO_2$/95% air, humidified cell culture incubator.

Assay Day 0:

- Trypsinize the cells as described above.
- Resuspend pellet in 10 ml assay medium (EpiLife Medium with HKGS Kit but without hydrocortisone)
- Filter the cells though a 37 μm strainer.
- Count cells using a cell counter.
- Seed HEKa cells in 384-well view plates 3500 c/w/40 μL.
- Place the plates with lids on in a humidity chamber with lid (24.5×24.5 cm box added $H_2O$ in the bottom).
- Incubate plates over night at 37° C., 5% $CO_2$/95% air Assay Day 1:

- Prepare compound-containing source plate, i.e. titrations in DMSO to be transferred to the assay plate.
- Add 80 nL compounds and controls from the source plate to the assay plate (with cells).
- Add 40 μL stimulation (recombinant human interleukin (IL) 4, 13, 22 at 10 ng/mL and Interferon-gamma at 1 ng/mL) in medium with supplement, but without hydrocortisone.
- Incubate plates at 37° C., 5% $CO_2$/95% air for 2 days.

Assay Day 3:

- Remove plates from incubation and equilibrate to room temperature for 30 minutes.
- Transfer 8 μL supernatant to white proxi 384-well plates for CCL2 detection.
- Add 8 μL media to the detection plate.
- Add 4 μL CCL2 HTRF detection reagent (to the white proxi 384w).
- Seal and incubate for 4 hours and read in a plate reader.

Data Analysis and Calculations

CCL2 concentration in the supernatants is measured using homogeneous time-resolved fluorescence resonance (TR-FRET). The assay is quantified by measuring fluorescence at 665 nm (proportional to CCL2 concentration) and 620 nm (control). A ratio 665/620*1000 is calculated.

% Effect:

The capacity of the test compound to inhibit CCL2 release is normalized to the signal in the control wells with keratinocytes incubated with 0.1% DMSO (0%) and 10 μM Terfenadine (100%), which fully inhibits the CCL2 release.

2. Keratinocyte IL-8 Release

Inhibition of IL-8 release from IL-17A and TNFα-induced primary human keratinocytes LEO Pharma Open Innovation assay number 1250 openinnovation.leo-pharma.com Disease Relevance The inflammatory skin disease psoriasis is characterized by cytokines IL-17A and TNFα. In the present assay, primary human keratinocytes are stimulated with a mixture of these cytokines, and the release of IL-8 (also called CXCL8) is measured in the culture supernatant by proximity homogenous time-resolved fluorescence (HTRF). The purpose of the assay is to measure if the test compound is able to inhibit the levels of IL-8 released by the keratinocytes, indicating that it is able to inhibit part of the inflammation occurring in cells.

Compounds which inhibit keratinocyte IL-8 secretion may be expected to have efficacy in psoriasis.

A known steroid, Betamethasone, inhibits IL-8 release in this assay with an $EC_{50}$ of approximately 10 nM, and an Emax (plateau of the fitted curve) of approximately 50%. A high Emax indicates that the compound inhibits a large proportion of the IL-8 secretion. A low $EC_{50}$ value indicates that the compound is potent and performs the inhibition at low concentrations.

| Key assay parameters | Description |
|---|---|
| Human epidermal keratinocytes, adult (HEKa) | Cells are frozen in passage 2. Cells are used in passage 3-5 |
| IL-17A and TNFα | Psoriasis-like stimulation: Recombinant human interleukin (IL) 17A and tumor necrosis factor alpha (TNFα) both at 10 ng/mL |
| Effect | Inhibition of IL-17A/TNFα-induced IL-8 release from HEKa |
| Positive control (~100% effect) | No stimulation and 0.1% DMSO |
| Negative control (~0% effect) | IL-17A/TNFα stimulation and 0.1% DMSO |
| Reference compound | Betamethasone (CAS: 378-44-9) |
| Incubation time | 72 h |
| Capacity, run-time and requirements | The assay takes 3 days to perform. |

Method Description
Cell Culture:

HEKa are human epidermal keratinocytes isolated from adult skin (See Cell Culture Method described for Keratinocyte CCL2 release above).

Assay Day 0:

Detach the cells as described above.

Resuspend pellet in 10 ml EpiLife Medium with HKGS Kit but without hydrocortisone Filter the cells though a 37 μm strainer.

Count cells using a cell counter.

Seed Human Epidermal Keratinocytes, adult (HEKa) cells in 384-well view plates 3500 c/w/40 μL. Use cell media with supplement but without hydrocortisone as assay medium.

Place the plates with lids on in a humidity chamber with lid (24.5×24.5 cm box added $H_2O$ in the bottom).

Incubate plates over night at 37° C., 5% $CO_2$/95% air.

Assay Day 1:

Prepare compound-containing source plate, i.e. titrations in DMSO to be transferred to the assay plate.

Empty the assay plate, and re-add 25 μL assay medium.

Add 75 nL compounds and controls from the source plate to the assay plate (with cells).

Add 25 μL assay medium and incubate for 2 hours.

Add 25 μL stimulation mix in assay medium (recombinant human interleukin 17A and Tumor necrosis factor-alpha) to give a final concentration of 10 ng/mL of both cytokines.

Incubate plates at 37° C., 5% $CO_2$/95% air for 3 days.

Assay Day 4:

Remove plates from incubation and equilibrate to room temperature for 30 minutes.

Transfer 2 μL supernatant to white proxi 384-well plates for IL-8 detection.

Add 2 μL assay medium

Prepare IL-8 HTRF mix (according to manufactory protocol) and add 2 μL pr well.

Seal and incubate for 3 hours and read fluorescence in a plate reader.

Data Analysis and Calculations

IL-8 concentration in the supernatant is measured using homogeneous time-resolved fluorescence resonance (TR-FRET). The assay is quantified by measuring fluorescence at 665 nm (proportional to IL8 concentration) and 620 nm (control). A ratio 665/620*1000 is calculated as a representation of the amount of IL-8 in the supernatant.

% Effect:

The capacity of the test compound to inhibit IL-8 release is normalized to the signal in the negative control wells with keratinocytes incubated with 0.1% DMSO (0%) and 10 μM Terfenadine (100%), which fully inhibits the release of IL-8.

3. PBMC IL-17 Assay

Inhibition of IL-17A secretion from human PBMC stimulated with antiCD3/antiCD28-coated beads. LEO Pharma Open Innovation assay number 1321

Disease Relevance

The inflammatory skin disease psoriasis is characterized by cytokines IL-17A and TNFα. In the present assay, human peripheral blood mononuclear cells (PBMC) are stimulated with beads coated with antibodies against CD3 and CD28 to activate the T-cell receptor, and stimulated with IL-23 to promote T-helper17 activity. The cells are incubated for three days, then the secreted level of IL-17A is measured in the culture supernatant using AlphaLISA and the amount of living cells is measured by addition of resazurin (Presto-Blue®) to identify compounds that inhibit cell proliferation or viability. The purpose of the assay is to measure if test compounds inhibit the secretion of IL-17A by the PBMC. Compounds which inhibit IL-17A secretion may be expected to have efficacy in psoriasis.

The reference compound in this assay is the calcineurin inhibitor Tacrolimus and inhibits IL-17A release with an $EC_{50}$ of approximately 0.34 nM, and with an Emax (plateau of the fitted curve) of approximately 90%. A high Emax shows that the compound inhibits a large proportion of the secreted IL-17. A low $EC_{50}$ value indicates that the compound is potent and performs the inhibition at low concentrations.

Key Assay Parameters

| Parameter | Description |
|---|---|
| Cells | Human PBMC isolated from buffy coats and kept at −150° C. until day of assay |
| Stimulation | Beads coated with antibodies to CD3 and CD28 (T-cell activation/expansion kit Miltenyi Biotec cat no 130-091-441) One bead/cell. |
| Effect | Inhibition of IL-17A release |
| 0% effect of test compound | Bead stimulation, 0.1% DMSO |
| 100% effect of test compound | Bead stimulation, 0.1% DMSO, Terfenadine 10 uM |
| Reference compound | Tacrolimus (Cas no 104987-11-3-P) |
| Incubation time | 3 days |
| Capacity, run-time and requirements | The assay takes 3 days to perform. |

Method Description
PBMC Isolation:

PBMC are isolated from fresh human buffy coats by centrifugation on Lymphoprep® following instructions from Sebmate®

Cells are spun down and resuspended in freezing medium (RPMI640+20% FBS+5% DMSO)

Cells are frozen in aliquots of $8\times10^7$ cells/vial matching one 384 plate. Cells are placed in Coolcell box and placed in −80° C. freezer for one day. Vials are moved to the −150° C. freezer in a prechilled box.

Assay Day 1:

Prepare assay medium: RPMI1640+10% heat inactivated FBS and 1% pen/strep, supplemented with human IL-23, 20 ng/mL (R&D systems, cat no 1290-IL-010)

Test compounds: Prepare compound-containing source plate, i.e. titrations in DMSO to be transferred to the assay plate.

Add 70 nL compounds and controls from the source plate to the assay plate.

Thaw the cells by adding 1 vial to 20 ml warm assay medium

Centrifuge the cells down at 170 G in 10 minutes, remove the supernatant and resuspend in new medium.

Filter the cells though a 37 μm strainer.

Count the cells in the cell counter.

Beads (T Cell Activation/Expansion Kit-human, Miltenyi Biotech, cat. no. 130-091-441): Coat beads with antibodies (antiCD3 and antiCD28) according to the kit procedure.

Add the beads to the cells, one bead per cell, 2.1e+06 cells/ml. Use a pipette to mix the cells and beads carefully.

Seed the cell/bead mixture into the assay plate, 70 μL/well (1.3e+05 cells/well)

Place the plates in a humidity chamber with lid (24.5×24.5 cm box added $H_2O$ in the bottom).

Incubate plates at 37° C., 5% $CO_2$/95% air for 3 days.

Assay Day 4:

IL-17A concentration in the supernatants is measured using an alphaLISA kit (Perkin Elmer, cat no. AL219F).

Pretest to find optima dilution of samples: Test 5 μL supernatant from control wells and run IL-17A alphaLISA assay with only 2 hours of incubation.

When data are available, remove assay plates from incubation and equilibrate to room temperature for 30 minutes.

Transfer 5 μL or corrected amounts of supernatant to a 384-proxy plate

Add 5 μL alphaLISA acceptor beads.

Incubate 1 hour at room temperature

Add 5 μL donor beads

Incubate overnight at room temperature protected from light.

Add 7 μL PrestoBlue reagent (resazurin)/well to the assay plate and incubated for 2-4 hours at 37° C./5% $CO_2$. The fluorescence in the wells is measured (Ex615/Em 535).

Assay Day 5:

Read alphaLISA plate in a plate reader

Data Analysis and Calculations

IL-17A concentration in the supernatants is measured using an alphaLISA kit (Perkin Elmer, cat no. AL219F).

% Effect IL-17:

The capacity of the test compound to inhibit IL-17A release is normalized to the signal in the negative control wells treated with a toxic compound, Terfenadine.

The level of living cells in the wells is measured by the addition of PrestoBlue® and the conversion of Resazurin to Resorufin (fluorescent) in living cells is measured.

% Effect Viability/Proliferation:

The effect of the test compounds on viability/proliferation is normalized to the PrestoBlue signal in the negative control wells treated with a toxic compound, Terfenadine.

4 And 5. T-Cell IL-2 & IL-4 Assay

Inhibition of IL-4 and IL-2 secretion from human CD4-positive T-cells stimulated with antiCD2/antiCD3/antiCD28-coated beads. LEO Pharma Open Innovation assay number 1297, 1298, 1299.

Disease Relevance

The inflammatory skin disease atopic dermatitis is characterized by the T-cell cytokines IL-4, IL-13 and IL-22. In the present assay, human T-cells are stimulated with beads coated with antibodies against CD2, CD3 and CD28 to activate the T-cell receptor. Then the level of secreted of IL-4 is measured in the culture supernatant using electrochemiluminescence (MSD kits, Meso Scale Discovery), IL-2 is measured by proximity homogenous time-resolved fluorescence (HTRF) and the amount of living cells is measured by addition of resazurin (PrestoBlue®) to allow identifying compounds that inhibit T-cell proliferation or viability. The purpose of the assay is to measure if a test compound is able to inhibit the secretion of IL-4 by the T-cells, indicating that it is able to inhibit part of the inflammation occurring in the skin.

Compounds which inhibit IL-4 secretion may be expected to have efficacy in atopic dermatitis. Compounds which also inhibit IL-2 secretion have a broader immunosuppressive effect since IL-2 is an autocrine growth factor for T-cells. A known steroid, Betamethasone, inhibits IL-4 release in this assay with an $EC_{50}$ of approximately 15 nM, and with an Emax (plateau of the fitted curve) of approximately 80%. A high Emax shows that the compound is able to inhibit a large proportion of the secreted IL-4. A low $EC_{50}$ value indicates that the compound is potent and is able to perform the inhibition at low concentrations.

Key Assay Parameters

| Human CD4-postive T-cells isolated from buffy coats and kept at −150 degree C. until day of assay | |
|---|---|
| Stimulation | Beads coaled with antibodies to CD2, CD3 and CD28 (T-cell activation/expansion kit Miltenyi Biotec cat no 130-091- 441) One bead/cell. |
| Effect | Inhibition of IL-4 release from T-cells |
| 0% effect of test compound | Bead stimulation, 0.1% DMSO |
| 100% effect of test compound | Unstimulated cells, 0.1% DMSO |
| Reference compound | Betamethasone (CAS: 378-44-9) |
| Incubation time | 48 h |
| Capacity, run-time and requirements | The assay takes 3 days to perform. |

Method Description

CD4+ T-Cell Isolation:

Peripheral blood mononuclear cells (PBMC) are isolated from fresh human buffy coats by centrifugation on Lymphoprep® following instructions from Sebmate™ (Stemcell).

The cells are resuspended in 30 ml of PBS+2% Serum and counted.

CD4 positive T-cells are isolated from freshly isolated PBMC using EasySep™ humane CD4+ T-cell Isolation Kit (Catalog #17952) and following the manufacturer's protocol.

Cells are spun down and resuspended in freezing medium (X-vivo 15+10% FBS+5% DMSO)

Cells are frozen in aliquots of $3\times10^7$ cells/vial matching one 384 plate. Cells are place in Coolcell box and place in −80° C. freezer for one day then transferred to the −150° C. freezer in a prechilled box.

Assay Day 1:

Prepare assay medium: 500 ml X-Vivo 15+5 ml Glutamax (2 mM final)+5 ml pen/strep (100 U/ml final).

Add 5 μL medium to the wells of a 384 well plate (Greiner cat. No 788986).

CD4+ Cells: Thaw frozen cells from −150° C. freezer in 37° C. bath, and pipette the cells into 10 ml medium. Spin 10 min@170 g.

Resuspend pellet in 3.5 ml per $2.5\times10^7$ cells and add 10 μL per well to the plate (40000 cells/well)

Test compounds: Prepare compound-containing source plate, i.e. titrations in DMSO to be transferred to the assay plate.

Add 25 nL compounds and controls from the source plate to the assay plate (with cells).

Beads (T Cell Activation/Expansion Kit-human, Miltenyi Biotech, cat. no. 130-091-441): Coat beads with antibodies according to the kit procedure.

Add 10 μL beads to each well except for the negative controls. One bead per cell. Add 10 μL medium to the negative controls.

Incubate plates at 37° C., 5% CO/95% air for 2 days.

Assay Day 3:

Remove plates from incubation and equilibrate to room temperature for 30 minutes.

IL-4 concentration in 10 μL supernatant is measured using an MSD IL-4 384-plate kit (Custom made) according to manufacturer protocol.

IL-2 concentrations in the supernatant is measured by an IL-2 HTRF kit, CisBio, cat. No 62HIL02PEH.

Add 4 μL medium to white proxi 384-well plates

Add 1 μL supernatant.

Add 4 μL mHTRF mix (each diluted 1:300 in 2/3 reconstitution buffer and 1/3 assay medium).

Spin the plates for 1 minute at 170 g

Seal and incubate overnight and read fluorescence in a plate reader

The amount of viable cells is measured by PrestoBlue® reagent

Add 15 μL diluted PrestoBlue® reagent (resazurin) corresponding to 2.5 μL Prestoblue/well to the assay plate.

Incubate overnight at 37° C./5% $CO_2$. The fluorescence in the wells is measured (Ex615/Em 535).

Data Analysis and Calculations

IL-4 concentration in the supernatants is measured using electrochemiluminescence (MSD kits, Meso Scale Discovery). IL-2 concentration in the supernatants is measured using homogeneous time-resolved fluorescence resonance (TR-FRET). The assay is quantified by measuring fluorescence at 665 nm (proportional to IL-2 concentration) and 620 nm (control). A ratio 665/620*1000 is calculated.

% Effect for IL-2 and IL-4:

The capacity of the test compound to inhibit IL-4 and IL-2 release is normalized to the signal in the negative control wells with un-stimulated T-cells.

The level of living cells in the wells is measured by the addition of PrestoBlue® and the conversion of Resazurin to Resorufin (fluorescent) in living cells is measured.

% Effect for Viability/Proliferation:

The effect of the test compounds on viability/proliferation is normalized to the PrestoBlue signal in the negative control wells treated with a toxic compound, Terfenadine.

Ex Vivo Study: Predicting Patient Response to Oncology Drugs

ROK-DRPS-001—Drug Response Summary (Jun. 19, 2020)

Glioblastoma Multiforme (GBM) Drug Response Pilot

KIYATEC, Inc., Greenville, S.C., USA

1. Project Description/Summary

This project involves an ex vivo drug response screen for 3 ROKiT Pharma test agents and Temozolomide in 3 previously dissociated and cryopreserved GBM samples.

2. Technical Conduct 2.1 Three previously processed GBM patient samples were chosen to be used in this study.

| ID | New or Relapse | IDH1 status | MGMT | Grade |
|---|---|---|---|---|
| BNA99 | New | wild type | methylated | high |
| BNB04 | Recurrent | wild type | unknown | high |
| BNB18 | New | wild type | unmethylated | high |

IDH1: isocitrate dehydrogenase-1;
MGMT: (O[6]-methylguanine-DNA methyltransferase)

2.2 1-2 vials of each sample were thawed, and cells were seeded as 3D spheroids in one 384-well plate per sample.

2.3 24 hours after seeding, images were taken of all wells and drugs/controls were added.

Test Compounds: KYN-001, KYN-146, KYN-149, 10-point dose curve at 1:3 dilution starting at 100 μM and ending at 0.005 μM Vehicles: Media+0.5% DMSO, Media+1% DMSO Positive controls; 10% DMSO and 2% DMSO Wells containing only vehicle and no cells were used as blanks 2.4 Cell viability was measured 4 days post drug treatment with CellTiter-Glo 3D assay.

Images were taken of all wells prior to addition of CellTiter Glo reagent.

2.5 Following the blanking of raw data and the removal of outliers (defined by software analysis and highlighted in red in raw data files), $IC_{50}$ values were determined using nonlinear regression (normalized to untreated control) in GraphPad Prism.

The $IC_{50}$ values are expressed in μM and are defined as the concentration of drug where cell viability is reduced by half.

3. Summary of Experimental Results 3.1 Drug response to the test compounds and TMZ is listed in the table below:

| | $IC_{50}$ (μM) | | |
|---|---|---|---|
| Drug | BNA99 | BNB04 | BNB18 |
| 1 [KYN-001] | 14.95 | 10.89 | 1.329 |
| 20 [KYN-146] | 19.13 | 23.67 | 4.556 |
| 27 [KYN-149] | 8.867 | 4.31 | 0.6343 |
| TMZ | NR | MR | R |

3.2 The RLUs (Relative Light Unit) were high for the cells from each GBM sample, indicating proliferation/viability throughout the assay duration.

3.3 Z-factors reflected successful assays for all samples and drugs.

3.4 TMZ Response:

NR: Non-responder

MR: Moderate responder

R: Responder

Discussion

The three GBM cell samples used in this study, namely BNA99, BNB04 and BNB18, displayed three distinct growth characteristics when grown into 3D spheroids as shown in FIG. 14. These cells range from resistant (BNA99), to moderately resistant (BNB04) and sensitive (BNB18) to the clinical drug Temozolomide (TMZ). In the presence of the test compounds 1, 20 and 27 the spheroids of all three cell lines were disrupted causing cell death and dispersion into the culture medium. These events were clearly demonstrated from images (FIG. 14) taken prior to addition of CellTiter Glo reagent which was used to quantify the cell viability by measuring the level of ATP of the live cells.

The test compounds showed moderate to potent inhibition of these GBM 3D spheroid cell samples with $IC_{50}$ value of 27 at sub-micromolar range in the sensitive line BNB18 ($IC_{50}$=0.63 μM). As predicted the test compounds were active towards sensitive GBM line BNB18 but less active towards BNB04 spheroids and much less active towards BNA99 spheroids. Despite this, the test compounds, particularly 27, were shown to be relatively active towards the TMZ resistant cells (BNA99) with $IC_{50}$ value of 8.86 μM while TMZ showed no response to this cell line.

The results from this study reveal that the test compounds, particularly 27, are promising candidates for the development of new anticancer drugs.

Summary

- Assay was successful for all drugs and samples based on z-factors and RLU signals
- $IC_{50}$ values indicated varying sensitivities to KYN-001, KYN-146, and KYN-149 for all 3 samples.
- TMZ response varied for all 3 samples across all 3 response categories.
- Bright field images of spheroids match CellTiterGlo Results (data not shown).
- 27 [KYN-149] more effective than 1 [KYN-001] and 20 [KYN-146] towards all three GBM 3D-spheroid sample types (NR, MR and R).

REFERENCE

Shuford, S., et al., 2019. Prospective Validation of an Ex Vivo, Patient-Derived 3D Spheroid Model for Response Predictions in Newly Diagnosed Ovarian Cancer, Nature Scientific Reports, 9:11153|https://doi.org/10.1038/s41598-019-47578-7

Compound 27 [KYN-149] Maximum Tolerable Dose—LD/50 Single Dose Oral Administration Report Evaluation was conducted by Kynan Pharma, USA Study Purpose:

To ascertain initial information regarding the toxicity and tolerability of compound 27.

Study Design:

- A single administration of orally formulated maximum dose, 2000 mg/kg was given to 5 BalbC mice. Observation was carried out for 5 days.
- Experimentalist: Tiziana Palumbo, Matt Kiosea
- Dates of testing: Jun. 8-12, 2020

Method:

- Compound 27 was weighed out and diluted into the same SEDDS vehicle used for S1. The SEDDS vehicle is composed of the following components:
  - Labrasol (30%)
  - PEG-400 (20%)
  - Kolliphore RH-40 (30%)
  - Labrafil (20%)
- The concentration of 27 in SEDDS was 200 mg/mL which would translate to a 2000 mg/kg oral dose for a 20 g mouse administered 200 ul. Oral administration was administered to 5 mice and the animals were carefully observed for signs of toxicity in the first hour then sporadically over 5 days.

Results:

All five mice survived and showed no immediate signs of distress. During the remaining days of observation, No distress or any other discomfort was recorded.

Conclusions

The results of the LD/50 study indicate that compound 27 has a high degree of oral tolerability in the given formulation. 2000 mg/kg is the maximum dose recommended for testing toxicological effects per FDA recommendations Preliminary Investigation of the Effect of Compound 27 [KYN-149] in B16F10 Xenografted Mice.

Evaluation was conducted by Kynan Pharma, USA

Objectives

- Observe and assess the effect of oral administration of 27 on animal wellbeing.
- Quantify levels of 27 in tissues (plasma, tumor, liver, spleen and brain) to assess the compound bioaccumulation and distribution.

Method

B16F10 cells (25×10$^5$ cells/mouse) were injected subcutaneously into the right flank of female BALB/c mice aged 7-8 weeks. Mice (n=10) were divided into 2 groups and given daily oral suspension of 27 (treated group), or vehicle (control group) for 15 days. The treated group was orally given a suspension of 27 at 900 mg/kg. The control group was given the vehicle suspension (SEDDS). Measurements performed on days 0, 9 and 15 only. Tissues (plasma, tumor, liver, spleen and brain) were harvested within 3 hours of final treatment. Biopsies of tumor tissues for histopathology were obtained subsequently.

Tissue samples from the tumors of both treated and control mice were fixed with formalin. Histopathological examination of these tumor samples was performed by Lore Laboratory, CA, USA.

Concentrations of 27 in different tissues were determined using LC/MS/MS spectrometry.

Results

Mice showed no signs of toxic effect at 900 mg/kg of 27. Concentration of 27 in different tissues are determined as shown in table 1 and presented graphically as shown in FIGS. 15A and B.

TABLE 8

Measurement of compound 27 in mice tissues using mass spectrometry

| | Concentration of compound 27 in tissues | | | | |
|---|---|---|---|---|---|
| Animal | Plasma (ng/mL) | Tumor (μg/mg) | Liver (μg/mg) | Spleen (μg/mg) | Brain (μg/mg) |
| Control 1 | 0.0 | NA | 0 | 0 | 0 |
| Control 2 | 0.0 | 0 | 0 | NA | 0 |
| Control 3 | 0.0 | 0 | 0 | 0 | 0 |
| Treated 1 | 0.0 | 0 | 12.6 | 2 | 156 |
| Treated 2 | 0.0 | NA | 10.2 | 0 | 77 |
| Treated 3 | 8.4 | 0 | 1.0 | 0 | 35 |
| Treated 4 | 0.4 | 0 | 0.0 | 0 | 170 |
| Treated 5 | 0.0 | 11.6 | 0.0 | 0 | 48 |
| P-Value control vs treated | 0.22 | 0.54 | 0.36 | 0.65 | 0.004 |

NA = not acquired

FIG. 15. Concentrations of 27 in different tissue samples isolated from treated mice. Mice were orally administration of 900 mg/kg of 27 in SEDDS suspension or vehicle (control) daily for 15 days.

It was found that concentration of compound 27 was variously distributed in different tissues as shown in FIG. 15. Low plasma level of compound 27 can be explained as the compound being bound to plasma proteins such as albumin.

Histochemical Analysis of the Tumor Samples.

Preliminary investigation revealed that two out of five biopsies samples from five mice treated with 27 displayed melanomas as detailed below.

Treated 1.

It was found that the lesion was located deep in the dermis and panniculus. There was a sheet of pleomorphic round cells with occasional pigmented cytoplasm. These cells were predominantly degenerated or necrotic with adjacent areas of lytic necrosis (FIG. 16). Mixed inflammatory cells were noticed at the periphery.

Treated 2.

It was found that the lesion was located in the superficial and mid dermis. There was a sheet of pleomorphic round cells with occasional pigmented cytoplasm surrounded by lytic necrosis (FIG. 16). Mixed inflammatory cells were noticed at the periphery.

Histochemical Analysis of Tumor Samples from Treated 1 and 2 Mice.

These two tumors contained melanoma which grew rapidly from day 0 to 9. The tumors were subsequently diminished after day 10 indicating that it is possibly an effect of compound 27 (FIG. 16).

Histochemical Analysis of Samples from Treated 3, 4 and 5 Mice.

Histochemical analysis of these samples revealed predominantly melanocytes which expand subcutaneous and panniculus with mild mononuclear inflammation (FIG. 17). These findings consist with the lack of tumor growth as shown in Table 8 and FIG. 18.

TABLE 8

| Tumor volume ($mm^3$) in mice treated with compound 27 | | | |
|---|---|---|---|
| Compound 27 | Day 0 ($mm^3$) | Day 9 ($mm^3$) | Day 15 ($mm^3$) |
| Treated #1 | 109.29 | 132.59 | 5.31 |
| Treated #2 | 52.18 | 178.68 | 19.93 |
| Treated #3 | 58.45 | 37.38 | 35.03 |
| Treated #4 | 82.97 | 60.93 | 42.35 |
| Treated #5 | 66.82 | 47.3 | 39.44 |

FIG. 18. Effect of Compound 27 on melanoma B16F10 xenografted in BALB/c mice.

Histopathology Conclusions

- Except in two drug-administered tumors, (Treated 1 and Treated 2) the other samples were highly pigmented melanocytes with a round elongated nucleus and no mitotic activity.
- It may be that in those samples with no malignancy observed histologically, either there was no malignancy developed from the beginning or malignant tissue was not sampled and collected.
- Although most of the tissues analyzed were composed of melanocytes, two treated tissues contained melanoma that was necrotic and degenerative, possibly indicative of an effect of treatment. The lack of melanoma in control untreated tissues confound these findings.

OVERALL CONCLUSION

In conclusion, the study showed that the compound 27 had low toxicity when given orally, and had a high tendency to accumulate in the brain. This could be explained by the highly lipophilic property of the compound.

Histochemical analysis of tumor samples revealed that the melanoma cells xenografted in two out of five mice treated with 27 were lysed and/or underwent necrosis indicating the possible effectiveness of compound 27 in treatment of melanoma in vivo. However, further studies are required to determine further details of the pharmacokinetics of 27 and to assess anticancer efficacy in vivo.

The invention claimed is:

1. A process of synthesising a compound of formula (I):

Formula (I)

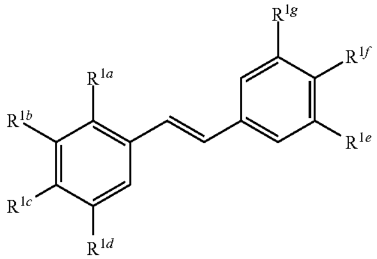

wherein:

$R^{1a}$ is independently allyl, crotyl, prenyl, benzyl or 2-alkenyl;

$R^{1b}$ is independently $CF_3$, $OR^2$ or $NHR^3$;

$R^{1c}$ is H;

$R^{1d}$ is independently OH, O-protecting group, $NHR^3$ or $NO_2$;

$R^{1e}$ is independently $C_1$-$C_6$ alkyl, OH, $OR^2$, $NO_2$, $NHR^3$, $NMeR^3$ or $SR^2$;

$R^{1f}$ is independently H, OH, O-protecting group, $NO_2$, $NHR^3$, $N(OH)(CO)CH_3$, $NHC{=}NH(NH_2)$ or COOH;

$R^{1g}$ is independently H, $C_1$-$C_6$ alkyl or OH;

$R^{1b}$ and $R^{1d}$ are not the same;

no more than one of $R^{1f}$ or $R^{1g}$ can be H;

$R^2$ is independently methyl, ethyl, propyl, isopropyl, butyl, isobutyl, t-butyl or trifluoromethyl;

protecting group is selected from the group consisting of COMe, t-$BuSi(CH_3)_2$, 2-(trimethylsilyl)ethoxymethyl (SEM), $CH(OEt)CH_3$, tetrahydropyranyl and $C(OEt)(CH_3)_2$;

$R^3$ is independently H, $CH_3$, (CO)H, (CO)Me, $SO_2Me$, $CH_2COOH$, $CH_2COOR^2$, $CO(CH_2)_nNH_2$, $CONH_2$, $CO(CH_2)_nCOOH$ or $COCOOR^4$, where n is 0, 1 or 2; and $R^4$ is $C_1$-$C_6$ alkyl;

or $R^{1e}$ and $R^{1f}$ form a five-membered heterocyclic ring containing a carbonyl group when $R^{1e}$ is independently OH, $NH_2$ or NHMe and $R^{1f}$ is $NH_2$, such that the nitrogen of $R^{1f}$ is bridged with the carbonyl group to the oxygen or nitrogen of $R^{1e}$ and $R^{1g}$ is H;

the process comprising:

i) a step of coupling a compound of formula (II) (Module A) with a compound of formula (III) (Module B) to afford a compound of formula (IV) (Module C):

Module A

Formula (II)

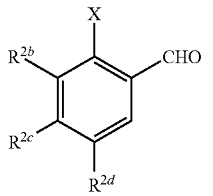

Module B

Formula (III)

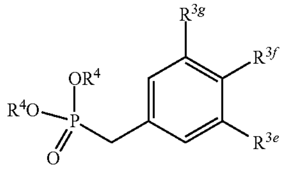

Module C

Formula (IV)

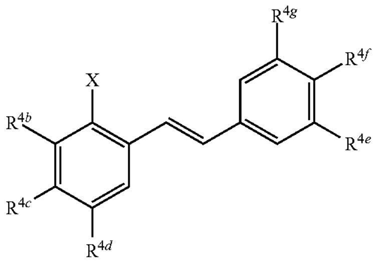

wherein, in Formula II (Module A):

$R^{2b}$ is independently $CF_3$, $OR^2$ or $NH_2$;

$R^{2c}$ is H;

$R^{2d}$ is independently O-protecting group or $NO_2$;

X is a halide or a hydroxyl group, wherein the halide is selected from the group consisting of F, Cl, Br, I, and At; and $R^2$ is independently methyl, ethyl, propyl, isopropyl, butyl, isobutyl, t-butyl or trifluoromethyl;

in Formula III (Module B):

$R^{3e}$ is independently $C_1$-$C_6$ alkyl, $OR^2$, $NO_2$ or $SR^2$;

$R^{3f}$ is independently H, O-protecting group, $NO_2$ or $COOR^2$;

$R^{3g}$ is independently H, $C_1$-$C_6$ alkyl, OH or $OR^2$;

no more than one of $R^{3f}$ or $R^{3g}$ can be H;

$R^2$ is independently methyl, ethyl, propyl, isopropyl, butyl, isobutyl, t-butyl or trifluoromethyl; and $R^4$ is $C_1$-$C_6$ alkyl;

or $R^{3e}$ and $R^{3f}$ form a five-membered heterocyclic ring containing a carbonyl group when $R^{3e}$ is OH, $NH_2$ or NHMe and $R^{3f}$ is $NH_2$, such that the nitrogen of $R^{3f}$ is bridged with the carbonyl group to the oxygen or nitrogen of $R^{3e}$ and $R^{3g}$ is H;

in Formula IV (Module C):

$R^{4b}$ is independently $CF_3$, $OR^2$ or $NH_2$;

$R^{4c}$ is H;

$R^{4d}$ is independently O-protecting group or $NO_2$;

$R^{4e}$ is independently $C_1$-$C_6$ alkyl, $OR^2$, $NO_2$ or $SR^2$;

$R^{4f}$ is independently H, O-protecting group, $NO_2$ or COOH;

$R^{4g}$ is independently H, $C_1$-$C_6$ alkyl, OH or $OR^2$;

no more than one of $R^{4f}$ or $R^{4g}$ can be H;

$R^2$ is independently methyl, ethyl, propyl, isopropyl, butyl, isobutyl, t-butyl or trifluoromethyl; and X is a halide or a hydroxyl group, wherein the halide is selected from the group consisting of F, Cl, Br, I, and At;

or $R^{4e}$ and $R^{4f}$ form a five-membered heterocyclic ring containing a carbonyl group when $R^{4e}$ is OH, $NH_2$ or NHMe and $R^{4f}$ is $NH_2$, such that the nitrogen of $R^{4f}$ is bridged with the carbonyl group to the oxygen or nitrogen of $R^{4e}$ and $R^{4g}$ is H;

wherein the protecting group is selected from the group consisting of COMe, t-$BuSi(CH_3)_2$, 2-(trimethylsilyl)ethoxymethyl (SEM), $CH(OEt)CH_3$, tetrahydropyranyl, or $C(OEt)(CH_3)_2$.

2. The process of claim 1, wherein:

i) when X in formula (IV) is a halide, the halide of formula (IV) undergoes a coupling reaction with one of the following:

a) a $R^{1a}$-substituted boronic acid compound or ester including a $R^{1a}$-substituted boronic acid pinacol ester;

b) a $R^{1a}$-substituted trifluoroborate compound including a potassium $R^{1a}$ substituted trifluoroborate; or c) a $R^{1a}$-substituted organostannane compound including a $R^{1a}$-substituted tributylstannane;

to form the compound of formula (I), wherein $R^{1a}$ is selected from the group consisting of allyl, crotyl, prenyl, benzyl or 2-alkenyl;

or ii) when X in formula (IV) is hydroxyl, the hydroxyl group of Formula (IV) is converted to a triflate (trifluoromethylsulfonate) group to form a triflate of formula (IV), and the triflate of formula (IV) undergoes a coupling reaction with one of the following:

a) a $R^{1a}$-substituted boronic acid compound or ester including a $R^{1a}$-substituted boronic acid pinacol ester;

b) a $R^{1a}$-substituted trifluoroborate compound including a potassium $R^{1a}$-substituted trifluoroborate; or c) a $R^{1a}$-substituted organostannane compound including a $R^{1a}$-substituted tributylstannane;

to form the compound of formula (I), wherein $R^{1a}$ is selected from the group consisting of allyl, crotyl, prenyl, benzyl or 2-alkenyl;

optionally wherein the coupling reaction i) and ii) is catalysed by a palladium compound in the presence of a base.

3. The process of claim 1, wherein:

in Formula (I):

$R^{1a}$ is independently allyl, crotyl, prenyl, benzyl or 2-alkenyl;

$R^{1b}$ is independently $CF_3$, $OR^2$, $NH_2$, NHC(O)H or NHC(O)Me;

$R^{1c}$ is H;

$R^{1d}$ is independently OH, $NH_2$, NHC(O)H, NHC(O)Me or $NO_2$;

$R^{1e}$ is independently $C_1$-$C_6$ alkyl, OH, $OR^2$, $NO_2$, NHC(O)H, NMe2, NHMe or $SR^2$;

$R^{1f}$ is independently H, OH, $NO_2$, $NH_2$, $NHSO_2Me$, NHC(O)H, NHC(O)Me, $NHCO(CH_2)NH_2$, NHCO $(CH_2)^{2c}OOH$, $NHCH^{2c}OOR^2$, N(OH)C(O)Me, $NHC{=}NH(NH_2)$ or COOH;

$R^{1g}$ is independently H, $C_1$-$C_6$ alkyl or OH;

$R^{1b}$ and $R^{1d}$ are not the same;

no more than one of $R^{1f}$ or $R^{1g}$ can be H;

$R^2$ is independently methyl, ethyl, propyl, isopropyl, butyl, isobutyl, t-butyl or trifluoromethyl;

or $R^{1e}$ and $R^{1f}$ form a five-membered heterocyclic ring containing a carbonyl group when $R^{1e}$ is OH, $NH_2$ or NHMe and $R^{1f}$ is $NH_2$, such that the nitrogen of $R^{1f}$ is bridged with the carbonyl group to the oxygen or nitrogen of $R^{1e}$, and $R^{1g}$ is H;

in Formula II (Module A):

$R^{2b}$ is independently $CF_3$, $OR^2$ or $NH_2$;

$R^{2c}$ is H;

$R^{2d}$ is independently O-protecting group or $NO_2$;

X is a halide or a hydroxyl group, wherein the halide is selected from the group consisting of F, Cl, Br, I and At;

$R^2$ is independently methyl, ethyl, propyl, isopropyl, butyl, isobutyl, t-butyl or trifluoromethyl;

in Formula III (Module B):

$R^{3e}$ is independently $C_1$-$C_6$ alkyl, $OR^2$, $NO_2$ or $SR^2$;

$R^{3f}$ is independently H, O-protecting group, $NO_2$ or $COOR^2$;

$R^{3g}$ is independently H, $C_1$-$C_6$ alkyl, OH or $OR^2$;

and no more than one of $R^{3f}$ or $R^{3g}$ can be H;

$R^2$ is independently methyl, ethyl, propyl, isopropyl, butyl, isobutyl, t-butyl or trifluoromethyl; and $R^4$ is $C_1$-$C_6$ alkyl;

or $R^{3e}$ and $R^{3f}$ form a five-membered heterocyclic ring containing a carbonyl group when $R^{3e}$ is OH, $NH_2$ or NHMe and $R^{3f}$ is $NH_2$, such that the nitrogen of $R^{3f}$ is bridged with the carbonyl group to the oxygen or nitrogen of $R^{3e}$ and $R^{3g}$ is H;

in Formula IV (Module C):

$R^{4b}$ is independently $CF_3$, $OR^2$ or $NH_2$;

$R^{4c}$ is H;

$R^{4d}$ is independently O-protecting group or $NO_2$;

$R^{4e}$ is independently $C_1$-$C_6$ alkyl, $OR^2$, $NO_2$, or $SR^2$;

$R^{4f}$ is independently H, O-protecting group, $NO_2$ or COOH;

$R^{4g}$ is independently H, $C_1$-$C_6$ alkyl, OH or $OR^2$;

no more than one of $R^{4f}$ or $R^{4g}$ can be H;

$R^2$ is independently methyl, ethyl, propyl, isopropyl, butyl, isobutyl, t-butyl or trifluoromethyl; and X is a halide or a hydroxyl group, wherein the halide is selected from the group consisting of F, Cl, Br, I, and At;

or $R^{4e}$ and $R^{4f}$ form a five-membered heterocyclic ring containing a carbonyl group when $R^{4e}$ is OH, $NH_2$ or NHMe and $R^{4f}$ is $NH_2$, such that the nitrogen of $R^{4f}$ is bridged with the carbonyl group to the oxygen or nitrogen of $R^{4e}$ and $R^{4g}$ is H;

wherein the protecting group is selected from the group consisting of COMe, t-$BuSi(CH_3)_2$, 2-(trimethylsilyl) ethoxymethyl (SEM), $CH(OEt)CH_3$, tetrahydropyranyl, or $C(OEt)(CH_3)_2$.

4. The process of claim 1, wherein:

in Formula (I):

$R^{1a}$ is independently allyl, crotyl, prenyl or benzyl;

$R^{1b}$ is independently $CF_3$, $OR^2$ or $NH_2$;

$R^{1c}$ is H;

$R^{1d}$ is independently OH or $NO_2$;

$R^{1e}$ is independently $C_1$-$C_6$ alkyl, OH, $OR^2$, $NO_2$ or $SR^2$;

$R^{1f}$ is independently H, OH, $NO_2$ or COOH;

$R^{1g}$ is independently H, $C_1$-$C_6$ alkyl or OH;

no more than one of $R^{1f}$ or $R^{1g}$ can be H; and $R^2$ is independently methyl, ethyl, propyl, isopropyl, butyl, isobutyl, t-butyl or trifluoromethyl;

or $R^{1e}$ and $R^{1f}$ form a five-membered heterocyclic ring containing a carbonyl group when $R^{1e}$ is OH, $NH_2$ or NHMe and $R^{1f}$ is $NH_2$, such that the nitrogen of $R^{1f}$ is bridged with the carbonyl group to the oxygen or nitrogen of $R^{1e}$ and $R^{1g}$ is H;

in Formula II (Module A):

$R^{2b}$ is independently $CF_3$, $OR^2$ or $NH_2$;

$R^{2c}$ is H;

$R^{2d}$ is independently O-protecting group or $NO_2$;

X is a halide or a hydroxyl group, wherein the halide is selected from the group consisting of F, Cl, Br, I and At; and $R^2$ is independently methyl, ethyl, propyl, isopropyl, butyl, isobutyl, t-butyl or trifluoromethyl;

in Formula III (Module B):

$R^{3e}$ is independently $C_1$-$C_6$ alkyl, $OR^2$, $NO_2$ or $SR^2$;

$R^{3f}$ is independently H, O-protecting group, $NO_2$ or $COOR^2$;

$R^{3g}$ is independently H, $C_1$-$C_6$ alkyl, OH or $OR^2$;

and no more than one of $R^{3f}$ or $R^{3g}$ can be H;

$R^2$ is independently methyl, ethyl, propyl, isopropyl, butyl, isobutyl, t-butyl or trifluoromethyl; and $R^4$ is $C_1$-$C_6$ alkyl;

or $R^{3e}$ and $R^{3f}$ form a five-membered heterocyclic ring containing a carbonyl group when $R^{3e}$ is OH, $NH_2$ or NHMe and $R^{3f}$ is $NH_2$, such that the nitrogen of $R^{3f}$ is bridged with the carbonyl group to the oxygen or nitrogen of $R^{3e}$ and $R^{3g}$ is H;

in Formula IV (Module C):

$R^{4b}$ is independently $CF_3$, $OR^2$ or $NH_2$;

$R^{4c}$ is H;

$R^{4d}$ is independently O-protecting group or $NO_2$;

$R^{4e}$ is independently $C_1$-$C_6$ alkyl, $OR^2$, $NO_2$ or $SR^2$;

$R^{4f}$ is independently H, O-protecting group, $NO_2$ or COOH;

$R^{4g}$ is independently H, $C_1$-$C_6$ alkyl, OH or $OR^2$;

$R^2$ is methyl, ethyl, propyl, isopropyl, butyl, isobutyl, t-butyl or trifluoromethyl; and X is a halide or a hydroxyl group, wherein the halide is selected from the group consisting of F, Cl, Br, I and At;

or $R^{4e}$ and $R^{4f}$ form a five-membered heterocyclic ring containing a carbonyl group when $R^{4e}$ is OH, $NH_2$ or NHMe and $R^{4f}$ is $NH_2$, such that the nitrogen of $R^{4f}$ is bridged with the carbonyl group to the oxygen or nitrogen of $R^{4e}$ and $R^{4g}$ is H;

wherein the protecting group is selected from the group consisting of COMe, t-$BuSi(CH_3)_2$, 2-(trimethylsilyl) ethoxymethyl (SEM), $CH(OEt)CH_3$, tetrahydropyranyl, or C(OEt) $(CH_3)_2$.

5. The process of claim 1, wherein the compound according to formula (I) is selected from the group consisting of:

1 [KYN-001]

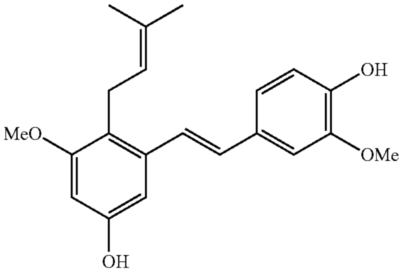

-continued
2 [KYN-138]
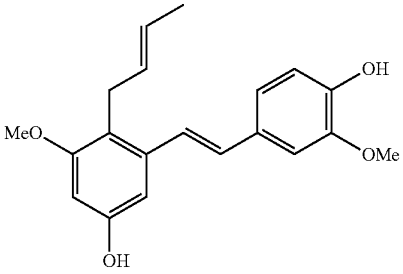
3 [KYN-139]
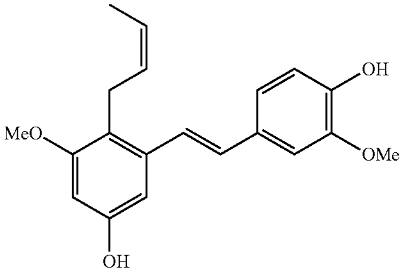
4 [KYN-140]
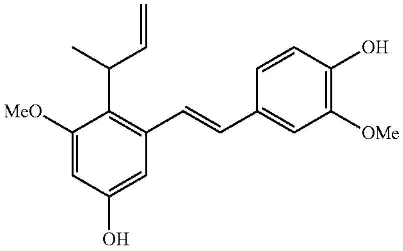
5 [KYN-153]
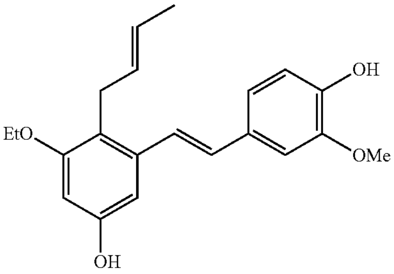
6 [KYN-134]
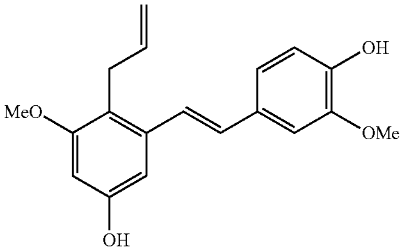
7 [KYN-136]
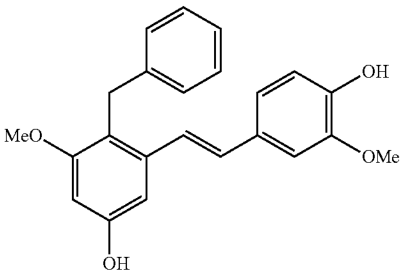
-continued
8 [KYN-119]
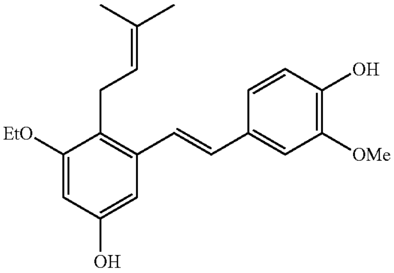
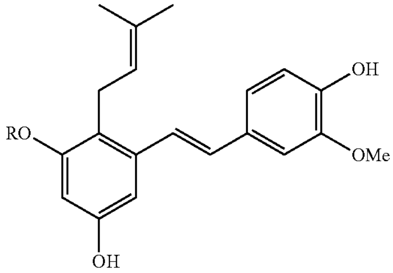
9 [KYN-130] R = n-propyl
10 [KYN-131] R = iso-propyl
11 [KYN-132] R = $CF_3$
12 [KYN-133]
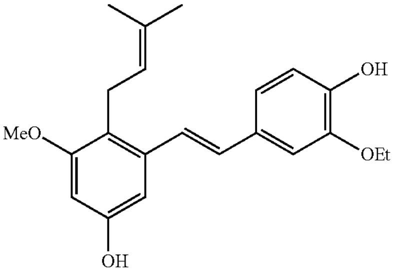
13 [KYN-114]
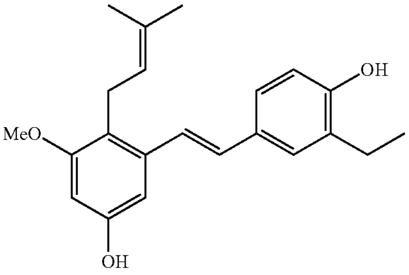
14 [KYN-118]
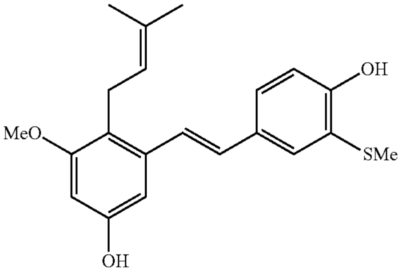

-continued
15 [KYN-158]
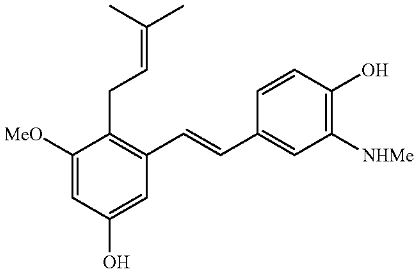
16 [KYN-157]
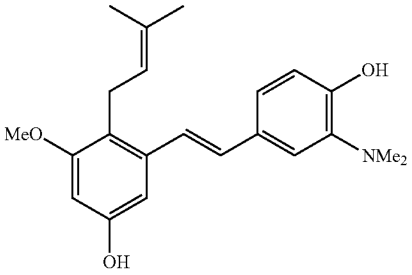
17 [KYN-120]
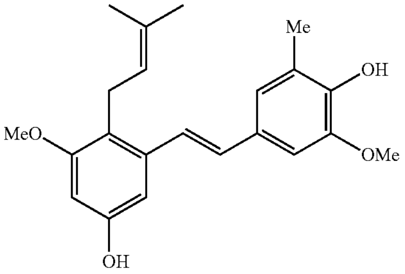
18 [KYN-156]
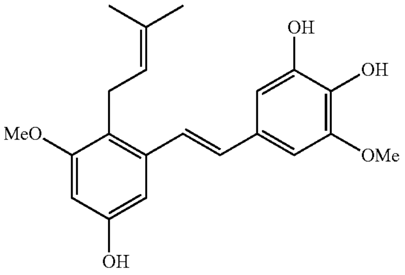
19 [KYN-160]
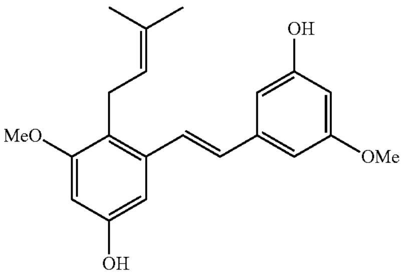
-continued
20 [KYN-146]
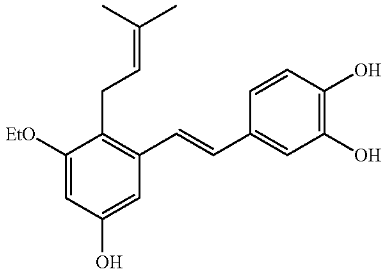
21 [KYN-154]
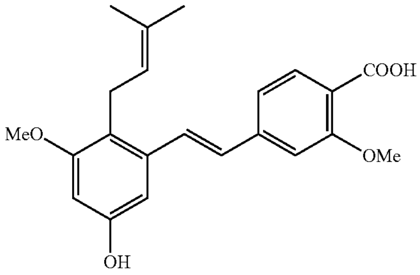
22 [KYN-124]
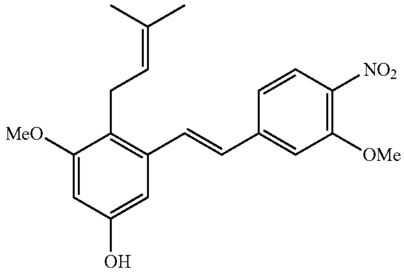
23 [KYN-125]
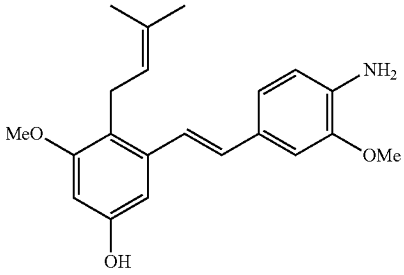
24 [KYN-141]
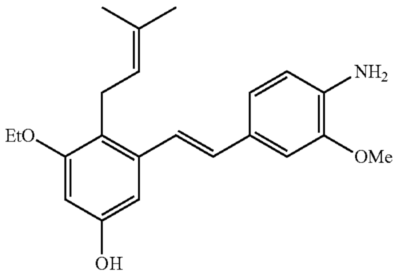

-continued
25 [KYN-137]
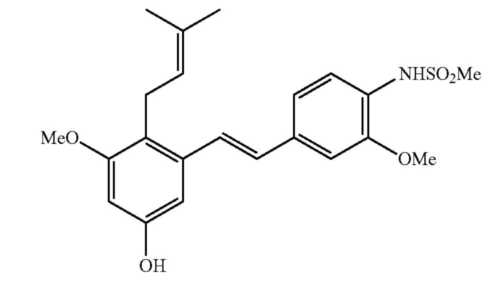
26 [KYN-129]
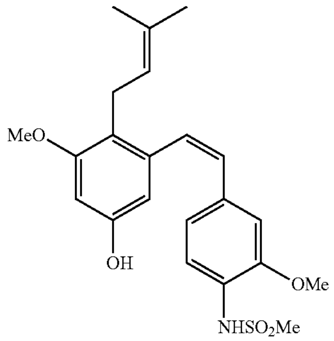
27 [KYN-149]
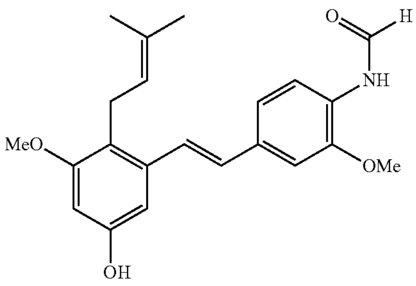
28 [KYN-143]
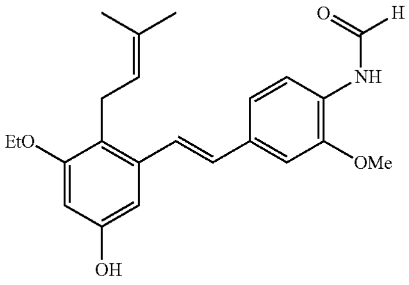
29 [KYN-128]
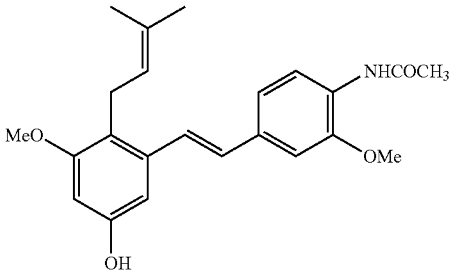
-continued
30 [KYN-142]
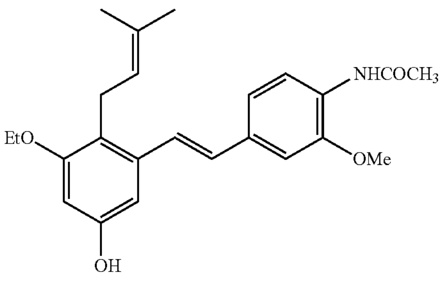
31 [KYN-151]
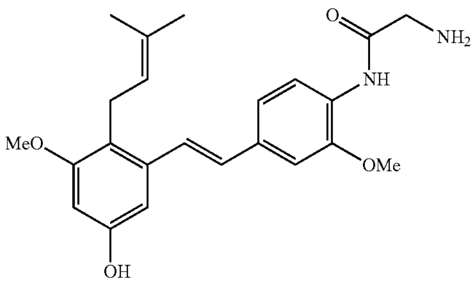
32 [KYN-148]
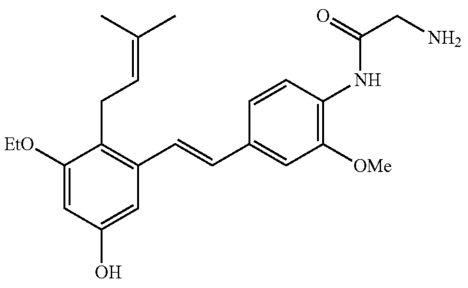
33 [KYN-126]
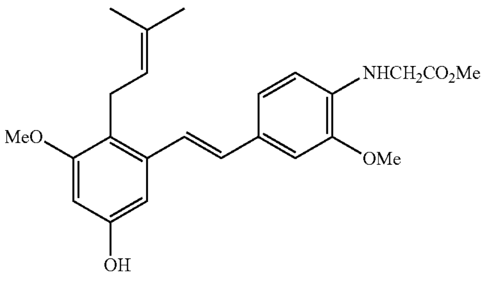
34 [KYN-147]
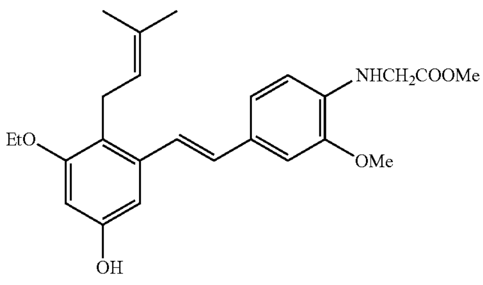

-continued
35 [KYN-152]
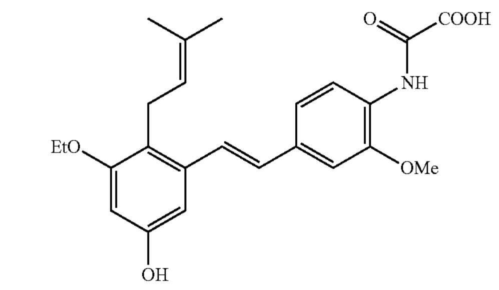
36 [KYN-150]
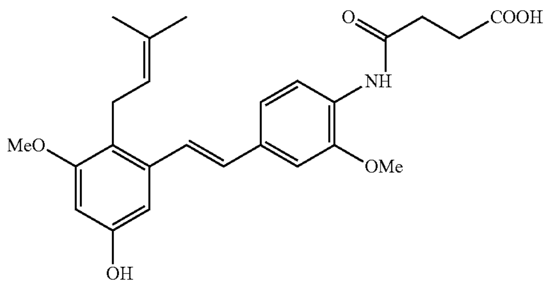
37 [KYN-144]
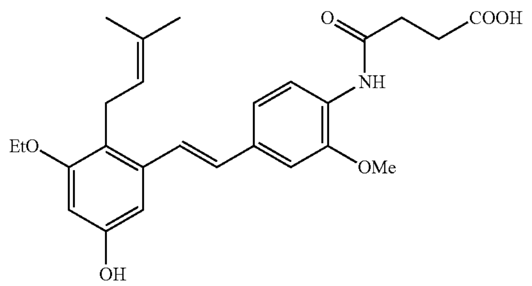
38 [KYN-155]
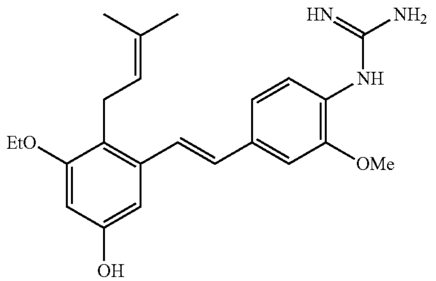
39 [KYN-165]
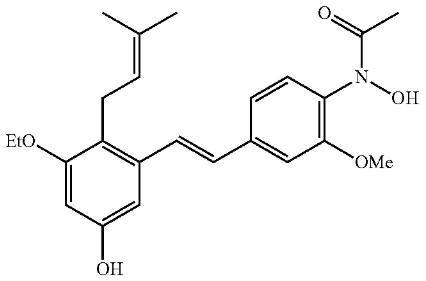
-continued
40 [KYN-159]
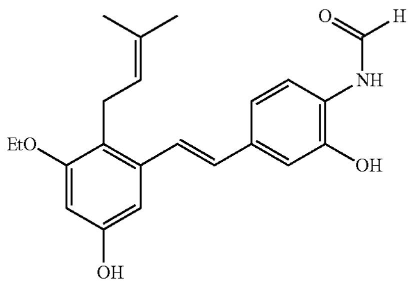
41 [KYN-161]
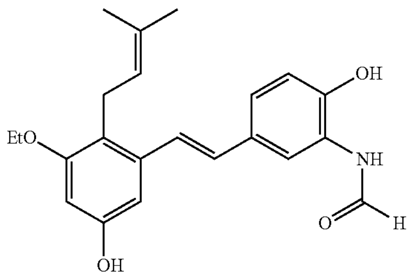
42 [KYN-162]
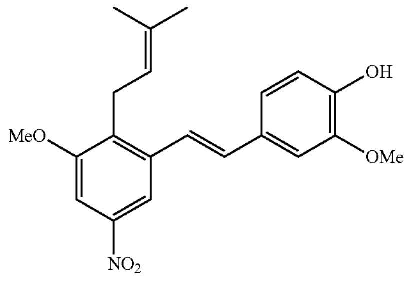
43 [KYN-163]
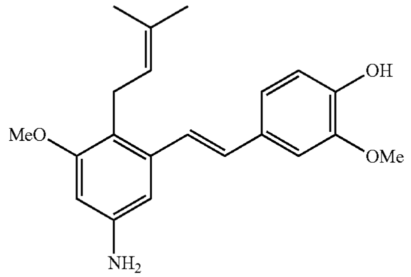
44 [KYN-164]
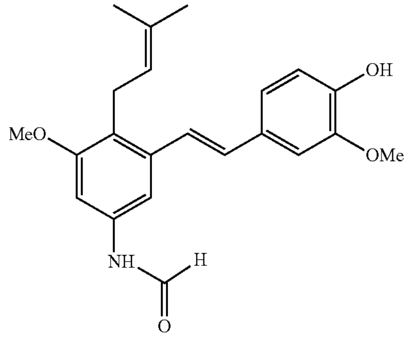

-continued

46 [KYN-145]

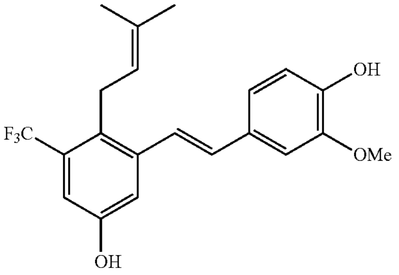

47 [KYN-167]

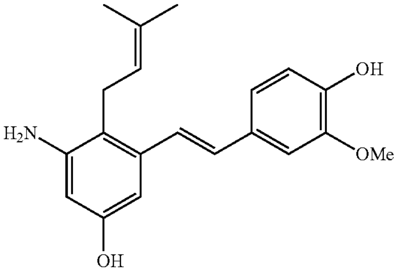

48 [KYN-168]

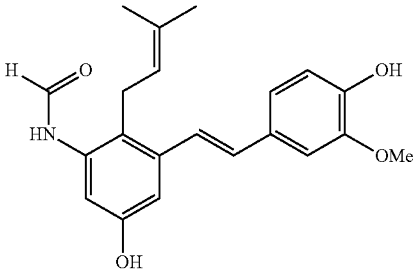

49 [KYN-169]

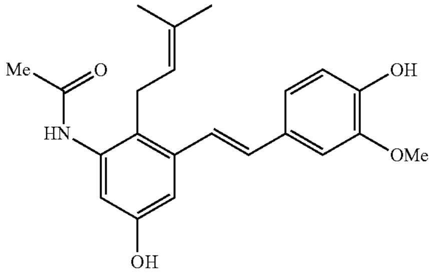

50 [KYN-170]

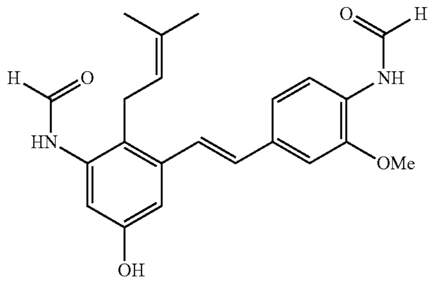

-continued

51 [KYN-166]

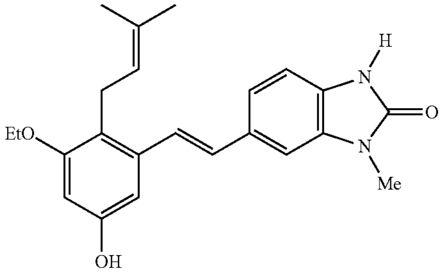

52 [KYN-171]

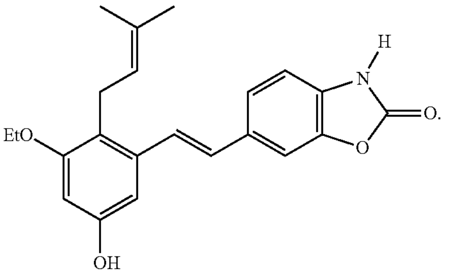

6. The process of claim 1, wherein in Formula (I):

$R^{1a}$ is allyl, crotyl, prenyl, benzyl or 2-alkenyl $R^{1b}$ is $OR^2$, NHC(O)Me or NHC(O)H;

$R^{1c}$ is H;

$R^{1d}$ is OH;

$R^{1e}$ is $OR^2$;

$R^{1f}$ is $NO_2$, $NHR^3$ or $NHC{=}NH(NH_2)$;

$R^{1g}$ is H;

$R^2$ is methyl, ethyl, propyl, isopropyl, butyl, isobutyl or t-butyl; and $R^3$ is H, (CO) H, (CO) Me, $SO_2Me$, $CH_2COOR^2$, $COCH_2NH_2$ or $CO(CH_2)_nCOOH$ (where n=0, 1 or 2);

in Formula (II):

$R^{2b}$ is $OR^2$ or $NH_2$;

$R^{2c}$ is H;

$R^{2d}$ is-O-protecting group;

X is a halide selected from the group consisting of F, Cl, Br, I and At; and $R^2$ is methyl, ethyl, propyl, isopropyl, butyl, isobutyl or t-butyl; and in Formula (III):

$R^{3e}$ is $OR^2$;

$R^{3f}$ is $NO_2$;

$R^{3g}$ is H;

$R^2$ is methyl, ethyl, propyl, isopropyl, butyl, isobutyl or t-butyl, and $R^4$ is $C_1$-$C_6$ alkyl;

in Formula (IV):

$R^{4b}$ is $OR^2$ or $NH_2$;

$R^{4c}$ is H;

$R^{4d}$ is O-protecting group;

$R^{4e}$ is $OR^2$;

$R^{4f}$ is $NO_2$;

$R^{4g}$ is H;

$R^2$ is methyl, ethyl, propyl, isopropyl, butyl, isobutyl or t-butyl, and

X is a halide selected from the group consisting of F, Cl, Br, I and At;

wherein the protecting group is selected from the group consisting of COMe, t-BuSi$(CH_3)_2$, 2-(trimethylsilyl) ethoxymethyl (SEM), CH(OEt)$CH_3$, tetrahydropyranyl, or C(OEt)$(CH_3)_2$; and wherein formula IV is coupled with a $R^{1a}$ boronic pinacol ester selected from the group consisting of 3-methylbut-2-enylboronic acid pinacol ester, crotylboronic acid pinacol ester, allylboronic acid pinacol ester and benzylboronic acid pinacol ester, catalysed by a palladium catalyst in the presence of a base, to produce the compound of formula (I).

7. The process of claim 1, wherein the compound according to formula (I) are selected for the group consisting of:

2 [KYN-138]

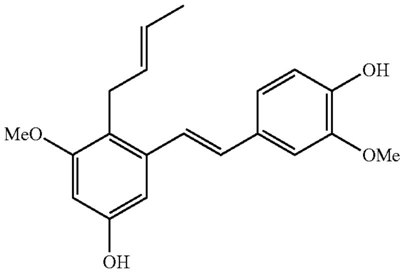

3 [KYN-139]

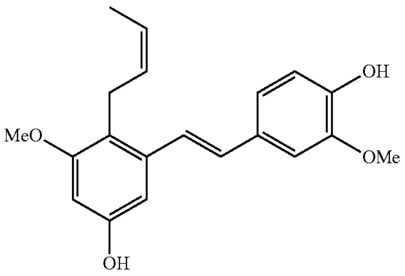

4 [KYN-140]

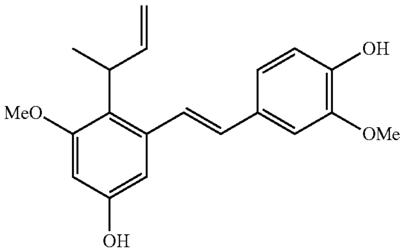

5 [KYN-153]

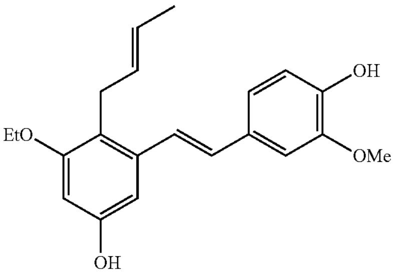

-continued

6 [KYN-134]

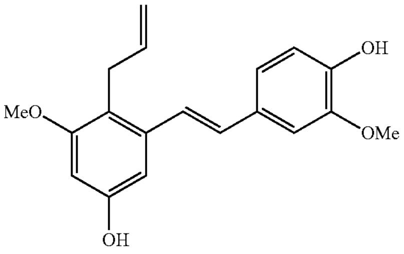

7 [KYN-136]

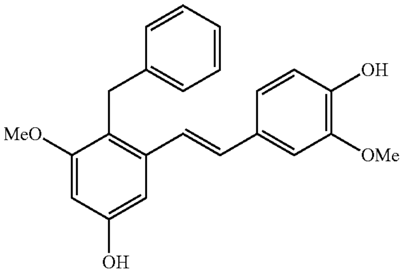

11 [KYN-132]

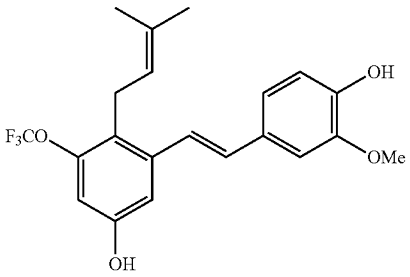

13 [KYN-114]

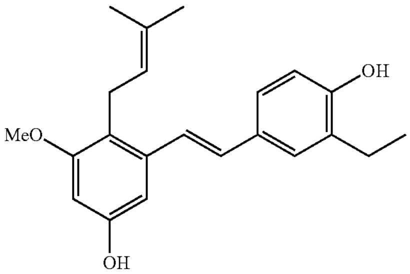

14 [KYN-118]

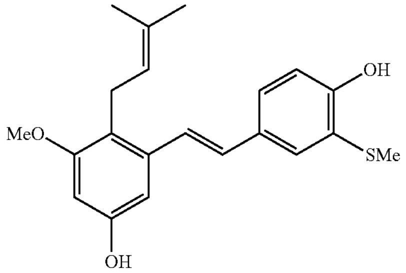

-continued
15 [KYN-158]
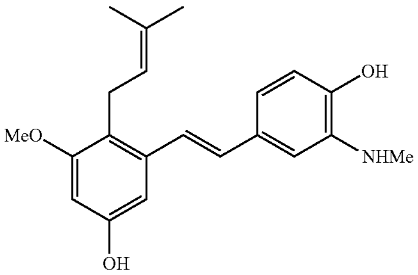
16 [KYN-157]
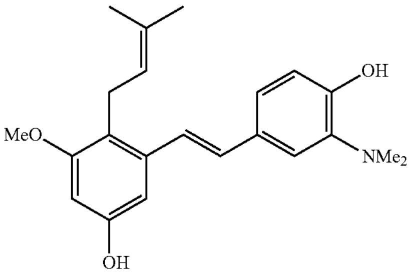
17 [KYN-120]
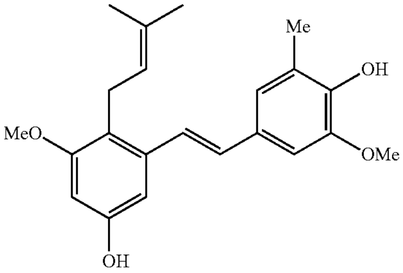
18 [KYN-156]
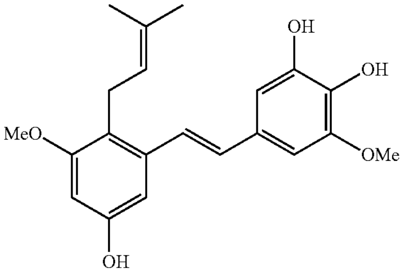
19 [KYN-160]
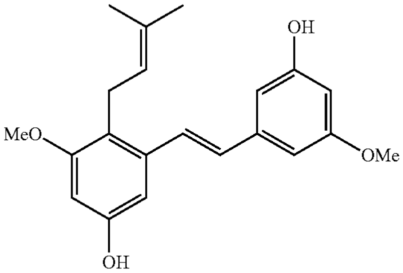
-continued
21 [KYN-154]
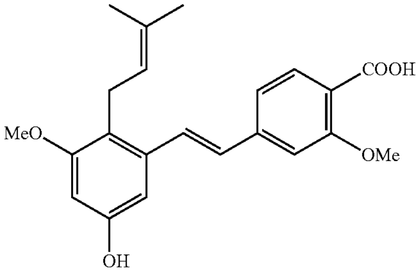
22 [KYN-124]
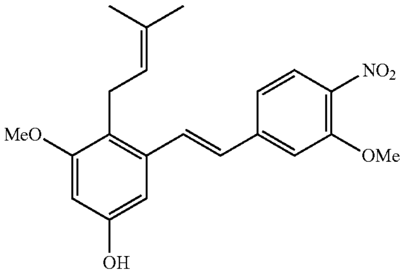
23 [KYN-125]
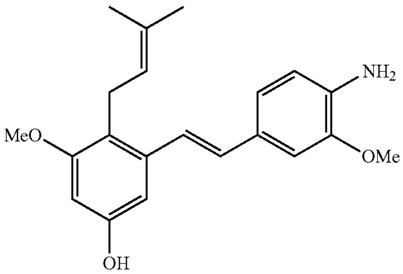
24 [KYN-141]
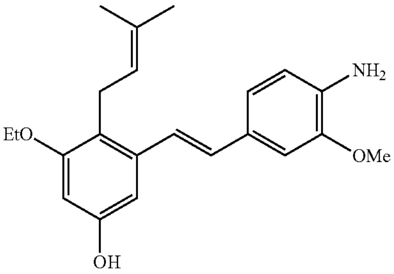
25 [KYN-137]
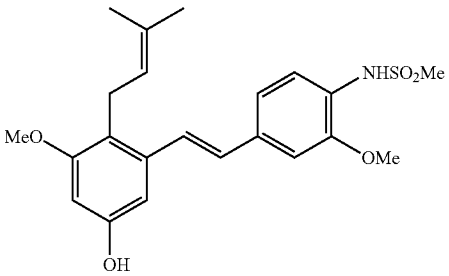

-continued
26 [KYN-129]
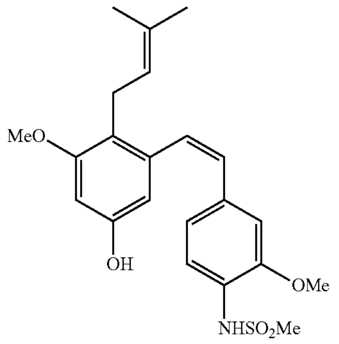
27 [KYN-149]
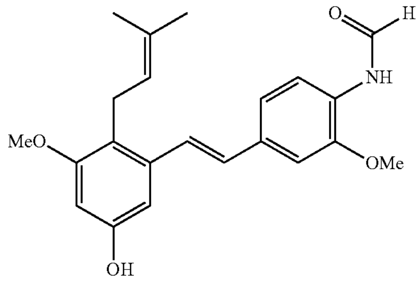
28 [KYN-143]
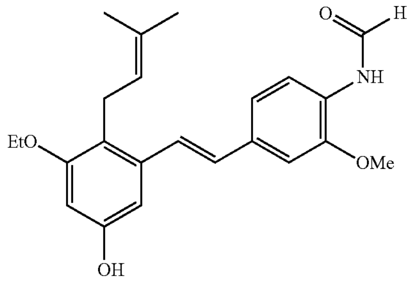
29 [KYN-128]
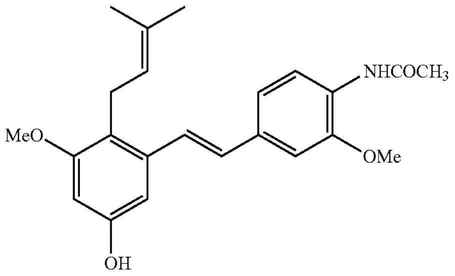
30 [KYN-142]
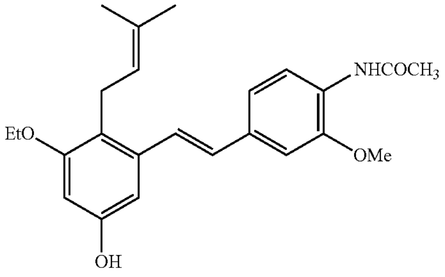
-continued
31 [KYN-151]
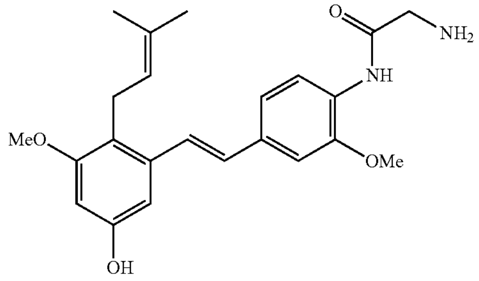
32 [KYN-148]
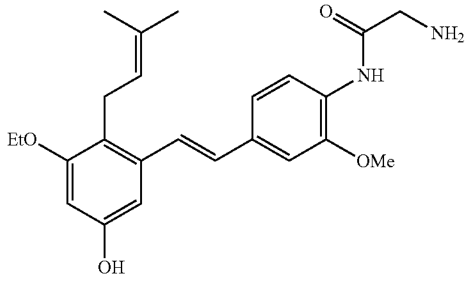
33 [KYN-126]
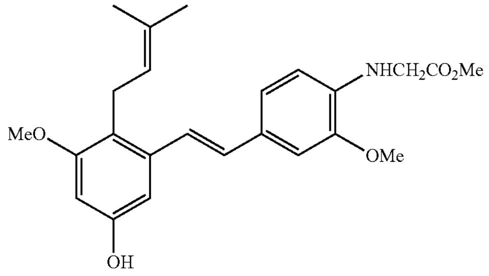
34 [KYN-147]
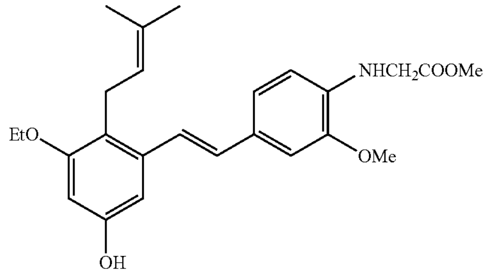
35 [KYN-152]
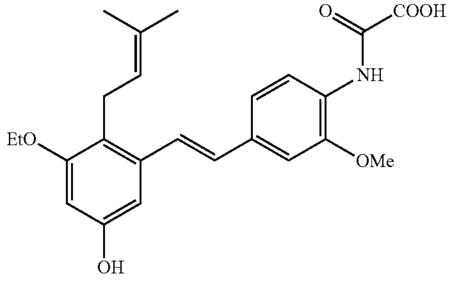

-continued
36 [KYN-150]
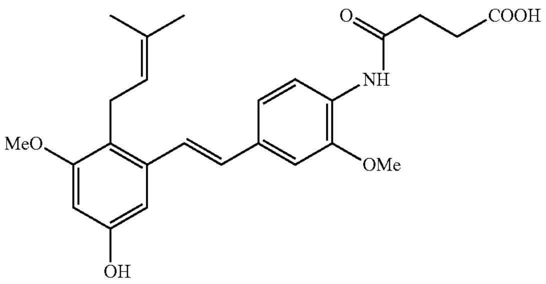
37 [KYN-144]
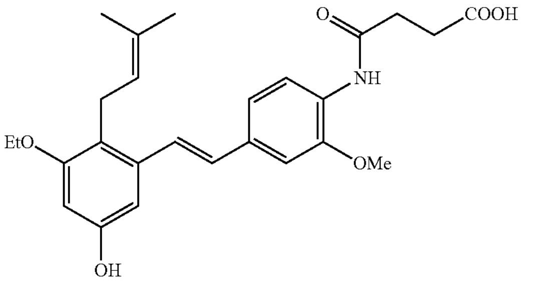
38 [KYN-155]
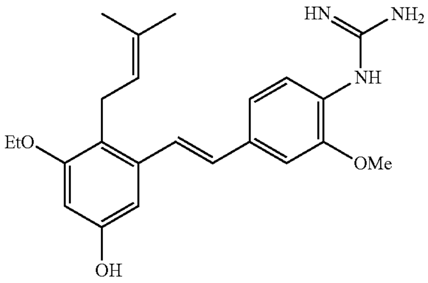
39 [KYN-165]
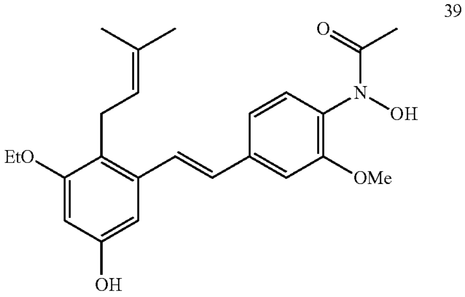
40 [KYN-159]
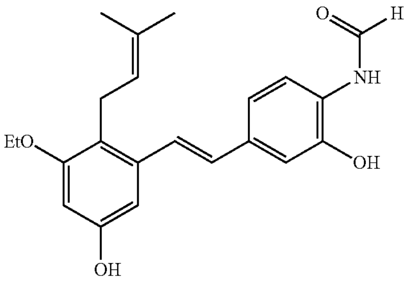
-continued
41 [KYN-161]
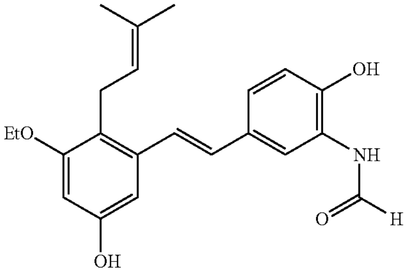
42 [KYN-162]
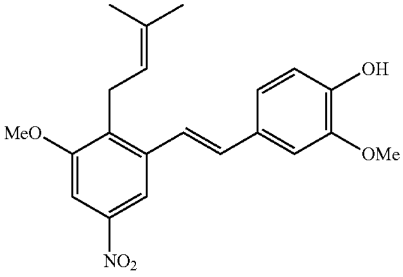
43 [KYN-163]
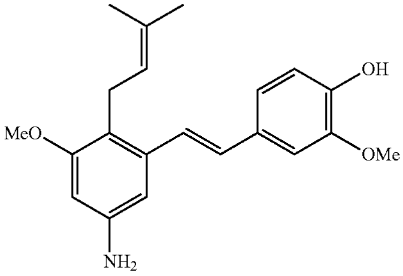
44 [KYN-164]
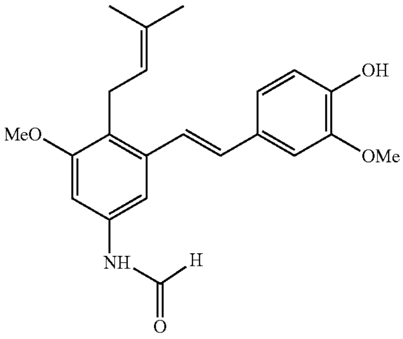
45 [KYN-112]
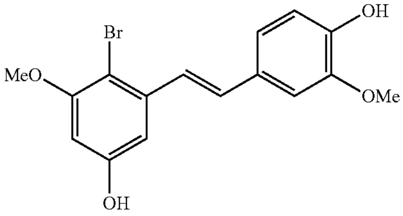

-continued

46 [KYN-145]

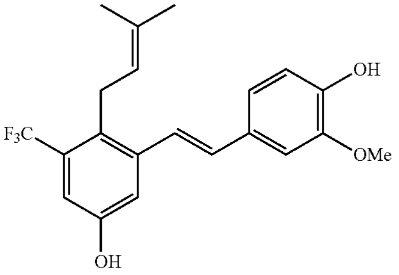

47 [KYN-167]

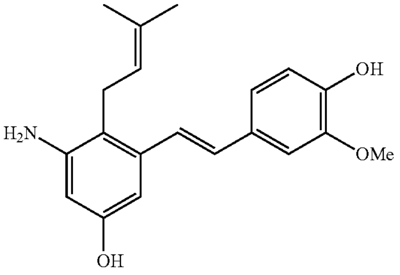

48 [KYN-168]

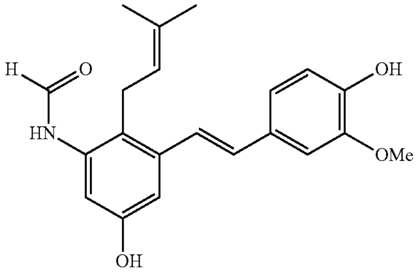

49 [KYN-169]

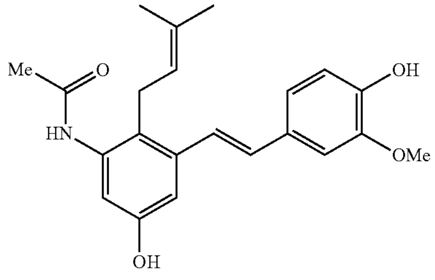

50 [KYN-170]

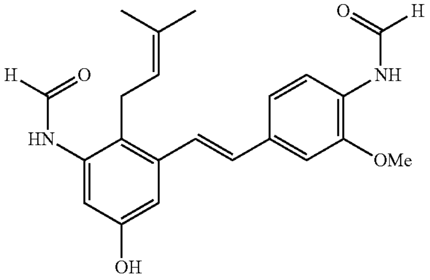

-continued

51 [KYN-166]

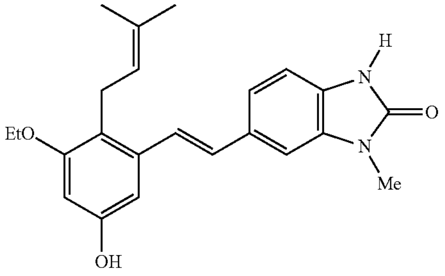

52 [KYN-171]

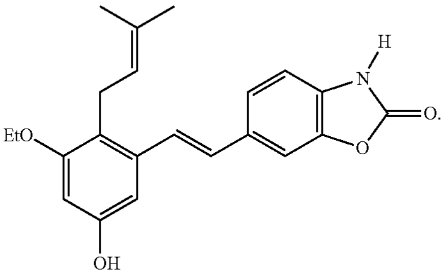

8. The process of claim 1, wherein the compound of formula (IV) or (I) undergoes one or more further reactions, selected from one or more of the following:

Reaction with one or more —$NH_2$, $NO_2$ and/or —OH substituents on formula (I);

Conversion of an —$NH_2$ substituents to methoxyoxoacetamido (—$NHC(O)C(O)OCH_3$) substituents by reaction of the compound containing the $NH_2$ substituent with methyl chlorooxoacetate in the presence of a base;

Conversion of one or more —OH substituents to methyl oxalate substituents by reaction of the compound containing the OH substituent with methyl chlorooxoacetate in the presence of a base;

Hydrolysis of one or more methoxyoxoacetamido substituents to a —NHC(O)C(O)OH substituents by reaction of the compound containing the N methoxyoxoacetamido substituent with a base;

Hydrolysis of one or more methyl oxalate substituents to —OH substituents by reaction of the compound containing the methyl oxalate substituent with a base;

Conversion of one or more —$NH_2$ substituents to guanidine (—$NHC(NH)NH_2$) substituents by reaction of the compound containing the $NH_2$ substituent with cyanamide in the presence of an acid;

Conversion of one or more —$NH_2$ substituents to formamide (—NHC(O)H) substituents by reaction of the compound containing the $NH_2$ substituent with ethyl formate;

Conversion of one or more —$NH_2$ substituents to an acetamido (—$NHC(O)CH_3$) substituents by reaction of the compound containing the $NH_2$ substituent with acetic anhydride in the presence of a base;

Conversion of one or more —$NH_2$ substituents to an amide derivative (—$NHC(O)CH^{2c}CH^{2c}(O)OH$) substituents by reaction of the compound containing the $NH_2$ substituent with succinic anhydride in the presence of a base;

Conversion of one or more —$NH_2$ substituents to methyl amine substituents (—NHMe) by reaction of the compound containing the $NH_2$ substituent with formaldehyde in the presence of triacetoxyborohydride;

Conversion of one or more —OH substituents to acetate (—OC(O)$CH_3$) substituents by reaction of the compound containing the —OH substituent with acetic anhydride in the presence of a base;

Hydrolysis of one or more acetate substituents may to form —OH substituents by reaction of the compound containing the acetate substituent with a base; or Reduction of one or more —$NO_2$ substituents to amine substituents by, for example, reaction of the compound containing the $NO_2$ substituent with Zn in the presence of ammonium chloride.

9. The process of claim 1, wherein the compound according to formula (II) is

A

Formula (II)

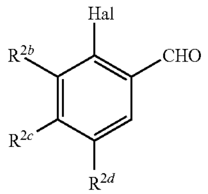

wherein $R^{2b}$ is OMe;

$R^{2c}$ is H;

$R^{2d}$ is OH or OSEM; and

Hal is Br;

which is prepared according to the following process:

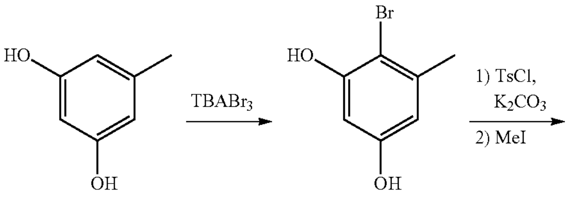

A1 A2

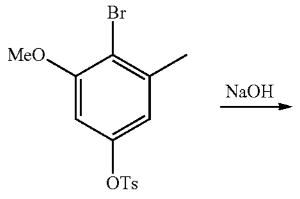

A3

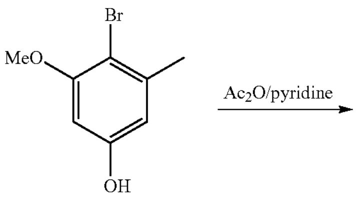

A4

-continued

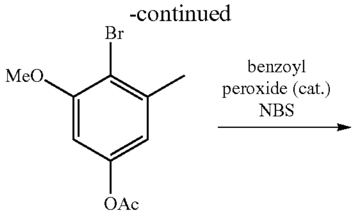

A5

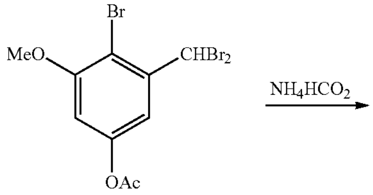

A6

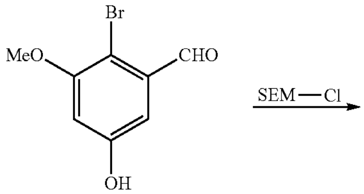

A7

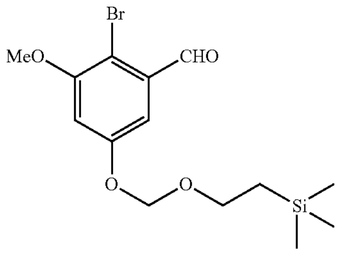

Module A wherein the compound according to formula (III) is

B

Formula (III)

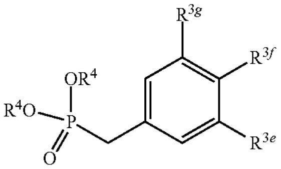

wherein $R^{3g}$ is H;

$R^{3f}$ is OSEM;

$R^{3e}$ is OMe; and $R^4$ is Et;

which is prepared according to the following process:

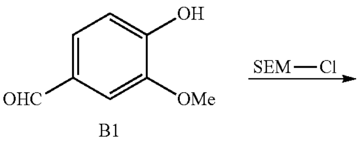

B1

-continued

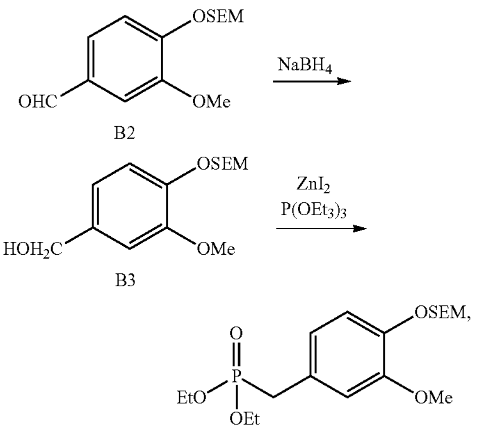

B2

B3

Module B and wherein formula (II) is Module A, formula (III) is Module B and formula (IV) is Module C according to the following:

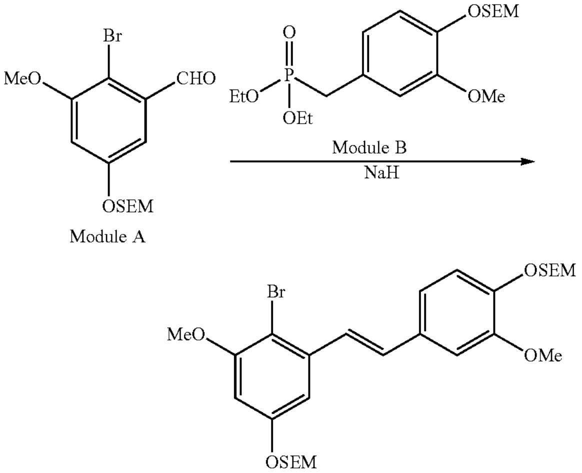

Module A

Module C wherein:

i) Module C is coupled with 3-methylbut-2-enylboronic acid pinacol ester in the presence of tetrakis (triphenylphosphine)palladium(0) and potassium carbonate to afford compound 1-1; and ii) compound 1-1 is treated with tetrabutylammonium fluoride to afford compound 1, according to the following:

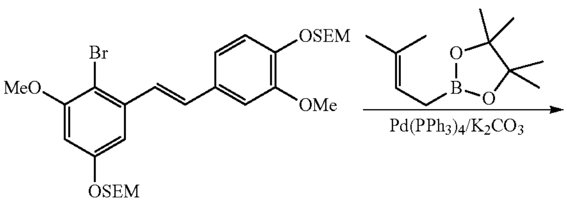

Module C

-continued

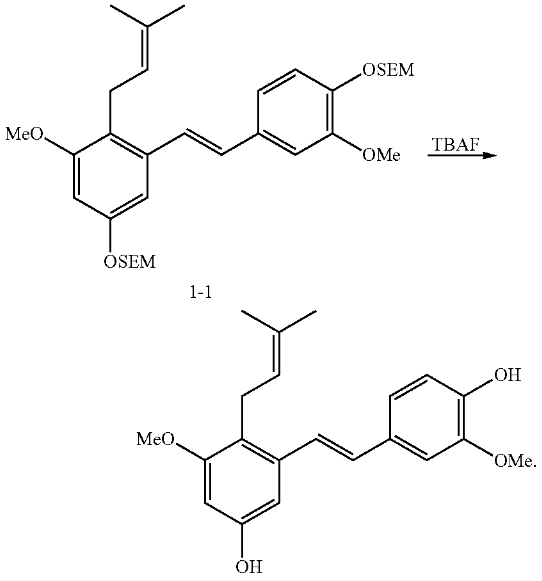

1-1

Compound 1

10. A compound according to formula (I)

Formula (I)

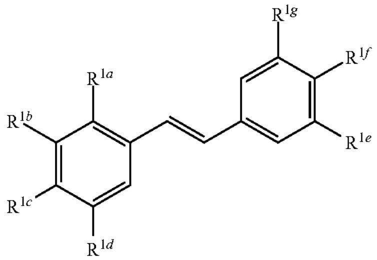

prepared by a process according to claim 1, wherein:

$R^{1a}$ is allyl, crotyl, prenyl, benzyl or 2-alkenyl;

$R^{1b}$ is $CF_3$, $OR^2$ or $NHR^3$;

$R^{1c}$ is H;

$R^{1d}$ is OH, O-protecting group, $NHR^3$ or $NO_2$;

$R^{1b}$ and $R^{1d}$ are not the same;

$R^{1e}$ is $C_1$-$C_6$ alkyl, OH, $OR^2$, $NO_2$, $NHR^3$, $NMeR^3$ or $SR^2$;

$R^{1f}$ is H, OH, O-protecting group, $NO_2$, $NHR^3$, NHC═NH($NH_2$), COOH or N(OH)(CO)$CH_3$;

$R^{1g}$ is H, $C_1$-$C_6$ alkyl or OH;

no more than one of $R^{1f}$ or $R^{1g}$ can be H;

$R^2$ is methyl, ethyl, propyl, isopropyl, butyl, isobutyl, t-butyl, trifluoromethyl or a O-protecting group;

protecting group is selected from the group consisting of COMe, t-BuSi($CH_3$)$_2$, 2-(trimethylsilyl) ethoxymethyl (SEM), CH(OEt)$CH_3$, tetrahydropyranyl, or C(OEt) ($CH_3$)$_2$;

$R^3$ is H, $CH_3$, (CO) H, (CO) Me, $SO_2Me$, $CH_2COOH$, $CH_2COOR^2$, $CO(CH_2)_nNH_2$, $CONH_2$, $CO(CH_2)_n$ COOH or $COCOOR^4$ (where n=0, 1 or 2); and $R^4$ is $C_1$-$C_6$ alkyl;

or $R^{1e}$ and $R^{1f}$ form a five-membered heterocyclic ring containing a carbonyl group when $R^{1e}$ is independently OH, $NH_2$ or NHMe and $R^{1f}$ is $NH_2$, such that the nitrogen of $R^{1f}$ is bridged with the carbonyl group to the oxygen or nitrogen of $R^{1e}$, and $R^{1g}$ is H.

11. A compound according to formula (I)

Formula (I)

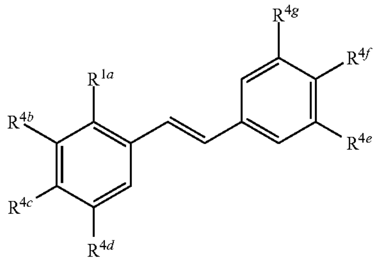

wherein:

$R^{1a}$ is allyl, crotyl, prenyl, benzyl or 2-alkenyl;

$R^{1b}$ is $CF_3$, $OR^2$ or $NHR^3$;

$R^{1c}$ is H;

$R^{1d}$ is OH, O-protecting group, $NO_2$ or $NHR^3$;

$R^{1e}$ is $C_1$-$C_6$ alkyl, OH, $OR^2$, $NO_2$, $NHR^3$, $NMeR^3$ or $SR^2$;

$R^{1f}$ is H, OH, O-protecting group, $NO_2$, $NHR^3$, NHC═NH($NH_2$), $COOR^2$, COOH or N(OH)(CO)$CH_3$;

$R^{1g}$ is H, $C_1$-$C_6$ alkyl or OH;

only one of $R^{1f}$ or $R^{1g}$ can be H;

$R^2$ is methyl, ethyl, propyl, isopropyl, butyl, isobutyl, t-butyl, trifluoromethyl or O-protecting group;

protecting group is selected from the group consisting of COMe, t-BuSi$(CH_3)_2$, 2-(trimethylsilyl) ethoxymethyl (SEM), CH(OEt)$CH_3$, tetrahydropyranyl, or C(OEt) $(CH_3)_2$;

$R^3$ is H, $CH_3$, (CO) H, (CO) Me, $SO_2Me$, $CH_2COOH$, $CH_2COOR^2$, $CO(CH_2)_nNH_2$, $CONH_2$, $CO(CH_2)_n$COOH or $COCOOR^4$ (where n=0, 1 or 2); and $R^4$ is $C_1$-$C_6$ alkyl;

or $R^{1e}$ and $R^{1f}$ form a five-membered heterocyclic ring containing a carbonyl group when $R^{1e}$ is independently OH, $NH_2$ or NHMe and $R^{1f}$ is $NH_2$, such that the nitrogen of $R^{1f}$ is bridged with the carbonyl group to the oxygen or nitrogen of $R^{1e}$; and $R^{1g}$ is H;

provided that:

i) when $R^{1a}$ is prenyl, $R^{1d}$ is OH or O-protecting group, $R^{1f}$ is OH or O-protecting group, $R^{1g}$ is H and $R^{1e}$ is OH or $OR^2$, then $R^{1b}$ cannot be $OR^2$ where $R^2$ is methyl, ethyl, propyl, isopropyl, butyl, isobutyl, t-butyl, or benzyl; and ii) $R^{1b}$ and Rid are not the same.

12. A compound of formula (I) according to claim 11 wherein:

$R^{1a}$ is allyl, prenyl or benzyl;

$R^{1b}$ is $CF_3$ or $OR^2$;

$R^{1c}$ is H;

$R^{1d}$ is OH, $NH_2$ or N(CO)H;

$R^{1e}$ is OH, $OR^2$, $NO_2$, $NHR^3$, $NMeR^3$ or SMe;

$R^{1f}$ is H, OH, $NO_2$, $NHR^3$, NHC═NH($NH_2$) or COOH;

$R^{1g}$ is H, $C_1$-$C_6$ alkyl or OH;

only one of $R^{1f}$ or $R^{1g}$ can be H;

$R^2$ is methyl, ethyl, propyl, isopropyl, butyl, isobutyl or t-butyl; and $R^3$ is H, $CH_3$, (CO) H, (CO) Me, $SO_2Me$, $CH_2COOR^2$, $COCH_2NH_2$ or $CO(CH_2)_n$COOH (where n=0, 1 or 2);

provided that:

i) when $R^{1a}$ is prenyl, $R^{1d}$ is OH, $R^{1f}$ is OH, $R^{1g}$ is H and $R^{1e}$ is OH or $OR^2$, then $R^{1b}$ cannot be $OR^2$ where $R^2$ is methyl, ethyl, isopropyl, propyl, butyl, isobutyl, tbutyl, or benzyl.

13. A compound according to claim 11 wherein formula (I) is a compound selected from the group consisting of:

2 [KYN-138]

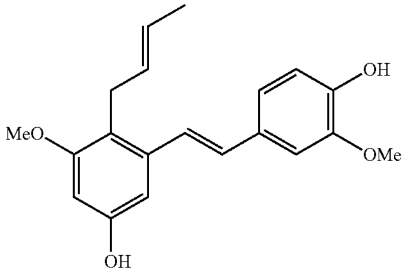

3 [KYN-139]

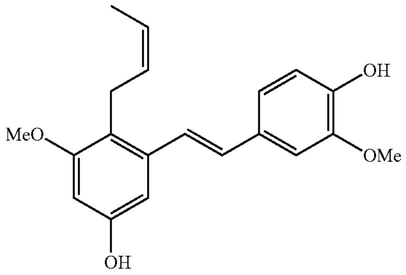

4 [KYN-140]

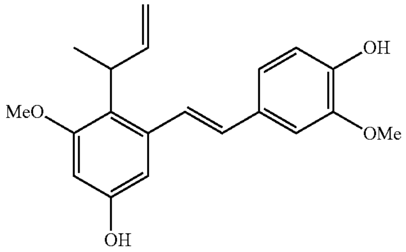

5 [KYN-153]

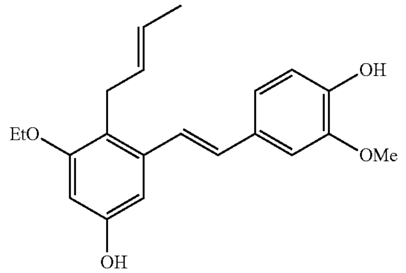

6 [KYN-134]

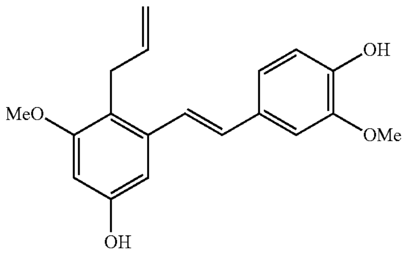

-continued
7 [KYN-136]
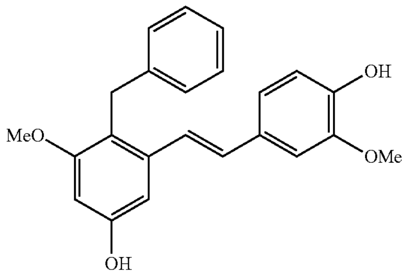
11 [KYN-132]
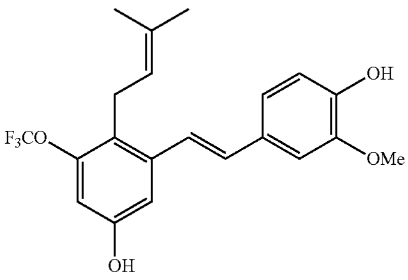
13 [KYN-114]
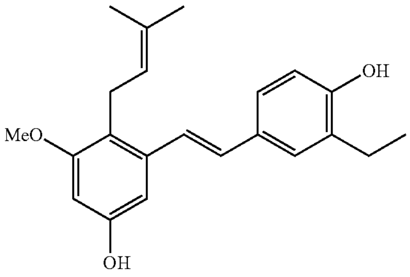
14 [KYN-118]
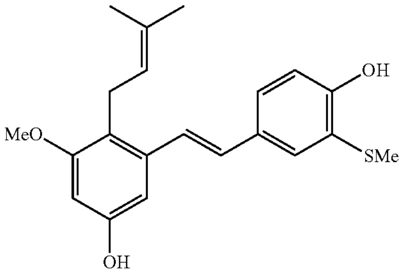
15 [KYN-158]
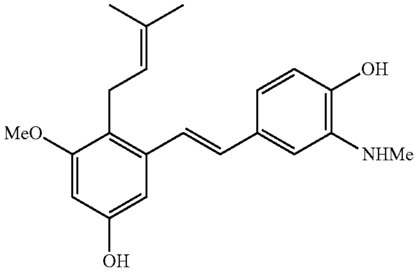
-continued
16 [KYN-157]
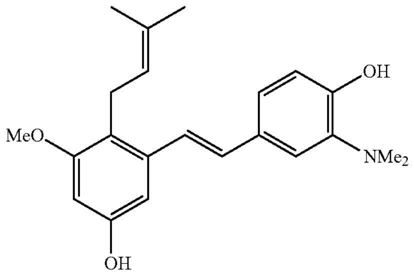
17 [KYN-120]
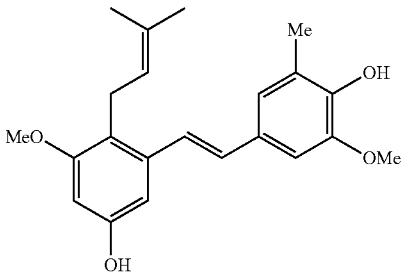
18 [KYN-156]
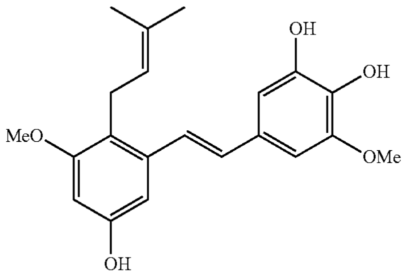
19 [KYN-160]
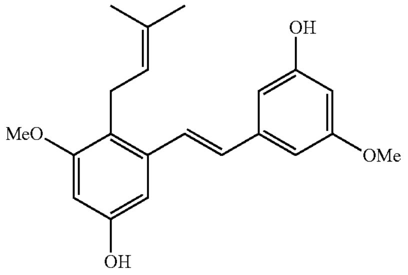
21 [KYN-154]
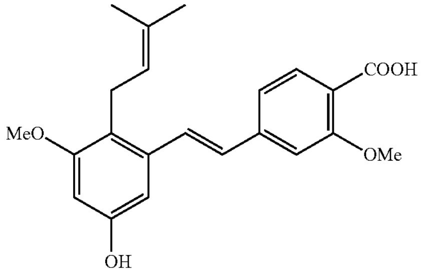

-continued
22 [KYN-124]
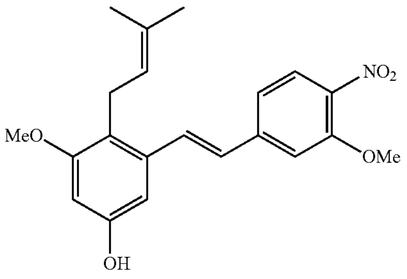
23 [KYN-125]
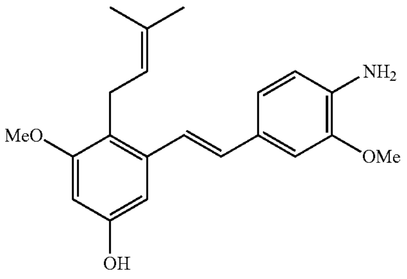
24 [KYN-141]
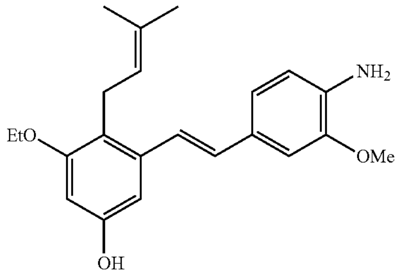
25 [KYN-137]
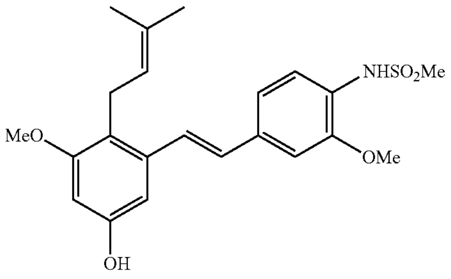
26 [KYN-129]
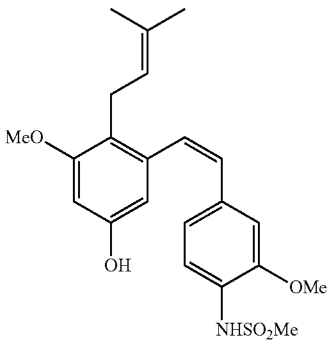
-continued
27 [KYN-149]
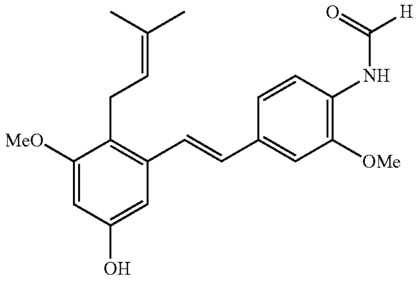
28 [KYN-143]
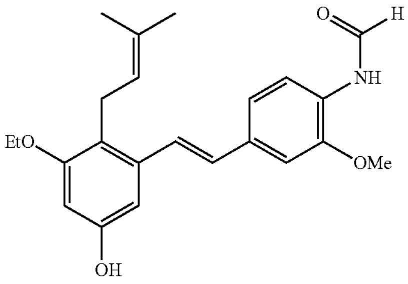
29 [KYN-128]
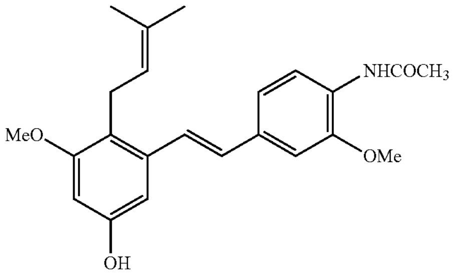
30 [KYN-142]
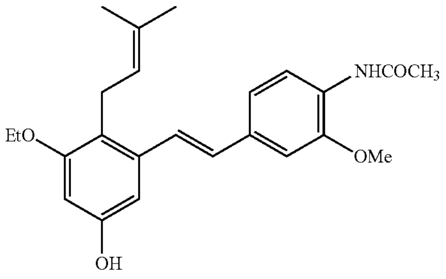
31 [KYN-151]
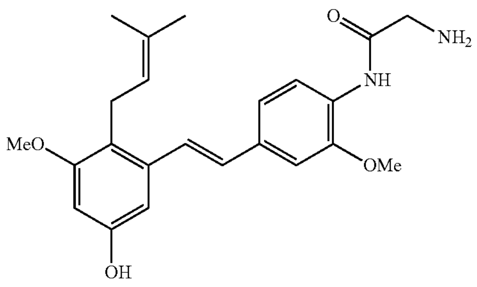

-continued
32 [KYN-148]
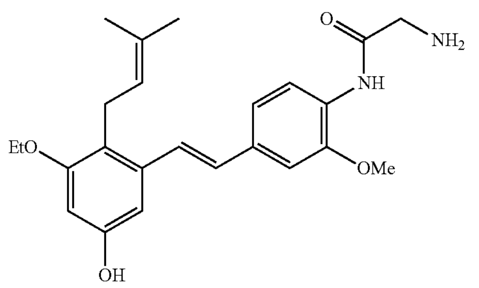
33 [KYN-126]
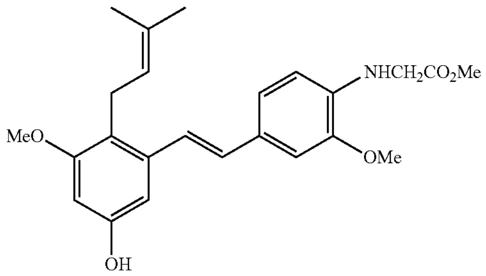
34 [KYN-147]
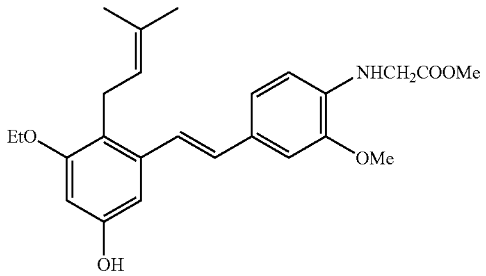
35 [KYN-152]
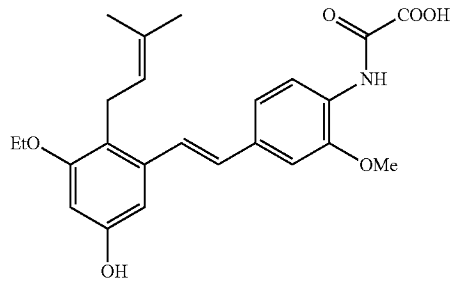
36 [KYN-150]
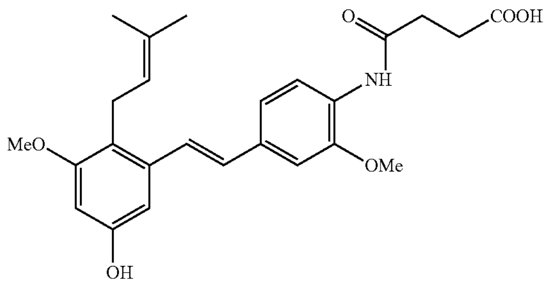
-continued
37 [KYN-144]
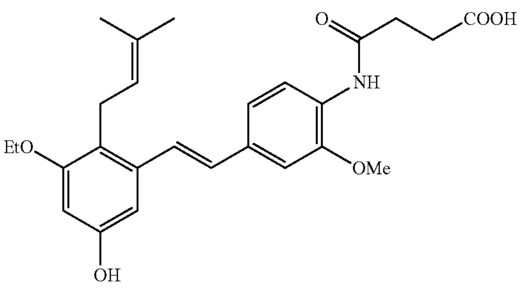
38 [KYN-155]
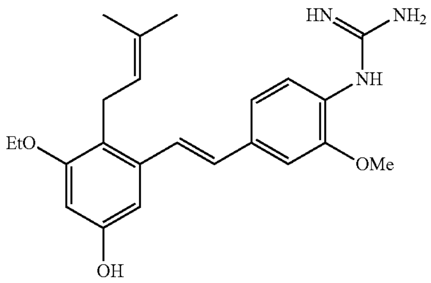
39 [KYN-165]
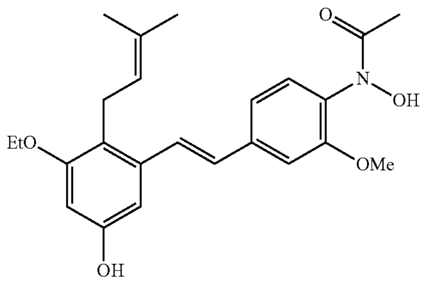
40 [KYN-159]
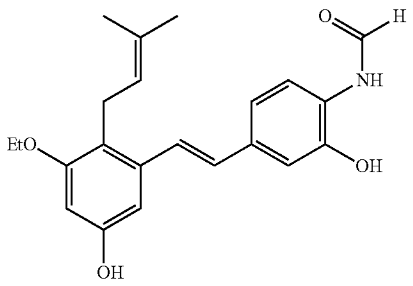
41 [KYN-161]
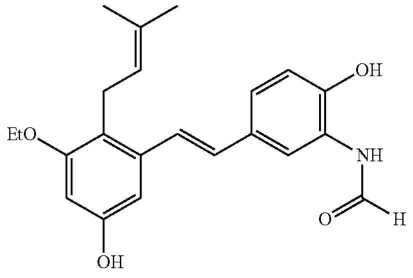

-continued
42 [KYN-162]
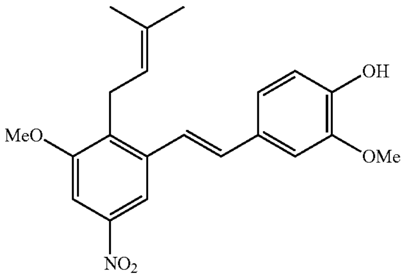
43 [KYN-163]
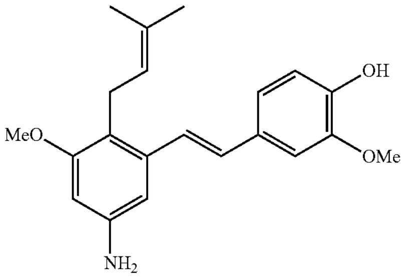
44 [KYN-164]
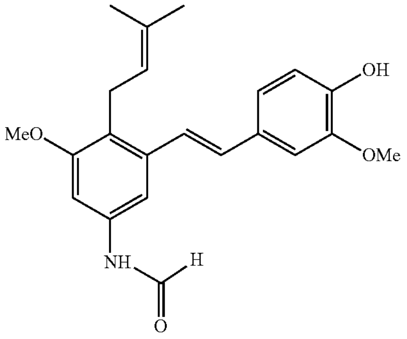
46 [KYN-145]
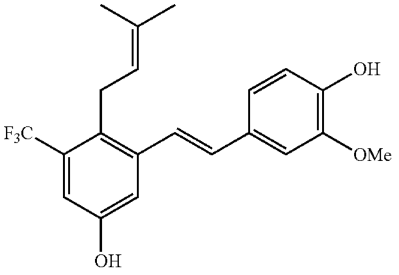
47 [KYN-167]
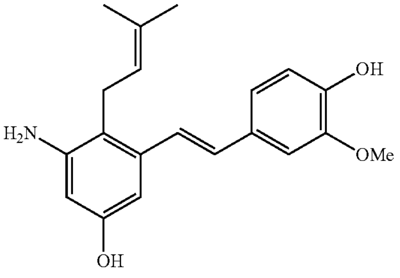
-continued
48 [KYN-168]
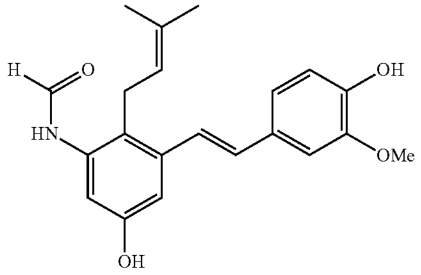
49 [KYN-169]
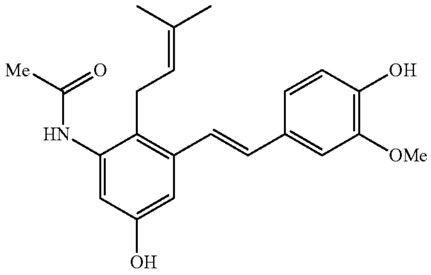
50 [KYN-170]
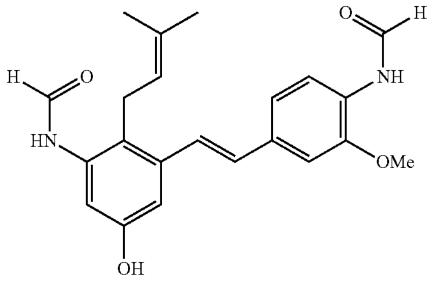
51 [KYN-166]
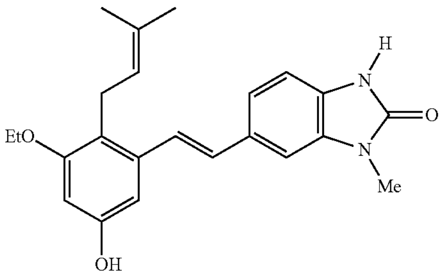
52 [KYN-171]
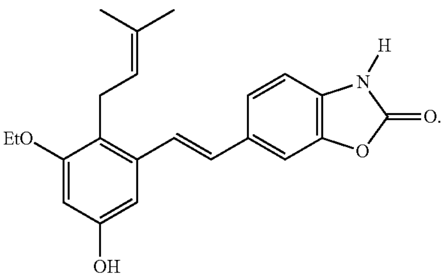
14. A compound according to claim 11 wherein in formula (I):
$R^{1a}$ is allyl, crotyl, prenyl or benzyl;
$R^{1b}$ is $CF_3$, $OR^2$ or $NHR^3$,
$R^{1c}$ is H;
$R^{1d}$ is OH, $NO_2$ or $NHR^3$;
$R^{1e}$ is $C_1$-$C_6$ alkyl, OH, $OR^2$, $NO_2$, $NHR^3$ or $SR^2$;

$R^{1f}$ is H, OH, O-protecting group, $NO_2$, $NHR^3$, NHC=NH($NH_2$), $COOR^2$ or COOH;

$R^{1g}$ is H, $C_1$-$C_6$ alkyl or OH;

$R^{1b}$ and $R^{1d}$ are not the same; and only one of $R^{1f}$ or $R^{1g}$ can be H;

wherein at least one of $R^{1b}$ or $R^{1d}$ is $CF_3$, $NO_2$ or $NHR^3$;

$R^2$ is methyl, ethyl, propyl, isopropyl, butyl, isobutyl, t-butyl, trifluoromethyl or O-protecting group;

protecting group is selected from the group consisting of COMe, t-BuSi$(CH_3)_2$, 2-(trimethylsilyl) ethoxymethyl (SEM), CH(OEt)$CH_3$, tetrahydropyranyl, or C(OEt) $(CH_3)_2$;

$R^3$ is H, $CH_3$, (CO) H, (CO) Me, $SO_2Me$, $CH_2COOH$, $CH_2COOR^2$, $CO(CH_2)_nNH_2$, $CONH_2$, $CO(CH_2)_n$ COOH or $COCOOR^4$ (where n is 0, 1 or 2); and $R^4$ is $C_1$-$C_6$ alkyl, wherein formula (I) includes a compound selected from the group consisting of:

11 [KYN-132]

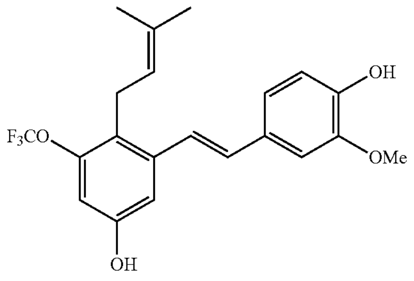

43 [KYN-163]

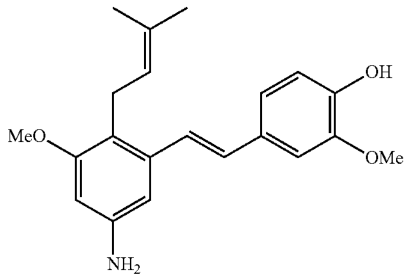

44 [KYN-164]

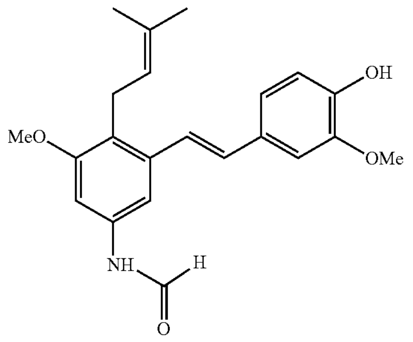

-continued

46 [KYN-145]

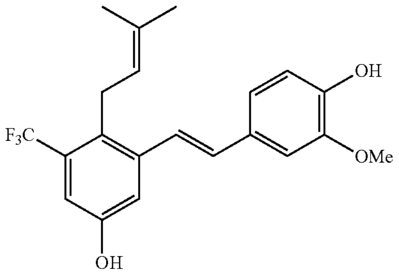

48 [KYN-168]

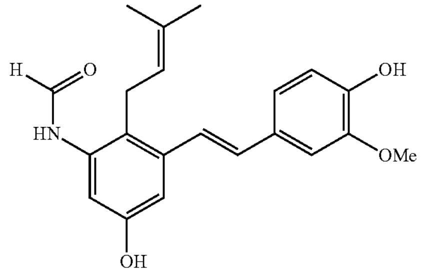

49 [KYN-169]

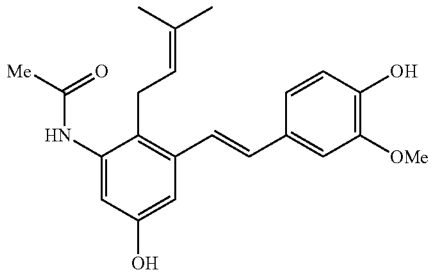

50 [KYN-170]

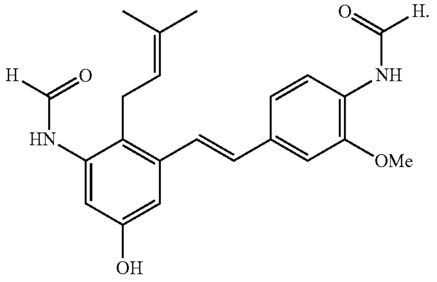

15. A compound according to claim 11 wherein in formula (I):

$R^{1a}$ is allyl, crotyl, prenyl or benzyl;

$R^{1b}$ is $CF_3$, $OR^2$ or $NHR^3$;

$R^{1c}$ is H;

$R^{1d}$ is OH, $NHR^3$ or $NO_2$;

$R^{1b}$ and $R^{1d}$ are not the same;

$R^{1e}$ is OH or $OR^2$;

$R^{1f}$ is $NO_2$, $NHR^3$, NHC=NH($NH_2$) or COOH;

$R^{1g}$ is H;

$R^2$ is methyl, ethyl, propyl, isopropyl, butyl, isobutyl, t-butyl or trifluoromethyl; and $R^3$ is H, $CH_3$, (CO)H, (CO)Me, $SO_2Me$, $CH_2COOH$, $CH_2COOR^2$, $COCH_2NH_2$, $CONH_2$ or $CO(CH_2)_n$ COOH (where n is 0, 1 or 2), wherein formula (I) is a compound selected from the group consisting of:

21 [KYN-154]
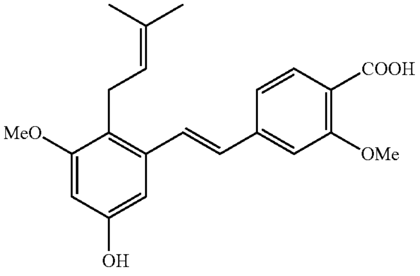
22 [KYN-124]
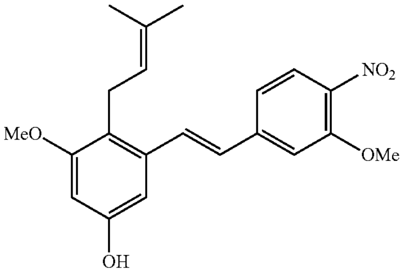
23 [KYN-125]
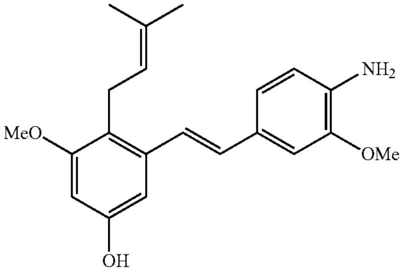
24 [KYN-141]
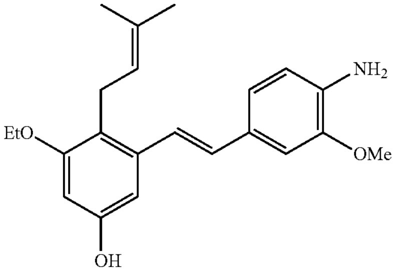
25 [KYN-137]
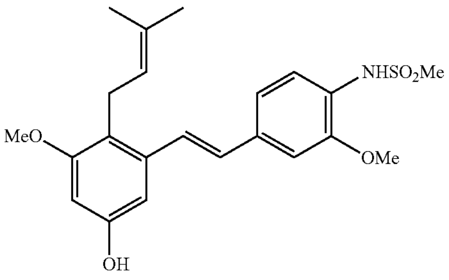
-continued
27 [KYN-149]
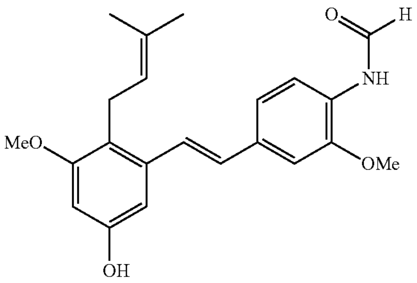
28 [KYN-143]
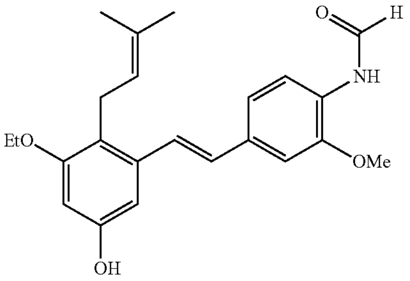
29 [KYN-128]
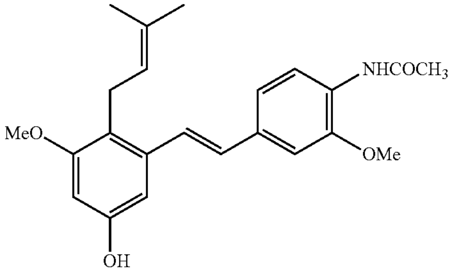
30 [KYN-142]
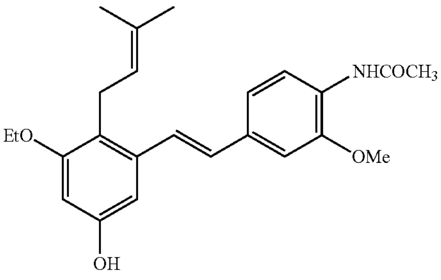
31 [KYN-151]
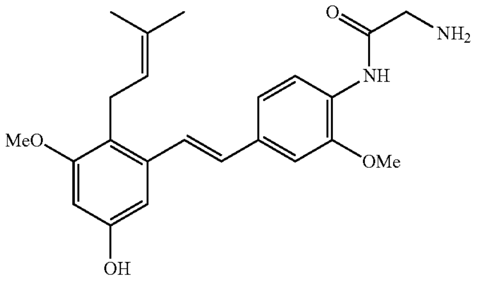

-continued

33 [KYN-126]

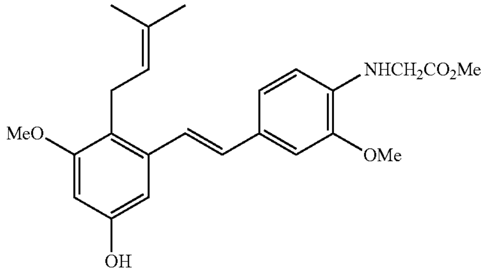

34 [KYN-147]

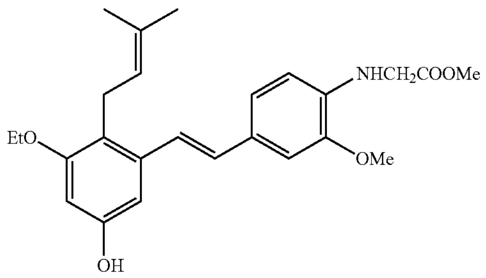

35 [KYN-152]

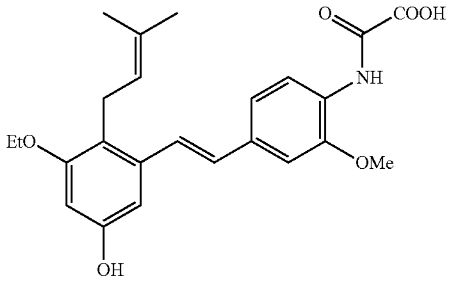

36 [KYN-150]

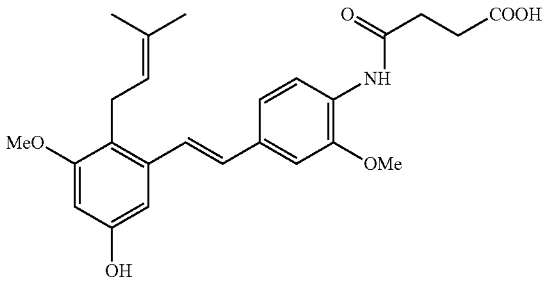

37 [KYN-144]

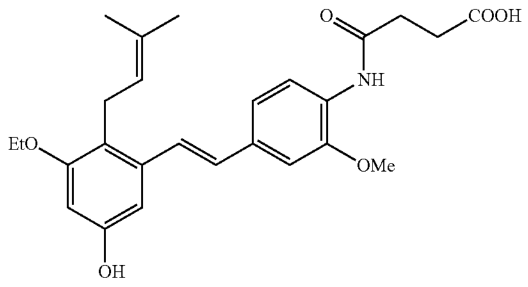

-continued

38 [KYN-155]

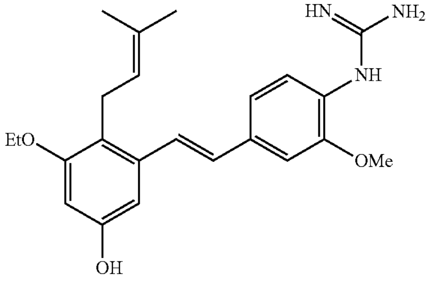

40 [KYN-159]

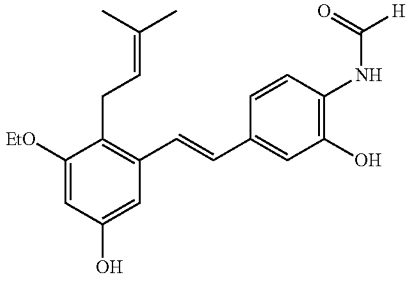

50 [KYN-170]

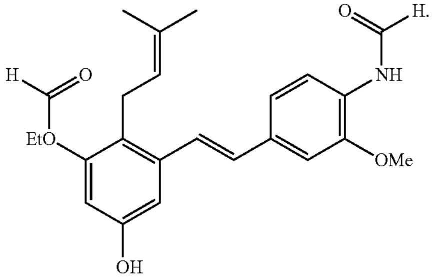

16. A compound according to claim 11 wherein in formula (I):

$R^{1a}$ is allyl, crotyl, prenyl or benzyl;

$R^{1b}$ is $CF_3$, $OR^2$ or $NHR^3$;

$R^{1c}$ is H;

$R^{1d}$ is OH, $NHR^3$ or $NO_2$;

$R^{1e}$ is $C_1$-$C_6$ alkyl, $NO_2$, NMe2, $NHR^3$ or $SR^2$;

$R^{1f}$ is OH or O-protecting group;

$R^{1g}$ is H;

$R^{1b}$ and $R^{1d}$ are not the same;

$R^2$ is methyl, ethyl, propyl, isopropyl, butyl, isobutyl, t-butyl, trifluoromethyl or O-protecting group;

protecting group is selected from the group consisting of COMe, t-BuSi$(CH_3)_2$, 2-(trimethylsilyl) ethoxymethyl (SEM), $CH(OEt)CH_3$, tetrahydropyranyl, or C(OEt)$(CH_3)_2$; and $R^3$ is H, $CH_3$, (CO)H, (CO)Me, $SO_2Me$, $CH_2COOH$, $CH_2COOR^2$, $COCH_2NH_2$, $CONH_2$ or $CO(CH_2)_n$COOH (where n is 0, 1 or 2), wherein formula (I) is a compound selected from the group consisting of:

13 [KYN-114]

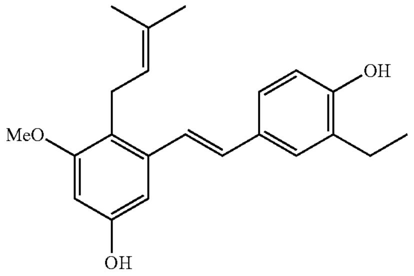

14 [KYN-118]

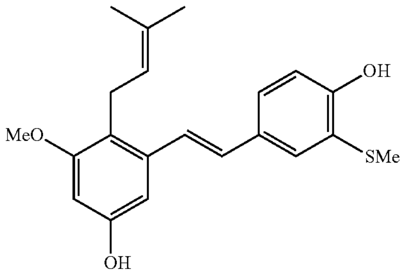

15 [KYN-158]

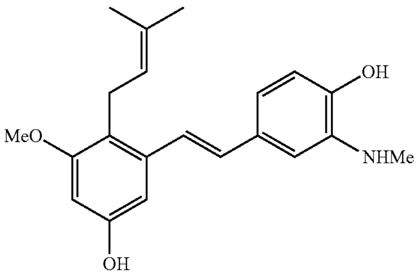

16 [KYN-157]

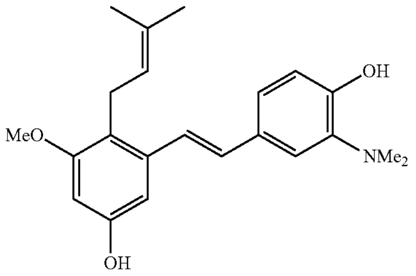

41 [KYN-161]

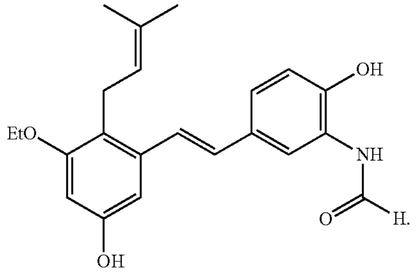

17. A compound according to claim 11 wherein in formula (I):

$R^{1a}$ is allyl, crotyl or benzyl;

$R^{1b}$ is $CF_3$, $OR^2$ or $NHR^3$;

$R^{1c}$ is H;

$R^{1d}$ is OH, $NHR^3$ or $NO_2$;

$R^{1e}$ is OH, $OR^2$, $NO_2$, $NHR^3$ or $SR^2$;

$R^{1f}$ is H, OH, $NO_2$, $NHR^3$, NHC═NH($NH_2$) or COOH;

$R^{1g}$ is H, $C_1$-$C_6$ alkyl or OH;

such that $R^{1b}$ and $R^{1d}$ are not the same;

and only one of $R^{1f}$ or $R^{1g}$ can be H;

$R^2$ is methyl, ethyl, propyl, isopropyl, butyl, isobutyl, t-butyl, trifluoromethyl or O-protecting group, wherein the protecting group is selected from the group consisting of COMe, t-BuSi($CH_3$)$_2$, 2-(trimethylsilyl) ethoxymethyl (SEM), CH(OEt)$CH_3$, tetrahydropyranyl, or C(OEt) ($CH_3$) 2; and $R^3$ is H, $CH_3$, (CO)H, (CO)Me, $SO_2$Me, $CH_2$COOH, $CH_2$COOR$^2$, COCH$_2$NH$_2$, CONH$_2$ or CO(CH$_2$)$_n$ COOH (where n is 0, 1 or 2).

18. A compound according to claim 11 wherein in formula (I):

$R^{1a}$ is allyl, crotyl, benzyl or 2-alkenyl;

$R^{1b}$ is $OR^2$;

$R^{1c}$ is H;

Rid is OH;

$R^{1e}$ is $OR^2$;

$R^{1f}$ is OH;

$R^{1g}$ is H; and $R^2$ is methyl, ethyl, propyl, isopropyl, butyl, isobutyl, t-butyl, trifluoromethyl or O-protecting group, wherein the protecting group is selected from the group consisting of COMe, t-BuSi($CH_3$)$_2$, 2-(trimethylsilyl) ethoxymethyl (SEM), CH(OEt)$CH_3$, tetrahydropyranyl, or C(OEt)($CH_3$) 2.

19. A compound according to claim 17 wherein formula (I) is a compound selected from the group consisting of:

2 [KYN-138]

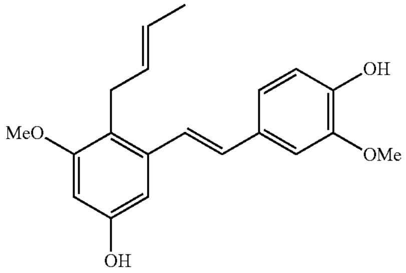

3 [KYN-139]

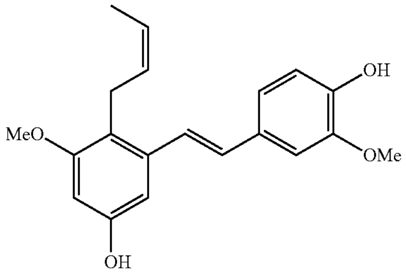

4 [KYN-140]

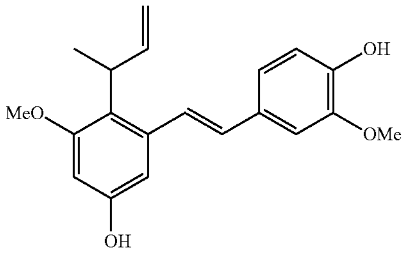

-continued

5 [KYN-153]

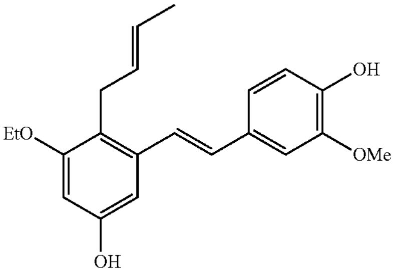

6 [KYN-134]

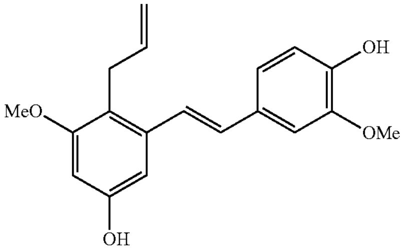

7 [KYN-136]

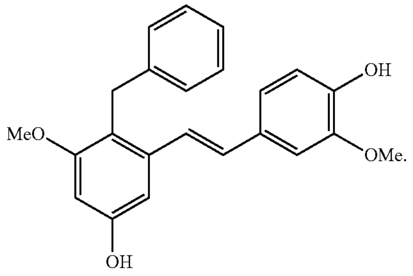

20. A compound according to claim 11 wherein in formula (I):

$R^{1a}$ is prenyl;

$R^{1b}$ is $OR^2$;

$R^{1c}$ is H;

$R^{1d}$ is OH;

$R^{1e}$ is $OR^2$;

$R^{1f}$ is $NHR^3$ or NHC═NH($NH_2$);

$R^{1g}$ is H;

$R^2$ is methyl, ethyl, propyl, isopropyl, butyl, isobutyl or t-butyl; and $R^3$ is H, $CH_3$, (CO)H, (CO)Me, $SO_2Me$, $CH_2COOR^2$, $COCH_2NH_2$ or $CO(CH_2)_nCOOH$ (where n is 0, 1 or 2).

21. A compound according to claim 11 wherein in formula (I):

$R^{1a}$ is prenyl;

$R^{1b}$ is $OR^2$;

$R^{1c}$ is H;

$R^{1d}$ is OH:

$R^{1e}$ is $OR^2$;

$R^{1f}$ is OH;

$R^{1g}$ is $C_1$-$C_6$ alkyl or OH; and $R^2$ is methyl, ethyl, propyl, isopropyl, butyl, isobutyl or t-butyl.

22. A compound according to claim 11 wherein in formula (I):

$R^{1a}$ is allyl, crotyl, prenyl or benzyl;

$R^{1b}$ is $CF_3$, $OR^2$ or $NHR^3$;

$R^{1c}$ is H;

$R^{1d}$ is OH, $NO_2$ or $NHR^3$;

Re is $C_1$-$C_6$ alkyl, OH, $OR^2$, $NO_2$, $NHR^3$ or $SR^2$;

$R^{1f}$ is H, OH, $OR^2$, $NO_2$, $NHR^3$, NHC═NH($NH_2$) or COOH;

$R^{1g}$ is H, $C_1$-$C_6$ alkyl or OH;

$R^2$ is methyl, ethyl, propyl, isopropyl, butyl, isobutyl, t-butyl, trifluoromethyl, or O-protecting group, wherein the protecting group is selected from the group consisting of COMe, t-BuSi($CH_3$)$_2$, 2-(trimethylsilyl) ethoxymethyl (SEM), CH(OEt)$CH_3$, tetrahydropyranyl, or C(OEt)($CH_3$)$_2$;

$R^3$ is H, $CH_3$, (CO)H, (CO)Me, $SO_2Me$, $CH_2COOH$, $CH_2COOR^2$, $CO(CH_2)_nNH_2$, $CONH_2$ or $CO(CH_2)_n$ COOH (where n is 0, 1 or 2);

only one of $R^{1f}$ or $R^{1g}$ can be H; and at least one of $R^{1e}$ or $R^{1f}$ is-NHC(O)H or NHC(O)Me.

23. A compound according to:

8 [KYN-119]

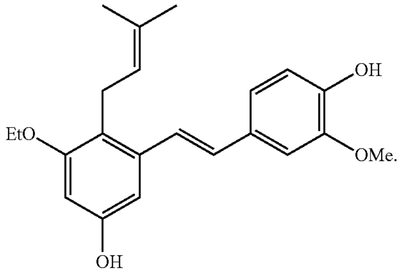

24. A compound according to:

20 [KYN-146]

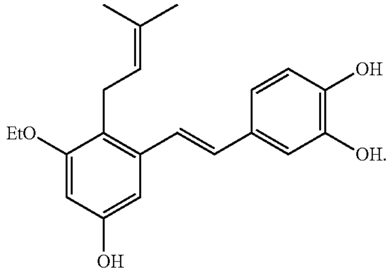

25. A method of treating a cancer comprising administering a therapeutically effective amount of a compound according to claim 11 or a pharmaceutically acceptable salt, solvate or pharmaceutical composition including said compound to a patient in need thereof wherein the cancer is selected from the group consisting of: skin cancer including melanoma; CNS cancer, ovarian cancer, renal cancer, prostate cancer, pancreatic cancer, bladder cancer, kidney cancer, hypo-pharynx cancer, pharynx cancer, tongue cancer, colon cancer, breast cancer, lung cancer, liver cancer, brain cancer, glioblastoma and osteoblastic sarcoma cell cancer, connective tissue sarcoma, Ewing's sarcoma, fibrosarcoma, leiomyosarcoma, liposarcoma, osteosarcoma and rhabdomyosarcoma, pharyngeal cancer and neuroblastomas.

26. A method of treating a skin disease and/or disorder comprising administering a therapeutically effective amount of a compound according to claim 11 or a pharmaceutically acceptable salt, solvate or pharmaceutical composition including said compound to a patient in need thereof.

27. The method of claim 26 wherein the skin disease and/or disorder is atopic dermatitis or psoriasis.

28. A method of treating a cancer comprising administering a therapeutically effective amount of a compound according to claim 23 or a pharmaceutically acceptable salt, solvate or pharmaceutical composition including said compound to a patient in need thereof wherein the cancer is selected from the group consisting of: skin cancer including melanoma; CNS cancer, ovarian cancer, renal cancer, prostate cancer, pancreatic cancer, bladder cancer, kidney cancer, hypo-pharynx cancer, pharynx cancer, tongue cancer, colon cancer, breast cancer, lung cancer, liver cancer, brain cancer, glioblastoma and osteoblastic sarcoma cell cancer, connective tissue sarcoma, Ewing's sarcoma, fibrosarcoma, leiomyosarcoma, liposarcoma, osteosarcoma and rhabdomyosarcoma, pharyngeal cancer and neuroblastomas.

29. A method of treating a skin disease and/or disorder comprising administering a therapeutically effective amount of a compound according to claim 23 or a pharmaceutically acceptable salt, solvate or pharmaceutical composition including said compound to a patient in need thereof.

30. The method of claim 29 wherein the skin disease and/or disorder is atopic dermatitis or psoriasis.

31. A method of treating a cancer comprising administering a therapeutically effective amount of a compound according to claim 24 or a pharmaceutically acceptable salt, solvate or pharmaceutical composition including said compound to a patient in need thereof wherein the cancer is selected from the group consisting of: skin cancer including melanoma; CNS cancer, ovarian cancer, renal cancer, prostate cancer, pancreatic cancer, bladder cancer, kidney cancer, hypo-pharynx cancer, pharynx cancer, tongue cancer, colon cancer, breast cancer, lung cancer, liver cancer, brain cancer, glioblastoma and osteoblastic sarcoma cell cancer, connective tissue sarcoma, Ewing's sarcoma, fibrosarcoma, leiomyosarcoma, liposarcoma, osteosarcoma and rhabdomyosarcoma, pharyngeal cancer and neuroblastomas.

32. A method of treating a skin disease and/or disorder comprising administering a therapeutically effective amount of a compound according to claim 24 or a pharmaceutically acceptable salt, solvate or pharmaceutical composition including said compound to a patient in need thereof.

33. The method of claim 32 wherein the skin disease and/or disorder is atopic dermatitis or psoriasis.

* * * * *